(12) United States Patent
Dave et al.

(10) Patent No.: US 12,161,670 B2
(45) Date of Patent: Dec. 10, 2024

(54) PHENOTYPIC MARKERS FOR CELL THERAPY AND RELATED METHODS

(71) Applicant: Juno Therapeutics, Inc., Seattle, WA (US)

(72) Inventors: Kedar Himanshu Dave, Seattle, WA (US); Todd Devries, Seattle, WA (US); Ronald James Hause, Jr., Seattle, WA (US); Ryan P. Larson, Seattle, WA (US); Christopher Glen Ramsborg, Seattle, WA (US); Claire L. Sutherland, Seattle, WA (US); Nathan K. Yee, Seattle, CA (US); Rachel K. Yost, Seattle, WA (US)

(73) Assignee: Juno Therapeutics, Inc., Seattle, WA (US)

( * ) Notice: Subject to any disclaimer, the term of this patent is extended or adjusted under 35 U.S.C. 154(b) by 557 days.

(21) Appl. No.: 16/770,510

(22) PCT Filed: Dec. 7, 2018

(86) PCT No.: PCT/US2018/064630
§ 371 (c)(1),
(2) Date: Jun. 5, 2020

(87) PCT Pub. No.: WO2019/113559
PCT Pub. Date: Jun. 13, 2019

(65) Prior Publication Data
US 2021/0128616 A1 May 6, 2021

Related U.S. Application Data

(60) Provisional application No. 62/716,967, filed on Aug. 9, 2018, provisional application No. 62/657,716, filed on Apr. 13, 2018, provisional application No. 62/643,165, filed on Mar. 14, 2018, provisional application No. 62/596,775, filed on Dec. 8, 2017.

(51) Int. Cl.
| | |
|---|---|
| *A61K 35/17* | (2015.01) |
| *A61P 35/00* | (2006.01) |
| *C07K 14/705* | (2006.01) |
| *C07K 14/725* | (2006.01) |
| *C07K 16/28* | (2006.01) |
| *C12N 5/0783* | (2010.01) |
| *C12N 15/85* | (2006.01) |
| *G01N 33/50* | (2006.01) |

(52) U.S. Cl.
CPC .............. *A61K 35/17* (2013.01); *A61P 35/00* (2018.01); *C07K 14/7051* (2013.01); *C07K 14/70521* (2013.01); *C07K 14/70578* (2013.01); *C07K 16/2803* (2013.01); *C12N 5/0636* (2013.01); *C12N 15/85* (2013.01); *G01N 33/5091* (2013.01); *C07K 2317/622* (2013.01); *C07K 2319/02* (2013.01); *C07K 2319/03* (2013.01); *C12N 2500/90* (2013.01); *C12N 2501/2302* (2013.01); *C12N 2501/2307* (2013.01); *C12N 2501/2315* (2013.01)

(58) Field of Classification Search
CPC ..... A61K 35/17; A61P 35/00; C07K 14/7051; C07K 14/70521; C07K 14/70578; C07K 16/2803; C12N 5/0636; C12N 15/85
USPC ...................................................... 424/93.21
See application file for complete search history.

(56) References Cited

U.S. PATENT DOCUMENTS

| | | |
|---|---|---|
| 4,452,773 A | 6/1984 | Molday |
| 4,690,915 A | 9/1987 | Rosenberg |
| 4,795,698 A | 1/1989 | Owen |
| 5,087,616 A | 2/1992 | Myers |
| 5,200,084 A | 4/1993 | Liberti |
| 5,219,740 A | 6/1993 | Miller |
| 5,994,136 A | 11/1999 | Naldini et al. |
| 6,013,516 A | 1/2000 | Verma et al. |
| 6,040,177 A | 3/2000 | Riddell et al. |
| 6,060,273 A | 5/2000 | Dirks et al. |
| 6,123,655 A | 9/2000 | Fell |
| 6,207,453 B1 | 3/2001 | Maass |
| 6,410,319 B1 | 6/2002 | Raubitschek |

(Continued)

FOREIGN PATENT DOCUMENTS

| | | |
|---|---|---|
| EP | 0452342 | 10/1991 |
| EP | 2537416 | 12/2012 |

(Continued)

OTHER PUBLICATIONS

US 8,252,592 B2, 08/2012, Sadelain (withdrawn)
(Continued)

*Primary Examiner* — Yan Xiao
(74) *Attorney, Agent, or Firm* — MORRISON & FOERSTER LLP

(57) ABSTRACT

Provided are methods, compositions and articles of manufacture for use in cell therapy involving the administration of one or more doses of a therapeutic T cell composition, and methods, compositions and articles of manufacture for use in the same. The cells of the T cell composition express recombinant receptors such as chimeric receptors, e.g. chimeric antigen receptors (CARs) or other transgenic receptors such as T cell receptors (TCRs). Features of the embodiments of the present disclosure, including the dose of cells or units of cells administered and/or the phenotype of administered cells, provide various advantages, such as consistent dosing, lower risk of toxicity and/or increased response in subjects administered the T cell compositions.

20 Claims, 35 Drawing Sheets
Specification includes a Sequence Listing.

(56) References Cited

U.S. PATENT DOCUMENTS

| | | |
|---|---|---|
| 6,451,995 B1 | 9/2002 | Cheung |
| 6,733,433 B1 | 5/2004 | Fell |
| 7,070,995 B2 | 7/2006 | Jensen |
| 7,265,209 B2 | 9/2007 | Jensen |
| 7,354,762 B2 | 4/2008 | Jensen |
| 7,446,179 B2 | 11/2008 | Jensen |
| 7,446,190 B2 | 11/2008 | Sadelain |
| 7,446,191 B2 | 11/2008 | Jensen |
| 8,008,450 B2 | 8/2011 | Williams et al. |
| 8,153,765 B2 | 4/2012 | Park et al. |
| 8,324,353 B2 | 12/2012 | Jensen |
| 8,339,645 B2 | 12/2012 | Nakawaki |
| 8,389,282 B2 | 3/2013 | Sadelain et al. |
| 8,479,118 B2 | 7/2013 | Lyndersay et al. |
| 8,603,477 B2 | 12/2013 | Afar et al. |
| 8,709,797 B2 | 4/2014 | Woods |
| 8,802,374 B2 | 8/2014 | Jensen |
| 8,911,993 B2 | 12/2014 | June et al. |
| 8,936,905 B2 | 1/2015 | Woods et al. |
| 9,565,854 B2 | 2/2017 | Woods |
| 11,413,310 B2 | 8/2022 | Albertson et al. |
| 2002/0131960 A1 | 9/2002 | Sadelain |
| 2002/0150914 A1 | 10/2002 | Anderse et al. |
| 2003/0170238 A1 | 9/2003 | Gruenberg et al. |
| 2003/0223994 A1 | 12/2003 | Hoogenboom et al. |
| 2004/0191260 A1 | 9/2004 | Reiter et al. |
| 2006/0034850 A1 | 2/2006 | Weidanz et al. |
| 2007/0092530 A1 | 4/2007 | Weidanz et al. |
| 2007/0116690 A1 | 5/2007 | Yang et al. |
| 2008/0171951 A1 | 7/2008 | Fell |
| 2009/0226474 A1 | 9/2009 | Weidanz et al. |
| 2009/0304679 A1 | 12/2009 | Weidanz |
| 2010/0260748 A1 | 10/2010 | Elkins et al. |
| 2011/0003380 A1 | 1/2011 | Miltenyi |
| 2012/0189622 A1 | 7/2012 | Tesar et al. |
| 2013/0149337 A1 | 6/2013 | Cooper et al. |
| 2013/0287748 A1 | 10/2013 | June |
| 2014/0294841 A1 | 10/2014 | Scheinberg et al. |
| 2014/0314795 A1 | 10/2014 | Riddell et al. |
| 2015/0283178 A1 | 10/2015 | June et al. |
| 2016/0046724 A1 | 2/2016 | Brogdon et al. |
| 2016/0122782 A1 | 5/2016 | Crisman et al. |
| 2016/0152723 A1 | 6/2016 | Chen et al. |
| 2016/0206656 A1 | 7/2016 | Gilbert et al. |
| 2016/0362472 A1 | 12/2016 | Bitter et al. |
| 2017/0037369 A1 | 2/2017 | Ramsborg et al. |
| 2017/0051035 A1 | 2/2017 | Payne et al. |
| 2023/0149458 A1 | 5/2023 | Albertson et al. |

FOREIGN PATENT DOCUMENTS

| | | | |
|---|---|---|---|
| WO | WO 1992/008796 | 5/1992 | |
| WO | WO 1994/028143 | 12/1994 | |
| WO | WO 1996/013593 | 5/1996 | |
| WO | WO 1996/018105 | 6/1996 | |
| WO | WO 1999/018129 | 4/1999 | |
| WO | WO 1999/060120 | 11/1999 | |
| WO | WO 2000/014257 | 3/2000 | |
| WO | WO 2000/038762 | 7/2000 | |
| WO | WO 2003/020763 | 3/2003 | |
| WO | WO 2003/068201 | 8/2003 | |
| WO | WO 2004/033685 | 4/2004 | |
| WO | WO 2006/000830 | 1/2006 | |
| WO | WO 2006/099875 | 9/2006 | |
| WO | WO 2009/072003 | 6/2009 | |
| WO | WO 2009/080829 | 7/2009 | |
| WO | WO 2010/033140 | 3/2010 | |
| WO | WO 2011/044186 | 4/2011 | |
| WO | WO 2012/062904 | 5/2012 | |
| WO | WO 2012/092612 | 7/2012 | |
| WO | WO 2012/129514 | 9/2012 | |
| WO | WO 2013/071154 | 5/2013 | |
| WO | WO 2013/123061 | 8/2013 | |
| WO | WO 2013/126726 | 8/2013 | |
| WO | WO 2013/166321 | 11/2013 | |
| WO | WO 2014/031687 | 2/2014 | |
| WO | WO 2014/055668 | 4/2014 | |
| WO | WO 2014/190273 | 11/2014 | |
| WO | WO 2014/210064 | 12/2014 | |
| WO | WO 2015/095895 | 6/2015 | |
| WO | WO 2015/157384 | 10/2015 | |
| WO | WO 2015/164675 | 10/2015 | |
| WO | WO 2016/019300 | 2/2016 | |
| WO | WO 2016/028896 | 2/2016 | |
| WO | WO 2016/033570 | 3/2016 | |
| WO | WO 2016/073602 | 5/2016 | |
| WO | WO 2016/090312 | 6/2016 | |
| WO | WO 2016/090320 | 6/2016 | |
| WO | WO 2016/090327 | 6/2016 | |
| WO | WO 2016/090329 | 6/2016 | |
| WO | WO 2016/164731 | 10/2016 | |
| WO | WO 2016/172606 | 10/2016 | |
| WO | WO 2016/191755 | 12/2016 | |
| WO | WO 2016/191756 | 12/2016 | |
| WO | WO 2017/035362 | 12/2016 | |
| WO | WO 2017/019848 | 2/2017 | |
| WO | WO 2017/049166 | 3/2017 | |
| WO | WO 2017/058850 | 4/2017 | |
| WO | WO-2017075389 A1 * | 5/2017 | ............. A61K 35/17 |
| WO | WO 2018/157171 | 8/2018 | |
| WO | WO 2018/170188 | 9/2018 | |
| WO | WO 2018/223101 | 12/2018 | |
| WO | WO 2019/032927 | 2/2019 | |
| WO | WO 2019/032929 | 2/2019 | |

OTHER PUBLICATIONS

"U.S. Appl. No. 17/846,868, filed Jun. 22, 2022, by Albertson et al. (Copy not provided). (Copy not submitted herewith pursuant to the waiver of 37 C.F. R. § 1.98(a)(2)(iii) issued by the Office on Sep. 21, 2004)".

Franke et al., "Antibodies against CD20 or B-cell receptor induce similar transcription patterns in human lymphoma cell lines," PLoS One.(2011) 6(2): e16596.

Kueberuwa et al., "CCR7+ selected gene-modified T cells maintain a central memory phenotype and display enhanced persistence in peripheral blood in vivo," J Immunother Cancer (2017) 5(14):1-14.

Law et al., "What does it take to bind CAR?," Mol Ther. (2005) 12(4):599-609.

Xu et al., "Closely related T-memory stem cells correlate with in vivo expansion of CAR.CD19-T cells and are preserved by IL-7 and IL-15," Blood (2014) 123(24):3750-3759.

Ali et al., "T cells expressing an anti-B-cell maturation antigen chimeric antigen receptor cause remissions of multiple myeloma," Blood (2016) 128 (13): 1688-1700.

Al-Lazikani et al., "Standard conformations for the canonical structures of immunoglobulins," J Mol Biol (1997) 273(4):927-948.

Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2: e93.

Barrett et al., "Chimeric Antigen Receptor Therapy for Cancer," Annu Rev Med (2014) 65:333-347.

Baum et al., "Retrovirus Vectors: Toward the plentivirus," Mol Ther (2006) 13:1050-1063.

Benson et al., "CS1-Directed monoclonal antibody therapy for multiple myeloma," J Clin Oncol (2012) 30(16):2012-2015.

Bersenev, "Crude versus defined CAR T-cell therapy product," dated May 1, 2016. Retrieved from the Internet: https://stemcellassays.com/2016/05/crude-versus-defined-car-t-cell-therapy-product/.

Boris-Lawrie et al., "Recent advances in retrovirus vector technology," Cur. Opin. Genet. Develop. (1993) 3:102-109.

Brash et al., "Strontium phosphate transfection of human cells in primary culture: stable expression of the simian virus 40 large-T-antigen gene in primary human bronchial epithelial cells," Mol. Cell Biol. (1987) 7: 2031-2034.

Brentjens et al. "Safety and persistence of adoptively transferred autologous CD19-targeted T cells in patients with relapsed or chemotherapy refractory B-cell leukemias," Blood (2011) 118(18): 4817-4828.

(56) References Cited

OTHER PUBLICATIONS

Brentjens et al., "CD19-targeted T cells rapidly induce molecular remissions in adults with chemotherapy-refractory acute lymphoblastic leukemia," Sci Transl Med. (2013) 5(177):177ra38.
Brudno et al., "Toxicities of chimeric antigen receptor T cells: recognition and management," Blood (2016) 127(26):3321-3330.
Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90:8033-8037.
Carceller et al., "Response Assessment in Paediatric Phase I Trials According to RECIST Guidelines: Survival Outcomes, Patterns of Progression and Relevance of Changes in Tumour Measurements," Pediatr Blood Cancer. (2016) 63(8):1400-1406.
Carlens et al., "Ex vivo T lymphocyte expansion for retroviral transduction: influence of serum-free media on variations in cell expansion rates and lymphocyte subset distribution," Exp Hematol (2000) 28(10): 1137-1146.
Carrillo et al., "The multiple sequence alighment problem in biology," SIAM Journal of Applied Mathematics (1988) 48(5):1073-1082.
Cavaletti et al., "Chemotherapy-induced peripheral neurotoxicity," Nat Rev Neurol (2010) 6(12):657-666.
Cavalieri et al., "Human T lymphocytes transduced by lentiviral vectors in the absence of TCR activation maintain an intact immune competence," Blood (2003) 102(2): 497-505.
Chaara et al., "RepSeq Data Representativeness and Robustness Assessment by Shannon Entropy," Front Immunol. (2018) 9:1038.
Cheadle et al., "Chimeric antigen receptors for T-cell based therapy," Methods Mol Biol (2012) 907:645-666.
Chervin et al., "Engineering higher affinity T cell receptors using a T cell display system," J Immunol Methods. (2008) 339(2): 175-84.
Cheson, "Staging and response assessment in lymphomas: the new Lugano classification," Chin Clin Oncol (2015) 4(1):5.
Cheson et al., "Recommendations for initial evaluation, staging, and response assessment of Hodgkin and non-Hodgkin lymphoma: the Lugano classification," J Clin Oncol (2014) 32(27):3059-3068.
Chicaybam et al., "An efficient low cost method for gene transfer to T lymphocytes," PLoS One (2013) 8(3): e60298.
Cho et al., "Human mammalian cell sorting using a highly integrated micro-fabricated fluorescence-activated cell sorter (µFACS)," Lab on a Chip (2010) 10:1567-1573.
Chothia et al.,. "The outline structure of the T-cell alpha beta receptor," EMBO J. (1988) 7(12): 3745-55.
Chu et al., "CS1-specific chimeric antigen receptor (CAR)-engineered natural killer cells enhance in vitro and in vivo antitumor activity against human multiple myeloma," Leukemia (2014) 28(4):917-927.
Clackson et al., "Making antibody fragments using phage display libraries," Nature (1991) 352(6336):624-628.
Cohen et al., "Recognition of Fresh Human Tumor by Human Peripheral Blood Lymphocytes Transduced with a Bicistronic Retroviral Vector Encoding a Murine Anti-p53 TCR," J Immunol (2005) 175(9):5799-5808.
Cohen et al., "Recombinant antibodies with MHC-restricted, peptide-specific, T-cell receptor-like specificity: new tools to study antigen presentation and TCR-peptide-MHC interactions," J Mol RecogN (2003) 16:324-332.
Cooper et al., "T-cell clones can be rendered specific for CD19: toward the selective augmentation of the graft-versus-B-lineage leukemia effect," Blood. (2003) 101:1637-1644.
Davila et al., "CD19 CAR-targeted T cells induce long-term remission and B Cell Aplasia in an immunocompetent mouse model of B cell acute lymphoblastic leukemia," PLoS One (2013) 8(4): e61338.
Davila et al., "Efficacy and toxicity management of 19-28z CAR T cell therapy in B cell acute lymphoblastic leukemia," Science Translational Medicine (2014) 6(224):224ra25.
Davila et al., "How do CARs work?: Early insights from recent clinical studies targeting CD19," Oncoimmunology (2012) 1(9):1577-1583.

De Felipe et al., "Targeting of proteins derived from self-processing polyproteins containing multiple signal sequences," Trafic (2004) 5(8):616-626.
De Felipe, "Skipping the co-expression problem: the new 2A "CHYSEL" technology," Genetics Vaccines and Therapy (2004) 2:13.
Dull, T. et al. (Nov. 1998) "A Third-Generation Lentivirus Vector with a Conditional Packaging System," J. Viral. 72:8463-8471.
Eisenhauer et al., "New response evaluation criteria in solid tumours: Revised RECIST guideline (version 1.1)," EJC (2009) 45(2):P228-247.
Fedorov et al., "PD-1- and CTLA-4-Based Inhibitory Chimeric Antigen Receptors (iCARs) Divert Off-Target Immunotherapy Responses," Sci Transl Medicine (2013) 5(215):215ra172.
Foon et al., "Immunologic classification of leukemia and lymphoma," Blood (1986) 68(1):1-31.
Fraietta et al., "Biomarkers of Response to Anti-CD19 Chimeric Antigen Receptor (CAR) T-Cell Therapy in Patients with Chronic Lymphocytic Leukemia," Blood (2016) 128(22):57.
Fraietta et al., "Determinants of response and resistance to CD19 chimeric antigen receptor (CAR) T cell therapy of chronic lymphocytic leukemia," Nat Med. (May 2018) 24(5):563-571. Epub Apr. 30, 2018.
Fraietta et al., "Identification of functional determinants of response and resistance to CD19 chimeric antigen receptor (CAR) T-cell therapy if chronic lymphocytic leukemia," Blood (2017) 130:3181.
Frecha et al., "Advances in the field of lentivector-based transduction of T and B lymphocytes for gene therapy," Mol Ther (2010) 18(10):1748-1757.
Friedl et al., " T lymphocyte locomotion in a three-dimensional collagen matrix: Expression and function of cell adhesion molecules," J Immunol. (1995) 154: 4973-4985.
Gardner et al., "Intent to treat leukemia remission by CD19CAR T cells of defined formulation and dose in children and young adults," Blood (2017) 129(25):3322-3331.
Garfall et al., "Immunotherapy with chimeric antigen receptors for multiple myeloma," Discov Med (2014) 17(91):37-46.
Godin et al., "Microfluidics and photonics for Bio-System-on-a-Chip: A review of advancements in technology towards a microfluidic flow cytometry chip," J Biophotonics (2008) 1(5):355-376.
Grupp et al., "Chimeric Antigen Receptor-Modified T Cells for Acute Lymphoid Leukemia," N Engl J Med (2013) 368:1509-1518.
Hackett et al., "A transposon and transposase system for human application," Molecular Therapy: The Journal of the American Society of Gene Therapy (2010) 18:674-683.
Hallek et al., "Guidelines for the diagnosis and treatment of chronic lymphocytic leukemia: a report from the International Workshop on Chronic Lymphocytic Leukemia updating the National Cancer Institute—Working Group 1996 guidelines," Blood (2008) 111(12):5446-5456.
Hermans et al., "The VITAL assay: a versatile fluorometric technique for assessing CTL- and NKT-mediated cytotoxicity against multiple targets in vitro and in vivo," J Immunol Methods (2004) 285(1):25-40.
Holler et al., "In vitro evolution of a T cell receptor with high affinity for peptide/MHC," Proc Natl Acad Sci U S A. (2000) 97(10): 5387-5392.
Holler et al., "TCRs with high affinity for foreign pMHC show self-reactivity," Nat Immunol. Jan. 2003;4(1):55-62.
Honegger et al., "Yet another numbering scheme for immunoglobulin variable domains: an automatic modeling and analysis tool," J Mol Biol (2001) 309(3):657-670.
Huang et al., "DNA transposons for modification of human primary T lymphocytes," Methods Mol Biol (2009) 506: 115-126.
Hudecek et al., "Receptor affinity and extracellular domain modifications affect tumor recognition by ROR1-specific chimeric antigen receptor T cells," Clin Cancer Res (2013) 19(12):3153-3164.
Hudecek et al., "The nonsignaling extracellular spacer domain of chimeric antigen receptors is decisive for in vivo antitumor activity," Cancer Immunol Res (2015) 3(2):125-135.
Janeway et al., Immunobiology: The Immune System in Health and Disease, 3rd ED., Current Biology Publications (1997), p. 4:33.

(56) References Cited

OTHER PUBLICATIONS

Jensen et al., "Antitransgene rejection responses contribute to attenuated persistence of adoptively transferred CD20/CD19-specific chimeric antigen receptor redirected T cells in humans," Biol Blood Marrow Transplant (2010) 16(9):1245-1256.
Johnson et al., "Imaging for Staging and Response Assessment in Lymphoma," Radiology (2015) 276(2):323-338.
Johnston, et al., "Biolistic transformation: microbes to mice," Nature (1990) 346: 776-777.
Jores et al., "Resolution of hypervariable regions in T-cell receptor beta chains by a modified Wu-Kabat index of amino acid diversity.," PNAS (1990) 87(23):9138-9142.
Kindt et al., "Antigens and Antibodies," in Chapter 4 of Kuby Immunology, 6th ed., W.H. Freeman and Co., N.Y, (2007) pp. 91, 14 pages.
Klaver et al., "Adoptive T-cell therapy: A need for standard immune monitoring," (2015) Immunotherapy 7(5)513-33.
Klebanoff et al., "Sorting through subsets: which T-cell populations mediate highly effective adoptive immunotherapy?," J Immunother. (2012) 35(9): 651-660.
Kochenderfer et al., "B-cell depletion and remissions of malignancy along with cytokine-associated toxicity in a clinical trial of anti-CD19 chimeric-antigen-receptor-transduced T cells," Blood (2012) 119(12):2709-2720.
Kochenderfer et al., "Construction and preclinical evaluation of an anti-CD19 chimeric antigen receptor," J. Immunotherapy (2009) 32(7): 689-702.
Kochenderfer et al., "Treating B-cell cancer with T cells expressing anti-CD19 chimeric antigen receptors," Nature Reviews Clinical Oncology (2013) 10:267-276.
Koste et al., "T-cell receptor transfer into human T cells with ecotropic retroviral vectors," Gene Therapy (2014) 21: 533-538.
Kotb, "Bacterial pyrogenic exotoxins as superantigens," Clin Microbiol Rev. (1995) 8(3):411-426.
Kurucz et al., "A bacterially expressed single-chain Fv construct from the 2B4 T-cell receptor," Proc Natl Acad Sci U S A. (1993) 90(9): 3830-3834.
Lamers et al., "Immune responses to transgene and retroviral vector in patients treated with ex vivo-engineered T cells," Blood (2011) 117(1):72-82.
Lee et al., "Current concepts in the diagnosis and management of cytokine release syndrome," Blood (2014) 124(2):188-195.
Lefranc et al., "IMGT unique numbering for immunoglobulin and T cell receptor variable domains and Ig superfamily V-like domains," Dev Comp Immunol (2003) 27(1):55-77.
Levine et al., "Global manufacturing of CAR T cell therapy" Mol. Ther. Methods & Clin. Dev. (2016) 4: 92-101.
Li et al., "Directed evolution of human T-cell receptors with picomolar affinities by phage display," Nature Biotechnology (2005) 23:349-354.
Ling et al., "B-cell and plasma cell antigens: new and previously defined clusters," Leucocyte typing III. (1987) 302-355.
Liu et al., "Inclusion of Strep-tag II in design of antigen receptors for T-cell immunotherapy," Nature Biotechnology (2016) 34(4):430-434.
Lupton et al., "Dominant positive and negative selection using a hygromycin phosphotransferase-Thymidine kinase dusion gene," Molecular and cellular biology (1991) 11(6):3374-3378.
Maccallum et al., "Antibody-antigen interactions: contact analysis and binding site topography," J Mol Biol (1996) 262(5):732-745.
Manuri et al., "piggyBac transposon/transposase system to generate CD19-specific T cells for the treatment of B-lineage malignancies," Hum Gene Ther (2010) 21(4): 427-437.
Martin et al., "Modeling antibody hypervariable loops: a combined algorithm," PNAS (1989) 86(23):9268-9272.
Methods in Molecular Medicine, vol. 58: Metastasis Research Protocols, vol. 2: Cell Behavior In Vitro and In Vivo, p. 17-25 Edited by: S. A. Brooks and U. Schumacher © Humana Press Inc., Totowa, NJ.
Miller et al., "Improved retroviral vectors for gene transfer and expression," BioTechniques (1989) 7:980-990.
Miller et al., "Retrovirus packaging cells," Human Gene Therapy (1990) 1:5-14.
Mock et al., "Automated manufacturing of chimeric antigen receptor T cells for adoptive immunotherapy using CliniMACS Prodify," Cytotherapy (2016) 18(8):1002-1011.
Monsky et al. "Semi-Automated Volumetric Quantification of Tumor Necrosis in Soft Tissue Sarcoma Using Contrast Enhanced MRI," Anticancer Res. (2012) 32(11): 4951-4961.
Naldini et al., "In vivo gene delivery and stable transduction of nondividing cells by a lentiviral vector," Science. (1996) Apr. 12;272(5259):263-7.
Naldini et al., "Lentiviruses as gene transfer agents for delivery to non-dividing cells", Curr Opin Biotechnol., Oct. 9, (1998); 5:457-63.
Park et al,, "Adoptive transfer of chimeric antigen receptor re-directed cytolytic T lymphocyte clones in patients with neuroblastoma," Molecular Therapy (2007) 15(4):825-833.
Park et al., "Treating cancer with genetically engineered T cells," Trends Biotechnol. (2011) 29(11): 550-557.
Parkhurst et al., "Characterization of genetically modified T-cell receptors that recognize the CEA:691-699 peptide in the context of HLA-A2.1 on human colorectal cancer cells," Clin Cancer Res (2009) 15:169-180.
Porter et al., "Chimeric antigen receptor T cells persist and induce sustained remissions in relapsed refractory chronic lymphocytic leukemia," Sc.i Trans. Med. (2015) 7(303): 303ra139.
Portolano et al., "Lack of promiscuity in autoantigen-specific H and L chain combinations as revealed by human H and L chain "roulette"," J Immunol (1993) 150(3):880-887.
Riddell et al., "The Fred Hutchinson Cancer Research Center and the University of Washington School of Medicine, Department of Medicine, Division of Oncology Oct. 7, 1991," Human Gene Therapy (1992) 3:319-338.
Rosenberg, et al., "Cell transfer immunotherapy for metastatic solid cancer—what clinicians need to know," Nat Rev Clin Oncol. (2011) 8(10):577-85.
Sadelain et al., "The basic principles of chimeric antigen receptor design," Cancer Discov. (2013) 3(4): 388-398.
Savoldo et al., "CD28 costimulation improves expansion and persistence of chimeric antigen receptor-modified T cells in lymphoma patients," JCI (2011) 121(5):1822-1826.
Scarpa et al., "Characterization of recombinant helper retroviruses from Moloney-based vectors in ecotropic and amphotropic packaging cell lines," Virology (1991) 180:849-852.
Schlueter et al., "Specificity and Binding Properties of a Single-chain T Cell Receptor," J Mol Biol (1996) 859-869.
Schuler et al., SYFPEITHI, Database for Searching and T-Cell Epitope Prediction. in Immunoinformatics Methods in Molecular Biology, (2007) 409(1): 75-93.
Sharma et al., "Efficient sleeping beauty DNA transposition from DNA minicircles," Molec Ther Nucl Acids (2013) 2, e74.
Singh et al., "ProPred: prediction of HLA-DR binding sites," Bioinformatics. (2001) 17(12): 1236-1237.
Soo Hoo et al., "Characterization of a single-chain T-cell receptor expressed in *Escherichia coli*," Proc Natl Acad Sci U S A. (1992) 89(10): 4759-4763.
Tai et al., "Antibody-Based Therapies in Multiple Myeloma," Bone Marrow Research (2010) vol. 2011. Article ID 924058.
Terakura et al., "Generation of CD19-chimeric antigen receptor modified CD8+ T cells derived from virus-specific central memory T cells," Blood (2012) 1:72-82.
Themeli et al., "Generation of tumor-targeted human T lymphocytes from induced pluripotent stem cells for cancer therapy," Nat Biotechnol. (2013) 31(10): 928-933.
Tsukahara et al., "CD19 target-engineered T-cells accumulate at tumor lesions in human B-cell lymphoma xenograft mouse models," Biochem Biophys Res Commun (2013) 438(1): 84-89.
Turtle et al., "Anti-CD19 Chimeric Antigen Receptor-Modified T Cell Therapy for B Cell Non-Hodgkin Lyphoma and Chronic Lyphocytic Leukemia: Fludarabine and Cyclophosphamide Lyphodeple-

(56) References Cited

OTHER PUBLICATIONS tion Imprives In Vivo Expansion and Persistence of CAR-T Cells and Clinical Outcomes," Blood (2015) 126:184.
Turtle et al., "CD19 CAR-T cells of defined CD4+:CD8+ composition in adult B cell All patients," J. Clin. Invest. (2016) 126(6):2123-38.
Turtle et al., "Engineered T cells for anti-cancer therapy," Curr. Opin. Immunol. (2012) 24(5): 633-39.
Turtle et al., "Immunotherapy of non-Hodgkin's lymphoma with a defined ratio of CD8+ and CD4+ CD19-specific chimeric antigen receptor-modified T cells," Sci Transl Med (2016) 8(355):355ra116.
Van Tendeloo et al., "High-level transgene expression in primary human T lymphocytes and adult bone marrow CD34+ cells via electroporation-mediated gene delivery," Gene Therapy (2000) 7(16): 1431-1437).
Varela-Rohena et al., "Control of HIV-1 immune escape by CD8 T cells expressing enhanced T-cell receptor," Nature Medicine (2008) 14(12):1390-1395.
Verhoeyen et al., "Lentiviral vector gene transfer into human T cells," Methods Mol Biol. (2009) 506: 97-114.
Wadhwa et al., "Receptor mediated glycotargeting," J. Drug Targeting (1995) 3: 111.
Wang et al., "Phenotypic and functional attributes of lentivirus-modified CD19-specific human CD8+ central memory T cells manufactured at clinical scale," J Immunother. (2012) 35(9):689-701.
Wu et al., "Adoptive T-cell therapy using autologous tumor-infiltrating lymphocytes for metastatic melanoma: current status and future outlook," Cancer (2012) 18(2): 160-175.
Wulfing et al., "Correctly folded T-cell receptor fragments in the periplasm of *Escherichia coli*. Influence of folding catalysts," J Mol Biol. (1994) 242(5): 655-669.
Xu et al., "Cytokine release syndrome in cancer immunotherapy with chimeric antigen receptor engineered T cells," Cancer Letters (2014) 343(2):172-178.
Xu et al., "Multiparameter comparative analysis reveals differential impacts of various cytokines on CART cell phenotype and function ex vivo and in vivo," Oncotarget (2016) 7(50):82354-82368.
Xue et al., "Single-cell multiplexed cytokine profiling of CD19 CAR-T cells reveals a diverse landscape of polyfunctional antigen-specific response," Immunother Cancer. (2017) 5(1): 85.
Zheng et al., "Protein L: a novel reagent for the detection of chimeric antigen receptor (CAR) expression by flow cytometry," J Transl Med (2012) 10:29, 6 pages.
Zufferey et al., "Multiply attenuated lentiviral vector achieves efficient gene delivery in vivo," Nat Biotechnol. (1997) Sep;15(9):871-875.
Avdic et al., "Human Cytomegalovirus-Encoded Human Interleukin-10 (IL-10) Homolog Amplifies Its Immunomodulatory Potential by Upregulating Human IL-10 in Monocytes," J Virol. (2016) 90(8): 3819-3827.
Chen et al. "Anti-CD19 Chimeric Antigen Receptor T Cells Improve Responses to Chemotherapy-Refractory Mantle Cell Lymphoma: A Case Report," Blood (2016) 128(22): 5393.
Sommermeyer et al., "Chimeric antigen receptor-modified T cells derived from defined CD8+ and CD4+ subsets confer superior antitumor reactivity in vivo," Leukemia (2016) 30: 492-500.
Supplementary Materials for Turtle et al., Immunotherapy of Non-Hodgkin's Lymphoma with a Defined Ratio of CDS+ and CD4+ CD19-specific Chimeric Antigen Receptor-modified T cells. Science Translational Medicine, 2016. vol. 8 (155) 355ra116, 16 pages.
Turtle et al. "Addition of fludarabine to cyclophosphamide lymphodepletion improves in vivo expansion of CD19 chimeric antigen receptor-modified T cells and clinical outcome in adults with B cell acute lymphoblastic leukemia." Blood 126.23 (2015): 3773.

\* cited by examiner

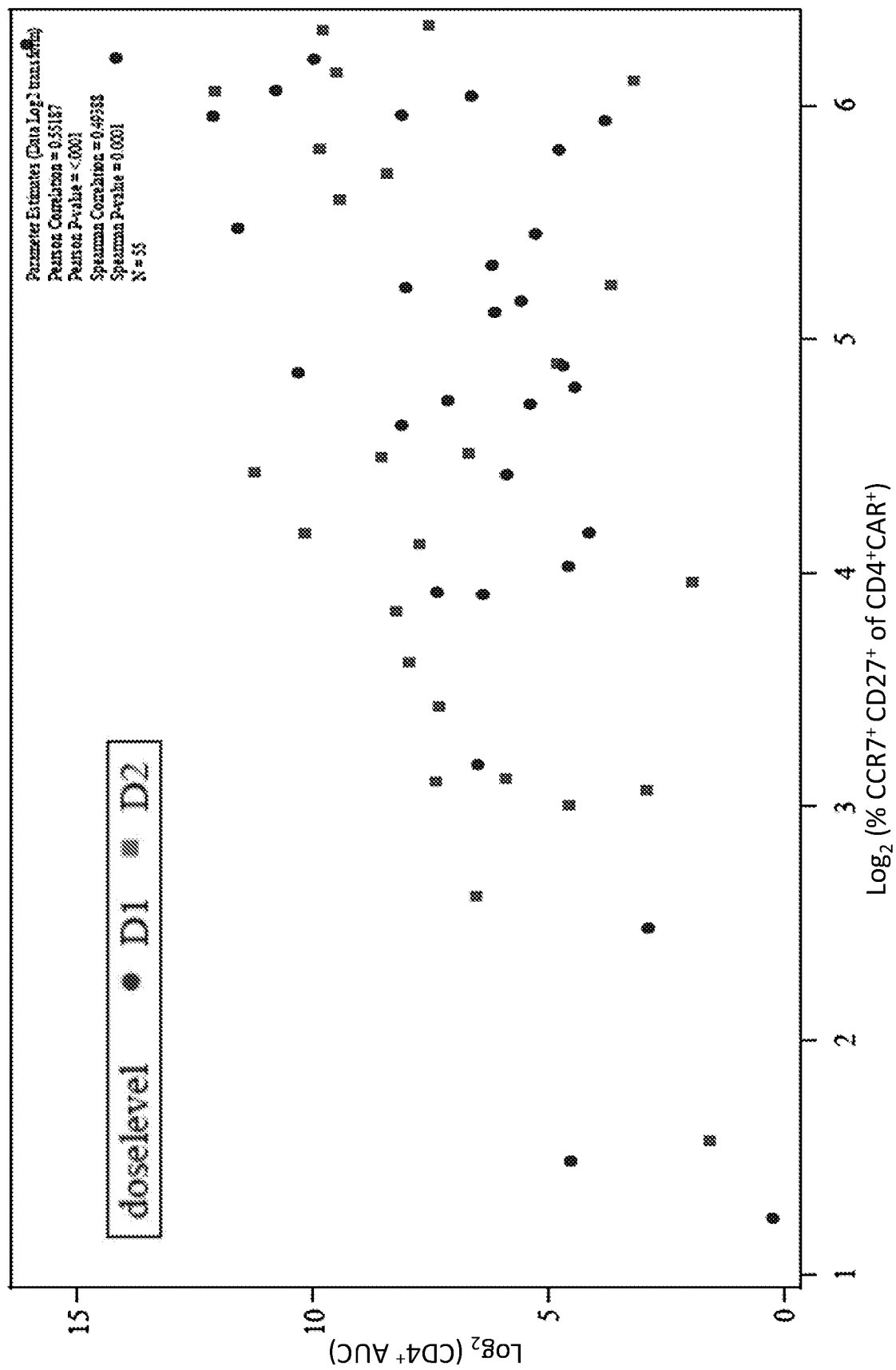

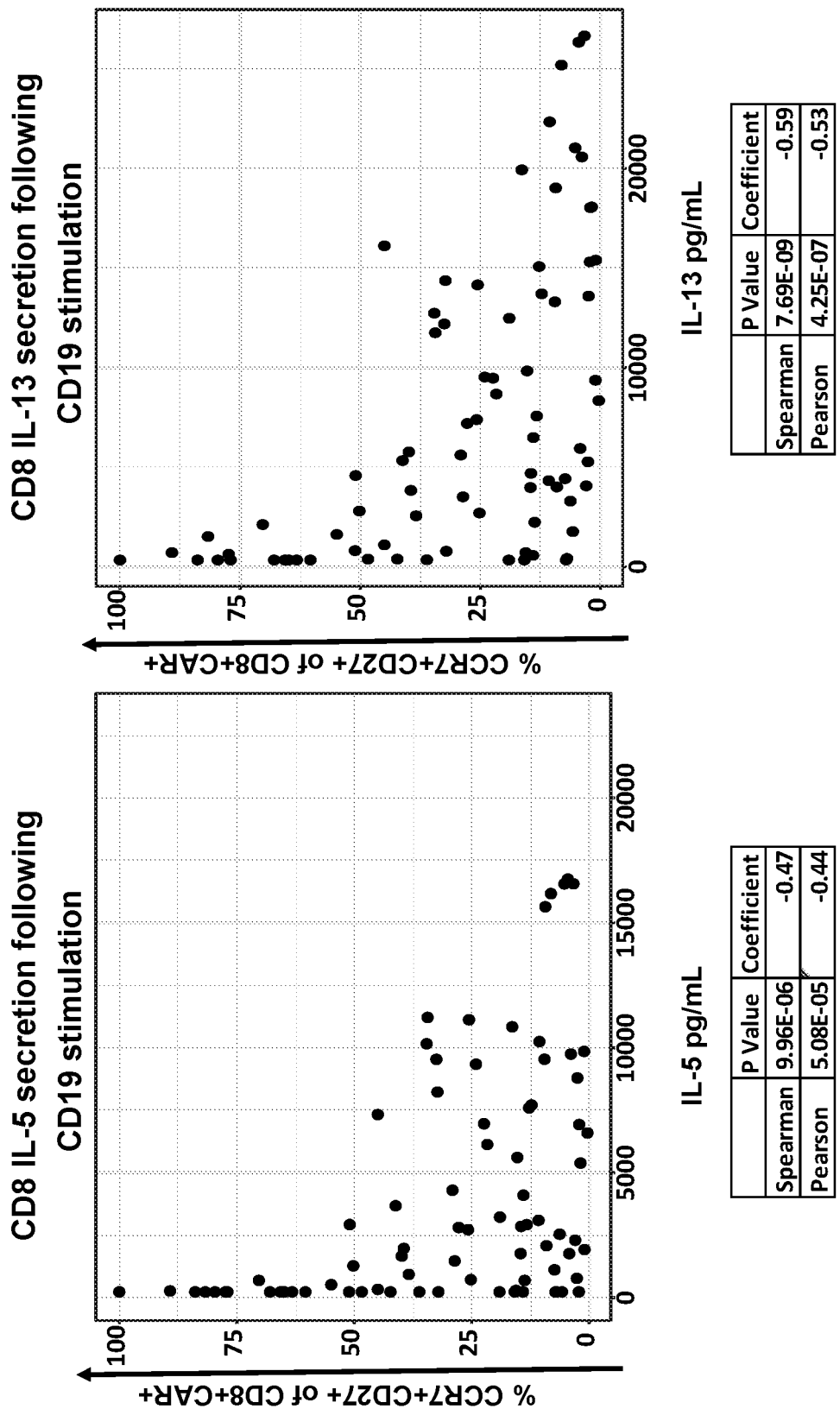

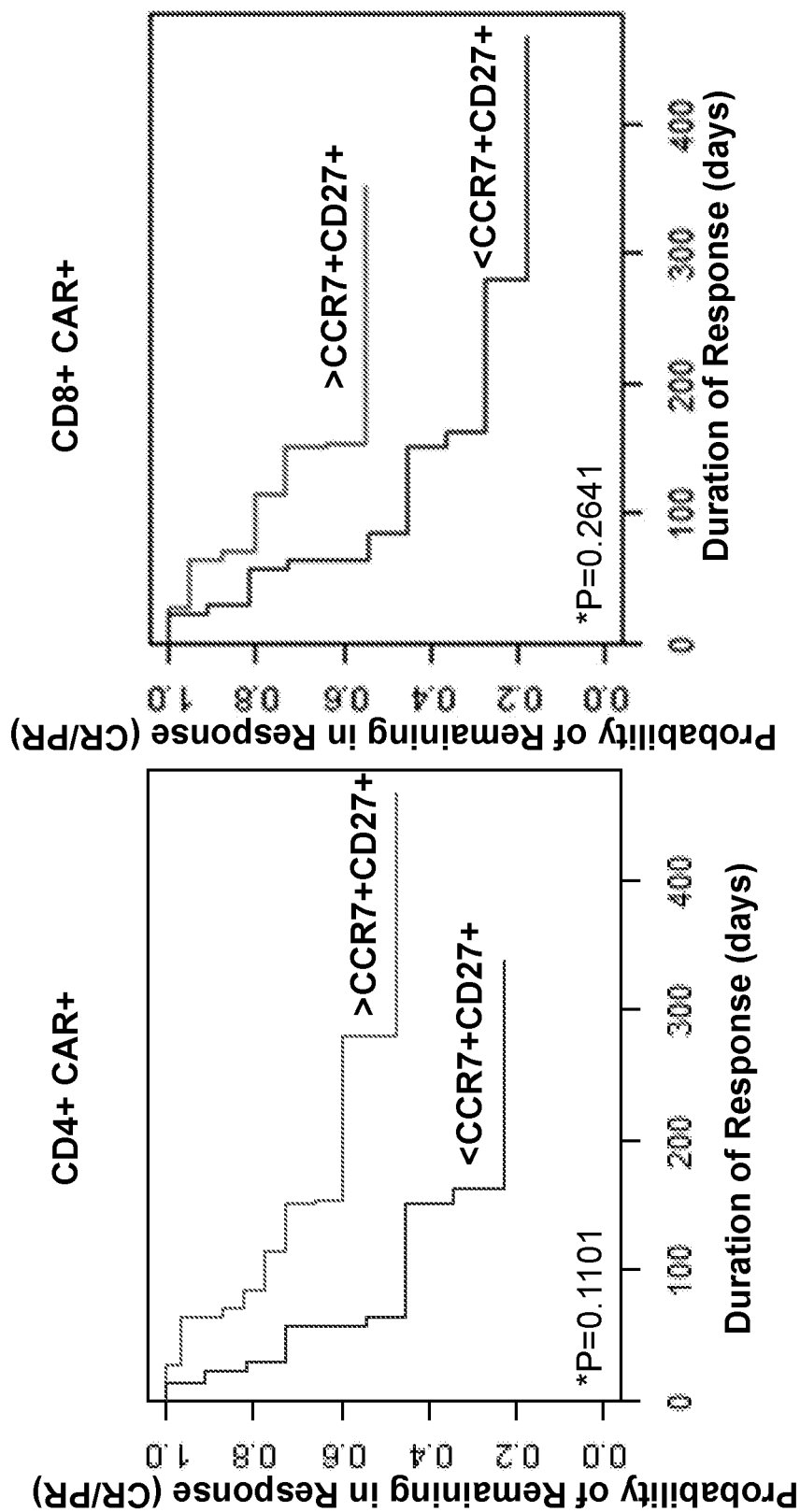

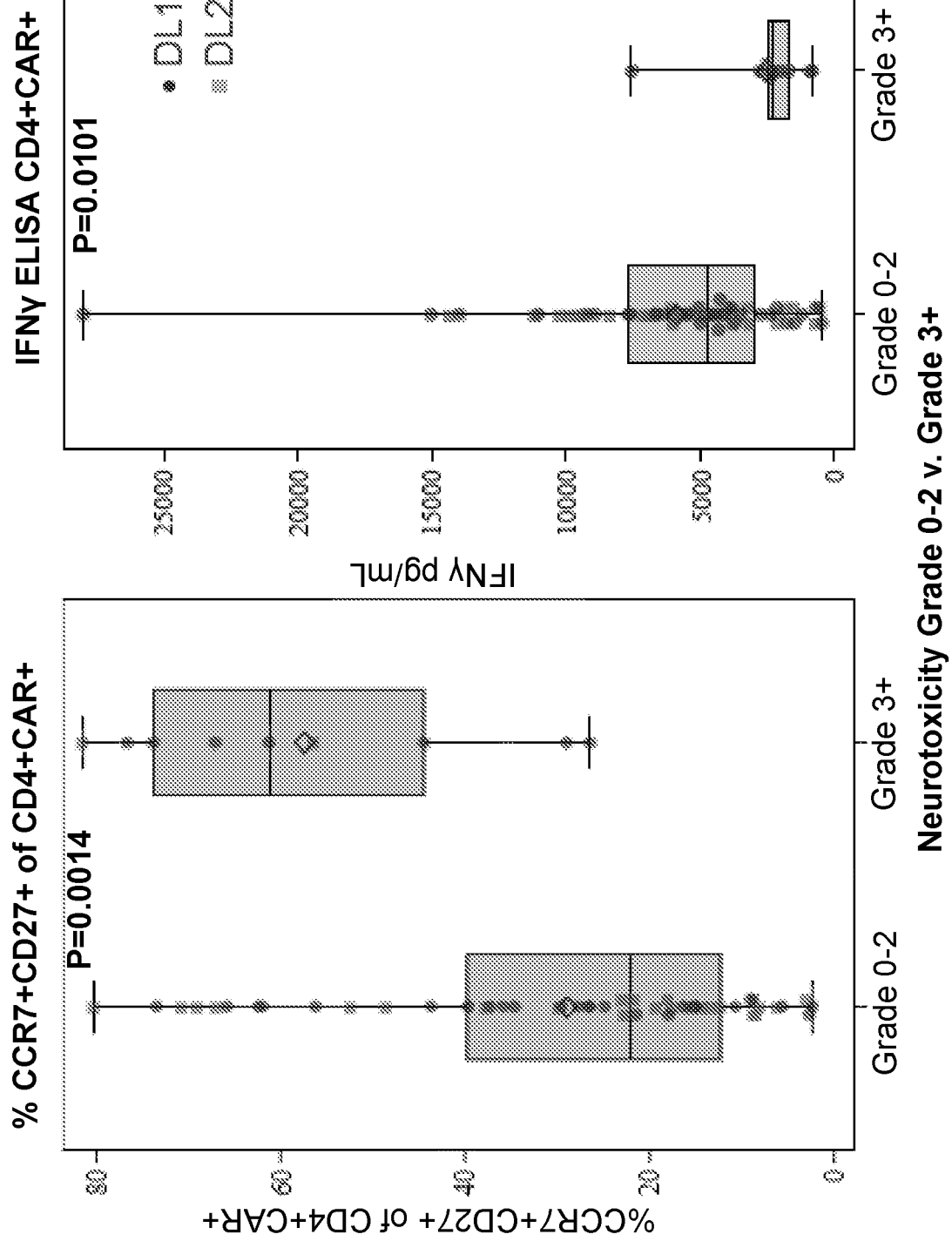

SEQUENCE LISTING

<160> NUMBER OF SEQ ID NOS: 59

<210> SEQ ID NO 1
<211> LENGTH: 12
<212> TYPE: PRT
<213> ORGANISM: Artificial Sequence
<220> FEATURE:
<223> OTHER INFORMATION: Spacer (IgG4hinge) (aa)

<400> SEQUENCE: 1

Glu Ser Lys Tyr Gly Pro Pro Cys Pro Pro Cys Pro
1               5                   10

<210> SEQ ID NO 2
<211> LENGTH: 36
<212> TYPE: DNA
<213> ORGANISM: Artificial Sequence
<220> FEATURE:
<223> OTHER INFORMATION: Spacer (IgG4hinge) (nt)

<400> SEQUENCE: 2
gaatctaagt acggaccgcc ctgcccccct tgccct                              36

<210> SEQ ID NO 3
<211> LENGTH: 119
<212> TYPE: PRT
<213> ORGANISM: Artificial Sequence
<220> FEATURE:
<223> OTHER INFORMATION: Hinge-CH3 spacer

<400> SEQUENCE: 3

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Gln Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
        115

<210> SEQ ID NO 4
<211> LENGTH: 229
<212> TYPE: PRT
<213> ORGANISM: Artificial Sequence
<220> FEATURE:
<223> OTHER INFORMATION: Hinge-CH2-CH3 spacer

<400> SEQUENCE: 4

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys
225

<210> SEQ ID NO 5
<211> LENGTH: 282
<212> TYPE: PRT
<213> ORGANISM: Artificial Sequence
<220> FEATURE:
<223> OTHER INFORMATION: IgD-hinge-Fc

<400> SEQUENCE: 5

Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
            20                  25                  30

Thr Thr Arg Asn Thr Gly Arg Gly Gly Glu Glu Lys Lys Lys Glu Lys
        35                  40                  45

Glu Lys Glu Glu Gln Glu Glu Arg Glu Thr Lys Thr Pro Glu Cys Pro
    50                  55                  60

Ser His Thr Gln Pro Leu Gly Val Tyr Leu Leu Thr Pro Ala Val Gln
65                  70                  75                  80

Asp Leu Trp Leu Arg Asp Lys Ala Thr Phe Thr Cys Phe Val Val Gly
                85                  90                  95

Ser Asp Leu Lys Asp Ala His Leu Thr Trp Glu Val Ala Gly Lys Val
            100                 105                 110

Pro Thr Gly Gly Val Glu Glu Gly Leu Leu Glu Arg His Ser Asn Gly
        115                 120                 125

Ser Gln Ser Gln His Ser Arg Leu Thr Leu Pro Arg Ser Leu Trp Asn
    130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
        195                 200                 205

Met Trp Leu Glu Asp Gln Arg Glu Val Asn Thr Ser Gly Phe Ala Pro
    210                 215                 220

Ala Arg Pro Pro Gln Pro Gly Ser Thr Thr Phe Trp Ala Trp Ser
225                 230                 235                 240

Val Leu Arg Val Pro Ala Pro Ser Pro Gln Pro Ala Thr Tyr Thr
                245                 250                 255

Cys Val Val Ser His Glu Asp Ser Arg Thr Leu Leu Asn Ala Ser Arg
            260                 265                 270

Ser Leu Glu Val Ser Tyr Val Thr Asp His
        275                 280

<210> SEQ ID NO 6
<211> LENGTH: 24
<212> TYPE: PRT
<213> ORGANISM: Artificial Sequence
<220> FEATURE:
<223> OTHER INFORMATION: T2A

<400> SEQUENCE: 6

Leu Glu Gly Gly Gly Glu Gly Arg Gly Ser Leu Leu Thr Cys Gly Asp
1               5                   10                  15

Val Glu Glu Asn Pro Gly Pro Arg

<210> SEQ ID NO 7
<211> LENGTH: 357
<212> TYPE: PRT
<213> ORGANISM: Artificial Sequence
<220> FEATURE:
<223> OTHER INFORMATION: tEGFR

<400> SEQUENCE: 7

```
Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Val Val Ala Leu Gly
            340                 345                 350

Ile Gly Leu Phe Met
```

-continued

```
<210> SEQ ID NO 8
<211> LENGTH: 27
<212> TYPE: PRT
<213> ORGANISM: Homo sapiens
<220> FEATURE:
<223> OTHER INFORMATION: CD28 (amino acids 153-179 of Accession No.
      P10747)

<400> SEQUENCE: 8

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 9
<211> LENGTH: 66
<212> TYPE: PRT
<213> ORGANISM: Homo sapiens
<220> FEATURE:
<223> OTHER INFORMATION: CD28 (amino acids 114-179 of Accession No.
      P10747)

<400> SEQUENCE: 9

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val
65

<210> SEQ ID NO 10
<211> LENGTH: 41
<212> TYPE: PRT
<213> ORGANISM: Homo sapiens
<220> FEATURE:
<223> OTHER INFORMATION: CD28 (amino acids 180-220 of P10747)

<400> SEQUENCE: 10

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 11
<211> LENGTH: 41
<212> TYPE: PRT
<213> ORGANISM: Artificial Sequence
<220> FEATURE:
<223> OTHER INFORMATION: CD28 (LL to GG)

<400> SEQUENCE: 11

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30
```

Pro Arg Asp Phe Ala Ala Tyr Arg Ser
        35                  40

<210> SEQ ID NO 12
<211> LENGTH: 42
<212> TYPE: PRT
<213> ORGANISM: Homo sapiens
<220> FEATURE:
<223> OTHER INFORMATION: 4-1BB (amino acids 214-255 of Q07011.1)

<400> SEQUENCE: 12

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 13
<211> LENGTH: 112
<212> TYPE: PRT
<213> ORGANISM: Artificial Sequence
<220> FEATURE:
<223> OTHER INFORMATION: CD3 zeta

<400> SEQUENCE: 13

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 14
<211> LENGTH: 112
<212> TYPE: PRT
<213> ORGANISM: Artificial Sequence
<220> FEATURE:
<223> OTHER INFORMATION: CD3 zeta

<400> SEQUENCE: 14

Arg Val Lys Phe Ser Arg Ser Ala Glu Pro Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 15
<211> LENGTH: 112
<212> TYPE: PRT
<213> ORGANISM: Artificial Sequence
<220> FEATURE:
<223> OTHER INFORMATION: CD3 zeta

<400> SEQUENCE: 15

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 16
<211> LENGTH: 335
<212> TYPE: PRT
<213> ORGANISM: Artificial Sequence
<220> FEATURE:
<223> OTHER INFORMATION: tEGFR

<400> SEQUENCE: 16

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

```
Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
        275                 280                 285

Pro Asn Cys Thr Tyr Gly Cys Thr Gly Pro Gly Leu Glu Gly Cys Pro
    290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335

<210> SEQ ID NO 17
<211> LENGTH: 18
<212> TYPE: PRT
<213> ORGANISM: Artificial Sequence
<220> FEATURE:
<223> OTHER INFORMATION: T2A

<400> SEQUENCE: 17

Glu Gly Arg Gly Ser Leu Leu Thr Cys Gly Asp Val Glu Glu Asn Pro
1               5                   10                  15

Gly Pro

<210> SEQ ID NO 18
<211> LENGTH: 22
<212> TYPE: PRT
<213> ORGANISM: Artificial Sequence
<220> FEATURE:
<223> OTHER INFORMATION: P2A

<400> SEQUENCE: 18

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 19
<211> LENGTH: 19
<212> TYPE: PRT
<213> ORGANISM: Artificial Sequence
<220> FEATURE:
<223> OTHER INFORMATION: P2A

<400> SEQUENCE: 19

Ala Thr Asn Phe Ser Leu Leu Lys Gln Ala Gly Asp Val Glu Glu Asn
1               5                   10                  15

Pro Gly Pro

<210> SEQ ID NO 20
```

```
<211> LENGTH: 20
<212> TYPE: PRT
<213> ORGANISM: Artificial Sequence
<220> FEATURE:
<223> OTHER INFORMATION: E2A

<400> SEQUENCE: 20

Gln Cys Thr Asn Tyr Ala Leu Leu Lys Leu Ala Gly Asp Val Glu Ser
1               5                   10                  15

Asn Pro Gly Pro
            20

<210> SEQ ID NO 21
<211> LENGTH: 22
<212> TYPE: PRT
<213> ORGANISM: Artificial Sequence
<220> FEATURE:
<223> OTHER INFORMATION: F2A

<400> SEQUENCE: 21

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 22
<211> LENGTH: 10
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (5)...(9)
<223> OTHER INFORMATION: SGGGG is repeated 5 times

<400> SEQUENCE: 22

Pro Gly Gly Gly Ser Gly Gly Gly Gly Pro
1               5                   10

<210> SEQ ID NO 23
<211> LENGTH: 17
<212> TYPE: PRT
<213> ORGANISM: Artificial Sequence
<220> FEATURE:
<223> OTHER INFORMATION: Linker

<400> SEQUENCE: 23

Gly Ser Ala Asp Asp Ala Lys Lys Asp Ala Ala Lys Lys Asp Gly Lys
1               5                   10                  15

Ser

<210> SEQ ID NO 24
<211> LENGTH: 66
<212> TYPE: DNA
<213> ORGANISM: Artificial Sequence
<220> FEATURE:
<223> OTHER INFORMATION: GMCSFR alpha chain signal sequence

<400> SEQUENCE: 24
atgcttctcc tggtgacaag ccttctgctc tgtgagttac cacacccagc attcctcctg    60
atccca                                                               66

<210> SEQ ID NO 25
<211> LENGTH: 22
```

```
<212> TYPE: PRT
<213> ORGANISM: Artificial Sequence
<220> FEATURE:
<223> OTHER INFORMATION: GMCSFR alpha chain signal sequence

<400> SEQUENCE: 25

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 26
<211> LENGTH: 18
<212> TYPE: PRT
<213> ORGANISM: Artificial Sequence
<220> FEATURE:
<223> OTHER INFORMATION: CD8 alpha signal peptide

<400> SEQUENCE: 26

Met Ala Leu Pro Val Thr Ala Leu Leu Leu Pro Leu Ala Leu Leu Leu
1               5                   10                  15

His Ala

<210> SEQ ID NO 27
<211> LENGTH: 15
<212> TYPE: PRT
<213> ORGANISM: Artificial Sequence
<220> FEATURE:
<223> OTHER INFORMATION: Hinge

<400> SEQUENCE: 27

Glu Pro Lys Ser Cys Asp Lys Thr His Thr Cys Pro Pro Cys Pro
1               5                   10                  15

<210> SEQ ID NO 28
<211> LENGTH: 12
<212> TYPE: PRT
<213> ORGANISM: Artificial Sequence
<220> FEATURE:
<223> OTHER INFORMATION: Hinge

<400> SEQUENCE: 28

Glu Arg Lys Cys Cys Val Glu Cys Pro Pro Cys Pro
1               5                   10

<210> SEQ ID NO 29
<211> LENGTH: 61
<212> TYPE: PRT
<213> ORGANISM: Artificial Sequence
<220> FEATURE:
<223> OTHER INFORMATION: Hinge

<400> SEQUENCE: 29

Glu Leu Lys Thr Pro Leu Gly Asp Thr His Thr Cys Pro Arg Cys Pro
1               5                   10                  15

Glu Pro Lys Ser Cys Asp Thr Pro Pro Cys Pro Arg Cys Pro Glu
                20                  25                  30

Pro Lys Ser Cys Asp Thr Pro Pro Cys Pro Arg Cys Pro Glu Pro
            35                  40                  45

Lys Ser Cys Asp Thr Pro Pro Cys Pro Arg Cys Pro
        50                  55                  60

<210> SEQ ID NO 30
<211> LENGTH: 12
```

```
<212> TYPE: PRT
<213> ORGANISM: Artificial Sequence
<220> FEATURE:
<223> OTHER INFORMATION: Hinge

<400> SEQUENCE: 30

Glu Ser Lys Tyr Gly Pro Pro Cys Pro Ser Cys Pro
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Hinge

<400> SEQUENCE: 31

Glu Ser Lys Tyr Gly Pro Pro Cys Pro Pro Cys Pro
1               5                   10

<210> SEQ ID NO 32
<211> LENGTH: 9
<212> TYPE: PRT
<213> ORGANISM: Artificial Sequence
<220> FEATURE:
<223> OTHER INFORMATION: Hinge

<400> SEQUENCE: 32

Tyr Gly Pro Pro Cys Pro Pro Cys Pro
1               5

<210> SEQ ID NO 33
<211> LENGTH: 10
<212> TYPE: PRT
<213> ORGANISM: Artificial Sequence
<220> FEATURE:
<223> OTHER INFORMATION: Hinge

<400> SEQUENCE: 33

Lys Tyr Gly Pro Pro Cys Pro Pro Cys Pro
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Hinge

<400> SEQUENCE: 34

Glu Val Val Val Lys Tyr Gly Pro Pro Cys Pro Pro Cys Pro
1               5                   10

<210> SEQ ID NO 35
<211> LENGTH: 11
<212> TYPE: PRT
<213> ORGANISM: Artificial Sequence
<220> FEATURE:
<223> OTHER INFORMATION: CDR L1

<400> SEQUENCE: 35

Arg Ala Ser Gln Asp Ile Ser Lys Tyr Leu Asn
1               5                   10

<210> SEQ ID NO 36
<211> LENGTH: 7
<212> TYPE: PRT
```

```
-continued

<213> ORGANISM: Artificial Sequence
<220> FEATURE:
<223> OTHER INFORMATION: CDR L2

<400> SEQUENCE: 36

Ser Arg Leu His Ser Gly Val
1               5

<210> SEQ ID NO 37
<211> LENGTH: 9
<212> TYPE: PRT
<213> ORGANISM: Artificial Sequence
<220> FEATURE:
<223> OTHER INFORMATION: CDR L3

<400> SEQUENCE: 37

Gly Asn Thr Leu Pro Tyr Thr Phe Gly
1               5

<210> SEQ ID NO 38
<211> LENGTH: 5
<212> TYPE: PRT
<213> ORGANISM: Artificial Sequence
<220> FEATURE:
<223> OTHER INFORMATION: CDR H1

<400> SEQUENCE: 38

Asp Tyr Gly Val Ser
1               5

<210> SEQ ID NO 39
<211> LENGTH: 16
<212> TYPE: PRT
<213> ORGANISM: Artificial Sequence
<220> FEATURE:
<223> OTHER INFORMATION: CDR H2

<400> SEQUENCE: 39

Val Ile Trp Gly Ser Glu Thr Thr Tyr Tyr Asn Ser Ala Leu Lys Ser
1               5                   10                  15

<210> SEQ ID NO 40
<211> LENGTH: 7
<212> TYPE: PRT
<213> ORGANISM: Artificial Sequence
<220> FEATURE:
<223> OTHER INFORMATION: CDR H3

<400> SEQUENCE: 40

Tyr Ala Met Asp Tyr Trp Gly
1               5

<210> SEQ ID NO 41
<211> LENGTH: 120
<212> TYPE: PRT
<213> ORGANISM: Artificial Sequence
<220> FEATURE:
<223> OTHER INFORMATION: VH

<400> SEQUENCE: 41

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
                20                  25                  30

Gly Val Ser Trp Ile Arg Gln Pro Pro Arg Lys Gly Leu Glu Trp Leu
            35                  40                  45
```

```
Gly Val Ile Trp Gly Ser Glu Thr Thr Tyr Tyr Asn Ser Ala Leu Lys
        50                  55                  60

Ser Arg Leu Thr Ile Ile Lys Asp Asn Ser Lys Ser Gln Val Phe Leu
 65                  70                  75                  80

Lys Met Asn Ser Leu Gln Thr Asp Asp Thr Ala Ile Tyr Tyr Cys Ala
                    85                  90                  95

Lys His Tyr Tyr Tyr Gly Gly Ser Tyr Ala Met Asp Tyr Trp Gly Gln
                    100                 105                 110

Gly Thr Ser Val Thr Val Ser Ser
                    115                 120

<210> SEQ ID NO 42
<211> LENGTH: 107
<212> TYPE: PRT
<213> ORGANISM: Artificial Sequence
<220> FEATURE:
<223> OTHER INFORMATION: VL

<400> SEQUENCE: 42

Asp Ile Gln Met Thr Gln Thr Thr Ser Ser Leu Ser Ala Ser Leu Gly
 1               5                  10                  15

Asp Arg Val Thr Ile Ser Cys Arg Ala Ser Gln Asp Ile Ser Lys Tyr
                    20                  25                  30

Leu Asn Trp Tyr Gln Gln Lys Pro Asp Gly Thr Val Lys Leu Leu Ile
                35                  40                  45

Tyr His Thr Ser Arg Leu His Ser Gly Val Pro Ser Arg Phe Ser Gly
            50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Tyr
                    85                  90                  95

Thr Phe Gly Gly Gly Thr Lys Leu Glu Ile Thr
                    100                 105

<210> SEQ ID NO 43
<211> LENGTH: 245
<212> TYPE: PRT
<213> ORGANISM: Artificial Sequence
<220> FEATURE:
<223> OTHER INFORMATION: scFv

<400> SEQUENCE: 43

Asp Ile Gln Met Thr Gln Thr Thr Ser Ser Leu Ser Ala Ser Leu Gly
 1               5                  10                  15

Asp Arg Val Thr Ile Ser Cys Arg Ala Ser Gln Asp Ile Ser Lys Tyr
                    20                  25                  30

Leu Asn Trp Tyr Gln Gln Lys Pro Asp Gly Thr Val Lys Leu Leu Ile
                35                  40                  45

Tyr His Thr Ser Arg Leu His Ser Gly Val Pro Ser Arg Phe Ser Gly
            50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Tyr
                    85                  90                  95

Thr Phe Gly Gly Gly Thr Lys Leu Glu Ile Thr Gly Ser Thr Ser Gly
                    100                 105                 110

Ser Gly Lys Pro Gly Ser Gly Glu Gly Ser Thr Lys Gly Glu Val Lys
```

```
                115                 120                 125
Leu Gln Glu Ser Gly Pro Gly Leu Val Ala Pro Ser Gln Ser Leu Ser
            130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
                195                 200                 205

Ser Leu Gln Thr Asp Asp Thr Ala Ile Tyr Tyr Cys Ala Lys His Tyr
            210                 215                 220

Tyr Tyr Gly Gly Ser Tyr Ala Met Asp Tyr Trp Gly Gln Gly Thr Ser
225                 230                 235                 240

Val Thr Val Ser Ser
            245

<210> SEQ ID NO 44
<211> LENGTH: 11
<212> TYPE: PRT
<213> ORGANISM: Artificial Sequence
<220> FEATURE:
<223> OTHER INFORMATION: CDR L1

<400> SEQUENCE: 44

Lys Ala Ser Gln Asn Val Gly Thr Asn Val Ala
1               5                   10

<210> SEQ ID NO 45
<211> LENGTH: 7
<212> TYPE: PRT
<213> ORGANISM: Artificial Sequence
<220> FEATURE:
<223> OTHER INFORMATION: CDR L2

<400> SEQUENCE: 45

Ser Ala Thr Tyr Arg Asn Ser
1               5

<210> SEQ ID NO 46
<211> LENGTH: 9
<212> TYPE: PRT
<213> ORGANISM: Artificial Sequence
<220> FEATURE:
<223> OTHER INFORMATION: CDR L3

<400> SEQUENCE: 46

Gln Gln Tyr Asn Arg Tyr Pro Tyr Thr
1               5

<210> SEQ ID NO 47
<211> LENGTH: 5
<212> TYPE: PRT
<213> ORGANISM: Artificial Sequence
<220> FEATURE:
<223> OTHER INFORMATION: CDR H1

<400> SEQUENCE: 47

Ser Tyr Trp Met Asn
1               5
```

```
<210> SEQ ID NO 48
<211> LENGTH: 17
<212> TYPE: PRT
<213> ORGANISM: Artificial Sequence
<220> FEATURE:
<223> OTHER INFORMATION: CDR H2

<400> SEQUENCE: 48

Gln Ile Tyr Pro Gly Asp Gly Asp Thr Asn Tyr Asn Gly Lys Phe Lys
1               5                   10                  15
Gly

<210> SEQ ID NO 49
<211> LENGTH: 13
<212> TYPE: PRT
<213> ORGANISM: Artificial Sequence
<220> FEATURE:
<223> OTHER INFORMATION: CDR H3

<400> SEQUENCE: 49

Lys Thr Ile Ser Ser Val Val Asp Phe Tyr Phe Asp Tyr
1               5                   10

<210> SEQ ID NO 50
<211> LENGTH: 122
<212> TYPE: PRT
<213> ORGANISM: Artificial Sequence
<220> FEATURE:
<223> OTHER INFORMATION: VH

<400> SEQUENCE: 50

Glu Val Lys Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Phe Cys
                85                  90                  95

Ala Arg Lys Thr Ile Ser Ser Val Val Asp Phe Tyr Phe Asp Tyr Trp
            100                 105                 110

Gly Gln Gly Thr Thr Val Thr Val Ser Ser
        115                 120

<210> SEQ ID NO 51
<211> LENGTH: 108
<212> TYPE: PRT
<213> ORGANISM: Artificial Sequence
<220> FEATURE:
<223> OTHER INFORMATION: VL

<400> SEQUENCE: 51

Asp Ile Glu Leu Thr Gln Ser Pro Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Pro Leu Ile
        35                  40                  45
```

```
Tyr Ser Ala Thr Tyr Arg Asn Ser Gly Val Pro Asp Arg Phe Thr Gly
         50                  55                  60

Ser Gly Ser Gly Thr Asp Phe Thr Leu Thr Ile Thr Asn Val Gln Ser
 65              70                  75                      80

Lys Asp Leu Ala Asp Tyr Phe Cys Gln Gln Tyr Asn Arg Tyr Pro Tyr
                 85                  90                  95

Thr Ser Gly Gly Gly Thr Lys Leu Glu Ile Lys Arg
            100                 105

<210> SEQ ID NO 52
<211> LENGTH: 15
<212> TYPE: PRT
<213> ORGANISM: Artificial Sequence
<220> FEATURE:
<223> OTHER INFORMATION: Linker

<400> SEQUENCE: 52

Gly Gly Gly Gly Ser Gly Gly Gly Ser Gly Gly Gly Gly Ser
 1               5                  10                  15

<210> SEQ ID NO 53
<211> LENGTH: 245
<212> TYPE: PRT
<213> ORGANISM: Artificial Sequence
<220> FEATURE:
<223> OTHER INFORMATION: scFv

<400> SEQUENCE: 53

Glu Val Lys Leu Gln Gln Ser Gly Ala Glu Leu Val Arg Pro Gly Ser
 1               5                  10                  15

Ser Val Lys Ile Ser Cys Lys Ala Ser Gly Tyr Ala Phe Ser Ser Tyr
             20                  25                  30

Trp Met Asn Trp Val Lys Gln Arg Pro Gly Gln Gly Leu Glu Trp Ile
         35                  40                  45

Gly Gln Ile Tyr Pro Gly Asp Gly Asp Thr Asn Tyr Asn Gly Lys Phe
     50                  55                  60

Lys Gly Gln Ala Thr Leu Thr Ala Asp Lys Ser Ser Ser Thr Ala Tyr
 65                  70                  75                  80

Met Gln Leu Ser Gly Leu Thr Ser Glu Asp Ser Ala Val Tyr Phe Cys
                 85                  90                  95

Ala Arg Lys Thr Ile Ser Ser Val Val Asp Phe Tyr Phe Asp Tyr Trp
             100                 105                 110

Gly Gln Gly Thr Thr Val Thr Val Ser Ser Gly Gly Gly Gly Ser Gly
         115                 120                 125

Gly Gly Ser Gly Gly Gly Gly Ser Asp Ile Glu Leu Thr Gln Ser
     130                 135                 140

Pro Lys Phe Met Ser Thr Ser Val Gly Asp Arg Val Ser Val Thr Cys
145                 150                 155                 160

Lys Ala Ser Gln Asn Val Gly Thr Asn Val Ala Trp Tyr Gln Gln Lys
                165                 170                 175

Pro Gly Gln Ser Pro Lys Pro Leu Ile Tyr Ser Ala Thr Tyr Arg Asn
            180                 185                 190

Ser Gly Val Pro Asp Arg Phe Thr Gly Ser Gly Ser Gly Thr Asp Phe
        195                 200                 205

Thr Leu Thr Ile Thr Asn Val Gln Ser Lys Asp Leu Ala Asp Tyr Phe
    210                 215                 220

Cys Gln Gln Tyr Asn Arg Tyr Pro Tyr Thr Ser Gly Gly Gly Thr Lys
```

```
<210> SEQ ID NO 54
<211> LENGTH: 12
<212> TYPE: PRT
<213> ORGANISM: Artificial Sequence
<220> FEATURE:
<223> OTHER INFORMATION: HC-CDR3

<400> SEQUENCE: 54

His Tyr Tyr Tyr Gly Gly Ser Tyr Ala Met Asp Tyr
1               5                   10

<210> SEQ ID NO 55
<211> LENGTH: 7
<212> TYPE: PRT
<213> ORGANISM: Artificial Sequence
<220> FEATURE:
<223> OTHER INFORMATION: LC-CDR2

<400> SEQUENCE: 55

His Thr Ser Arg Leu His Ser
1               5

<210> SEQ ID NO 56
<211> LENGTH: 9
<212> TYPE: PRT
<213> ORGANISM: Artificial Sequence
<220> FEATURE:
<223> OTHER INFORMATION: LC-CDR3

<400> SEQUENCE: 56

Gln Gln Gly Asn Thr Leu Pro Tyr Thr
1               5

<210> SEQ ID NO 57
<211> LENGTH: 735
<212> TYPE: DNA
<213> ORGANISM: Artificial Sequence
<220> FEATURE:
<223> OTHER INFORMATION: Sequence encoding scFv

<400> SEQUENCE: 57
```

| | |
|---|---|
| gacatccaga tgacccagac cacctccagc ctgagcgcca gcctgggcga ccgggtgacc | 60 |
| atcagctgcc gggccagcca ggacatcagc aagtacctga actggtatca gcagaagccc | 120 |
| gacggcaccg tcaagctgct gatctaccac accagccggc tgcacagcgg cgtgcccagc | 180 |
| cggtttagcg gcagcggctc cggcaccgac tacagcctga ccatctccaa cctggaacag | 240 |
| gaagatatcg ccacctactt ttgccagcag ggcaacacac tgccctacac ctttggcggc | 300 |
| ggaacaaagc tggaaatcac cggcagcacc tccggcagcg gcaagcctgg cagcggcgag | 360 |
| ggcagcacca agggcgaggt gaagctgcag gaaagcggcc ctggcctggt ggcccccagc | 420 |
| cagagcctga gcgtgacctg caccgtgagc ggcgtgagcc tgcccgacta cggcgtgagc | 480 |
| tggatccggc agccccccag gaagggcctg aatggctggg gcgtgatctg ggcagcgag | 540 |
| accacctact acaacagcgc cctgaagagc cggctgacca tcatcaagga caacagcaag | 600 |
| agccaggtgt tcctgaagat gaacagcctg cagaccgacg acaccgccat ctactactgc | 660 |
| gccaagcact actactacgg cggcagctac gccatggact actggggcca gggcaccagc | 720 |
| gtgaccgtga gcagc | 735 |

```
<210> SEQ ID NO 58
<211> LENGTH: 5
<212> TYPE: PRT
<213> ORGANISM: Artificial Sequence
<220> FEATURE:
<223> OTHER INFORMATION: Hinge
<220> FEATURE:
<221> NAME/KEY: VARIANT
<222> LOCATION: (1)...(1)
<223> OTHER INFORMATION: Xaa is glycine, cysteine or arginine
<220> FEATURE:
<221> NAME/KEY: VARIANT
<222> LOCATION: (4)...(4)
<223> OTHER INFORMATION: Xaa is cysteine or threonine

<400> SEQUENCE: 58

Xaa Pro Pro Xaa Pro
1               5

<210> SEQ ID NO 59
<211> LENGTH: 18
<212> TYPE: PRT
<213> ORGANISM: Artificial Sequence
<220> FEATURE:
<223> OTHER INFORMATION: Linker

<400> SEQUENCE: 59

Gly Ser Thr Ser Gly Ser Gly Lys Pro Gly Ser Gly Glu Gly Ser Thr
1               5                   10                  15

Lys Gly
```

PHENOTYPIC MARKERS FOR CELL THERAPY AND RELATED METHODS

CROSS-REFERENCE TO RELATED APPLICATIONS

This application is a National Stage application under 35 U.S.C. § 371 of International Application No. PCT/US2018/064630, filed on Dec. 7, 2018, which claims priority from U.S. provisional application No. 62/596,775, filed Dec. 8, 2017, entitled "PHENOTYPIC MARKERS FOR CELL THERAPY AND RELATED METHODS," U.S. provisional application No. 62/643,165, filed Mar. 14, 2018, entitled "PHENOTYPIC MARKERS FOR CELL THERAPY AND RELATED METHODS," U.S. provisional application No. 62/657,716, filed Apr. 13, 2018, entitled "PHENOTYPIC MARKERS FOR CELL THERAPY AND RELATED METHODS," and U.S. provisional application No. 62/716,967, filed Aug. 9, 2018, entitled "PHENOTYPIC MARKERS FOR CELL THERAPY AND RELATED METHODS," the contents of which are incorporated by reference in their entirety.

INCORPORATION BY REFERENCE OF SEQUENCE LISTING

The present application is being filed along with a Sequence Listing in electronic format. The Sequence Listing is provided as a file entitled 735042014500SeqList.txt, created Jun. 1, 2020, which is 35,501 bytes in size. The information in the electronic format of the Sequence Listing is incorporated by reference in its entirety.

FIELD

The present disclosure relates to cell therapy involving the administration of one or more doses of a therapeutic T cell composition, and methods, compositions and articles of manufacture for use in the same. The cells of the T cell composition express recombinant receptors such as chimeric receptors, e.g. chimeric antigen receptors (CARs) or other transgenic receptors such as T cell receptors (TCRs). Features of the embodiments of the present disclosure, including the dose of cells or units of cells administered and/or the phenotype of administered cells, provide various advantages, such as consistent dosing, lower risk of toxicity and/or increased response in subjects administered the T cell compositions.

BACKGROUND

Various immunotherapy and/or cell therapy methods are available for treating diseases and conditions. For example, adoptive cell therapies (including those involving the administration of cells expressing chimeric receptors specific for a disease or disorder of interest, such as chimeric antigen receptors (CARs) and/or other recombinant antigen receptors, as well as other adoptive immune cell and adoptive T cell therapies) can be beneficial in the treatment of cancer or other diseases or disorders. Improved approaches are needed. Provided are methods and articles of manufacture that meet such needs.

SUMMARY

Provided herein are therapeutic compositions containing T cells expressing a recombinant receptor, wherein at least at or about, or at or about, 40%, 50%, 60%, 70%, 80%, 85%, 90%, 91%, 92%, 93%, 94%, 95%, 96%, 97%, 98%, 99% or 100% of the total number of T cells in the composition or of the total number of T cells in the composition expressing the recombinant receptor, are surface positive for CCR7 and/or CD27. In some embodiments, at least at or about, or at or about 50% of the total number of T cells in the composition or of the total number of T cells in the composition expressing the recombinant receptor are surface positive for CCR7 and/or CD27. In some embodiments, at least at or about, or at or about 60% of the total number of T cells in the composition or of the total number of T cells in the composition expressing the recombinant receptor are surface positive for CCR7 and/or CD27. In some embodiments, at least at or about, or at or about 70% of the total number of T cells in the composition or of the total number of T cells in the composition expressing the recombinant receptor are surface positive for CCR7 and/or CD27. In some embodiments, at least at or about, or at or about 80% of the total number of T cells in the composition or of the total number of T cells in the composition expressing the recombinant receptor are surface positive for CCR7 and/or CD27.

In some embodiments, the T cells in the composition and/or expressing the recombinant receptor comprise or consist of CD8+ T cells; the T cells in the composition and/or expressing the recombinant receptor comprise or consist of CD4+ T cells; the T cells in the composition and/or expressing the recombinant receptor comprise or consist of CD8+ and CD4+ T cells; the T cells in the composition and/or expressing the recombinant receptor comprise or consist of at least at or about 30%, 50% 95%, 96%, 97%, 98%, or 99% or 100% CD8+ T cells; the T cells in the composition and/or expressing the recombinant receptor comprise or consist of at least at or about 30%, 50% 95%, 96%, 97%, 98%, or 99% or 100% CD4+ T cells; and/or the T cells in the composition and/or expressing the recombinant receptor comprise or consist of approximately 1:1 or approximately between 1:3 and 3:1 or approximately between 1:2 and 2:1, CD4+:CD8+ T cells.

Provided herein are methods, compositions, and articles of manufacture involving or comprising a unit dose of cells based on a defined number, such as a subtype of CD8+ T cells or a subtype of CD4+ T cells or cells thereof expressing a recombinant receptor, or a ratio of such subtype of CD8+ and CD4+ T cells. In some embodiments, the total number of T cells in the composition, or the total number of T cells in the composition expressing the recombinant receptor, are surface positive for CCR7. In some embodiments, the total number of T cells in the composition, or the total number of T cells in the composition expressing the recombinant receptor, are surface positive for CD27. In some embodiments, the total number of T cells in the composition, or the total number of T cells in the composition expressing the recombinant receptor, are surface positive for CCR7 and CD27. In some embodiments, the composition comprises one or more unit doses of cells.

In some embodiments, the subtype of cells is positive for a cell surface marker, such as a marker of a central memory phenotype and/or in which the cell surface marker is CCR7 and/or CD27. In some embodiments, the provided methods, compositions and articles of manufacture are for use in connection with cell therapy, such as engineered T cell therapy for the treatment of diseases and conditions, including various tumors.

Provided herein are articles of manufacture. In some embodiments, the provided articles of manufacture includes a container, comprising one or more unit doses of cells, present in one or more therapeutic composition, the unit dose comprising a plurality of CD8+ and/or CD4+ T cells expressing (optionally engineered to express) a recombinant receptor, wherein a unit dose of cells comprises a defined number of recombinant receptor-expressing CD8+ T cells that express (optionally surface express) C—C chemokine receptor type 7 (CCR7) (receptor+/CD8+/CCR7+ cells) and/or a defined number of recombinant receptor-expressing CD4+ T cells that express CCR7 (receptor+/CD4+/CCR7+ cells) and/or a defined ratio of receptor+/CD8+/CCR7+ cells to receptor+/CD4+/CCR7+ cells and/or a defined ratio of receptor+/CD8+/CCR7+ cells and/or receptor+/CD4+/CCR7+ cells to another subset of cells in the composition; and instructions for administering to a subject having a disease or condition, the therapeutic composition, optionally one or more unit doses thereof and/or a volume corresponding to such one or more of unit doses.

Provided herein are articles of manufacture. In some embodiments, the provided articles of manufacture includes a container, comprising one or more unit doses of cells, present in one or more therapeutic composition, the unit dose comprising a plurality of CD8+ and/or CD4+ T cells expressing (optionally engineered to express) a recombinant receptor, wherein a unit dose of cells comprises a defined number of recombinant receptor-expressing CD8+ T cells that express (optionally surface express) cluster of differentiation 27 (CD27) (receptor+/CD8+/CD27+ cells) and/or a defined number of recombinant receptor-expressing CD4+ T cells that express CD27 (receptor+/CD4+/CD27+ cells) and/or a defined ratio of receptor+/CD8+/CD27+ cells to receptor+/CD4+/CD27+ cells and/or a defined ratio of receptor+/CD8+/CD27+ cells and/or receptor+/CD4+/CD27+ cells to another subset of cells in the composition; and instructions for administering to a subject having a disease or condition, the therapeutic composition, optionally one or more unit doses thereof and/or a volume corresponding to such one or more of unit doses.

Also provided herein are therapeutic compositions. In some embodiments, the therapeutic composition comprises T cells expressing a recombinant receptor, wherein at least at or about, or at or about, 80%, 85%, 90%, 91%, 92%, 93%, 94%, 95%, 96%, 97%, 98%, 99% or 100% of the total number of T cells in the composition (or of the total number of T cells in the composition expressing the recombinant receptor), are surface positive for CCR7 and/or CD27, optionally wherein: the T cells in the composition and/or expressing the recombinant receptor comprise or consist of CD8+ T cells; the T cells in the composition and/or expressing the recombinant receptor comprise or consist of CD4+ T cells; the T cells in the composition and/or expressing the recombinant receptor comprise or consist of CD8+ and CD4+ T cells; the T cells in the composition and/or expressing the recombinant receptor comprise or consist of at least at or about 30%, 50% 95%, 96%, 97%, 98%, or 99% or 100% CD8+ T cells; the T cells in the composition and/or expressing the recombinant receptor comprise or consist of at least at or about 30%, 50% 95%, 96%, 97%, 98%, or 99% or 100% CD4+ T cells; the T cells in the composition and/or expressing the recombinant receptor comprise or consist of approximately 1:1 or approximately between 1:3 and 3:1 or approximately between 1:2 and 2:1, CD4+:CD8+ T cells.

In some embodiments, the unit dose of cells comprises any of the therapeutic compositions described herein.

In some embodiments, the unit dose of cells comprises a defined number of CD8+/CCR7+ cells; and/or wherein the unit dose of cells comprises a defined number of CD4+/CCR7+ cells. In some embodiments, the unit dose of cells comprises a defined number of CD8+/CD27+ cells; and/or wherein the unit dose of cells comprises a defined number of CD4+/CD27+ cells. In some embodiments, the unit dose of cells comprises a defined number of CD8+/CCR7+/CD27+ cells; and/or wherein the unit dose of cells comprises a defined number of CD4+/CCR7+/CD27+ cells.

In some embodiments, the unit dose or composition comprises between at or about $1 \times 10^5$ and at or about $1 \times 10^8$, between at or about $5 \times 10^5$ and at or about $1 \times 10^7$, or between at or about $1 \times 10^6$ and at or about $1 \times 10^7$ total CD8+ cells that express the recombinant receptor (receptor+/CD8+ cells) or total CD4+ cells that express the recombinant receptor (receptor+/CD4+ cells), total receptor+/CD8+/CCR7+ cells, total receptor+/CD4+/CCR7+ cells, total receptor+/CD8+/CD27+ cells, or total receptor+/CD4+/CD27+ cells, each inclusive, and/or the unit dose or composition comprises no more than about $1 \times 10^8$, no more than about $5 \times 10^7$, no more than about $1 \times 10^7$, no more than about $5 \times 10^6$, no more than about $1 \times 10^6$, or no more than about $5 \times 10^5$ total receptor+/CD8+ cells or total receptor+/CD4+ cells, total receptor+/CD8+/CCR7+ cells, total receptor+/CD4+/CCR7+ cells, total receptor+/CD8+/CD27+ cells, or total receptor+/CD4+/CD27+ cells.

In some embodiments, the unit dose comprises at least about $3 \times 10^6$, $4 \times 10^6$, $5 \times 10^6$, $6 \times 10^6$, $7 \times 10^6$, $8 \times 10^6$, $9 \times 10^6$, or $1 \times 10^7$ total receptor+/CD8+/CCR7+ cells or total receptor+/CD8+/CD27+ cells and/or at least about $3 \times 10^6$, $4 \times 10^6$, $5 \times 10^6$, $6 \times 10^6$, $7 \times 10^6$, $8 \times 10^6$, $9 \times 10^6$, or $1 \times 10^7$ total receptor+/CD4+/CCR7+ cells or total receptor+/CD4+/CD27+. In some embodiments, the unit dose comprises between at or about $3 \times 10^6$ and at or about $2.5 \times 10^7$, between at or about $4 \times 10^6$ and at or about $2 \times 10^7$, or between at or about $5 \times 10^6$ and at or about $1 \times 10^7$ total receptor+/CD8+/CCR7+ cells or total receptor+/CD8+/CD27+ cells and/or between at or about $3 \times 10^6$ and at or about $2.5 \times 10^7$, between at or about $4 \times 10^6$ and at or about $2 \times 10^7$, or between at or about $5 \times 10^6$ and at or about $1 \times 10^7$ total receptor+/CD4+/CCR7+ cells or total receptor+/CD4+/CD27+, each inclusive. In some embodiments, at least 15%, 20%, 30%, 40%, 50%, 60%, 70%, 80% or 90% of the total receptor+ cells in the unit dose, or between about 15% and 90%, between about 20% and 80%, between about 30% and 70%, or between about 40% and 60%, each inclusive, of the total receptor+ cells in the unit dose are receptor+/CD8+/CCR7+ or receptor+/CD8+/CD27+; or at least 15%, 20%, 30%, 40%, 50%, 60%, 70%, 80% or 90% of the total receptor+ cells in the unit dose, or between about 15% and 90%, between about 20% and 80%, between about 30% and 70%, or between about 40% and 60%, each inclusive, of the total receptor+ cells in the unit dose are receptor+/CD4+/CCR7+ or receptor+/CD4+/CD27+.

In some embodiments, the unit dose of cells or composition comprises a defined ratio of receptor+/CD8+/CCR7+ cells to receptor+/CD4+/CCR7+ cells, which ratio optionally is or is approximately 1:1 or is between approximately 1:3 and approximately 3:1.

In some embodiments, the unit dose of cells or composition comprises a defined ratio of receptor+/CD8+/CD27+ cells to receptor+/CD4+/CD27+ cells, which ratio optionally is or is approximately 1:1 or is between approximately 1:3 and approximately 3:1. In some embodiments, the defined number or ratio is further based on expression or absence of expression of CCR7 and/or CD45RA on the cells. In some embodiments, the defined number of cells further express or do not express CCR7 and/or CD45RA, optionally wherein the defined number of cells further are CCR7+ or CD45RA− cells.

In some embodiments, the defined number or ratio is further based on expression or absence of expression of CD27 and/or CD45RA on the cells. In some embodiments, the defined number of cells further express or do not express CD27 and/or CD45RA, optionally wherein the defined number of cells further are CD27$^+$ or CD45RA$^-$ cells. In some embodiments, the defined number further comprises cells that express or do not express CD27 and/or CD45RA, optionally wherein the defined number further comprises CD27$^+$ or CD45RA$^-$ cells. In some embodiments, the unit dose of cells or composition comprises a defined number of receptor$^+$/CD8$^+$/CCR7$^+$/CD27$^+$ cells and/or receptor$^+$/CD8$^+$/CCR7$^+$/CD45RA$^-$ cells. In some embodiments, the unit dose of cells or composition comprises a defined number of receptor$^+$/CD4$^+$/CCR7$^+$/CD27$^+$ cells and/or receptor$^+$/CD4$^+$/CCR7$^+$/CD45RA$^-$ cells.

In some embodiments, at least 15%, 20%, 30%, 40%, 50%, 60%, 70%, 80% or 90% of the total receptor$^+$ cells in the unit dose, or between about 15% and 90%, between about 20% and 80%, between about 30% and 70%, or between about 40% and 60%, each inclusive, of the total receptor$^+$ cells in the unit dose are receptor$^+$/CD8$^+$/CCR7$^+$/CD27$^+$, receptor$^+$/CD8$^+$/CCR7$^+$/CD45RA$^-$, receptor$^+$/CD4$^+$/CCR7$^+$/CD27$^+$ or receptor$^+$/CD4$^+$/CCR7$^+$/CD45RA$^-$.

Also provided herein are articles of manufacture, that include: a container, comprising one or more unit doses of cells, present in one or more therapeutic composition, the unit dose comprising a plurality of CD8$^+$ and/or CD4$^+$ T cells expressing, optionally engineered to express, a recombinant receptor, wherein a unit dose of cells comprises a defined number of recombinant receptor-expressing CD8$^+$ T cells that express CCR7 and CD27 (receptor$^+$/CD8$^+$/CCR7$^+$/CD27$^+$ cells) and/or a defined number of recombinant receptor-expressing CD4$^+$ T cells that express CCR7 and CD27 (receptor$^+$/CD4$^+$/CCR7$^+$/CD27$^+$ cells) and/or a defined ratio of receptor$^+$/CD8$^+$/CCR7$^+$/CD27$^+$ cells to receptor$^+$/CD4$^+$/CCR7$^+$/CD27$^+$ cells and/or a defined ratio of receptor$^+$/CD8$^+$/CCR7$^+$/CD27$^+$ cells and/or receptor$^+$/CD4$^+$/CCR7$^+$/CD27$^+$ cells to another subset of cells in the composition; and instructions for administering to a subject having a disease or condition, the therapeutic composition, optionally one or more unit doses thereof and/or a volume corresponding to such one or more of unit doses. In some embodiments, the unit dose of cells comprises a defined number of CD8$^+$/CCR7$^+$/CD27$^+$ cells. In some embodiments, the unit dose of cells comprises a defined number of CD4$^+$/CCR7$^+$/CD27$^+$ cells. In some embodiments, the unit dose comprises between at or about 1×10$^5$ and at or about 1×10$^8$, between at or about 5×10$^5$ and at or about 1×10$^7$, or between at or about 1×10$^6$ and at or about 1×10$^7$ total CD8$^+$ cells that express the recombinant receptor (receptor$^+$/CD8$^+$ cells) or total CD4$^+$ cells that express the recombinant receptor (receptor$^+$/CD4$^+$ cells), total receptor$^+$/CD8$^+$/CCR7$^+$/CD27$^+$ cells, or total receptor$^+$/CD4$^+$/CCR7$^+$/CD27$^+$ cells, each inclusive. In some embodiments, the unit dose comprises no more than about 1×10$^8$, no more than about 5×10$^7$, no more than about 1×10$^7$, no more than about 5×10$^6$, no more than about 1×10$^6$, or no more than about 5×10$^5$ total receptor$^+$/CD8$^+$ cells or total receptor$^+$/CD4$^+$ cells, total receptor$^+$/CD8$^+$/CCR7$^+$/CD27$^+$ cells, or total receptor$^+$/CD4$^+$/CCR7$^+$/CD27$^+$ cells.

In some embodiments, the unit dose comprises at least about 3×10$^6$, 4×10$^6$, 5×10$^6$, 6×10$^6$, 7×10$^6$, 8×10$^6$, 9×10$^6$, or 1×10$^7$ total receptor$^+$/CD8$^+$/CCR7$^+$/CD27$^+$ cells and/or at least about 3×10$^6$, 4×10$^6$, 5×10$^6$, 6×10$^6$, 7×10$^6$, 8×10$^6$, 9×10$^6$, or 1×10$^7$ total receptor$^+$/CD4$^+$/CCR7$^+$/CD27$^+$ cells.

In some embodiments, the unit dose comprises between at or about 3×10$^6$ and at or about 2.5×10$^7$, between at or about 4×10$^6$ and at or about 2×10$^7$, or between at or about 5×10$^6$ and at or about 1×10$^7$ total receptor$^+$/CD8$^+$/CCR7$^+$/CD27$^+$ cells and/or between at or about 3×10$^6$ and at or about 2.5×10$^7$, between at or about 4×10$^6$ and at or about 2×10$^7$, or between at or about 5×10$^6$ and at or about 1×10$^7$ total receptor$^+$/CD4$^+$/CCR7$^+$/CD27$^+$ cells, each inclusive. In some embodiments, at least 15%, 20%, 30%, 40%, 50%, 60%, 70%, 80% or 90% of the total receptor$^+$ cells in the unit dose, or between about 15% and 90%, between about 20% and 80%, between about 30% and 70%, or between about 40% and 60%, each inclusive, of the total receptor$^+$ cells in the unit dose are receptor$^+$/CD8$^+$/CCR7$^+$/CD27$^+$ or receptor$^+$/CD4$^+$/CCR7$^+$/CD27$^+$.

In some embodiments, the unit dose of cells comprises a defined ratio of receptor$^+$/CD8$^+$/CCR7$^+$/CD27$^+$ cells to receptor$^+$/CD4$^+$/CCR7$^+$/CD27$^+$ cells, which ratio optionally is or is approximately 1:1 or is between approximately 1:3 and approximately 3:1.

In some embodiments, the defined number or ratio is further based on expression or absence of expression of CD45RA on the cells. In some embodiments, the defined number of cells further express or do not express CD45RA, optionally wherein the defined number of cells further are CD45RA$^-$ cells. In some embodiments, the defined number further comprises cells that express or do not express CD45RA, optionally wherein the defined number further comprises CD45RA$^-$ cells.

In some embodiments, among a plurality of articles or unit doses or compositions, optionally produced according to the same method, the number or ratio of cells that express CCR7 (CCR7$^+$ cells) in the unit dose varies by no more than 40%, by no more than 30%, by no more than 20%, by no more than 10% or by no more than 5%.

In some embodiments, the unit dose or number of cells expressing the recombinant receptor comprises between at or about 1×10$^5$ and at or about 5×10$^8$, between at or about 1×10$^5$ and at or about 1×10$^8$, between at or about 5×10$^5$ and at or about 1×10$^7$, or between at or about 1×10$^6$ and at or about 1×10$^7$ total CD3$^+$ cells that express the recombinant receptor (receptor$^+$/CD3$^+$ cells) or total CD3$^+$ cells, each inclusive. In some embodiments, the unit dose or number of cells expressing the recombinant receptor comprises no more than about 5×10$^8$, no more than about 1×10$^8$, no more than about 5×10$^7$, no more than about 1×10$^7$, no more than about 5×10$^6$, no more than about 1×10$^6$, or no more than about 5×10$^5$ total receptor$^+$/CD3$^+$ cells or total CD3$^+$ cells.

In some embodiments, the total number of CD3$^+$ cells, total number of receptor$^+$/CD3$^+$ cells, total number of receptor$^+$/CD8$^+$ cells, total number of receptor$^+$/CD4$^+$ cells, total number of receptor$^+$/CD8$^+$/CCR7$^+$ cells, total number of receptor$^+$/CD4$^+$/CCR7$^+$ cells, total number of receptor$^+$/CD8$^+$/CD27$^+$ cells, total number of receptor$^+$/CD4$^+$/CD27$^+$ cells, total number of receptor$^+$/CD8$^+$/CCR7$^+$/CD27$^+$ cells, total number of receptor$^+$/CD4$^+$/CCR7$^+$/CD27$^+$ cells, total number of receptor$^+$/CD8$^+$/CCR7$^+$/CD45RA$^-$ cells and/or receptor$^+$/CD4$^+$/CCR7$^+$/CD45RA$^-$ cells is the total number of such cells that are live or viable. In some embodiments, the total number of CD3$^+$ cells, total number of receptor$^+$/CD3$^+$ cells, total number of receptor$^+$/CD8$^+$ cells, total number of receptor$^+$/CD4$^+$ cells, total number of receptor$^+$/CD8$^+$/CCR7$^+$ cells, total number of receptor$^+$/CD4$^+$/CCR7$^+$ cells, total number of receptor$^+$/CD8$^+$/CD27$^+$ cells, total number of receptor$^+$/CD4$^+$/CD27$^+$ cells, total number of receptor$^+$/CD8$^+$/CCR7$^+$/CD27$^+$ cells, total number of receptor$^+$/CD4$^+$/CCR7$^+$/CD27$^+$ cells, total number of receptor$^+$/

CD8+/CCR7+/CD45RA− cells and/or receptor+/CD4+/CCR7+/CD45RA− cells is the total number of such cells that do not express an apoptotic marker and/or is the total number of such cells that are apoptotic marker negative (−), wherein the apoptotic marker is Annexin V or activated Caspase 3.

In some embodiments, the instructions specify administering a plurality of unit doses contained in a plurality of separate compositions. In some embodiments, the plurality of separate compositions comprise a first composition comprising one of the CD8+ T cells and the CD4+ T cells and a second composition comprising the other of the CD8+ T cells and the CD4+ T cells. In some embodiments, the first composition comprises the CD8+ T cells. In some embodiments, the first composition comprises the CD4+ T cells.

In some embodiments, the instructions specify administering the composition containing CD8+ T cells or one or more unit doses thereof and/or a volume corresponding to such one or more of unit doses and the composition containing CD4+ T cells or one or more unit doses thereof and/or a volume corresponding to such one or more of unit doses, no more than 2 hours, no more than 1 hour, no more than 30 minutes, no more than 15 minutes, no more than 10 minutes or no more than 5 minutes apart or simultaneously.

In some embodiments, the instructions specify administering the composition containing CD8+ T cells or one or more unit doses thereof and/or a volume corresponding to such one or more of unit doses, prior to administering the composition containing CD4+ cells or one or more unit doses thereof and/or a volume corresponding to such one or more of unit doses. In some embodiments, the instructions specify administering the composition containing CD4+ T cells or one or more unit doses thereof and/or a volume corresponding to such one or more of unit doses, prior to administering the composition containing CD8+ cells or one or more unit doses thereof and/or a volume corresponding to such one or more of unit doses.

In some embodiments, the recombinant receptor is or comprises a chimeric receptor and/or a recombinant antigen receptor. In some embodiments, the recombinant receptor is capable of binding to a target antigen that is associated with, specific to, and/or expressed on a cell or tissue of a disease, disorder or condition. In some embodiments, the disease, disorder or condition is an infectious disease or disorder, an autoimmune disease, an inflammatory disease, or a tumor or a cancer. In some embodiments, the target antigen is a tumor antigen.

In some embodiments, the target antigen is selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD138, CD171, epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), G Protein Coupled Receptor 5D (GPCR5D), Her2/neu (receptor tyrosine kinase erbB2), Her3 (erb-B3), Her4 (erb-B4), erbB dimers, Human high molecular weight-melanoma-associated antigen (HMW-MAA), hepatitis B surface antigen, Human leukocyte antigen A1 (HLA-AI), Human leukocyte antigen A2 (HLA-A2), IL-22 receptor alpha(IL-22Ra), IL-13 receptor alpha 2 (IL-13Ra2), kinase insert domain receptor (kdr), kappa light chain, L1 cell adhesion molecule (L1CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, mesothelin, c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), vascular endothelial growth factor receptor (VEGFR), vascular endothelial growth factor receptor 2 (VEGFR2), Wilms Tumor 1 (WT-1), a pathogen-specific antigen, or an antigen associated with a universal tag, and/or biotinylated molecules, and/or molecules expressed by HIV, HCV, HBV or other pathogens.

In some embodiments, the recombinant receptor is or comprises a functional non-TCR antigen receptor or a TCR or antigen-binding fragment thereof. In some embodiments, the recombinant receptor is a chimeric antigen receptor (CAR).

In some embodiments, the recombinant receptor comprises an extracellular domain comprising an antigen-binding domain. In some embodiments, the antigen-binding domain is or comprises an antibody or an antibody fragment thereof, which optionally is a single chain fragment. In some embodiments, the fragment comprises antibody variable regions joined by a flexible linker. In some embodiments, the fragment comprises an scFv.

In some embodiments, the recombinant receptor comprises an intracellular signaling region. In some embodiments, the intracellular signaling region comprises an intracellular signaling domain. In some embodiments, the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM). In some embodiments, the intracellular signaling domain is or comprises an intracellular signaling domain of a CD3 chain, optionally a CD3-zeta (CD3ζ) chain, or a signaling portion thereof.

In some embodiments, the recombinant receptor further comprises a transmembrane domain disposed between the extracellular domain and the intracellular signaling region. In some embodiments, the intracellular signaling region further comprises a costimulatory signaling domain. In some embodiments, the costimulatory signaling domain comprises an intracellular signaling domain of a T cell costimulatory molecule or a signaling portion thereof. In some embodiments, the costimulatory signaling domain comprises an intracellular signaling domain of a CD28, a 4-1BB or an ICOS or a signaling portion thereof. In some embodiments, the costimulatory signaling domain is between the transmembrane domain and the intracellular signaling domain.

In some embodiments, the T cells are primary T cells obtained from a subject. In some embodiments, the T cells are autologous to the subject. In some embodiments, the T cells are allogeneic to the subject.

Also provided herein are methods of treatment. In some embodiments, the methods of treatment involve administering to a subject having a disease or condition one or more unit doses of any therapeutic composition described herein or a therapeutic composition comprising a plurality of CD8$^+$ and/or CD4$^+$ T cells engineered to express a recombinant receptor and/or a volume corresponding to such unit doses. In some embodiments, the unit dose of cells comprises a defined number of recombinant receptor-expressing CD8$^+$ T cells that express C—C chemokine receptor type 7 (CCR7) (receptor$^+$/CD8$^+$/CCR7$^+$ cells) and/or a defined number of recombinant receptor-expressing CD4$^+$ T cells that express CCR7 (receptor$^+$/CD4$^+$/CCR7$^+$ cells) and/or a defined ratio of receptor$^+$/CD8$^+$/CCR7$^+$ cells to receptor$^+$/CD4$^+$/CCR7$^+$ cells and/or a defined ratio of receptor$^+$/CD8$^+$/CCR7$^+$ cells and/or receptor$^+$/CD4$^+$/CCR7$^+$ cells to another subset of cells in the composition; and/or among a group of subjects treated according to the method, the number or ratio of cells that express CCR7 (CCR7$^+$ cells) in the unit dose varies by no more than 40%, by no more than 30%, by no more than 20%, by no more than 10% or by no more than 5%.

Also provided herein are methods of treatment. In some embodiments, the methods of treatment involve administering to a subject having a disease or condition one or more unit doses of a therapeutic composition described herein or a therapeutic composition comprising a plurality of CD8$^+$ and/or CD4$^+$ T cells engineered to express a recombinant receptor and/or a volume corresponding to such unit doses, optionally wherein: the unit dose of cells comprises a defined number of recombinant receptor-expressing CD8$^+$ T cells that express cluster of differentiation 27 (CD27) (receptor$^+$/CD8$^+$/CD27$^+$ cells) and/or a defined number of recombinant receptor-expressing CD4$^+$ T cells that express CD27 (receptor$^+$/CD4$^+$/CD27$^+$ cells) and/or a defined ratio of receptor$^+$/CD8$^+$/CD27$^+$ cells to receptor$^+$/CD4$^+$/CD27$^+$ cells and/or a defined ratio of receptor$^+$/CD8$^+$/CD27$^+$ cells and/or receptor$^+$/CD4$^+$/CD27$^+$ cells to another subset of cells in the composition; and/or among a group of subjects treated according to the method, the number or ratio of cells that express CD27 (CD27$^+$ cells) in the unit dose varies by no more than 40%, by no more than 30%, by no more than 20%, by no more than 10% or by no more than 5%.

In some embodiments, the unit dose of cells comprises a defined number of CD8$^+$/CD27$^+$ cells. In some embodiments, the unit dose of cells comprises a defined number of CD4$^+$/CD27$^+$ cells.

In some embodiments, the unit dose of cells comprises a defined number of CD8$^+$/CCR7$^+$ cells. In some embodiments, the unit dose of cells comprises a defined number of CD4$^+$/CCR7$^+$ cells. In some embodiments, the unit dose comprises between at or about 1×10$^5$ and at or about 1×10$^8$, between at or about 5×10$^5$ and at or about 1×10$^7$, or between at or about 1×10$^6$ and at or about 1×10$^7$ total CD8$^+$ cells that express the recombinant receptor (receptor$^+$/CD8$^+$ cells) or total CD4$^+$ cells that express the recombinant receptor (receptor$^+$/CD4$^+$ cells), total receptor$^+$/CD8$^+$/CCR7$^+$ cells, total receptor$^+$/CD4$^+$/CCR7$^+$ cells, total receptor$^+$/CD8$^+$/CD27$^+$ cells, or total receptor$^+$/CD4$^+$/CD27$^+$ cells, each inclusive. In some embodiments, the unit dose comprises no more than about 1×10$^8$, no more than about 5×10$^7$, no more than about 1×10$^7$, no more than about 5×10$^6$, no more than about 1×10$^6$, or no more than about 5×10$^5$ total receptor$^+$/CD8$^+$ cells or total receptor$^+$/CD4$^+$ cells, total receptor$^+$/CD8$^+$/CCR7$^+$ cells, total receptor$^+$/CD4$^+$/CCR7$^+$ cells, total receptor$^+$/CD8$^+$/CD27$^+$ cells, or total receptor$^+$/CD4$^+$/CD27$^+$ cells.

In some embodiments, the unit dose comprises at least about 3×10$^6$, 4×10$^6$, 5×10$^6$, 6×10$^6$, 7×10$^6$, 8×10$^6$, 9×10$^6$, or 1×10$^7$ total receptor$^+$/CD8$^+$/CCR7$^+$ cells or total receptor$^+$/CD8$^+$/CD27$^+$ cells and/or at least about 3×10$^6$, 4×10$^6$, 5×10$^6$, 6×10$^6$, 7×10$^6$, 8×10$^6$, 9×10$^6$, or 1×10$^7$ total receptor$^+$/CD4$^+$/CCR7$^+$ cells or total receptor$^+$/CD4$^+$/CD27$^+$. In some embodiments, the unit dose comprises between at or about 3×10$^6$ and at or about 2.5×10$^7$, between at or about 4×10$^6$ and at or about 2×10$^7$, or between at or about 5×10$^6$ and at or about 1×10$^7$ total receptor$^+$/CD8$^+$/CCR7$^+$ cells or total receptor$^+$/CD8$^+$/CD27$^+$ cells and/or between at or about 3×10$^6$ and at or about 2.5×10$^7$, between at or about 4×10$^6$ and at or about 2×10$^7$, or between at or about 5×10$^6$ and at or about 1×10$^7$ total receptor$^+$/CD4$^+$/CCR7$^+$ cells or total receptor$^+$/CD4$^+$/CD27$^+$, each inclusive. In some embodiments, at least 15%, 20%, 30%, 40%, 50%, 60%, 70%, 80% or 90% of the total receptor$^+$ cells in the unit dose, or between about 15% and 90%, between about 20% and 80%, between about 30% and 70%, or between about 40% and 60%, each inclusive, of the total receptor$^+$ cells in the unit dose are receptor$^+$/CD8$^+$/CCR7$^+$ or receptor$^+$/CD8$^+$/CD27$^+$; or at least 15%, 20%, 30%, 40%, 50%, 60%, 70%, 80% or 90% of the total receptor$^+$ cells in the unit dose, or between about 15% and 90%, between about 20% and 80%, between about 30% and 70%, or between about 40% and 60%, each inclusive, of the total receptor$^+$ cells in the unit dose are receptor$^+$/CD4$^+$/CCR7$^+$ or receptor$^+$/CD4$^+$/CD27$^+$.

In some embodiments, the unit dose of cells comprises a defined ratio of receptor$^+$/CD8$^+$/CCR7$^+$ cells to receptor$^+$/CD4$^+$/CCR7$^+$ cells, which ratio optionally is or is approximately 1:1 or is between approximately 1:3 and approximately 3:1.

In some embodiments, the defined number or ratio is further based on expression or absence of expression of CD27 and/or CD45RA on the cells. In some embodiments, the unit dose of cells comprises a defined number of receptor$^+$/CD8$^+$/CCR7$^+$/CD27$^+$ cells and/or receptor$^+$/CD8$^+$/CCR7$^+$/CD45RA$^-$ cells. In some embodiments, the unit dose of cells comprises a defined number of receptor$^+$/CD4$^+$/CCR7$^+$/CD27$^+$ cells and/or receptor$^+$/CD4$^+$/CCR7$^+$/CD45RA$^-$ cells. In some embodiments, the unit dose of cells comprises a defined ratio of receptor$^+$/CD8$^+$/CD27$^+$ cells to receptor$^+$/CD4$^+$/CD27$^+$ cells, which ratio optionally is or is approximately 1:1 or is between approximately 1:3 and approximately 3:1. In some embodiments, the defined number or ratio is further based on expression or absence of expression of CCR7 and/or CD45RA on the cells. In some embodiments, at least 15%, 20%, 30%, 40%, 50%, 60%, 70%, 80% or 90% of the total receptor$^+$ cells in the unit dose, or between about 15% and 90%, between about 20% and 80%, between about 30% and 70%, or between about 40% and 60%, each inclusive, of the total receptor$^+$ cells in the unit dose are receptor$^+$/CD8$^+$/CCR7$^+$/CD27$^+$ or receptor$^+$/CD8$^+$/CCR7$^+$/CD45RA$^-$.

In some embodiments, also provided are methods of treatment, wherein the methods involve administering to a subject having a disease or condition one or more unit doses of any compositions described herein.

In some embodiments, the unit dose of cells comprises a defined number of recombinant receptor-expressing CD8$^+$ T cells that express CCR7 and CD27 (receptor$^+$/CD8$^+$/CCR7$^+$/CD27$^+$ cells) and/or a defined number of recombinant receptor-expressing CD4$^+$ T cells that express CCR7 and CD27 (receptor$^+$/CD4$^+$/CCR7$^+$/CD27$^+$ cells) and/or a defined ratio of receptor+/CD8+/CCR7+/CD27+ cells to receptor+/CD4+/CCR7+/CD27+ cells and/or a defined ratio of receptor+/CD8+/CCR7+/CD27+ cells and/or receptor+/CD4+/CCR7+/CD27+ cells to another subset of cells in the composition; and among a group of subjects treated according to the method, the number or ratio of cells that express CCR7 (CCR7+ cells) in the unit dose varies by no more than 40%, by no more than 30%, by no more than 20%, by no more than 10% or by no more than 5%.

Also provided herein are methods of treatment, wherein the methods involve administering to a subject having a disease or condition a therapeutic composition comprising a plurality of CD8+ and/or CD4+ T cells engineered to express a recombinant receptor and/or a volume corresponding to such unit doses. In some embodiments, the unit dose of cells comprises a defined number of recombinant receptor-expressing CD8+ T cells that express CCR7 and CD27 (receptor+/CD8+/CCR7+/CD27+ cells) and/or a defined number of recombinant receptor-expressing CD4+ T cells that express CCR7 and CD27 (receptor+/CD4+/CCR7+/CD27+ cells) and/or a defined ratio of receptor+/CD8+/CCR7+/CD27+ cells to receptor+/CD4+/CCR7+/CD27+ cells and/or a defined ratio of receptor+/CD8+/CCR7+/CD27+ cells and/or receptor+/CD4+/CCR7+/CD27+ cells to another subset of cells in the composition; and among a group of subjects treated according to the method, the number or ratio of cells that express CCR7 (CCR7+ cells) in the unit dose varies by no more than 40%, by no more than 30%, by no more than 20%, by no more than 10% or by no more than 5%.

In some embodiments, the unit dose of cells comprises a defined number of CD8+/CCR7+/CD27+ cells. In some embodiments, the unit dose of cells comprises a defined number of CD4+/CCR7+/CD27+ cells. In some embodiments, the unit dose comprises between at or about $1 \times 10^5$ and at or about $1 \times 10^8$, between at or about $5 \times 10^5$ and at or about $1 \times 10^7$, or between at or about $1 \times 10^6$ and at or about $1 \times 10^7$ total CD8+ cells that express the recombinant receptor (receptor+/CD8+ cells) or total CD4+ cell that express the recombinant receptor (receptor+/CD4+ cells), total receptor+/CD8+/CCR7+/CD27+ cells, or total receptor+/CD4+/CCR7+/CD27+ cells, each inclusive. In some embodiments, the unit dose comprises no more than about $1 \times 10^8$, no more than about $5 \times 10^7$, no more than about $1 \times 10^7$, no more than about $5 \times 10^6$, no more than about $1 \times 10^6$, or no more than about $5 \times 10^5$ total receptor+/CD8+ cells or total receptor+/CD4+ cells, total receptor+/CD8+/CCR7+/CD27+ cells, or total receptor+/CD4+/CCR7+/CD27+ cells.

In some embodiments, the unit dose comprises at least about $3 \times 10^6$, $4 \times 10^6$, $5 \times 10^6$, $6 \times 10^6$, $7 \times 10^6$, $8 \times 10^6$, $9 \times 10^6$, or $1 \times 10^7$ total receptor+/CD8+/CCR7+/CD27+ cells; and/or at least about $3 \times 10^6$, $4 \times 10^6$, $5 \times 10^6$, $6 \times 10^6$, $7 \times 10^6$, $8 \times 10^6$, $9 \times 10^6$, or $1 \times 10^7$ total receptor+/CD4+/CCR7+/CD27+ cells. In some embodiments, the unit dose comprises between at or about $3 \times 10^6$ and at or about $2.5 \times 10^7$, between at or about $4 \times 10^6$ and at or about $2 \times 10^7$, or between at or about $5 \times 10^6$ and at or about $1 \times 10^7$ total receptor+/CD8+/CCR7+/CD27+ cells; and/or between at or about $3 \times 10^6$ and at or about $2.5 \times 10^7$, between at or about $4 \times 10^6$ and at or about $2 \times 10^7$, or between at or about $5 \times 10^6$ and at or about $1 \times 10^7$ total receptor+/CD4+/CCR7+/CD27+ cells, each inclusive. In some embodiments, at least 15%, 20%, 30%, 40%, 50%, 60%, 70%, 80% or 90% of the total receptor+ cells in the unit dose, or between about 15% and 90%, between about 20% and 80%, between about 30% and 70%, or between about 40% and 60%, each inclusive, of the total receptor+ cells in the unit dose are receptor+/CD8+/CCR7+/CD27+ or receptor+/CD4+/CCR7+/CD27+.

In some embodiments, the unit dose of cells comprises a defined ratio of receptor+/CD8+/CCR7+/CD27+ cells to receptor+/CD4+/CCR7+/CD27+ cells, which ratio optionally is or is approximately 1:1 or is between approximately 1:3 and approximately 3:1.

In some embodiments, the defined number or ratio is further based on expression or absence of expression of CD45RA on the cells. In some embodiments, the defined number or ratio is further based on the number of CD45RA− cells. In some embodiments, the defined number of cells further express or do not express CD45RA, optionally wherein the defined number of cells further are CD45RA− cells.

In some embodiments, the unit dose comprises between at or about $1 \times 10^5$ and at or about $5 \times 10^8$, between at or about $1 \times 10^5$ and at or about $1 \times 10^8$, between at or about $5 \times 10^5$ and at or about $1 \times 10^7$, or between at or about $1 \times 10^6$ and at or about $1 \times 10^7$ total CD3+ cells that express the recombinant receptor (receptor+/CD3+ cells) or total CD3+ cells, each inclusive. In some embodiments, the unit dose comprises no more than about $5 \times 10^8$, no more than about $1 \times 10^8$, no more than about $5 \times 10^7$, no more than about $1 \times 10^7$, no more than about $5 \times 10^6$, no more than about $1 \times 10^6$, or no more than about $5 \times 10^5$ total receptor+/CD3+ cells or total CD3+ cells.

In some embodiments, the total number of CD3+ cells, total number of receptor+/CD3+ cells, total number of receptor+/CD8+ cells, total number of receptor+/CD4+ cells, total number of receptor+/CD8+/CCR7+ cells, total number of receptor+/CD4+/CCR7+ cells, total number of receptor+/CD8+/CD27+ cells, total number of receptor+/CD4+/CD27+ cells, total number of receptor+/CD8+/CCR7+/CD27+ cells, total number of receptor+/CD4+/CCR7+/CD27+ cells, total number of receptor+/CD8+/CCR7+/CD45RA− cells and/or receptor+/CD4+/CCR7+/CD45RA− cells is the total number of such cells that are live or viable. In some embodiments, the total number of CD3+ cells, total number of receptor+/CD3+ cells, total number of receptor+/CD8+ cells, total number of receptor+/CD4+ cells, total number of receptor+/CD8+/CCR7+ cells, total number of receptor+/CD4+/CCR7+ cells, total number of receptor+/CD8+/CD27+ cells, total number of receptor+/CD4+/CD27+ cells, total number of receptor+/CD8+/CCR7+/CD27+ cells, total number of receptor+/CD4+/CCR7+/CD27+ cells, total number of receptor+/CD8+/CCR7+/CD45RA− cells and/or receptor+/CD4+/CCR7+/CD45RA− cells is the total number of such cells that do not express an apoptotic marker and/or is the total number of such cells that are apoptotic marker negative (−), wherein the apoptotic marker is Annexin V or activated Caspase 3.

In some embodiments, the method involves administering a plurality of unit doses contained in a plurality of separate compositions.

In some embodiments, the plurality of separate compositions comprise a first composition comprising one of the CD8+ T cells and the CD4+ T cells and a second composition comprising the other of the CD8+ T cells and the CD4+ T cells. In some embodiments, the first composition comprises the CD8+ T cells. In some embodiments, the first composition comprises the CD4+ T cells.

In some embodiments, the method involves administering the composition containing CD8+ T cells or one or more unit doses thereof and/or a volume corresponding to such one or more of unit doses and the composition containing CD4+ T cells or one or more unit doses thereof and/or a volume corresponding to such one or more of unit doses, no more than 2 hours, no more than 1 hour, no more than 30 minutes, no more than 15 minutes, no more than 10 minutes or no more than 5 minutes apart or simultaneously.

In some embodiments, the method involves administering the composition containing CD8+ T cells or one or more unit doses thereof and/or a volume corresponding to such one or more of unit doses, prior to administering the composition containing CD4+ cells or one or more unit doses thereof and/or a volume corresponding to such one or more of unit doses. In some embodiments, the method involves administering the composition containing CD4+ T cells or one or more unit doses thereof and/or a volume corresponding to such one or more of unit doses, prior to administering the composition containing CD8+ cells or one or more unit doses thereof and/or a volume corresponding to such one or more of unit doses.

In some embodiments, the recombinant receptor is or comprises a chimeric receptor and/or a recombinant antigen receptor. In some embodiments, the recombinant receptor is capable of binding to a target antigen that is associated with, specific to, and/or expressed on a cell or tissue of a disease, disorder or condition. In some embodiments, the disease, disorder or condition is an infectious disease or disorder, an autoimmune disease, an inflammatory disease, or a tumor or a cancer. In some embodiments, the target antigen is a tumor antigen.

In some embodiments, the target antigen is selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD138, CD171, epidermal growth factor protein (EGFR), type III epidermal growth factor receptor mutation (EGFR VIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), G Protein Coupled Receptor 5D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22Ra), IL-13 receptor alpha 2 (IL-13Ra2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, mesothelin, c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), vascular endothelial growth factor receptor (VEGFR), vascular endothelial growth factor receptor 2 (VEGFR2), Wilms Tumor 1 (WT-1), a pathogen-specific antigen, or an antigen associated with a universal tag, and/or biotinylated molecules, and/or molecules expressed by HIV, HCV, HBV or other pathogens.

In some embodiments, the recombinant receptor is or comprises a functional non-TCR antigen receptor or a TCR or antigen-binding fragment thereof. In some embodiments, the recombinant receptor is a chimeric antigen receptor (CAR).

In some embodiments, the recombinant receptor comprises an extracellular domain comprising an antigen-binding domain. In some embodiments, the antigen-binding domain is or comprises an antibody or an antibody fragment thereof, which optionally is a single chain fragment. In some embodiments, the fragment comprises antibody variable regions joined by a flexible linker. In some embodiments, wherein the fragment comprises an scFv.

In some embodiments, the recombinant receptor comprises an intracellular signaling region. In some embodiments, the intracellular signaling region comprises an intracellular signaling domain. In some embodiments, the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM). In some embodiments, the intracellular signaling domain is or comprises an intracellular signaling domain of a CD3 chain, optionally a CD3-zeta (CD3ζ) chain, or a signaling portion thereof.

In some embodiments, the recombinant receptor further comprises a transmembrane domain disposed between the extracellular domain and the intracellular signaling region. In some embodiments, the intracellular signaling region further comprises a costimulatory signaling domain. In some embodiments, the costimulatory signaling domain comprises an intracellular signaling domain of a T cell costimulatory molecule or a signaling portion thereof. In some embodiments, the costimulatory signaling domain comprises an intracellular signaling domain of a CD28, a 4-1BB or an ICOS or a signaling portion thereof. In some embodiments, the costimulatory signaling domain is between the transmembrane domain and the intracellular signaling domain.

In some embodiments, the T cells are primary T cells obtained from a subject. In some embodiments, the T cells are autologous to the subject. In some embodiments, the T cells are allogeneic to the subject.

Also provided herein are methods of determining a dose unit of engineered T cells for treating a subject. In some embodiments, the method comprises assessing, in a therapeutic composition comprising a plurality of CD8+ and/or CD4+ T cells engineered to express a recombinant receptor, the number, percentage or ratio of T cells that express the recombinant receptor and CCR7 (receptor+/CCR7+). In some embodiments, the method comprises, based on the number, percentage or ratio of receptor+/CCR7+ cells, determining one or more unit doses of cells for administration to a subject having a disease or conditions, wherein the unit dose comprises a defined number of recombinant receptor-expressing CD8+ T cells that express C—C chemokine receptor type 7 (CCR7) (receptor+/CD8+/CCR7+ cells) and/or a defined number of recombinant receptor-expressing CD4+ T cells that express CCR7 (receptor+/CD4+/CCR7+ cells) and/or a defined ratio of receptor+/CD8+/CCR7+ cells to receptor+/CD4+/CCR7+ cells and/or a defined ratio of receptor+/CD8+/CCR7+ cells and/or receptor+/CD4+/CCR7+ cells to another subset of cells in the composition.

Also provided herein are methods of determining a dose unit of engineered T cells for treating a subject. In some embodiments, the method involves (a) assessing, in a therapeutic composition comprising a plurality of $CD8^+$ and/or $CD4^+$ T cells engineered to express a recombinant receptor, the number, percentage or ratio of T cells that express the recombinant receptor and CD27 (receptor$^+$/CD27$^+$); and (b) based on the number, percentage or ratio of receptor$^+$/CD27$^+$ cells, determining one or more unit doses of cells for administration to a subject having a disease or conditions, wherein the unit dose comprises a defined number of recombinant receptor-expressing $CD8^+$ T cells that express cluster of differentiation 27 (CD27) (receptor$^+$/CD8$^+$/CD27$^+$ cells) and/or a defined number of recombinant receptor-expressing $CD4^+$ T cells that express CD27 (receptor$^+$/CD4$^+$/CD27$^+$ cells) and/or a defined ratio of receptor$^+$/CD8$^+$/CD27$^+$ cells to receptor$^+$/CD4$^+$/CD27$^+$ cells and/or a defined ratio of receptor$^+$/CD8$^+$/CD27$^+$ cells and/or receptor$^+$/CD4$^+$/CD27$^+$ cells to another subset of cells in the composition.

Also provided herein are methods of producing a composition comprising a unit dose of a T cell composition. In some embodiments, the method comprises assessing, in a therapeutic composition comprising a plurality of $CD8^+$ and/or $CD4^+$ T cells engineered to express a recombinant receptor, the number, percentage or ratio of T cells that express the recombinant receptor and CCR7 and CD27 (receptor$^+$/CCR7$^+$/CD27$^+$). In some embodiments, the method comprises filling a container with all or a portion of the composition and optionally another solution to achieve a unit dose of the T cell composition, wherein the unit dose comprises a defined number of recombinant receptor-expressing $CD8^+$ T cells that express C—C chemokine receptor type 7 (CCR7) (receptor$^+$/CD8$^+$/CCR7$^+$ cells) and/or a defined number of recombinant receptor-expressing $CD4^+$ T cells that express CCR7 (receptor$^+$/CD4$^+$/CCR7$^+$ cells) and/or a defined ratio of receptor$^+$/CD8$^+$/CCR7$^+$ cells to receptor$^+$/CD4$^+$/CCR7$^+$ cells and/or a defined ratio of receptor$^+$/CD8$^+$/CCR7$^+$ cells and/or receptor$^+$/CD4$^+$/CCR7$^+$ cells to another subset of cells in the composition. In some embodiments, the method comprises filling a container with all or a portion of the composition and optionally another solution to achieve a unit dose of the T cell composition, wherein the unit dose comprises a defined number of recombinant receptor-expressing $CD8^+$ T cells that express cluster of differentiation 27 (CD27) (receptor$^+$/CD8$^+$/CD27$^+$ cells) and/or a defined number of recombinant receptor-expressing $CD4^+$ T cells that express CD27 (receptor$^+$/CD4$^+$/CD27$^+$ cells) and/or a defined ratio of receptor$^+$/CD8$^+$/CD27$^+$ cells to receptor$^+$/CD4$^+$/CD27$^+$ cells and/or a defined ratio of receptor$^+$/CD8$^+$/CD27$^+$ cells and/or receptor$^+$/CD4$^+$/CD27$^+$ cells to another subset of cells in the composition.

Also provided herein are methods of producing a therapeutic composition comprising a unit dose of a T cell composition. In some embodiments, the method comprises filling a container with all or a portion of a T cell composition, the T cell composition comprising T cells comprising a recombinant receptor that specifically binds an antigen associated with a disease or condition, to achieve a unit dose of the T cell composition, wherein the unit dose comprises a defined number of recombinant receptor-expressing $CD8^+$ T cells that express C—C chemokine receptor type 7 (CCR7) (receptor$^+$/CD8$^+$/CCR7$^+$ cells) and/or a defined number of recombinant receptor-expressing $CD4^+$ T cells that express CCR7 (receptor$^+$/CD4$^+$/CCR7$^+$ cells) and/or a defined ratio of receptor$^+$/CD8$^+$/CCR7$^+$ cells to receptor$^+$/CD4$^+$/CCR7$^+$ cells and/or a defined ratio of receptor$^+$/CD8$^+$/CCR7$^+$ cells and/or receptor$^+$/CD4$^+$/CCR7$^+$ cells to another subset of cells in the composition.

Also provided herein are methods of producing a therapeutic composition comprising a unit dose of a T cell composition. In some embodiments, the method comprises filling a container with all or a portion of a T cell composition, the T cell composition comprising T cells comprising a recombinant receptor that specifically binds an antigen associated with a disease or condition, to achieve a unit dose of the T cell composition, wherein the unit dose comprises a defined number of recombinant receptor-expressing $CD8^+$ T cells that express cluster of differentiation 27 (CD27) (receptor$^+$/CD8$^+$/CD27$^+$ cells) and/or a defined number of recombinant receptor-expressing $CD4^+$ T cells that express CD27 (receptor$^+$/CD4$^+$/CD27$^+$ cells) and/or a defined ratio of receptor$^+$/CD8$^+$/CD27$^+$ cells to receptor$^+$/CD4$^+$/CD27$^+$ cells and/or a defined ratio of receptor$^+$/CD8$^+$/CD27$^+$ cells and/or receptor$^+$/CD4$^+$/CD27$^+$ cells to another subset of cells in the composition.

In some embodiments, the unit dose of cells comprises a defined number of $CD8^+$/CCR7$^+$ cells. In some embodiments, the unit dose of cells comprises a defined number of $CD4^+$/CCR7$^+$ cells.

In some embodiments, the unit dose comprises between at or about $1 \times 10^5$ and at or about $1 \times 10^8$, between at or about $5 \times 10^5$ and at or about $1 \times 10^7$, or between at or about $1 \times 10^6$ and at or about $1 \times 10^7$ total $CD8^+$ cells that express the recombinant receptor (receptor$^+$/CD8$^+$ cells) or total $CD4^+$ cell that express the recombinant receptor (receptor$^+$/CD4$^+$ cells), total receptor$^+$/CD8$^+$/CCR7$^+$ cells, total receptor$^+$/CD4$^+$/CCR7$^+$ cells, total receptor$^+$/CD8$^+$/CD27$^+$ cells, or total receptor$^+$/CD4$^+$/CD27$^+$ cells, each inclusive. In some embodiments, the unit dose comprises no more than about $1 \times 10^8$, no more than about $5 \times 10^7$, no more than about $1 \times 10^7$, no more than about $5 \times 10^6$, no more than about $1 \times 10^6$, or no more than about $5 \times 10^5$ total receptor$^+$/CD8$^+$ cells or total receptor$^+$/CD4$^+$ cells, total receptor$^+$/CD8$^+$/CCR7$^+$ cells, total receptor$^+$/CD4$^+$/CCR7$^+$ cells, total receptor$^+$/CD8$^+$/CD27$^+$ cells, or total receptor$^+$/CD4$^+$/CD27$^+$ cells.

In some embodiments, the unit dose comprises at least about $3 \times 10^6$, $4 \times 10^6$, $5 \times 10^6$, $6 \times 10^6$, $7 \times 10^6$, $8 \times 10^6$, $9 \times 10^6$, or $1 \times 10^7$ total receptor$^+$/CD8$^+$/CCR7$^+$ cells or total receptor$^+$/CD8$^+$/CD27$^+$ cells and/or at least about $3 \times 10^6$, $4 \times 10^6$, $5 \times 10^6$, $6 \times 10^6$, $7 \times 10^6$, $8 \times 10^6$, $9 \times 10^6$, or $1 \times 10^7$ total receptor$^+$/CD4$^+$/CCR7$^+$ cells or total receptor$^+$/CD4$^+$/CD27$^+$. In some embodiments, the unit dose comprises between at or about $3 \times 10^6$ and at or about $2.5 \times 10^7$, between at or about $4 \times 10^6$ and at or about $2 \times 10^7$, or between at or about $5 \times 10^6$ and at or about $1 \times 10^7$ total receptor$^+$/CD8$^+$/CCR7$^+$ cells or total receptor$^+$/CD8$^+$/CD27$^+$ cells and/or between at or about $3 \times 10^6$ and at or about $2.5 \times 10^7$, between at or about $4 \times 10^6$ and at or about $2 \times 10^7$, or between at or about $5 \times 10^6$ and at or about $1 \times 10^7$ total receptor$^+$/CD4$^+$/CCR7$^+$ cells or total receptor$^+$/CD4$^+$/CD27$^+$, each inclusive. In some embodiments, at least 15%, 20%, 30%, 40%, 50%, 60%, 70%, 80% or 90% of the total receptor$^+$ cells in the unit dose, or between about 15% and 90%, between about 20% and 80%, between about 30% and 70%, or between about 40% and 60%, each inclusive, of the total receptor$^+$ cells in the unit dose are receptor$^+$/CD8$^+$/CCR7$^+$ or receptor$^+$/CD8$^+$/CD27$^+$; or at least 15%, 20%, 30%, 40%, 50%, 60%, 70%, 80% or 90% of the total receptor$^+$ cells in the unit dose, or between about 15% and 90%, between about 20% and 80%, between about 30% and 70%, or between about 40% and 60%, each inclusive, of the total receptor$^+$ cells in the unit dose are receptor$^+$/CD4$^+$/CCR7$^+$ or receptor$^+$/CD4$^+$/CD27$^+$.

In some embodiments, the unit dose of cells comprises a defined ratio of receptor$^+$/CD8$^+$/CCR7$^+$ cells to receptor$^+$/CD4$^+$/CCR7$^+$ cells, which ratio optionally is or is approximately 1:1 or is between approximately 1:3 and approximately 3:1.

In some embodiments, the unit dose further comprises a defined number of cells comprising cells that express or do not express CD27 and/or CD45, optionally wherein the unit dose further comprises a defined number of cells comprising CD27$^+$ or CD45RA$^-$ cells.

In some embodiments, the methods further comprise assessing in the therapeutic composition the number, percentage or ratio of T cells that express or do not express CD27 and/or CD45RA, optionally the number, percentage or ratio of T cells that are CD27$^+$ or CD45RA$^-$.

In some embodiments, the unit dose of cells comprises a defined number of receptor$^+$/CD8$^+$/CCR7$^+$/CD27$^+$ cells and/or receptor$^+$/CD8$^+$/CCR7$^+$/CD45RA$^-$ cells. In some embodiments, the unit dose of cells comprises a defined number of receptor$^+$/CD4$^+$/CCR7$^+$/CD27$^+$ cells and/or receptor$^+$/CD4$^+$/CCR7$^+$/CD45RA$^-$ cells.

In some embodiments, at least 15%, 20%, 30%, 40%, 50%, 60%, 70%, 80% or 90% of the total receptor$^+$ cells in the unit dose, or between about 15% and 90%, between about 20% and 80%, between about 30% and 70%, or between about 40% and 60%, each inclusive, of the total receptor$^+$ cells in the unit dose are receptor$^+$/CD8$^+$/CCR7$^+$/CD27$^+$, receptor$^+$/CD8$^+$/CCR7$^+$/CD45RA$^-$, receptor$^+$/CD4$^+$/CCR7$^+$/CD27$^+$ or receptor$^+$/CD4$^+$/CCR7$^+$/CD45RA$^-$.

Also provided herein are methods of determining a unit dose of engineered T cells for treating a subject. In some embodiments, the method comprises assessing, in a therapeutic composition comprising a plurality of CD8$^+$ and/or CD4$^+$ T cells engineered to express a recombinant receptor, the number, percentage or ratio of T cells that express the recombinant receptor and CCR7 and CD27 (receptor$^+$/CCR7$^+$/CD27$^+$). In some embodiments, the method comprises, based on the number, percentage or ratio of receptor$^+$/CCR7$^+$/CD27$^+$ cells, determining one or more unit doses of cells for administration to a subject having a disease or conditions, wherein the unit dose comprises a defined number of recombinant receptor-expressing CD8$^+$ T cells that express CCR7 and CD27 (receptor$^+$/CD8$^+$/CCR7$^+$/CD27$^+$ cells) and/or a defined number of recombinant receptor-expressing CD4$^+$ T cells that express CCR7 and CD27 (receptor$^+$/CD4$^+$/CCR7$^+$/CD27$^+$ cells) and/or a defined ratio of receptor$^+$/CD8$^+$/CCR7$^+$/CD27$^+$ cells to receptor$^+$/CD4$^+$/CCR7$^+$/CD27$^+$ cells and/or a defined ratio of receptor$^+$/CD8$^+$/CCR7$^+$/CD27$^+$ cells and/or receptor$^+$/CD4$^+$/CCR7$^+$/CD27$^+$ cells to another subset of cells in the composition.

Also provided herein are methods of producing a composition comprising a unit dose of a T cell composition. In some embodiments, the method comprises assessing, in a therapeutic composition comprising a plurality of CD8$^+$ and/or CD4$^+$ T cells engineered to express a recombinant receptor, the number, percentage or ratio of T cells that express the recombinant receptor and CCR7 and CD27 (receptor$^+$/CCR7$^+$/CD27$^+$). In some embodiments, the method comprises filling a container with all or a portion of the composition and optionally another solution to achieve a unit dose of the T cell composition, wherein the unit dose comprises a defined number of recombinant receptor-expressing CD8$^+$ T cells that express CCR7 and CD27 (receptor$^+$/CD8$^+$/CCR7$^+$/CD27$^+$ cells) and/or a defined number of recombinant receptor-expressing CD4$^+$ T cells that express CCR7 and CD27 (receptor$^+$/CD4$^+$/CCR7$^+$/CD27$^+$ cells) and/or a defined ratio of receptor$^+$/CD8$^+$/CCR7$^+$/CD27$^+$ cells to receptor$^+$/CD4$^+$/CCR7$^+$/CD27$^+$ cells and/or a defined ratio of receptor$^+$/CD8$^+$/CCR7$^+$/CD27$^+$ cells and/or receptor$^+$/CD4$^+$/CCR7$^+$/CD27$^+$ cells to another subset of cells in the composition.

Also provided herein are methods of producing a therapeutic composition comprising a unit dose of a T cell composition. In some embodiments, the method comprises filling a container with all or a portion of a T cell composition, the T cell composition comprising T cells comprising a recombinant receptor that specifically binds an antigen associated with a disease or condition, to achieve a unit dose of the T cell composition, wherein the unit dose comprises a defined number of recombinant receptor-expressing CD8$^+$ T cells that express CCR7 and CD27 (receptor$^+$/CD8$^+$/CCR7$^+$/CD27$^+$ cells) and/or a defined number of recombinant receptor-expressing CD4$^+$ T cells that express CCR7 and CD27 (receptor$^+$/CD4$^+$/CCR7$^+$/CD27$^+$ cells) and/or a defined ratio of receptor$^+$/CD8$^+$/CCR7$^+$/CD27$^+$ cells to receptor$^+$/CD4$^+$/CCR7$^+$/CD27$^+$ cells and/or a defined ratio of receptor$^+$/CD8$^+$/CCR7$^+$/CD27$^+$ cells and/or receptor$^+$/CD4$^+$/CCR7$^+$/CD27$^+$ cells to another subset of cells in the composition.

In some embodiments, the unit dose of cells comprises a defined number of CD8$^+$/CCR7$^+$/CD27$^+$ cells. In some embodiments, the unit dose of cells comprises a defined number of CD4$^+$/CCR7$^+$/CD27$^+$ cells.

In some embodiments, the unit dose comprises between at or about $1\times10^5$ and at or about $1\times10^8$, between at or about $5\times10^5$ and at or about $1\times10^7$, or between at or about $1\times10^6$ and at or about $1\times10^7$ total CD8$^+$ cells that express the recombinant receptor (receptor$^+$/CD8$^+$ cells) or total CD4$^+$ cell that express the recombinant receptor (receptor$^+$/CD4$^+$ cells), total receptor$^+$/CD8$^+$/CCR7$^+$/CD27$^+$ cells, or total receptor$^+$/CD4$^+$/CCR7$^+$/CD27$^+$ cells, each inclusive. In some embodiments, the unit dose comprises no more than about $1\times10^8$, no more than about $5\times10^7$, no more than about $1\times10^7$, no more than about $5\times10^6$, no more than about $1\times10^6$, or no more than about $5\times10^5$ total receptor$^+$/CD8$^+$ cells or total receptor$^+$/CD4$^+$ cells, total receptor$^+$/CD8$^+$/CCR7$^+$/CD27$^+$ cells, or total receptor$^+$/CD4$^+$/CCR7$^+$/CD27$^+$ cells.

In some embodiments, the unit dose comprises at least about $3\times10^6$, $4\times10^6$, $5\times10^6$, $6\times10^6$, $7\times10^6$, $8\times10^6$, $9\times10^6$, or $1\times10^7$ total receptor$^+$/CD8$^+$/CCR7$^+$/CD27$^+$ cells and/or at least about $3\times10^6$, $4\times10^6$, $5\times10^6$, $6\times10^6$, $7\times10^6$, $8\times10^6$, $9\times10^6$, or $1\times10^7$ total receptor$^+$/CD4$^+$/CCR7$^+$/CD27$^+$ cells. In some embodiments, the unit dose comprises between at or about $3\times10^6$ and at or about $2.5\times10^7$, between at or about $4\times10^6$ and at or about $2\times10^7$, or between at or about $5\times10^6$ and at or about $1\times10^7$ total receptor$^+$/CD8$^+$/CCR7$^+$/CD27$^+$ cells and/or between at or about $3\times10^6$ and at or about $2.5\times10^7$, between at or about $4\times10^6$ and at or about $2\times10^7$, or between at or about $5\times10^6$ and at or about $1\times10^7$ total receptor$^+$/CD4$^+$/CCR7$^+$/CD27$^+$ cells, each inclusive. In some embodiments, at least 15%, 20%, 30%, 40%, 50%, 60%, 70%, 80% or 90% of the total receptor$^+$ cells in the unit dose, or between about 15% and 90%, between about 20% and 80%, between about 30% and 70%, or between about 40% and 60%, each inclusive, of the total receptor$^+$ cells in the unit dose are receptor$^+$/CD8$^+$/CCR7$^+$/CD27$^+$ or receptor$^+$/CD4$^+$/CCR7$^+$/CD27$^+$.

In some embodiments, the unit dose of cells comprises a defined ratio of receptor$^+$/CD8$^+$/CCR7$^+$/CD27$^+$ cells to receptor$^+$/CD4$^+$/CCR7$^+$/CD27$^+$ cells, which ratio optionally is or is approximately 1:1 or is between approximately 1:3 and approximately 3:1.

In some embodiments, the unit dose further comprises a defined number of cells comprising cells that express or do not express CD45, optionally wherein the unit dose further comprises a defined number of cells comprising CD45RA− cells. In some embodiments, the method further comprises assessing in the therapeutic composition the number, percentage or ratio of T cells that express or do not express CD45RA, optionally the number, percentage or ratio of T cells that are CD45RA−.

Also provided are methods for generating a cell composition comprising genetically engineered cells. In some embodiments, the method involves providing, from a biological sample from a subject, an input composition comprising a target percentage of $CD8^+$ T cells that express or do not express CCR7, CD27 and/or CD45RA and/or a target percentage of $CD4^+$ T cells that express or do not express CCR7, CD27 and/or CD45RA. In some embodiments, the method involves introducing, into the input composition, a polynucleotide encoding a recombinant receptor. In some embodiments, the method involves stimulating the cells in the input composition, prior to, during and/or subsequent to said introducing, wherein stimulating comprises incubating the cells in the presence of one or more stimulating agents, said stimulating results in activation and/or proliferation of the cells. In some embodiments, the method produces an output composition comprising a defined ratio of recombinant receptor-expressing (receptor$^+$) $CD8^+$ T cells that express or do not express CCR7, CD27 and/or CD45RA to receptor$^+$/$CD4^+$ T cells that express or do not express CCR7, CD27 and/or CD45RA, and/or a defined ratio of receptor$^+$/$CD8^+$ T cells that express or do not express CCR7, CD27 and/or CD45RA and/or receptor$^+$/$CD4^+$ T cells that express or do not express CCR7, CD27 and/or CD45RA to another subset of cells in the composition.

Also provided are methods for generating a cell composition comprising genetically engineered cells. In some embodiments, the method involves introducing, into an input composition, a polynucleotide encoding a recombinant receptor, wherein the input composition comprises a target percentage of $CD8^+$ T cells that express or do not express CCR7, CD27 and/or CD45RA and/or a target percentage of $CD4^+$ T cells that express or do not express CCR7, CD27 and/or CD45RA provided from a biological sample from a subject, and the input composition is stimulated, prior to, during and/or subsequent to said introducing by incubating the cells in the presence of one or more stimulating agents, said stimulation results in activation and/or proliferation of the cells; and wherein the method produces an output composition comprising a defined ratio of recombinant receptor-expressing (receptor$^+$) $CD8^+$ T cells that express or do not express CCR7, CD27 and/or CD45RA to receptor$^+$/$CD4^+$ T cells that express or do not express CCR7, CD27 and/or CD45RA and/or a defined ratio of receptor$^+$/$CD8^+$ T cells that express or do not express CCR7, CD27 and/or CD45RA and/or receptor$^+$/$CD4^+$ T cells that express or do not express CCR7, CD27 and/or CD45RA to another subset of cells in the composition.

Also provided are methods for generating a cell composition comprising genetically engineered cells. In some embodiments, the method involves isolating, from a biological sample obtained from a subject, a target number of $CD8^+$ T cells that express or do not express CCR7, CD27 and/or CD45RA and/or a target number of $CD4^+$ T cells that express or do not express CCR7, CD27 and/or CD45RA, thereby generating an input composition. In some embodiments, the method involves introducing, into the input composition, a polynucleotide encoding a recombinant receptor. In some embodiments, the method involves stimulating the cells in the input composition, prior to, during and/or subsequent to said introducing, wherein stimulating comprises incubating the cells in the presence of one or more stimulating agents, said stimulating results in activation and/or proliferation of the cells. In some embodiments, the method produces an output composition comprising a defined ratio of recombinant receptor-expressing (receptor$^+$) $CD8^+$ T cells that express or do not express CCR7, CD27 and/or CD45RA to receptor$^+$/$CD4^+$ T cells that express or do not express CCR7, CD27 and/or CD45RA and/or a defined ratio of receptor$^+$/$CD8^+$ T cells that express or do not express CCR7, CD27 and/or CD45RA and/or receptor$^+$/$CD4^+$ T cells that express or do not express CCR7, CD27 and/or CD45RA to another subset of cells in the composition.

Also provided are methods for generating a cell composition comprising genetically engineered cells. In some embodiments, the method involves introducing, into an input composition, a polynucleotide encoding a recombinant receptor, wherein the input composition is generated by isolating, from a biological sample obtained from a subject, a target number of $CD8^+$ T cells that express or do not express CCR7, CD27 and/or CD45RA and/or a target number of $CD4^+$ T cells that express or do not express CCR7, CD27 and/or CD45RA, and the input composition is stimulated, prior to, during and/or subsequent to said introducing by incubating the cells in the presence of one or more stimulating agents, said stimulation results in activation and/or proliferation of the cells; and wherein the method produces an output composition comprising a defined ratio of recombinant receptor-expressing (receptor$^+$) $CD8^+$ T cells that express or do not express CCR7, CD27 and/or CD45RA to receptor$^+$/$CD4^+$ T cells that express or do not express CCR7, CD27 and/or CD45RA and/or a defined ratio of receptor$^+$/$CD8^+$ T cells that express or do not express CCR7, CD27 and/or CD45RA and/or receptor$^+$/$CD4^+$ T cells that express or do not express CCR7, CD27 and/or CD45RA to another subset of cells in the composition.

In some embodiments, the input composition comprises a target percentage of $CD8^+$ T cells that express or do not express CCR7, CD27 and/or CD45RA and/or a target percentage of $CD4^+$ T cells that express or do not express CCR7, CD27 and/or CD45RA.

In some embodiments, the input composition comprises a target percentage of $CD4^+/CCR7^+$, $CD4^+/CD27^+$, $CD4^+/CCR7^+/CD27^+$, $CD4^+/CCR7^+/CD45RA-$, $CD4^+/CCR7^+/CD45RA^+$, $CD8^+/CCR7^+$, $CD8^+/CD27^+$, $CD8^+/CCR7^+/CD27^+$, $CD8^+/CCR7^+/CD45RA-$ and/or $CD8^+/CCR7^+/CD45RA^+$ cells.

In some embodiments, the output composition comprises a defined ratio of receptor$^+$/$CD8^+/CCR7^+$, receptor$^+$/$CD8^+/CD27^+$, receptor$^+$/$CD8^+/CCR7^+/CD27^+$, receptor$^+$/$CD8^+/CCR7^+/CD45RA-$ and/or receptor$^+$/$CD8^+/CCR7^+/CD45RA^+$ cells, to receptor$^+$/$CD4^+/CCR7^+$, receptor$^+$/$CD4^+/CD27^+$, receptor$^+$/$CD4^+/CCR7^+/CD27^+$, receptor$^+$/$CD4^+/CCR7^+/CD45RA-$ and/or receptor$^+$/$CD4^+/CCR7^+/CD45RA^+$ cells; or a defined ratio of receptor$^+$/$CD8^+/CCR7^+$, receptor$^+$/$CD8^+/CD27^+$, receptor$^+$/$CD8^+/CCR7^+/CD27^+$, receptor$^+$/$CD8^+/CCR7^+/CD45RA-$ and/or receptor$^+$/$CD8^+/CCR7^+/CD45RA^+$ cells and/or receptor$^+$/$CD4^+/CCR7^+$, receptor$^+$/$CD4^+/CD27^+$, receptor$^+$/$CD4^+/CCR7^+/CD27^+$, receptor$^+$/$CD4^+/CCR7^+/CD45RA-$ and/or receptor$^+$/$CD4^+/CCR7^+/CD45RA^+$ cells to another subset of cells in the composition.

In some embodiments, the methods also involve determining one or more unit doses of a T cell composition for administration to a subject having a disease or condition, wherein the unit dose comprises all or a portion of the output composition that comprises: a defined number of recombinant receptor-expressing CD8$^+$ T cells that express C—C chemokine receptor type 7 (CCR7) (receptor$^+$/CD8$^+$/CCR7$^+$ cells) and/or a defined number of recombinant receptor-expressing CD4$^+$ T cells that express CCR7 (receptor$^+$/CD4$^+$/CCR7$^+$ cells) and/or a defined ratio of receptor$^+$/CD8$^+$/CCR7$^+$ cells to receptor$^+$/CD4$^+$/CCR7$^+$ cells and/or a defined ratio of receptor$^+$/CD8$^+$/CCR7$^+$ cells and/or receptor$^+$/CD4$^+$/CCR7$^+$ cells to another subset of cells in the composition; a defined number of recombinant receptor-expressing CD8$^+$ T cells that express cluster of differentiation 27 (CD27) (receptor$^+$/CD8$^+$/CD27$^+$ cells) and/or a defined number of recombinant receptor-expressing CD4$^+$ T cells that express CD27 (receptor$^+$/CD4$^+$/CD27$^+$ cells) and/or a defined ratio of receptor$^+$/CD8$^+$/CD27$^+$ cells to receptor$^+$/CD4$^+$/CD27$^+$ cells and/or a defined ratio of receptor$^+$/CD8$^+$/CD27$^+$ cells and/or receptor$^+$/CD4$^+$/CD27$^+$ cells to another subset of cells in the composition; or a defined number of recombinant receptor-expressing CD8$^+$ T cells that express CCR7 and CD27 (receptor$^+$/CD8$^+$/CCR7$^+$/CD27$^+$ cells) and/or a defined number of recombinant receptor-expressing CD4$^+$ T cells that express CCR7 and CD27 (receptor$^+$/CD4$^+$/CCR7$^+$/CD27$^+$ cells) and/or a defined ratio of receptor$^+$/CD8$^+$/CCR7$^+$/CD27$^+$ cells to receptor$^+$/CD4$^+$/CCR7$^+$/CD27$^+$ cells and/or a defined ratio of receptor$^+$/CD8$^+$/CCR7$^+$/CD27$^+$ cells and/or receptor$^+$/CD4$^+$/CCR7$^+$/CD27$^+$ cells to another subset of cells in the composition.

In some embodiments, the unit dose of cells comprises a defined number of CD8$^+$/CCR7$^+$ cells, CD4$^+$/CCR7$^+$ cells, CD8$^+$/CD27$^+$ cells, CD4$^+$/CD27$^+$ cells, CD8$^+$/CCR7$^+$/CD27$^+$ cells and/or CD4$^+$/CCR7$^+$/CD27$^+$ cells.

In some embodiments, the unit dose comprises between at or about $1\times10^5$ and at or about $1\times10^8$, between at or about $5\times10^5$ and at or about $1\times10^7$, or between at or about $1\times10^6$ and at or about $1\times10^7$, each inclusive, total receptor$^+$/CD8$^+$ cells or total receptor$^+$/CD4$^+$ cells, total receptor$^+$/CD8$^+$/CCR7$^+$ cells, total receptor$^+$/CD4$^+$/CCR7$^+$ cells, total receptor$^+$/CD8$^+$/CD27$^+$ cells, total receptor$^+$/CD4$^+$/CD27$^+$ cells, total receptor$^+$/CD8$^+$/CCR7$^+$/CD27$^+$ cells, or total receptor$^+$/CD4$^+$/CCR7$^+$/CD27$^+$ cells.

In some embodiments, the unit dose comprises at least about $3\times10^6$, $4\times10^6$, $5\times10^6$, $6\times10^6$, $7\times10^6$, $8\times10^6$, $9\times10^6$, or $1\times10^7$ total receptor$^+$/CD8$^+$/CCR7$^+$ cells or total receptor$^+$/CD8$^+$/CD27$^+$ cells; and/or at least about $3\times10^6$, $4\times10^6$, $5\times10^6$, $6\times10^6$, $7\times10^6$, $8\times10^6$, $9\times10^6$, or $1\times10^7$ total receptor$^+$/CD4$^+$/CCR7$^+$ cells or total receptor$^+$/CD4$^+$/CD27$^+$; and/or at least about $3\times10^6$, $4\times10^6$, $5\times10^6$, $6\times10^6$, $7\times10^6$, $8\times10^6$, $9\times10^6$, or $1\times10^7$ total receptor$^+$/CD8$^+$/CCR7$^+$/CD27$^+$ cells and/or at least about $3\times10^6$, $4\times10^6$, $5\times10^6$, $6\times10^6$, $7\times10^6$, $8\times10^6$, $9\times10^6$, or $1\times10^7$ total receptor$^+$/CD4$^+$/CCR7$^+$/CD27$^+$ cells.

In some embodiments, the unit dose comprises between at or about $3\times10^6$ and at or about $2.5\times10^7$, between at or about $4\times10^6$ and at or about $2\times10^7$, or between at or about $5\times10^6$ and at or about $1\times10^7$ total receptor$^+$/CD8$^+$/CCR7$^+$ cells or total receptor$^+$/CD8$^+$/CD27$^+$ cells; and/or between at or about $3\times10^6$ and at or about $2.5\times10^7$, between at or about $4\times10^6$ and at or about $2\times10^7$, or between at or about $5\times10^6$ and at or about $1\times10^7$ total receptor$^+$/CD4$^+$/CCR7$^+$ cells or total receptor$^+$/CD4$^+$/CD27$^+$, and/or between at or about $3\times10^6$ and at or about $2.5\times10^7$, between at or about $4\times10^6$ and at or about $2\times10^7$, or between at or about $5\times10^6$ and at or about $1\times10^7$ total receptor$^+$/CD8$^+$/CCR7$^+$/CD27$^+$ cells and/or between at or about $3\times10^6$ and at or about $2.5\times10^7$, between at or about $4\times10^6$ and at or about $2\times10^7$, or between at or about $5\times10^6$ and at or about $1\times10^7$ total receptor$^+$/CD4$^+$/CCR7$^+$/CD27$^+$ cells, each inclusive.

In some embodiments, at least 15%, 20%, 30%, 40%, 50%, 60%, 70%, 80% or 90% of the total receptor$^+$ cells in the unit dose, or between about 15% and 90%, between about 20% and 80%, between about 30% and 70%, or between about 40% and 60%, each inclusive, of the total receptor$^+$ cells in the unit dose are receptor$^+$/CD8$^+$/CCR7$^+$ or receptor$^+$/CD8$^+$/CD27$^+$; and/or at least 15%, 20%, 30%, 40%, 50%, 60%, 70%, 80% or 90% of the total receptor$^+$ cells in the unit dose, or between about 15% and 90%, between about 20% and 80%, between about 30% and 70%, or between about 40% and 60%, each inclusive, of the total receptor$^+$ cells in the unit dose are receptor$^+$/CD4$^+$/CCR7$^+$ or receptor$^+$/CD4$^+$/CD27$^+$; and/or at least 15%, 20%, 30%, 40%, 50%, 60%, 70%, 80% or 90% of the total receptor$^+$ cells in the unit dose, or between about 15% and 90%, between about 20% and 80%, between about 30% and 70%, or between about 40% and 60%, each inclusive, of the total receptor$^+$ cells in the unit dose are receptor$^+$/CD8$^+$/CCR7$^+$/CD27$^+$ or receptor$^+$/CD4$^+$/CCR7$^+$/CD27$^+$.

In some embodiments, the unit dose of cells comprises a defined ratio of receptor$^+$/CD8$^+$/CCR7$^+$ cells to receptor$^+$/CD4$^+$/CCR7$^+$ cells, which ratio optionally is or is approximately 1:1 or is between approximately 1:3 and approximately 3:1; and/or a defined ratio of receptor$^+$/CD8$^+$/CD27$^+$ cells to receptor$^+$/CD4$^+$/CD27$^+$ cells, which ratio optionally is or is approximately 1:1 or is between approximately 1:3 and approximately 3:1; and/or a defined ratio of receptor$^+$/CD8$^+$/CCR7$^+$/CD27$^+$ cells to receptor$^+$/CD4$^+$/CCR7$^+$/CD27$^+$ cells, which ratio optionally is or is approximately 1:1 or is between approximately 1:3 and approximately 3:1.

In some embodiments, the unit dose further comprises a defined number of cells comprising cells that express or do not express CD45, optionally wherein the unit dose further comprises a defined number of cells comprising CD45RA− cells. In some embodiments, the unit dose of cells comprises a defined number of receptor$^+$/CD4$^+$/CCR7$^+$/CD45RA− cells and/or receptor$^+$/CD8$^+$/CCR7$^+$/CD45RA− cells.

In some embodiments, at least 15%, 20%, 30%, 40%, 50%, 60%, 70%, 80% or 90% of the total receptor$^+$ cells in the unit dose, or between about 15% and 90%, between about 20% and 80%, between about 30% and 70%, or between about 40% and 60%, each inclusive, of the total receptor$^+$ cells in the unit dose are receptor$^+$/CD4$^+$/CCR7$^+$/CD45RA− or receptor$^+$/CD8$^+$/CCR7$^+$/CD45RA−.

In some embodiments, the methods further comprise, prior to the providing or isolating, determining the number, number per volume, number per weight, and/or percentage of the CD8$^+$ T cells that express or do not express CCR7, CD27 and/or CD45RA and/or CD4$^+$ T cells that express or do not express CCR7, CD27 and/or CD45RA.

In some embodiments, the one or more stimulating agent is capable of activating T cells, CD4$^+$ T cells and/or CD8$^+$ T cells; is capable of inducing a signal through a TCR complex; and/or is capable of inducing proliferation of T cells, CD4$^+$ T cells and/or CD8$^+$ T cells.

In some embodiments, the one or more stimulating agent comprises a primary agent that binds to a member of a TCR complex, optionally that specifically binds to CD3. In some embodiments, the one or more stimulating agent further comprises a secondary agent that specifically binds to a T cell costimulatory molecule. In some embodiments, the costimulatory molecule is selected from the group consisting of CD28, CD137 (4-1-BB), OX40, or ICOS. In some embodiments, the primary and secondary agents comprise antibodies, optionally wherein the one or more stimulating agent comprises incubation with an anti-CD3 antibody and an anti-CD28 antibody. In some embodiments, the one or more stimulating agents are present on the surface of a solid support, optionally a bead. In some embodiments, the one or more stimulating agent is selected from the group consisting of CD3-binding molecules; CD28-binding molecules; recombinant IL-2; recombinant IL-15; and recombinant IL-7, a vaccine comprising an antigen specifically recognized by the antigen receptor, and an anti-idiotype antibody that specifically binds the antigen receptor or combinations thereof.

In some embodiments, the therapeutic composition is any of the compositions described herein.

In some embodiments, the method further comprises administering to a subject having a disease or condition, the therapeutic composition, optionally one or more unit doses thereof and/or a volume corresponding to such one or more of the unit doses.

In some embodiments, among a group of subjects treated according to the method, the number or ratio of cells that express CCR7 (CCR7$^+$ cells) in the unit dose varies by no more than 40%, by no more than 30%, by no more than 20%, by no more than 10% or by no more than 5%.

In some embodiments, the unit dose comprises between at or about $1\times10^5$ and at or about $5\times10^8$, between at or about $1\times10^5$ and at or about $1\times10^8$, between at or about $5\times10^5$ and at or about $1\times10^7$, or between at or about $1\times10^6$ and at or about $1\times10^7$ total CD3$^+$ cells that express the recombinant receptor (receptor$^+$/CD3$^+$ cells) or total CD3$^+$ cells, each inclusive. In some embodiments, the unit dose comprises no more than about $5\times10^8$, no more than about $1\times10^8$, no more than about $5\times10^7$, no more than about $1\times10^7$, no more than about $5\times10^6$, no more than about $1\times10^6$, or no more than about $5\times10^5$ total receptor$^+$/CD3$^+$ cells or total CD3$^+$ cells.

In some embodiments, the total number of CD3$^+$ cells, total number of receptor$^+$/CD3$^+$ cells, total number of receptor$^+$/CD8$^+$ cells, total number of receptor$^+$/CD4$^+$ cells, total number of receptor$^+$/CD8$^+$/CCR7$^+$ cells, total number of receptor$^+$/CD4$^+$/CCR7$^+$ cells, total number of receptor$^+$/CD8$^+$/CD27$^+$ cells, total number of receptor$^+$/CD4$^+$/CD27$^+$ cells, total number of receptor$^+$/CD8$^+$/CCR7$^+$/CD27$^+$ cells, total number of receptor$^+$/CD4$^+$/CCR7$^+$/CD27$^+$ cells, total number of receptor$^+$/CD8$^+$/CCR7$^+$/CD45RA$^-$ cells and/or receptor$^+$/CD4$^+$/CCR7$^+$/CD45RA$^-$ cells is the total number of such cells that are live or viable. In some embodiments, the total number of CD3$^+$ cells, total number of receptor$^+$/CD3$^+$ cells, total number of receptor$^+$/CD8$^+$ cells, total number of receptor$^+$/CD4$^+$ cells, total number of receptor$^+$/CD8$^+$/CCR7$^+$ cells, total number of receptor$^+$/CD4$^+$/CCR7$^+$ cells, total number of receptor$^+$/CD8$^+$/CD27$^+$ cells, total number of receptor$^+$/CD4$^+$/CD27$^+$ cells, total number of receptor$^+$/CD8$^+$/CCR7$^+$/CD27$^+$ cells, total number of receptor$^+$/CD4$^+$/CCR7$^+$/CD27$^+$ cells, total number of receptor$^+$/CD8$^+$/CCR7$^+$/CD45RA$^-$ cells and/or receptor$^+$/CD4$^+$/CCR7$^+$/CD45RA$^-$ cells is the total number of such cells that do not express an apoptotic marker and/or is the total number of such cells that are apoptotic marker negative (−), wherein the apoptotic marker is Annexin V or activated Caspase 3.

In some embodiments, the method involves administering a plurality of unit doses contained in a plurality of separate compositions.

In some embodiments, the plurality of separate compositions comprise a first composition comprising one of the CD8$^+$ T cells and the CD4$^+$ T cells and a second composition comprising the other of the CD8$^+$ T cells and the CD4$^+$ T cells. In some embodiments, the first composition comprises the CD8$^+$ T cells. In some embodiments, the first composition comprises the CD4$^+$ T cells.

In some embodiments, the method involves administering the composition containing CD8$^+$ T cells or one or more unit doses thereof and/or a volume corresponding to such one or more of unit doses and the composition containing CD4$^+$ T cells or one or more unit doses thereof and/or a volume corresponding to such one or more of unit doses, no more than 2 hours, no more than 1 hour, no more than 30 minutes, no more than 15 minutes, no more than 10 minutes or no more than 5 minutes apart or simultaneously.

In some embodiments, the method involves administering the composition containing CD8$^+$ T cells or one or more unit doses thereof and/or a volume corresponding to such one or more of unit doses, prior to administering the composition containing CD4$^+$ cells or one or more unit doses thereof and/or a volume corresponding to such one or more of the unit doses. In some embodiments, the method involves administering the composition containing CD4$^+$ T cells or one or more unit doses thereof and/or a volume corresponding to such one or more of unit doses, prior to administering the composition containing CD8$^+$ cells or one or more unit doses thereof and/or a volume corresponding to such one or more of unit doses.

In some embodiments, the recombinant receptor is or comprises a chimeric receptor and/or a recombinant antigen receptor. In some embodiments, the recombinant receptor is capable of binding to a target antigen that is associated with, specific to, and/or expressed on a cell or tissue of a disease, disorder or condition. In some embodiments, the disease, disorder or condition is an infectious disease or disorder, an autoimmune disease, an inflammatory disease, or a tumor or a cancer. In some embodiments, the target antigen is a tumor antigen.

In some embodiments, the target antigen is selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD138, CD171, epidermal growth factor protein (EGFR), type III epidermal growth factor receptor mutation (EGFR viii), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), G Protein Coupled Receptor 5D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22Ra), IL-13 receptor alpha 2 (IL-13Ra2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, mesothelin, c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), vascular endothelial growth factor receptor (VEGFR), vascular endothelial growth factor receptor 2 (VEGFR2), Wilms Tumor 1 (WT-1), a pathogen-specific antigen, or an antigen associated with a universal tag, and/or biotinylated molecules, and/or molecules expressed by HIV, HCV, HBV or other pathogens.

In some embodiments, the recombinant receptor is or comprises a functional non-TCR antigen receptor or a TCR or antigen-binding fragment thereof. In some embodiments, the recombinant receptor is a chimeric antigen receptor (CAR). In some embodiments, the recombinant receptor comprises an extracellular domain comprising an antigen-binding domain. In some embodiments, the antigen-binding domain is or comprises an antibody or an antibody fragment thereof, which optionally is a single chain fragment. In some embodiments, the fragment comprises antibody variable regions joined by a flexible linker. In some embodiments, the fragment comprises an scFv.

In some embodiments, the recombinant receptor comprises an intracellular signaling region. In some embodiments, the intracellular signaling region comprises an intracellular signaling domain. In some embodiments, the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM). In some embodiments, the intracellular signaling domain is or comprises an intracellular signaling domain of a CD3 chain, optionally a CD3-zeta (CD3ζ) chain, or a signaling portion thereof.

In some embodiments, the recombinant receptor further comprises a transmembrane domain disposed between the extracellular domain and the intracellular signaling region.

In some embodiments, the intracellular signaling region further comprises a costimulatory signaling domain. In some embodiments, the costimulatory signaling domain comprises an intracellular signaling domain of a T cell costimulatory molecule or a signaling portion thereof. In some embodiments, the costimulatory signaling domain comprises an intracellular signaling domain of a CD28, a 4-1BB or an ICOS or a signaling portion thereof. In some embodiments, the costimulatory signaling domain is between the transmembrane domain and the intracellular signaling domain.

In some embodiments, the T cells are primary T cells obtained from a subject. In some embodiments, the T cells are autologous to the subject. In some embodiments, the T cells are allogeneic to the subject.

In some aspects of any of the embodiments provided herein, the cells in a provided therapeutic composition or a unit dose are associated with certain functional attributes, including certain recombinant receptor (e.g. CAR)-dependent activities that depend on an activity or presence of the recombinant receptor, e.g. an activity induced or mediated in the presence of antigen recognized by the recombinant receptor. In some embodiments, a functional attribute includes production of higher levels of a cytokine, e.g., IL-2. In some aspects of any of the embodiments provided herein, the functional attribute includes production of lower levels of a cytokine, e.g., IFNγ or IL-13. In some embodiments, the higher or lower levels of such cytokines are with reference to a reference composition in which is contained a non-defined number of cells of a particular phenotype and/or in which cells of a particular phenotype are not at a particular defined ratio according to embodiments provided herein. In some embodiments, a reference composition is one in which is contained a greater frequency or number of T cells having an effector or differentiated phenotype.

In some aspects, upon administration of a therapeutic composition or a unit dose to one of a group of subjects according to any of the embodiments provided herein, a plurality of subjects among the group of subjects exhibits one or more features associated with increased efficacy, persistence and/or reduced toxicity following the administration. In some embodiments, a plurality of subjects among the group of subjects is likely to exhibit and/or is associated with, pharmacokinetic parameters, reduced likelihood of development of a toxicity or an adverse event, and/or a particular response, efficacy or survival outcome. In some embodiments, the subject is a subject suspected of having a disease or condition. In some embodiments, the one or more features are improved compared to a similar group of subjects treated with the reference composition in which is contained a non-defined number of cells of a particular phenotype and/or in which cells of a particular phenotype are not at a particular defined ratio according to embodiments provided herein. In some embodiments, a reference composition is one in which is contained a greater frequency or number of T cells having an effector or differentiated phenotype.

In some aspects, upon administration of a therapeutic composition or a unit dose to one of a group of subjects according to any of the embodiments provided herein, a plurality of subjects among the group of subjects is likely to exhibit and/or is associated with particular pharmacokinetic parameters, such as maximum (peak) plasma concentration ($C_{max}$), the peak time (i.e. when maximum plasma concentration ($C_{max}$) occurs; $T_{max}$), the minimum plasma concentration (i.e. the minimum plasma concentration between doses of a therapeutic agent, e.g., CAR$^+$ T cells; $C_{min}$), the elimination half-life ($T_{1⁄2}$) and area under the curve (i.e. the area under the curve generated by plotting time versus plasma concentration of the therapeutic agent CAR$^+$ T cells; AUC). In some aspects, upon administration of a therapeutic composition or a unit dose, a plurality of subjects among the group is likely to exhibit or is associated with increased maximum (peak) plasma concentration ($C_{max}$) of the administered cells. In some embodiments, long term persistence of cells of the therapeutic composition or unit dose are observed in a plurality of subjects among the group.

In some aspects, upon administration of a therapeutic composition or a unit dose to one of a group of subjects according to any of the embodiments provided herein, a plurality of subjects among the group of subjects is likely to exhibit and/or is associated with a reduced likelihood of development of a toxicity or an adverse event, such as cytokine release syndrome (CRS) or severe CRS (sCRS) or neurotoxicity (NT) or severe NT (sNT).

In some aspects, upon administration of a therapeutic composition or a unit dose to one of a group of subjects according to any of the embodiments provided herein, a plurality of subjects among the group of subjects is likely to exhibit and/or is associated with a particular response, efficacy or survival outcome, such as partial response (PR) or partial remission, complete response (CR) or complete remission, progression-free survival (PFS), objective response (OR), overall survival (OS), event-free survival (EFS), increased duration of response (DOR) or increased survival rate. In some aspects, upon administration of a therapeutic composition or a unit dose, a plurality of subjects among the group is likely to exhibit or is associated with increased progression-free survival (PFS).

In some embodiments of any of the provided embodiments, the methods and/or uses and/or administration of a unit dose of cells according to the articles of manufacture, achieve certain outcomes and/or are associated with certain reduced risks of toxicity, e.g., in the population of subjects treated according to the methods or according to information provided in the article of manufacture. In some aspects, at least 35%, at least 40% at least 50%, or at least 60%, of subjects treated according to the method achieve a complete response (CR) or complete remission, progression-free survival (PFS), objective response (OR), overall survival (OS), event-free survival (EFS), or a response that is durable for greater than 3 months, greater than 6 months or greater than 12 months. In certain embodiments of any of the provided methods, greater than or greater than about 50% of the subjects treated according to the method do not exhibit a grade 3 or greater cytokine release syndrome (CRS) or a grade 3 or greater neurotoxicity. In some embodiments, such subjects do not exhibit early onset CRS and/or neurotoxicity, such as do not exhibit onset of CRS earlier than 3 days following initiation of the administration and/or do not exhibit onset of neurotoxicity earlier than 5 days following initiation of the administration. In some embodiments of any of the provided methods, greater than or greater than about 30%, 35%, 40%, or 50% of the subjects treated according to the method do not exhibit any grade of cytokine release syndrome (CRS) or neurotoxicity.

Also provided are output compositions produced by any of the methods described herein.

Also provided are unit doses determined or produced by any of the methods described herein.

Also provided are pharmaceutical compositions comprising any of the unit doses described herein. In some embodiments, the pharmaceutical compositions also include a pharmaceutical carrier.

Also provided are methods of treatment, comprising administering to a mammalian subject all or a portion of any of the output compositions, unit doses or pharmaceutical compositions described herein.

Also provided are uses of all or a portion of any of the output compositions, unit doses or pharmaceutical compositions described herein for treating cancer.

Also provided are uses of all or a portion of any of the output compositions, unit doses or pharmaceutical compositions described herein in the manufacture of a medicament for treating cancer.

Also provided are all or a portion of any of the output compositions, unit doses or pharmaceutical compositions described herein for use in treating cancer.

Provided herein are therapeutic cell compositions containing T cells expressing a recombinant receptor that binds to an antigen, wherein, following stimulation with a stimulatory agent: at least at or about, or at or about, 70%, 80%, 85%, 90%, 91%, 92%, 93%, 94%, 95%, 96%, 97%, 98%, 99% or 100% of the total number of CD4+ T cells in the composition expressing the recombinant receptor are able to produce a cytokine selected from interleukin 2 (IL-2) and/or TNF-alpha; and/or at least at or about, or at or about, 10%, 15%, 20%, 25%, 30%, 40%, 50%, 60% or more of the total number of CD4+ T cells in the composition expressing the recombinant receptor are polyfunctional for producing two or more cytokines selected from among interferon-gamma (IFN-gamma), interleukin 2 (IL-2) and TNF-alpha. In some embodiments, at least at or about, or at or about, 70%, 80%, 85%, 90%, 91%, 92%, 93%, 94%, 95%, 96%, 97%, 98%, 99% or 100% of the total number of CD4+ T cells in the composition expressing the recombinant receptor are able to produce a cytokine selected from interleukin 2 (IL-2) and/or TNF-alpha. In some embodiments, at least at or about, or at or about, 10%, 15%, 20%, 25%, 30%, 40%, 50%, 60% or more of the total number of CD4+ T cells in the composition expressing the recombinant receptor are polyfunctional for producing two or more cytokines selected from among interferon-gamma (IFN-gamma), interleukin 2 (IL-2) and TNF-alpha. In some embodiments, at least at or about, or at or about, 10%, 15%, 20%, 25%, 30%, 40%, 50%, 60% or more of the total number of CD4+ T cells in the composition expressing the recombinant receptor are polyfunctional for producing the cytokines interferon-gamma (IFN-gamma), interleukin 2 (IL-2) and TNF-alpha.

In some embodiments, the stimulatory agent is a non-specific or non-antigen-dependent T cell stimulatory agent. In some embodiments, the non-specific or non-antigen dependent T cell stimulatory agent is a polyclonal stimulatory agent. In some embodiments, the non-specific or non-antigen dependent stimulatory agent comprises PMA/ionomycin, anti-CD3/anti-CD28, phytohemagglutinin (PHA) or concanavalin A (ConA). In some embodiments, the non-specific or non-antigen dependent T cell stimulatory agent comprises PMA/ionomycin. In some embodiments, the stimulatory agent specifically binds the recombinant receptor, optionally wherein the stimulatory agent is an antigen-specific stimulatory reagent and/or contains the antigen or a portion thereof specifically recognized by the recombinant receptor. In some embodiments, production of the cytokines is measured in an intracellular cytokine assay.

In some embodiments, the composition contains at least at or about, or at or about, 40%, 50%, 60%, 70%, 80%, 85%, 90%, 91%, 92%, 93%, 94%, 95%, 96%, 97%, 98%, 99% or 100% of the total number of T cells in the composition or of the total number of T cells in the composition expressing the recombinant receptor, are surface positive for CCR7 and/or CD27, optionally further negative for surface expression of CD45RA.

In some embodiments, the T cells are primary cells obtained from a subject. In some embodiments, the subject has a cancer, optionally wherein the cancer is a leukemia or a lymphoma. In some embodiments, the subject is a subject that, at the time of obtaining the cells, is identified or known to have a high tumor burden. In some embodiments, the subject has high tumor burden if a sum of product dimensions (SPD) of a tumor in the subject is above at or about 30 $cm^2$, 40 $cm^2$, 50 $cm^2$, 60 $cm^2$ or 70 $cm^2$; and/or the subject has high tumor burden if C reactive protein (CRP) in a biological sample, optionally a serum sample, from the subject is above at or about 5 miligrams per liter, 10 miligrams per liter, 15 miligrams per liter, 20 miligrams per liter, 25 miligrams per liter, 30 miligrams per liter, 40 miligrams per liter or 50 miligrams per liter. In some embodiments, the subject has high tumor burden if the SPD of a tumor in the subject is above at or about 50 $cm^2$. In some embodiments, the subject has high tumor burden if the CRP is above at or about 20 miligrams per liter in the biological sample.

In some embodiments, the therapeutic cell composition is enriched in CD4+ T cells and/or at least at or about 60%, at least at or about 70%, at least at or about 80%, at least at or about 90%, at least at or about 95%, at least at or about 97% of the total recombinant receptor+ cells in the engineered composition, or between about 60% and 99%, between about 75% and 99%, between about 85% and 99%, or between about 90% and 99%, each inclusive, of the total cells in the composition are CD4+. In some embodiments, the therapeutic cell composition is enriched in CD3+ T cell, is enriched in CD4+ and CD8+ T cells and/or at least at or about 60%, at least at or about 70%, at least at or about 80%, at least at or about 90%, at least at or about 95%, at least at or about 97% of the total recombinant receptor+ cells in the engineered composition, or between about 60% and 99%, between about 75% and 99%, between about 85% and 99%, or between about 90% and 99%, each inclusive, of the total cells in the composition are CD3+ or CD4+ and CD8+. In some embodiments, the therapeutic cell composition contains CD4+ and CD8+ T cells at a ratio of CD4+ to CD8+ T cells that is between approximately 1:3 and approximately 3:1, optionally between approximately 1:2 and 2:1.

In some embodiments, the recombinant receptor is or contains a chimeric receptor and/or a recombinant antigen receptor. In some embodiments, the recombinant receptor is capable of binding to a target antigen that is associated with, specific to, and/or expressed on a cell or tissue of a disease, disorder or condition. In some embodiments, the disease, disorder or condition is an infectious disease or disorder, an autoimmune disease, an inflammatory disease, or a tumor or a cancer. In some embodiments, the target antigen is a tumor antigen. In some embodiments, the target antigen is selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22Ra), IL-13 receptor alpha 2 (IL-13Ra2), kinase insert domain receptor (kdr), kappa light chain, L1 cell adhesion molecule (L1-CAM), CE7 epitope of L-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens.

In some embodiments, the recombinant receptor is or contains a functional non-TCR antigen receptor or a TCR or antigen-binding fragment thereof. In some embodiments, the recombinant receptor is a chimeric antigen receptor (CAR). In some embodiments, the recombinant receptor contains an extracellular domain containing an antigen-binding domain and an intracellular signaling region containing an intracellular signaling domain. In some embodiments, the antigen-binding domain is or contains an antibody or an antibody fragment thereof, which optionally is a single chain fragment. In some embodiments, the fragment contains antibody variable regions joined by a flexible linker. In some embodiments, the fragment comprises an scFv. In some embodiments, the intracellular signaling domain is or contains a primary signaling domain, a signaling domain that is capable of inducing a primary activation signal in a T cell, a signaling domain of a T cell receptor (TCR) component, and/or a signaling domain containing an immunoreceptor tyrosine-based activation motif (ITAM). In some embodiments, the intracellular signaling domain is or contains an intracellular signaling domain of a CD3 chain, optionally a CD3-zeta (CD3ζ) chain, or a signaling portion thereof. In some embodiments, the recombinant receptor further contains a transmembrane domain disposed between the extracellular domain and the intracellular signaling region. In some embodiments, the intracellular signaling region further contains a costimulatory signaling domain. In some embodiments, the costimulatory signaling domain contains an intracellular signaling domain of a T cell costimulatory molecule or a signaling portion thereof. In some embodiments, the costimulatory signaling domain contains an intracellular signaling domain of a CD28, a 4-1BB or an ICOS or a signaling portion thereof. In some embodiments, the costimulatory signaling domain is between the transmembrane domain and the intracellular signaling domain.

In some embodiments, the T cells are primary T cells obtained from a subject. In some embodiments, the T cells are autologous to the subject.

Provided herein are articles of manufacture, including a container containing a therapeutic cell composition described herein, and instructions for administering to a subject having a disease or condition, the therapeutic cell composition, optionally one or more unit doses thereof and/or a volume corresponding to such one or more unit doses. In some embodiments, the instructions specify administering a plurality of unit doses contained in a plurality of separate compositions. In some embodiments, the plurality of separate compositions contain a first composition containing the therapeutic cell composition containing one of CD8+ T cells and CD4+ T cells and a second composition containing the other of the CD8+ T cells and the CD4+ T cells, said second composition containing cells expressing the recombinant receptor or a recombinant receptor specific for the antigen or for a cell expressed by the disease or condition optionally wherein the second composition is any composition described herein. In some embodiments, the instructions specify administering the composition containing CD8+ T cells or one or more unit doses thereof and/or a volume corresponding to such one or more of unit doses and the composition containing CD4⁺ T cells or one or more unit doses thereof and/or a volume corresponding to such one or more of unit doses within no more than 48 hours apart, within no more than 36 hours apart, within no more than 24 hours apart, within no more than 12 hours apart, within no more than 6 hours apart, within no more than 2 hours apart, within no more than 1 hour apart or simultaneously. In some embodiments, the instructions specify administering the composition containing CD8⁺ T cells or one or more unit doses thereof and/or a volume corresponding to such one or more of unit doses, prior to administering the composition containing CD4⁺ cells or one or more unit doses thereof and/or a volume corresponding to such one or more of unit doses.

Provided herein are methods of treatment, the method including administering to a subject having a disease or condition one or more unit doses of a therapeutic cell composition described herein. In some embodiments, the therapeutic composition is a first therapeutic cell composition containing one of CD8+ T cells and CD4+ T cells and the one or more units doses further contains a second therapeutic cell composition containing the other of the CD8+ T cells and CD4+ cells, said second composition containing cells expressing the recombinant receptor or a recombinant receptor specific for the antigen or for a cell expressed by the disease or condition, optionally wherein the second composition is any composition described herein.

In some embodiments, at least at or about, or at or about, 40%, 50%, 60%, 70%, 80%, 85%, 90%, 91%, 92%, 93%, 94%, 95%, 96%, 97%, 98%, 99% or 100% of the total number of T cells in the second therapeutic cell composition or of the total number of T cells in the composition expressing the recombinant receptor, are surface positive for CCR7 and/or CD27, optionally further negative for surface expression of CD45RA. In some embodiments, the second therapeutic cell composition is enriched in CD8+ T cells and/or at least at or about 60%, at least at or about 70%, at least at or about 80%, at least at or about 90%, at least at or about 95%, at least at or about 97% of the total recombinant receptor⁺ cells in the engineered composition, or between about 60% and 99%, between about 75% and 99%, between about 85% and 99%, or between about 90% and 99%, each inclusive, of the total cells in the composition are CD8⁺.

In some embodiments, the first therapeutic composition and second therapeutic composition are administered within at or about 48 hours, within at or about 36 hours, within at or about 24 hours, within at or about 12 hours, within at or about 6 hours, within at or about 2 hours or within at or about 1 hour of each other. In some embodiments, the second therapeutic cell composition containing the CD8+ T cells is administered before the first composition containing CD4+ T cells. In some embodiments, the one or more unit dose of cells contains a defined ratio of CD4+ to CD8+ T cells, which ratio is or is approximately 1:3 and approximately 3:1, optionally that is or is approximately 1:2 and 2:1, optionally that is or is about 1:1.

Provided herein are methods for treatment of a subject, the method including (A) assaying an engineered cell composition containing T cells expressing a recombinant receptor for a factor indicative of the function or phenotype of engineered cells in the composition, the factor selected from (i) the percentage of T cells expressing the recombinant receptor that are surface positive for CCR7 and/or CD27, and optionally surface negative for CD45RA; and/or (ii) the percentage of CD4+ T cells expressing the recombinant receptor that are able to produce IL-2, TNF-alpha, and/or IFN-gamma following stimulation with a stimulatory agent; and (B) administering to a subject having a disease or condition a therapy, the administering selected from: (1) if a factor indicative of the function or phenotype of cells of the engineered T cell composition is at or above a threshold value, administering to the subject one or more unit doses of cells of an engineered cell composition containing T cells expressing a recombinant receptor; or (2) if the factor indicative of the function or phenotype of cells of the engineered T cell composition is below a threshold value of the factor, administering a therapy selected from (a) one or more unit doses of cells of the engineered cell composition and an agent capable of increasing expansion, proliferation or efficacy of T cells of the engineered cell composition in the subject, (b) an increased dose of cells of the engineered cell composition, optionally increased compared to the one or more unit dose administered to a similarly situated subject having the same disease or condition but exhibiting the threshold value of the factor or greater; or (c) an alternative therapeutic treatment for treating the disease or condition other than one or more unit doses of the engineered cell composition, wherein the threshold value of the factor is selected from (i) at or about 40%, 50%, 60%, 70%, 80%, 85%, 90%, 91%, 92%, 93%, 94%, 95%, 96%, 97%, 98%, 99% or 100% of the total number of T cells in the composition or of the total number of T cells in the composition expressing the recombinant receptor, are surface positive for CCR7 and/or CD27; and/or (ii) at or about 70%, 80%, 85%, 90%, 91%, 92%, 93%, 94%, 95%, 96%, 97%, 98%, 99% or 100% of the total number of CD4+ T cells in the composition expressing the recombinant receptor are able to produce interleukin 2 (IL-2) or TNF-alpha following stimulation with a stimulatory agent; and/or (iii) at or about 10%, 15%, 20%, 25%, 30%, 40%, 50%, 60% or more of the total number of CD4+ T cells in the composition expressing the recombinant receptor are polyfunctional for producing two or more cytokines selected from among interferon-gamma (IFN-gamma), interleukin 2 (IL-2) and TNF-alpha following stimulation with a stimulatory agent.

Provided herein are methods for treatment of a subject, the methods including administering to a subject having a disease or condition a therapy, the administering selected from: (1) if a factor indicative of a function or phenotype of cells of an engineered cell composition containing T cells expressing a recombinant receptor is at or above a threshold value, administering to the subject one or more unit doses of cells of the engineered T cell composition; or (2) if the factor indicative of the function or phenotype of cells of the engineered T cell composition is below a threshold value of the factor, administering a therapy selected from (a) one or more unit doses of cells of the engineered cell composition and an agent capable of increasing expansion, proliferation or efficacy of T cells of the engineered cell composition in the subject, (b) an increased dose of cells of the engineered cell composition, optionally increased compared to the one or more unit doses administered to a similarly situated subject having the same disease or condition but exhibiting the threshold value of the factor or greater; or (c) an alternative therapeutic treatment for treating the disease or condition other than a dose of the engineered cell composition, wherein the threshold value of the factor is selected from (i) at or about 40%, 50%, 60%, 70%, 80%, 85%, 90%, 91%, 92%, 93%, 94%, 95%, 96%, 97%, 98%, 99% or 100% of the total number of T cells in the composition or of the total number of T cells in the composition expressing the recombinant receptor, are surface positive for CCR7 and/or CD27; and/or (ii) at or about 70%, 80%, 85%, 90%, 91%, 92%, 93%, 94%, 95%, 96%, 97%, 98%, 99% or 100% of the total number of CD4+ T cells in the composition expressing the recombinant receptor are able to produce interleukin 2 (IL-2) or TNF-alpha following stimulation with a stimulatory agent; and/or (iii) at or about 10%, 15%, 20%, 25%, 30%, 40%, 50%, 60% or more of the total number of CD4+ T cells in the composition expressing the recombinant receptor are polyfunctional for producing two or more cytokines selected from among interferon-gamma (IFN-gamma), interleukin 2 (IL-2) and TNF-alpha following stimulation with a stimulatory agent.

In some embodiments, cells of the cell composition are autologous to the subject. In some embodiments, at least 35%, at least 40%, at least 50%, at least 60% or at least 70%, or at least 75% of the subjects treated according to the method achieve progression free survival for at least 3 months, at least 4 months, at least 5 months, at least 6 months, at least 9 months or at least 12 months following administration of the one or more unit doses. In some embodiments, at least 35%, at least 40%, at least 50%, at least 60% or at least 70%, or at least 75% of the subjects treated according to the method do not achieve disease progression for at least at or about 3 months, at least at or about 4 months, at least at or about 5 months, at least at or about 6 months, at least at or about 9 months or at least at or about 12 months following administration of the one or more unit doses. In some embodiments, subjects treated according to the method achieve a pharmacokinetic property of cells of the cell composition in a biological sample, optionally a blood or serum sample, that is improved, on average, compared to a group of similarly situated subjects having the same disease or condition and administered a similar dose of an autologous cell composition comprising T cells expressing the recombinant receptor but in which the factor indicative of function or phenotype of cells is below the threshold value. In some embodiments, the pharmacokinetic property is the total exposure over time (AUC) or peak number of cells in the biological sample.

Provided herein are methods of predicting likelihood of response to a therapeutic T cell composition, the method including: (a) assaying an engineered cell composition containing T cells expressing a recombinant receptor for a factor indicative of the function or phenotype of engineered cells in the composition, the factor selected from (i) the percentage of T cells expressing the recombinant receptor that are surface positive for CCR7 and/or CD27, and optionally surface negative for CD45RA; and/or (ii) the percentage of CD4+ T cells expressing the recombinant receptor that are able to produce IL-2, TNF-alpha, and/or IFN-gamma following stimulation with a stimulatory agent; and (b) determining the likelihood of response following administration of a cell therapy containing a dose of the engineered cells, wherein if the factor is at or above a threshold value identifying the subject as likely to achieve a durable response or progression free survival, optionally for at least 3 months, following administration the therapy; or if the factor is below a threshold value identifying the subject as not likely to exhibit a durable response or progression free survival to the therapy, wherein the threshold value of the factor is selected from: (i) at or about 40%, 50%, 60%, 70%, 80%, 85%, 90%, 91%, 92%, 93%, 94%, 95%, 96%, 97%, 98%, 99% or 100% of the total number of T cells in the composition or of the total number of T cells in the composition expressing the recombinant receptor, are surface positive for CCR7 and/or CD27; and/or (ii) at or about 70%, 80%, 85%, 90%, 91%, 92%, 93%, 94%, 95%, 96%, 97%, 98%, 99% or 100% of the total number of CD4+ T cells in the composition expressing the recombinant receptor are able to produce interleukin 2 (IL-2) or TNF-alpha following stimulation with a stimulatory agent; and/or (iii) at or about 10%, 15%, 20%, 25%, 30%, 40%, 50%, 60% or more of the total number of CD4+ T cells in the composition expressing the recombinant receptor are polyfunctional for producing two or more cytokines selected from among interferon-gamma (IFN-gamma), interleukin 2 (IL-2) and TNF-alpha following stimulation with a stimulatory agent.

In some embodiments, cells of the cell composition are autologous to the subject. In some embodiments, if the subject is identified as likely to achieve a durable response or progression free survival to the therapy, administering to the subject one or more unit doses of cells of the engineered T cell composition. In some embodiments, the one or more unit doses contain between at or about $1\times10^5$ and at or about $5\times10^8$, between at or about $1\times10^5$ and at or about $1\times10^8$, between at or about $5\times10^5$ and at or about $1\times10^7$, or between at or about $1\times10^6$ and at or about $1\times10^7$ total T cells that express the recombinant receptor (receptor$^+$/T cells) or total T cells, each inclusive. In some embodiments, the one or more unit doses contains no more than about $5\times10^8$, no more than about $1\times10^8$, no more than about $5\times10^7$, no more than about $1\times10^7$, no more than about $5\times10^6$, no more than about $1\times10^6$, or no more than about $5\times10^5$ total receptor$^+$/T cells or total T cells. In some embodiments, the threshold value of the factor is at or about 40%, 50%, 60%, 70%, 80%, 85%, 90%, 91%, 92%, 93%, 94%, 95%, 96%, 97%, 98%, 99% or 100% of the total number of T cells in the composition or of the total number of T cells in the composition expressing the recombinant receptor, are surface positive for CCR7 and/or CD27. In some embodiments, the threshold value of the factor is at or about 40%, 50%, 60%, 70%, 80%, 85%, 90%, 91%, 92%, 93%, 94%, 95%, 96%, 97%, 98%, 99% or 100% of the total number of T cells in the composition or of the total number of T cells in the composition expressing the recombinant receptor, are surface positive for CCR7 and/or CD27. In some embodiments, the threshold value of the factor is at or about 70%, 80%, 85%, 90%, 91%, 92%, 93%, 94%, 95%, 96%, 97%, 98%, 99% or 100% of the total number of CD4+ T cells in the composition expressing the recombinant receptor are able to produce a cytokine selected from interleukin 2 (IL-2) and/or TNF-alpha. In some embodiments, the threshold value of the factor is at or about, 10%, 15%, 20%, 25%, 30%, 40%, 50%, 60% or more of the total number of CD4+ T cells in the composition expressing the recombinant receptor are polyfunctional for producing two or more cytokines selected from among interferon-gamma (IFN-gamma), interleukin 2 (IL-2) and TNF-alpha. In some embodiments, the threshold value of the factor is at or about, 10%, 15%, 20%, 25%, 30%, 40%, 50%, 60% or more of the total number of CD4+ T cells in the composition expressing the recombinant receptor are polyfunctional for producing the cytokines interferon-gamma (IFN-gamma), interleukin 2 (IL-2) and TNF-alpha.

In some embodiments, if the subject is identified as not likely to achieve a durable response or progression free survival, administering to the subject a therapy selected from (a) a dose of cells of the engineered cell composition and an agent capable of increasing expansion, proliferation or efficacy of T cells of the engineered cell composition in the subject, (b) an increased dose of cells of the engineered cell composition, optionally increased compared to a dose administered to a similarly situated subject having the same disease or condition but exhibiting a likelihood of achieving progression free survival or a durable response to the cell therapy; or (c) an alternative therapeutic treatment for treating the disease or condition other than a dose of the engineered cell composition.

In some embodiments, the method includes administration of a therapy containing a dose of cells of the engineered cell composition and an agent capable of increasing expansion, proliferation or efficacy of T cells of the engineered cell composition in the subject, wherein the agent is an anti-idiotype antibody or antigen-binding fragment thereof specific to the CAR, an immune checkpoint inhibitor, a modulator of a metabolic pathway, an adenosine receptor antagonist, a kinase inhibitor, an anti-TGFβ antibody or an anti-TGFβR antibody or a cytokine. In some embodiments, the agent is administered prior to, concurrently or after the administration of the therapeutic T cell composition.

In some embodiments, the subject is a subject that, at the time of the assaying and/or prior to the administering, is identified or known to have a high tumor burden. In some embodiments, the subject has high tumor burden if a sum of product dimensions (SPD) of a tumor in the subject is above at or about 30 cm$^2$, 40 cm$^2$, 50 cm$^2$, 60 cm$^2$ or 70 cm$^2$; and/or the subject has high tumor burden if C reactive protein (CRP) in a biological sample, optionally a serum sample, from the subject is above at or about 5 miligrams per liter, 10 miligrams per liter, 15 miligrams per liter, 20 miligrams per liter, 25 miligrams per liter, 30 miligrams per liter, 40 miligrams per liter or 50 miligrams per liter. In some embodiments, the subject has high tumor burden if the SPD of a tumor in the subject is above at or about 50 cm$^2$. In some embodiments, the subject has high tumor burden if the CRP is above at or about 20 miligrams per liter in the biological sample.

In some embodiments, the stimulatory agent is a non-specific or non-antigen-dependent T cell stimulatory agent. In some embodiments, the non-specific or non-antigen dependent T cell stimulatory agent is a polyclonal stimulatory agent. In some embodiments, the the non-specific or non-antigen dependent stimulatory agent contains PMA/ionomycin, anti-CD3/anti-CD28, phytohemagglutinin (PHA) or concanavalin A (ConA). In some embodiments, the non-specific or non-antigen dependent T cell stimulatory agent contains PMA/ionomycin. In some embodiments, the stimulatory agent specifically binds the recombinant receptor, optionally wherein the stimulatory agent is an antigen-specific stimulatory reagent and/or comprises the antigen or a portion thereof specifically recognized by the recombinant receptor. In some embodiments, production of the cytokines is measured in an intracellular cytokine assay.

In some embodiments, the recombinant receptor is or contains a chimeric receptor and/or a recombinant antigen receptor. In some embodiments, the recombinant receptor is capable of binding to a target antigen that is associated with, specific to, and/or expressed on a cell or tissue of a disease, disorder or condition. In some embodiments, the disease, disorder or condition is an infectious disease or disorder, an autoimmune disease, an inflammatory disease, or a tumor or a cancer. In some embodiments, the target antigen is a tumor antigen. In some embodiments, the target antigen is selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22Ra), IL-13 receptor alpha 2 (IL-13Ra2), kinase insert domain receptor (kdr), kappa light chain, L1 cell adhesion molecule (L1-CAM), CE7 epitope of L-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens.

In some embodiments, the recombinant receptor is or comprises a functional non-TCR antigen receptor or a TCR or antigen-binding fragment thereof. In some embodiments, the recombinant receptor is a chimeric antigen receptor (CAR). In some embodiments, the recombinant receptor contains an extracellular domain containing an antigen-binding domain and an intracellular signaling region containing an intracellular signaling domain. In some embodiments, the antigen-binding domain is or contains an antibody or an antibody fragment thereof, which optionally is a single chain fragment. In some embodiments, the fragment contains antibody variable regions joined by a flexible linker. In some embodiments, the fragment comprises an scFv. In some embodiments, the intracellular signaling domain is or contains a primary signaling domain, a signaling domain that is capable of inducing a primary activation signal in a T cell, a signaling domain of a T cell receptor (TCR) component, and/or a signaling domain containing an immunoreceptor tyrosine-based activation motif (ITAM). In some embodiments, the intracellular signaling domain is or contains an intracellular signaling domain of a CD3 chain, optionally a CD3-zeta (CD3ζ) chain, or a signaling portion thereof. In some embodiments, the recombinant receptor further contains a transmembrane domain disposed between the extracellular domain and the intracellular signaling region. In some embodiment, the intracellular signaling region further contains a costimulatory signaling domain. In some embodiments, the costimulatory signaling domain contains an intracellular signaling domain of a T cell costimulatory molecule or a signaling portion thereof. In some embodiments, the costimulatory signaling domain contains an intracellular signaling domain of a CD28, a 4-1BB or an ICOS or a signaling portion thereof. In some embodiments, the costimulatory signaling domain is between the transmembrane domain and the intracellular signaling domain.

In some embodiments, the T cells are primary T cells obtained from a subject. In some embodiments, the T cells are autologous to the subject.

Provided herein are methods of producing a therapeutic T cell composition, including (a) incubating an input composition under stimulating conditions, thereby generating a stimulated composition, wherein the input composition containing a defined number of T cells that do not express an apoptotic marker (apoptotic marker negative (−)); and (b) introducing a recombinant receptor into cells from the stimulated composition thereby generating an engineered cell composition, wherein the introducing includes contacting the cells of the stimulated composition with an agent comprising a polynucleotide encoding the recombinant receptor. In some embodiments, the apoptotic marker negative T cells are or contain apoptotic marker negative $CD3^+$ cells, apoptotic marker negative $CD8^+$ cells, apoptotic marker negative CD4+ cells, or apoptotic marker negative CD8+ cells and apoptotic marker negative CD4+ cells. In some embodiments, the apoptotic marker is Annexin V. In some embodiments, the apoptotic marker is activated Caspase 3. In some embodiments, the defined number of T cells contains at least $50 \times 10^6$ of the apoptotic marker negative T cells, optionally apoptotic marker negative CD4+ and/or apoptotic marker negative CD8+ T cells. In some embodiments, the defined number of T cells contains at least $100 \times 10^6$ of the apoptotic marker negative T cells, optionally apoptotic marker negative CD4+ and/or apoptotic marker negative CD8+ T cells. In some embodiments, the defined number of T cells includes between at or about $100 \times 10^6$ and at or about $500 \times 10^6$ apoptotic marker negative T cells, optionally apoptotic marker negative CD4+ and/or apoptotic marker negative CD8+ T cells. In some embodiments, the defined number of T cells includes at or about $300 \times 10^6$, apoptotic marker negative T cells, optionally apoptotic marker negative CD4+ and/or apoptotic marker negative CD8+ T cells.

In some embodiments, the percentage of apoptotic marker negative T cells as a percentage of the total T cells in the input composition is greater than or greater than about 70%, greater than or greater than about 80%, greater than or greater than about 90%, or greater than or greater than about 95%. In some embodiments, prior to the incubating, isolating, selecting or enriching apoptotic marker negative T cells, optionally apoptotic marker negative CD4+ and/or apoptotic marker negative CD8+ T cells from a biological sample.

Provided herein are methods of producing a therapeutic T cell composition, the method including (a) isolating, selecting or enriching, from a biological sample, a population of T cells that do not express an apoptotic marker (apoptotic marker negative (−)), optionally apoptotic marker negative CD4+ and/or apoptotic marker negative CD8+ T cells, thereby obtaining an input composition; (b) incubating the input composition under stimulating conditions, thereby generating a stimulated composition; and (c) introducing a recombinant receptor into cells from the stimulated composition thereby generating an engineered cell composition, wherein the introducing comprises contacting the cells of the stimulated composition with an agent comprising a polynucleotide encoding the recombinant receptor.

In some embodiments, the biological sample primary T cells obtained from a subject. In some embodiments, the subject is a human subject. In some embodiments, the biological sample is or contains a whole blood sample, a buffy coat sample, a peripheral blood mononuclear cell (PBMC) sample, an unfractionated T cell sample, a lymphocyte sample, a white blood cell sample, an apheresis product, or a leukapheresis product. In some embodiments, the biological sample contains an apheresis product or a leukapheresis product. In some embodiments, the T cells are isolated, selected or enriched from the biological sample no more than 36 hours after it is obtained from a subject. In some embodiments, the biological sample is cryofozen in the presence of a cryoprotectant no more than 36 hours after it is obtained from the subject and thawed prior to isolating, selecting or enriching the cells, optionally wherein the cryofrozen sample is thawed immediately prior to or within not more than 6 hours, no more than 4 hours, no more than 2 hours or no more than 1 hour prior to the isolating, selecting or enriching the cells.

In some embodiments, the incubation is performed in the presence of one or more cytokines, optionally in a serum free medium. In some embodiments, the one or more cytokines are selected from recombinant IL-2, recombinant IL-7, and/or recombinant IL-15. In some embodiments, the one or more cytokines comprise: between 10 and 200 IU/mL recombinant IL-2; between 100 IU/mL and 1,000 IU/mL recombinant IL-7; and/or between 10 and 200 IU/mL recombinant IL-15. In some embodiments, the stimulatory reagent contains a primary agent that specifically binds to a member of a TCR complex, optionally that specifically binds to CD3, optionally wherein the primary agent is an antibody or an antigen-binding fragment thereof. In some embodiments, the stimulatory reagent further contains a secondary agent that specifically binds to a T cell costimulatory molecule, optionally wherein the costimulatory molecule is selected from CD28, CD137 (4-1-BB), OX40, or ICOS, optionally wherein the secondary agent is an antibody or an antigen-binding fragment thereof. In some embodiments, the stimulatory reagent includes incubation with an anti-CD3 antibody and an anti-CD28 antibody, or an antigen-binding fragment thereof. In some embodiments, the primary agent and/or secondary agent are present on the surface of a solid support. In some embodiments, the solid support is or comprises a bead. In some embodiments, the primary agent and secondary agent are immobilized or reversibly bound on the surface of an oligomeric particle reagent comprising a plurality of streptavidin or streptavidin mutein molecules.

In some embodiments, the input composition is incubated under stimulating conditions for between 12 hours and 36 hours, inclusive, optionally at or about 24 hours. In some embodiments, the contacting is carried out by viral transduction, optionally with a retroviral vector, optionally a lentiviral vector.

In some embodiments, the method further includes cultivating the engineered composition under conditions to promote proliferation and/or expansion of the engineered cells, thereby producing an output composition comprising the engineered T cells. In some embodiments, the cultivating is performed in the presence of one or more cytokines, optionally in a serum free medium. In some embodiments, the one or more cytokines are selected from recombinant IL-2, recombinant IL-7, and/or recombinant IL-15. In some embodiments, the one or more cytokines contains: between 50 and 400 IU/mL recombinant IL-2; between 100 IU/mL and 2,000 IU/mL recombinant IL-7; and/or between 50 and 400 IU/mL recombinant IL-15.

In some embodiments, the input composition contains CD4+ T cells and CD8+ T cells at a ratio of between 2:1 and 1:2 CD4+ to CD8+ T cells; or the input composition contains apoptotic marker negative CD4+ T cells and apoptotic marker negative CD8+ T cells at a ratio of between 2:1 and 1:2 CD4+ to CD8+ T cells. In some embodiments, the CD4+ T cell and CD8+ T cells are separately selected, isolated or enriched from the same biological sample or a sample therefrom and combined prior to the incubating. In some embodiments, the recombinant receptor is a chimeric antigen receptor (CAR).

In some embodiments, the output composition contains at least at or about 40%, 50%, 60%, 70%, 80%, 85%, 90%, 91%, 92%, 93%, 94%, 95%, 96%, 97%, 98%, 99% or 100% of the total number of T cells in the composition or of the total number of T cells in the composition expressing the recombinant receptor, are surface positive for CCR7 and/or CD27; and/or at least at or about 70%, 80%, 85%, 90%, 91%, 92%, 93%, 94%, 95%, 96%, 97%, 98%, 99% or 100% of the total number of CD4+ T cells in the composition expressing the recombinant receptor are able to produce interleukin 2 (IL-2) or TNF-alpha following stimulation with a stimulatory agent; and/or at least at or about 10%, 15%, 20%, 25%, 30%, 40%, 50%, 60% or more of the total number of CD4+ T cells in the composition expressing the recombinant receptor are polyfunctional for producing two or more cytokines selected from among interferon-gamma (IFN-gamma), interleukin 2 (IL-2) and TNF-alpha following stimulation with a stimulatory agent. In some embodiments, the stimulatory agent is a non-specific or non-antigen-dependent T cell stimulatory agent. In some embodiments, the non-specific or non-antigen dependent T cell stimulatory agent is a polyclonal stimulatory agent. In some embodiments, the non-specific or non-antigen dependent stimulatory agent comprises PMA/ionomycin, anti-CD3/anti-CD28, phytohemagglutinin (PHA) or concanavalin A (ConA). In some embodiments, the non-specific or non-antigen dependent T cell stimulatory agent contains PMA/ionomycin. In some embodiments, the stimulatory agent specifically binds the recombinant receptor, optionally wherein the stimulatory agent is an antigen-specific stimulatory reagent and/or contains the antigen or a portion thereof specifically recognized by the recombinant receptor. In some embodiments, production of the cytokines is measured in an intracellular cytokine assay.

BRIEF DESCRIPTION OF THE DRAWINGS

FIGS. 3D-3J, depict plots of the percentage CCR7$^+$ or CCR7$^+$CD27$^+$CD4$^+$ or CD8$^+$ CAR$^+$ T cells against pharmacokinetic parameters (AUC$_{0-28}$ and C$_{max}$) of CD4$^+$ CAR$^+$ T cells (FIGS. 3A, 3D-3F) and CD8$^+$ CAR$^+$ T cells (FIGS. 3G-3J), with the correlation coefficients and associated p-values.

FIGS. 5A-5B depict a plot of the percentage of CCR7$^+$CD27$^+$ cells among CD8$^+$ CAR$^+$ cells against IL-5 (FIG. 5A) and IL-13 (FIG. 5B) secretion by the CD4$^+$ CAR$^+$ composition upon stimulation with the antigen recognized by the CAR (CD19).

FIGS. 6A-6D show the Kaplan-Meier survival curves for subjects who were administered CAR$^+$ T cell compositions, divided into groups that were administered compositions containing a percentage of CCR7$^+$CD27$^+$ CAR$^+$ T cells among CD4$^+$ CAR$^+$ T cells (FIG. 6A for progression free survival, FIG. 6C for duration of response) and among CD8$^+$ CAR$^+$ T cells (FIG. 6B for progression free survival, FIG. 6D for duration of response) that is above or below a certain threshold level.

FIGS. 7C-7D show boxplots depicting the percentage of CCR7$^+$CD27$^+$ cells among CD4$^+$ CAR$^+$ cells (FIG. 7C) or IFNγ secretion by CD4$^+$ CAR$^+$ cells (FIG. 7D) in cell compositions administered to for subjects as a function of whether the subject went on to develop neurotoxicity (NT; grade 0-2 vs. grade 3 or higher).

FIG. 11A depicts the percentage of CD4$^+$ and CD8$^+$ T cells positive for both CCR7 and CD27. FIG. 11B depicts the percentage of CCR7$^+$CD27$^+$ cells for CD4$^+$ CAR$^+$ T cells. FIG. 11C depicts the percentage of CCR7$^+$CD27$^+$ cells for CD8$^+$ CAR$^+$ T cells. FIG. 11D displays the percentage of CCR7$^+$CD27$^+$ cells generated from a representative donor from an exemplary expanded process at various days during the process of manufacture, including activation at day 1 (activation d1), transduction at day 2 (transduction d2), and at various timed after initiation of cultivation (d4 INOC+2, d6 INOC+4, d7 INOC+5).

DETAILED DESCRIPTION

Figure 1A:
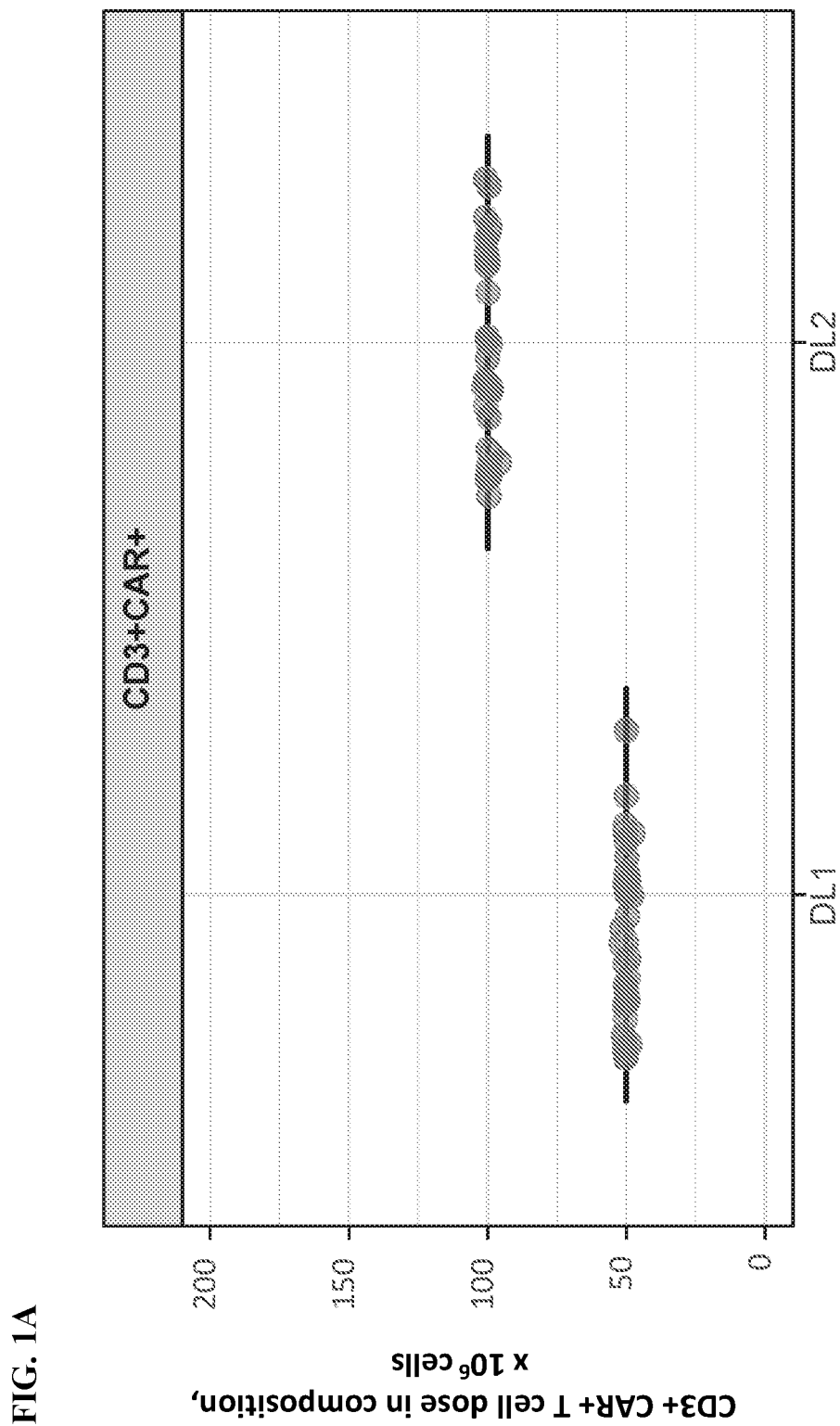
FIG. 1A shows the number of CD3$^+$ CAR$^+$ T cells present in CAR T cell compositions for administration at DL1 and DL2.

Provided herein are methods, compositions, and articles of manufacture for use in connection with cell therapy, such as engineered T cell therapy for the treatment of diseases and conditions, including various tumors. The provided embodiments relate to therapeutic T cell compositions containing engineered T cells such as those engineered to express recombinant proteins such as expressing recombinant receptors designed to recognize and/or specifically bind to molecules associated with the disease or condition and result in a response, such as an immune response against such molecules upon binding to such molecules. The receptors may include chimeric receptors, e.g., chimeric antigen receptors (CARs), and other transgenic antigen receptors including transgenic T cell receptors (TCRs).

The provided embodiments in some aspects relate to aspects in which cell phenotypes, e.g., the presence and/or expression of a surface marker, and/or the absence or lack of expression of a surface marker, is related to function or activity of the therapeutic T cell composition, pharmacokinetic parameters, e.g., exposure or maximum cell concentration, risk of the likelihood of developing a toxicity, such as cytokine release syndrome (CRS) or neurotoxicity (NT) and/or an outcome of the cell therapy, e.g., response to the cell therapy, in a subject administered the T cell composition and/or may provide information about the potency of the therapeutic T cell composition. In some aspects, the provided embodiments are based on the observation that certain cell phenotypes, e.g., expression of one or more surface markers, production of one or more cytokines are associated with pharmacokinetic parameters, likelihood of response and/or likelihood of developing a toxicity. In some embodiments, the expression and/or absence of expression of cell surface markers such as C—C chemokine receptor type 7 (CCR7), CD27 and CD45RA or combinations thereof in the T cell composition for administration, e.g., drug composition, are positively or negatively correlated with pharmacokinetic parameters and/or response or toxicity outcomes. In some aspects, it is observed herein that phenotype and functional attributes associated with a less differentiated T cell product or of a product enriched in naïve-like or central memory T cell subsets correlate with or exhibit a relationship with improved pharmacokinetic properties or responses, such as durability of response and/or progression free survival, following administration to a subject.

Aspects of the provided embodiments also relate to administering or providing a unit dose containing a number, ratio, percentage and/or proportion of cells, that is a function of the number of cells of a certain phenotype, such as a phenotype indicative of a cell population, including for use in connection with dosing of the therapeutic T cell composition. In some aspects, the provided embodiments allow for consistent dosing and/or administration. In some aspects, the provided embodiments may be used to assess the likelihood of a certain outcome and/or value of a certain pharmacokinetic parameter, risk of toxicity and/or response, potency or efficacy of the cell therapy. In some aspects, the provided methods can control, ameliorate or reduce the risk of toxicity in a subject administered a dose of the therapeutic T cell composition, while ensuring potency of the T cell composition. Also provided are articles of manufacture containing the cells and designed for administration according to such dosing regimens.

In some embodiments, the provided methods, doses, unit doses, compositions, and articles of manufacture are based on observations that it can be advantageous to take into account certain phenotypes, e.g., expression of surface markers, and combinations thereof when determining appropriate dose of cell therapy and/or releasing or generating cell compositions for therapy. In certain available methods, doses are based on numbers of particular cell types, such as those engineered to exhibit a particular activity, such as those positive for an engineered receptor. For example, in certain available methods and doses, dose is based upon an observed or suspected relationship between the number (or number per patient weight) of viable engineered T cells, or of a subset thereof, such as of viable, cytotoxic (e.g., $CD8^+$) engineered T cells. In various contexts, such numbers can have a relationship with efficacy and/or safety outcomes, such as response and/or risk of toxicities, such as neurotoxicity, cerebral edema and CRS. Provided herein are embodiments based on the observation that nonetheless, such metrics in some contexts do not consistently adequately associate with pharmacological parameters in the subject, risk of toxicities, CRS or NT, particularly without taking into account other variables. Accordingly, approaches for defining dose and evaluating product for release that rely on such metrics alone may not be entirely satisfactory. For example, such approaches may in some contexts fail to reach a certain therapeutic range or window, for safe and effective cell therapy. Provided herein are methods (including treatment, dosing, dose-determination and assay methods), therapeutic compositions, and articles of manufacture that address such shortcomings.

In some aspects, the provided embodiments permit the administration of a controlled and consistent dose of cells, thereby minimizing variation in efficacy and/or safety outcomes in the subjects. In some aspects, controlling the dose of cells based on a defined number, ratio, percentage and/or proportions of particular subset of cells, e.g., based on cell phenotypes, permit the understanding of the impact of a subset of cells having particular phenotypes on the health, potency and/or efficacy of the cells contained in the therapeutic compositions. Such approaches can be used to determine and/or calculate consistent and precise effective doses of the cells in the cell therapy and/or control the pharmacokinetic parameters of the cell therapy. Provided are methods of determining such doses, including unit doses for administration, based on the number, ratio, percentage and/or proportions of cells expressing particular surface markers and/or having particular phenotypes, articles of manufacture and kits containing doses determined using such methods and instructions for administration, and related methods of treatment. In some aspects, the provided embodiments allow the identification of attributes of cells in the engineered cell composition and potential association with pharmacokinetics (PK) and clinical outcomes such as response and toxicity, based on the consistency and tight control of the number of $CD4^+$ and $CD8^+$ $CAR^+$ T cells, and optionally subsets thereof that are $CCR7^+$, $CD27^+$ and/or CD45RA−, in the therapeutic composition for administration in subjects. Such consistency and tight control of the total number of CARP cells in the cell composition for administration can provide the basis for strategies to assess and control other aspects of the cells in the engineered cell composition for administration.

In some aspects, the provided embodiments permits the administration of $CAR^+$ T cell compositions that exhibit low variability, are pure and contain a precise dose, allowing identification of relationships between various cell attributes and clinical outcomes, such as response and toxicity. In some aspects, the provided embodiments are based on the observation that cell populations expressing markers associated with certain phenotypes, such as a less differentiated phenotype, exhibit certain functional profiles (e.g., cytokine production). In some aspects, $CCR7^+CD27^+CD4^+$ CAR T cells produce reduced IFNγ and increased IL-2, and, in some aspects, $CCR7^+CD27^+CD8^+$ CAR T cells produce reduced IL-5 and IL-13, such as upon antigen-specific stimulation of the CAR. In some embodiments, administered cell compositions containing $CAR^+$ T cells in which a certain percentage of cells in the composition exhibit a less differentiated state and/or are $CCR7^+CD27^+$ are associated with desirable or improved pharmacokinetic parameters, safety events and increased durable response, such as compared to compositions containing a lower percentage of such cell populations.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. DOSES AND DOSE DETERMINATION IN THERAPEUTIC T CELL COMPOSITIONS

Provided herein are methods, compositions, and articles of manufacture for use in connection with cell therapy, such as engineered T cell therapy for the treatment of diseases and conditions, including various tumors. The provided embodiments relate to methods of determining a dose for administration to a subject, related methods of treatment, compositions containing doses of cells and related article of manufacture and kits. The provided embodiments in some aspects relate to aspects in which cell phenotypes, e.g., the presence and/or expression of a surface marker, the absence or lack of expression of a surface marker and/or the ability to produce one or more cytokines (e.g. IL-2), of the cells in the composition for administration, is related to, correlated with or associated with values or measurements of pharmacokinetic parameters, e.g., exposure or maximum cell concentration. In some aspects, the phenotypes and/or parameters are also related to correlated with or associated with activity and/or function of the cells and/or the likelihood of developing a toxicity, such as cytokine release syndrome (CRS) or neurotoxicity (NT) and/or an outcome of the cell therapy, e.g., response to the cell therapy, in a subject administered the T cell composition, such as durability of response and progression free survival.

In some aspects, the provided embodiments, involve determining and/or administering a dose of the cell composition, e.g., one or more unit doses of a cell composition and/or a volume corresponding to such unit doses. In some aspects, the dose of cells is enriched for, e.g. has a high or relatively high percentage of, biologically active engineered T cells having a particular phenotype. In some aspects, the dose is based upon the number of biologically active engineered T cells having a particular phenotype. In some aspects, biologically active refers to a property of cells not programmed to undergo cell death, e.g., non-apoptotic cells or cells not showing indications of entry into an apoptotic pathway. In some aspects, dose is based upon number of biologically active engineered CD8+ T cells having a particular phenotype, and/or, where dose is based upon total numbers of biologically active engineered T cells having a particular phenotype.

In some embodiments, the methods ensure that a unit dose encompasses a relatively consistent numbers, proportion, ratio and/or percentage of engineered cells having a particular phenotype in one or more particular compositions. In some aspects, the consistency is associated with or related to a relatively consistent activity, function, pharmacokinetic parameters, toxicity outcome and/or response outcome. In some embodiments, the percentage of engineered cells capable of consistent activity, function, pharmacokinetic parameters, toxicity outcome, and/or response outcome (e.g., durable response, durable progression free survival) is or includes at least at or about, or at or about, 40%, 50%, 60%, 70%, 80%, 85%, 90%, 91%, 92%, 93%, 94%, 95%, 96%, 97%, 98%, 99% or 100% of the total number of engineered cells (e.g., T cells) in the composition or of the total number of engineered cells (e.g., T cells) in the composition expressing the recombinant receptor, surface positive for CCR7 and/or CD27, optionally further negative for surface expression of CD45RA. In some embodiments, the engineered cells (e.g., T cells) are further negative for an apoptotic marker, such as activated caspase 3 or annexin V. In some embodiments, the percentage of engineered cells capable of consistent activity, function, pharmacokinetic parameters, toxicity outcome, and/or response outcome (e.g., durable response, durable progression free survival) is or includes at least at or about, or at or about, 75%, 80%, 85%, 90%, 95%, 96%, 97%, 98%, or 99% of the total number of engineered cells (e.g., T cells) in the composition or of the total number of engineered cells (e.g., T cells) in the composition expressing the recombinant receptor, negative for markers of apoptosis (e.g., caspase-3, annexin V). In some embodiments, the percentage of engineered cells capable of consistent activity, function, pharmacokinetic parameters, toxicity outcome, and/or response outcome (e.g., durable response, durable progression free survival) is or includes at least at or about, or at or about, 70%, 80%, 85%, 90%, 91%, 92%, 93%, 94%, 95%, 96%, 97%, 98%, 99% or 100% of the total number of engineered CD4+ T cells in the composition or the total number of engineered CD4+ T cells expressing the recombinant receptor capable of producing a cytokine selected from interleukin 2 (IL-2) and/or TNF-alpha. In some embodiments, the percentage of engineered cells capable of consistent activity, function, pharmacokinetic parameters, toxicity outcome, and/or response outcome (e.g., durable response, durable progression free survival) is or includes at least at or about, or at or about, 10%, 15%, 20%, 25%, 30%, 40%, 50%, 60% or more of the total number of engineered CD4+ T cells in the composition or the total number of engineered CD4+ T cells expressing the recombinant receptor are polyfunctional for producing two or more cytokines selected from among interferon-gamma (IFN-gamma), interleukin 2 (IL-2) and TNF-alpha. In some embodiments, the engineered cells of the composition capable of consistent activity, function, pharmacokinetic parameters, toxicity outcome, and/or response outcome (e.g., durable response, durable progression free survival) are or include one or more phenotypes described herein. Thus, in some embodiments, the percentage of engineered cells capable of consistent activity, function, pharmacokinetic parameters, toxicity outcome, and/or response outcome (e.g., durable response, durable progression free survival) is or includes a combination of percentages of phenotypes. In some embodiments, the composition to be used as a therapeutic composition is selected based on the percentage of cells including one or more phenotypes in the composition (e.g., output composition).

In some aspects, in a plurality of subjects, compositions and/or doses, the numbers, proportion, ratio and/or percentage, are relatively consistent, e.g., the number or ratio of cells that have a particular phenotype, e.g., express CCR7 (CCR7+) and/or have the ability to produce one or more cytokines, in the composition or unit dose, varies by no more than 40%, by no more than 30%, by no more than 20%, by no more than 10% or by no more than 5%. In some aspects the number or ratio of cells that have a particular phenotype, e.g., express CCR7 (CCR7+) and/or the ability to produce one or more cytokines, in the composition or unit dose, varies by no more than 20% or no more than 10% or no more than 5% from an average of said number or ratio in a plurality of T cell compositions produced by the process and/or varies from such average by no more than one standard deviation or varies by no more than 20% or no more than 10% or no more than 5% among a plurality of T cell compositions or doses determined.

In some embodiments, the methods involve determining and/or administering one or more unit doses of cells, e.g., engineered T cells expressing a recombinant receptor such as a CAR. In some aspects, the methods involve administering one or more unit doses of cells in which the one or more unit doses of cells are enriched in, and/or contain a high or relatively high percentage of cells having a particular phenotype, such as particular surface marker phenotype and/or indicating functional activity, such as the ability to produce one or more cytokines. In some aspects, the unit dose is determined based on the number, percentage, ratio, frequency and/or proportion of a particular subset of engineered T cells, e.g., cells having a particular phenotype, such as particular surface marker phenotype and/or indicating functional activity, such as the ability to produce one or more cytokines. In some embodiments, an engineered or therapeutic cell composition can be produced by a method that results in an output composition containing or enriched for cells having such phenotypes or functional attributes, such as compared to the starting material or input composition used to generate the engineered output composition. Exemplary phenotype and functional attributes of cells of an engineered or therapeutic cell composition, such as an output composition produced in accord with methods for generating engineered cells, including in one or more unit doses of any such composition, are described herein.

In some aspects, the cell marker includes markers indicative of cell health, viability and/or apoptotic state of the cells. In some aspects, exemplary markers include CD3, CD4, CD8, CCR7, CD27, CD45RA, annexin V, or activated caspase 3. In some aspects, exemplary markers include CCR7, CD27 and/or CD45RA. In some aspects, exemplary markers include CCR7 and/or CD27. In some aspects, an exemplary marker is CCR7. In some aspects, an exemplary marker is CD27.

In some aspects, the provided methods also involve assessing the therapeutic composition for cell phenotypes, e.g., expression of the markers, e.g. CD3, CD4, CD8, CCR7, CD27, CD45RA, annexin V, or activated caspase 3. In some embodiments, the phenotype includes antigen-specific functions. In some embodiments, the phenotype includes production or secretion of a cytokine, e.g., upon stimulation with an antigen that the recombinant receptor, e.g., CAR, specifically binds and/or recognizes. In some embodiments, the phenotype includes production of cytokines, e.g., cytokines associated with particular cell types, such as cytokines associated with Th1, Th2, Th17 and/or Treg subtypes.

In some aspects, the provided methods involve determining a suitable dose, e.g., one or more unit doses of a therapeutic composition containing engineered T cells for administration to a subject having a disease or condition. In some aspects, the methods also involve assessing the number, percentage, ratio, frequency and/or proportion of a particular subset of engineered T cells, e.g., cells having a particular phenotype, such as particular surface marker phenotype, in a therapeutic composition containing engineered T cells. In some embodiments, the provided methods involve assessing, in a therapeutic composition comprising a plurality of $CD8^+$ and/or $CD4^+$ T cells engineered to express a recombinant receptor, the number, percentage or ratio of T cells that express the recombinant receptor and CCR7 (receptor$^+$/CCR7$^+$).

In some embodiments, the provided methods involve assessing, in a therapeutic composition comprising a plurality of $CD8^+$ and/or $CD4^+$ T cells engineered to express a recombinant receptor, the number, percentage or ratio of T cells that express or do not express CD27 and/or CD45RA. Other exemplary phenotypic markers for assessment and/or methods for assessment are described below, e.g., in Section I.A. In some aspects, the unit dose can be determined based on any of the assessments. In some aspects, the methods also involve assessing the number, percentage, ratio, frequency and/or proportion of the cells expressing the recombinant receptor (e.g., CAR) or a surrogate marker of the recombinant receptor. The doses, e.g., one or more unit doses, can be determined based on the assessment for the number, percentage, ratio, frequency and/or proportion any of the phenotypic markers described herein.

A. Determining Cell Phenotypes

In some embodiments, cell phenotypes, or the level or percentage of such phenotypes in a composition of cells, correlate to or are associated with activity and/or function of the cells and/or the likelihood of developing a toxicity, such as cytokine release syndrome (CRS) or neurotoxicity (NT) and/or an outcome of the cell therapy, e.g., response to the cell therapy, in a subject administered the T cell composition, such as durability of response and progression free survival. In some embodiments, compositions including cells with specific phenotypes, and, more particularly, percentages of cells with such specific phenotypes, correlate with clinical outcomes, such as durable response and/or progression free survival. In some embodiments, the phenotype is determined by assessing the presence or absence of one or more specific molecules, including surface molecules and/or molecules that may accumulate or be produced by the cells or a subpopulation of cells within a T cell composition. In some embodiments, the phenotype, directly or inversely, indicates or is indicative of a biological activity of the cells or of a population of cells within the T cell composition. In some embodiments, phenotype may include cell activity, such as production of a factor (e.g., cytokine) in response to a stimulus. In certain embodiments, assessment of a cell composition is performed to identify, detect, or quantify a phenotype of the cell composition. In particular embodiments, a measurement of a cell composition is performed to identify, detect, or quantify the presence, absence, degree of expression or level of a specific molecule.

It is contemplated that the phenotype of the cell composition (e.g., engineered T cell composition) can, in some cases, depend upon many factors, including, but not limited to, the phenotype of the starting cellular material (e.g., apheresis product or leukapheresis product) used to generate the cell composition and the phenotype of the cellular material undergoing processing to generate the cell composition. Thus, in some embodiments, phenotype is assessed in cells of the starting material and/or the material undergoing processing to generate the cell composition, as well as the final cell composition.

In some embodiments, the phenotype is indicative of viability of a cell. In some embodiments, the phenotype is indicative of absence of apoptosis, absence of early stages of apoptosis or absence of late stages of apoptosis. In some embodiments, the phenotype is the absence of a factor indicative of absence of apoptosis, early apoptosis or late stages of apoptosis. In some embodiments, the phenotype is a phenotype of a sub-population or subset of T cells, such as recombinant receptor-expressing T cells (e.g. $CAR^+$ T cells), $CD8^+$ T cells, or $CD4^+$ T cells. In some embodiments, the phenotype is a phenotype of cells that are not activated and/or that lack or are reduced for or low for expression of one or more activation marker. In some embodiments, the phenotype is a phenotype of cells that are not exhausted and/or that lack or are reduced for or low for expression of one or more exhaustion markers.

In some embodiments, the phenotype is indicated by the presence, absence, or level of expression in a cell of one or more specific molecules, such as certain surface markers indicative of the phenotype, e.g., surface proteins, intracellular markers indicative of the phenotype, or nucleic acids indicative of the phenotype or other molecules or factors indicative of the phenotype. In some embodiments, the phenotype is or comprises a positive or negative expression of the one or more of specific molecules. In some embodiments, the specific molecules include, but are not limited to, a surface marker, e.g., a membrane glycoprotein or a receptor; a marker associated with apoptosis or viability; or a specific molecule that indicates the status of an immune cells, e.g., a marker associated with activation, exhaustion, or a mature or naïve phenotype. In some embodiments, any known method for assessing or measuring, counting, and/or quantifying cells based on specific molecules can be used to determine the number of cells of the phenotype.

In some embodiments, a phenotype is or includes a positive or negative expression of one or more specific molecules in a cell. In some embodiments, the positive expression is indicated by a detectable amount of the specific molecule in the cell. In certain embodiments, the detectable amount is any detected amount of the specific molecule in the cell. In particular embodiments, the detectable amount is an amount greater than a background, e.g., background staining, signal, etc., in the cell. In certain embodiments, the positive expression is an amount of the specific molecule that is greater than a threshold, e.g., a predetermined threshold. Likewise, in particular embodiments, a cell with negative expression of a specific molecule may be any cell not determined to have positive expression, or is a cell that lacks a detectable amount of the specific molecule or a detectable amount of the specific molecule above background. In some embodiments, the cell has negative expression of a specific molecule if the amount of the specific molecule is below a threshold. One of skill in the art will understand how to define a threshold to define positive and/or negative expression for a specific molecule as a matter of routine skill, and that the thresholds may be defined according to specific parameters of, for example, but not limited to, the assay or method of detection, the identity of the specific molecule, reagents used for detection, and instrumentation.

Examples of methods that can be used to detect a specific molecule and/or analyze a phenotype of the cells include, but are not limited to, biochemical analysis; immunochemical analysis; image analysis; cytomorphological analysis; molecule analysis such as PCR, sequencing, high-throughput sequencing, determination of DNA methylation; proteomics analysis such as determination of protein glycosylation and/or phosphorylation pattern; genomics analysis; epigenomics analysis (e.g., ChIP-seq or ATAC-seq); transcriptomics analysis (e.g., RNA-seq); and any combination thereof. In some embodiments, the methods can include assessment of immune receptor repertoire, e.g., repertoire of T cell receptors (TCRs). In some aspects, determination of any of the phenotypes can be assessed in high-throughput, automated and/or by single-cell-based methods. In some aspects, large-scale or genome-wide methods, can be used to identify one or more molecular signatures. In some aspects, large-scale or genome-wide methods, can be used to identify molecular signatures that are associated with outcomes of therapy, e.g., efficacy and safety, or pharmacokinetic parameters. In some aspects, one or more molecular signatures, e.g., expression of specific RNA or proteins in the cell, can be determined. In some embodiments, molecular features of the phenotype analyzed by image analysis, PCR (including the standard and all variants of PCR), microarray (including, but not limited to DNA microarray, MMchips for microRNA, protein microarray, cellular microarray, antibody microarray, and carbohydrate array), sequencing, biomarker detection, or methods for determining DNA methylation or protein glycosylation pattern. In particular embodiments, the specific molecule is a polypeptide, i.e. a protein. In some embodiments, the specific molecule is a polynucleotide.

In some embodiments, positive or negative expression of a specific molecule is determined by incubating cells with one or more antibodies or other binding agent that specifically bind to one or more surface markers expressed or expressed (marker+) at a relatively higher level (marker$^{high}$) on the positively or negatively selected cells, respectively. In particular embodiments, the positive or negative expression is determined by flow cytometry, immunohistochemistry, or any other suitable method for detecting specific markers.

In particular embodiments, expression of a specific molecule is assessed with flow cytometry. Flow cytometry is a laser- or impedance-based, biophysical technology employed in cell counting, cell sorting, biomarker detection and protein engineering, by suspending cells in a stream of fluid and passing them by an electronic detection apparatus. It allows simultaneous multiparametric analysis of the physical and chemical characteristics of up to thousands of particles per second.

The data generated by flow-cytometers can be plotted in a single dimension, to produce a histogram, or in two-dimensional dot plots or even in three dimensions. The regions on these plots can be sequentially separated, based on fluorescence intensity, by creating a series of subset extractions, termed "gates." Specific gating protocols exist for diagnostic and clinical purposes especially in relation to immunology. Plots are often made on logarithmic scales. Because different fluorescent dyes' emission spectra overlap, signals at the detectors have to be compensated electronically as well as computationally. Data accumulated using the flow cytometer can be analyzed using software, e.g., JMP (statistical software), WinMDI, Flowing Software, and web-based Cytobank), Cellcion, FCS Express, FlowJo, FACSDiva, CytoPaint (aka Paint-A-Gate), VenturiOne, CellQuest Pro, Infinicyt or Cytospec.

Flow Cytometry is a standard technique in the art and one of skill would readily understand how to design or tailor protocols to detect one or more specific molecules and analyze the data to determine the expression of one or more specific molecules in a population of cells. Standard protocols and techniques for flow cytometry are found in Loyd "Flow Cytometry in Microbiology; Practical Flow Cytometry by Howard M. Shapiro; Flow Cytometry for Biotechnology by Larry A. Sklar, Handbook of Flow Cytometry Methods by J. Paul Robinson, et al., Current Protocols in Cytometry, Wiley-Liss Pub, Flow Cytometry in Clinical Diagnosis, v4, (Carey, McCoy, and Keren, eds), ASCP Press, 2007, Ormerod, M. G. (ed.) (2000) Flow Cytometry—A practical approach. 3rd edition. Oxford University Press, Oxford, UK, Ormerod, M. G. (1999) Flow Cytometry. 2nd edition. BIOS Scientific Publishers, Oxford., and Flow Cytometry—A basic introduction. Michael G. Ormerod, 2008.

In some embodiments, cells are sorted by phenotype for further analysis. In some embodiments, cells of different phenotypes within the same cell composition are sorted by Fluorescence-activated cell sorting (FACS). FACS is a specialized type of flow cytometry that allows for sorting a heterogeneous mixture of cells into two or more containers, one cell at a time, based upon the specific light scattering and fluorescent characteristics of each cell. It is a useful scientific instrument as it provides fast, objective and quantitative recording of fluorescent signals from individual cells as well as physical separation of cells of particular interest.

In some embodiments, the phenotype includes the number of total T cells or the number of total CD3$^+$ T cells. In particular embodiments, a T cell composition, e.g., a therapeutic T cell composition that contains cells that express a recombinant receptor or a CAR, may include one or more different subtypes of T cells. In some embodiments, the phenotype is or includes the identity of a T cell subtype. Different populations or subtypes of T cells include, but are not limited to effector T cells, helper T cells, memory T cell, Regulatory T cells, naïve T cells, CD4$^+$ cells, and CD8$^+$ T cells. In certain embodiments, a T cell sub-type may be identified by detecting the presence or absence of a specific molecule. In certain embodiments, the specific molecule is a surface marker that can be used to identify a T cell subtype.

In some embodiments, the phenotype is positive or high level expression of one or more specific molecule that are surface markers, e.g., CD3, CD4, CD8, CD28, CD62L, CCR7, CD27, CD127, CD4, CD8, CD45RA, and/or CD45RA$^+$. In certain embodiments, the phenotype is a surface marker of T cells or of a subpopulation or subset of T cells, such as based on positive surface marker expression of one or more surface markers, e.g., CD3$^+$, CD4$^+$, CD8$^+$, CD28$^+$, CD62L$^+$, CCR7$^+$, CD27$^+$, CD127$^+$, CD4$^+$, CD8$^+$, CD45RA$^+$, and/or CD45RA$^+$. In some embodiments, the phenotype is positive or high level expression of one or more specific molecule that are surface markers, e.g., C—C chemokine receptor type 7 (CCR7), Cluster of Differentiation 27 (CD27), Cluster of Differentiation 28 (CD28), and Cluster of Differentiation 45 RA (CD45RA). In certain embodiments, the phenotype markers include CCR7, CD27, CD28, CD44, CD45RA, CD62L, and L-selectin. In some embodiments, the phenotype is negative or the absence of expression of one or more specific molecule that are surface markers, e.g., CD3, CD4, CD8, CD28, CD62L, CCR7, CD27, CD127, CD4, CD8, CD45RA, and/or CD45RO. In certain embodiments, the phenotype is a surface marker of T cells or of a subpopulation or subset of T cells, such as based on the absence of surface marker expression of one or more surface markers, e.g., CD3$^-$, CD4$^-$, CD8$^-$, CD28$^-$, CD62L$^-$, CCR7$^-$, CD27$^-$, CD127$^-$, CD4$^-$, CD8$^-$, CD45RA$^-$, and/or CD45RO$^-$. In some embodiments, the phenotype is negative or the absence of expression of one or more specific molecule that are surface markers, e.g., C—C chemokine receptor type 7 (CCR7), Cluster of Differentiation 27 (CD27), Cluster of Differentiation 28 (CD28), and Cluster of Differentiation 45 RA (CD45RA). In certain embodiments, the phenotype markers include CCR7, CD27, CD28, CD44, CD45RA, CD62L, and L-selectin.

In certain embodiments, the phenotype is or includes positive or negative expression of CD27, CCR7 and/or CD45RA. In some embodiments, the phenotype is CCR7$^+$. In some embodiments, the phenotype is CD27$^+$. In some embodiments, the phenotype is CCR7$^+$/CD27$^+$. In some embodiments, the phenotype is CD45RA$^-$. In some embodiments, the phenotype is CCR7$^+$/CD45RA$^-$. In some embodiments, the phenotype is CD27$^+$/CD45RA$^-$. In some embodiments, the phenotype is CCR7$^+$/CD27$^+$/CD45RA$^-$.

In certain embodiments, the surface marker indicates expression of a recombinant receptor, e.g., a CAR. In particular embodiments, the surface marker is expression of the recombinant receptor, e.g. CAR, which, in some aspects, can be determined using an antibody, such as an anti-idiotype antibody. In some embodiments, the surface marker that indicates expression of the recombinant receptor is a surrogate marker. In particular embodiments, such a surrogate marker is a surface protein that has been modified to have little or no activity. In certain embodiments, the surrogate marker is encoded on the same polynucleotide that encodes the recombinant receptor. In some embodiments, the nucleic acid sequence encoding the recombinant receptor is operably linked to a nucleic acid sequence encoding a marker, optionally separated by an internal ribosome entry site (IRES), or a nucleic acid encoding a self-cleaving peptide or a peptide that causes ribosome skipping, such as a 2A sequence, such as a T2A (e.g., SEQ ID NOS: 6 and 17), a P2A (e.g., SEQ ID NOS: 18 and 19), a E2A (e.g., SEQ ID NO: 20) or a F2A (e.g., SEQ ID NO: 21). Extrinsic marker genes may in some cases be utilized in connection with engineered cells to permit detection or selection of cells and, in some cases, also to promote cell suicide.

Exemplary surrogate markers can include truncated cell surface polypeptides, such as a truncated human epidermal growth factor receptor 2 (tHER2), a truncated epidermal growth factor receptor (EGFRt, exemplary EGFRt sequence set forth in SEQ ID NO:7 or 16) or a prostate-specific membrane antigen (PSMA) or modified form thereof. EGFRt may contain an epitope recognized by the antibody cetuximab (Erbitux®) or other therapeutic anti-EGFR antibody or binding molecule, which can be used to identify or select cells that have been engineered with the EGFRt construct and a recombinant receptor, such as a chimeric antigen receptor (CAR), and/or to eliminate or separate cells expressing the receptor. See U.S. Pat. No. 8,802,374 and Liu et al., Nature Biotech. 2016 April; 34(4): 430-434). In some aspects, the marker, e.g. surrogate marker, includes all or part (e.g., truncated form) of CD34, a NGFR, or epidermal growth factor receptor (e.g., tEGFR). In some embodiments, the nucleic acid encoding the marker is operably linked to a polynucleotide encoding for a linker sequence, such as a cleavable linker sequence, e.g., T2A. For example, a marker, and optionally a linker sequence, can be any as disclosed in PCT Pub. No. WO2014031687. For example, the marker can be a truncated EGFR (tEGFR) that is, optionally, linked to a linker sequence, such as a T2A cleavable linker sequence. An exemplary polypeptide for a truncated EGFR (e.g. tEGFR) comprises the sequence of amino acids set forth in SEQ ID NO: 7 or 16 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7 or 16.

In some embodiments, the marker is or comprises a fluorescent protein, such as green fluorescent protein (GFP), enhanced green fluorescent protein (EGFP), such as superfold GFP, red fluorescent protein (RFP), such as tdTomato, mCherry, mStrawberry, AsRed2, DsRed or DsRed2, cyan fluorescent protein (CFP), blue green fluorescent protein (BFP), enhanced blue fluorescent protein (EBFP), and yellow fluorescent protein (YFP), and variants thereof, including species variants, monomeric variants, and codon-optimized and/or enhanced variants of the fluorescent proteins. In some embodiments, the marker is or comprises an enzyme, such as a luciferase, the lacZ gene from *E. coli*, alkaline phosphatase, secreted embryonic alkaline phosphatase (SEAP), chloramphenicol acetyl transferase (CAT). Exemplary light-emitting reporter genes include luciferase (luc), β-galactosidase, chloramphenicol acetyltransferase (CAT), β-glucuronidase (GUS) or variants thereof.

In certain embodiments, the phenotype comprises expression, e.g. surface expression, of one or more of the surface markers CD3, CD4, CD8, and/or a recombinant receptor (e.g. CAR) or its surrogate marker indicating or correlating to expression of a recombinant receptor (e.g. CAR).

In particular embodiments, the phenotype is identified by the expression of one or more specific molecules that are surface markers. In certain embodiments, the phenotype is or includes positive or negative expression of CD3, CD4, CD8, and/or a recombinant receptor, e.g. a CAR. In certain embodiments, the recombinant receptor is a CAR. In particular embodiments the phenotype comprises CD3$^+$/CAR$^+$, CD4$^+$/CAR$^+$, and/or CD8$^+$/CAR$^+$.

In certain embodiments, the phenotype is or includes positive or negative expression of CD27, CCR7 and/or CD45RA, and/or a recombinant receptor, e.g. a CAR. In some embodiments, the phenotype is CCR7$^+$/CAR$^+$. In some embodiments, the phenotype is CD27$^+$/CAR$^+$. In some embodiments, the phenotype is CCR7$^+$/CD27$^+$/CAR$^+$. In some embodiments, the phenotype is CD45RA$^-$/CAR$^+$. In some embodiments, the phenotype is CCR7$^+$/CD45RA$^-$/CAR$^+$. In some embodiments, the phenotype is CD27$^+$/CD45RA$^-$/CAR$^+$. In some embodiments, the phenotype is CCR7$^+$/CD27$^+$/CD45RA$^-$/CAR$^+$.

In some embodiments, the phenotype is viability. In certain embodiments, the phenotype is the positive expression of a marker that indicates that the cell undergoes normal functional cellular processes and/or has not undergone or is not under the process of undergoing necrosis or programmed cell death. In some embodiments, viability can be assessed by the redox potential of the cell, the integrity of the cell membrane, or the activity or function of mitochondria. In some embodiments, viability is the absence of a specific molecule associated with cell death, or the absence of the indication of cell death in an assay.

In some embodiments, the phenotype is or comprises cell viability. In certain embodiments, the viability of cells can be detected, measured, and/or assessed by a number of means that are routine in the art. Non-limiting examples of such viability assays include, but are not limited to, dye uptake assays (e.g., calcein AM assays), XTT cell viability assays, and dye exclusion assays (e.g., trypan blue, Eosin, or propidium dye exclusion assays). Viability assays are useful for determining the number or percentage (e.g., frequency) of viable cells in a cell dose, a cell composition, and/or a cell sample. In particular embodiments, the phenotype comprises cell viability along with other features, e.g., recombinant receptor expression.

In certain embodiments, the phenotype is or includes cell viability, viable $CD3^+$, viable $CD4^+$, viable $CD8^+$, viable $CD3^+/CAR^+$, viable $CD4^+/CAR^+$, viable $CD8^+/CAR^+$, viable $CD4^+/CCR7^+/CAR^+$, viable $CD8^+/CD27^+/CAR^+$, viable $CD4^+/CD27^+/CAR^+$, viable $CD8^+/CCR7^+/CD27^+/CAR^+$, viable $CD4^+/CCR7^+/CD27^+/CAR^+$, viable $CD8^+/CCR7^+/CD45RA^-/CAR^+$ or viable $CD4^+/CCR7^+/CD45RA^-$ or a combination thereof.

In particular embodiments, the phenotype is or includes an absence of apoptosis and/or an indication the cell is undergoing the apoptotic process. Apoptosis is a process of programmed cell death that includes a series of stereotyped morphological and biochemical events that lead to characteristic cell changes and death. These changes include blebbing, cell shrinkage, nuclear fragmentation, chromatin condensation, chromosomal DNA fragmentation, and global mRNA decay. Apoptosis is a well characterized process, and specific molecules associated with various stages are well known in the art.

In some embodiments, the phenotype is the absence of an early stage of apoptosis, and/or an absence of an indicator and/or a specific molecule associated with an early stage of apoptosis. In the early stages of apoptosis, changes in the cellular and mitochondrial membrane become apparent. Biochemical changes are also apparent in the cytoplasm and nucleus of the cell. For example, the early stages of apoptosis can be indicated by activation of certain caspases, e.g., 2, 8, 9, and 10. In particular embodiments, the phenotype is the absence of a late stage of apoptosis, and/or an absence of an indicator and/or a specific molecule associated with a late stage of apoptosis. The middle to late stages of apoptosis are characterized by further loss of membrane integrity, chromatin condensation and DNA fragmentation, and include biochemical events such as activation of caspases 3, 6, and 7.

In certain embodiments, the phenotype is the negative expression of one or more factors associated with apoptosis, including pro-apoptotic factors known to initiate apoptosis, e.g., members of the death receptor pathway, activated members of the mitochondrial (intrinsic) pathway, such as Bcl-2 family members, e.g., Bax, Bad, and Bid, and caspases. In some embodiments, the phenotype is a negative or low amount of a marker of apoptosis. In certain embodiments, the phenotype is the negative expression of a marker of apoptosis. In certain embodiments, the phenotype is the absence of an indicator, e.g., an Annexin V molecule, which will preferentially bind to cells undergoing apoptosis when incubated with or contacted to a cell composition. In some embodiments, the phenotype is or includes the expression of one or more markers that are indicative of an apoptotic state in the cell.

In some embodiments, the phenotype is the negative (or low) expression of a specific molecule that is a marker for apoptosis. Various apoptosis markers are known to those of ordinary skill in the art and include, but are not limited to, an increase in activity of one or more caspases i.e. an activated caspase (e.g., an active caspase), an increase in PARP cleavage, activation and/or translocation of Bcl-2 family proteins, members of the cell death pathway, e.g., Fas and FADD, presence of nuclear shrinkage (e.g., monitored by microscope) and presence of chromosome DNA fragmentation (e.g., presence of chromosome DNA ladder) or with apoptosis assays that include TUNEL staining, and Annexin V staining.

Caspases are enzymes that cleave proteins after an aspartic acid residue, the term is derived from "cysteine-aspartic acid proteases." Caspases are involved in apoptosis, thus activation of caspases, such as caspase-3 is indicative of an increase or revival of apoptosis. In certain embodiments, caspase activation can be detected by methods known to the person of ordinary skill. In some embodiments, an antibody that binds specifically to an activated caspase (i.e., binds specifically to the cleaved polypeptide) can be used to detect caspase activation. In another example, a fluorochrome inhibitor of caspase activity (FLICA) assay can be utilized to detect caspase-3 activation by detecting hydrolysis of acetyl Asp-Glu-Val-Asp 7-amido-4-methylcoumarin (Ac-DEVD-AMC) by caspase-3 (i.e., detecting release of the fluorescent 7-amino-4-methylcoumarin (AMC)). FLICA assays can be used to determine caspase activation by a detecting the product of a substrate processed by multiple caspases (e.g., FAM-VAD-FMK FLICA). Other techniques include The CASPASE-GLO® caspase assays (PROMEGA) that use luminogenic caspase-8 tetrapeptide substrate (Z-LETD-aminoluciferin), the caspase-9 tetrapeptide substrate (Z-LEHD-aminoluciferin), the caspase-3/7 substrate (Z-DEVD-aminoluciferin), the caspase-6 substrate (Z-VEID-aminoluciferin), or the caspase-2 substrate (Z-VDVAD-aminoluciferin).

In certain embodiments, the phenotype is or includes negative expression of activated caspase-1, activated caspase-2, activated caspase-3, activated caspase-7, activated caspase-8, activated caspase-9, activated caspase-10 and/or activated caspase-13 in a cell. In particular embodiments, the phenotype is or includes activated caspase $3^-$. In some embodiments, the proform (zymogen cleaved) form of a caspase, such as any above, also is a marker indicating the presence of apoptosis. In some embodiments, the phenotype is or includes the absence of or negative expression of a proform of a caspase, such as the proform of caspase-3.

In some embodiments, the marker of apoptosis is cleaved the Poly ADP-ribose polymerase 1 (PARP). PARP is cleaved by caspase during early stages of apoptosis. Thus, detection of a cleaved PARP peptide is a marker for apoptosis. In particular embodiments, the phenotype is or includes positive or negative expression of cleaved PARP.

In some embodiments, the marker of apoptosis is a reagent that detects a feature in a cell that is associated with apoptosis. In certain embodiments, the reagent is an annexin V molecule. During the early stages of apoptosis the lipid phosphatidylserine (PS) translocates from the inner to the outer leaflet of the plasma membrane. PS is normally restricted to the internal membrane in healthy and/or non-apoptotic cells. Annexin V is a protein that preferentially binds phosphatidylserine (PS) with high affinity. When conjugated to a fluorescent tag or other reporter, Annexin V can be used to rapidly detect this early cell surface indicator of apoptosis. In some embodiments, the presence of PS on the outer membrane will persist into the late stages of apoptosis. Thus in some embodiments, annexin V staining is an indication of both early and late stages of apoptosis. In certain embodiments, an Annexin, e.g. Annexin V, is tagged with a detectable label and incubated with, exposed to, and/or contacted with cells of a cell composition to detect cells that are undergoing apoptosis, for example by flow cytometry. In some embodiments, fluorescence tagged annexins, e.g., annexin V, are used to stain cells for flow cytometry analysis, for example with the annexin $^-$V/7$^-$ AAD assay. Alternative protocols suitable for apoptosis detection with annexin include techniques and assays that utilize radiolabeled annexin V. In certain embodiments, the phenotype is or includes negative staining by annexin, e.g. annexin V$^-$. In particular embodiments, the phenotype is or includes the absence of PS on the outer plasma membrane. In certain embodiments, the phenotype is or includes cells that are not bound by annexin e.g. annexin V. In certain embodiments, the cell that lacks detectable PS on the outer membrane is annexin V$^-$. In particular embodiments, the cell that is not bound by annexin V$^-$ in an assay, e.g., flow cytometry after incubation with labeled annexin V, is annexin V$^-$.

In particular embodiments, the phenotype is annexin V$^-$, annexin V$^-$ CD3$^+$, annexin V$^-$CD4$^+$, annexin V$^-$ CD8$^+$, annexin V$^-$ CD3$^+$/CAR$^+$, annexin V$^-$ CD4$^+$/CAR$^+$, annexin V$^-$ CD8$^+$/CAR$^+$, activated caspase 3$^-$, activated caspase 3$^-$/CD3$^+$, activated caspase 3$^-$/CD4$^+$, activated caspase 3$^-$/CD8$^+$, activated caspase 3$^-$/CD3$^+$/CAR$^+$, activated caspase 3$^-$/CD4$^+$/CAR$^+$, activated caspase 3$^-$/CD8$^+$/CAR$^+$, annexin V$^-$/CD4$^+$/CCR7$^+$/CAR$^+$, annexin V$^-$/CD8$^+$/CD27$^+$/CAR$^+$, annexin V$^-$/CD4$^+$/CD27$^+$/CAR$^+$, annexin V$^-$/CD8$^+$/CCR7$^+$/CD27$^+$/CAR$^+$, annexin V$^-$/CD4$^+$/CCR7$^+$/CD27$^+$/CAR$^+$, annexin V$^-$/CD8$^+$/CCR7$^+$/CD45RA$^-$/CAR$^+$ or annexin V$^-$/CD4$^+$/CCR7$^+$/CD45RA$^-$; activated caspase 3$^-$/CD4$^+$/CCR7$^+$/CAR$^+$, activated caspase 3$^-$/CD8$^+$/CD27$^+$/CAR$^+$, activated caspase 3$^-$/CD4$^+$/CD27$^+$/CAR$^+$, activated caspase 3$^-$/CD8$^+$/CCR7$^+$/CD27$^+$/CAR$^+$, activated caspase 3$^-$/CD4$^+$/CCR7$^+$/CD27$^+$/CAR$^+$, activated caspase 3$^-$/CD8$^+$/CCR7$^+$/CD45RA$^-$/CAR$^+$ or activated caspase 3$^-$/CD4$^+$/CCR7$^+$/CD45RA$^-$ or a combination thereof.

Particular embodiments contemplate that cells positive for expression of a marker for apoptosis are undergoing programmed cell death, show reduced or no immune function, and have diminished capabilities if any to undergo activation, expansion, and/or bind to an antigen to initiate, perform, or contribute to an immune response or activity. In particular embodiments, the phenotype is defined by negative expression for an activated caspase and/or negative staining with annexin V.

In certain embodiments, the phenotype is or includes activated caspase 3$^-$ (caspase 3$^-$) and/or annexin V.

Among the phenotypes are the expression or surface expression of one or more markers generally associated with one or more sub-types or subpopulations of T cells, or phenotypes thereof. T cell subtypes and subpopulations may include CD4$^+$ and/or of CD8$^+$ T cells and subtypes thereof that may include naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), $T_{EMRA}$ cells or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some aspects, among the phenotypes include expression or markers or functions, e.g. antigen-specific functions such as cytokine secretion, that are associated with a less differentiated cell subset or a more differentiated subset. In some embodiments, the phenotypes are those associated with a less differentiated subset, such as one or more of CCR7$^+$, CD27$^+$ and interleukin-2 (IL-2) production. In some aspects, less differentiated subsets can also be related to therapeutic efficacy, self-renewal, survival functions or graft-versus-host disease. In some embodiments, the phenotypes are those associated with a more differentiated subset, such as one or more of interferon-gamma (IFN-γ) or IL-13 production. In some aspects, more differentiated subsets can also be related to senescence and effector function.

In some embodiments, the phenotype is or includes a phenotype of a memory T cell or memory T cell subset exposed to their cognate antigen. In some embodiments the phenotype is or includes a phenotype of a memory T cell (or one or more markers associated therewith), such as a $T_{CM}$ cell, a $T_{EM}$ cell, or a $T_{EMRA}$ cell, a $T_{SCM}$ cell, or a combination thereof. In particular embodiments, the phenotype is or includes the expression of one or more specific molecules that is a marker for memory and/or memory T cells or subtypes thereof. In some aspects, exemplary phenotypes associated with $T_{CM}$ cells can include one or more of CD45RA$^-$, CD62L$^+$, CCR7$^+$ and CD95$^+$. In some aspects, exemplary phenotypes associated with $T_{EM}$ cells can include one or more of CD45RA$^-$, CD62L$^-$, CCR7$^-$ and CD95$^+$.

In particular embodiments, the phenotype is or includes the expression of one or more specific molecules that is a marker for naïve T cells.

In some embodiments, the phenotype is or includes a memory T cell or a naïve T cell. In certain embodiments, the phenotype is the positive or negative expression of one or more specific molecules that are markers for memory. In some embodiments, the memory marker is a specific molecule that may be used to define a memory T cell population.

In some embodiments, the phenotype is or includes a phenotype of or one or more marker associated with a non-memory T cell or sub-type thereof; in some aspects, it is or includes a phenotype or marker(s) associated with a naïve cell. In some embodiments, the phenotype is CCR7$^+$/CD27$^+$/CD28$^+$/CD45RA$^+$. In certain embodiments, the phenotype is or includes CCR7$^+$/CD45RA$^+$. In some embodiments, the phenotype is or includes a phenotype of a central memory T cell. In particular embodiments, the phenotype is or includes CCR7$^+$/CD27$^+$/CD28$^+$/CD45RA$^-$. In some embodiments, the phenotype is or includes CCR7$^-$/CD27$^+$/CD28$^+$/CD45RA$^-$. In certain embodiments, the phenotype is or includes that of a $T_{EMRA}$ cell or a $T_{SCM}$ cell. In certain embodiments, the phenotype is or includes CD45RA$^+$. In particular embodiments, the phenotype is or includes CCR7$^-$/CD27$^-$/CD28$^-$/CD45RA$^+$. In some embodiments, the phenotype is or includes one of CD27$^+$/CD28$^+$, CD27$^-$/CD28$^+$, CD27$^+$/CD28$^-$, or CD27$^-$/CD28$^-$. In some embodiments, the phenotype is CCR7$^+$/CD27$^+$/CD45RA$^+$. In certain embodiments, the phenotype is or includes CCR7$^+$/CD45RA$^+$. In particular embodiments, the phenotype is or includes CCR7$^+$/CD27$^+$/CD45RA$^-$. In some embodiments, the phenotype is or includes CCR7$^-$/CD27$^+$/CD45RA$^-$. In certain embodiments, the phenotype is or includes CD45RA$^+$. In particular embodiments, the phenotype is or includes CCR7$^-$/CD27$^-$/CD45RA$^+$.

In some embodiments the phenotype is or includes any of the foregoing phenotypic properties and further includes the expression of a recombinant receptor, such as phenotype associated with a memory T cell or memory subtype and that expresses a CAR, or a phenotype associated with a naïve cell that expresses a CAR. In certain embodiments, the phenotype is or includes that of a central memory T cell or stem central memory T cell that expresses a CAR. In particular embodiments, the phenotype is or includes that of an effector memory cell that expresses a CAR. In some embodiments, the phenotype is or includes that of a $T_{EMRA}$ cell that expresses a CAR. In particular embodiments, the phenotype is or includes CAR+/CCR7+/CD27+/CD28+/CD45RA−; CAR+/CCR7−/CD27+/CD28+/CD45RA−; CAR+/CCR7−/CD27−/CD28−/CD45RA+; CAR+/CD27+/CD28+; CAR+/CD27−/CD28+; CAR+/CD27+/CD28−; or CAR+/CD27−/CD28−. In particular embodiments, the phenotype is or includes CAR+/CCR7+/CD27+/CD45RA−; CAR+/CCR7−/CD27+/CD45RA−; CAR+/CCR7−/CD27−/CD28−/CD45RA+; CAR+/CD27+; CAR+/CD27−; CAR+/CD27+/CD28−; or CAR+/CD27−/CD28−.

In certain embodiments, the phenotype is or includes a phenotype of a T cell that is negative for a marker of apoptosis. In certain embodiments, the phenotype is or includes a naïve cell that is negative for a marker of apoptosis. In some embodiments, the marker of apoptosis is activated caspase 3. In some embodiments, the marker of apoptosis is positive staining by annexin V.

In particular embodiments, the phenotype is or includes that of a memory T cell or subtype thereof that is negative for a marker of apoptosis that expresses a CAR. In particular embodiments, the phenotype is or includes that of a memory T cell or particular subtype that is negative for a marker of apoptosis that expresses a CAR. In certain embodiments, the phenotype is or includes a naïve cell that is negative for a marker of apoptosis that expresses a CAR. In certain embodiments, the phenotype is or includes that of a central memory T cell or $T_{SCM}$ ell or naïve cell that is negative for a marker of apoptosis that expresses a CAR. In particular embodiments, the phenotype is or includes that of an effector memory cell that is negative for a marker of apoptosis that expresses a CAR. In certain embodiments, the phenotype is or includes annexin V−/CAR+/CCR7+/CD27+/CD28+/CD45RA−; annexin V−/CAR+/CCR7−/CD27+/CD28+/CD45RA−; annexin V−/CAR+/CCR7−/CD27−/CD28−/CD45RA+; annexin V−/CAR+/CD27+/CD28+; annexin V−/CAR+/CD27−/CD28+; annexin V−/CAR+/CD27+/CD28−; or annexin V−/CAR+/CD27−/CD28−. In certain embodiments, the phenotype is or includes activated caspase 3−/CAR+/CCR7+/CD27+/CD28+/CD45RA−; activated caspase 3−/CAR+/CCR7−/CD27+/CD28+/CD45RA−; activated caspase 3−/CAR+/CCR7−/CD27−/CD28−/CD45RA+; activated caspase 3−/CAR+/CD27+/CD28+; activated caspase 3−/CAR+/CD27−/CD28+; activated caspase 3−/CAR+/CD27+/CD28−; or activated caspase 3−/CAR+/CD27−/CD28−. In certain embodiments, the phenotype is or includes annexin V−/CAR+/CCR7+/CD27+/CD45RA−; annexin V−/CAR+/CCR7−/CD27+/CD45RA−; annexin V−/CAR+/CCR7−/CD27−/CD45RA+; annexin V−/CAR+/CD27+/CD28+; annexin V−/CAR+/CD27−/CD28+; annexin V−/CAR+/CD27+; or annexin V−/CAR+/CD27−. In certain embodiments, the phenotype is or includes activated caspase 3−/CAR+/CCR7+/CD27+/CD45RA−; activated caspase 3−/CAR+/CCR7−/CD27+/CD45RA−; activated caspase 3−/CAR+/CCR7−/CD27−/CD45RA+; activated caspase 3−/CAR+/CD27+/CD28+; activated caspase 3−/CAR+/CD27−/CD28+; activated caspase 3−/CAR+/CD27+; or activated caspase 3−/CAR+/CD27−.

In particular embodiments, the phenotype is or includes CD27+/CD28+, CD27−/CD28+, CD27+/CD28−, CD27−/CD28−, or a combination thereof. In some embodiments, the phenotype is or includes CAR+/CD27+/CD28+, CAR+/CD27−/CD28+, CAR+/CD27+/CD28−, CAR+/CD27−/CD28−, or a combination thereof. In certain embodiments, the phenotype is or includes activated caspase 3−/CAR+/CD27+/CD28+, activated caspase 3−/CAR+/CD27−/CD28+, activated caspase 3−/CAR+/CD27+/CD28−, activated caspase 3−/CAR+/CD27−/CD28−, or a combination thereof. In particular embodiments, the phenotype is or includes annexin V−/CAR+/CD27+/CD28+, annexin V−/CAR+/CD27−/CD28+, annexin V−/CAR+/CD27+/CD28−, annexin V−/CAR+/CD27−/CD28−, or a combination thereof. In particular embodiments, the phenotype is or includes CD27+, CD27+, CD27−, or a combination thereof. In some embodiments, the phenotype is or includes CAR+/CD27+, CAR+/CD27−, CAR+/CD27+, CAR+/CD27−, or a combination thereof. In certain embodiments, the phenotype is or includes activated caspase 3−/CAR+/CD27+, activated caspase 3−/CAR+/CD27−, activated caspase 3−/CAR+/CD27+, activated caspase 3−/CAR+/CD27−, or a combination thereof. In particular embodiments, the phenotype is or includes annexin V−/CAR+/CD27+, annexin V−/CAR+/CD27−, annexin V−/CAR+/CD27+, annexin V−/CAR+/CD27−, or a combination thereof.

In particular embodiments, the phenotype is or includes CCR7+/CD28+, CCR7−/CD28+, CCR7+/CD28−, CCR7−/CD28−, or a combination thereof. In some embodiments, the phenotype is or includes CAR+/CCR7+/CD28+, CAR+/CCR7−/CD28+, CAR+/CCR7+/CD28−, CAR+/CCR7−/CD28−, or a combination thereof. In certain embodiments, the phenotype is or includes activated caspase 3−/CAR+/CCR7+/CD28+, activated caspase 3−/CAR+/CCR7−/CD28+, activated caspase 3−/CAR+/CCR7+/CD28−, activated caspase 3−/CAR+/CCR7−/CD28−, or a combination thereof. In particular embodiments, the phenotype is or includes annexin V−/CAR+/CCR7+/CD28+, annexin V−/CAR+/CCR7−/CD28+, annexin V−/CAR+/CCR7+/CD28−, annexin V−/CAR+/CCR7−/CD28−, or a combination thereof. In particular embodiments, the phenotype is or includes CCR7+, CCR7−, CCR7+, CCR7−, or a combination thereof. In some embodiments, the phenotype is or includes CAR+/CCR7+, CAR+/CCR7−, CAR+/CCR7+, CAR+/CCR7−, or a combination thereof. In certain embodiments, the phenotype is or includes activated caspase 3−/CAR+/CCR7+, activated caspase 3−/CAR+/CCR7−, activated caspase 3−/CAR+/CCR7+, activated caspase 3−/CAR+/CCR7−, or a combination thereof. In particular embodiments, the phenotype is or includes annexin V−/CAR+/CCR7+, annexin V−/CAR+/CCR7−, annexin V−/CAR+/CCR7+, annexin V−/CAR+/CCR7−, or a combination thereof.

In some embodiments, the phenotype is or includes positive or negative expression of a marker of exhaustion. In certain embodiments, the phenotype is or includes positive or negative expression of a specific molecule that is associated with exhaustion. In certain embodiments, the specific molecule is any molecule that is associated with exhaustion or a quality associated with exhaustion, e.g., poor effector function or inhibitory receptor expression. In particular embodiments, the phenotype is positive or negative expression of an immune checkpoint inhibitor. In particular embodiments, marker of exhaustion is CTLA-4, FOXP3, PD-1, TIGIT, LAB-3, 2B4, BTLA, TIM3, VISTA, or CD96, or a combination thereof. In certain embodiments, the phenotype is the positive or negative expression of CTLA-4, FOXP3, PD-1, TIGIT, LAB-3, 2B4, BTLA, TIM3, VISTA, or CD96, or a combination thereof. In particular embodiments, the phenotype is positive or negative expression of PD1 and/or FOXP3.

In some embodiments, the phenotype is or includes positive or negative expression of an exhaustion marker in a CD3+ cell that expresses a recombinant receptor or a CAR. In particular embodiments, the phenotype is or includes positive or negative expression of an exhaustion marker in a CD4+ cell that expresses a recombinant receptor or a CAR. In some embodiments, the phenotype is or includes positive or negative expression of an exhaustion marker and CD3+ and positive expression of a recombinant receptor or a CAR. In particular embodiments, the phenotype is or includes positive or negative expression of an exhaustion marker in a CD4$^+$ cell that expresses a recombinant receptor or a CAR. In some embodiments, the phenotype is or includes positive or negative expression of an exhaustion marker in a CD8$^+$ cell that expresses a recombinant receptor or a CAR. In particular embodiments, the exhaustion marker is one or more of CTLA-4, FOXP3, PD-1, TIGIT, LAB-3, 2B4, BTLA, TIM3, VISTA, or CD96. In particular embodiments, the exhaustion marker is PD1 and/or FOXP3.

In particular embodiments, the phenotype is or includes PD1$^-$/CD3$^+$, PD1$^-$/CD4$^+$, PD1$^-$/CD8$^+$, PD1$^-$/CD3$^+$/CAR$^+$, PD1$^-$/CD4$^+$/CAR$^+$, PD1$^-$/CD8$^+$/CAR$^+$, PD1/annexin V$^-$, PD1$^-$/annexin V$^-$/CD3$^+$, PD1$^-$/annexin V$^-$/CD4$^+$, PD1$^-$/annexin V$^-$/CD8$^+$, PD1$^-$/annexin V/$^-$CD3$^+$/CAR$^+$, PD1$^-$/annexin V$^-$/CD4$^+$/CAR$^+$, PD1$^-$/annexin V$^-$/CD8$^+$/CAR$^+$, PD1$^-$/activated caspase 3$^-$, PD1$^-$/activated caspase 3$^-$/CD3$^+$, PD1$^-$/activated caspase 3$^-$/CD4$^+$, PD1$^-$/activated caspase 3$^-$/CD8$^+$, PD1/activated caspase 3$^-$/CD3$^+$/CAR$^+$, PD1/activated caspase 3$^-$/CD4$^+$/CAR$^+$, PD1/activated caspase 3$^-$/CD8$^+$/CAR$^+$, or a combination thereof.

In certain embodiments, the phenotype is or includes FOXP3$^-$/CD3$^+$, FOXP3-CD4$^+$, FOXP3$^-$/CD8$^+$, FOXP3$^-$/CD3$^+$/CAR$^+$, FOXP3$^-$/CD4$^+$/CAR$^+$, FOXP3$^-$/CD8$^+$/CAR$^+$, FOXP3$^-$/annexin V$^-$, FOXP3$^-$/annexin V$^-$/CD3$^+$, FOXP3$^-$/annexin V$^-$/CD4$^+$, FOXP3$^-$/annexin V$^-$/CD8$^+$, FOXP3$^-$/annexin V/$^-$CD3$^+$/CAR$^+$, FOXP3$^-$/annexin V$^-$/CD4$^+$/CAR$^+$, FOXP3$^-$/annexin V$^-$/CD8$^+$/CAR$^+$, FOXP3$^-$/activated caspase 3$^-$, FOXP3$^-$/activated caspase 3$^-$/CD3$^+$, FOXP3$^-$/activated caspase 3$^-$/CD4$^+$, FOXP3$^-$/activated caspase 3$^-$/CD8$^+$, FOXP3$^-$/activated caspase 3$^-$/CD3$^+$/CAR$^+$, FOXP3$^-$/activated caspase 3$^-$/CD4$^+$/CAR$^+$, FOXP3$^-$/activated caspase 3$^-$/CD8$^+$/CAR$^+$, or a combination thereof.

In certain embodiments, the phenotype is the negative expression of a specific molecule that is associated with T cell activation. In some embodiments, the phenotype is or includes the negative expression of one or more of a specific molecule that is an activation marker. In general, T cell activation requires two simultaneous signals. The first is binding of the T cell receptor complex (TCR) to a major histocompatibility complex (MHC) molecule carrying a peptide antigen. The second is provided by the binding of the co-stimulatory receptor CD28 to proteins in the surface of the APC, such as B7-2 or B7-1. In certain embodiments, the specific molecule is associated with TCR activation, e.g., is activated, altered, or expressed as a result of T cell activation. In some embodiments, the specific molecule is associated with activation of a CD28 receptor, e.g., a molecule that is activated, altered, or expressed as a result of T cell activation.

In particular embodiments, the phenotype is or includes the negative expression of one or more of a specific molecule that is an activation marker. In certain embodiments, the activation marker is one or more of CD25, CD26, CD27, CD28, CD30, CD71, CD154, CD40L, CD127, LAG3, Ki67, or a combination thereof. In certain embodiments, the phenotype is the negative or positive expression of one or more of CD25, CD26, CD27, CD28, CD30, CD71, CD154, CD40L, CD127, LAG3, or Ki67. In certain embodiments, the phenotype is or includes the expression of CD25, CD127, LAG3, Ki67, or a combination thereof.

In some embodiments, the phenotype is or includes positive or negative expression of an activation marker in a CD3$^+$ cell that expresses a recombinant receptor or a CAR. In particular embodiments, the phenotype is or includes positive or negative expression of activation marker in a CD4$^+$ cell that expresses a recombinant receptor or a CAR. In some embodiments, the phenotype is or includes positive or negative expression of activation marker in a CD8$^+$ cell that expresses a recombinant receptor or a CAR. In particular embodiments, the activation marker is one or more of CD25, CD26, CD27, CD28, CD30, CD71, CD154, CD40L, CD127, LAG3, or Ki67. In particular embodiments, the activation marker is CD25, CD127, LAG3, Ki67, or a combination thereof.

In particular embodiments, the phenotype is or includes positive or negative expression of an activation marker and CD3$^+$, CD4$^+$, CD8$^+$, CD3$^+$/CAR$^+$, CD4$^+$/CAR$^+$, CD8$^+$/CAR$^+$, annexin V$^-$, annexin V$^-$/CD3$^+$, annexin V$^-$/CD4$^+$, annexin V$^-$/CD8$^+$, annexin V/$^-$CD3$^+$/CAR$^+$, annexin V$^-$/CD4$^+$/CAR$^+$, annexin V$^-$/CD8$^+$/CAR$^+$, activated caspase 3$^-$, activated caspase 3$^-$/CD3$^+$, activated caspase 3$^-$/CD4$^+$, activated caspase 3$^-$CD8$^+$, activated caspase 3$^-$/CD3$^+$/CAR$^+$, activated caspase 3$^-$/CD4$^+$/CAR$^+$, activated caspase 3$^-$/CD8$^+$/CAR$^+$, or a combination thereof.

In some embodiments, the phenotype is assessed by a response to a stimulus, for example a stimulus that triggers, induces, stimulates, or prolongs an immune cell function. In certain embodiments, the cells are incubated in the presence of stimulating conditions or a stimulatory agent, the phenotype is or includes the response to the stimulation. In particular embodiments, the phenotype is or includes the production or secretion of a soluble factor in response to one or more stimulations. In some embodiments, the phenotype is or includes a lack or production or secretion of a soluble factor in response to one or more stimulations. In certain embodiments, the soluble factor is a cytokine. In some embodiments, the cytokine is IL-2. In some embodiments, the cytokine is TNFa.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells. In some embodiments, the cells are stimulated and the phenotype is determined by whether or not a soluble factor, e.g., a cytokine or a chemokine, is produced or secreted. In some embodiments, the stimulation is nonspecific, i.e., is not an antigen-specific stimulation. In some embodiments, the stimulation comprises PMA and ionomycin. In some embodiments, cells are incubated in the presence of stimulating conditions or a stimulatory agent for about 1 hour, about 2 hours, about 3 hours, about 4 hours, about 5 hours, about 6 hours, about 7 hours, about 8 hours, about 9 hours, about 10 hours, about 11 hours, about 12 hours, about 18 hours, about 24 hours, about 48 hours, or for a duration of time between 1 hour and 4 hours, between 1 hour and 12 hours, between 12 hours and 24 hours, or for more than 24 hours.

In some embodiments, the cells are stimulated with an agent that is an antigen or an epitope thereof that is specific to the recombinant receptor, or is an antibody or fragment thereof that binds to and/or recognizes the recombinant receptor, or a combination thereof. In some embodiments, the recombinant receptor is a CAR, and the agent is an antigen or an epitope thereof that is specific to the CAR, or is an antibody or fragment thereof that binds to and/or recognizes the CAR, or a combination thereof. In particular embodiments, the cells are stimulated by incubating the cells in the presence of target cells with surface expression of the antigen that is recognized by the CAR. In certain embodiments, the recombinant receptor is a CAR, and the agent is an antibody or an active fragment, variant, or portion thereof that binds to the CAR. In certain embodiments, the antibody or the active fragment, variant, or portion thereof that binds to the CAR is an anti-idiotypic (anti-ID) antibody.

In some embodiments, the stimulating conditions or agents include one or more agent, e.g., ligand, which is capable of stimulating or activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to a solid support such as a bead, and/or one or more cytokines. In some embodiments, the one or more agents are PMA and ionomycin.

In particular embodiments, the phenotype is or includes the production or secretion of a cytokine in response to one or more of stimulations. The production and/or the secretion of cytokines contributes to immune responses, and is involved in different processes including the induction of anti-viral proteins and the induction of T cell proliferation. Cytokines are not pre-formed factors but are rapidly produced and secreted in response to cellular activation. The production or secretion of cytokines may be measured, detected, and/or quantified by any suitable technique known in the art.

In certain embodiments, the phenotype is the production of one or more cytokines. In some embodiments, the production of two or more cytokines from the same cell can be indicative of polyfunctional features of such cells. In particular embodiments, the production of one or more cytokines is measured, detected, and/or quantified by intracellular cytokine staining. Intracellular cytokine staining (ICS) by flow cytometry is a technique well-suited for studying cytokine production at the single-cell level. It detects the production and accumulation of cytokines within the endoplasmic reticulum after cell stimulation, allowing for the identification of cell populations that are positive or negative for production of a particular cytokine or for the separation of high producing and low producing cells based on a threshold. In some embodiments, as described above, the stimulation can be performed using nonspecific stimulation, e.g., is not an antigen-specific stimulation. For example, PMA/ionomycin can be used for nonspecific cell stimulation. In some embodiments, the stimulation can be performed by an agent that is an antigen or an epitope thereof that is specific to the recombinant receptor (e.g., CAR), or is an antibody or fragment thereof that binds to and/or recognizes the recombinant receptor, or a combination thereof. ICS can also be used in combination with other flow cytometry protocols for immunephenotyping using cell surface markers or with MHC multimers to access cytokine production in a particular subgroup of cells, making it an extremely flexible and versatile method. Other single-cell techniques for measuring or detecting cytokine production include, but are not limited to ELISPOT, limiting dilution, and T cell cloning.

In some embodiments, the phenotype is the production of a cytokine, such as following stimulation of the recombinant receptor with an antigen specific to and/or recognized by the recombinant receptor. In particular embodiments, the phenotype is the lack of the production of the cytokine, such as following stimulation of the recombinant receptor with an antigen specific to and/or recognized by the recombinant receptor. In particular embodiments, the phenotype is positive for or is a high level of production of a cytokine. In certain embodiments, the phenotype is negative for or is a low level of production of a cytokine. Cytokines may include, but are not limited to, interleukin-1 (IL-1), IL-1β, IL-2, sIL-2Ra, IL-3, IL-5, IL-6, IL-7, IL-8, IL-13, IL-12, IL-13, IL 27, IL-33, IL-35, TNF, tumor necrosis factor alpha (TNF-α), CXCL2, CCL2, CCL3, CCL5, CCL17, CCL24, PGD2, LTB4, interferon gamma (IFN-γ), granulocyte macrophage colony stimulating factor (GM-CSF), macrophage inflammatory protein (MIP)-1α, MIP-1β, Flt-3L, fracktalkine, and/or IL-5. In some embodiments, the phenotype includes production of cytokines, e.g., cytokines associated with particular cell types, such as cytokines associated with Th1, Th2, Th17 and/or Treg subtypes. In some embodiments, exemplary Th1-related cytokines include IL-2, IFN-γ, and transforming growth factor beta (TGF-β), and in some cases are involved in cellular immune responses. In some embodiments, exemplary Th2-related cytokines include IL-4, IL-5, IL-6, IL-10 and IL-13, and in some cases are associated with humoral immunity and anti-inflammatory properties. In some embodiments, exemplary Th17-related cytokines include IL-17A and IL-17F, and in some cases are involved in recruiting neutrophils and macrophages, e.g., during an inflammatory reaction.

In some embodiments, the phenotype is or includes the production of a cytokine. In certain embodiments, the phenotype is or includes the production of more than one cytokine (e.g., polyfunctional). In certain embodiments, the phenotype is or includes a lack of a production of one or more cytokines. In certain embodiments, the phenotype is or includes the production, or lack thereof, of one or more of IL-2, IL-5, IL-13, IFN-gamma, or TNF-alpha. In certain embodiments, the phenotype is or includes the production, or lack thereof, of one or more of IL-2, IL-13, IFN-gamma, or TNF-alpha. In some embodiments, the phenotype is the presence of a production, and/or the presence of a high level of production of the cytokine. In some embodiments, the phenotype is a low, reduced, or absent production of a cytokine.

In some embodiments, the phenotype is or includes the internal (intracellular) production of a cytokine, for example, as assessed in the presence of a stimulatory agent or under stimulatory conditions when secretion is prevented or inhibited. In some embodiments, the stimulatory agent is nonspecific stimulatory agent, e.g., a stimulatory agent that does not bind to an antigen binding domain, for example on a recombinant receptor (e.g., CAR). In some embodimetns, the stimulatory agent is PMA/ionomycin, which can act as a nonspecific stimulatory agent. In some embodiments, the stimulatory agent is a specific stimulatory agent, e.g., is a stimulatory agent that is an antigen or an epitope thereof that is specific to the recombinant receptor (e.g., CAR), or is an antibody or fragment thereof that binds to and/or recognizes the recombinant receptor, or a combination thereof. In particular embodiments, the phenotype is or includes the lack or absence of an internal production of a cytokine. In certain embodiments, the phenotype is or includes the internal amount of one or more cytokines when the production of more than one cytokines as assessed with an ICS assay. In certain embodiments, the phenotype is or includes the internal amount of one or more of IL-2, IL-5, IL-13, IFN-gamma, or TNF-alpha as assessed with an ICS assay. In some embodiments, the phenotype is or includes a low internal amount or a lack of a detectable amount of one or more cytokines as assessed with an ICS assay. In certain embodiments, phenotype is or includes a low internal amount or a lack of a detectable amount of IL-2, IL-5, IL-13, IFN-gamma, or TNF-alpha as assessed with an ICS assay. In some embodiments, the phenotype includes assessment of multiple cytokines, e.g., by multiplexed assays or assays to assess polyfunctionality (see, e.g., Xue et al., (2017) Journal for ImmunoTherapy of Cancer 5:85). In some embodiments, the lack of cytokine expression is inversely correlated with or associated with activity and/or function of the cells and/or durability of response and progression free survival. In some embodiments, cells with reduced, minimal or no cytokine production, assessed according to any known method or method described herein, are reduced in the cell composition (e.g., output composition, therapeutic cell composition).

Particular embodiments contemplate that the phenotype may include the production of a cytokine or a lack of or a low amount of production for a cytokine. This may depend on several factors that include, but are not limited to, the identity of the cytokine, the assay performed to detect the cytokine, and the stimulatory agent or condition used with the assay. For example, in some embodiments it is contemplated that the phenotype is or includes a lack of, or a low level of IL-13 production as indicated by ICS while in some embodiments, the phenotype is or includes production of IFN-gamma as indicated by ICS.

In some embodiments, the phenotype is or includes production of one or more cytokines and either $CD3^+$, $CD4^+$, $CD8^+$, $CD3^+/CAR^+$, $CD4^+/CAR^+$, $CD8^+/CAR^+$, annexin $V^-$, annexin $V^-$ $CD3^+$, annexin $V^-CD4^+$, annexin $V^-$ $CD8^+$, annexin $V^-CD3^+/CAR^+$, annexin $V^-$ $CD4^+/CAR^+$, annexin $V^-$ $CD8^+/CAR^+$, activated caspase $3^-$, activated caspase $3^-/CD3^+$, activated caspase $3^-/CD4^+$, activated caspase $3^-/CD8^+$, activated caspase $3^-/CD3^+/CAR^+$, activated caspase $3^-/CD4^+/CAR^+$, or activated caspase $3^-/CD8^+/CAR^+$, or a combination thereof. In particular embodiments, the phenotype is or includes production of one or more cytokines in $CD4^+/CAR^+$ and/or $CD8^+/CAR^+$. In some embodiments, the one or more cytokines are IL-2, IFN-gamma, and/or TNF-alpha. In some embodiments, the phenotype is or includes production of IL-2 in $CD4^+/CAR^+$ cells. In some embodiments, the phenotype is or includes production of TNF-alpha in $CD4^+/CAR^+$ cells. In some embodiments, the phenotype is or includes production of IL-2 and TNF-alpha in $CD4^+/CAR^+$ cells. In some embodiments, the phenotype is or includes production of IL-2 and IFN-gamma in $CD4^+/CAR^+$ cells. In some embodiments, the phenotype is or includes production of TNF-alpha in $CD8^+/CAR^+$ cells. In some embodiments, the phenotype is or includes production of IFN-gamma and TNF-alpha in $CD8^+/CAR^+$ cells. In some embodiments, the phenotype is or includes production of IL-2 in activated caspase $3^-/CD4^+/CAR^+$ cells. In some embodiments, the phenotype is or includes production of TNF-alpha in activated caspase $3^-/CD4^+/CAR^+$ cells. In some embodiments, the phenotype is or includes production of IL-2 and TNF-alpha in activated caspase $3^-/CD4^+/CAR^+$ cells. In some embodiments, the phenotype is or includes production of IL-2 and IFN-gamma in activated caspase $3^-/CD4^+/CAR^+$ cells. In some embodiments, the phenotype is or includes production of TNF-alpha in activated caspase $3^-/CD8^+/CAR^+$ cells. In some embodiments, the phenotype is or includes production of IFN-gamma and TNF-alpha in activated caspase $3^-/CD8^+/CAR^+$ cells. In some embodiments, the phenotype is or includes production of TNF-alpha in annexin $V^-/CD4^+/CAR^+$ cells. In some embodiments, the phenotype is or includes production of IL-2 and TNF-alpha in annexin $V^-/CD4^+/CAR^+$ cells. In some embodiments, the phenotype is or includes production of IL-2 and IFN-gamma in annexin $V^-/CD4^+/CAR^+$ cells. In some embodiments, the phenotype is or includes production of TNF-alpha in annexin $V^-/CD8^+/CAR^+$ cells. In some embodiments, the phenotype is or includes production of IFN-gamma and TNF-alpha in annexin $V^-/CD8^+/CAR^+$ cells. In some embodiments, the phenotypes described in this paragraph are positively correlated with durable response and progression free survival. Thus, in some embodiments, cells including these phenotypes are maximized or increased in the cell composition (e.g., output composition, therapeutic cell composition). In some embodiments, the cell composition includes at least at or about, or at or about, 70%, 80%, 85%, 90%, 91%, 92%, 93%, 94%, 95%, 96%, 97%, 98%, 99% or 100% of the total number of $CD4^+$ T cells, such as engineered CD4 T cells expressing a recombinant receptor (e.g., CAR), in the composition that are capable of producing a cytokine selected from interleukin 2 (IL-2) and/or TNF-alpha. In some embodiments, the cell composition includes at least at or about, or at or about, 10%, 15%, 20%, 25%, 30%, 40% or more, of the total number of $CD4^+$ T cells, such as engineered CD4 T cells expressing a recombinant receptor (e.g., CAR), in the composition polyfunctional for producing two or more cytokines selected from among interferon-gamma (IFN-gamma), interleukin 2 (IL-2) and TNF-alpha.

In some embodiments, the phenotype is or includes a lack of production of one or more cytokines. In certain embodiments, the phenotype is or includes a lack of a production of one or more cytokines and either $CD3^+$, $CD4^+$, $CD8^+$, $CD3^+/CAR^+$, $CD4^+/CAR^+$, $CD8^+/CAR^+$, annexin $V^-$, annexin $V^-$ $CD3^+$, annexin $V^-CD4^+$, annexin $V^-$ $CD8^+$, annexin $V^-CD3^+/CAR^+$, annexin $V^-$ $CD4^+/CAR^+$, annexin $V^-$ $CD8^+/CAR^+$, activated caspase $3^-$, activated caspase $3^-/CD3^+$, activated caspase $3^-/CD4^+$, activated caspase $3^-/CD8^+$, activated caspase $3^-/CD3^+/CAR^+$, activated caspase $3^-/CD4^+/CAR^+$, or activated caspase $3^-/CD8^+/CAR^+$, or a combination thereof. In some embodiments, the one or more cytokines are IL-2, IFN-gamma, and/or TNF-alpha. In some embodiments, the phenotype is or includes the lack of production of IL-2 in activated caspase $3^-/CD4^+/CAR^+$ cells. In some embodiments, the phenotype is or includes the lack of production of TNF-alpha in activated caspase $3^-/CD4^+/CAR^+$ cells. In some embodiments, the phenotype is or includes the lack of production of IL-2 and TNF-alpha in activated caspase $3^-/CD4^+/CAR^+$ cells. In some embodiments, the phenotype is or includes the lack of production of IL-2 and IFN-gamma in activated caspase $3^-/CD4^+/CAR^+$ cells. In some embodiments, the phenotype is or includes the lack of production of TNF-alpha in activated caspase $3^-/CD8^+/CAR^+$ cells. In some embodiments, the phenotype is or includes the lack of production of INF-gamma and TNF-alpha in activated caspase $3^-/CD8^+/CAR^+$ cells. In some embodiments, the phenotypes described in this paragraph are negatively correlated with durable response and progression free survival. Thus, in some embodiments, cells including these phenotypes are minimized or reduced in the cell composition (e.g., output composition, therapeutic cell composition). For example, in some embodiments, cells including the phenotype of this paragraph compose less than 2%, 5%, 10%, 15,%, 20,%, or 25% of the total cells in the cell composition (e.g., output composition, therapeutic cell composition).

In particular embodiments, the phenotype is or includes the presence or absence of an internal amount of one or more of IL-2, IL-13, IFN-gamma, or TNF-alpha as assessed with an ICS assay and one or more specific markers for a subset of cells or cells of a particular cell type. In some embodiments, the phenotype is or includes production, or lack thereof, of one or more of IL-2, IL-13, IFN-gamma, or TNF-alpha and $CD4^+/CAR^+$ and/or $CD8^+/CAR^+$. In certain embodiments, the phenotype is or includes production of IL-2 and CD4$^+$/CAR$^+$ and/or CD8$^+$/CAR$^+$. In some embodiments, the phenotype is or includes a lack of or low production of IL-2 and CD4$^+$/CAR$^+$ and/or CD8$^+$/CAR$^+$. In some embodiments, the phenotype is or includes production of IL-13 and CD4$^+$/CAR$^+$ and/or CD8$^+$/CAR$^+$. In some embodiments, the phenotype is or includes production of IL-13 and CD4$^+$/CAR$^+$ and/or CD8$^+$/CAR$^+$. In certain embodiments, the phenotype is or includes the lack of or low production of IL-13 and CD4$^+$/CAR$^+$ and/or CD8$^+$/CAR$^+$. In some embodiments, the phenotype is or includes production of IFN-gamma and CD4$^+$/CAR$^+$ and/or CD8$^+$/CAR$^+$. In certain embodiments, the phenotype is or includes production of TNF-alpha and CD4$^+$/CAR$^+$ and/or CD8$^+$/CAR$^+$. In certain embodiments, the phenotype is or includes a lack of or low production of TNF-alpha and CD4$^+$/CAR$^+$ and/or CD8$^+$/CAR$^+$.

Any one or more the phenotypes, alone or in combination, can be assessed or determined in accord with the provided methods. In some embodiments, the phenotype is CD3$^+$, CD3$^+$/CAR$^+$, CD4$^+$/CAR$^+$, CD8$^+$/CAR$^+$, or a combination thereof.

In certain embodiments, the phenotype is or includes CD3$^+$. In certain embodiments, the phenotype is or includes CD3$^+$/CAR$^+$. In some embodiments, the phenotype is or includes CD8$^+$/CAR$^+$. In certain embodiments, the phenotype is or includes CD4$^+$/CAR$^+$.

In particular embodiments, the phenotype is or includes Annexin-/CD3$^+$/CAR$^+$. In some embodiments, the phenotype is or includes Annexin-/CD4$^+$/CAR$^+$ In particular embodiments, the phenotype is Annexin-CD8$^+$/CAR.

In particular embodiments, the phenotype is or includes a lack of or a low amount of intracellular IL-2 and CD4$^+$/CAR$^+$. In particular embodiments, the phenotype is a lack of or a low amount of intracellular IL-13 and CD4$^+$/CAR$^+$. In some embodiments, the phenotype is a lack of or a low amount of intracellular expression of IL-13 and CD8$^+$/CAR$^+$ cells. In particular embodiments, the phenotype is a lack of or a low amount of intracellular TNF-alpha CD4$^+$/CAR$^+$.

In certain embodiments, the phenotype is or includes CD8$^+$/CAR$^+$. In certain embodiments, the phenotype is or includes annexin-CD8$^+$/CAR$^+$.

In some embodiments, the phenotype comprises an indicator of production of one or a combination of cytokines, optionally non-specific to the antigen or the recombinant receptor and/or that is polyclonally produced, wherein the one or more cytokines is IL-2, IL-13, IL-17, IFN-gamma or TNF-alpha. In some embodiments, the indicator of production is measured in an assay, optionally an intracellular cytokine staining assay, comprising incubating a sample of the T cell composition with a polyclonal agent, an antigen-specific agent or an agent that binds the recombinant receptor, optionally CAR. In some embodiments, the agent is or comprises PMA and ionomycin or is or comprises a T cell receptor or T cell receptor complex agonist. In some embodiments, the phenotype comprises negative expression of an activation marker, wherein the activation marker is selected from among CD25, CD127, LAG3, Ki67 and combinations thereof. In some embodiments, the phenotype comprises negative expression of an exhaustion marker, wherein the exhaustion maker is a PD1 or FOXP3 gene product or a combination thereof. In some embodiments, the phenotype comprises a naïve phenotype or a memory phenotype, optionally wherein the memory phenotype comprises a T effector memory phenotype, a T central memory phenotype, or a T effector memory phenotype expressing CD45RA (Temra).

In some embodiments, the recombinant receptor-dependent (e.g., CAR) activity is a measure of the production or accumulation of a proinflammatory cytokine, optionally, one of or a combination of TNF-alpha, IFN-gamma, and IL-2. In some embodiments, a reference measure is the average of the measure among a plurality, optionally at least 10, at least 15, at least 20, of reference therapeutic T cell compositions comprising the recombinant receptor (e.g., CAR) in which: (i) each of the reference therapeutic T cell compositions has been observed or determined to result in an acceptable safety profile following administration to a subject, optionally wherein the subject has a disease or condition expressing or associated with the antigen; and/or (ii) each of the reference therapeutic T cell compositions has been observed or determined to result in a desired efficacy following administration to a subject, optionally wherein the subject has a disease or condition expressing or associated with the antigen.

In certain embodiments, a number, multiple, or fraction of cells of a particular phenotype of a cell composition is determined, measured, obtained, detected, observed, and/or identified. In some embodiments, the cell composition is a T cell composition. In certain embodiments, the cell composition contains cells that express a recombinant receptor, e.g., a CAR. In particular embodiments, the cell composition is a therapeutic T composition containing cells that express a recombinant receptor that may be administered to a subject to treat a disease or condition. In certain embodiments, the number of cells of the phenotype is the total amount of cells of the phenotype of the cell composition. In certain embodiments, the number of cells of the phenotype is the total number of cells of the phenotype present in a dose of the cell composition. In particular embodiments, the number of cells of the phenotype is the number of cells of the phenotype present in a sample of the cell composition. In some embodiments, the number of the cells of the phenotype may be expressed as a frequency, ratio, and/or a percentage of cells of the phenotype present in the cell composition, or a dose or a sample thereof.

In particular embodiments, the number, multiple, or fraction of the cells of a phenotype is transformed, for example to compress the range of relevant values of the number, multiple, or fraction. In some embodiments, the transformation is any application of a deterministic mathematical function to each point in a data set, such as, each data point x is replaced with the transformed value y=f(x), where f is a function. In general, transforms may be applied so that the data appear to more closely meet the assumptions of a statistical inference procedure that is to be applied, or to improve the interpretability or appearance of graphs. In most cases the function that is used to transform the data is invertible, and generally is continuous. The transformation is usually applied to a collection of comparable measurements. Examples of suitable transformations include, but are not limited to, logarithm and square root transformation, reciprocal transformations, and power transformations. In certain embodiments, the number, multiple, or fraction of the cells of a phenotype is transformed by a logarithmic transformation. In certain embodiments, the logarithmic transformation is a common log ($\log_{10}(x)$), a natural log ($\ln(x)$) or a binary log ($\log_2(x)$).

B. Determining Dosing and Administration

The therapeutic composition or a dose thereof, in some embodiments contains the cells in amounts effective to treat or prevent the disease or condition, such as a therapeutically effective or prophylactically effective amount. In some embodiments, the composition includes the cells in an amount effective to reduce burden of the disease or condition. In some embodiments, the composition includes cells in an amount that provides more consistent outcome, e.g., response and/or safety outcomes, among a group of subjects administered the composition, and/or more consistent pharmacokinetic parameters. In some embodiments, the composition includes the cells in an amount effective to promote durable response and/or progression free survival. In some aspects, the provided methods involve assessing a therapeutic composition containing T cells for cell phenotypes, and determining doses based on such outcomes.

In some embodiments, the dose is determined to encompass a relatively consistent number, proportion, ratio and/or percentage of engineered cells having a particular phenotype in one or more particular compositions. In some aspects, the consistency is associated with or related to a relatively consistent activity, function, pharmacokinetic parameters, toxicity outcome and/or response outcome. In some aspects, in a plurality of subjects, compositions and/or doses the numbers, proportion, ratio and/or percentage, are relatively consistent, e.g., the number or ratio of cells that have a particular phenotoype, e.g., express CCR7 ($CCR7^+$) or, that produce a cytokine, for example, produce IL-2, TNF-alpha, or IFN-gamma, in the composition or unit dose, varies by no more than 40%, by no more than 30%, by no more than 20%, by no more than 10% or by no more than 5%. In some aspects the number or ratio of cells that have a particular phenotoype, e.g., express CCR7 ($CCR7^+$), in the compositon or unit dose, varies by no more than 20% or no more than 10% or no more than 5% from an average of said number or ratio in a plurality of T cell compositions produced by the process and/or varies from such average by no more than one standard deviation or varies by no more than 20% or no more than 10% or no more than 5% among a plurality of T cell compositions or doses determined. In some embodiments, the plurality of subjects includes at least 10 subjects, such as at least 15, at least 20, at least 25, at least 30, at least 40, at least 50, at least 60, at least 70, at least 80, at least 90, at least 100 or more subjects.

In some aspects, the dose, e.g., one or more unit dose(s) is determined based on the number, percentage, ratio, frequency and/or proportion of a particular subset of engineered T cells, e.g., cells having a particular phenotype, such as particular surface marker phenotype. In some aspects, the cell phenotype is determined based on expression and/or absence of expression of particular cell markers, e.g., surface markers. In some aspects, the cell marker includes markers indicative of viability and/or apoptotic state of the cells. In some aspects, exemplary markers include CD3, CD4, CD8, CCR7, CD27, CD45RA, annexin V, or activated caspase 3. In some aspects, an exemplary marker is CCR7. In some aspects, an exemplary marker is CD27. In some aspects, exemplary markers include CCR7 and/or CD27. In some aspects, exemplary markers include CCR7, CD27 and/or CD45RA.

In some embodiments, provided are methods involving administering to a subject one or more unit doses of a therapeutic T cell composition, such as any described herein and/or any unit dose determined by the methods provided herein.

In some embodiments, provided are methods involving administering to a subject having a disease or condition a unit dose of a T cell composition comprising cells comprising a recombinant receptor, such as a chimeric antigen receptor (CAR), that specifically binds to an antigen associated with the disease or condition, wherein either a defined number of total recombinant receptor-expressing cells (receptor$^+$) of the therapeutic composition, total $CD8^+$ recombinant receptor-expressing cells (receptor$^+$/$CD8^+$) are administered and/or a unit dose of such cells is administered in which the unit dose contains a defined number, percentage, ratio, frequency and/or proportion of cells with a certain phenotype, e.g., $CCR7^+$/$CD4^+$, $CCR7^+$/$CD8^+$, $CD27^+$/$CD4^+$, $CD27^+$/$CD8^+$, $CD45RA^+$/$CD4^+$, $CD45RA^+$/$CD8^+$, $CCR7^-$/$CD4^+$, $CCR7^-$/$CD8^+$, $CD27^-$/$CD4^+$, $CD27^-$/$CD8^+$, $CD45RA^-$/$CD4^+$, $CD45RA^-$/$CD8^+$, $CCR7^+$/$CD27^+$/$CD4^+$, $CCR7^+$/$CD27^+$/$CD8^+$, $CCR7^+$/$CD45RA^-$/$CD4^+$, $CCR7^+$/$CD45RA^-$/$CD8^+$, $CCR7^-$/$CD45RA^-$/$CD4^+$, $CCR7^-$/$CD45RA^-$/$CD8^+$, $CCR7^-$/$CD27^-$/$CD4^+$, $CCR7^-$/$CD27^-$/$CD8^+$.

In some embodiments, the unit dose of cells comprises a defined number of recombinant receptor-expressing $CD8^+$ T cells that express C—C chemokine receptor type 7 (CCR7) (receptor$^+$/$CD8^+$/$CCR7^+$ cells) and/or a defined number of recombinant receptor-expressing $CD4^+$ T cells that express CCR7 (receptor$^+$/$CD4^+$/$CCR7^+$ cells) and/or a defined ratio of receptor$^+$/$CD8^+$/$CCR7^+$ cells to receptor$^+$/$CD4^+$/$CCR7^+$ cells and/or a defined ratio of receptor$^+$/$CD8^+$/$CCR7^+$ cells and/or receptor$^+$/$CD4^+$/$CCR7^+$ cells to another subset of cells in the composition. In some embodiments, the unit dose of cells comprises a defined number of $CD8^+$/$CCR7^+$ cells. In some embodiments, the unit dose of cells comprises a defined number of $CD4^+$/$CCR7^+$ cells. In some embodiments, the defined number or ratio is further based on expression or absence of expression of CD27 and/or CD45RA on the cells.

In some embodiments, the unit dose of cells comprises a defined number of recombinant receptor-expressing $CD8^+$ T cells that express cluster of differentiation 27 (CD27) (receptor$^+$/$CD8^+$/$CD27^+$ cells) and/or a defined number of recombinant receptor-expressing $CD4^+$ T cells that express CD27 (receptor$^+$/$CD4^+$/$CD27^+$ cells) and/or a defined ratio of receptor$^+$/$CD8^+$/$CD27^+$ cells to receptor$^+$/$CD4^+$/$CD27^+$ cells and/or a defined ratio of receptor$^+$/$CD8^+$/$CD27^+$ cells and/or receptor$^+$/$CD4^+$/$CD27^+$ cells to another subset of cells in the composition. In some embodiments, the unit dose of cells comprises a defined number of $CD8^+$/$CD27^+$ cells. In some embodiments, the unit dose of cells comprises a defined number of $CD4^+$/$CD27^+$ cells. In some embodiments, the defined number or ratio is further based on expression or absence of expression of CCR7 and/or CD45RA on the cells.

In some embodiments, the unit dose of cells comprises a defined number of recombinant receptor-expressing $CD8^+$ T cells that express CCR7 and CD27 (receptor$^+$/$CD8^+$/$CCR7^+$/$CD27^+$ cells) and/or a defined number of recombinant receptor-expressing $CD4^+$ T cells that express CCR7 and CD27 (receptor$^+$/$CD4^+$/$CCR7^+$/$CD27^+$ cells) and/or a defined ratio of receptor$^+$/$CD8^+$/$CCR7^+$/$CD27^+$ cells to receptor$^+$/$CD4^+$/$CCR7^+$/$CD27^+$ cells and/or a defined ratio of receptor$^+$/$CD8^+$/$CCR7^+$/$CD27^+$ cells and/or receptor$^+$/$CD4^+$/$CCR7^+$/$CD27^+$ cells to another subset of cells in the composition. In some embodiments, the unit dose of cells comprises a defined number of $CD8^+$/$CCR7^+$/$CD27^+$ cells. In some embodiments, the unit dose of cells comprises a defined number of $CD4^+$/$CCR7^+$/$CD27^+$ cells. In some embodiments, the defined number or ratio is further based on expression or absence of expression of CD45RA on the cells.

In some embodiments, the number of cells in the unit dose is the number of cells or number of recombinant receptor-expressing or CAR-expressing cells, or number, percentage, ratio, frequency and/or proportion of such cells of a certain phenotype, e.g. cells that express or do not express one or more markers selected from CD3 CD4, CD8, CCR7, CD27, CD45RA, annexin V, or activated caspase 3, that it is desired to administer to a particular subject in a dose, such as a subject from which the cells have been derived. In some embodiments, the number of cells in the unit dose is the number of cells or number of recombinant receptor-expressing or CAR-expressing cells, or number, percentage, ratio, frequency and/or proportion of such cells of a certain phenotype, e.g., CCR7$^+$, CD27$^+$, CD45RA$^+$, CD45RA$^-$, CD4$^+$, CD8$^+$, CD3$^+$, apoptosis marker negative (e.g. Annexin V$^-$ or Caspase 3) cells, or cells that are positive or negative for one or more of any of the foregoing.

In some embodiments, the number of cells in the unit dose is the number of cells or number of recombinant receptor-expressing or CAR-expressing cells, or number, percentage, ratio and/or proportion of such cells of a certain phenotype, e.g., CCR7$^+$/CD4$^+$, CCR7$^+$/CD8$^+$, CD27$^+$/CD4$^+$, CD27$^+$/CD8$^+$, CD45RA$^+$/CD4$^+$, CD45RA$^+$/CD8$^+$, CCR7$^-$/CD4$^+$, CCR7$^-$/CD8$^+$, CD27$^-$/CD4$^+$, CD27$^-$/CD8$^+$, CD45RA$^-$/CD4$^+$, CD45RA$^-$/CD8$^+$, CCR7$^+$/CD27$^+$/CD4$^+$, CCR7$^+$/CD27$^+$/CD8$^+$, CCR7$^+$/CD45RA$^-$/CD4$^+$, CCR7$^+$/CD45RA$^-$/CD8$^+$, CCR7$^-$/CD45RA$^-$/CD4$^+$, CCR7$^-$/CD45RA$^-$/CD8$^+$, CCR7$^-$/CD27$^-$/CD4$^+$, CCR7$^-$/CD27$^-$/CD8$^+$; and apoptosis marker negative (e.g. Annexin V$^-$ or Caspase 3) cells, that it is desired to administer to a particular subject in a dose, such as a subject from which the cells have been derived. In some embodiments, the unit dose contains a defined number of cells or number of recombinant receptor-expressing or CAR-expressing cells, or number, percentage, ratio and/or proportion of such cells of a certain phenotype e.g., CCR7$^+$/CD4$^+$, CCR7$^+$/CD8$^+$, CD27$^+$/CD4$^+$, CD27$^+$/CD8$^+$, CD45RA$^+$/CD4$^+$, CD45RA$^+$/CD8$^+$, CCR7$^-$/CD4$^+$, CCR7$^-$/CD8$^+$, CD27$^-$/CD4$^+$, CD27$^-$/CD8$^+$, CD45RA$^-$/CD4$^+$, CD45RA$^-$/CD8$^+$, CCR7$^+$/CD27$^+$/CD4$^+$, CCR7$^+$/CD27$^+$/CD8$^+$, CCR7$^+$/CD45RA$^-$/CD4$^+$, CCR7$^+$/CD45RA$^-$/CD8$^+$, CCR7$^-$/CD45RA$^-$/CD4$^+$, CCR7$^-$/CD45RA$^-$/CD8$^+$, CCR7$^-$/CD27$^-$/CD4$^+$, CCR7$^-$/CD27$^-$/CD8$^+$; and apoptosis marker negative (e.g. Annexin V$^-$ or Caspase 3) cells, and/or any subset thereof.

In some embodiments, the unit dose is determined based on the number of cells or cell type(s) and/or a frequency, ratio, and/or percentage of cells or cell types, e.g., individual populations, phenotypes, or subtypes, in the cell composition, such as those with the phenotypes of annexin V$^-$/CCR7$^+$/CAR$^+$; annexin V$^-$/CCR7$^+$/CAR$^+$/CD4$^+$; annexin V$^-$/CCR7$^+$/CAR$^+$/CD8$^+$; annexin V$^-$/CD27$^+$/CAR$^+$; annexin V$^-$/CD27$^+$/CAR$^+$/CD4$^+$; annexin V$^-$/CD27$^+$/CAR$^+$/CD8$^+$; annexin V$^-$/CCR7$^+$/CD27$^+$/CAR$^+$; annexin V$^-$/CCR7$^+$/CD27$^+$/CAR$^+$/CD4$^+$; annexin V$^-$/CCR7$^+$/CD27$^+$/CAR$^+$/CD8$^+$; annexin V$^-$/CCR7$^+$/CD45RA$^-$/CAR$^+$; annexin V$^-$/CCR7$^+$/CD45RA$^-$/CAR$^+$/CD4$^+$; annexin V$^-$/CCR7$^+$/CD45RA$^-$/CAR$^+$/CD8$^+$; annexin V$^-$/CCR7$^-$/CD45RA$^-$/CAR$^+$; annexin V$^-$/CCR7$^-$/CD45RA$^-$/CAR$^+$/CD4$^+$; annexin V$^-$/CCR7$^-$/CD45RA$^-$/CAR$^+$/CD8$^+$; annexin V$^-$/CCR7$^-$/CD27$^-$/CAR$^+$; annexin V$^-$/CCR7$^-$/CD27$^-$/CAR$^+$/CD4$^+$; annexin V$^-$/CCR7$^-$/CD27$^-$/CAR$^+$/CD8$^+$; activated caspase 3$^-$/CCR7$^+$/CAR$^+$; activated caspase 3$^-$/CCR7$^+$/CAR$^+$/CD4$^+$; activated caspase 3$^-$/CCR7$^+$/CAR$^+$/CD8$^+$; activated caspase 3$^-$/CD27$^+$/CAR$^+$; activated caspase 3$^-$/CD27$^+$/CAR$^+$/CD4$^+$; activated caspase 3$^-$/CD27$^+$/CAR$^+$/CD8$^+$; activated caspase 3$^-$/CCR7$^+$/CD27$^+$/CAR$^+$; activated caspase 3$^-$/CCR7$^+$/CD27$^+$/CAR$^+$/CD4$^+$; activated caspase 3$^-$/CCR7$^+$/CD27$^+$/CAR$^+$/CD8$^+$; activated caspase 3$^-$/CCR7$^+$/CD45RA$^-$/CAR$^+$; activated caspase 3$^-$/CCR7$^+$/CD45RA$^-$/CAR$^+$/CD4$^+$; activated caspase 3$^-$/CCR7$^+$/CD45RA$^-$/CAR$^+$/CD8$^+$; activated caspase 3$^-$/CCR7$^-$/CD45RA$^-$/CAR$^+$; activated caspase 3$^-$/CCR7$^-$/CD45RA-CAR$^+$/CD4$^+$; activated caspase 3$^-$/CCR7$^-$/CD45RA$^-$/CAR$^+$/CD8$^+$; activated caspase 3$^-$/CCR7$^-$/CD27$^-$/CAR$^+$; activated caspase 3$^-$/CCR7$^-$/CD27$^-$/CAR$^+$/CD4$^+$; and/or activated caspase 3$^-$/CCR7$^-$/CD27$^-$/CAR$^+$/CD8$^+$; or a combination thereof.

In some embodiments, the unit dose comprises between at or about $1\times10^5$ and at or about $1\times10^8$, between at or about $5\times10^5$ and at or about $1\times10^7$, or between at or about $1\times10^6$ and at or about $1\times10^7$ total CD8$^+$ cells that express the recombinant receptor (receptor$^+$/CD8$^+$ cells) or total CD4$^+$ cell that express the recombinant receptor (receptor$^+$/CD4$^+$ cells), total receptor$^+$/CD8$^+$/CCR7$^+$ cells, total receptor$^+$/CD4$^+$/CCR7$^+$ cells, total receptor$^+$/CD8$^+$/CD27$^+$ cells, or total receptor$^+$/CD4$^+$/CD27$^+$ cells, each inclusive. In some embodiments, the unit dose comprises no more than about $1\times10^8$, no more than about $5\times10^7$, no more than about $1\times10^7$, no more than about $5\times10^6$, no more than about $1\times10^6$, or no more than about $5\times10^5$ total receptor$^+$/CD8$^+$ cells or total receptor$^+$/CD4$^+$ cells, total receptor$^+$/CD8$^+$/CCR7$^+$ cells, total receptor$^+$/CD4$^+$/CCR7$^+$ cells, total receptor$^+$/CD8$^+$/CD27$^+$ cells, or total receptor$^+$/CD4$^+$/CD27$^+$ cells.

In some embodiments, the unit dose comprises between at or about $5\times10^5$ and at or about $5\times10^7$, between at or about $1\times10^6$ and at or about $1\times10^7$, or between at or about $5\times10^6$ and at or about $1\times10^7$ total receptor$^+$/CD8$^+$/CCR7$^+$ cells or receptor$^+$/CD4$^+$/CCR7$^+$ cells, each inclusive. In some embodiments, the unit dose comprises at least or at least about $5\times10^7$, $1\times10^7$, $5\times10^6$, $1\times10^6$, or at least about $5\times10^5$ total receptor$^+$/CD8$^+$/CCR7$^+$ cells or receptor$^+$/CD4$^+$/CCR7$^+$ cells.

In some embodiments, the unit dose comprises between at or about $5\times10^5$ and at or about $5\times10^7$, between at or about $1\times10^6$ and at or about $1\times10^7$, or between at or about $5\times10^6$ and at or about $1\times10^7$ total receptor$^+$/CD8$^+$/CD27$^+$ cells or receptor$^+$/CD4$^+$/CD27$^+$ cells, each inclusive. In some embodiments, the unit dose comprises at least or at least about $5\times10^7$, $1\times10^7$, $5\times10^6$, $1\times10^6$, or at least about $5\times10^5$ total receptor$^+$/CD8$^+$/CD27$^+$ cells or receptor$^+$/CD4$^+$/CD27$^+$ cells.

In some embodiments, the unit dose comprises at least at or about $1\times10^6$, $2\times10^6$, $3\times10^6$, $4\times10^6$, $5\times10^6$, $6\times10^6$, $7\times10^6$, $8\times10$, $1\times10^6$, or $1\times10^7$ total receptor/CD8$^+$/CCR7$^+$ cells and/or at least at or about $1\times10^6$, $2\times10^6$, $3\times10^6$, $4\times10^6$, $5\times10^6$, $6\times10^6$, $7\times10^6$, $8\times10^6$, $9\times10^6$, or $1\times10^7$ total receptor$^+$/CD4$^+$/CCR7$^+$ cells, each inclusive. In some embodiments, the unit dose comprises between at or about $3\times10^6$ and at or about $2.5\times10^7$, between at or about $4\times10^6$ and at or about $2\times10^7$, or between at or about $5\times10^6$ and at or about $1\times10^7$ total receptor$^+$/CD8$^+$/CCR7$^+$ cells and/or between at or about $3\times10^6$ and at or about $2.5\times10^7$, between at or about $4\times10^6$ and at or about $2\times10^7$, or between at or about $5\times10^6$ and at or about $1\times10^7$ total receptor$^+$/CD4$^+$/CCR7$^+$ cells, each inclusive.

In some embodiments, the unit dose comprises at least at or about $1\times10^6$, $2\times10^6$, $3\times10^6$, $4\times10^6$, $5\times10^6$, $6\times10^6$, $7\times10^6$, $8\times1\times10^6$, $9\times10^6$, or $1\times10^7$ total receptor/CD8$^+$/CD27$^+$ cells and/or at least at or about $1\times10^6$, $2\times10^6$, $3\times10^6$, $4\times10^6$, $5\times10^6$, $6\times10^6$, $7\times10^6$, $8\times10^6$, $9\times10^6$, or $1\times10^7$ total receptor$^+$/CD4$^+$/CD27$^+$ cells, each inclusive. In some embodiments, the unit dose comprises unit dose comprises between at or about $3\times10^6$ and at or about $2.5\times10^7$, between at or about $4\times10^6$ and at or about $2\times10^7$, or between at or about $5\times10^6$ and at or about $1\times10^7$ total receptor$^+$/CD8$^+$/CD27$^+$ cells and/or between at or about $3\times10^6$ and at or about $2.5\times10^7$, between at or about $4\times10^6$ and at or about $2\times10^7$, or between at or about $5\times10^6$ and at or about $1\times10^7$ total receptor$^+$/CD4$^+$/CD27$^+$ cells, each inclusive.

In some embodiments, the unit dose comprises between at or about $5\times10^5$ and at or about $5\times10^7$, between at or about $1\times10^6$ and at or about $1\times10^7$, or between at or about $5\times10^6$ and at or about $1\times10^7$ total receptor$^+$/CD8$^+$/CCR7$^+$/CD27$^+$ cells or receptor$^+$/CD4$^+$/CCR7$^+$/CD27$^+$ cells, each inclusive. In some embodiments, the unit dose comprises at least or at least at or about $5\times10^7$, $1\times10^7$, $5\times10^6$, $1\times10^6$, or at least at or about $5\times10^5$ total receptor$^+$/CD8$^+$/CCR7$^+$/CD27$^+$ cells or receptor$^+$/CD4$^+$/CCR7$^+$/CD27$^+$ cells.

In some embodiments, the unit dose comprises at least at or about $1\times10^6$, $2\times10^6$, $3\times10^6$, $4\times10^6$, $5\times10^6$, $6\times10^6$, $7\times10^6$, $8\times10^6$, $9\times10^6$, or $1\times10^7$ total receptor$^+$/CD8$^+$/CCR7$^+$/CD27$^+$ cells and/or at least at or about $1\times10^6$, $2\times10^6$, $3\times10^6$, $4\times10^6$, $5\times10^6$, $6\times10^6$, $7\times10^6$, $8\times10^6$, $9\times10^6$, or $1\times10^7$ total receptor$^+$/CD4$^+$/CCR7$^+$/CD27$^+$ cells, each inclusive. In some embodiments, the unit dose comprises between at or about $3\times10^6$ and at or about $2.5\times10^7$, between at or about $4\times10^6$ and at or about $2\times10^7$, or between at or about $5\times10^6$ and at or about $1\times10^7$ total receptor$^+$/CD8$^+$/CCR7$^+$/CD27$^+$ cells and/or between at or about $3\times10^6$ and at or about $2.5\times10^7$, between at or about $4\times10^6$ and at or about $2\times10^7$, or between at or about $5\times10^6$ and at or about $1\times10^7$ total receptor$^+$/CD4$^+$/CCR7$^+$/CD27$^+$ cells, each inclusive.

In some embodiments, the unit dose of cells comprises a defined ratio of receptor$^+$/CD8$^+$/CCR7$^+$ cells to receptor$^+$/CD4$^+$/CCR7$^+$ cells, which ratio optionally is or is approximately 1:1 or is between approximately 1:3 and approximately 3:1.

In some embodiments, the unit dose of cells comprises a defined ratio of receptor$^+$/CD8$^+$/CD27$^+$ cells to receptor$^+$/CD4$^+$/CD27$^+$ cells, which ratio optionally is or is approximately 1:1 or is between approximately 1:3 and approximately 3:1.

In some embodiments, the unit dose comprises between at or about $1\times10^5$ and at or about $1\times10^8$, between at or about $5\times10^5$ and at or about $1\times10^7$, or between at or about $1\times10^6$ and at or about $1\times10^7$ total CD8$^+$ cells that express the recombinant receptor (receptor$^+$/CD8$^+$ cells) or total CD4$^+$ cell that express the recombinant receptor (receptor$^+$/CD4$^+$ cells), total receptor$^+$/CD8$^+$/CCR7$^+$/CD27$^+$ cells, or total receptor$^+$/CD4$^+$/CCR7$^+$/CD27$^+$ cells, each inclusive. In some embodiments, the unit dose comprises no more than at or about $1\times10^8$, no more than at or about $5\times10^7$, no more than at or about $1\times10^7$, no more than at or about $5\times10^6$, no more than at or about $1\times10^6$, or no more than at or about $5\times10^5$ total receptor$^+$/CD8$^+$ cells or total receptor$^+$/CD4$^+$ cells, total receptor$^+$/CD8$^+$/CCR7$^+$/CD27$^+$ cells, or total receptor$^+$/CD4$^+$/CCR7$^+$/CD27$^+$ cells.

In some embodiments, the unit dose of cells comprises a defined ratio of receptor$^+$/CD8$^+$/CCR7$^+$/CD27$^+$ cells to receptor$^+$/CD4$^+$/CCR7$^+$/CD27$^+$ cells, which ratio optionally is or is approximately 1:1 or is between approximately 1:3 and approximately 3:1.

In some embodiments, the unit dose comprises between at or about $1\times10^5$ and at or about $5\times10^8$, between at or about $1\times10^5$ and at or about $1\times10^8$, between at or about $5\times10^5$ and at or about $1\times10^7$, or between at or about $1\times10^6$ and at or about $1\times10^7$ total CD3$^+$ cells that express the recombinant receptor (receptor$^+$/CD3$^+$ cells) or total CD3$^+$ cells, each inclusive. In some embodiments, the unit dose comprises no more than at or about $5\times10^8$, no more than at or about $1\times10^8$, no more than at or about $5\times10^7$, no more than at or about $1\times10^7$, no more than at or about $5\times10^6$, no more than at or about $1\times10^6$, or no more than at or about $5\times10^5$ total receptor$^+$/CD3$^+$ cells or total CD3$^+$ cells.

In some embodiments, the total number of CD3$^+$ cells, total number of receptor$^+$/CD3$^+$ cells, total number of receptor$^+$/CD8$^+$ cells, total number of receptor$^+$/CD4$^+$ cells, total number of receptor$^+$/CD8$^+$/CCR7$^+$ cells, total number of receptor$^+$/CD4$^+$/CCR7$^+$ cells, total number of receptor$^+$/CD8$^+$/CD27$^+$ cells, total number of receptor$^+$/CD4$^+$/CD27$^+$ cells, total number of receptor$^+$/CD8$^+$/CCR7$^+$/CD27$^+$ cells, total number of receptor$^+$/CD4$^+$/CCR7$^+$/CD27$^+$ cells, total number of receptor$^+$/CD8$^+$/CCR7$^+$/CD45RA$^-$ cells and/or receptor$^+$/CD4$^+$/CCR7$^+$/CD45RA$^-$ cells is the total number of such cells that are live or viable. In some embodiments, the total number of CD3$^+$ cells, total number of receptor$^+$/CD3$^+$ cells, total number of receptor$^+$/CD8$^+$ cells, total number of receptor$^+$/CD4$^+$ cells, total number of receptor$^+$/CD8$^+$/CCR7$^+$ cells, total number of receptor$^+$/CD4$^+$/CCR7$^+$ cells, total number of receptor$^+$/CD8$^+$/CD27$^+$ cells, total number of receptor$^+$/CD4$^+$/CD27$^+$ cells, total number of receptor$^+$/CD8$^+$/CCR7$^+$/CD27$^+$ cells, total number of receptor$^+$/CD4$^+$/CCR7$^+$/CD27$^+$ cells, total number of receptor$^+$/CD8$^+$/CCR7$^+$/CD45RA$^-$ cells and/or receptor$^+$/CD4$^+$/CCR7$^+$/CD45RA$^-$ cells is the total number of such cells that do not express an apoptotic marker and/or is the total number of such cells that are apoptotic marker negative (−), wherein the apoptotic marker is Annexin V or activated Caspase 3.

In some embodiments, in any of the composition comprising T cells expressing a recombinant receptor provided herein, at least at or about, or at or about, 15%, 20%, 30%, 40%, 50%, 60%, 70%, 80%, 85%, 90%, 91%, 92%, 93%, 94%, 95%, 96%, 97%, 98%, 99% or 100% of the total number of T cells in the composition (or of the total number of T cells in the composition expressing the recombinant receptor), are surface positive for CCR7 and/or CD27.

In some embodiments, in any of the composition comprising T cells expressing a recombinant receptor provided herein, at least at or about, or at or about, 70%, 80%, 85%, 90%, 91%, 92%, 93%, 94%, 95%, 96%, 97%, 98%, 99% or 100% of the total number of T cells in the composition (or of the total number of T cells in the composition expressing the recombinant receptor), are able to produce a cytokine selected from interleukin 2 (IL-2) and/or TNF-alpha. In some embodiments, the T cell able to produce IL-2 and/or TNF-alpha is a CD4$^+$ T cell.

In some embodiments, in any of the composition comprising T cells expressing a recombinant receptor provided herein, at least at or about, or at or about, 15%, 20%, 30%, 40%, 50%, 60%, 70%, 80% or 90% of the total receptor$^+$ cells in the unit dose, or between at or about 15% and at or about 90%, between at or about 20% and at or about 80%, between at or about 30% and at or about 70%, or between at or about 40% and at or about 60%, each inclusive, of the total receptor$^+$ cells in the unit dose are receptor$^+$/CD8$^+$/CCR7$^+$ or receptor$^+$/CD8$^+$/CD27$^+$. In some embodiments, in any of the composition comprising T cells expressing a recombinant receptor provided herein, at least at or about 15%, 20%, 30%, 40%, 50%, 60%, 70%, 80% or 90% of the total receptor$^+$ cells in the unit dose, or between at or about 15% and at or about 90%, between at or about 20% and at or about 80%, between at or about 30% and at or about 70%, or between at or about 40% and at or about 60%, each inclusive, of the total receptor$^+$ cells in the unit dose are receptor$^+$/CD4$^+$/CCR7$^+$ or receptor$^+$/CD4$^+$/CD27$^+$. In some embodiments, at least at or about 15%, 20%, 30%, 40%, 50%, 60%, 70%, 80% or 90% of the total receptor$^+$ cells in the unit dose, or between at or about 15% and at or about 90%, between at or about 20% and at or about 80%, between at or about 30% and at or about 70%, or between at or about 40% and at or about 60%, each inclusive, of the total receptor$^+$ cells in the unit dose are receptor$^+$/CD8$^+$/CCR7$^+$/

CD27$^+$, receptor$^+$/CD8$^+$/CCR7$^+$/CD45RA$^-$, receptor$^+$/CD4$^+$/CCR7$^+$/CD27$^+$ or receptor$^+$/CD4$^+$/CCR7$^+$/CD45RA$^-$.

In some embodiments, in any of the composition comprising T cells expressing a recombinant receptor provided herein, at least at or about 50%, 60%, 70%, 80% or 90% of the total receptor$^+$/CD8$^+$ cells in the composition or unit dose are or the unit dose, or between at or about 50% and at or about 90%, between at or about 60% and at or about 90%, between at or about 70% and at or about 80%, each inclusive, of the total receptor$^+$/CD8$^+$ cells in the composition or the unit dose are receptor$^+$/CD8$^+$/CCR7$^+$ or receptor$^+$/CD8$^+$/CD27$^+$ or receptor$^+$/CD8$^+$/CCR7$^+$/CD27$^+$. In some embodiments, in any of the composition comprising T cells expressing a recombinant receptor provided herein, at least at or about 50%, 60%, 70%, 80% or 90% of the total receptor$^+$/CD4$^+$ cells in the composition or unit dose are or the unit dose, or between at or about 50% and at or about 90%, between at or about 60% and at or about 90%, between at or about 70% and at or about 80%, each inclusive, of the total receptor$^+$/CD4$^+$ cells in the composition or the unit dose are receptor$^+$/CD4$^+$/CCR7$^+$ or receptor$^+$/CD4$^+$/CD27$^+$ or receptor$^+$/CD4$^+$/CCR7$^+$/CD27$^+$. receptor$^+$/CD8$^+$/CCR7$^+$/CD27$^+$, receptor$^+$/CD8$^+$/CCR7$^+$/CD45RA$^-$, receptor$^+$/CD4$^+$/CCR7$^+$/CD27$^+$ or receptor$^+$/CD4$^+$/CCR7$^+$/CD45RA$^-$. In some embodiments, at least at or about 50%, 60%, 70%, 80% or 90% of the total receptor$^+$/CD8$^+$ cells in the composition are receptor$^+$/CD8$^+$/CCR7$^+$/CD27$^+$; or at least at or about 15%, 20%, 30%, 40%, 50%, 60%, 70%, 80% or 90% of the total receptor$^+$/CD4$^+$ cells in the composition are receptor$^+$/CD4$^+$/CCR7$^+$/CD27$^+$.

In some embodiments, the unit dose comprises between at or about $1 \times 10^5$ and at or about $1 \times 10^8$, between at or about $5 \times 10^5$ and at or about $1 \times 10^7$, or between at or about $1 \times 10^6$ and at or about $1 \times 10^7$ total CD8$^+$ cells that express the recombinant receptor (receptor$^+$/CD8$^+$ cells) or total CD4$^+$ cell that express the recombinant receptor (receptor$^+$/CD4$^+$ cells), total receptor$^+$/CD8$^+$/CCR7$^+$ cells, total receptor$^+$/CD4$^+$/CCR7$^+$ cells, total receptor$^+$/CD8$^+$/CD27$^+$ cells, or total receptor$^+$/CD4$^+$/CD27$^+$ cells, each inclusive. In some embodiments, the unit dose comprises no more than at or about $1 \times 10^8$, no more than at or about $5 \times 10^7$, no more than at or about $1 \times 10^7$, no more than at or about $5 \times 10^6$, no more than at or about $1 \times 10^6$, or no more than at or about $5 \times 10^5$ total receptor$^+$/CD8$^+$ cells or total receptor$^+$/CD4$^+$ cells, total receptor$^+$/CD8$^+$/CCR7$^+$ cells, total receptor$^+$/CD4$^+$/CCR7$^+$ cells, total receptor$^+$/CD8$^+$/CD27$^+$ cells, or total receptor$^+$/CD4$^+$/CD27$^+$ cells.

In some embodiments, the unit dose of cells comprises a defined ratio of receptor$^+$/CD8$^+$/CCR7$^+$ cells to receptor$^+$/CD4$^+$/CCR7$^+$ cells, which ratio optionally is or is approximately 1:1 or is between approximately 1:3 and approximately 3:1.

In some embodiments, the unit dose comprises between at or about $1 \times 10^5$ and at or about $1 \times 10^8$, between at or about $5 \times 10^5$ and at or about $1 \times 10^7$, or between at or about $1 \times 10^6$ and at or about $1 \times 10^7$ total CD8$^+$ cells that express the recombinant receptor (receptor$^+$/CD8$^+$ cells) or total CD4$^+$ cell that express the recombinant receptor (receptor$^+$/CD4$^+$ cells), total receptor$^+$/CD8$^+$/CCR7$^+$/CD27$^+$ cells, or total receptor$^+$/CD4$^+$/CCR7$^+$/CD27$^+$ cells, each inclusive. In some embodiments, the unit dose comprises no more than at or about $1 \times 10^8$, no more than at or about $5 \times 10^7$, no more than at or about $1 \times 10^7$, no more than at or about $5 \times 10^6$, no more than at or about $1 \times 10^6$, or no more than at or about $5 \times 10^5$ total receptor$^+$/CD8$^+$ cells or total receptor$^+$/CD4$^+$ cells, total receptor$^+$/CD8$^+$/CCR7$^+$/CD27$^+$ cells, or total receptor$^+$/CD4$^+$/CCR7$^+$/CD27$^+$ cells.

In some embodiments, the unit dose of cells comprises a defined ratio of receptor$^+$/CD8$^+$/CCR7$^+$/CD27$^+$ cells to receptor$^+$/CD4$^+$/CCR7$^+$/CD27$^+$ cells, which ratio optionally is or is approximately 1:1 or is between approximately 1:3 and approximately 3:1.

In some embodiments, the provided methods involve administering a dose containing a defined number of cells. In some embodiments, the dose, such as the defined number of cells, such as a defined number of CAR$^+$ cells that are CCR7$^+$/CD4$^+$, CCR7$^+$/CD8$^+$, CD27$^+$/CD4$^+$, CD27$^+$/CD8$^+$, CD45RA$^+$/CD4$^+$, CD45RA$^+$/CD8$^+$, CCR7$^-$/CD4$^+$, CCR7$^-$/CD8$^+$, CD27$^-$/CD4$^+$, CD27$^-$/CD8$^+$, CD45RA$^-$/CD4$^+$, CD45RA$^-$/CD8$^+$, CCR7$^+$/CD27$^+$/CD4$^+$, CCR7$^+$/CD27$^+$/CD8$^+$, CCR7$^+$/CD45RA$^-$/CD4$^+$, CCR7$^+$/CD45RA$^-$/CD8$^+$, CCR7$^-$/CD45RA$^-$/CD4$^+$, CCR7$^-$/CD45RA$^-$/CD8$^+$, CCR7$^-$/CD27$^-$/CD4$^+$, or CCR7$^-$/CD27$^-$/CD8$^+$, is between or between about $5.0 \times 10^6$ and $2.25 \times 10^7$, $5.0 \times 10^6$ and $2.0 \times 10^7$, $5.0 \times 10^6$ and $1.5 \times 10^7$, $5.0 \times 10^6$ and $1.0 \times 10^7$, $5.0 \times 10^6$ and $7.5 \times 10^6$, $7.5 \times 10^6$ and $2.25 \times 10^7$, $7.5 \times 10^6$ and $2.0 \times 10^7$, $7.5 \times 10^6$ and $1.5 \times 10^7$, $7.5 \times 10^6$ and $1.0 \times 10^7$, $1.0 \times 10^7$ and $2.25 \times 10^7$, $1.0 \times 10^7$ and $2.0 \times 10^7$, $1.0 \times 10^7$ and $1.5 \times 10^7$, $1.5 \times 10^7$ and $2.25 \times 10^7$, $1.5 \times 10^7$ and $2.0 \times 10^7$, $2.0 \times 10^7$ and $2.25 \times 10^7$. In some embodiments, such dose, such as such defined number of cells refers to the total recombinant-receptor expressing cells in the administered composition. In some aspects, the defined number of recombinant receptor-expressing cells that are administered are cells that are apoptotic marker negative($-$) and optionally wherein the apoptotic marker is Annexin V or activated Caspase 3.

In some embodiments, the dose of cells of the unit dose contains a number of cells, such as a defined number of cells, between at least or at least about $5 \times 10^6$, $6 \times 10^6$, $7 \times 10^6$, $8 \times 10^6$, $9 \times 10^6$, $10 \times 10^6$ and about $15 \times 10^6$ recombinant-receptor expressing cells, such as recombinant-receptor expressing cells that are CCR7$^+$/CD4$^+$, CCR7$^+$/CD8$^+$, CD27$^+$/CD4$^+$, CD27$^+$/CD8$^+$, CD45RA$^+$/CD4$^+$, CD45RA$^+$/CD8$^+$, CCR7$^-$/CD4$^+$, CCR7$^-$/CD8$^+$, CD27$^-$/CD4$^+$, CD27$^-$/CD8$^+$, CD45RA$^-$/CD4$^+$, CD45RA$^-$/CD8$^+$, CCR7$^+$/CD27$^+$/CD4$^+$, CCR7$^+$/CD27$^+$/CD8$^+$, CCR7$^+$/CD45RA$^-$/CD4$^+$, CCR7$^+$/CD45RA$^-$/CD8$^+$, CCR7$^-$/CD45RA$^-$/CD4$^+$, CCR7$^-$/CD45RA$^-$/CD8$^+$, CCR7$^-$/CD27$^-$/CD4$^+$, or CCR7$^-$/CD27$^-$/CD8$^+$, and/or that are apoptotic marker negative($-$) and optionally wherein the apoptotic marker is Annexin V or activated Caspase 3.

In some embodiments, a dose of cells is administered to subjects in accord with the provided methods, and/or with the provided articles of manufacture or compositions. In some embodiments, the size or timing of the doses is determined as a function of the particular disease or condition in the subject. In some cases, the size or timing of the doses for a particular disease in view of the provided description may be empirically determined.

In some embodiments, the dose of cells comprises between at or about $2 \times 10^5$ of the cells/kg and at or about $2 \times 10^6$ of the cells/kg, such as between at or about $4 \times 10^5$ of the cells/kg and at or about $1 \times 10^6$ of the cells/kg or between at or about $6 \times 10^5$ of the cells/kg and at or about $8 \times 10^5$ of the cells/kg. In some embodiments, the dose of cells comprises no more than $2 \times 10^5$ of the cells (e.g. antigen-expressing, such as CAR-expressing cells) per kilogram body weight of the subject (cells/kg), such as no more than at or about $3 \times 10^5$ cells/kg, no more than at or about $4 \times 10^5$ cells/kg, no more than at or about $5 \times 10^5$ cells/kg, no more than at or about $6 \times 10^5$ cells/kg, no more than at or about $7 \times 10^5$ cells/kg, no more than at or about $8 \times 10^5$ cells/kg, no more than at or about $9 \times 10^5$ cells/kg, no more than at or about $1 \times 10^6$ cells/kg, or no more than at or about $2 \times 10^6$ cells/kg. In some embodiments, the dose of cells comprises at least or at least about or at or about $2 \times 10^5$ of the cells (e.g. antigen-expressing, such as CAR-expressing cells) per kilogram body weight of the subject (cells/kg), such as at least or at least about or at or about $3 \times 10^5$ cells/kg, at least or at least about or at or about $4 \times 10^5$ cells/kg, at least or at least about or at or about $5 \times 10^5$ cells/kg, at least or at least about or at or about $6 \times 10^5$ cells/kg, at least or at least about or at or about $7 \times 10^5$ cells/kg, at least or at least about or at or about $8 \times 10^5$ cells/kg, at least or at least about or at or about $9 \times 10^5$ cells/kg, at least or at least about or at or about $1 \times 10^6$ cells/kg, or at least or at least about or at or about $2 \times 10^6$ cells/kg.

In certain embodiments, the cells, or individual populations of sub-types of cells, are administered to the subject at a range of at or about 0.1 million to at or about 100 billion cells and/or that amount of cells per kilogram of body weight of the subject, such as, e.g., at or about 0.1 million to at or about 50 billion cells (e.g., at or about 5 million cells, at or about 25 million cells, at or about 500 million cells, at or about 1 billion cells, at or about 5 billion cells, at or about 20 billion cells, at or about 30 billion cells, at or about 40 billion cells, or a range defined by any two of the foregoing values), at or about 1 million to at or about 50 billion cells (e.g., at or about 5 million cells, at or about 25 million cells, at or about 500 million cells, at or about 1 billion cells, at or about 5 billion cells, at or about 20 billion cells, at or about 30 billion cells, at or about 40 billion cells, or a range defined by any two of the foregoing values), such as at or about 10 million to at or about 100 billion cells (e.g., at or about 20 million cells, at or about 30 million cells, at or about 40 million cells, at or about 60 million cells, at or about 70 million cells, at or about 80 million cells, at or about 90 million cells, at or about 10 billion cells, at or about 25 billion cells, at or about 50 billion cells, at or about 75 billion cells, at or about 90 billion cells, or a range defined by any two of the foregoing values), and in some cases at or about 100 million cells to at or about 50 billion cells (e.g., at or about 120 million cells, at or about 250 million cells, at or about 350 million cells, at or about 450 million cells, at or about 650 million cells, at or about 800 million cells, at or about 900 million cells, at or about 3 billion cells, at or about 30 billion cells, at or about 45 billion cells) or any value in between these ranges and/or per kilogram of body weight of the subject. Dosages may vary depending on attributes particular to the disease or disorder and/or patient and/or other treatments. In some embodiments, the dose of cells is a flat dose of cells or fixed dose of cells such that the dose of cells is not tied to or based on the body surface area or weight of a subject.

In some embodiments, for example, where the subject is a human, the dose includes fewer than about $5 \times 10^8$ total recombinant receptor (e.g., CAR)-expressing cells, T cells, or peripheral blood mononuclear cells (PBMCs), e.g., in the range of at or about $1 \times 10^6$ to at or about $5 \times 10^8$ such cells, such as at or about $2 \times 10^6$, $5 \times 10^6$, $1 \times 10^7$, $5 \times 10^7$, $1 \times 10^8$, $1.5 \times 10^8$, or $5 \times 10^8$ total such cells, or the range between any two of the foregoing values. In some embodiments, for example, where the subject is a human, the dose includes more than at or about $1 \times 10^6$ total recombinant receptor (e.g., CAR)-expressing cells, T cells, or peripheral blood mononuclear cells (PBMCs) and fewer than at or about $2 \times 10^9$ total recombinant receptor (e.g., CAR)-expressing cells, T cells, or peripheral blood mononuclear cells (PBMCs), e.g., in the range of at or about $2.5 \times 10^7$ to at or about $1.2 \times 10^9$ such cells, such as at or about $2.5 \times 10^7$, $5 \times 10^7$, $1 \times 10^8$, $1.5 \times 10^8$ total such cells, or the range between any two of the foregoing values.

In some embodiments, the dose of genetically engineered cells comprises from at or about $1 \times 10^5$ to at or about $5 \times 10^8$ total CAR-expressing (CAR-expressing) T cells, from at or about $1 \times 10^5$ to at or about $2.5 \times 10^8$ total CAR-expressing T cells, from at or about $1 \times 10^5$ to at or about $1 \times 10^8$ total CAR-expressing T cells, from at or about $1 \times 10^5$ to at or about $5 \times 10^7$ total CAR-expressing T cells, from at or about $1 \times 10^5$ to at or about $2.5 \times 10^7$ total CAR-expressing T cells, from at or about $1 \times 10^5$ to at or about $1 \times 10^7$ total CAR-expressing T cells, from at or about $1 \times 10^5$ to at or about $5 \times 10^6$ total CAR-expressing T cells, from at or about $1 \times 10^5$ to at or about $2.5 \times 10^6$ total CAR-expressing T cells, from at or about $1 \times 10^5$ to at or about $1 \times 10^6$ total CAR-expressing T cells, from at or about $1 \times 10^6$ to at or about $5 \times 10^8$ total CAR-expressing T cells, from at or about $1 \times 10^6$ to at or about $2.5 \times 10^8$ total CAR-expressing T cells, from at or about $1 \times 10^6$ to at or about $1 \times 10^8$ total CAR-expressing T cells, from at or about $1 \times 10^6$ to at or about $5 \times 10^7$ total CAR-expressing T cells, from at or about $1 \times 10^6$ to at or about $2.5 \times 10^7$ total CAR-expressing T cells, from at or about $1 \times 10^6$ to at or about $1 \times 10^7$ total CAR-expressing T cells, from at or about $1 \times 10^6$ to at or about $5 \times 10^6$ total CAR-expressing T cells, from at or about $1 \times 10^6$ to at or about $2.5 \times 10^6$ total CAR-expressing T cells, from at or about $2.5 \times 10^6$ to at or about $5 \times 10^8$ total CAR-expressing T cells, from at or about $2.5 \times 10^6$ to at or about $2.5 \times 10^8$ total CAR-expressing T cells, from at or about $2.5 \times 10^6$ to at or about $1 \times 10^8$ total CAR-expressing T cells, from at or about $2.5 \times 10^6$ to at or about $5 \times 10^7$ total CAR-expressing T cells, from at or about $2.5 \times 10^6$ to at or about $2.5 \times 10^7$ total CAR-expressing T cells, from at or about $2.5 \times 10^6$ to at or about $1 \times 10^7$ total CAR-expressing T cells, from at or about $2.5 \times 10^6$ to at or about $5 \times 10^6$ total CAR-expressing T cells, from at or about $5 \times 10^6$ to at or about $5 \times 10^8$ total CAR-expressing T cells, from at or about $5 \times 10^6$ to at or about $2.5 \times 10^8$ total CAR-expressing T cells, from at or about $5 \times 10^6$ to at or about $1 \times 10^8$ total CAR-expressing T cells, from at or about $5 \times 10^6$ to at or about $5 \times 10^7$ total CAR-expressing T cells, from at or about $5 \times 10^6$ to at or about $2.5 \times 10^7$ total CAR-expressing T cells, from at or about $5 \times 10^6$ to at or about $1 \times 10^7$ total CAR-expressing T cells, from at or about $1 \times 10^7$ to at or about $5 \times 10^8$ total CAR-expressing T cells, from at or about $1 \times 10^7$ to at or about $2.5 \times 10^8$ total CAR-expressing T cells, from at or about $1 \times 10^7$ to at or about $1 \times 10^8$ total CAR-expressing T cells, from at or about $1 \times 10^7$ to at or about $5 \times 10^7$ total CAR-expressing T cells, from at or about $1 \times 10^7$ to at or about $2.5 \times 10^7$ total CAR-expressing T cells, from at or about $2.5 \times 10^7$ to at or about $5 \times 10^8$ total CAR-expressing T cells, from at or about $2.5 \times 10^7$ to at or about $2.5 \times 10^8$ total CAR-expressing T cells, from at or about $2.5 \times 10^7$ to at or about $1 \times 10^8$ total CAR-expressing T cells, from at or about $2.5 \times 10^7$ to at or about $5 \times 10^7$ total CAR-expressing T cells, from at or about $5 \times 10^7$ to at or about $5 \times 10^8$ total CAR-expressing T cells, from at or about $5 \times 10^7$ to at or about $2.5 \times 10^8$ total CAR-expressing T cells, from at or about $5 \times 10^7$ to at or about $1 \times 10^8$ total CAR-expressing T cells, from at or about $1 \times 10^8$ to at or about $5 \times 10^8$ total CAR-expressing T cells, from at or about $1 \times 10^8$ to at or about $2.5 \times 10^8$ total CAR-expressing T cells, from at or about $2.5 \times 10^8$ to at or about $5 \times 10^8$ total CAR-expressing T cells. In some embodiments, the dose of genetically engineered cells comprises from or from about $2.5 \times 10^7$ to at or about 1.5×10⁸ total CAR-expressing T cells, such as from or from about 5×10⁷ to or to about 1×10⁸ total CAR-expressing T cells.

In some embodiments, the dose of genetically engineered cells comprises at least at or about $1\times10^5$ CAR-expressing cells, at least at or about $2.5\times10^5$ CAR-expressing cells, at least at or about $5\times10^5$ CAR-expressing cells, at least at or about $1\times10^6$ CAR-expressing cells, at least at or about $2.5\times10^6$ CAR-expressing cells, at least at or about $5\times10^6$ CAR-expressing cells, at least at or about $1\times10^7$ CAR-expressing cells, at least at or about $2.5\times10^7$ CAR-expressing cells, at least at or about $5\times10^7$ CAR-expressing cells, at least at or about $1\times10^8$ CAR-expressing cells, at least at or about $1.5\times10^8$ CAR-expressing cells, at least at or about $2.5\times10^8$ CAR-expressing cells, or at least at or about $5\times10^8$ CAR-expressing cells.

In some embodiments, the cell therapy comprises administration of a dose comprising a number of cell from or from about $1\times10^5$ to or to about $5\times10^8$ total recombinant receptor-expressing cells, total T cells, or total peripheral blood mononuclear cells (PBMCs), from or from about $5\times10^5$ to or to about $1\times10^7$ total recombinant receptor-expressing cells, total T cells, or total peripheral blood mononuclear cells (PBMCs) or from or from about $1\times10^6$ to or to about $1\times10^7$ total recombinant receptor-expressing cells, total T cells, or total peripheral blood mononuclear cells (PBMCs), each inclusive. In some embodiments, the cell therapy comprises administration of a dose of cells comprising a number of cells at least or at least about $1\times10^5$ total recombinant receptor-expressing cells, total T cells, or total peripheral blood mononuclear cells (PBMCs), such at least or at least $1\times10^6$, at least or at least about $1\times10^7$, at least or at least about $1\times10^8$ of such cells. In some embodiments, the number is with reference to the total number of CD3⁺ or CD8⁺, in some cases also recombinant receptor-expressing (e.g. CAR⁺) cells. In some embodiments, the cell therapy comprises administration of a dose comprising a number of cell from or from about $1\times10^5$ to or to about $5\times10^8$ CD3⁺ or CD8⁺ total T cells or CD3⁺ or CD8⁺ recombinant receptor-expressing cells, from or from about $5\times10^5$ to or to about $1\times10^7$ CD3 or CD8⁺ total T cells or CD3⁺ or CD8⁺ recombinant receptor-expressing cells, or from or from about $1\times10^6$ to or to about $1\times10^7$ CD3⁺ or CD8⁺ total T cells or CD3⁺ or CD8⁺ recombinant receptor-expressing cells, each inclusive. In some embodiments, the cell therapy comprises administration of a dose comprising a number of cell from or from about $1\times10^5$ to or to about $5\times10^8$ total CD3⁺/CAR⁺ or CD8⁺/CAR⁺ cells, from or from about $5\times10^5$ to or to about $1\times10^7$ total CD3⁺/CAR⁺ or CD8⁺/CAR⁺ cells, or from or from about $1\times10^6$ to or to about $1\times10^7$ total CD3⁺/CAR⁺ or CD8⁺/CAR⁺ cells, each inclusive.

In some embodiments, the T cells of the dose include CD4⁺ T cells, CD8⁺ T cells or CD4⁺ and CD8⁺ T cells.

In some embodiments, for example, where the subject is human, the CD8⁺ T cells of the dose, including in a dose including CD4⁺ and CD8⁺ T cells, includes between at or about $1\times10^6$ and at or about $5\times10^8$ total recombinant receptor (e.g., CAR)-expressing CD8⁺ cells, e.g., in the range of from at or about $5\times10^6$ to at or about $1\times10^8$ such cells, such as $1\times10^7$, $2.5\times10^7$, $5\times10^7$, $7.5\times10^7$, $1\times10^8$, $1.5\times10^8$, or $5\times10^8$ total such cells, or the range between any two of the foregoing values. In some embodiments, the patient is administered multiple doses, and each of the doses or the total dose can be within any of the foregoing values. In some embodiments, the dose of cells comprises the administration of from or from about $1\times10^7$ to or to about $0.75\times10^8$ total recombinant receptor-expressing CD8⁺ T cells, from or from about $1\times10^7$ to or to about $5\times10^7$ total recombinant receptor-expressing CD8⁺ T cells, from or from about $1\times10^7$ to or to about $0.25\times10^8$ total recombinant receptor-expressing CD8⁺ T cells, each inclusive. In some embodiments, the dose of cells comprises the administration of at or about $1\times10^7$, $2.5\times10^7$, $5\times10^7$, $7.5\times10^7$, $1\times10^8$, $1.5\times10^8$, $2.5\times10^8$, or $5\times10^8$ total recombinant receptor-expressing CD8⁺ T cells.

In some embodiments, the dose of cells, e.g., recombinant receptor-expressing T cells, is administered to the subject as a single dose or is administered only one time within a period of two weeks, one month, three months, six months, 1 year or more.

In the context of adoptive cell therapy, administration of a given "dose" encompasses administration of the given amount or number of cells as a single composition and/or single uninterrupted administration, e.g., as a single injection or continuous infusion, and also encompasses administration of the given amount or number of cells as a split dose or as a plurality of compositions, provided in multiple individual compositions or infusions, over a specified period of time, such as over no more than 3 days. Thus, in some contexts, the dose is a single or continuous administration of the specified number of cells, given or initiated at a single point in time. In some contexts, however, the dose is administered in multiple injections or infusions over a period of no more than three days, such as once a day for three days or for two days or by multiple infusions over a single day period.

Thus, in some aspects, the cells of the dose are administered in a single pharmaceutical composition. In some embodiments, the cells of the dose are administered in a plurality of compositions, collectively containing the cells of the dose.

In some embodiments, the term "split dose" refers to a dose that is split so that it is administered over more than one day. This type of dosing is encompassed by the present methods and is considered to be a single dose.

Thus, the dose of cells may be administered as a split dose, e.g., a split dose administered over time. For example, in some embodiments, the dose may be administered to the subject over 2 days or over 3 days. Exemplary methods for split dosing include administering 25% of the dose on the first day and administering the remaining 75% of the dose on the second day. In other embodiments, 33% of the dose may be administered on the first day and the remaining 67% administered on the second day. In some aspects, 10% of the dose is administered on the first day, 30% of the dose is administered on the second day, and 60% of the dose is administered on the third day. In some embodiments, the split dose is not spread over more than 3 days.

In some embodiments, cells of the dose may be administered by administration of a plurality of compositions or solutions, such as a first and a second, optionally more, each containing some cells of the dose. In some aspects, the plurality of compositions, each containing a different population and/or sub-types of cells, are administered separately or independently, optionally within a certain period of time. For example, the populations or sub-types of cells can include CD8⁺ and CD4⁺ T cells, respectively, and/or CD8⁺- and CD4⁺-enriched populations, respectively, e.g., CD4⁺ and/or CD8⁺ T cells each individually including cells genetically engineered to express the recombinant receptor. In some embodiments, the administration of the dose comprises administration of a first composition comprising a dose of CD8⁺ T cells or a dose of CD4⁺ T cells and administration of a second composition comprising the other of the dose of CD4⁺ T cells and the CD8⁺ T cells.

In some embodiments, the administration of the composition or dose, e.g., administration of the plurality of cell compositions, involves administration of the cell compositions separately. In some aspects, the separate administrations are carried out simultaneously, or sequentially, in any order. In some embodiments, the dose comprises a first composition and a second composition, and the first composition and second composition are administered 0 to 12 hours apart, 0 to 6 hours apart or 0 to 2 hours apart. In some embodiments, the initiation of administration of the first composition and the initiation of administration of the second composition are carried out no more than 2 hours, no more than 1 hour, or no more than 30 minutes apart, no more than 15 minutes, no more than 10 minutes or no more than 5 minutes apart. In some embodiments, the initiation and/or completion of administration of the first composition and the completion and/or initiation of administration of the second composition are carried out no more than 2 hours, no more than 1 hour, or no more than 30 minutes apart, no more than 15 minutes, no more than 10 minutes or no more than 5 minutes apart.

In some embodiments, the first composition, e.g., first composition of the dose, comprises $CD4^+$ T cells. In some embodiments, the first composition, e.g., first composition of the dose, comprises $CD8^+$ T cells. In some embodiments, the first composition is administered prior to the second composition. In some embodiments, the second composition, e.g., second composition of the dose, comprises $CD4^+$ T cells. In some embodiments, the second composition, e.g., second composition of the dose, comprises $CD8^+$ T cells.

In some embodiments, the dose or composition of cells includes a defined or target ratio of $CD4^+$ cells expressing a recombinant receptor to $CD8^+$ cells expressing a recombinant receptor and/or of $CD4^+$ cells to $CD8^+$ cells, which ratio optionally is approximately 1:1 or is between approximately 1:3 and approximately 3:1, such as approximately 1:1. In some aspects, the administration of a composition or dose with the target or desired ratio of different cell populations (such as $CD4^+$:$CD8^+$ ratio or $CAR^+CD4^+$:$CAR^+CD8^+$ ratio, e.g., 1:1) involves the administration of a cell composition containing one of the populations and then administration of a separate cell composition comprising the other of the populations, where the administration is at or approximately at the target or desired ratio. In some aspects, administration of a dose or composition of cells at a defined ratio leads to improved expansion, persistence and/or antitumor activity of the T cell therapy.

In some embodiments, the subject receives multiple doses, e.g., two or more doses or multiple consecutive doses, of the cells. In some embodiments, two doses are administered to a subject. In some embodiments, the subject receives the consecutive dose, e.g., second dose, is administered approximately 4, 5, 6, 7, 8, 9, 10, 11, 12, 13, 14, 15, 16, 17, 18, 19, 20 or 21 days after the first dose. In some embodiments, multiple consecutive doses are administered following the first dose, such that an additional dose or doses are administered following administration of the consecutive dose. In some aspects, the number of cells administered to the subject in the additional dose is the same as or similar to the first dose and/or consecutive dose. In some embodiments, the additional dose or doses are larger than prior doses.

In some aspects, the size of the first and/or consecutive dose is determined based on one or more criteria such as response of the subject to prior treatment, e.g. chemotherapy, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

In some aspects, the time between the administration of the first dose and the administration of the consecutive dose is about 9 to about 35 days, about 14 to about 28 days, or 15 to 27 days. In some embodiments, the administration of the consecutive dose is at a time point more than about 14 days after and less than about 28 days after the administration of the first dose. In some aspects, the time between the first and consecutive dose is about 21 days. In some embodiments, an additional dose or doses, e.g. consecutive doses, are administered following administration of the consecutive dose. In some aspects, the additional consecutive dose or doses are administered at least about 14 and less than about 28 days following administration of a prior dose. In some embodiments, the additional dose is administered less than about 14 days following the prior dose, for example, 4, 5, 6, 7, 8, 9, 10, 11, 12, or 13 days after the prior dose. In some embodiments, no dose is administered less than about 14 days following the prior dose and/or no dose is administered more than about 28 days after the prior dose.

In some embodiments, the dose of cells, e.g., recombinant receptor-expressing cells, comprises two doses (e.g., a double dose), comprising a first dose of the T cells and a consecutive dose of the T cells, wherein one or both of the first dose and the second dose comprises administration of the split dose of T cells.

In some embodiments, the dose of cells is generally large enough to be effective in reducing disease burden.

In some embodiments, the cells are administered at a desired dosage, which in some aspects includes a desired dose or number of cells or cell type(s) and/or a desired ratio of cell types. Thus, the dosage of cells in some embodiments is based on a total number of cells (or number per kg body weight) and a desired ratio of the individual populations or sub-types, such as the $CD4^+$ to $CD8^+$ ratio. In some embodiments, the dosage of cells is based on a desired total number (or number per kg of body weight) of cells in the individual populations or of individual cell types. In some embodiments, the dosage is based on a combination of such features, such as a desired number of total cells, desired ratio, and desired total number of cells in the individual populations.

In some embodiments, the populations or sub-types of cells, such as $CD8^+$ and $CD4^+$ T cells, are administered at or within a tolerated difference of a desired dose of total cells, such as a desired dose of T cells. In some aspects, the desired dose is a desired number of cells or a desired number of cells per unit of body weight of the subject to whom the cells are administered, e.g., cells/kg. In some aspects, the desired dose is at or above a minimum number of cells or minimum number of cells per unit of body weight. In some aspects, among the total cells, administered at the desired dose, the individual populations or sub-types are present at or near a desired output ratio (such as $CD4^+$ to $CD8^+$ ratio), e.g., within a certain tolerated difference or error of such a ratio.

In some embodiments, the cells are administered at or within a tolerated difference of a desired dose of one or more of the individual populations or sub-types of cells, such as a desired dose of $CD4^+$ cells and/or a desired dose of $CD8^+$ cells. In some aspects, the desired dose is a desired number of cells of the sub-type or population, or a desired number of such cells per unit of body weight of the subject to whom the cells are administered, e.g., cells/kg. In some aspects, the desired dose is at or above a minimum number of cells of the population or sub-type, or minimum number of cells of the population or sub-type per unit of body weight.

Thus, in some embodiments, the dosage is based on a desired fixed dose of total cells and a desired ratio, and/or based on a desired fixed dose of one or more, e.g., each, of the individual sub-types or sub-populations. Thus, in some embodiments, the dosage is based on a desired fixed or minimum dose of T cells and a desired ratio of $CD4^+$ to $CD8^+$ cells, and/or is based on a desired fixed or minimum dose of $CD4^+$ and/or $CD8^+$ cells.

In some embodiments, the cells are administered at or within a tolerated range of a desired output ratio of multiple cell populations or sub-types, such as $CD4^+$ and $CD8^+$ cells or sub-types. In some aspects, the desired ratio can be a specific ratio or can be a range of ratios. For example, in some embodiments, the desired ratio (e.g., ratio of $CD4^+$ to $CD8^+$ cells) is between at or about 1:5 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1), such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9:1:2, 1:2.5, 1:3, 1:3.5, 1:4, 1:4.5, or 1:5. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

In particular embodiments, the numbers and/or concentrations of cells refer to the number of recombinant receptor (e.g., CAR)-expressing cells. In other embodiments, the numbers and/or concentrations of cells refer to the number or concentration of all cells, T cells, or peripheral blood mononuclear cells (PBMCs) administered.

In some aspects, the size of the dose is determined based on one or more criteria such as response of the subject to prior treatment, e.g. chemotherapy, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

In some embodiments, the methods also include administering one or more additional doses of cells expressing a chimeric antigen receptor (CAR) and/or lymphodepleting therapy, and/or one or more steps of the methods are repeated. In some embodiments, the one or more additional dose is the same as the initial dose. In some embodiments, the one or more additional dose is different from the initial dose, e.g., higher, such as 2-fold, 3-fold, 4-fold, 5-fold, 6-fold, 7-fold, 8-fold, 9-fold or 10-fold or more higher than the initial dose, or lower, such as e.g., 2-fold, 3-fold, 4-fold, 5-fold, 6-fold, 7-fold, 8-fold, 9-fold or 10-fold or more lower than the initial dose. In some embodiments, administration of one or more additional doses is determined based on response of the subject to the initial treatment or any prior treatment, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

C. Methods of Treatment

Provided herein are methods of treatment, e.g., including administering any of the engineered cells or compositions containing engineered cells described herein, including one or more doses, e.g., a unit doses or any compositions containing one or more unit doses described herein. In some aspects, also provided are methods of administering any of the engineered cells or compositions containing engineered cells or unit doses described herein to a subject, such as a subject that has a disease or disorder. In some aspects, also provided are uses of any of the engineered cells or compositions containing engineered cells described herein for treatment of a disease or disorder. In some aspects, also provided are uses of any of the engineered cells or compositions containing engineered cells or unit doses described herein for the manufacture of a medicament for the treatment of a disease or disorder. In some aspects, also provided are any of the engineered cells or compositions containing engineered cells or unit doses described herein, for use in treatment of a disease or disorder, or for administration to a subject having a disease or disorder.

The engineered cells expressing a recombinant receptor, such as a chimeric antigen receptor (CAR), or compositions comprising the same, are useful in a variety of therapeutic, diagnostic and prophylactic indications. For example, the engineered cells or compositions comprising the engineered cells are useful in treating a variety of diseases and disorders in a subject. Such methods and uses include therapeutic methods and uses, for example, involving administration of the engineered cells, or compositions containing the same, to a subject having a disease, condition, or disorder, such as a tumor or cancer. In some embodiments, the engineered cells or compositions comprising the same are administered in an effective amount to effect treatment of the disease or disorder. Uses include uses of the engineered cells or compositions in such methods and treatments, and in the preparation of a medicament in order to carry out such therapeutic methods. In some embodiments, the methods are carried out by administering the engineered cells, or compositions comprising the same, to the subject having or suspected of having the disease or condition. In some embodiments, the methods thereby treat the disease or condition or disorder in the subject.

Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338.

The disease or condition that is treated can be any in which expression of an antigen is associated with and/or involved in the etiology of a disease condition or disorder, e.g. causes, exacerbates or otherwise is involved in such disease, condition, or disorder. Exemplary diseases and conditions can include diseases or conditions associated with malignancy or transformation of cells (e.g. cancer), autoimmune or inflammatory disease, or an infectious disease, e.g. caused by a bacterial, viral or other pathogen. Exemplary antigens, which include antigens associated with various diseases and conditions that can be treated, are described above. In particular embodiments, the chimeric antigen receptor or transgenic TCR specifically binds to an antigen associated with the disease or condition.

Among the diseases, conditions, and disorders are tumors, including solid tumors, hematologic malignancies, and melanomas, and including localized and metastatic tumors, infectious diseases, such as infection with a virus or other pathogen, e.g., HIV, HCV, HBV, CMV, HPV, and parasitic disease, and autoimmune and inflammatory diseases. In some embodiments, the disease, disorder or condition is a tumor, cancer, malignancy, neoplasm, or other proliferative disease or disorder. In some embodiments, the disease or condition is a B cell malignancy. In some embodiments, the B cell malignancy is a leukemia or a lymphoma. Such diseases include but are not limited to leukemia, lymphoma, e.g., acute myeloid (or myelogenous) leukemia (AML), chronic myeloid (or myelogenous) leukemia (CML), acute lymphocytic (or lymphoblastic) leukemia (ALL), chronic lymphocytic leukemia (CLL), hairy cell leukemia (HCL), small lymphocytic lymphoma (SLL), Mantle cell lymphoma (MCL), Marginal zone lymphoma, Burkitt lymphoma, Hodgkin lymphoma (HL), non-Hodgkin lymphoma (NHL), Anaplastic large cell lymphoma (ALCL), follicular lymphoma, refractory follicular lymphoma, diffuse large B-cell lymphoma (DLBCL) and multiple myeloma (MM). In some embodiments, disease or condition is a B cell malignancy selected from among acute lymphoblastic leukemia (ALL), adult ALL, chronic lymphoblastic leukemia (CLL), non-Hodgkin lymphoma (NHL), and Diffuse Large B-Cell Lymphoma (DLBCL). In some embodiments, the disease or condition is NHL and the NHL is selected from the group consisting of aggressive NHL, diffuse large B cell lymphoma (DLBCL), NOS (de novo and transformed from indolent), primary mediastinal large B cell lymphoma (PMBCL), T cell/histocyte-rich large B cell lymphoma (TCHRBCL), Burkitt's lymphoma, mantle cell lymphoma (MCL), and/or follicular lymphoma (FL), optionally, follicular lymphoma Grade 3B (FL3B).

In some aspects, the disease or condition is acute lymphoblastic leukemia (ALL), adult ALL, chronic lymphoblastic leukemia (CLL), non-Hodgkin lymphoma (NHL), or Diffuse Large B-Cell Lymphoma (DLBCL). In some cases, the disease or condition is an NHL, such as or including an NHL that is an aggressive NHL, diffuse large B cell lymphoma (DLBCL), NOS (de novo and transformed from indolent), primary mediastinal large B cell lymphoma (PMBCL), T cell/histocyte-rich large B cell lymphoma (TCHRBCL), Burkitt's lymphoma, mantle cell lymphoma (MCL), and/or follicular lymphoma (FL), optionally, follicular lymphoma Grade 3B (FL3B). In some aspects, the recombinant receptor, such as a CAR, specifically binds to an antigen associated with the disease or condition or expressed in cells of the environment of a lesion associated with the B cell malignancy. Antigens targeted by the receptors in some embodiments include antigens associated with a B cell malignancy, such as any of a number of known B cell marker. In some embodiments, the antigen targeted by the receptor is CD20, CD19, CD22, ROR1, CD45, CD21, CD5, CD33, Igkappa, Iglambda, CD79a, CD79b or CD30, or combinations thereof.

In some embodiments, the disease or condition is a myeloma, such as a multiple myeloma. In some aspects, the recombinant receptor, such as a CAR, specifically binds to an antigen associated with the disease or condition or expressed in cells of the environment of a lesion associated with the multiple myeloma. Antigens targeted by the receptors in some embodiments include antigens associated with multiple myeloma. In some aspects, the antigen, e.g., the second or additional antigen, such as the disease-specific antigen and/or related antigen, is expressed on multiple myeloma, such as B cell maturation antigen (BCMA), G protein-coupled receptor class C group 5 member D (GPRC5D), CD38 (cyclic ADP ribose hydrolase), CD138 (syndecan-1, syndecan, SYN-1), CS-1 (CS1, CD2 subset 1, CRACC, SLAMF7, CD319, and 19A24), BAFF-R, TACI and/or FcRH5. Other exemplary multiple myeloma antigens include CD56, TIM-3, CD33, CD123, CD44, CD20, CD40, CD74, CD200, EGFR, 02-Microglobulin, HM1.24, IGF-1R, IL-6R, TRAIL-R1, and the activin receptor type IIA (Ac-tRIIA). See Benson and Byrd, J. Clin. Oncol. (2012) 30(16): 2013-15; Tao and Anderson, Bone Marrow Research (2011): 924058; Chu et al., Leukemia (2013) 28(4):917-27; Garfall et al., Discov Med. (2014) 17(91):37-46. In some embodiments, the antigens include those present on lymphoid tumors, myeloma, AIDS-associated lymphoma, and/or post-transplant lymphoproliferations, such as CD38. Antibodies or antigen-binding fragments directed against such antigens are known and include, for example, those described in U.S. Pat. Nos. 8,153,765; 8,603,477, 8,008,450; U.S. Pub. No. US20120189622 or US20100260748; and/or International PCT Publication Nos. WO2006099875, WO2009080829 or WO2012092612 or WO2014210064. In some embodiments, such antibodies or antigen-binding fragments thereof (e.g. scFv) are contained in multispecific antibodies, multispecific chimeric receptors, such as multispecific CARs, and/or multispecific cells.

In some embodiments, the disease or disorder is associated with expression of G protein-coupled receptor class C group 5 member D (GPRC5D) and/or expression of B cell maturation antigen (BCMA).

In some embodiments, the disease or disorder is a B cell-related disorder. In some of any of the provided embodiments of the provided methods, the disease or disorder associated with BCMA is an autoimmune disease or disorder. In some of any of the provided embodiments of the provided methods, the autoimmune disease or disorder is systemic lupus erythematosus (SLE), lupus nephritis, inflammatory bowel disease, rheumatoid arthritis, ANCA associated vasculitis, idiopathic thrombocytopenia purpura (ITP), thrombotic thrombocytopenia purpura (TTP), autoimmune thrombocytopenia, Chagas' disease, Grave's disease, Wegener's granulomatosis, poly-arteritis nodosa, Sjögren's syndrome, pemphigus vulgaris, scleroderma, multiple sclerosis, psoriasis, IgA nephropathy, IgM polyneuropathies, vasculitis, diabetes mellitus, Reynaud's syndrome, anti-phospholipid syndrome, Goodpasture's disease, Kawasaki disease, autoimmune hemolytic anemia, myasthenia gravis, or progressive glomerulonephritis.

In some embodiments, the disease or disorder is a cancer. In some embodiments, the cancer is a GPRC5D-expressing cancer. In some embodiments, the cancer is a plasma cell malignancy and the plasma cell malignancy is multiple myeloma (MM) or plasmacytoma. In some embodiments, the cancer is multiple myeloma (MM). In some embodiments, the cancer is a relapsed/refractory multiple myeloma.

In some embodiments, the disease or condition is an infectious disease or condition, such as, but not limited to, viral, retroviral, bacterial, and protozoal infections, immunodeficiency, Cytomegalovirus (CMV), Epstein-Barr virus (EBV), adenovirus, BK polyomavirus. In some embodiments, the disease or condition is an autoimmune or inflammatory disease or condition, such as arthritis, e.g., rheumatoid arthritis (RA), Type I diabetes, systemic lupus erythematosus (SLE), inflammatory bowel disease, psoriasis, scleroderma, autoimmune thyroid disease, Grave's disease, Crohn's disease, multiple sclerosis, asthma, and/or a disease or condition associated with transplant.

In some embodiments, the antigen associated with the disease or disorder or includes αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22Ra), IL-13 receptor alpha 2 (IL-13Ra2), kinase insert domain receptor (kdr), kappa light chain, L1 cell adhesion molecule (L1-CAM), CE7 epitope of L-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen is or includes CD20, CD19, CD22, ROR1, CD45, CD21, CD5, CD33, Igkappa, Iglambda, CD79a, CD79b or CD30.

In some embodiments, the antigen is or includes a pathogen-specific or pathogen-expressed antigen. In some embodiments, the antigen is a viral antigen (such as a viral antigen from HIV, HCV, HBV, etc.), bacterial antigens, and/or parasitic antigens.

In some embodiments, the cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

The cells can be administered by any suitable means, for example, by bolus infusion, by injection, e.g., intravenous or subcutaneous injections, intraocular injection, periocular injection, subretinal injection, intravitreal injection, transseptal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration. In some embodiments, a given dose is administered by a single bolus administration of the cells. In some embodiments, it is administered by multiple bolus administrations of the cells, for example, over a period of no more than 3 days, or by continuous infusion administration of the cells. In some embodiments, administration of the cell dose or any additional therapies, e.g., the lymphodepleting therapy, intervention therapy and/or combination therapy, is carried out via outpatient delivery.

For the prevention or treatment of disease, the appropriate dosage may depend on the type of disease to be treated, the type of cells or recombinant receptors, the severity and course of the disease, whether the cells are administered for preventive or therapeutic purposes, previous therapy, the subject's clinical history and response to the cells, and the discretion of the attending physician. The compositions and cells are in some embodiments suitably administered to the subject at one time or over a series of treatments.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents include a cytokine, such as IL-2, for example, to enhance persistence. In some embodiments, the methods comprise administration of a chemotherapeutic agent.

In some embodiments, the methods comprise administration of a chemotherapeutic agent, e.g., a conditioning chemotherapeutic agent, for example, to reduce tumor burden prior to the administration.

Preconditioning subjects with immunodepleting (e.g., lymphodepleting) therapies in some aspects can improve the effects of adoptive cell therapy (ACT).

Thus, in some embodiments, the methods include administering a preconditioning agent, such as a lymphodepleting or chemotherapeutic agent, such as cyclophosphamide, fludarabine, or combinations thereof, to a subject prior to the initiation of the cell therapy. For example, the subject may be administered a preconditioning agent at least 2 days prior, such as at least 3, 4, 5, 6, or 7 days prior, to the initiation of the cell therapy. In some embodiments, the subject is administered a preconditioning agent no more than 7 days prior, such as no more than 6, 5, 4, 3, or 2 days prior, to the initiation of the cell therapy.

In some embodiments, the subject is preconditioned with cyclophosphamide at a dose between or between about 20 mg/kg and 100 mg/kg, such as between or between about 40 mg/kg and 80 mg/kg. In some aspects, the subject is preconditioned with or with about 60 mg/kg of cyclophosphamide. In some embodiments, the cyclophosphamide can be administered in a single dose or can be administered in a plurality of doses, such as given daily, every other day or every three days. In some embodiments, the cyclophosphamide is administered once daily for one or two days. In some embodiments, where the lymphodepleting agent comprises cyclophosphamide, the subject is administered cyclophosphamide at a dose between or between about 100 mg/m$^2$ and 500 mg/m$^2$, such as between or between about 200 mg/m$^2$ and 400 mg/m$^2$ or 250 mg/m$^2$ and 350 mg/m$^2$, inclusive. In some instances, the subject is administered about 300 mg/m$^2$ of cyclophosphamide. In some embodiments, the cyclophosphamide can be administered in a single dose or can be administered in a plurality of doses, such as given daily, every other day or every three days. In some embodiments, cyclophosphamide is administered daily, such as for 1-5 days, for example, for 3 to 5 days. In some instances, the subject is administered about 300 mg/m$^2$ of cyclophosphamide, daily for 3 days, prior to initiation of the cell therapy.

In some embodiments, where the lymphodepleting agent comprises fludarabine, the subject is administered fludarabine at a dose between or between about 1 mg/m$^2$ and 100 mg/m$^2$, such as between or between about 10 mg/m$^2$ and 75 mg/m$^2$, 15 mg/m$^2$ and 50 mg/m$^2$, 20 mg/m$^2$ and 40 mg/m$^2$, or 24 mg/m$^2$ and 35 mg/m$^2$, inclusive. In some instances, the subject is administered about 30 mg/m$^2$ of fludarabine. In some embodiments, the fludarabine can be administered in a single dose or can be administered in a plurality of doses, such as given daily, every other day or every three days. In some embodiments, fludarabine is administered daily, such as for 1-5 days, for example, for 3 to 5 days. In some instances, the subject is administered about 30 mg/m$^2$ of fludarabine, daily for 3 days, prior to initiation of the cell therapy.

In some embodiments, the lymphodepleting agent comprises a combination of agents, such as a combination of cyclophosphamide and fludarabine. Thus, the combination of agents may include cyclophosphamide at any dose or administration schedule, such as those described above, and fludarabine at any dose or administration schedule, such as those described above. For example, in some aspects, the subject is administered 60 mg/kg (~2 g/m$^2$) of cyclophosphamide and 3 to 5 doses of 25 mg/m$^2$ fludarabine prior to the first or subsequent dose.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable known methods, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells is measured by assaying expression and/or secretion of one or more cytokines, such as CD107a, IFNγ, IL-2, and TNF. In some aspects the biological activity is measured by assessing clinical outcome, such as reduction in tumor burden or load.

In certain embodiments, the engineered cells are further modified in any number of ways, such that their therapeutic or prophylactic efficacy is increased. For example, the engineered CAR or TCR expressed by the population can be conjugated either directly or indirectly through a linker to a targeting moiety. The practice of conjugating compounds, e.g., the CAR or TCR, to targeting moieties is known. See, for instance, Wadwa et al., J. Drug Targeting 3: 1 1 1 (1995), and U.S. Pat. No. 5,087,616.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agent includes a cytokine, such as IL-2, for example, to enhance persistence.

D. Monitoring or Assessing Therapy with Therapeutic T Cell Compositions

1. Assessing Pharmacokinetics (PK) of Engineered Cells, e.g. Peak Cell Levels and Patient Factors In some embodiments, the method includes assessment of the exposure, number, concentration, persistence and proliferation of the T cells, e.g., T cells administered for the T cell based therapy. In some embodiments, the method includes assessment of the exposure, number or level of engineered T cells, e.g., T cells administered for the T cell based therapy, or subset thereof, such as CD3$^+$ cells, CD4$^+$ cells, CD8$^+$ cells, CD3$^+$ CAR$^+$ cells, CD4$^+$ CAR$^+$ cells or CD8$^+$ CAR$^+$ cells. In some embodiments, the exposure, or prolonged expansion and/or persistence of the cells, and/or changes in cell phenotypes or functional activity of the cells, e.g., cells administered for immunotherapy, e.g. T cell therapy, in the methods provided herein, can be measured by assessing the characteristics of the T cells in vitro or ex vivo. In some embodiments, such assays can be used to determine or confirm the function of the T cells used for the immunotherapy, e.g. T cell therapy, before or after administering the cell therapy provided herein.

In some aspects, the exposure, number, concentration, persistence and proliferation relate to pharmacokinetic parameters. In some cases, pharmacokinetics can be assessed by measuring such parameters as the maximum (peak) plasma concentration ($C_{max}$), the peak time (i.e. when maximum plasma concentration ($C_{max}$) occurs; $T_{max}$), the minimum plasma concentration (i.e. the minimum plasma concentration between doses of a therapeutic agent, e.g., $CAR^+$ T cells; $C_{min}$), the elimination half-life ($T_{1/2}$) and area under the curve (i.e. the area under the curve generated by plotting time versus plasma concentration of the therapeutic agent $CAR^+$ T cells; AUC), following administration. The concentration of a particular therapeutic agent, e.g., $CAR^+$ T cells, in the plasma following administration can be measured using any method known in the art suitable for assessing concentrations of the therapeutic agents, e.g., $CAR^+$ T cells, in samples of blood, or any methods described herein. For example, nucleic acid-based methods, such as quantitative PCR (qPCR) or flow cytometry-based methods, or other assays, such as an immunoassay, ELISA, or chromatography/mass spectrometry-based assays can be used.

In some embodiments, the pharmacokinetics (PK) of administered cells, e.g., $CAR^+$ T cell composition, are determined to assess the availability, e.g., bioavailability, of the administered cells. In some embodiments, the determined pharmacokinetic parameters of the administered cells include maximum (peak) plasma concentrations ($C_{max}$), such as $C_{max}$ of $CD3^+$ $CAR^+$ cells, $CD4^+$ $CAR^+$ cells and or $CD8^+$ $CAR^+$ T cells; the time point at which $C_{max}$ is achieved ($T_{max}$), such as the $T_{max}$ of $CD3^+$ $CAR^+$ cells, $CD4^+$ $CAR^+$ cells and or $CD8^+$ $CAR^+$ T cells, and or area under the curve (AUC), such as the $AUC_{0-28}$, of $CD3^+$ $CAR^+$ cells, $CD4^+$ $CAR^+$ cells and or $CD8^+$ $CAR^+$ T cells. In some embodiments, the pharmacokinetic parameter is peak $CD3^+$ $CAR^+$ T cell concentration ($C_{max}$ $CD3^+$ $CAR^+$ T cells), or $CD8^+$ $CAR^+$ T cell concentration ($C_{max}$ $CD8^+$ $CAR^+$ T cells). In some embodiments, the pharmacokinetic parameter is $AUC_{0-28}$, of $CD3^+$ $CAR^+$ T cells, ($AUC_{0-28}$ $CD3^+$ $CAR^+$ T cells), or $AUC_{0-28}$, of $CD8^+$ $CAR^+$ T cells, (AUC0-28 $CD8^+$ $CAR^+$ T cells), In some embodiments, "exposure" can refer to the body exposure of a therapeutic agent, e.g., $CAR^+$ T cells in the plasma (blood or serum) after administration of the therapeutic agent over a certain period of time. In some embodiments exposure can be set forth as the area under the therapeutic agent concentration-time curve (AUC) as determined by pharmacokinetic analysis after administration of a dose of the therapeutic agent, e.g., $CAR^+$ T cells. In some cases, the AUC is expressed in cells*days/µL, for cells administered in cell therapy, or in corresponding units thereof. In some embodiments, the AUC is measured as an average AUC in a patient population, such as a sample patient population, e.g., the average AUC from one or more patient(s). In some embodiments, systemic exposure refers to the area under the curve (AUC) within a certain period of time, e.g., from day 0 to day 1, 2, 3, 4, 5, 6, 7, 8, 9, 10, 11, 12, 13, 14, 21, 28 days or more, or week 1, 2, 3, 4, 5, 6, 7, 8, 9, 10, 11, 12, 13, 14, 15 or more, or month 1, 2, 3, 4, 5, 6, 7, 8, 9, 10, 11, 12, 18, 24, 48 or more. In some embodiments, the AUC is measured as an AUC from day 0 to day 28 ($AUC_{0-28}$) after administration of the therapeutic agent, e.g., $CAR^+$ T cells, including all measured data and data extrapolated from measured pharmacokinetic (PK) parameters, such as an average AUC from a patient population, such as a sample patient population. In some embodiments, to determine exposure over time, e.g., AUC for a certain period of time, such as $AUC_{0-28}$, a therapeutic agent concentration-time curve is generated, using multiple measurements or assessment of parameters, e.g., cell concentrations, over time, e.g., measurements taken every 1, 2, 3, 4, 5, 6, 7, 8, 9, 10, 11, 12, 13, 14, 21 or 28 days or more.

In some embodiments, the presence and/or amount of cells expressing the recombinant receptor (e.g., CAR-expressing cells administered for T cell based therapy) in the subject following the administration of the T cells and before, during and/or after the administration of the therapy is detected. In some aspects, nucleic acid-based methods, such as quantitative PCR (qPCR), are used to assess the quantity of cells expressing the recombinant receptor (e.g., CAR-expressing cells administered for T cell based therapy) in the blood or serum or organ or tissue sample (e.g., disease site, e.g., tumor sample) of the subject. In some aspects, persistence is quantified as copies of DNA or plasmid encoding the receptor, e.g., CAR, per microgram of DNA, or as the number of receptor-expressing, e.g., CAR-expressing, cells per microliter of the sample, e.g., of blood or serum, or per total number of peripheral blood mononuclear cells (PBMCs) or white blood cells or T cells per microliter of the sample. In some embodiments, the primers or probe used for qPCR or other nucleic acid-based methods are specific for binding, recognizing and/or amplifying nucleic acids encoding the recombinant receptor, and/or other components or elements of the plasmid and/or vector, including regulatory elements, e.g., promoters, transcriptional and/or post-transcriptional regulatory elements or response elements, or markers, e.g., surrogate markers. In some embodiments, the primers can be specific for regulatory elements, such as the woodchuck hepatitis virus post-transcriptional regulatory element (WPRE). In some examples, the presence and/or amount of cells expressing the recombinant receptor is expressed as copies of the nucleic acid sequence (e.g., transgene sequence) encoding the CAR or a nucleic acid sequence operably connected to the CAR-encoding sequences, per mass of DNA (e.g., copies/µg of DNA); AUC of the curve of copies/µg of DNA over time, maximum or peak copies/µg of DNA following treatment, or copies/µg of DNA at day 1, 2, 3, 4, 5, 6, 7, 8, 9, 10, 11, 12, 13, 14, 15, 16, 17, 18, 19, 20 or 21, or week 1, 2, 3, 4, 5, 6, 7, 8, 9, 10, 11, or 12 or more post-treatment or initiation thereof.

In some embodiments, the cells are detected in the subject at or at least at 4, 14, 15, 27, or 28 days following the administration of the T cells, e.g., CAR-expressing T cells. In some aspects, the cells are detected at or at least at 2, 4, or 6 weeks following, or 3, 6, or 12, 18, or 24, or 30 or 36 months, or 1, 2, 3, 4, 5, or more years, following the administration of the T cells, e.g., CAR-expressing T cells.

In some embodiments, the peak levels and/or AUC are assessed and/or the sample is obtained from the subject at a time that is at least 8 days, 9 days, 10 days, 11 days, 12 days, 13 days, 14 days, 15 days, 16 days, 17 days, 18 days, 19 days, 20 days or 21 days after initiation of administration of the genetically engineered cells. In some embodiments the peak levels and/or AUC are assessed and/or the sample is obtained from the subject at a time that is between or between about 11 to 22 days, 12 to 18 days or 14 to 16 days, each inclusive, after initiation of administration of the genetically engineered cells.

The exposure, e.g., number or concentration of cells, e.g. T cells administered for T cell therapy, indicative of expansion and/or persistence, may be stated in terms of maximum numbers or concentration of the cells to which the subject is exposed, duration of detectable cells or cells above a certain number or percentage, area under the curve (AUC) for number or concentration of cells over time, and/or combinations thereof and indicators thereof. Such outcomes may be assessed using known methods, such as qPCR to detect copy number of nucleic acid encoding the recombinant receptor compared to total amount of nucleic acid or DNA in the particular sample, e.g., blood, serum, plasma or tissue, such as a tumor sample, and/or flow cytometric assays detecting cells expressing the receptor generally using antibodies specific for the receptors. Cell-based assays may also be used to detect the number or percentage or concentration of functional cells, such as cells capable of binding to and/or neutralizing and/or inducing responses, e.g., cytotoxic responses, against cells of the disease or condition or expressing the antigen recognized by the receptor.

In some aspects, increased exposure of the subject to the cells includes increased expansion of the cells. In some embodiments, the receptor expressing cells, e.g. CAR-expressing cells, expand in the subject following administration of the T cells, e.g., CAR-expressing T cells.

In some embodiments, cells expressing the receptor are detectable in the serum, plasma, blood or tissue, e.g., tumor sample, of the subject, e.g., by a specified method, such as qPCR or flow cytometry-based detection method, at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 or more days following administration of the T cells, e.g., CAR-expressing T cells, for at least at or about 2, 3, 4, 5, 6, 7, 8, 9, 10, 11, 12, 13, 14, 15, 16, 17, 18, 19, 20, 21, 22, 23, or 24 or more weeks following the administration of the T cells, e.g., CAR-expressing T cells.

In some aspects, at least at or about $1\times10^2$, at least at or about $1\times10^3$, at least at or about $1\times10^4$, at least at or about $1\times10^5$, or at least at or about $1\times10^6$ or at least at or about $5\times10^6$ or at least at or about $1\times10^7$ or at least at or about $5\times10^7$ or at least at or about $1\times10^8$ recombinant receptor-expressing, e.g., CAR-expressing cells, and/or at least 10, 25, 50, 100, 200, 300, 400, or 500, or 1000 receptor-expressing cells per microliter, e.g., at least 10 per microliter, are detectable or are present in the subject or fluid, plasma, serum, tissue, or compartment thereof, such as in the blood, e.g., peripheral blood, or disease site, e.g., tumor, thereof. In some embodiments, such a number or concentration of cells is detectable in the subject for at least at or about 20 days, at least at or about 40 days, or at least at or about 60 days, or at least at or about 3, 4, 5, 6, 7, 8, 9, 10, 11, or 12 months, or at least 2 or 3 years, following administration of the T cells, e.g., CAR-expressing T cells. Such cell numbers may be as detected by flow cytometry-based or quantitative PCR-based methods and extrapolation to total cell numbers using known methods. See, e.g., Brentjens et al., *Sci Transl Med.* 2013 5(177), Park et al, *Molecular Therapy* 15(4):825-833 (2007), Savoldo et al., *JCI* 121(5):1822-1826 (2011), Davila et al., (2013) *PLoS ONE* 8(4):e61338, Davila et al., *Oncoimmunology* 1(9): 1577-1583 (2012), Lamers, *Blood* 2011 117:72-82, Jensen et al., *Biol Blood Marrow Transplant* 2010 September; 16(9): 1245-1256, Brentjens et al., *Blood* 2011 118(18):4817-4828.

In some aspects, the copy number of nucleic acid encoding the recombinant receptor, e.g., vector copy number, per 100 cells, for example in the peripheral blood or bone marrow or other compartment, as measured by immunohistochemistry, PCR, and/or flow cytometry, is at least 0.01, at least 0.1, at least 1, or at least 10, at about 1 week, about 2 weeks, about 3 weeks, about 4 weeks, about 5 weeks, or at least about 6 weeks, or at least about 2, 3, 4, 5, 6, 7, 8. 9, 10, 11, or 12 months or at least 2 or 3 years following administration of the cells, e.g., CAR-expressing T cells. In some embodiments, the copy number of the vector expressing the receptor, e.g. CAR, per microgram of genomic DNA is at least 100, at least 1000, at least 5000, or at least 10,000, or at least 15,000 or at least 20,000 at a time about 1 week, about 2 weeks, about 3 weeks, or at least about 4 weeks following administration of the T cells, e.g., CAR-expressing T cells or at least 2, 3, 4, 5, 6, 7, 8, 9, 10, 11, or 12 months or at least 2 or 3 years following such administration.

In some aspects, the receptor, e.g. CAR, expressed by the cells, is detectable by quantitative PCR (qPCR) or by flow cytometry in the subject, plasma, serum, blood, tissue and/or disease site thereof, e.g., tumor site, at a time that is at least at or about 3 months, at least at or about 6 months, at least at or about 12 months, at least at or about 1 year, at least at or about 2 years, at least at or about 3 years, or more than 3 years, following the administration of the cells, e.g., following the initiation of the administration of the T cells. In some embodiments, the area under the curve (AUC) for concentration of receptor- (e.g., CAR-) expressing cells in a fluid, plasma, serum, blood, tissue, organ and/or disease site, e.g. tumor site, of the subject over time following the administration of the T cells, e.g., CAR-expressing T cells, is measured.

Also provided are methods of assessing likelihood of a response or a durable response. In some embodiments, the methods involve detecting, in a biological sample from a subject, peak levels of one or more inflammatory marker and/or peak levels of genetically engineered cells comprising T cells expressing a chimeric antigen receptor (CAR), wherein the subject has been previously administered a dose of the genetically engineered cells for treating a disease or condition. In some embodiments, the methods involve comparing, individually, the peak levels to a threshold value, thereby determining a likelihood that a subject will achieve a durable response to the administration of the genetically engineered cells.

In some embodiments, the subject is likely to achieve a response or a durable response if the peak levels of the one or more inflammatory marker is below a threshold value and the subject is not likely to achieve a durable response if the peak levels of the one or more inflammatory marker is above a threshold value. In some embodiments, the subject is likely to achieve a durable response if the peak level of the genetically engineered cells is within a therapeutic range between a lower threshold value and an upper threshold value and the subject is not likely to achieve a durable response if the peak level of the genetically engineered cells is below the lower threshold value or is above the upper threshold value.

In some cases, the provided embodiments involve assessing parameters, such as attributes, factors, characteristic of the patient and/or the disease or condition, and/or expression of biomarkers. In some embodiments, the assessed parameters are associated with and/or correlated with pharmacokinetic parameters, response, durable response and/or development of toxicity. In some embodiments, the parameters include patient factors or patient attributes. In some embodiments, the assessed parameters are correlated with the phenotype of the cell compositions disclosed herein. In some embodiments, the assessed parameters indicate whether the output composition will have the necessary cellular composition (e.g., percentage of cell phenotypes) correlated with progression free survival and/or durable response. In some embodiments, the assessed parameters can be used to predict the likelihood of producing an output composition useful for therapeutic administration. In some embodiments, patients with high disease burden, for example those with high SPD (e.g., a value of greater than or equal to 50 cm$^2$) or CRP values (e.g., a value greater than or equal to 20 mg/L), are less likely to produce output compositions useful for therapeutic administration. In some embodiments, patients with low disease burden, for example those with low SPD (e.g., a value of less than 50 cm$^2$) or CRP values (e.g., a value less than 20 mg/L), are more likely to produce output compositions useful for therapeutic administration. In some embodiments, the parameters include attributes, factors, characteristic of the disease or condition. In some embodiments, the parameters are assessed prior to treatment, e.g., prior to administration of the cell therapy. In some embodiments, the parameters are assessed after treatment, e.g., after administration of one or more doses of the cell therapy.

In some embodiments, the parameter is or includes pharmacokinetic parameters, e.g., maximum (peak) plasma concentration ($C_{max}$), the peak time (i.e., when maximum plasma concentration ($C_{max}$) occurs; $T_{max}$), the minimum plasma concentration (i.e., the minimum plasma concentration between doses of a therapeutic agent, e.g., CAR$^+$ T cells; $C_{min}$), the elimination half-life ($T_{1/2}$) and area under the curve (i.e., the area under the curve generated by plotting time versus plasma concentration of the therapeutic agent CAR$^+$ T cells; AUC; such as AUC$_{0-28}$).

In some embodiments, the parameter is or includes one or more factors indicative of the state of the patient and/or the disease or condition of the patient. In some embodiments, the parameter is indicative of tumor burden. In some embodiments, the factor indicative of tumor burden is a volumetric measure of tumor(s). In some embodiments, the volumetric measure is a measure of the lesion(s), such as the tumor size, tumor diameter, tumor volume, tumor mass, tumor load or bulk, tumor-related edema, tumor-related necrosis, and/or number or extent of metastases. In some embodiments, the volumetric measure of tumor is a bidimensional measure. For example, in some embodiments, the area of lesion(s) are calculated as the product of the longest diameter and the longest perpendicular diameter of all measurable tumors. In some cases, the volumetric measure of tumor is a unidimensional measure. In some cases, the size of measurable lesions is assessed as the longest diameter. In some embodiments, the sum of the products of diameters (SPD), longest tumor diameters (LD), sum of longest tumor diameters (SLD), necrosis, tumor volume, necrosis volume, necrosis-tumor ratio (NTR), peritumoral edema (PTE), and edema-tumor ratio (ETR) is measured.

Exemplary methods for measuring and assessing tumor burden include those described in, e.g., Carceller et al., Pediatr Blood Cancer. (2016) 63(8):1400-1406 and Eisenhauer et al., Eur J Cancer. (2009) 45(2):228-247. In some embodiments, the volumetric is a sum of the products of diameters (SPD) measured by determining the sum of the products of the largest perpendicular diameters of all measurable tumors. In some aspects, the tumor or lesion is measured in one dimension with the longest diameter (LD) and/or by determining the sum of longest tumor diameters (SLD) of all measurable lesions. In some embodiments, the volumetric measure of tumor is a volumetric quantification of tumor necrosis, such as necrosis volume and/or necrosis-tumor ratio (NTR), see Monsky et al., Anticancer Res. (2012) 32(11): 4951-4961. In some aspects, the volumetric measure of tumor is a volumetric quantification of tumor-related edema, such as peritumoral edema (PTE) and/or edema-tumor ratio (ETR). In some embodiments, measuring can be performed using imaging techniques such as computed tomography (CT), positron emission tomography (PET), and/or magnetic resonance imaging (MRI) of the subject.

In some embodiments, the volumetric measure is SPD and in some cases, development of toxicity, e.g., CRS or NT, is correlated with the SPD value that is above a threshold value. In some embodiments, the volumetric measure is SPD, and the threshold value is or is about 30 cm$^2$, is or is about 40 cm$^2$, is or is about 50 cm$^2$, is or is about 60 cm$^2$, or is or is about 70 cm$^2$. In some embodiments, the volumetric measure is SPD and the threshold value is or is about 30 cm$^2$, is or is about 40 cm$^2$, is or is about 50 cm$^2$, is or is about 60 cm$^2$, or is or is about 70 cm$^2$.

In some embodiments, the volumetric measure of tumor is determined at a screening session, such as a routine assessment or blood draw to confirm and/or identify the condition or disease in the subject.

In some aspects, the parameter, e.g., measurements of tumor burden, correlates to and/or is associated with pharmacokinetic parameters. In some embodiments, the parameter, including pharmacokinetic parameters, is associated with response and/or durable response, and/or a risk for developing toxicity, e.g., CRS or neurotoxicity (NT).

In some embodiments, the parameter is or includes at least one or a panel of biomarkers. In some embodiments, expression and/or presence of the biomarker is associated with and/or correlated with pharmacokinetic parameters, response, durable response and/or development of toxicity. In some embodiments, the parameter is compared to a particular reference value, e.g., those associated with response and/or durable response, and/or a risk for developing toxicity, e.g., CRS or neurotoxicity (NT). In some embodiments, the methods also involve administering an agent capable of modulating CAR$^+$ T cell expansion, proliferation, and/or activity, to the subject, based on the assessment of patient factors and/or biomarkers.

In some aspects, the embodiments involve obtaining a biological sample for detecting the parameter and/or assessing the presence of and/or or detecting the parameter. In some embodiments, the biological sample is obtained generally within 4 hours to 12 months of administration of the cell therapy, or a first administration or dose thereof, or after the initiation of any of the foregoing, such as generally within or within about 1, 2, 3, 4, 5, 6, 7, 8, 9, 10, 11, 12, 13, 14, 21, 28, 30, 60 or 90 or more days, 2, 3, 4, 5, 6, 7, 8, 9, 10, 11, 12, 13, 14, 15 or more weeks, or 1, 2, 3, 4, 5, 6, 7, 8, 9, 10, 11, 12, 18, 24, 48 or more months, after administration of the cell therapy, or a first administration or dose thereof, or after the initiation of any of the foregoing. In some embodiments, the parameter is assessed or measured in a subject prior to administration of the cell therapy or soon after administration of the cell therapy, or a first administration or dose thereof, or after the initiation of any of the foregoing, such as generally within 4 hours to 3 days of administration of the cell therapy, or a first administration or dose thereof, or after the initiation of any of the foregoing, such as generally within or about 1 day, 2 days or 3 days after administration of the cell therapy, or a first administration or dose thereof, or after the initiation of any of the foregoing. In some embodiments, the parameter is assessed or measured. In some embodiments, the parameter is assessed generally within 4 hours to 12 months of administration of the cell therapy, or a first administration or dose thereof, or after the initiation of any of the foregoing, such as generally within or within about 1, 2, 3, 4, 5, 6, 7, 8, 9, 10, 11, 12, 13, 14, 21, 28, 30, 60 or 90 or more days, 2, 3, 4, 5, 6, 7, 8, 9, 10, 11, 12, 13, 14, 15 or more weeks, or 1, 2, 3, 4, 5, 6, 7, 8, 9, 10, 11, 12, 18, 24, 48 or more months, after administration of the cell therapy, or a first administration or dose thereof, or after the initiation of any of the foregoing.

In some aspects, the parameter, e.g., patient factor and/or biomarker, correlates to and/or is associated with pharmacokinetic parameters. In some embodiments, the parameter, including pharmacokinetic parameters, is associated with response and/or durable response, and/or a risk for developing toxicity, e.g., CRS or neurotoxicity (NT).

In some embodiments, the parameter is a biomarker. In some embodiments, the parameter is or includes the expression of the biomarker and/or the number, concentration, and/or percentage of cells that express a particular biomarker. In some embodiments, the parameter includes biomarkers or each biomarker in a panel that comprises a plurality of biomarkers. In some embodiments, the biomarker is or comprises a cytokine and/or other serum or blood factor, such as any as described herein. In some embodiments, the biomarker or each biomarker in a panel is a cytokine, which, in some cases, can be a chemokine. In some embodiments, the biomarkers or each biomarker in a panel comprises a soluble receptor. In some embodiments, the biomarkers or each biomarker in a panel comprises a soluble serum protein. Exemplary biomarkers or panel of biomarkers is described herein.

In some embodiments, the parameter is or includes levels and/or concentrations of a blood analyte. In some embodiments, the parameter is or includes levels and/or concentrations of an inflammatory marker. In some embodiments, the blood analyte and/or inflammatory marker is or includes levels and/or concentrations of interleukin-7 (IL-7), IL-15, macrophage inflammatory protein (MIP-1a). In some embodiments, the blood analyte and/or inflammatory marker is or includes levels and/or concentrations of IL-6, IL-1β, IL-16, interferon gamma (IFN-γ), tumor necrosis factor alpha (TNF-α), MIP-1α, MIP-1β, Monocyte chemoattractant protein-1 (MCP-1), and C—X—C motif chemokine 10 (CXCL10). In some embodiments, the blood analyte and/or inflammatory marker is or includes levels and/or concentrations of ferritin, C-reactive protein (CRP), D-dimer (fibrin degradation product), IL-6, IL-10, IL-15, IL-16, TNF-α, MIP-1α, and MIP-1β. In some embodiments, the blood analyte and/or inflammatory marker is or includes levels and/or concentrations of LDH, Ferritin, CRP, IL-6, IL-8, IL-10, TNF-α, IFN-α2, MCP-1 and/or MIP-1β. In some embodiments, the blood analyte and/or inflammatory marker is or includes levels and/or concentrations of CRP, Serum Amyloid A1 (SAA-1), IL-2, IL-6, IL-10, IL-15, TNF-α, MIP-1α, MIP-1β, MCP-1, CXCL10 and C—C Motif Chemokine Ligand 13 (CCL13). In some embodiments, the blood analyte and/or inflammatory marker is or includes levels and/or concentrations of LDH, ferritin, CRP, D-dimer, SAA-1, IL-6, IL-10, IL-15, IL-16, TNF-α, IFN-γ and/or MIP-1α.

In some embodiments, an inflammatory marker is or includes the level or presence of C-reactive protein (CRP), erythrocyte sedimentation rate (ESR), albumin, ferritin, 32 microglobulin (β2-M), or lactate dehydrogenase (LDH) is detected and assessed. In some embodiments, the inflammatory marker is assessed using an immune assay. For example, an enzyme-linked immunosorbent assay (ELISA), enzyme immunoassay (EIA), radioimmunoassay (RIA), surface plasmon resonance (SPR), Western Blot, Lateral flow assay, immunohistochemistry, protein array or immuno-PCR (iPCR) can be used to detect the inflammatory marker.

In some embodiments, using the articles of manufacture include detecting an inflammatory marker indicative of tumor burden. In some cases, the assaying or assessing of an inflammatory marker is using flow cytometry. In some cases, the reagent is a soluble protein that binds the inflammatory marker. In some example, the reagent is a protein that binds C-reactive protein (CRP), erythrocyte sedimentation rate (ESR), albumin, ferritin, β2 microglobulin (β2-M), or lactate dehydrogenase (LDH).

In some embodiments, the biomarker, e.g., inflammatory marker is or includes C-reactive protein (CRP). In some embodiments, CRP is assessed using an in vitro enzyme-linked immunosorbent assay to obtain a quantitative measurement of human CRP from a sample such as serum, plasma, or blood. In some examples, CRP is detected using a human Enzyme-Linked Immunosorbent Assay (ELISA). In some embodiments, the biomarker, e.g. inflammatory marker is or includes erythrocyte sedimentation rate (ESR). In some embodiments, ESR is assessed by measuring the distance (in millimeters per hour) that red cells have fallen after separating from the plasma in a vertical pipette or tube. In some embodiments the biomarker is or includes albumin. In some aspects, albumin is assessed using a colorimetric test or an in vitro enzyme-linked immunosorbent assay. In some examples, albumin is detected using a human Enzyme-Linked Immunosorbent Assay (ELISA). In some embodiments, the biomarker, e.g., inflammatory marker, is or includes ferritin or 2 microglobulin. In some embodiments, ferritin or 2 microglobulin is assessed using an immunoassay or detected using an ELISA. In some aspects, the biomarker, e.g., inflammatory marker, is or includes lactate dehydrogenase (LDH), and LDH is assessed using a colorimetric test or an in vitro enzyme-linked immunosorbent assay.

In some embodiments, the parameter is LDH and in some cases, development of toxicity, e.g., CRS or NT, is correlated with the LDH value that is above a threshold value. In some embodiments, the inflammatory marker is LDH and the threshold value is or is about 300 units per liter, is or is about 400 units per liter, is or is about 500 units per liter or is or is about 600 units per liter.

In some embodiments, the parameter or biomarker is LDH. In some embodiments, the biomarker is LDH and the threshold value is 500 U/L or higher. In some embodiments, the parameter or biomarker is SPD. In some embodiments, the parameter is SPD, and the threshold value is or is about 50 cm$^2$ or higher. In some embodiments, biomarker or parameters are SPD and LDH, and the threshold values are SPD of 50 cm$^2$ or higher and LDH of 500 U/L or higher. In some embodiments, the biomarkers or parameters are associated with increased risk of developing CRS or NT. In some embodiments, a measurement of the parameter or marker that is above the threshold value, e.g., SPD of 50 cm$^2$ or higher and LDH of 500 U/L or higher, are associated with an approximately 2-, 3⁻, 4-, 5-, 6-, 7-, 8-, 9-, 10-fold or more increased risk of developing CRS or NT, such as any grade CRS or NT. In some embodiments, a measurement of the parameter or marker that is below the threshold value, e.g., SPD of lower than 500 cm$^2$ and LDH of lower than 500 U/L, are associated with an approximately 2-, 3-, 4-, 5-, 6-, 7-, 8-, 9-10-fold or more decreased risk of developing CRS or NT, such as any grade CRS or NT.

2. Assessing Response, Efficacy and Survival

In some aspects, the methods involve determining the association or relationship between the dose of cells having a particular cell phenotype, e.g., CCR7$^+$ cells, and response, efficacy and/or survival in subjects administered such doses of cells.

In some aspects, response rates in subjects, such as subjects with NHL, are based on the Lugano criteria. (Cheson et al., (2014) JCO 32(27):3059-3067; Johnson et al., (2015) Radiology 2:323-338; Cheson, B. D. (2015) Chin Clin Oncol 4(1):5). In some aspects, response assessment utilizes any of clinical, hematologic, and/or molecular methods. In some aspects, response assessed using the Lugano criteria involves the use of positron emission tomography (PET)-computed tomography (CT) and/or CT as appropriate. PET-CT evaluations may further comprise the use of fluorodeoxyglucose (FDG) for FDG-avid lymphomas. In some aspects, where PET-CT will be used to assess response in FDG-avid histologies, a 5-point scale may be used. In some respects, the 5-point scale comprises the following criteria: 1, no uptake above background; 2, uptake≤mediastinum; 3, uptake>mediastinum but ≤liver; 4, uptake moderately >liver; 5, uptake markedly higher than liver and/or new lesions; X, new areas of uptake unlikely to be related to lymphoma.

In some aspects, a complete response (CR) as described using the Lugano criteria involves a complete metabolic response and a complete radiologic response at various measureable sites. In some aspects, these sites include lymph nodes and extralymphatic sites, wherein a CR is described as a score of 1, 2, or 3 with or without a residual mass on the 5-point scale, when PET-CT is used. In some aspects, in Waldeyer's ring or extranodal sites with high physiologic uptake or with activation within spleen or marrow (e.g., with chemotherapy or myeloid colony-stimulating factors), uptake may be greater than normal mediastinum and/or liver. In this circumstance, complete metabolic response may be inferred if uptake at sites of initial involvement is no greater than surrounding normal tissue even if the tissue has high physiologic uptake. In some aspects, response is assessed in the lymph nodes using CT, wherein a CR is described as no extralymphatic sites of disease and target nodes/nodal masses must regress to ≤1.5 cm in longest transverse diameter of a lesion (LDi). Further sites of assessment include the bone marrow wherein PET-CT-based assessment should indicate a lack of evidence of FDG-avid disease in marrow and a CT-based assessment should indicate a normal morphology, which if indeterminate should be IHC negative. Further sites may include assessment of organ enlargement, which should regress to normal. In some aspects, nonmeasured lesions and new lesions are assessed, which in the case of CR should be absent (Cheson et al., (2014) JCO 32(27):3059-3067; Johnson et al., (2015) Radiology 2:323-338; Cheson, B. D. (2015) Chin Clin Oncol 4(1):5).

In some aspects, a partial response (PR) as described using the Lugano criteria involves a partial metabolic and/or radiological response at various measureable sites. In some aspects, these sites include lymph nodes and extralymphatic sites, wherein a PR is described as a score of 4 or 5 with reduced uptake compared with baseline and residual mass(es) of any size, when PET-CT is used. At interim, such findings can indicate responding disease. At the end of treatment, such findings can indicate residual disease. In some aspects, response is assessed in the lymph nodes using CT, wherein a PR is described as ≥50% decrease in SPD of up to 6 target measureable nodes and extranodal sites. If a lesion is too small to measure on CT, 5 mm×5 mm is assigned as the default value; if the lesion is no longer visible, the value is 0 mm×0 mm; for a node>5 mm×5 mm, but smaller than normal, actual measurements are used for calculation. Further sites of assessment include the bone marrow wherein PET-CT-based assessment should indicate residual uptake higher than uptake in normal marrow but reduced compared with baseline (diffuse uptake compatible with reactive changes from chemotherapy allowed). In some aspects, if there are persistent focal changes in the marrow in the context of a nodal response, consideration should be given to further evaluation with MRI or biopsy, or an interval scan. In some aspects, further sites may include assessment of organ enlargement, where the spleen must have regressed by >50% in length beyond normal. In some aspects, nonmeasured lesions and new lesions are assessed, which in the case of PR should be absent/normal, regressed, but no increase. No response/stable disease (SD) or progressive disease (PD) can also be measured using PET-CT and/or CT based assessments. (Cheson et al., (2014) JCO 32(27):3059-3067; Johnson et al., (2015) Radiology 2:323-338; Cheson, B. D. (2015) Chin Clin Oncol 4(1):5).

In some respects, progression-free survival (PFS) is described as the length of time during and after the treatment of a disease, such as cancer, that a subject lives with the disease but it does not get worse. In some aspects, objective response (OR) is described as a measurable response. In some aspects, objective response rate (ORR) is described as the proportion of patients who achieved CR or PR. In some aspects, overall survival (OS) is described as the length of time from either the date of diagnosis or the start of treatment for a disease, such as cancer, that subjects diagnosed with the disease are still alive. In some aspects, event-free survival (EFS) is described as the length of time after treatment for a cancer ends that the subject remains free of certain complications or events that the treatment was intended to prevent or delay. These events may include the return of the cancer or the onset of certain symptoms, such as bone pain from cancer that has spread to the bone, or death.

In some embodiments, the measure of duration of response (DOR) includes the time from documentation of tumor response to disease progression. In some embodiments, the parameter for assessing response can include durable response, e.g., response that persists after a period of time from initiation of therapy. In some embodiments, durable response is indicated by the response rate at approximately 1, 2, 3, 4, 5, 6, 7, 8, 9, 10, 11, 12, 18 or 24 months after initiation of therapy. In some embodiments, the response is durable for greater than 3 months or greater than 6 months.

In some aspects, the RECIST criteria is used to determine objective tumor response; in some aspects, in solid tumors. (Eisenhauer et al., European Journal of Cancer 45 (2009) 228-247.) In some aspects, the RECIST criteria is used to determine objective tumor response for target lesions. In some respects, a complete response as determined using RECIST criteria is described as the disappearance of all target lesions and any pathological lymph nodes (whether target or non-target) must have reduction in short axis to <10 mm. In other aspects, a partial response as determined using RECIST criteria is described as at least a 30% decrease in the sum of diameters of target lesions, taking as reference the baseline sum diameters. In other aspects, progressive disease (PD) is described as at least a 20% increase in the sum of diameters of target lesions, taking as reference the smallest sum on study (this includes the baseline sum if that is the smallest on study). In addition to the relative increase of 20%, the sum must also demonstrate an absolute increase of at least 5 mm (in some aspects the appearance of one or more new lesions is also considered progression). In other aspects, stable disease (SD) is described as neither sufficient shrinkage to qualify for PR nor sufficient increase to qualify for PD, taking as reference the smallest sum diameters while on study.

In some aspects, the administration in accord with the provided methods, and/or with the provided articles of manufacture or compositions, generally reduces or prevents the expansion or burden of the disease or condition in the subject. For example, where the disease or condition is a tumor, the methods generally reduce tumor size, bulk, metastasis, percentage of blasts in the bone marrow or molecularly detectable cancer and/or improve prognosis or survival or other symptom associated with tumor burden.

Disease burden can encompass a total number of cells of the disease in the subject or in an organ, tissue, or bodily fluid of the subject, such as the organ or tissue of the tumor or another location, e.g., which would indicate metastasis. For example, tumor cells may be detected and/or quantified in the blood or bone marrow in the context of certain hematological malignancies. Disease burden can include, in some embodiments, the mass of a tumor, the number or extent of metastases and/or the percentage of blast cells present in the bone marrow.

In some embodiments, a subject has leukemia. The extent of disease burden can be determined by assessment of residual leukemia in blood or bone marrow.

In some aspects, response rates in subjects, such as subjects with CLL, are based on the International Workshop on Chronic Lymphocytic Leukemia (IWCLL) response criteria (Hallek, et al., Blood 2008, Jun. 15; 111(12): 5446-5456). In some aspects, these criteria are described as follows: complete remission (CR), which in some aspects requires the absence of peripheral blood clonal lymphocytes by immunophenotyping, absence of lymphadenopathy, absence of hepatomegaly or splenomegaly, absence of constitutional symptoms and satisfactory blood counts; complete remission with incomplete marrow recovery (CRi), which in some aspects is described as CR above, but without normal blood counts; partial remission (PR), which in some aspects is described as ≥50% fall in lymphocyte count, ≥50% reduction in lymphadenopathy or ≥50% reduction in liver or spleen, together with improvement in peripheral blood counts; progressive disease (PD), which in some aspects is described as ≥50% rise in lymphocyte count to ≥5×10$^9$/L, ≥50% increase in lymphadenopathy, ≥50% increase in liver or spleen size, Richter's transformation, or new cytopenias due to CLL; and stable disease, which in some aspects is described as not meeting criteria for CR, CRi, PR or PD.

In some embodiments, the subject exhibits a durable response following administration of a cell therapy comprising one more unit doses (or unit dose) of the cells of the composition. In some embodiments, a durable response is a length of time, usually in months, during which a subject displays a partial or complete response as a result of treatment. In some embodiments, the durable response coincides with an improvement in overall survival.

In some embodiments, the subject exhibits progression free survival (PFS) following administration of a cell therapy comprising one more unit doses (or unit dose) of the cells of the composition. In some embodiments, progression free survival is determined by measuring the length of time after treatment or the start of treatment (e.g., after administration of a cell therapy comprising one more unit doses (or unit dose) of the cells of the composition) where the disease does not worsen. In some embodiments, when the disease is cancer, progression free survival refers to the cancer failing to worsen or spread. In some embodiments, progression free survival coincides with a durable response.

In some embodiments, the subjects exhibits a CR or OR if, within 1 month of the administration of the dose of cells, lymph nodes in the subject are less than at or about 20 mm in size, less than at or about 10 mm in size or less than at or about 10 mm in size.

In some embodiments, an index clone of the CLL is not detected in the bone marrow of the subject (or in the bone marrow of greater than 50%, 60%, 70%, 80%, 90% or more of the subjects treated according to the methods. In some embodiments, an index clone of the CLL is assessed by IgH deep sequencing. In some embodiments, the index clone is not detected at a time that is at or about or at least at or about 1, 2, 3, 4, 5, 6, 12, 18 or 24 months following the administration of the cells.

In some embodiments, a subject exhibits morphologic disease if there are greater than or equal to 5% blasts in the bone marrow, for example, as detected by light microscopy, such as greater than or equal to 10% blasts in the bone marrow, greater than or equal to 20% blasts in the bone marrow, greater than or equal to 30% blasts in the bone marrow, greater than or equal to 40% blasts in the bone marrow or greater than or equal to 50% blasts in the bone marrow. In some embodiments, a subject exhibits complete or clinical remission if there are less than 5% blasts in the bone marrow.

In some embodiments, a subject may exhibit complete remission, but a small proportion of morphologically undetectable (by light microscopy techniques) residual leukemic cells are present. A subject is said to exhibit minimum residual disease (MRD) if the subject exhibits less than 5% blasts in the bone marrow and exhibits molecularly detectable cancer. In some embodiments, molecularly detectable cancer can be assessed using any of a variety of molecular techniques that permit sensitive detection of a small number of cells. In some aspects, such techniques include PCR assays, which can determine unique Ig/T-cell receptor gene rearrangements or fusion transcripts produced by chromosome translocations. In some embodiments, flow cytometry can be used to identify cancer cell based on leukemia-specific immunophenotypes. In some embodiments, molecular detection of cancer can detect as few as 1 leukemia cell in 100,000 normal cells. In some embodiments, a subject exhibits MRD that is molecularly detectable if at least or greater than 1 leukemia cell in 100,000 cells is detected, such as by PCR or flow cytometry. In some embodiments, the disease burden of a subject is molecularly undetectable or MRD$^-$, such that, in some cases, no leukemia cells are able to be detected in the subject using PCR or flow cytometry techniques.

In some aspects, the disease or condition persists following administration of the first dose and/or administration of the first dose is not sufficient to eradicate the disease or condition in the subject.

In some embodiments, the method reduces the burden of the disease or condition, e.g., number of tumor cells, size of tumor, duration of patient survival or event-free survival, to a greater degree and/or for a greater period of time as compared to the reduction that would be observed with a comparable method using an alternative dosing regimen, such as one in which the subject receives one or more alternative therapeutic agents and/or one in which the subject does not receive a dose of cells and/or a lymphodepleting agent in accord with the provided methods, and/or with the provided articles of manufacture or compositions. In some embodiments, an alternative dose of cells is referred to as a reference composition. In some embodiments, the reference composition contains a non-defined number of cells or cells of a particular phenotype and/or cells of a particular phenotype not at a particular defined ratio according to embodiments provided herein. In some embodiments, the reference composition is one in which is contained a greater frequency or number of T cells having an effector or differentiated phenotype. In some embodiments, the burden of a disease or condition in the subject is detected, assessed, or measured. Disease burden may be detected in some aspects by detecting the total number of disease or disease-associated cells, e.g., tumor cells, in the subject, or in an organ, tissue, or bodily fluid of the subject, such as blood or serum. In some aspects, survival of the subject, survival within a certain time period, extent of survival, presence or duration of event-free or symptom-free survival, or relapse-free survival, is assessed. In some embodiments, any symptom of the disease or condition is assessed. In some embodiments, the measure of disease or condition burden is specified.

In some embodiments, the event-free survival rate or overall survival rate of the subject is improved by the methods, as compared with other methods, for example, methods in which the subject receives one or more alternative therapeutic agents and/or one in which the subject does not receive a dose of cells (e.g., receives a reference composition) and/or a lymphodepleting agent in accord with the provided methods, and/or with the provided articles of manufacture or compositions. For example, in some embodiments, event-free survival rate or probability for subjects treated by the methods at 6 months following the dose is greater than about 40%, greater than about 50%, greater than about 60%, greater than about 70%, greater than about 80%, greater than about 90%, or greater than about 95%. In some aspects, overall survival rate is greater than about 40%, greater than about 50%, greater than about 60%, greater than about 70%, greater than about 80%, greater than about 90%, or greater than about 95%. In some embodiments, the subject treated with the methods exhibits event-free survival, relapse-free survival, or survival to at least 6 months, or at least 1, 2, 3, 4, 5, 6, 7, 8, 9, or 10 years. In some embodiments, the time to progression is improved, such as a time to progression of greater than at or about 6 months, or at least 1, 2, 3, 4, 5, 6, 7, 8, 9, or 10 years.

In some embodiments, following treatment by the method, the probability of relapse is reduced as compared to other methods, for example, methods in which the subject receives one or more alternative therapeutic agents and/or one in which the subject does not receive a dose of cells (e.g., receives a reference composition) and/or a lymphodepleting agent in accord with the provided methods, and/or with the provided articles of manufacture or compositions. For example, in some embodiments, the probability of relapse at 6 months following the first dose is less than about 80%, less than about 70%, less than about 60%, less than about 50%, less than about 40%, less than about 30%, less than about 20%, or less than about 10%.

In some cases, the pharmacokinetics of administered cells, e.g., adoptively transferred cells are determined to assess the availability, e.g., bioavailability of the administered cells. Methods for determining the pharmacokinetics of adoptively transferred cells may include drawing peripheral blood from subjects that have been administered engineered cells, and determining the number or ratio of the engineered cells in the peripheral blood. Approaches for selecting and/or isolating cells may include use of chimeric antigen receptor (CAR)-specific antibodies (e.g., Brentjens et al., Sci. Transl. Med. 2013 March; 5(177): 177ra38) Protein L (Zheng et al., J. Transl. Med. 2012 February; 10:29), epitope tags, such as Strep-Tag sequences, introduced directly into specific sites in the CAR, whereby binding reagents for Strep-Tag are used to directly assess the CAR (Liu et al. (2016) Nature Biotechnology, 34:430; international patent application Pub. No. WO2015095895) and monoclonal antibodies that specifically bind to a CAR polypeptide (see international patent application Pub. No. WO2014190273). Extrinsic marker genes may in some cases be utilized in connection with engineered cell therapies to permit detection or selection of cells and, in some cases, also to promote cell suicide. A truncated epidermal growth factor receptor (EGFRt) in some cases can be co-expressed with a transgene of interest (a CAR or TCR) in transduced cells (see e.g. U.S. Pat. No. 8,802,374). EGFRt may contain an epitope recognized by the antibody cetuximab (Erbitux®) or other therapeutic anti-EGFR antibody or binding molecule, which can be used to identify or select cells that have been engineered with the EGFRt construct and another recombinant receptor, such as a chimeric antigen receptor (CAR), and/or to eliminate or separate cells expressing the receptor. See U.S. Pat. No. 8,802,374 and Liu et al., Nature Biotech. 2016 April; 34(4): 430-434).

In some embodiments, the number of $CAR^+$ T cells in a biological sample obtained from the patient, e.g., blood, can be determined at a period of time after administration of the cell therapy, e.g., to determine the pharmacokinetics of the cells. In some embodiments, number of $CAR^+$ T cells, optionally $CAR^+$ $CD8^+$ T cells and/or $CAR^+CD4^+$ T cells, detectable in the blood of the subject, or in a majority of subjects so treated by the method, is greater than 1 cells per µL, greater than 5 cells per µL or greater than per 10 cells per µL.

3. Assessing Toxicity

In some aspects, the methods involve determining the association or relationship between the dose of cells having a particular cell phenotype, e.g., $CCR7^+$ cells, and toxicity outcome, e.g., development of cytokine release syndrome (CRS) or neurotoxicity (NT) in subjects administered such doses of cells.

In some aspects, the toxic outcome is or is associated with or indicative of cytokine release syndrome (CRS) or severe CRS (sCRS). CRS, e.g., sCRS, can occur in some cases following adoptive T cell therapy and administration to subjects of other biological products. See Davila et al., Sci Transl Med 6, 224ra25 (2014); Brentjens et al., Sci. Transl. Med. 5, 177ra38 (2013); Grupp et al., N. Engl. J. Med. 368, 1509-1518 (2013); and Kochenderfer et al., Blood 119, 2709-2720 (2012); Xu et al., Cancer Letters 343 (2014) 172-78.

Typically, CRS is caused by an exaggerated systemic immune response mediated by, for example, T cells, B cells, NK cells, monocytes, and/or macrophages. Such cells may release a large amount of inflammatory mediators such as cytokines and chemokines. Cytokines may trigger an acute inflammatory response and/or induce endothelial organ damage, which may result in microvascular leakage, heart failure, or death. Severe, life-threatening CRS can lead to pulmonary infiltration and lung injury, renal failure, or disseminated intravascular coagulation. Other severe, life-threatening toxicities can include cardiac toxicity, respiratory distress, neurologic toxicity and/or hepatic failure. In some aspects, fever, especially high fever (≥38.5° C. or ≥101.3° F.), is associated with CRS. In some cases, features or symptoms of CRS mimic infection. In some embodiments, infection is also considered in subjects presenting with CRS symptoms, and monitoring by cultures and empiric antibiotic therapy can be administered. Other symptoms associated with CRS can include cardiac dysfunction, adult respiratory distress syndrome, renal and/or hepatic failure, coagulopathies, disseminated intravascular coagulation, and capillary leak syndrome.

CRS may be treated using anti-inflammatory therapy such as an anti-IL-6 therapy, e.g., anti-IL-6 antibody, e.g., tocilizumab, or antibiotics or other agents as described. Outcomes, signs and symptoms of CRS are known and include those described herein. In some embodiments, where a particular dosage regimen or administration effects or does not effect a given CRS-associated outcome, sign, or symptom, particular outcomes, signs, and symptoms and/or quantities or degrees thereof may be specified.

In the context of administering CAR-expressing cells, CRS typically occurs 6-20 days after infusion of cells that express a CAR. See Xu et al., Cancer Letters 343 (2014) 172-78. In some cases, CRS occurs less than 6 days or more than 20 days after CAR T cell infusion. The incidence and timing of CRS may be related to baseline cytokine levels or tumor burden at the time of infusion. Commonly, CRS involves elevated serum levels of interferon (IFNγ)-γ, tumor necrosis factor (TNF)-α, and/or interleukin (IL)-2. Other cytokines that may be rapidly induced in CRS are IL-1β, IL-6, IL-8, and IL-1β.

Exemplary outcomes associated with CRS include fever, rigors, chills, hypotension, dyspnea, acute respiratory distress syndrome (ARDS), encephalopathy, ALT/AST elevation, renal failure, cardiac disorders, hypoxia, neurologic disturbances, and death. Neurological complications include delirium, seizure-like activity, confusion, word-finding difficulty, aphasia, and/or becoming obtunded. Other CRS-related outcomes include fatigue, nausea, headache, seizure, tachycardia, myalgias, rash, acute vascular leak syndrome, liver function impairment, and renal failure. In some aspects, CRS is associated with an increase in one or more factors such as serum-ferritin, d-dimer, aminotransferases, lactate dehydrogenase and triglycerides, or with hypofibrinogenemia or hepatosplenomegaly.

In some embodiments, outcomes associated with CRS include one or more of: persistent fever, e.g., fever of a specified temperature, e.g., greater than at or about 38 degrees Celsius, for two or more, e.g., three or more, e.g., four or more days or for at least three consecutive days; fever greater than at or about 38 degrees Celsius; elevation of cytokines, such as a max fold change, e.g., of at least at or about 75, compared to pre-treatment levels of at least two cytokines (e.g., at least two of the group consisting of interferon gamma (IFNγ), GM-CSF, IL-6, IL-1β, Flt-3L, fracktalkine, and IL-5, and/or tumor necrosis factor alpha (TNFα)), or a max fold change, e.g., of at least at or about 250 of at least one of such cytokines; and/or at least one clinical sign of toxicity, such as hypotension (e.g., as measured by at least one intravenous vasoactive pressor); hypoxia (e.g., plasma oxygen ($PO_2$) levels of less than at or about 90%); and/or one or more neurologic disorders (including mental status changes, obtundation, and seizures). In some embodiments, neurotoxicity (NT) can be observed concurrently with CRS.

Exemplary CRS-related outcomes include increased or high serum levels of one or more factors, including cytokines and chemokines and other factors associated with CRS. Exemplary outcomes further include increases in synthesis or secretion of one or more of such factors. Such synthesis or secretion can be by the T cell or a cell that interacts with the T cell, such as an innate immune cell or B cell.

In some embodiments, the CRS-associated serum factors or CRS-related outcomes include inflammatory cytokines and/or chemokines, including interferon gamma (IFN-γ), TNF-a, IL-1β, IL-2, IL-6, IL-7, IL-8, IL-1β, IL-12, sIL-2Ra, granulocyte macrophage colony stimulating factor (GM-CSF), macrophage inflammatory protein (MIP)-1, tumor necrosis factor alpha (TNFα), IL-6, and IL-1β, IL-1β, IL-8, IL-2, MIP-1, Flt-3L, fracktalkine, and/or IL-5. In some embodiments, the factor or outcome includes C reactive protein (CRP). In addition to being an early and easily measurable risk factor for CRS, CRP also is a marker for cell expansion. In some embodiments, subjects that are measured to have high levels of CRP, such as ≥15 mg/dL, have CRS. In some embodiments, subjects that are measured to have high levels of CRP do not have CRS. In some embodiments, a measure of CRS includes a measure of CRP and another factor indicative of CRS.

In some embodiments, one or more inflammatory cytokines or chemokines are monitored before, during, or after CAR treatment. In some aspects, the one or more cytokines or chemokines include IFN-γ, TNF-α, IL-2, IL-1β, IL-6, IL-7, IL-8, IL-1β, IL-12, sIL-2Ra, granulocyte macrophage colony stimulating factor (GM-CSF), or macrophage inflammatory protein (MIP). In some embodiments, IFN-γ, TNF-α, and IL-6 are monitored.

CRS criteria that appear to correlate with the onset of CRS to predict which patients are more likely to be at risk for developing sCRS have been developed (see Davilla et al. Science translational medicine. 2014; 6(224):224ra25). Factors include fevers, hypoxia, hypotension, neurologic changes, elevated serum levels of inflammatory cytokines, such as a set of seven cytokines (IFNγ, IL-5, IL-6, IL-1β, Flt-3L, fractalkine, and GM-CSF) whose treatment-induced elevation can correlate well with both pretreatment tumor burden and sCRS symptoms. Other guidelines on the diagnosis and management of CRS are known (see e.g., Lee et al, Blood. 2014; 124(2):188-95). In some embodiments, the criteria reflective of CRS grade are those detailed in Table 1 below.

TABLE 2

Exemplary Grading Criteria for CRS

| Grade | Description of Symptoms |
|---|---|
| 1 Mild | Not life-threatening, require only symptomatic treatment such as antipyretics and anti-emetics (e.g., fever, nausea, fatigue, headache, myalgias, malaise) |
| 2 Moderate | Require and respond to moderate intervention: Oxygen requirement < 40%, or Hypotension responsive to fluids or low dose of a single vasopressor, or Grade 2 organ toxicity (by CTCAE v4.0) |
| 3 Severe | Require and respond to aggressive intervention: Oxygen requirement ≥ 40%, or Hypotension equiring high dose of a single vasopressor (e.g., norepinephrine ≥ 20 μg/kg/min, dopamine ≥ 10 μg/kg/min, phenylephrine ≥ 200 μg/kg/min, or epinephrine), or Hypotension requiring multiple vasopressors (e.g., vasopressin + one of the above agents, or combination vasopressors equivalent to ≥20 μg/kg/min norepinephrine), or Grade 3 organ toxicity or Grade 4 transaminitis (by CTCAE v4.0) |
| 4 Life-threatening | Life-threatening: Requirement for ventilator support, or Grade 4 organ toxicity (excluding transaminitis) |
| 5 Fatal | Death |

In some aspects, a criteria reflective of CRS grade are those detailed in Table 3 below.

TABLE 3

Exemplary Grading Criteria for CRS

| Symptoms/Signs | Grade 1 (mild) | Grade 2 (moderate) | Grade 3 (severe) | Grade 4 (life-threatening) |
|---|---|---|---|---|
| | CRS grade is defined by the most severe symptom (excluding fever) | | | |
| Temperature ≥ 38.5° C./101.3° F. | Any | Any | Any | Any |
| Systolic blood pressure ≤ 90 mm Hg | N/A | Responds to fluid or single low-dose vasopressor | Needs high-dose or multiple vasopressors | Life-threatening |
| Need for oxygen to reach SaO$_2$ > 90% | N/A | FiO2 < 40% | FiO$_2$ ≥ 40% | Needs ventilator support |
| Organ toxicity | N/A | Grade 2 | Grade 3 or transaminitis | Grade 4 (excluding transaminitis) |

In some embodiments, a subject is deemed to develop "severe CRS" ("sCRS") in response to or secondary to administration of a cell therapy or dose of cells thereof, if, following administration, the subject displays: (1) fever of at least 38 degrees Celsius for at least three days; (2) cytokine elevation that includes either (a) a max fold change of at least 75 for at least two of the following group of seven cytokines compared to the level immediately following the administration: interferon gamma (IFNγ), GM-CSF, IL-6, IL-1β, Flt-3L, fracktalkine, and IL-5 and/or (b) a max fold change of at least 250 for at least one of the following group of seven cytokines compared to the level immediately following the administration: interferon gamma (IFNγ), GM-CSF, IL-6, IL-1β, Flt-3L, fracktalkine, and IL-5; and (c) at least one clinical sign of toxicity such as hypotension (requiring at least one intravenous vasoactive pressor) or hypoxia (PO$_2$<90%) or one or more neurologic disorder(s) (including mental status changes, obtundation, and/or seizures). In some embodiments, severe CRS includes CRS with a grade of 3 or greater, such as set forth in Table 2 or Table 3.

In some embodiments, outcomes associated with severe CRS or grade 3 CRS or greater, such as grade 4 or greater, include one or more of: persistent fever, e.g., fever of a specified temperature, e.g., greater than at or about 38 degrees Celsius, for two or more, e.g., three or more, e.g., four or more days or for at least three consecutive days; fever greater than at or about 38 degrees Celsius; elevation of cytokines, such as a max fold change, e.g., of at least at or about 75, compared to pre-treatment levels of at least two cytokines (e.g., at least two of the group consisting of interferon gamma (IFNγ), GM-CSF, IL-6, IL-1β, Flt-3L, fracktalkine, and IL-5, and/or tumor necrosis factor alpha (TNFα)), or a max fold change, e.g., of at least at or about 250 of at least one of such cytokines; and/or at least one clinical sign of toxicity, such as hypotension (e.g., as measured by at least one intravenous vasoactive pressor); hypoxia (e.g., plasma oxygen (PO$_2$) levels of less than at or about 90%); and/or one or more neurologic disorders (including mental status changes, obtundation, and seizures). In some embodiments, severe CRS includes CRS that requires management or care in the intensive care unit (ICU).

In some embodiments, the CRS, such as severe CRS, encompasses a combination of (1) persistent fever (fever of at least 38 degrees Celsius for at least three days) and (2) a serum level of CRP of at least at or about 20 mg/dL. In some embodiments, the CRS encompasses hypotension requiring the use of two or more vasopressors or respiratory failure requiring mechanical ventilation. In some embodiments, the dosage of vasopressors is increased in a second or subsequent administration.

In some embodiments, severe CRS or grade 3 CRS encompasses an increase in alanine aminotransferase, an increase in aspartate aminotransferase, chills, febrile neutropenia, headache, left ventricular dysfunction, encephalopathy, hydrocephalus, and/or tremor.

The method of measuring or detecting the various outcomes may be specified.

In some aspects, the toxic outcome is or is associated with neurotoxicity. In some embodiments, symptoms associated with a clinical risk of neurotoxicity include confusion, delirium, expressive aphasia, obtundation, myoclonus, lethargy, altered mental status, convulsions, seizure-like activity, seizures (optionally as confirmed by electroencephalogram [EEG]), elevated levels of beta amyloid (A3), elevated levels of glutamate, and elevated levels of oxygen radicals. In some embodiments, neurotoxicity is graded based on severity (e.g., using a Grade 1-5 scale (see, e.g., Guido Cavaletti & Paola Marmiroli *Nature Reviews Neurology* 6, 657-666 (December 2010); National Cancer Institute-Common Toxicity Criteria version 4.03 (NCI-CTCAE v4.03).

In some instances, neurologic symptoms may be the earliest symptoms of sCRS. In some embodiments, neurologic symptoms are seen to begin 5 to 7 days after cell therapy infusion. In some embodiments, duration of neurologic changes may range from 3 to 19 days. In some cases, recovery of neurologic changes occurs after other symptoms of sCRS have resolved. In some embodiments, time or degree of resolution of neurologic changes is not hastened by treatment with anti-IL-6 and/or steroid(s).

In some embodiments, a subject is deemed to develop "severe neurotoxicity" in response to or secondary to administration of a cell therapy or dose of cells thereof, if, following administration, the subject displays symptoms that limit self-care (e.g. bathing, dressing and undressing, feeding, using the toilet, taking medications) from among: 1) symptoms of peripheral motor neuropathy, including inflammation or degeneration of the peripheral motor nerves; 2) symptoms of peripheral sensory neuropathy, including inflammation or degeneration of the peripheral sensory nerves, dysesthesia, such as distortion of sensory perception, resulting in an abnormal and unpleasant sensation, neuralgia, such as intense painful sensation along a nerve or a group of nerves, and/or paresthesia, such as functional disturbances of sensory neurons resulting in abnormal cutaneous sensations of tingling, numbness, pressure, cold and warmth in the absence of stimulus. In some embodiments, severe neurotoxicity includes neurotoxicity with a grade of 3 or greater, such as set forth in Table 4.

TABLE 4

Exemplary Grading Criteria for neurotoxicity

| Grade | Description of Symptoms |
|---|---|
| 1<br>Asymptomatic or Mild | Mild or asymptomatic symptoms |
| 2<br>Moderate | Presence of symptoms that limit instrumental activities of daily living (ADL), such as preparing meals, shopping for groceries or clothes, using the telephone, managing money |
| 3<br>Severe | Presence of symptoms that limit self-care ADL, such as bathing, dressing and undressing, feeding self, using the toilet, taking medications |
| 4<br>Life-threatening | Symptoms that are life-threatening, requiring urgent intervention |
| 5<br>Fatal | Death |

In some embodiments, the methods reduce symptoms associated with CRS or neurotoxicity compared to other methods. In some aspects, the provided methods reduce symptoms, outcomes or factors associated with CRS, including symptoms, outcomes or factors associated with severe CRS or grade 3 or higher CRS, compared to other methods. For example, subjects treated according to the present methods may lack detectable and/or have reduced symptoms, outcomes or factors of CRS, e.g. severe CRS or grade 3 or higher CRS, such as any described, e.g. set forth in Table 1 or Table 2. In some embodiments, subjects treated according to the present methods may have reduced symptoms of neurotoxicity, such as limb weakness or numbness, loss of memory, vision, and/or intellect, uncontrollable obsessive and/or compulsive behaviors, delusions, headache, cognitive and behavioral problems including loss of motor control, cognitive deterioration, and autonomic nervous system dysfunction, and sexual dysfunction, compared to subjects treated by other methods. In some embodiments, subjects treated according to the present methods may have reduced symptoms associated with peripheral motor neuropathy, peripheral sensory neuropathy, dysethesia, neuralgia or paresthesia.

In some embodiments, the methods reduce outcomes associated with neurotoxicity including damages to the nervous system and/or brain, such as the death of neurons. In some aspects, the methods reduce the level of factors associated with neurotoxicity such as beta amyloid (Aβ), glutamate, and oxygen radicals.

In some embodiments, the toxicity outcome is a dose-limiting toxicity (DLT). In some embodiments, the toxic outcome is a dose-limiting toxicity. In some embodiments, the toxic outcome is the absence of a dose-limiting toxicity. In some embodiments, a dose-limiting toxicity (DLT) is defined as any grade 3 or higher toxicity as assessed by any known or published guidelines for assessing the particular toxicity, such as any described above and including the National Cancer Institute (NCI) Common Terminology Criteria for Adverse Events (CTCAE) version 4.0.

In some embodiments, the low rate, risk or likelihood of developing a toxicity, e.g. CRS or neurotoxicity or severe CRS or neurotoxicity, e.g. grade 3 or higher CRS or neurotoxicity, observed with administering a dose of T cells in accord with the provided methods, and/or with the provided articles of manufacture or compositions, permits administration of the cell therapy on an outpatient basis. In some embodiments, the administration of the cell therapy, e.g. dose of T cells (e.g. CAR⁺ T cells) in accord with the provided methods, and/or with the provided articles of manufacture or compositions, is performed on an outpatient basis or does not require admission to the subject to the hospital, such as admission to the hospital requiring an overnight stay.

In some aspects, subjects administered the cell therapy, e.g. dose of T cells (e.g. CAR⁺ T cells) in accord with the provided methods, and/or with the provided articles of manufacture or compositions, including subjects treated on an outpatient basis, are not administered an intervention for treating any toxicity prior to or with administration of the cell dose, unless or until the subject exhibits a sign or symptom of a toxicity, such as of a neurotoxicity or CRS. Exemplary agents for treating, delaying, attenuating or ameliorating a toxicity are described herein.

In some embodiments, if a subject administered the cell therapy, e.g. dose of T cells (e.g. CAR⁺ T cells), including subjects treated on an outpatient basis, exhibits a fever the subject is given or is instructed to receive or administer a treatment to reduce the fever. In some embodiments, the fever in the subject is characterized as a body temperature of the subject that is (or is measured at) at or above a certain threshold temperature or level. In some aspects, the threshold temperature is that associated with at least a low-grade fever, with at least a moderate fever, and/or with at least a high-grade fever. In some embodiments, the threshold temperature is a particular temperature or range. For example, the threshold temperature may be at or about or at least at or about 38, 39, 40, 41, or 42 degrees Celsius, and/or may be a range of at or about 38 degrees Celsius to at or about 39 degrees Celsius, a range of at or about 39 degrees Celsius to at or about 40 degrees Celsius, a range of at or about 40 degrees Celsius to at or about 41 degrees, or a range of at or about 41 degrees Celsius to at or about 42 degrees Celsius.

In some embodiments, the treatment designed to reduce fever includes treatment with an antipyretic. An antipyretic may include any agent, e.g., compound, composition, or ingredient, that reduces fever, such as one of any number of agents known to have antipyretic effects, such as NSAIDs (such as ibuprofen, naproxen, ketoprofen, and nimesulide), salicylates, such as aspirin, choline salicylate, magnesium salicylate, and sodium salicylate, paracetamol, acetaminophen, Metamizole, Nabumetone, Phenaxone, antipyrine, febrifuges. In some embodiments, the antipyretic is acetaminophen. In some embodiments, acetaminophen can be administered at a dose of 12.5 mg/kg orally or intravenously up to every four hours. In some embodiments, it is or comprises ibuprofen or aspirin.

In some embodiments, if the fever is a sustained fever, the subject is administered an alternative treatment for treating the toxicity, such as any described in Section II below. For subjects treated on an outpatient basis, the subject is instructed to return to the hospital if the subject has and/or is determined to or to have a sustained fever. In some embodiments, the subject has, and/or is determined to or considered to have, a sustained fever if he or she exhibits a fever at or above the relevant threshold temperature, and where the fever or body temperature of the subject is not reduced, or is not reduced by or by more than a specified amount (e.g., by more than 1° C., and generally does not fluctuate by about, or by more than about, 0.5° C., 0.4° C., 0.3° C., or 0.2° C.), following a specified treatment, such as a treatment designed to reduce fever such as treatment with an antipyretic, e.g. NSAID or salicylates, e.g. ibuprofen, acetaminophen or aspirin. For example, a subject is considered to have a sustained fever if he or she exhibits or is determined to exhibit a fever of at least at or about 38 or 39 degrees Celsius, which is not reduced by or is not reduced by more than at or about 0.5° C., 0.4° C., 0.3° C., or 0.2° C., or by at or about 1%, 2%, 3%, 4%, or 5%, over a period of 6 hours, over a period of 8 hours, or over a period of 12 hours, or over a period of 24 hours, even following treatment with the antipyretic such as acetaminophen. In some embodiments, the dosage of the antipyretic is a dosage ordinarily effective in such as subject to reduce fever or fever of a particular type such as fever associated with a bacterial or viral infection, e.g., a localized or systemic infection.

In some embodiments, the subject has, and/or is determined to or considered to have, a sustained fever if he or she exhibits a fever at or above the relevant threshold temperature, and where the fever or body temperature of the subject does not fluctuate by about, or by more than about, 1° C., and generally does not fluctuate by about, or by more than about, 0.5° C., 0.4° C., 0.3° C., or 0.2° C. Such absence of fluctuation above or at a certain amount generally is measured over a given period of time (such as over a 24-hour, 12-hour, 8-hour, 6-hour, 3-hour, or 1-hour period of time, which may be measured from the first sign of fever or the first temperature above the indicated threshold). For example, in some embodiments, a subject is considered to or is determined to exhibit sustained fever if he or she exhibits a fever of at least at or about or at least at or about 38 or 39 degrees Celsius, which does not fluctuate in temperature by more than at or about 0.5° C., 0.4° C., 0.3° C., or 0.2° C., over a period of 6 hours, over a period of 8 hours, or over a period of 12 hours, or over a period of 24 hours.

In some embodiments, the fever is a sustained fever; in some aspects, the subject is treated at a time at which a subject has been determined to have a sustained fever, such as within one, two, three, four, five six, or fewer hours of such determination or of the first such determination following the initial therapy having the potential to induce the toxicity, such as the cell therapy, such as dose of T cells, e.g. CAR+ T cells.

In some embodiments, one or more interventions or agents for treating the toxicity, such as a toxicity-targeting therapies, is administered at a time at which or immediately after which the subject is determined to or confirmed to (such as is first determined or confirmed to) exhibit sustained fever, for example, as measured according to any of the aforementioned embodiments. In some embodiments, the one or more toxicity-targeting therapies is administered within a certain period of time of such confirmation or determination, such as within 30 minutes, 1 hour, 2 hours, 3 hours, 4 hours, 6 hours, or 8 hours thereof.

II. METHODS OF GENERATING ENGINEERED CELL COMPOSITIONS

Among the provided embodiments are methods for generating or producing a cell composition that contains genetically engineered cells. In some embodiments, the methods produce an output cell composition containing cells that express a recombinant receptor, such as a CAR, which in some cases is a therapeutic T cell composition, such as for use in accord with methods for treating a subject having a disease or conditions. In some embodiments, features of one or more steps of the process for producing an engineered cell composition can result in output compositions enriched for cells having certain features or phenotypes as described, such as enriched compared to the feature of phenotype in cells of a starting material used for producing the engineered cell compositions. In some embodiments, engineered or therapeutic T cell compositions, such as output compositions generated or produced by a method provided herein, exhibit phenotype and functional attributes associated with a less differentiated T cell product or of a product enriched in naïve-like or central memory T cell subsets and/or a more functionally active T cell product, which, in some cases, correlate with improved pharmacokinetic properties or responses, such as durability of response and/or progression free survival, when administered to subjects. Also provided are therapeutic T cell compositions, e.g. output compositions, comprising T cells expressing a recombinant receptor in which cells of the composition are enriched in or exhibit a certain percentage of cells having one or more phenotypic or functional attributes as described, including attributes associated with a less differentiated T cell product or of a product enriched in naïve-like or central memory T cell subsets and/or a more functionally active T cell product.

In some embodiments, the methods involve generating or producing a cell composition (e.g., therapeutic T cell composition) via a process that includes one or more processing or further processing steps, such as steps for cryopreservation, the isolation, separation, selection, activation or stimulation, transduction, cultivation, expansion, washing, suspension, dilution, concentration, and/or formulation of the cells. In some embodiments, the methods of generating or producing a cell composition (e.g., therapeutic T cell composition) include isolating cells from a subject, preparing, processing, culturing under one or more stimulating conditions. In some embodiments, the method includes processing steps carried out in an order in which: cells, e.g. primary cells (e.g., T cells), are first isolated, such as selected or separated, from a biological sample (e.g., blood sample, apheresis sample, leukapheresis sample); selected cells are incubated with viral vector particles for transduction, optionally subsequent to a step of stimulating the isolated cells in the presence of a stimulation reagent; culturing the transduced cells, such as to expand the cells; formulating the transduced cells in a composition and introducing the composition into a provided container. In some embodiments, the cell composition is administered to the patient, for example as a unit dose. In some embodiments, the cell composition comprising the generated engineered cells is re-introduced into the same subject, before or after cryopreservation. In some embodiments, the cells during one or more steps of the steps, including before and/or after isolation, selection, transduction and/or cultivation, the cells can be cryopreserved, and subsequently thawed.

In some embodiments, the one or more processing steps can include one or more of (a) washing a biological sample containing cells (e.g., a whole blood sample, a buffy coat sample, a peripheral blood mononuclear cells (PBMC) sample, an unfractionated T cell sample, a lymphocyte sample, a white blood cell sample, an apheresis product, or a leukapheresis product), (b) isolating, e.g. selecting, from the sample a desired subset or population of cells (e.g., CD4+ and/or CD8+ T cells), for example, by incubation of cells with a selection or immunoaffinity reagent for immunoaffinity-based separation; c) incubating the isolated cells, such as selected cells, with viral vector particles, (d) culturing, cultivating or expanding the cells using such methods as described and (e) formulating the transduced cells, such as in a pharmaceutically acceptable buffer, cryopreservative or other suitable medium. In some embodiments, the methods can further include (e) stimulating cells by exposing cells to stimulating conditions, which can be performed prior to, during and/or subsequent to the incubation of cells with viral vector particles. In some embodiments, one or more further step of washing or suspending step, such as for dilution, concentration and/or buffer exchange of cells, can also be carried out prior to or subsequent to any of the above steps. In some aspects, the resulting engineered cell composition (e.g., therapeutic T cell composition) is introduced into one or more containers. In some embodiments, the cell composition is administered to the patient, for example as a unit dose.

In some aspects, the methods can be employed to generate a cell composition with particular properties, features and/or characteristics, such as cell phenotypes, e.g., the presence and/or expression of a surface marker, and/or the absence or lack of expression of a surface marker, of the cells in the composition for administration. In some aspects, the particular properties, features and/or characteristics, e.g., cell phenotypes, are associated with a desired outcome in therapy, e.g., a desired response or safety outcome and/or exhibiting desired pharmacokinetic parameters associated with such desired outcomes. In some embodiments, the methods also include determination and/or generation of a unit dose, such as a unit dose of the cell composition generated using the methods described herein, e.g., for administration to a subject. In some aspects, the cell compositions and/or unit doses thereof, produced according to the methods described herein, can be used for therapeutic applications, e.g., for administering to a subject for cell-based therapy, e.g., including any methods of treatment described herein. In some aspects, the cell compositions and/or unit dose described herein can achieve or be associated with particular desired outcomes of therapy, e.g., a desired response or safety outcome and/or exhibiting desired pharmacokinetic parameters associated with such desired outcomes. In some embodiments, the methods for generating a cell composition include generating or producing an input composition for use in the steps described herein to generate or produce a cell composition. In some aspects, the methods involve generating or producing an input composition. In some embodiments, the one or momethods for generating an input composition are or include processing steps that can include one or more of (a) washing a biological sample containing cells (e.g., a whole blood sample, a buffy coat sample, a peripheral blood mononuclear cells (PBMC) sample, an unfractionated T cell sample, a lymphocyte sample, a white blood cell sample, an apheresis product, or a leukapheresis product), (b) isolating, e.g. selecting, from the sample a desired subset or population of cells (e.g., CD4+ and/or CD8+ T cells), for example, by incubation of cells with a selection or immunoaffinity reagent for immunoaffinity-based separation. In some embodiments, the input composition is generated via a process that includes one or more processing steps, such as steps for the isolation, separation, selection. Thus, in some embodiments, the input composition is generated in the first steps of a general process for generating or producing a cell composition. In some aspects, the cells for engineering using the methods, such as the cells in the input composition, are any cells described herein, e.g., in Section II.A. In some aspects, the input composition is generated based on a target number or percentage of CD8$^+$ and/or CD4$^+$ T cells obtained from a subject for therapy, that express, e.g., express on the surface of the cell, or do not express, one or more markers associated with certain cell phenotypes, including markers associated or indicative of a less differentiated cell phenotype and/or markers associated with or indicative of a memory cell subtype. In some aspects, the input composition contains a target percentage of T cells that express or do not express CCR7, CD27 and/or CD45RA and/or a target percentage of CD4$^+$ T cells that express or do not express CCR7, CD27 and/or CD45RA. In some embodiments, the input composition contains a target number or percentage (e.g., at, at least, or about 75%, 80%, 85%, 90%, 95%, 96%, 97%, 98%, 99% or more) of T cells (e.g., CD4+ and CD8+ T cells) that do not express markers of apoptosis (e.g., activated caspase-3, annexin V).

In some aspects, the input composition is subject to genetic engineering, e.g., by introduction of one or more agents comprising a polynucleotide encoding a recombinant receptor (e.g., a chimeric antigen receptor; CAR) or a portion thereof and/or other molecules, such as any polynucleotides or nucleic acids, or one or more agents containing a polynucleotide described herein, e.g., in Section I.C.3. In some aspects, the cells in the input composition are engineered by introducing one or more agents and/or polynucleotide, such as those described herein, e.g., in Section II.C.3. In some embodiments, the input composition is stimulated, prior to, during and/or subsequent to said introducing by incubating the cells in the presence of one or more stimulating agents, said stimulation results in activation and/or proliferation of the cells. In some embodiments, the stimulation can be carried out using any of the methods of stimulation described herein, e.g., in Section II.B. In some embodiments, the input composition is used in any of the processing or further processing steps for generating or producing a cell composition.

In some aspects, the methods produce an output composition comprising genetically engineered cells, e.g., engineered T cells expressing a recombinant receptor, e.g., a chimeric antigen receptor (CAR). In some aspects, the output composition contains a defined ratio, frequency and/or number of engineered cells that that express, e.g., express on the surface of the cell, or do not express, one or more markers associated with certain cell phenotypes, including markers associated or indicative of a less differentiated cell phenotype and/or markers associated with or indicative of a memory cell subtype. In some aspects, the output composition contains a defined ratio of recombinant receptor-expressing (receptor$^+$) CD8$^+$ T cells that express or do not express CCR7, CD27 and/or CD45RA to receptor$^+$/CD4$^+$ T cells that express or do not express CCR7, CD27 and/or CD45RA and/or a defined ratio of receptor$^+$/CD8$^+$ T cells that express or do not express CCR7, CD27 and/or CD45RA and/or receptor$^+$/CD4$^+$ T cells that express or do not express CCR7, CD27 and/or CD45RA to another subset of cells in the composition. In some embodiments, the output composition contains T cells that do not express markers of apoptosis (e.g., caspase-3, annexin V). In some embodiments, the output composition contains a target number or percentage (e.g., at, at least, or about 75%, 80%, 85%, 90%, 95%, 96%, 97%, 98%, 99% or more) of T cells that do not express markers of apoptosis (e.g., caspase-3, annexin V). In some embodiments, the output composition contains a target number or percentage of T cells that produce cytokines following stimulation. In some embodiments, the stimulation is recombinant receptor (e.g., CAR) antigen specific. In some embodiments, the stimulation is not recombinant receptor (e.g., CAR) antigen specific, for example, stimulation involving PMA/ionomycin. In some embodiments, the cytokines produced are or include IL-2, TNFα, and/or IFNg. In some embodiments, the cytokines produced are or include IL-2 and/or TNFα. In some aspects, a desired output composition, e.g., containing a defined ratio of cells based on certain characteristics and/or phenotypes, can be generated by the methods described herein.

In some embodiments, the methods also involve, prior to generating the input composition, the providing or isolating, determining the number, number per volume, number per weight, and/or percentage of the CD8$^+$ T cells that express or do not express CCR7, CD27 and/or CD45RA and/or CD4$^+$ T cells that express or do not express CCR7, CD27 and/or CD45RA. In some embodiments, the method includes determining the number, number per volume, number per weight, and/or percentage of T cells (e.g., CD4$^+$, CD8$^+$ T cells) that do not express markers of apoptosis (e.g., caspase-3, annexin V).

In particular embodiments, the genetic engineering is or includes transfection or transduction of cells from the input composition to introduce an agent containing a nucleic acid, e.g., a polynucleotide encoding a recombinant receptor, e.g., a chimeric antigen receptor (CAR). In some embodiments, generating an output cell composition includes one or more steps of activating or stimulating cells of the input composition; genetically engineering, transducing or transfecting the cells from the input composition; and/or expanding the transfected cells; thereby resulting in output cell composition having a defined ratio of recombinant receptor-expressing (receptor$^+$) CD8$^+$ T cells that express or do not express CCR7, CD27 and/or CD45RA to receptor$^+$/CD4$^+$ T cells that express or do not express CCR7, CD27 and/or CD45RA and/or a defined ratio of receptor$^+$/CD8$^+$ T cells that express or do not express CCR7, CD27 and/or CD45RA and/or receptor$^+$/CD4$^+$ T cells that express or do not express CCR7, CD27 and/or CD45RA to another subset of cells in the composition. In some embodiments, the one or more steps results in an output cell composition containing a target number or percentage of T cells that produce cytokines following stimulation. In some embodiments, the cytokines produced are or include IL-2, TNFα, and/or IFNg. In some embodiments, the cytokines produced are or include IL-2 and/or TNFα.

In some embodiments, the provided methods are carried out such that one, more, or all steps in the preparation of cells for clinical use, e.g., in adoptive cell therapy, are carried out without exposing the cells to non-sterile conditions and without the need to use a sterile room or cabinet. In some embodiments of such a process, the cells are isolated, separated or selected, transduced, washed, optionally activated or stimulated and formulated, all within a closed system. In some aspects of such a process, the cells are expressed from a closed system and introduced into one or more of the biomaterial vessels. In some embodiments, the methods are carried out in an automated fashion. In some embodiments, one or more of the steps is carried out apart from the closed system or device.

In some embodiments, a closed system is used for carrying out one or more of the other processing steps of a method for manufacturing, generating or producing a cell therapy. In some embodiments, one or more or all of the processing steps, e.g., isolation, selection and/or enrichment, processing, incubation in connection with transduction and engineering, and formulation steps is carried out using a system, device, or apparatus in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps. In one example, the system is a system as described in International Patent Application, Publication Number WO2009/072003, or US 20110003380 A1. In one example, the system is a system as described in International Publication Number WO2016/073602.

A. Isolation or Selection of Cells from Samples

In some embodiments, the processing steps include isolation of cells or compositions thereof from biological samples, such as those obtained from or derived from a subject, such as one having a particular disease or condition or in need of a cell therapy or to which cell therapy will be administered. In some aspects, the subject is a human, such as a subject who is a patient in need of a particular therapeutic intervention, such as the adoptive cell therapy for which cells are being isolated, processed, and/or engineered. Accordingly, the cells in some embodiments are primary cells, e.g., primary human cells. In some embodiments, the cells comprise CD4+ and CD8+ T cells. In some embodiments, the cells comprise CD4+ or CD8+ T cells. The samples include tissue, fluid, and other samples taken directly from the subject. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product, also referred to herein as an apheresis or leukapheresis sample. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions.

In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

The cells generally are eukaryotic cells, such as mammalian cells, and typically are human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, $CD4^+$ cells, $CD8^+$ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, and re-introducing them into the same subject, before or after cryopreservation.

Among the sub-types and subpopulations of T cells and/or of $CD4^+$ and/or of $CD8^+$ T cells are naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components. In some embodiments, the methods include density-based cell separation methods, such as the preparation of white blood cells from peripheral blood by lysing the red blood cells and centrifugation through a Percoll or Ficoll gradient.

In some embodiments, at least a portion of the selection step includes incubation of cells with a selection reagent. The incubation with a selection reagent or reagents, e.g., as part of selection methods which may be performed using one or more selection reagents for selection of one or more different cell types based on the expression or presence in or on the cell of one or more specific molecules, such as surface markers, e.g., surface proteins, intracellular markers, or nucleic acid. In some embodiments, any known method using a selection reagent or reagents for separation based on such markers may be used. In some embodiments, the selection reagent or reagents result in a separation that is affinity- or immunoaffinity-based separation. For example, the selection in some aspects includes incubation with a reagent or reagents for separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner. In some embodiments, the selection and/or other aspects of the process is as described in International Patent Application Publication Number WO/2015/164675.

In some aspects of such processes, a volume of cells is mixed with an amount of a desired affinity-based selection reagent. The immunoaffinity-based selection can be carried out using any system or method that results in a favorable energetic interaction between the cells being separated and the molecule specifically binding to the marker on the cell, e.g., the antibody or other binding partner on the solid surface, e.g., particle. In some embodiments, methods are carried out using particles such as beads, e.g. magnetic beads, that are coated with a selection agent (e.g. antibody) specific to the marker of the cells. The particles (e.g. beads) can be incubated or mixed with cells in a container, such as a tube or bag, while shaking or mixing, with a constant cell density-to-particle (e.g., bead) ratio to aid in promoting energetically favored interactions. In other cases, the methods include selection of cells in which all or a portion of the selection is carried out in the internal cavity of a centrifugal chamber, for example, under centrifugal rotation. In some embodiments, incubation of cells with selection reagents, such as immunoaffinity-based selection reagents, is performed in a centrifugal chamber. In certain embodiments, the isolation or separation is carried out using a system, device, or apparatus described in International Patent Application, Publication Number WO2009/072003, or US 20110003380 A1. In one example, the system is a system as described in International Publication Number WO2016/073602.

In some embodiments, by conducting such selection steps or portions thereof (e.g., incubation with antibody-coated particles, e.g., magnetic beads) in the cavity of a centrifugal chamber, the user is able to control certain parameters, such as volume of various solutions, addition of solution during processing and timing thereof, which can provide advantages compared to other available methods. For example, the ability to decrease the liquid volume in the cavity during the incubation can increase the concentration of the particles (e.g. bead reagent) used in the selection, and thus the chemical potential of the solution, without affecting the total number of cells in the cavity. This in turn can enhance the pairwise interactions between the cells being processed and the particles used for selection. In some embodiments, carrying out the incubation step in the chamber, e.g., when associated with the systems, circuitry, and control as described herein, permits the user to effect agitation of the solution at desired time(s) during the incubation, which also can improve the interaction.

In some embodiments, at least a portion of the selection step is performed in a centrifugal chamber, which includes incubation of cells with a selection reagent. In some aspects of such processes, a volume of cells is mixed with an amount of a desired affinity-based selection reagent that is far less than is normally employed when performing similar selections in a tube or container for selection of the same number of cells and/or volume of cells according to manufacturer's instructions. In some embodiments, an amount of selection reagent or reagents that is/are no more than 5%, no more than 10%, no more than 15%, no more than 20%, no more than 25%, no more than 50%, no more than 60%, no more than 70% or no more than 80% of the amount of the same selection reagent(s) employed for selection of cells in a tube or container-based incubation for the same number of cells and/or the same volume of cells according to manufacturer's instructions is employed.

In some embodiments, for selection, e.g., immunoaffinity-based selection of the cells, the cells are incubated in the cavity of the chamber in a composition that also contains the selection buffer with a selection reagent, such as a molecule that specifically binds to a surface marker on a cell that it desired to enrich and/or deplete, but not on other cells in the composition, such as an antibody, which optionally is coupled to a scaffold such as a polymer or surface, e.g., bead, e.g., magnetic bead, such as magnetic beads coupled to monoclonal antibodies specific for CD4 and CD8. In some embodiments, as described, the selection reagent is added to cells in the cavity of the chamber in an amount that is substantially less than (e.g. is no more than 5%, 10%, 20%, 30%, 40%, 50%, 60%, 70% or 80% of the amount) as compared to the amount of the selection reagent that is typically used or would be necessary to achieve about the same or similar efficiency of selection of the same number of cells or the same volume of cells when selection is performed in a tube with shaking or rotation. In some embodiments, the incubation is performed with the addition of a selection buffer to the cells and selection reagent to achieve a target volume with incubation of the reagent of, for example, 10 mL to 200 mL, such as at least or about at least or about or 10 mL, 20 mL, 30 mL, 40 mL, 50 mL, 60 mL, 70 mL, 80 mL, 90 mL, 100 mL, 150 mL or 200 mL. In some embodiments, the selection buffer and selection reagent are pre-mixed before addition to the cells. In some embodiments, the selection buffer and selection reagent are separately added to the cells. In some embodiments, the selection incubation is carried out with periodic gentle mixing condition, which can aid in promoting energetically favored interactions and thereby permit the use of less overall selection reagent while achieving a high selection efficiency.

In some embodiments, the total duration of the incubation with the selection reagent is from 5 minutes to 6 hours or from about 5 minutes to about 6 hours, such as 30 minutes to 3 hours, for example, at least or about at least 30 minutes, 60 minutes, 120 minutes or 180 minutes.

In some embodiments, the incubation generally is carried out under mixing conditions, such as in the presence of spinning, generally at relatively low force or speed, such as speed lower than that used to pellet the cells, such as from 600 rpm to 1700 rpm or from about 600 rpm to about 1700 rpm (e.g. at or about or at least 600 rpm, 1000 rpm, or 1500 rpm or 1700 rpm), such as at an RCF at the sample or wall of the chamber or other container of from 80 g to 100 g or from about 80 g to about 100 g (e.g. at or about or at least 80 g, 85 g, 90 g, 95 g, or 100 g). In some embodiments, the spin is carried out using repeated intervals of a spin at such low speed followed by a rest period, such as a spin and/or rest for 1, 2, 3, 4, 5, 6, 7, 8, 9, or 10 seconds, such as a spin at approximately 1 or 2 seconds followed by a rest for approximately 5, 6, 7, or 8 seconds.

In some embodiments, such process is carried out within the entirely closed system to which the chamber is integral. In some embodiments, this process (and in some aspects also one or more additional step, such as a previous wash step washing a sample containing the cells, such as an apheresis sample) is carried out in an automated fashion, such that the cells, reagent, and other components are drawn into and pushed out of the chamber at appropriate times and centrifugation effected, so as to complete the wash and binding step in a single closed system using an automated program.

In some embodiments, after the incubation and/or mixing of the cells and selection reagent and/or reagents, the incubated cells are subjected to a separation to select for cells based on the presence or absence of the particular reagent or reagents. In some embodiments, the separation is performed in the same closed system in which the incubation of cells with the selection reagent was performed. In some embodiments, after incubation with the selection reagents, incubated cells, including cells in which the selection reagent has bound are transferred into a system for immunoaffinity-based separation of the cells. In some embodiments, the system for immunoaffinity-based separation is or contains a magnetic separation column.

Such separation steps can be based on positive selection, in which the cells having bound the reagents, e.g. antibody or binding partner, are retained for further use, and/or negative selection, in which the cells having not bound to the reagent, e.g., antibody or binding partner, are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

In some embodiments, the process steps further include negative and/or positive selection of the incubated and cells, such as using a system or apparatus that can perform an affinity-based selection. In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker+) at a relatively higher level (marker$^{high}$) on the positively or negatively selected cells, respectively. Multiple rounds of the same selection step, e.g., positive or negative selection step, can be performed. In certain embodiments, the positively or negatively selected fraction subjected to the process for selection, such as by repeating a positive or negative selection step. In some embodiments, selection is repeated twice, three times, four times, five times, six times, seven times, eight times, nine times or more than nine times. In certain embodiments, the same selection is performed up to five times. In certain embodiments, the same selection step is performed three times.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types. In certain embodiments, one or more separation steps are repeated and/or performed more than once. In some embodiments, the positively or negatively selected fraction resulting from a separation step is subjected to the same separation step, such as by repeating the positive or negative selection step. In some embodiments, a single separation step is repeated and/or performed more than once, for example, to increase the yield of positively selected cells, to increase the purity of negatively selected cells, and/or to further remove the positively selected cells from the negatively selected fraction. In certain embodiments, one or more separation steps are performed and/or repeated two times, three times, four times, five times, six times, seven times, eight times, nine times, ten times, or more than ten times. In certain embodiments, the one or more selection steps are performed and/or repeated between one and ten times, between one and five times, or between three and five times. In certain embodiments, one or more selection steps are repeated three times.

For example, in some aspects, specific subpopulations of T cells, such as cells positive or expressing high levels of one or more surface markers, e.g., CD28+, CD62L+, CCR7+, CD27+, CD127+, CD4+, CD8+, CD45RA+, and/or CD45RO+ T cells, are isolated by positive or negative selection techniques. In some embodiments, such cells are selected by incubation with one or more antibody or binding partner that specifically binds to such markers. In some embodiments, the antibody or binding partner can be conjugated, such as directly or indirectly, to a solid support or matrix to effect selection, such as a magnetic bead or paramagnetic bead. For example, CD3+, CD28+ T cells can be positively selected using anti-CD3/anti-CD28 conjugated magnetic beads (e.g., DYNABEADS® M-450 CD3/CD28 T Cell Expander, and/or ExpACT® beads).

In some embodiments, T cells are separated from a PBMC sample by negative selection of markers expressed on non-T cells, such as B cells, monocytes, or other white blood cells, such as CD14. In some aspects, a CD4+ or CD8+ selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naïve, memory, and/or effector T cell subpopulations.

In some embodiments, CD8+ T cells are further enriched for or depleted of naïve, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See Terakura et al., (2012) Blood. 1:72-82; Wang et al. (2012) J Immunother. 35(9):689-701. In some embodiments, combining TCM-enriched CD8+ T cells and CD4+ T cells further enhances efficacy.

In embodiments, memory T cells are present in both CD62L+ and CD62L− subsets of CD8+ peripheral blood lymphocytes. PBMC can be enriched for or depleted of CD62L−CD8+ and/or CD62L+CD8+ fractions, such as using anti-CD8 and anti-CD62L antibodies.

In some embodiments, the enrichment for central memory T ($T_{CM}$) cells is based on positive or high surface expression of CD45RO, CD62L, CCR7, CD28, CD3, and/or CD127; in some aspects, it is based on negative selection for cells expressing or highly expressing CD45RA and/or granzyme B. In some aspects, isolation of a CD8+ population enriched for $T_{CM}$ cells is carried out by depletion of cells expressing CD4, CD14, CD45RA, and positive selection or enrichment for cells expressing CD62L. In one aspect, enrichment for central memory T ($T_{CM}$) cells is carried out starting with a negative fraction of cells selected based on CD4 expression, which is subjected to a negative selection based on expression of CD14 and CD45RA, and a positive selection based on CD62L.

Such selections in some aspects are carried out simultaneously and in other aspects are carried out sequentially, in either order. In some aspects, the same CD4 expression-based selection step used in preparing the CD8+ T cell population or subpopulation, also is used to generate the CD4+ T cell population or sub-population, such that both the positive and negative fractions from the CD4-based separation are retained and used in subsequent steps of the methods, optionally following one or more further positive or negative selection steps. In some embodiments, the selection for the CD4+ T cell population and the selection for the CD8+ T cell population are carried out simultaneously. In some embodiments, the CD4+ T cell population and the selection for the CD8+ T cell population are carried out sequentially, in either order. In some embodiments, methods for selecting cells can include those as described in published U.S. App. No. US20170037369. In some embodiments, the selected CD4+ T cell population and the selected CD8+ T cell population may be combined subsequent to the selecting. In some aspects, the selected CD4+ T cell population and the selected CD8+ T cell population may be combined in a container or a bag, such as a bioreactor bag. In some embodiments, the selected CD4+ T cell population and the selected CD8+ T cell population are separately processed, whereby the selected CD4+ T cell population is enriched in CD4+ T cells and incubated with a stimulatory reagent (e.g. anti-CD3/anti-CD28 magnetic beads), transduced with a viral vector encoding a recombinant protein (e.g. CAR) and cultivated under conditions to expand T cells and the selected CD8+ T cell population is enriched in CD8+ T cell and incubated with a stimulatory reagent (e.g. anti-CD3/anti-CD28 magnetic beads), transduced with a viral vector encoding a recombinant protein (e.g. CAR), the same recombinant protein as for engineering of the CD4+ T cells from the same donor, and cultivated under conditions to expand T cells, such as in accord with the provided methods.

In particular embodiments, a biological sample, e.g., a sample of PBMCs or other white blood cells, are subjected to selection of CD4+ T cells, where both the negative and positive fractions are retained. In certain embodiments, CD8+ T cells are selected from the negative fraction. In some embodiments, a biological sample is subjected to selection of CD8+ T cells, where both the negative and positive fractions are retained. In certain embodiments, CD4+ T cells are selected from the negative fraction.

In a particular example, a sample of PBMCs or other white blood cell sample is subjected to selection of CD4+ T cells, where both the negative and positive fractions are retained. The negative fraction then is subjected to negative selection based on expression of CD14 and CD45RA or CD19, and positive selection based on a marker characteristic of central memory T cells, such as CD62L or CCR7, where the positive and negative selections are carried out in either order.

CD4+ T helper cells may be sorted into naïve, central memory, and effector cells by identifying cell populations that have cell surface antigens. CD4+ lymphocytes can be obtained by standard methods. In some embodiments, naïve CD4+ T lymphocytes are CD45RO−, CD45RA+, CD62L+, or CD4+ T cells. In some embodiments, central memory CD4+ T cells are CD62L+ and CD45RO+. In some embodiments, effector CD4+ T cells are CD62L− and CD45RO−.

In one example, to enrich for CD4+ T cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher © Humana Press Inc., Totowa, NJ).

In some aspects, the sample or composition of cells to be separated is incubated with a selection reagent containing small, magnetizable or magnetically responsive material, such as magnetically responsive particles or microparticles, such as paramagnetic beads (e.g., such as Dynalbeads or MACS® beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials for use in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other example and also may be used.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some aspects, separation is achieved in a procedure in which the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In some embodiments, the affinity-based selection is via magnetic-activated cell sorting (MACS) (Miltenyi Biotec, Auburn, CA). Magnetic Activated Cell Sorting (MACS), e.g., CliniMACS systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, magnetizable particles or antibodies conjugated to cleavable linkers, etc. In some embodiments, the magnetizable particles are biodegradable.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotic), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood is automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) *J Immunother.* 35(9): 651-660, Terakura et al. (2012) Blood. 1:72-82, and Wang et al. (2012) *J Immunother.* 35(9):689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) *Lab Chip* 10, 1567-1573; and Godin et al. (2008) J Biophoton. 1(5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after selection, isolation, incubation, and/or engineering. In some embodiments, the methods include steps for freezing, e.g., crypreserving, the cells either before or after selection isolation, or enrichment. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are generally then frozen to −80° C. at a rate of 1° per minute and stored in the vapor phase of a liquid nitrogen storage tank. In some embodiments, the cells are enclosed in a bag suitable for cryopreservation (for example, CryoMacs® Freezing Bags, Miltenyi Biotec). In some embodiments, the cells are enclosed in a vial suitable for cryopreservation (for example, CellSeal® Vials, Cook Regentec). In some embodiments, the steps and/or reagents for freezing are or include any of the steps and/or reagents for freezing that are described herein.

In some embodiments of the methods described herein, it is beneficial to cryopreserve a sample (e.g., apheresis or leukapheresis product) prior to selection, isolation, incubation, and/or engineering so as to reduce, minimize, or prevent cell death. Non-limiting cyroprotection methods for reducing, minimizing, or preventing cell death and preserving cell viability are described below. In some embodiments, the sample containing cells (e.g., a whole blood sample, a buffy coat sample, a peripheral blood mononuclear cells (PBMC) sample, an unfractionated T cell sample, a lymphocyte sample, a white blood cell sample, an apheresis product, or a leukapheresis product) is cryopreserved and/or cryoprotected (e.g., frozen) and then thawed prior to any steps for isolating, selecting, activating, stimulating, engineering, transducing, transfecting, incubating, culturing, harvesting, formulating a population of the cells, and/or administering the formulated cell population to a subject. In particular embodiments, an apheresis product or a leukapheresis product is cryopreserved and/or cryoprotected (e.g., frozen) and then thawed before being subject to a cell selection or isolation step (e.g., a T cell selection or isolation step) as described above. In some embodiments, after a cryopreserved and/or cryoprotected apheresis product or leukapheresis product is subject to a cell (e.g., T cell) selection or isolation step, no additional cryopreservation and/or cryoprotection step is performed during or between any of the subsequent steps, such as the steps of activating, stimulating, engineering, transducing, transfecting, incubating, culturing, harvesting, formulating a population of the cells, and/or administering the formulated cell population to a subject. For example, T cells selected from a thawed cryopreserved and/or cryoprotected apheresis product or leukapheresis product are not again cryopreserved and/or cryoprotected before being thawed for a downstream process, such as T cell activation/stimulation or transduction. In some embodiments, after a cryopreserved and/or cryoprotected apheresis product or leukapheresis product is subject to a cell (e.g., T cell) selection or isolation step, an additional cryopreservation and/or cryoprotection step is performed during or between any of the subsequent steps, such as the steps of activating, stimulating, engineering, transducing, transfecting, incubating, culturing, harvesting, formulating a population of the cells, and/or administering the formulated cell population to a subject. For example, T cells selected from a thawed cryopreserved and/or cryoprotected apheresis product or leukapheresis product are again cryopreserved and/or cryoprotected before being thawed for a downstream process, such as T cell activation/stimulation or transduction.

In particular embodiments, the cryopreserved and/or cryoprotected apheresis product or leukapheresis product is banked (e.g., without T cell selection before freezing the sample), which, in some aspects, can allow more flexibility for subsequent processing steps. In one aspect, banking cells before selection increases cell yields for a downstream process, and banking cells earlier may mean they are healthier and may be easier to meet manufacturing success criteria. In some embodiments, the banked cells are more robust in further processing steps, such as in a step or further step for generating or producing a cell composition compared to cells that were not banked. In another aspect, once thawed, the cryopreserved and/or cryoprotected apheresis product or leukapheresis product can be subject to one or more different selection methods. Advantages of this approach are, among other things, to enhance the availability, efficacy, and/or other aspects of cells of a cell therapy for treatment of a disease or condition of a subject, such as in the donor of the sample and/or another recipient.

In some embodiments, the cryopreservation of the blood sample, apheresis sample, or leukapheresis sample occurs within 1, 2, 3, 4, 5, 10, 15, 20, 24, 30, 32, 34, 36, 38, 40, 42, 44, 46, 48, 50 hours of the sample being obtained from the subject. In embodiments, the cryopreservation of the blood sample, apheresis sample, or leukapheresis sample occurs within 1 day, 2 days, or 3 days of the sample being obtained from the subject.

In some embodiments, the sample containing cells (e.g., blood sample, apheresis product or leukapheresis product) is washed in order to remove one or more anti-coagulants, such as heparin, added during apheresis or leukapheresis. In some embodiments, the sample (e.g., blood sample, apheresis sample, leukapheresis sample) undergoes selection, isolation and/or enrichment and the selected, isolated, and/or enriched cells are cryopresrved. In some embodiments, the isolated, selected, and/or enriched cells are T cells, such as any T cell described herein. In some embodiments, the enriched T cell compositions are frozen, e.g., cryopreserved and/or cryofrozen, after isolation, selection and/or enrichment. In particular embodiments, a composition of enriched CD4+ T cells are frozen, e.g., cryopreserved and/or cryofrozen, after isolation, selection and/or enrichment. In certain embodiments, a composition of enriched CD8+ T cells are frozen, e.g., cryopreserved and/or cryofrozen, after isolation, selection and/or enrichment. In some embodiments, the enriched T cells are frozen e.g., cryopreserved and/or cryofrozen, prior to any steps of incubating, activating, stimulating, engineering, transducing, transfecting, cultivating, expanding, harvesting, and/or formulating the composition of cells. In particular embodiments, a composition of enriched CD4+ T cells is frozen e.g., cryopreserved and/or cryofrozen, prior to any steps of incubating, activating, stimulating, engineering, transducing, transfecting, cultivating, expanding, harvesting, and/or formulating the composition of cells. In some embodiments, a composition of enriched CD8+ T cells are frozen e.g., cryopreserved and/or cryofrozen, prior to any steps of incubating, activating, stimulating, engineering, transducing, transfecting, cultivating, expanding, harvesting, and/or formulating the composition of cells. In particular embodiments, the one or more cryofrozen input compositions are stored, e.g., at or at about −80° C., for between 12 hours and 7 days, between 24 hours and 120 hours, or between 2 days and 5 days. In particular embodiments, the one or more cryofrozen input compositions are stored at or at about −80° C., for an amount of time of less than 10 days, 9 days, 8 days, 7 days, 6 days, or 5 days, 4 days, 3 days, 2 days, or 1 day. In some embodiments, the one or more cryofrozen input compositions are stored at or at about −80° C., for or for about 1 day, 2 days, 3 days, 4 days, 5 days, or 6 days.

In some embodiments, the sample (e.g. apheresis or leukapheresis sample) is collected and cryopreserved and/or cryoprotected prior to or without prior cell selection (e.g., without prior T cell selection, such as selection by chromatography), at a time after the donor is diagnosed with a disease or condition. In some aspects, the time of cryopreservation also is before the donor has received one or more of the following: any initial treatment for the disease or condition, any targeted treatment or any treatment labeled for treatment for the disease or condition, or any treatment other than radiation and/or chemotherapy. In some embodiments, the sample is collected after a first relapse of a disease following initial treatment for the disease, and before the donor or subject receives subsequent treatment for the disease. The initial and/or subsequent treatments may be a therapy other than a cell therapy. In some embodiments, the collected cells may be used in a cell therapy following initial and/or subsequent treatments. In one aspect, the cryopreserved and/or cryoprotected sample without prior cell selection may help reduce up-front costs, such as those associated with non-treatment patients in a randomized clinic trial who may crossover and require treatment later.

In some embodiments, the sample (e.g. apheresis or leukapheresis sample) is collected and cryopreserved and/or cryoprotected prior to or without prior cell selection (e.g., without prior T cell selection, such as selection by chromatography), at a time after a second relapse of a disease following a second line of treatment for the disease, and before the donor or subject receives subsequent treatment for the disease. In some embodiments, patients are identified as being likely to relapse after a second line of treatment, for example, by assessing certain risk factors. In some embodiments, the risk factors are based on disease type and/or genetics, such as double-hit lymphoma, primary refractory cancer, or activated B-cell lymphoma. In some embodiments, the risk factors are based on clinical presentation, such as early relapse after first-line treatment, or other poor prognostic indicators after treatment (e.g., IPI (International Prognostic Index)>2).

In some embodiments, the sample (e.g. apheresis or leukapheresis sample) is collected and cryopreserved and/or cryoprotected prior to or without prior cell selection (e.g., without prior T cell selection, such as selection by chromatography), at a time before the donor or subject is diagnosed with a disease. In some aspects, the donor or subject may be determined to be at risk for developing a disease. In some aspects, the donor or subject may be a healthy subject. In certain cases, the donor or subject may elect to bank or store cells without being deemed at risk for developing a disease or being diagnosed with a disease in the event that cell therapy is required at a later stage in life. In some embodiments, a donor or subject may be deemed at risk for developing a disease based on factors such as genetic mutations, genetic abnormalities, genetic disruptions, family history, protein abnormalities (such as deficiencies with protein production and/or processing), and lifestyle choices that may increase the risk of developing a disease. In some embodiments, the cells are collected as a prophylactic.

By allowing donors to store their cells at a stage when the donors, and thus their cells, have not undergone extensive treatment for a disease and/or prior to contracting of a disease or condition or diagnosis thereof, such cells may have certain advantages for use in cell therapy compared to cells harvested after one or after multiple rounds of treatment. For example, cells harvested before one or more rounds of treatment may be healthier, may exhibit higher levels of certain cellular activities, may grow more rapidly, and/or may be more receptive to genetic manipulation than cells that have undergone several rounds of treatment. Another example of an advantage according to embodiments described herein may include convenience. For example, by collecting, optionally processing, and storing a donor's cells before they are needed for cell therapy, the cells would be readily available if and when a recipient later needs them. This could increase apheresis lab capacity, providing technicians with greater flexibility for scheduling the apheresis collection process.

In some embodiments, the cryopreserved cells (e.g., selected cells or cells in a sample (e.g., blood sample, apheresis sample, leukapheresis sample)) may be stored for an amount of time under 1, 2, 3, 4, 5, 6, 7, 8, 9, or 10 days, or an amount of time under 1, 2, 3, 4, 5, 6, 7, 8 weeks, or for an amount of time at least 1, 2, 3, 4, 5, 6, 7, or 8 weeks, or for more than 8 weeks. In some embodiments, the cryopreserved cells (e.g., selected cells or cells in a sample (e.g., blood sample, apheresis sample, leukapheresis sample)) may be stored for an amount of time greater than or about 1 month, 2 months, 3 months, 4 months, 5 months, 6 months, 12 months or longer. After storage, the cells (e.g., selected cells or cells in a sample (e.g., blood sample, apheresis sample, leukapheresis sample)) may be thawed and the processing may be resumed from the same point in the process. In some embodiments, the cells are cryoprotected and stored prior to further processing, e.g., incubation under stimulating conditions. In particular embodiments, cultivated and/or formulated populations cells are cryoprotected and stored prior to being administered to as subject, e.g., as an autologous cell therapy.

In particular embodiments, the cells are frozen, e.g., following a washing step, e.g., to remove plasma and platelets. In some embodiments, the cells are frozen prior to, subsequent to, and/or during any of the steps associated with manufacturing and/or generating cells, e.g., CD4+ and/or CD8+ T cells, that express a recombinant receptor, e.g., a CAR. In certain embodiments, such steps may include any steps associated with the generation of engineered cells, including but not limited to, selection and/or isolation of a subset of cells, e.g., CD4+ and/or CD8+ T cells, the stimulation and/or expansion of cells, e.g. T cells or a subset thereof, or transfection or transduction of the cells. In some embodiments, the cells are cells of an apheresis sample collected from a subject, prior to the selection and/or isolation of cells, the stimulation and/or expansion of cells, or transfection or transduction of the cells. In particular embodiments, the cells are frozen after the completion of an engineering process, e.g., after a process involving one or more steps of isolation, selections, stimulation, activation, transduction, transfection, and/or expansion.

In some embodiments, the cells are suspended in a freezing solution, e.g., a cryoprotectant and/or a solution containing a cryoprotectant. Any of a variety of known freezing solutions and parameters in some aspects may be used, including freezing solutions containing cryopreservation or vitrification medium or solutions containing cryoprotectant. Suitable cryoprotectants include, but are not limited to, dimethyl sulfoxide (DMSO), glycerol, a glycol, a propylene glycol, an ethylene glycol, propanediol, polyethylene glycol (PEG), 1, 2-propanediol (PROH) or a mixture thereof. In some examples, the cryopreservation solution can contain one or more non-cell permeating cryopreservative, including but not limited to, polyvinyl pyrrolidone, a hydroxyethyl starch, a polysaccharide, a monosaccharide, an alginate, trehalose, raffinose, dextran, human serum albumin, Ficoll, lipoproteins, polyvinyl pyrrolidone, hydroxyethyl starch, autologous plasma or a mixture thereof. In some embodiments, the cells are suspended in a freezing solution with a final concentration of cryoprotectant of between about 1% and about 20%, between about 3% and about 9%, or between about 6% and about 9% by volume, each inclusive. In certain embodiments, the final concentration of cryoprotectant in the freezing solution is about 3%, about 4%, about 5%, about 5.5%, about 6%, about 6.5%, about 7%, about 7.5%, about 8%, about 8.5%, about 9%, about 9.5%, or about 10% by volume.

In some embodiments, the cells, e.g., are frozen at particular cell density, e.g., a known or controlled cell density. In certain embodiments, the cell density during the freezing process may affect cell death and/or cell damage that occurs during and/or due to the freezing process. For example, in particular embodiments, cell density affects equilibrium, e.g., osmotic equilibrium, with surroundings during the freezing process. In some embodiments, this equilibrium is, includes, and/or results in dehydration. In certain embodiments, the dehydration is or includes cellular dehydration that occurs with contact, combination, and/or incubation with a freezing solution, e.g., DMSO and/or a DMSO containing solution. In particular embodiments, the dehydration is or includes dehydration resulting from the nucleation and enlargement of ice crystals in extracellular space, such as by reducing the effective liquid water concentration exposed to the cells. In some embodiments, the cells are frozen at a cell density that results in slower and/or less rapid dehydration than cells that are frozen at a different, e.g., higher or lower, cell density. In some embodiments, the cells are frozen at a cell density that results in about, at least, or at 5%, 10%, 20%, 25%, 30%, 40%, 50%, 60%, 70%, 80%, 90%, 100%, 125%, 150%, 175%, 200%, 1-fold, 2-fold, 3-fold, 4-fold, 5-fold, 10-fold, 50-fold, or 100-fold slower dehydration that cells frozen at a different cell density, e.g., higher or lower, under the same or similar conditions.

In some embodiments, the cryoprotectant is DMSO. In particular embodiments, the cells are suspended in a freezing solution with a final concentration of DMSO of between about 1% and about 20%, between about 3% and about 9%, or between about 6% and about 9% by volume, each inclusive. In certain embodiments, the final concentration of DMSO in the freezing solution is about 3%, about 4%, about 5%, about 5.5%, about 6%, about 6.5%, about 7%, about 7.5%, about 8%, about 8.5%, about 9%, about 9.5%, or about 10% by volume.

In particular embodiments, the cells are suspended in a freezing solution at a density of between or between about $0.1\times10^6$ cells/mL and about $5,000\times10^6$ cells/mL, between or between about $1\times10^6$ cells/mL and about $500\times10^6$ cells/mL, between or between about $5\times10^6$ cells/mL and about $150\times10^6$ cells/mL, between or between about $10\times10^6$ cells/mL and about $70\times10^6$ cells/mL, or between or between about $15\times10^6$ cells/mL and about $60\times10^6$ cells/mL, each inclusive. In some embodiments, the cells are viable cells.

In certain embodiments, the cells are suspended in a freezing solution at a density of between or between about $1\times10^6$ cells/mL and about $1\times10^8$ cells/mL, between about $1\times10^6$ cells/mL and about $2\times10^7$ cells/mL, between about $1\times10^7$ cells/mL and about $5\times10^7$ cells/mL, or between about $1\times10^7$ cells/mL and $5\times10^7$ cells/mL, each inclusive. In certain embodiments, the cells are suspended in the freezing solution at a density of about $1\times10^6$ cells/mL, about $2\times10^6$ cells/mL, about $5\times10^6$ cells/mL, about $1\times10^7$ cells/mL, about $1.5\times10^7$ cells/mL, about $2\times10^7$ cells/mL, about $2.5\times10^7$ cells/mL, about $2.5\times10^7$ cells/mL, about $2.5\times10^7$ cells/mL, about $3\times10^7$ cells/mL, about $3.5\times10^7$ cells/mL, about $4\times10^7$ cells/mL, about $4.5\times10^7$ cells/mL, or about $5\times10^7$ cells/mL, each inclusive. In certain embodiments, the cells are suspended in the freezing solution at a density of between about $1.5\times10^7$ cells/mL and about $6\times10^7$ cells/mL, inclusive. In certain embodiments, the cells are suspended in a freezing solution at a density of at least about $1\times10^7$ cells/mL. In particular embodiments, the cells are suspended in a freezing solution at a density of at least about $1.5\times10^7$ cells/mL. In some embodiments, the cells are viable cells.

In some embodiments, the cells are frozen in a container. In certain embodiments, the container is a freezing container and/or a cryoprotectant container. Containers suitable for cryofreezing include, but are not limited to vials, bags, e.g., plastic bags, and canes. In particular embodiments, cells, e.g., cells of the same cell composition such as a cell composition containing CAR expressing cells, are frozen in 1, 2, 3, 4, 5, 6, 7, 8, 9 10, or more than 10 separate containers. For example, in some embodiments, the cells and/or a composition of cells are suspended in a volume, e.g., such as in a solution, a freezing solution, and/or a cryoprotectant, and that is larger than a volume suitable for a container, and so the volume is placed in two or more containers. In some embodiments, the volume is, is about, or less than 100 mL, 50 mL, 25 mL, 20 mL, 15 mL, 10 mL, 5 mL, or less than 5 mL, and the cells are frozen in two, three, four, five six, seven, eight, nine, ten, or more than ten separate vials. In particular embodiments, the same volume of cells is placed into each vial. In some embodiments, the vials are identical vials, e.g., vials of the same make, model, and/or manufacturing lot. In particular embodiments, the volume is, is about, or greater than 10 mL, 15 mL, 20 mL, 25 mL, 30 mL, 40 mL, 50 mL, 60 mL, 70 mL, 80 mL, 90 mL, 100 mL, 120 mL, 150 mL, 200 mL, or more than 200 mL and the cells are frozen in two, three, four, five six, seven, eight, nine, ten, or more than ten separate bags. In particular embodiments, the same volume of cells is placed into each bag. In some embodiments, the bags are identical bags, e.g., bags of the same make, model, and/or manufacturing lot.

In some embodiments, the container is a vial. In certain embodiments, the container is a vial with a fill volume of, of about, or of at least 0.5 mL, 1 mL, 2 mL, 3 mL, 4 mL, 5 mL, 6 mL, 7 mL, 8 mL, 9 mL, 10 mL, 11 mL, 12 mL, 13 mL, 14 mL, 15 mL, 16 mL, 17 mL, 18 mL, 19 mL, 20 mL, 25 mL, 30 mL, 35 mL, 40 mL, 45 mL, or 50 mL. In some embodiments, the vial has a fill volume of between 1 mL and 120 mL, 1 mL and 20 mL, 1 mL and 5 mL, lmL and 10 mL, 1 mL and 40 mL, or 20 mL and 40 mL, each inclusive. In some embodiments, the vial is a freezing vial, cryoprotectant vial, and/or a cryovial. Suitable vials are known, and include but are not limited to CellSeal® Vials (Cook Regentec), and vials described in U.S. Pat. Nos: U.S. Pat. Nos. 8,936,905, 9,565,854 and 8,709,797, hereby incorporated by reference in their entirety.

In particular embodiments, the container is a bag. In certain embodiments, the container is a bag with a fill volume of, of about, or of at least 0.5 mL, 1 mL, 2 mL, 3 mL, 4 mL, 5 mL, 6 mL, 7 mL, 8 mL, 9 mL, 10 mL, 11 mL, 12 mL, 13 mL, 14 mL, 15 mL, 16 mL, 17 mL, 18 mL, 19 mL, 20 mL, 25 mL, 30 mL, 35 mL, 40 mL, 45 mL, or 50 mL. In some embodiments, the bag has a fill volume of between 1 mL and 120 mL, 1 mL and 20 mL, 1 mL and 5 mL, 1 mL and 40 mL, 20 mL and 40 mL, 1 mL and 70 mL, or 50 mL and 70 mL, each inclusive. In some embodiments, the bag is filled with a volume of, of about, or less than 100 mL, 75 mL, 70 mL, 50 mL, 25 mL, 20 mL, or 10 mL. Suitable bags are known, and include but are not limited to CryoMacs® Freezing Bags (Miltenyi Biotec). In certain embodiments, the volume is the volume at room temperature. In some embodiments, the volume is the volume between 37° C. and 4° C., 16° C. and 27° C., inclusive, or at, at about, or at least 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., or 37° C. In some embodiments, the volume is the volume at 25° C.

In some embodiments, cells in a volume of media or solution, e.g., freezing solution, of between 1 mL and 20 mL are frozen in one or more vials, inclusive. In some embodiments, the one or more vials have a fill volume of between 1 mL and 5 mL, inclusive. In certain embodiments, cells in a volume of media or solution, e.g., freezing solution, of between 20 mL and 120 mL, inclusive, are frozen in one or more bags. In particular embodiments, the one or more bags have a fill volume of between 20 mL and 40 mL, inclusive. In some embodiments, cells in a volume of media or solution, e.g., freezing solution, of 120 mL or greater are frozen in one or more bags. In certain embodiments, the one or more bags have a fill volume of between 50 mL and 70 mL, inclusive.

In certain embodiments, the cells are frozen in solution, e.g., freezing solution, that is placed in a container, e.g., a bag or a vial, at a surface area to volume ratio. In particular embodiments, the surface area to volume ratio is from or from about 0.1 cm$^{-1}$ to 100 cm$^{-1}$; 1 cm$^{-1}$ to 50 cm$^{-1}$, 1 cm$^{-1}$ to 20 cm$^{-1}$, 1 cm$^{-1}$ to 10 cm$^{-1}$, 2 cm$^{-1}$ to 10 cm$^{-1}$, 3 cm$^{-1}$ to 7 cm, or 3 cm$^{-1}$ to 6 cm$^{-1}$, each inclusive. In particular embodiments, the surface area to volume ratio is between or between about 3 cm$^{-1}$ to 6 cm$^{-1}$. In some embodiments, the surface area to volume ratio is, is about, or is at least 3 cm$^{-1}$, 4 cm$^{-1}$, 5 cm, 6 cm$^{-1}$, or 7 cm$^{-1}$.

In some embodiments, transfer to cryopreservation medium is associated with one or more processing steps that can involve washing of the sample, e.g., engineered cell composition, such as to remove the media and/or replacing the cells in an appropriate cryopreservation buffer or media for subsequent freezing. In certain embodiments, the transfer to the cryopreservation medium is fully automated on a clinical-scale level in a closed and sterile system. In certain embodiments the transfer to the cryopreservation medium carried out using CliniMACS system (Miltenyi Biotec).

In some embodiments, the cells are thawed. In particular embodiments, the cells are thawed rapidly, e.g., rapidly as possible without overheating the cells or exposing cells to high temperatures such as above 37° C. In some embodiments, rapid thawing reduces and/or prevents exposure of the cells to high concentrations of cryoprotectant and/or DMSO. In particular embodiments, the rate at which thawing occurs may be affected by properties of the container, e.g., the vial and/or the bag, that the cells are frozen and thawed in. In particular embodiments, the cells are thawed at a temperature of, of about, or less than 37° C., 35° C., 32° C., 30° C., 29° C., 28° C., 27° C., 26° C., 25° C., 24° C., 23° C., 22° C., 21° C., 20° C., or 15° C., or between 15° C. and 30° C., between 23° C. and 28° C., or between 24° C. and 26° C., each inclusive. In some embodiments, the cells are thawed on a heat block or in a water bath. In certain embodiments, the cells are not thawed on a heat block or water bath. In some embodiments, the cells are thawed at room temperature. In some embodiments, the thickness of container the walls effects the rate of cell thawing, such as for example cells in containers with thick walls thaw at a slower rate than in containers with thinner walls. In some embodiments, containers having a low ratio of surface area to volume have a slow and/or uneven rate of thawing. In some embodiments, cryopreserved cells are rapidly thawed in a containing having a surface area to volume ratio is, is about, or is at least 1 cm$^{-1}$, 2 cm$^{-1}$, 3 cm$^{-1}$, 4 cm$^{-1}$, 5 cm$^{-1}$, 6 cm$^{-1}$, or 7 cm$^{-1}$, 8 cm$^{-1}$, 9 cm$^{-1}$, or 10 cm$^{-1}$. In particular embodiments, the cells are thawed in, in about, or in less than 120 minutes, 90 minutes, 60 minutes, 45 minutes, 30 minutes, 25 minutes, 20 minutes, 15 minutes, or ten minutes. In some embodiments, the cells are thawed for between 10 minutes and 60 minutes, 15 minutes and 45 minutes, or 15 minutes and 25 minutes, each inclusive. In particular embodiments, the cells are thawed in, in about, or in less than 20 minutes.

In certain embodiments, the thawed cells are rested, e.g., incubated or cultured, prior to administration or prior to any subsequent engineering and/or processing steps. In some embodiments, the cells are rested in low and/or undetectable amounts of cryoprotectant, or in the absence of cryoprotectant, e.g., DMSO. In particular embodiments, the thawed cells are rested after or immediately after washing steps, e.g., to remove cryoprotectant and/or DMSO. In some embodiments, the resting is or includes culture and/or incubation at or at about 37° C. In some embodiments, the resting is performed in the absence of any reagents, e.g., stimulatory reagents, bead reagents, or recombinant cytokines, used with and/or associated with any processing or engineering step. In some embodiments, the cells are rested for, for about, or for at least 5 minutes, 10 minutes, 15 minutes, 30 minutes, 1 hour, 2 hours, 3 hours, 4 hours, 5 hours, 6 hours, 8 hours, 12 hours, 18 hours, or 24 hours. In certain embodiments, the cells are rested for, for about, or for at least 2 hours.

In some embodiments, the cells are frozen, e.g., cryopreserved, either before, during, or after said methods for processing and/or engineering the cells. In some embodiments, the freeze and subsequent thaw step removes granulocytes and, to some extent, monocytes in the cell population. The cells are generally then frozen to −80° C. at a rate of 1° per minute and stored in the vapor phase of a liquid nitrogen storage tank. In some embodiments, the cells are actively and/or effectively cooled at a rate of or of about 1° per minute using a controlled rate freezer. In some embodiments, cells can be frozen with a controlled rate freezer. In some aspects, the controlled rate freezers are used to freeze cells with programmed cooling profiles, e.g. profiles with multiple cooling and/or heating rates. Such freezing profiles may be programmed to control nucleation, e.g., ice formation, for example to reduce intracellular ice formation.

In some embodiments, features of the frozen cells including any of the cells and compositions as described, such as cell compositions at a particular concentration or cell density, frozen in the presence of a cryoprotectant and/or filled into a container at a particular volume or surface to volume ratio, include improved, increased, and/or faster expansion; improved increased, and/or enhanced cell survival and reduced instances of cell death, e.g., necrosis, programmed cell death, and/or apoptosis; improved, enhanced, and/or increased activity, e.g., cytolytic activity; and/or reduced instance of senescence or quiescence after thawing than cells frozen by alternate means.

In particular embodiments, the cells are frozen at a cell density and/or a surface area to volume ratio provided herein and have reduced cell death, e.g., necrosis and/or apoptosis, during and/or resulting from the freezing, cryofreezing, and/or cryopreservation, as compared to cells frozen at a different cell density and/or a different surface area to volume ratio under the same or similar conditions. In particular embodiments, the cells are frozen at a cell density and/or a surface area to volume ratio provided herein and have reduced delayed cell death, e.g., a reduction in the amount of cells that die, e.g., via necrosis, programmed cell death, or apoptosis, within 48 hours after freezing, cryofreezing, and/or cryopreservation, e.g. after the thawing of the frozen cells. In certain embodiments, at least or about 5%, 10%, 20%, 25%, 30%, 40%, 50%, 60%, 70%, 80%, 90%, or 99% less cells die during and/or resulting from freezing and/or cryopreservation as compared to cells that are frozen at a different cell density and/or a different surface area to volume ratio under the same or similar conditions. In certain embodiments, less than 40%, 30%, 25%, 20%, 15%, 10%, 5%, 1%, 0.1%, or 0.01% of the cells frozen at the provided cell density and/or a surface area to volume ratio die during or as a result from freezing, cryofreezing, and/or cryopreservation.

In some embodiments, the cells are frozen at a cell density and/or a surface area to volume ratio provided herein and have reduced instances of senescence or quiescence due to and/or resulting from the freezing, cryofreezing, and/or cryopreservation, as compared to cells frozen at a different a different cell density and/or a different surface area to volume ratio under the same or similar conditions. In particular embodiments, at least or about 5%, 10%, 20%, 25%, 30%, 40%, 50%, 60%, 70%, 80%, 90%, or 99% less cells are senescent and/or quiescent cells as compared to cells frozen at a different cell density and/or a different surface area to volume ratio under the same or similar conditions. In certain embodiments, the cells are frozen at the provided cell density and/or surface area to volume ratio and less than 40%, 30%, 25%, 20%, 15%, 10%, 5%, 1%, 0.1%, or 0.01% of the cells become senescent and/or quiescent as a result from freezing, cryofreezing, and/or cryopreservation.

In certain embodiments, the cells are frozen, e.g., cryopreserved, at a cell density and/or surface area to volume ratio provided herein and have improved, faster, and/or more rapid expansion, e.g., under stimulatory conditions such as by incubation with a stimulatory reagent described herein, after the cells are thawed, as compared to cells frozen at a different cell density and/or surface area to volume ratio under the same or similar conditions. In particular embodiments, the cells expand at a rate that is faster and/or more rapid by, by about, or by at least 5%, 10%, 20%, 25%, 30%, 40%, 50%, 60%, 70%, 80%, 90%, 100%, 150%, 200%, 1-fold, 1.5 fold, 2-fold, 3-fold, 4-fold, 5-fold, or 10-fold as compared to cells frozen at a different cell density and/or a different surface area to volume ratio under the same or similar conditions. For example, in some embodiments, the thawed cells reach a threshold expansion, e.g., a predetermined cell number, density, or factor such as a 2-fold expansion, in, in about, or in at least 5% 10%, 20%, 25%, 30%, 40%, 50%, 60%, 70%, 80%, 90%, 95%, or 99%, less time than thawed cells that were frozen at a different cell density and/or a different surface area to volume ratio under the same or similar conditions.

In some embodiments, the cells are frozen, e.g., cryopreserved, at the cell density and have improved, increased, and/or more cytolytic activity, e.g., such as measured by any assay for measuring cytolytic activity described herein, after the cells are thawed, as compared to cells frozen at a different cell density, e.g., a higher or lower density, under the same or similar conditions. In particular embodiments, the cytolytic activity is increased by, by about, or by at least 5%, 10%, 20%, 25%, 30%, 40%, 50%, 60%, 70%, 80%, 90%, 100%, 150%, 200%, 1-fold, 1.5 fold, 2-fold, 3-fold, 4-fold, 5-fold, or 10-fold as compared to cells frozen at a different density under the same or similar conditions. Exemplary methods and systems for cryogenic storage and processing of cells from a sample, such as an apheresis sample, can include those described in International published application no. WO2018170188. In some embodiments, the method and systems involve collecting apheresis before the patient needs cell therapy, and then subjecting the apheresis sample to cryopreservation for later use in a process for engineering the cells, e.g. T cells, with a recombinant receptor (e.g. CAR). In some cases, such processes can include those described herein. In some embodiments, an apheresis sample is collected from a subject and cryopreserved prior to subsequent T cell selection, activation, stimulation, engineering, transduction, transfection, incubation, culturing, harvest, formulation of a population of the cells, and/or administration of the formulated cell population to a subject. In such examples, the cryopreserved apheresis sample is thawed prior to subjecting the sample to one or more selection steps, such as any as described herein.

In some embodiments, the cryopreserved and/or cryoprotected sample of cells (e.g. apheresis or leukapheresis sample), such as a sample of cells that has not been subject to a prior cell selection (e.g., without prior T cell selection, such as selection by chromatography) is thawed prior to its use for downstream processes for manufacture of a cell population for cell therapy, for example, a T cell population containing CAR+ T cells. In some embodiments, such a cryopreserved and/or cryoprotected sample of cells (e.g. apheresis or leukapheresis sample) is used in connection with the process provided herein for engineered a T cell therapy, such as a CAR+ T cell therapy. In particular examples, no further step of cryopreservation is carried out prior to or during the harvest/formulation steps.

1. Features of the Input Composition

In some embodiments, the input composition includes T cells isolated or selected from a biological sample, e.g. a apheresis sample, leukapheresis sample. In some embodiments, the input composition may be cryopreserved according to any of the methods described herein. In particular embodiments, the input composition comprises a population of enriched CD3+ T cells, e.g., viable CD3+ T cells. In some embodiments, at least 60%, at least 65%, at least 70%, at least 75%, at least 80%, at least 85%, at least 90%, at least 95%, at least 98%, at least 99%, at least 99.5%, at least 99.9%, or at or at about 100% of the cells of the input composition are CD3+ T cells, e.g., viable CD3+ T cells. In some embodiments, the input composition consists essentially of CD3+ T cells, e.g., viable CD3+ T cells. In some embodiments, the input composition is enriched in CD4+ cells and/or is enriched in CD8+ cells.

In certain embodiments, the input composition is a population of cells enriched for enriched CD4+ T cells and CD8+ T cells, e.g., CD4+ T cells and CD8+ T cells. In particular embodiments, the input composition is or includes at least 60%, at least 65%, at least 70%, at least 75%, at least 80%, at least 85%, at least 90%, at least 95%, at least 98%, at least 99%, at least 99.5%, at least 99.9%, or at or at about 100% cells that are CD4+ or CD8+ T cells. In some embodiments, the input composition consists essentially of CD4+ and CD8+ T cells.

In certain embodiments, the input composition is a population of enriched CD4+ T cells. In particular embodiments, at least 60%, at least 65%, at least 70%, at least 75%, at least 80%, at least 85%, at least 90%, at least 95%, at least 98%, at least 99%, at least 99.5%, at least 99.9%, or at or at about 100% of the cells of the input composition are CD4+ T cells. In some embodiments, the input composition consists essentially of CD4+ T cells.

In certain embodiments, the input composition is a population of enriched CD8+ T cells. In particular embodiments, at least 60%, at least 65%, at least 70%, at least 75%, at least 80%, at least 85%, at least 90%, at least 95%, at least 98%, at least 99%, at least 99.5%, at least 99.9%, or at or at about 100% of the cells of the input composition are CD8+ T cells. In some embodiments, the input composition consists essentially of CD8+ T cells.

In some embodiments, cells from a population of enriched CD4+ T cells and cells from a population of enriched CD8+ T cells are mixed, combined, and/or pooled to generate an input composition containing CD4+ T cells and CD8+ T cells. In certain embodiments, the populations of enriched CD4+ T cells and CD8+ T cells are pooled, mixed, and/or combined prior to stimulating cells, e.g., culturing the cells under stimulating conditions such as described in Section II-B. In certain embodiments, the populations of enriched CD4+ and CD8+ T cells are pooled, mixed, and/or combined subsequent to isolating, enriching, and/or selecting the CD4+ and CD8+ T cells from a biological sample. In particular embodiments, the populations of enriched CD4+ and CD8+ T cells are pooled, mixed, and/or combined subsequent to freezing, e.g., cryopreserving, and thawing the populations of enriched CD4+ and CD8+ T cells.

In certain embodiments, the input composition is produced, generated, or made by mixing, pooling, and/or combining cells from a population of enriched CD4+ cells with cells from a population of enriched CD8+ cells. In certain embodiments, the population of enriched CD4+ T cells contains at least 60%, 65%, 70%, 75%, 80%, 85%, 90%, 95%, 98%, 99%, or 99.9% CD4+ T cells. In particular embodiments, the population of enriched CD4+ T cells contains 100% CD4+ T cells or contains about 100% CD4+ T cells. In certain embodiments, the population of enriched T cells includes or contains less than 20%, less than 10%, less than 5%, less than 1%, less than 0.1%, or less than 0.01% CD8+ T cells, and/or contains no CD8+ T cells, and/or is free or substantially free of CD8+ T cells. In some embodiments, the populations of cells consist essentially of CD4+ T cells. In certain embodiments, the population of enriched CD8+ T cells contains at least 75%, 80%, 85%, 90%, 95%, 98%, 99%, or 99.9% CD8+ T cells, or contains or contains about 100% CD8+ T cells. In certain embodiments, the population of enriched CD8+ T cells includes or contains less than 20%, less than 10%, less than 5%, less than 1%, less than 0.1%, or less than 0.01% CD4+ T cells, and/or contains no CD4+ T cells, and/or is free or substantially free of CD4+ T cells. In some embodiments, the populations of cells consist essentially of CD8+ T cells.

In certain embodiments, CD4+ T cells and CD8+ T cells are pooled, mixed, and/or combined at a ratio of between 1:10 and 10:1, between 1:5 and 5:1, between 4:1 and 1:4, between 1:3 and 3:1, between 2:1 and 1:2, between 1.5:1 and 1:1.5, between 1.25:1 and 1:1.25, between 1.2:1 and 1:1.2, between 1.1:1 and 1:1.1, or about 1:1 or 1:1 CD4+ T cells to CD8+ T cells. In particular embodiments, viable CD4+ T cells and viable CD8+ T cells are pooled, mixed, and/or combined at a ratio of between 1:10 and 10:1, between 1:5 and 5:1, between 4:1 and 1:4, between 1:3 and 3:1, between 2:1 and 1:2, between 1.5:1 and 1:1.5, between 1.25:1 and 1:1.25, between 1.2:1 and 1:1.2, between 1.1:1 and 1:1.1, or about 1:1 or 1:1 CD4+ T cells to CD8+ T cells.

In particular embodiments, the input composition contains cells (e.g., T cells) that are not positive for an apoptotic marker. In some embodiments, the apoptotic marker is annexin V and/or activated caspase 3. In some embodiments, the cells contained in the input composition include or are annexin V$^-$, annexin V$^-$/CD3$^+$, annexin V$^-$/CD4$^+$, annexin V$^-$/CD8$^+$, annexin V$^-$/CD3$^+$, activated caspase 3$^-$, activated caspase 3$^-$/CD3$^+$, activated caspase 3$^-$/CD4$^+$, activated caspase 3$^-$/CD8$^+$, or a combination thereof.

In some embodiments, the input composition contains a target number or percentage (e.g., not greater than 5%, 10%, 20%, 30%, 40%, 50%, 60%, 70%, 80%, 90%, or 95%) of T cells that do not express markers of apoptosis (e.g., caspase-3, annexin V). In some embodiments, the input composition contains a target number or percentage of T cells that produce cytokines following stimulation. In some embodiments, the stimulation is not recombinant receptor (e.g., CAR) antigen specific, for example, stimulation involving PMA/ionomycin. In some embodiments, the cytokines produced are or include IL-2, TNFα, and/or IFNg. In some embodiments, the cytokines produced are or include IL-2 and/or TNFα. In some embodiments, the method involves providing, producing or generating an input composition. In some embodiments, the input composition comprising a target percentage of CD8$^+$ T cells that express or do not express CCR7, CD27 and/or CD45RA and/or a target percentage of CD4$^+$ T cells that express or do not express CCR7, CD27 and/or CD45RA. In some embodiments, the input composition contains T cells that do not express markers of apoptosis (e.g., caspase-3, annexin V).

In some aspects, the input composition can be generated by providing, from a biological sample from a subject, a cell composition containing a target percentage of CD8$^+$ T cells that express or do not express CCR7, CD27 and/or CD45RA. In some aspects, the input composition can be generated by providing, from a biological sample from a subject, a cell composition containing a target percentage of CD4$^+$ T cells that express or do not express CCR7, CD27 and/or CD45RA. In some aspects, the input composition can be generated after determining the number, number per volume, number per weight, and/or percentage of the CD8$^+$ T cells that express or do not express CCR7, CD27 and/or CD45RA and/or CD4$^+$ T cells that express or do not express CCR7, CD27 and/or CD45RA, and selecting a particular number, volume or weight of cells that, upon mixing with additional components, contains a target percentage of CD8$^+$ T cells that express or do not express CCR7, CD27 and/or CD45RA and/or a target percentage of CD4$^+$ T cells that express or do not express CCR7, CD27 and/or CD45RA. In some aspects, the input composition can be generated by mixing a cell composition containing CD4$^+$ T cells, and a cell composition containing CD8$^+$ T cells. In some embodiments, the input composition can be generated after determining the number, number per volume, number per weight, and/or percentage of the CD8$^+$ T cells that express or do not express CCR7, CD27, CD45RA and/or markers of apoptosis (e.g., caspase 3, annexin V) and/or CD4$^+$ T cells that express or do not express CCR7, CD27, CD45RA and/or markers of apoptosis (e.g., caspase 3, annexin V), and selecting a particular number, volume or weight of cells that, upon mixing with additional components, contains a target percentage of CD8$^+$ T cells that express or do not express CCR7, CD27, CD45RA and/or markers of apoptosis (e.g., caspase 3, annexin V) and/or a target percentage of CD4$^+$ T cells that express or do not express CCR7, CD27, CD45RA and/or markers of apoptosis (e.g., caspase 3, annexin V).

In some embodiments, the input composition can be generated by isolating, purifying, separating or selecting, from a biological sample obtained from a subject, a target number of CD8$^+$ T cells that express or do not express CCR7, CD27 and/or CD45RA and/or a target number of CD4$^+$ T cells that express or do not express CCR7, CD27 and/or CD45RA, thereby generating an input composition. In some embodiments, the input composition can be generated by isolating, purifying, separating or selecting, from a biological sample obtained from a subject, a target number of CD8$^+$ T cells that express or do not express CCR7, CD27, CD45RA and/or markers of apoptosis (e.g., caspase 3, annexin V) and/or a target number of CD4$^+$ T cells that express or do not express CCR7, CD27, CD45RA and/or markers of apoptosis (e.g., caspase 3, annexin V), thereby generating an input composition. In some aspects, such target number(s) of cells can be combined or mixed to generate an input composition that comprises a target percentage of CD8$^+$ T cells that express or do not express CCR7, CD27 and/or CD45RA and/or a target percentage of CD4$^+$ T cells that express or do not express CCR7, CD27 and/or CD45RA. In some aspects, such target number(s) of cells can be combined or mixed to generate an input composition that comprises a target percentage of CD8$^+$ T cells that express or do not express CCR7, CD27, CD45RA and/or markers of apoptosis (e.g., caspase 3, annexin V) and/or a target percentage of CD4$^+$ T cells that express or do not express CCR7, CD27, CD45RA and/or markers of apoptosis (e.g., caspase 3, annexin V).

In some aspects, the input composition comprises a target percentage of CD4$^+$/CCR7$^+$, CD4$^+$/CD27$^+$, CD4$^+$/CCR7$^+$/CD27$^+$, CD4$^+$/CCR7$^+$/CD45RA$^-$, CD4$^+$/CCR7$^+$/CD45RA$^+$, CD8$^+$/CCR7$^+$, CD8$^+$/CD27$^+$, CD8$^+$/CCR7$^+$/CD27$^+$, CD8$^+$/CCR7$^+$/CD45RA$^-$ and/or CD8$^+$/CCR7$^+$/CD45RA$^+$ cells. In some aspects, the input composition comprises a target percentage of CD4$^+$/CCR7$^+$, CD4$^+$/CD27$^+$, CD4$^+$/CCR7$^+$/CD27$^+$, CD4$^+$/CCR7$^+$/CD45RA$^-$, CD4$^+$/CCR7$^+$/CD45RA$^+$, CD8$^+$/CCR7$^+$, CD8$^+$/CD27$^+$, CD8$^+$/CCR7$^+$/CD27$^+$, CD8$^+$/CCR7$^+$/CD45RA$^-$ and/or CD8$^+$/CCR7$^+$/CD45RA$^+$ and apoptosis marker negative (e.g. Annexin V$^-$ or Caspase 3$^-$) cells.

In some embodiments, the input composition contains CD4$^+$ T cells and CD8$^+$ T cells. In certain embodiments, the input composition one or more subtypes or populations of CD4$^+$ and/or CD8$^+$ T cells. In certain embodiments, the one or more subtypes or populations include cells that that express, e.g., express on the surface of the cell, or do not express, one or more markers associated with certain cell phenotypes, including markers associated or indicative of a less differentiated cell phenotype and/or markers associated with or indicative of a memory cell subtype. In particular embodiments, the input composition contains CD4$^+$ T cells, and at least a portion of the CD4$^+$ T cells express markers associated with a less differentiated phenotype, such as CCR7 and/or CD27. In some embodiments, the input composition contains CD8$^+$ T cells, and at least a portion of the CD8$^+$ T cells express markers associated with a less differentiated phenotype, such as CCR7 and/or CD27. In particular embodiments, the input composition contains and/or has a fixed, preferred, target, defined, and/or controlled percentage or ratio of the cells exhibiting the particular phenotype, e.g., a target percentage of CD8$^+$ T cells that express or do not express CCR7, CD27 and/or CD45RA and/or a target percentage of CD4$^+$ T cells that express or do not express CCR7, CD27 and/or CD45RA.

In certain embodiments, the methods include one or more steps of mixing or combining cells or compositions of cells to generate or produce an input composition. In certain embodiments, the cells or cell compositions have been selected and/or isolated from a sample. In some embodiments, the cells of the input composition have been selected and/or isolated from a sample. In some embodiments, CD4$^+$ T cells and/or a composition of CD4$^+$ T cells are selected or isolated from a sample. In some embodiments, CD8$^+$ T cells and/or a composition of CD8$^+$ T cells are selected or isolated from a sample. In some embodiments, the sample is a biological sample, such as blood sample, apheresis sample, and/or leukapheresis sample. In certain embodiments, the sample is from a subject, e.g. a human subject. In particular embodiments, the composition of CD4$^+$ T cells and the composition of CD8$^+$ T cells are isolated and/or selected from the same sample. In certain embodiments, the composition of CD4$^+$ T cells and the composition of CD8$^+$ T cells are isolated and/or selected from samples taken or obtained from the same subject.

In some embodiments, the generation or production of an input composition includes one or more steps of assessing, characterizing, and/or identifying cells. In particular embodiments, the cells are assessed, characterized, and/or identified in a composition of CD4$^+$ T cells. In some embodiments, cells are assessed, characterized, and/or identified in a composition of CD8$^+$ T cells. In some embodiments, the cells are positive for a marker that indicates and/or is associated with a less differentiated cell phenotype or state and/or markers associated with or indicative of a memory cell subtype. In certain embodiments, the cells are negative for a marker that indicates and/or is associated with a more differentiated state in T cells. In particular embodiments, the cells from CD4$^+$ and CD8$^+$ T cell compositions are assessed, characterized, and/or identified to determine the amount, level, portion, and/or percentage of cells that are positive for one or more markers associated with less differentiated cell phenotype or state and/or markers associated with or indicative of a memory cell subtype and/or are negative for one or more markers associated with a more differentiated state. In certain embodiments, the cells from CD4$^+$ and CD8$^+$ T cell compositions are assessed, characterized, and/or identified to determine the amount, level, portion, and/or percentage of cells that exhibit the particular phenotypes, e.g., expression or lack of expression of the markers associated with a less differentiated cell phenotype or state and/or markers associated with or indicative of a memory cell subtype.

In some embodiments, the methods include one or more steps of mixing or combining a cell composition containing CD4$^+$ T cells with a cell composition containing CD8$^+$ T cells to generate or produce a cell composition, e.g., an input composition, with a target percentage of T cells that express or do not express CCR7, CD27 and/or CD45RA and/or a target percentage of CD4$^+$ T cells that express or do not express CCR7, CD27 and/or CD45RA. In some embodiments, the generation or production of the input composition includes one or more steps of: (i) isolating or selecting a composition of CD4$^+$ T cells and/or a composition of CD8$^+$ T cells from a sample, e.g., a biological sample; (ii) assessing, characterizing, and/or identifying the amount, level, portion, and/or percentage of cells that are positive or negative for one or more markers associated with a less differentiated cell phenotype or state and/or markers associated with or indicative of a memory cell subtype or a more differentiated subtype, e.g., CCR7, CD27 and/or CD45RA, in the composition of CD4$^+$ and/or CD8$^+$ T cells; and/or (iii) mixing or combining cells of a composition of CD4$^+$ T cells with cells of a composition of CD8$^+$ T cells at a target, defined, fixed, and/or preferred percentage of T cells that express or do not express CCR7, CD27 and/or CD45RA and/or percentage of CD4$^+$ T cells that express or do not express CCR7, CD27 and/or CD45RA in the input composition is different than the ratio that is present in the sample.

In some aspects, target percentage of CD4$^+$/CCR7$^+$, CD4$^+$/CD27$^+$, CD4$^+$/CCR7$^+$/CD27$^+$, CD4$^+$/CCR7$^+$/CD45RA$^-$, CD4$^+$/CCR7$^+$/CD45RA$^+$, CD8$^+$/CCR7$^+$, CD8$^+$/CD27$^+$, CD8$^+$/CCR7$^+$/CD27$^+$, CD8$^+$/CCR7$^+$/CD45RA$^-$ and/or CD8$^+$/CCR7$^+$/CD45RA$^+$ cells in the input composition, include, at least 15%, 20%, 30%, 40%, 50%, 60%, 70%, 80% or 90% of the total cells in the input composition, or between about 15% and 90%, between about 20% and 80%, between about 30% and 70%, or between about 40% and 60%, each inclusive, of the total cells in the input composition being CD4$^+$/CCR7$^+$, CD4$^+$/CD27$^+$, CD4$^+$/CCR7$^+$/CD27$^+$, CD4$^+$/CCR7$^+$/CD45RA$^-$, CD4$^+$/CCR7$^+$/CD45RA$^+$, CD8$^+$/CCR7$^+$, CD8$^+$/CD27$^+$, CD8$^+$/CCR7$^+$/CD27$^+$, CD8$^+$/CCR7$^+$/CD45RA$^-$ and/or CD8$^+$/CCR7$^+$/CD45RA$^+$.

In some embodiments, the target percentage of CCR7$^+$, CD27$^+$ and/or CCR7$^+$/CD27$^+$ cells in the input composition are at least 15%, 20%, 30%, 40%, 50%, 60%, 70%, 80% or 90% of the total cells in the input composition, or between about 15% and 90%, between about 20% and 80%, between about 30% and 70%, or between about 40% and 60%, each inclusive, of the total cells in the input composition being $CCR7^+$, $CD27^+$ and/or $CCR7^+/CD27^+$ cells.

In some embodiments, the methods include one or more steps of genetically engineering the cells of the input composition. In some embodiments, the genetic engineering includes one or more steps of incubating the cells of the input composition under conditions that activate and/or simulate the cells, delivering one or more agents comprising a nucleic acid molecule, e.g., a recombinant and/or heterologous nucleic acid molecule to the cells, expanding the cells by incubating the cells under activing or stimulating conditions, harvesting the cells, and/or storing the cells by freezing, e.g., cryopreservation. In some embodiments, the one or more steps of genetic engineering produce an output cell composition containing engineered cells. In certain embodiments, engineered cells of the output composition have a fixed, defined, and/or target ratio of recombinant receptor-expressing (receptor$^+$) $CD8^+$ T cells that express or do not express CCR7, CD27 and/or CD45RA to receptor$^+$/$CD4^+$ T cells that express or do not express CCR7, CD27 and/or CD45RA and/or a defined ratio of receptor$^+$/$CD8^+$ T cells that express or do not express CCR7, CD27 and/or CD45RA and/or receptor$^+$/$CD4^+$ T cells that express or do not express CCR7, CD27 and/or CD45RA to another subset of cells in the composition.

B. Activation and Stimulation of Cells

In some embodiments, the one or more processing steps include a step of stimulating the isolated cells, such as selected cell populations. In some embodiments, the cells are incubated and/or cultured prior to or in connection with genetic engineering. The incubation may be prior to or in connection with genetic engineering, such as genetic engineering resulting from embodiments of the transduction method described above. In some embodiments, the stimulation results in activation and/or proliferation of the cells, for example, prior to transduction. The incubation steps can include culture, cultivation, stimulation, activation, and/or propagation. The incubation and/or engineering may be carried out in a culture vessel, such as a unit, chamber, well, column, tube, tubing set, valve, vial, culture dish, bag, or other container for culture or cultivating cells. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

In some embodiments, the processing steps include incubations of cells, such as selected cells, in which the incubation steps can include culture, cultivation, stimulation, activation, and/or propagation of cells. In some embodiments, the compositions or cells are incubated in the presence of stimulating conditions or a stimulatory agent. Such conditions include those designed to induce proliferation, activation, and/or survival of cells in the population, to mimic antigen exposure, and/or to prime the cells for genetic engineering, such as for the introduction of a recombinant antigen receptor.

In some embodiments, the conditions for stimulation and/or activation can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of stimulating or activating an intracellular signaling domain of a TCR complex. In some aspects, the agent turns on or initiates TCR/CD3 intracellular signaling cascade in a T cell. Such agents can include agents suitable to deliver a primary signal, e.g., to initiate activation of an ITAM-induced signal, such as antibodies, such as those specific for a TCR, e.g. anti-CD3. In some embodiments, the stimulating conditions include one or more agent, e.g. ligand, which is capable of stimulating a costimulatory receptor, e.g., anti-CD28 or anti-4-1BB. In some embodiments, such agents and/or ligands may be, bound to solid support such as a bead, and/or one or more cytokines. Among the stimulating agents are anti-CD3/anti-CD28 beads (e.g., DYNABEADS® M-450 CD3/CD28 T Cell Expander, and/or ExpACT® beads). Optionally, the expansion method may further comprise the step of adding anti-CD3 and/or anti CD28 antibody to the culture medium (e.g., at a concentration of at least about 0.5 ng/ml). In some embodiments, the stimulating agents include IL-2, IL-7 and/or IL-15, for example, an IL-2 concentration of at least about 10 units/mL, at least about 50 units/mL, at least about 100 units/mL or at least about 200 units/mL.

In some embodiments, the one or more stimulating agent is capable of activating T cells, $CD4^+$ T cells and/or $CD8^+$ T cells; is capable of inducing a signal through a TCR complex; and/or is capable of inducing proliferation of T cells, $CD4^+$ T cells and/or $CD8^+$ T cells. In some embodiments, the one or more stimulating agent comprises a primary agent that binds to a member of a TCR complex, optionally that specifically binds to CD3. In some embodiments, the one or more stimulating agent further comprises a secondary agent that specifically binds to a T cell costimulatory molecule. In some embodiments, the costimulatory molecule is selected from the group consisting of CD28, CD137 (4-1-BB), OX40, or ICOS. In some embodiments, the primary and secondary agents comprise antibodies, optionally wherein the one or more stimulating agent comprises incubation with an anti-CD3 antibody and an anti-CD28 antibody. In some embodiments, the one or more stimulating agents are present on the surface of a solid support, optionally a bead. In some embodiments, the one or more stimulating agent is selected from the group consisting of CD3-binding molecules; CD28-binding molecules; recombinant IL-2; recombinant IL-15; and recombinant IL-7, a vaccine comprising an antigen specifically recognized by the antigen receptor, and an anti-idiotype antibody that specifically binds the antigen receptor or combinations thereof.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In embodiments, antigen-specific T cells, such as antigen-specific CD4+ and/or CD8+ T cells, are obtained by stimulating naïve or antigen specific T lymphocytes with antigen. For example, antigen-specific T cell lines or clones can be generated to cytomegalovirus antigens by isolating T cells from infected subjects and stimulating the cells in vitro with the same antigen.

In some aspects, incubation is carried out in accordance with techniques such as those described in U.S. Pat. No. 6,040,177 to Riddell et al., Klebanoff et al. (2012) J Immunother. 35(9): 651-660, Terakura et al. (2012) Blood. 1:72-82, and/or Wang et al. (2012) J Immunother. 35(9):689-701.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In some embodiments, at least a portion of the incubation in the presence of one or more stimulating conditions or stimulatory agents is carried out in the internal cavity of a centrifugal chamber, for example, under centrifugal rotation, such as described in International Publication Number WO2016/073602. In some embodiments, at least a portion of the incubation performed in a centrifugal chamber includes mixing with a reagent or reagents to induce stimulation and/or activation. In some embodiments, cells, such as selected cells, are mixed with a stimulating condition or stimulatory agent in the centrifugal chamber. In some aspects of such processes, a volume of cells is mixed with an amount of one or more stimulating conditions or agents that is far less than is normally employed when performing similar stimulations in a cell culture plate or other system.

In some embodiments, the stimulating agent is added to cells in the cavity of the chamber in an amount that is substantially less than (e.g. is no more than 5%, 10%, 20%, 30%, 40%, 50%, 60%, 70% or 80% of the amount) as compared to the amount of the stimulating agent that is typically used or would be necessary to achieve about the same or similar efficiency of selection of the same number of cells or the same volume of cells when selection is performed without mixing in a centrifugal chamber, e.g. in a tube or bag with periodic shaking or rotation. In some embodiments, the incubation is performed with the addition of an incubation buffer to the cells and stimulating agent to achieve a target volume with incubation of the reagent of, for example, about 10 mL to about 200 mL, or about 20 mL to about 125 mL, such as at least or about at least or about 10 mL, 20 mL, 30 mL, 40 mL, 50 mL, 60 mL, 70 mL, 80 mL, 90 mL, 100 mL, 105 mL, 110 mL, 115 mL, 120 mL, 125 mL, 130 mL, 135 mL, 140 mL, 145 mL, 150 mL, 160 mL, 170 mL, 180 mL, 190 mL, or 200 mL. In some embodiments, the incubation buffer and stimulating agent are pre-mixed before addition to the cells. In some embodiments, the incubation buffer and stimulating agent are separately added to the cells. In some embodiments, the stimulating incubation is carried out with periodic gentle mixing condition, which can aid in promoting energetically favored interactions and thereby permit the use of less overall stimulating agent while achieving stimulating and activation of cells.

In some embodiments, the incubation generally is carried out under mixing conditions, such as in the presence of spinning, generally at relatively low force or speed, such as speed lower than that used to pellet the cells, such as from 600 rpm to 1700 rpm or from about 600 rpm to about 1700 rpm (e.g. at or about or at least 600 rpm, 1000 rpm, or 1500 rpm or 1700 rpm), such as at an RCF at the sample or wall of the chamber or other container of from 80 g to 100 g or from about 80 g to about 100 g (e.g. at or about or at least 80 g, 85 g, 90 g, 95 g, or 100 g). In some embodiments, the spin is carried out using repeated intervals of a spin at such low speed followed by a rest period, such as a spin and/or rest for 1, 2, 3, 4, 5, 6, 7, 8, 9, or 10 seconds, such as a spin at approximately 1 or 2 seconds followed by a rest for approximately 5, 6, 7, or 8 seconds.

In some embodiments, the total duration of the incubation, e.g. with the stimulating agent, is between or between about 1 hour and 96 hours, 1 hour and 72 hours, 1 hour and 48 hours, 4 hours and 36 hours, 8 hours and 30 hours, 18 hours and 30 hours, or 12 hours and 24 hours, such as at least or about at least or about 6 hours, 12 hours, 18 hours, 24 hours, 36 hours or 72 hours. In some embodiments, the further incubation is for a time between or about between 1 hour and 48 hours, 4 hours and 36 hours, 8 hours and 30 hours or 12 hours and 24 hours, inclusive.

C. Genetic Engineering

In some embodiments, the processing steps include introduction of a nucleic acid molecule encoding a recombinant protein. In some embodiments, the cells, e.g., T cells, are genetically engineered to express a recombinant receptor. Among such recombinant proteins are recombinant receptors, such as any described in Section III. In some embodiments, the engineering is carried out by introducing polynucleotides that encode the recombinant receptor. Also provided are polynucleotides encoding a recombinant receptor, and vectors or constructs containing such nucleic acids and/or polynucleotides. Introduction of the nucleic acid molecules encoding the recombinant protein, such as recombinant receptor, in the cell may be carried out using any of a number of known vectors. Such vectors include viral and non-viral systems, including lentiviral and gammaretroviral systems, as well as transposon-based systems such as PiggyBac or Sleeping Beauty-based gene transfer systems. Exemplary methods include those for transfer of nucleic acids encoding the receptors, including via viral, e.g., retroviral or lentiviral, transduction, transposons, and electroporation.

In some embodiments, preparation of the engineered cells includes one or more culture and/or preparation steps. The cells for introduction of the nucleic acid encoding the transgenic receptor such as the CAR, may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

In certain embodiments, compositions of cells are engineered, e.g., transduced or transfected, prior to cultivating the cells, e.g., under conditions that promote proliferation and/or expansion. In particular embodiments, compositions of cells are engineered after the compositions have been stimulated, activated, and/or incubated under stimulating conditions. In particular embodiments, the compositions are stimulated compositions. In particular embodiments, the stimulated compositions have been previously cryopreserved and stored, and are thawed prior to engineering.

In some embodiments, gene transfer is accomplished by first stimulating the cell, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

In some embodiments, recombinant nucleic acids are transferred into cells using recombinant infectious virus particles, such as, e.g., vectors derived from simian virus 40 (SV40), adenoviruses, adeno-associated virus (AAV), and human immunodeficiency virus (HIV).

In some embodiments, recombinant nucleic acids are transferred into T cells via electroporation (see, e.g., Chicaybam et al, (2013) PLoS ONE 8(3): e60298 and Van Tedeloo et al. (2000) Gene Therapy 7(16): 1431-1437). In some embodiments, recombinant nucleic acids are transferred into T cells via transposition (see, e.g., Manuri et al. (2010) Hum Gene Ther 21(4): 427-437; Sharma et al. (2013) Molec Ther Nucl Acids 2, e74; and Huang et al. (2009) Methods Mol Biol 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

Other approaches and vectors for transfer of the nucleic acids encoding the recombinant products are those described, e.g., in international patent application, Publication No.: WO2014055668, and U.S. Pat. No. 7,446,190.

In some embodiments, the cells, e.g., T cells, may be transfected either during or after expansion e.g. with a T cell receptor (TCR) or a chimeric antigen receptor (CAR). This transfection for the introduction of the gene of the desired receptor can be carried out with any suitable retroviral vector, for example. The genetically modified cell population can then be liberated from the initial stimulus (the CD3/CD28 stimulus, for example) and subsequently be stimulated with a second type of stimulus e.g. via a de novo introduced receptor). This second type of stimulus may include an antigenic stimulus in form of a peptide/MHC molecule, the cognate (cross-linking) ligand of the genetically introduced receptor (e.g. natural ligand of a CAR) or any ligand (such as an antibody) that directly binds within the framework of the new receptor (e.g. by recognizing constant regions within the receptor). See, for example, Cheadle et al, "Chimeric antigen receptors for T-cell based therapy" Methods Mol Biol. 2012; 907:645-66 or Barrett et al., Chimeric Antigen Receptor Therapy for Cancer Annual Review of Medicine Vol. 65: 333-347 (2014).

In some cases, a vector may be used that does not require that the cells, e.g., T cells, are activated. In some such instances, the cells may be selected and/or transduced prior to activation. Thus, the cells may be engineered prior to, or subsequent to culturing of the cells, and in some cases at the same time as or during at least a portion of the culturing.

In some aspects, the cells further are engineered to promote expression of cytokines or other factors. Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., Mol. and Cell Biol., 11:6 (1991); and Riddell et al., Human Gene Therapy 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

In some embodiments, the introducing is carried out by contacting one or more cells of a composition with a nucleic acid molecule encoding the recombinant protein, e.g. recombinant receptor. In some embodiments, the contacting can be effected with centrifugation, such as spinoculation (e.g. centrifugal inoculation). Such methods include any of those as described in International Publication Number WO2016/073602. Exemplary centrifugal chambers include those produced and sold by Biosafe SA, including those for use with the Sepax® and Sepax® 2 system, including an A-200/F and A-200 centrifugal chambers and various kits for use with such systems. Exemplary chambers, systems, and processing instrumentation and cabinets are described, for example, in U.S. Pat. Nos. 6,123,655, 6,733,433 and Published U.S. Patent Application, Publication No.: US 2008/0171951, and published international patent application, publication no. WO 00/38762, the contents of each of which are incorporated herein by reference in their entirety. Exemplary kits for use with such systems include, but are not limited to, single-use kits sold by BioSafe SA under product names CS-430.1, CS-490.1, CS-600.1 or CS-900.2.

In some embodiments, the system is included with and/or placed into association with other instrumentation, including instrumentation to operate, automate, control and/or monitor aspects of the transduction step and one or more various other processing steps performed in the system, e.g. one or more processing steps that can be carried out with or in connection with the centrifugal chamber system as described herein or in International Publication Number WO2016/073602. This instrumentation in some embodiments is contained within a cabinet. In some embodiments, the instrumentation includes a cabinet, which includes a housing containing control circuitry, a centrifuge, a cover, motors, pumps, sensors, displays, and a user interface. An exemplary device is described in U.S. Pat. Nos. 6,123,655, 6,733,433 and US 2008/0171951.

In some embodiments, the system comprises a series of containers, e.g., bags, tubing, stopcocks, clamps, connectors, and a centrifuge chamber. In some embodiments, the containers, such as bags, include one or more containers, such as bags, containing the cells to be transduced and the viral vector particles, in the same container or separate containers, such as the same bag or separate bags. In some embodiments, the system further includes one or more containers, such as bags, containing medium, such as diluent and/or wash solution, which is pulled into the chamber and/or other components to dilute, resuspend, and/or wash components and/or compositions during the methods. The containers can be connected at one or more positions in the system, such as at a position corresponding to an input line, diluent line, wash line, waste line and/or output line.

In some embodiments, the chamber is associated with a centrifuge, which is capable of effecting rotation of the chamber, such as around its axis of rotation. Rotation may occur before, during, and/or after the incubation in connection with transduction of the cells and/or in one or more of the other processing steps. Thus, in some embodiments, one or more of the various processing steps is carried out under rotation, e.g., at a particular force. The chamber is typically capable of vertical or generally vertical rotation, such that the chamber sits vertically during centrifugation and the side wall and axis are vertical or generally vertical, with the end wall(s) horizontal or generally horizontal.

In some embodiments, the composition containing cells, viral particles and reagent can be rotated, generally at relatively low force or speed, such as speed lower than that used to pellet the cells, such as from 600 rpm to 1700 rpm or from about 600 rpm to about 1700 rpm (e.g. at or about or at least 600 rpm, 1000 rpm, or 1500 rpm or 1700 rpm). In some embodiments, the rotation is carried at a force, e.g., a relative centrifugal force, of from 100 g to 3200 g or from about 100 g to about 3200 g (e.g. at or about or at least at or about 100 g, 200 g, 300 g, 400 g, 500 g, 1000 g, 1500 g, 2000 g, 2500 g, 3000 g or 3200 g), as measured for example at an internal or external wall of the chamber or cavity. The term "relative centrifugal force" or RCF is generally understood to be the effective force imparted on an object or substance (such as a cell, sample, or pellet and/or a point in the chamber or other container being rotated), relative to the earth's gravitational force, at a particular point in space as compared to the axis of rotation. The value may be determined using well-known formulas, taking into account the gravitational force, rotation speed and the radius of rotation (distance from the axis of rotation and the object, substance, or particle at which RCF is being measured).

In some embodiments, during at least a part of the genetic engineering, e.g. transduction, and/or subsequent to the genetic engineering the cells are transferred to a container such as a bag, e.g., a bioreactor bag assembly, for culture of the genetically engineered cells, such as for cultivation or expansion of the cells, as described above. In some embodiments, the container for cultivation or expansion of the cells is a bioreactor bag, such as a perfusion bag.

1. Vectors and Methods

In some embodiments, the processing steps include introduction of a nucleic acid molecule encoding a recombinant protein, into the cell, and may be carried out using any of a number of known vectors. In some embodiments, the vector contains the nucleic acid encoding the recombinant receptor. In particular embodiments, the vector is a viral vector a non-viral vector. In some cases, the vector is a viral vector, such as a retroviral vector, e.g., a lentiviral vector or a gammaretroviral vector.

In some cases, the nucleic acid sequence encoding the recombinant receptor, e.g., chimeric antigen receptor (CAR) contains a signal sequence that encodes a signal peptide. Non-limiting exemplary examples of signal peptides include, for example, the GMCSFR alpha chain signal peptide, the CD8 alpha signal peptide, or the CD33 signal peptide.

In some embodiments, the vectors include viral vectors, e.g., retroviral or lentiviral, non-viral vectors or transposons, e.g. Sleeping Beauty transposon system, vectors derived from simian virus 40 (SV40), adenoviruses, adeno-associated virus (AAV), lentiviral vectors or retroviral vectors, such as gamma-retroviral vectors, retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV) or adeno-associated virus (AAV).

In some embodiments, the viral vector or the non-viral DNA contains a nucleic acid that encodes a heterologous recombinant protein. In some embodiments, the heterologous recombinant molecule is or includes a recombinant receptor, e.g., an antigen receptor, SB-transposons, e.g., for gene silencing, capsid-enclosed transposons, homologous double stranded nucleic acid, e.g., for genomic recombination or reporter genes (e.g., fluorescent proteins, such as GFP) or luciferase).

2 Preparation of Vial Vector Particles for Transduction

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) *Mol Ther Nucl* Acids 2, e93; Park et al., *Trends Biotechnol.* 2011 November 29(11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), or spleen focus forming virus (SFFV). In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known. Exemplary methods are described in, e.g., Wang et al. (2012) *J. Immunother.* 35(9): 689-701; Cooper et al. (2003) *Blood.* 101: 1637-1644; Verhoeyen et al. (2009) *Methods Mol Biol.* 506: 97-114; and Cavalieri et al. (2003) Blood. 102(2): 497-505.

In some embodiments, the viral vector particles contain a genome derived from a retroviral genome based vector, such as derived from a lentiviral genome based vector. In some aspects of the provided viral vectors, the heterologous nucleic acid encoding a recombinant receptor, such as a CAR, is contained and/or located between the 5' LTR and 3' LTR sequences of the vector genome.

In some embodiments, the viral vector genome is a lentivirus genome, such as an HIV-1 genome or an SIV genome. For example, lentiviral vectors have been generated by multiply attenuating virulence genes, for example, the genes env, vif, vpu and nef can be deleted, making the vector safer for therapeutic purposes. Lentiviral vectors are known. See Naldini et al., (1996 and 1998); Zufferey et al., (1997); Dull et al., 1998, U.S. Pat. Nos. 6,013,516; and 5,994,136). In some embodiments, these viral vectors are plasmid-based or virus-based, and are configured to carry the essential sequences for incorporating foreign nucleic acid, for selection, and for transfer of the nucleic acid into a host cell. Known lentiviruses can be readily obtained from depositories or collections such as the American Type Culture Collection ("ATCC"; 10801 University Blvd., Manassas, Va. 20110-2209), or isolated from known sources using commonly available techniques.

Non-limiting examples of lentiviral vectors include those derived from a lentivirus, such as Human Immunodeficiency Virus 1 (HIV-1), HIV-2, an Simian Immunodeficiency Virus (SIV), Human T-lymphotropic virus 1 (HTLV-1), HTLV-2 or equine infection anemia virus (E1AV). For example, lentiviral vectors have been generated by multiply attenuating the HIV virulence genes, for example, the genes env, vif, vpr, vpu and nef are deleted, making the vector safer for therapeutic purposes. Lentiviral vectors are known in the art, see Naldini et al., (1996 and 1998); Zufferey et al., (1997); Dull et al., 1998, U.S. Pat. Nos. 6,013,516; and 5,994,136). In some embodiments, these viral vectors are plasmid-based or virus-based, and are configured to carry the essential sequences for incorporating foreign nucleic acid, for selection, and for transfer of the nucleic acid into a host cell. Known lentiviruses can be readily obtained from depositories or collections such as the American Type Culture Collection ("ATCC"; 10801 University Blvd., Manassas, Va. 20110-2209), or isolated from known sources using commonly available techniques.

The viral vector genome is typically constructed in a plasmid form that can be transfected into a packaging or producer cell line. In any of such examples, the nucleic acid encoding a recombinant protein, such as a recombinant receptor, is inserted or located in a region of the viral vector, such as generally in a non-essential region of the viral genome. In some embodiments, the nucleic acid is inserted into the viral genome in the place of certain viral sequences to produce a virus that is replication defective.

Any of a variety of known methods can be used to produce retroviral particles whose genome contains an RNA copy of the viral vector genome. In some embodiments, at least two components are involved in making a virus-based gene delivery system: first, packaging plasmids, encompassing the structural proteins as well as the enzymes necessary to generate a viral vector particle, and second, the viral vector itself, i.e., the genetic material to be transferred. Biosafety safeguards can be introduced in the design of one or both of these components.

In some embodiments, the packaging plasmid can contain all retroviral, such as HIV-1, proteins other than envelope proteins (Naldini et al., 1998). In other embodiments, viral vectors can lack additional viral genes, such as those that are associated with virulence, e.g. vpr, vif, vpu and nef, and/or Tat, a primary transactivator of HIV. In some embodiments, lentiviral vectors, such as HIV-based lentiviral vectors, comprise only three genes of the parental virus: gag, pol and rev, which reduces or eliminates the possibility of reconstitution of a wild-type virus through recombination.

In some embodiments, the viral vector genome is introduced into a packaging cell line that contains all the components necessary to package viral genomic RNA, transcribed from the viral vector genome, into viral particles. Alternatively, the viral vector genome may comprise one or more genes encoding viral components in addition to the one or more sequences, e.g., recombinant nucleic acids, of interest. In some aspects, in order to prevent replication of the genome in the target cell, however, endogenous viral genes required for replication are removed and provided separately in the packaging cell line.

In some embodiments, a packaging cell line is transfected with one or more plasmid vectors containing the components necessary to generate the particles. In some embodiments, a packaging cell line is transfected with a plasmid containing the viral vector genome, including the LTRs, the cis-acting packaging sequence and the sequence of interest, i.e. a nucleic acid encoding an antigen receptor, such as a CAR; and one or more helper plasmids encoding the virus enzymatic and/or structural components, such as Gag, pol and/or rev. In some embodiments, multiple vectors are utilized to separate the various genetic components that generate the retroviral vector particles. In some such embodiments, providing separate vectors to the packaging cell reduces the chance of recombination events that might otherwise generate replication competent viruses. In some embodiments, a single plasmid vector having all of the retroviral components can be used.

In some embodiments, the retroviral vector particle, such as lentiviral vector particle, is pseudotyped to increase the transduction efficiency of host cells. For example, a retroviral vector particle, such as a lentiviral vector particle, in some embodiments is pseudotyped with a VSV-G glycoprotein, which provides a broad cell host range extending the cell types that can be transduced. In some embodiments, a packaging cell line is transfected with a plasmid or polynucleotide encoding a non-native envelope glycoprotein, such as to include xenotropic, polytropic or amphotropic envelopes, such as Sindbis virus envelope, GALV or VSV-G.

In some embodiments, the packaging cell line provides the components, including viral regulatory and structural proteins, that are required in trans for the packaging of the viral genomic RNA into lentiviral vector particles. In some embodiments, the packaging cell line may be any cell line that is capable of expressing lentiviral proteins and producing functional lentiviral vector particles. In some aspects, suitable packaging cell lines include 293 (ATCC CCL X), 293T, HeLA (ATCC CCL 2), D17 (ATCC CCL 183), MDCK (ATCC CCL 34), BHK (ATCC CCL-10) and Cf2Th (ATCCCRL 1430) cells.

In some embodiments, the packaging cell line stably expresses the viral protein(s). For example, in some aspects, a packaging cell line containing the gag, pol, rev and/or other structural genes but without the LTR and packaging components can be constructed. In some embodiments, a packaging cell line can be transiently transfected with nucleic acid molecules encoding one or more viral proteins along with the viral vector genome containing a nucleic acid molecule encoding a heterologous protein, and/or a nucleic acid encoding an envelope glycoprotein.

In some embodiments, the viral vectors and the packaging and/or helper plasmids are introduced via transfection or infection into the packaging cell line. The packaging cell line produces viral vector particles that contain the viral vector genome. Methods for transfection or infection are well known. Non-limiting examples include calcium phosphate, DEAE-dextran and lipofection methods, electroporation and microinjection.

When a recombinant plasmid and the retroviral LTR and packaging sequences are introduced into a special cell line (e.g., by calcium phosphate precipitation for example), the packaging sequences may permit the RNA transcript of the recombinant plasmid to be packaged into viral particles, which then may be secreted into the culture media. The media containing the recombinant retroviruses in some embodiments is then collected, optionally concentrated, and used for gene transfer. For example, in some aspects, after cotransfection of the packaging plasmids and the transfer vector to the packaging cell line, the viral vector particles are recovered from the culture media and titered by standard methods used by those of skill in the art.

In some embodiments, a retroviral vector, such as a lentiviral vector, can be produced in a packaging cell line, such as an exemplary HEK 293T cell line, by introduction of plasmids to allow generation of lentiviral particles. In some embodiments, a packaging cell is transfected and/or contains a polynucleotide encoding gag and pol, and a polynucleotide encoding a recombinant receptor, such as an antigen receptor, for example, a CAR. In some embodiments, the packaging cell line is optionally and/or additionally transfected with and/or contains a polynucleotide encoding a rev protein. In some embodiments, the packaging cell line is optionally and/or additionally transfected with and/or contains a polynucleotide encoding a non-native envelope glycoprotein, such as VSV-G. In some such embodiments, approximately two days after transfection of cells, e.g. HEK 293T cells, the cell supernatant contains recombinant lentiviral vectors, which can be recovered and titered.

Recovered and/or produced retroviral vector particles can be used to transduce target cells using the methods as described. Once in the target cells, the viral RNA is reverse-transcribed, imported into the nucleus and stably integrated into the host genome. One or two days after the integration of the viral RNA, the expression of the recombinant protein, e.g. antigen receptor, such as CAR, can be detected.

3. Nucleic Acids

In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

In some embodiments, the cells include one or more nucleic acids introduced via genetic engineering, and thereby express recombinant or genetically engineered products of such nucleic acids.

In some cases, the nucleic acid sequence encoding the recombinant receptor contains a signal sequence that encodes a signal peptide. In some aspects, the signal sequence may encode a signal peptide derived from a native polypeptide. In other aspects, the signal sequence may encode a heterologous or non-native signal peptide, such as the exemplary signal peptide of the GMCSFR alpha chain set forth in SEQ ID NO:25 and encoded by the nucleotide sequence set forth in SEQ ID NO:24. In some cases, the nucleic acid sequence encoding the recombinant receptor, e.g., chimeric antigen receptor (CAR) contains a signal sequence that encodes a signal peptide. Non-limiting exemplary examples of signal peptides include, for example, the GMCSFR alpha chain signal peptide set forth in SEQ ID NO: 25 and encoded by the nucleotide sequence set forth in SEQ ID NO:24, or the CD8 alpha signal peptide set forth in SEQ ID NO:26.

In some embodiments, the polynucleotide encoding the recombinant receptor contains at least one promoter that is operatively linked to control expression of the recombinant receptor. In some examples, the polynucleotide contains two, three, or more promoters operatively linked to control expression of the recombinant receptor.

In certain cases where nucleic acid molecules encode two or more different polypeptide chains, e.g., a recombinant receptor and a marker, each of the polypeptide chains can be encoded by a separate nucleic acid molecule. For example, two separate nucleic acids are provided, and each can be individually transferred or introduced into the cell for expression in the cell. In some embodiments, the nucleic acid encoding the recombinant receptor and the nucleic acid encoding the marker are operably linked to the same promoter and are optionally separated by an internal ribosome entry site (IRES), or a nucleic acid encoding a self-cleaving peptide or a peptide that causes ribosome skipping, which optionally is a T2A, a P2A, a E2A or a F2A. In some embodiments, the nucleic acids encoding the marker and the nucleic acid encoding the recombinant receptor are operably linked to two different promoters. In some embodiments, the nucleic acid encoding the marker and the nucleic acid encoding the recombinant receptor are present or inserted at different locations within the genome of the cell. In some embodiments, the polynucleotide encoding the recombinant receptor is introduced into a composition containing cultured cells, such as by retroviral transduction, transfection, or transformation.

In some embodiments, such as those where the polynucleotide contains a first and second nucleic acid sequence, the coding sequences encoding each of the different polypeptide chains can be operatively linked to a promoter, which can be the same or different. In some embodiments, the nucleic acid molecule can contain a promoter that drives the expression of two or more different polypeptide chains. In some embodiments, such nucleic acid molecules can be multicistronic (bicistronic or tricistronic, see e.g., U.S. Pat. No. 6,060,273). In some embodiments, transcription units can be engineered as a bicistronic unit containing an IRES (internal ribosome entry site), which allows coexpression of gene products ((e.g. encoding the marker and encoding the recombinant receptor) by a message from a single promoter.

Alternatively, in some cases, a single promoter may direct expression of an RNA that contains, in a single open reading frame (ORF), two or three genes (e.g. encoding the marker and encoding the recombinant receptor) separated from one another by sequences encoding a self-cleavage peptide (e.g., 2A sequences) or a protease recognition site (e.g., furin). The ORF thus encodes a single polypeptide, which, either during (in the case of 2A) or after translation, is processed into the individual proteins. In some cases, the peptide, such as a T2A, can cause the ribosome to skip (ribosome skipping) synthesis of a peptide bond at the C-terminus of a 2A element, leading to separation between the end of the 2A sequence and the next peptide downstream (see, for example, de Felipe, Genetic Vaccines and Ther. 2:13 (2004) and de Felipe et al. Traffic 5:616-626 (2004)). Various 2A elements are known. Examples of 2A sequences that can be used in the methods and system disclosed herein, without limitation, 2A sequences from the foot-and-mouth disease virus (F2A, e.g., SEQ ID NO: 21), equine rhinitis A virus (E2A, e.g., SEQ ID NO: 20), Thosea asigna virus (T2A, e.g., SEQ ID NO: 6 or 17), and porcine teschovirus-1 (P2A, e.g., SEQ ID NO: 18 or 19) as described in U.S. Patent Publication No. 20070116690.

Any of the recombinant receptors described herein can be encoded by polynucleotides containing one or more nucleic acid sequences encoding recombinant receptors, in any combinations or arrangements. For example, one, two, three or more polynucleotides can encode one, two, three or more different polypeptides, e.g., recombinant receptors. In some embodiments, one vector or construct contains a nucleic acid sequence encoding marker, and a separate vector or construct contains a nucleic acid sequence encoding a recombinant receptor, e.g., CAR. In some embodiments, the nucleic acid encoding the marker and the nucleic acid encoding the recombinant receptor are operably linked to two different promoters. In some embodiments, the nucleic acid encoding the recombinant receptor is present downstream of the nucleic acid encoding the marker.

In some embodiments, the vector backbone contains a nucleic acid sequence encoding one or more marker(s). In some embodiments, the one or more marker(s) is a transduction marker, surrogate marker and/or a selection marker.

In some embodiments, the marker is a transduction marker or a surrogate marker. A transduction marker or a surrogate marker can be used to detect cells that have been introduced with the polynucleotide, e.g., a polynucleotide encoding a recombinant receptor. In some embodiments, the transduction marker can indicate or confirm modification of a cell. In some embodiments, the surrogate marker is a protein that is made to be co-expressed on the cell surface with the recombinant receptor, e.g. CAR. In particular embodiments, such a surrogate marker is a surface protein that has been modified to have little or no activity. In certain embodiments, the surrogate marker is encoded on the same polynucleotide that encodes the recombinant receptor. In some embodiments, the nucleic acid sequence encoding the recombinant receptor is operably linked to a nucleic acid sequence encoding a marker, optionally separated by an internal ribosome entry site (IRES), or a nucleic acid encoding a self-cleaving peptide or a peptide that causes ribosome skipping, such as a 2A sequence, such as a T2A, a P2A, a E2A or a F2A. Extrinsic marker genes may in some cases be utilized in connection with engineered cell to permit detection or selection of cells and, in some cases, also to promote cell suicide.

Exemplary surrogate markers can include truncated cell surface polypeptides, such as a truncated human epidermal growth factor receptor 2 (tHER2), a truncated epidermal growth factor receptor (EGFRt, exemplary EGFRt sequence set forth in SEQ ID NO:7 or 16) or a prostate-specific membrane antigen (PSMA) or modified form thereof. EGFRt may contain an epitope recognized by the antibody cetuximab (Erbitux®) or other therapeutic anti-EGFR antibody or binding molecule, which can be used to identify or select cells that have been engineered with the EGFRt construct and a recombinant receptor, such as a chimeric antigen receptor (CAR), and/or to eliminate or separate cells expressing the receptor. See U.S. Pat. No. 8,802,374 and Liu et al., Nature Biotech. 2016 April; 34(4): 430-434). In some aspects, the marker, e.g. surrogate marker, includes all or part (e.g., truncated form) of CD34, a NGFR, a CD19 or a truncated CD19, e.g., a truncated non-human CD19, or epidermal growth factor receptor (e.g., tEGFR). In some embodiments, the nucleic acid encoding the marker is operably linked to a polynucleotide encoding for a linker sequence, such as a cleavable linker sequence, e.g., T2A. For example, a marker, and optionally a linker sequence, can be any as disclosed in PCT Pub. No. WO2014031687. For example, the marker can be a truncated EGFR (tEGFR) that is, optionally, linked to a linker sequence, such as a T2A cleavable linker sequence. An exemplary polypeptide for a truncated EGFR (e.g. tEGFR) comprises the sequence of amino acids set forth in SEQ ID NO: 7 or 16 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7 or 16.

In some embodiments, the marker is or comprises a fluorescent protein, such as green fluorescent protein (GFP), enhanced green fluorescent protein (EGFP), such as superfold GFP, red fluorescent protein (RFP), such as tdTomato, mCherry, mStrawberry, AsRed2, DsRed or DsRed2, cyan fluorescent protein (CFP), blue green fluorescent protein (BFP), enhanced blue fluorescent protein (EBFP), and yellow fluorescent protein (YFP), and variants thereof, including species variants, monomeric variants, and codon-optimized and/or enhanced variants of the fluorescent proteins. In some embodiments, the marker is or comprises an enzyme, such as a luciferase, the lacZ gene from *E. coli*, alkaline phosphatase, secreted embryonic alkaline phosphatase (SEAP), chloramphenicol acetyl transferase (CAT). Exemplary light-emitting reporter genes include luciferase (luc), β-galactosidase, chloramphenicol acetyltransferase (CAT), β-glucuronidase (GUS) or variants thereof.

In some embodiments, the marker is a selection marker. In some embodiments, the selection marker is or comprises a polypeptide that confers resistance to exogenous agents or drugs. In some embodiments, the selection marker is an antibiotic resistance gene. In some embodiments, the selection marker is an antibiotic resistance gene confers antibiotic resistance to a mammalian cell. In some embodiments, the selection marker is or comprises a Puromycin resistance gene, a Hygromycin resistance gene, a Blasticidin resistance gene, a Neomycin resistance gene, a Geneticin resistance gene or a Zeocin resistance gene or a modified form thereof.

D. Cultivating and/or Expansion of Cells

In some embodiments, cells that have been engineered using methods described herein can undergo one or more cultivating steps, e.g., cultivating cells under conditions that promote proliferation and/or expansion. In some embodiments, engineered cells are cultivated under conditions that promote proliferation and/or expansion subsequent to a step of genetically engineering, e.g., introducing a recombinant polypeptide to the cells by transduction or transfection. In particular embodiments, the cells are cultivated after the cells have been incubated under stimulating conditions and transduced or transfected with a recombinant polynucleotide, e.g., a polynucleotide encoding a recombinant receptor. In some embodiments, the cultivation produces one or more cultivated compositions of enriched T cells. In some embodiments, such conditions may be designed to induce proliferation, expansion, activation, and/or survival of cells in the population. In particular embodiments, the stimulating conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to promote growth, division, and/or expansion of the cells.

In some embodiments, the engineered cells are cultured in a container that can be filled, e.g. via the feed port, with cell media and/or cells for culturing of the added cells. The cells can be from any cell source for which culture of the cells is desired, for example, for expansion and/or proliferation of the cells.

In some aspects, the culture media is an adapted culture medium that supports that growth, cultivation, expansion or proliferation of the cells, such as T cells. In some aspects, the medium can be a liquid containing a mixture of salts, amino acids, vitamins, sugars or any combination thereof. In some embodiments, the culture media further contains one or more stimulating conditions or agents, such as to stimulate the cultivation, expansion or proliferation of cells during the incubation. In some embodiments, the stimulating condition is or includes one or more cytokines, such as selected from IL-2, IL-7 or IL-15. In some embodiments, the cytokine is a recombinant cytokine. In particular embodiments, the one or more cytokines are human recombinant cytokines. In certain embodiments, the one or more cytokines bind to and/or are capable of binding to receptors that are expressed by and/or are endogenous to T cells. In particular embodiments, the one or more cytokines is or includes a member of the 4-alpha-helix bundle family of cytokines. In some embodiments, members of the 4-alpha-helix bundle family of cytokines include, but are not limited to, interleukin-2 (IL-2), interleukin-4 (IL-4), interleukin-7 (IL-7), interleukin-9 (IL-9), interleukin 12 (IL-12), interleukin 15 (IL-15), granulocyte colony-stimulating factor (G-CSF), and granulocyte-macrophage colony-stimulating factor (GM-CSF). In some embodiments, the one or more cytokines is or includes IL-15. In particular embodiments, the one or more cytokines is or includes IL-7. In particular embodiments, the one or more cytokines is or includes recombinant IL-2.

In some embodiments, the concentration of the one or more cytokine in the culture media during the culturing or incubation, independently, is from or from about 1 IU/mL to 1500 IU/mL, such as from or from about 1 IU/mL to 100 IU/mL, 2 IU/mL to 50 IU/mL, 5 IU/mL to 10 IU/mL, 10 IU/mL to 500 IU/mL, 50 IU/mL to 250 IU/mL or 100 IU/mL to 200 IU/mL, 50 IU/mL to 1500 IU/mL, 100 IU/mL to 1000 IU/mL or 200 IU/mL to 600 IU/mL. In some embodiments, the concentration of the one or more cytokine, independently, is at least or at least about 1 IU/mL, 5 IU/mL, 10 IU/mL, 50 IU/mL, 100 IU/mL, 200 IU/mL, 500 IU/mL, 1000 IU/mL or 1500 IU/mL.

In some aspects, the cells are incubated for at least a portion of time after transfer of the engineered cells and culture media. In some embodiments, the stimulating conditions generally include a temperature suitable for the growth of primary immune cells, such as human T lymphocytes, for example, at least about 25 degrees Celsius, generally at least about 30 degrees, and generally at or about 37 degrees Celsius. In some embodiments, the composition of enriched T cells is incubated at a temperature of 25 to 38° C., such as 30 to 37° C., for example at or about 37° C.±2° C. In some embodiments, the incubation is carried out for a time period until the culture, e.g. cultivation or expansion, results in a desired or threshold density, concentration, number or dose of cells. In some embodiments, the incubation is carried out for a time period until the culture, e.g. cultivation or expansion, results in a desired or threshold density, concentration, number or dose of viable cells. In some embodiments, the incubation is greater than or greater than about or is for about or 24 hours, 48 hours, 72 hours, 96 hours, 5 days, 6 days, 7 days, 8 days, 9 days or more.

In some embodiments, the cells are incubated under conditions to maintain a target amount of carbon dioxide in the cell culture. In some aspects, this ensures optimal cultivation, expansion and proliferation of the cells during the growth. In some aspects, the amount of carbon dioxide (CO2) is between 10% and 0% (v/v) of said gas, such as between 8% and 2% (v/v) of said gas, for example an amount of or about 5% (v/v) CO2.

In particular embodiments, the cultivation is performed in a closed system. In certain embodiments, the cultivation is performed in a closed system under sterile conditions. In particular embodiments, the cultivation is performed in the same closed system as one or more steps of the provided systems. In some embodiments the composition of enriched T cells is removed from a closed system and placed in and/or connected to a bioreactor for the cultivation. Examples of suitable bioreactors for the cultivation include, but are not limited to, GE Xuri W25, GE Xuri W5, Sartorius BioSTAT RM 20 I50, Finesse SmartRocker Bioreactor Systems, and Pall XRS Bioreactor Systems. In some embodiments, the bioreactor is used to perfuse and/or mix the cells during at least a portion of the cultivation step.

In some embodiments, cells cultivated while enclosed, connected, and/or under control of a bioreactor undergo expansion during the cultivation more rapidly than cells that are cultivated without a bioreactor, e.g., cells that are cultivated under static conditions such as without mixing, rocking, motion, and/or perfusion. In some embodiments, cells cultivated while enclosed, connected, and/or under control of a bioreactor reach or achieve a threshold expansion, cell count, and/or density within 14 days, 10 days, 9 days, 8 days, 7 days, 6 days, 5 days, 4 days, 3 days, 2 days, 60 hours, 48 hours, 36 hours, 24 hours, or 12 hours. In some embodiments, cells cultivated while enclosed, connected, and/or under control of a bioreactor reach or achieve a threshold expansion, cell count, and/or density at least 50%, at least 60%, at least 70%, at least 80%, at least 90%, at least 95%, at least 100%, at least 150%, at least 1-fold, at least 2-fold, at least 3-fold, at least 4-fold, at least 5-fold than cells cultivated in an exemplary and/or alternative process where cells are not cultivated while enclosed, connected, and/or under control of a bioreactor.

In some embodiments, the mixing is or includes rocking and/or motioning. In some embodiments, cells are incubated using containers, e.g., bags, which are used in connection with a bioreactor. In some cases, the bioreactor can be subject to motioning or rocking, which, in some aspects, can increase oxygen transfer. Motioning the bioreactor may include, but is not limited to rotating along a horizontal axis, rotating along a vertical axis, a rocking motion along a tilted or inclined horizontal axis of the bioreactor or any combination thereof. In some embodiments, at least a portion of the incubation is carried out with rocking. The rocking speed and rocking angle may be adjusted to achieve a desired agitation. In some embodiments the rock angle is or is about 20°, 19°, 18°, 17°, 16°, 15°, 14°, 13°, 12°, 11°, 10°, 9°, 8°, 7° 6°, 5°, 4°, 3°, 2° or 1°. In certain embodiments, the rock angle is between 6-16°. In other embodiments, the rock angle is between 7-16°. In other embodiments, the rock angle is between 8-12°. In some embodiments, the rock rate is 1, 2, 3, 4, 5, 6, 7, 8, 9, 10, 11, 1 12, 13, 14 15, 16, 17, 18, 19, 20, 21, 22, 23, 24, 25, 26, 27, 28, 29, 30, 31, 32, 33, 34, 35, 36, 37, 38, 39, 40 rpm. In some embodiments, the rock rate is between 4 and 12 rpm, such as between 4 and 6 rpm, inclusive. At least a portion of the cell culture expansion is performed with a rocking motion, such as at an angle of between 5° and 10°, such as 6°, at a constant rocking speed, such as a speed of between 5 and 15 RPM, such as 6 RMP or 10 RPM.

In some embodiments, a composition comprising cells, such as engineered T cells, e.g. engineered CD4+ T cells or engineered CD8+ T cells, or engineered cells of any phenotype as described herein, is cultivated in the presence of a surfactant. In particular embodiments, cultivating the cells of the composition reduces the amount of shear stress that may occur during the cultivation, e.g., due to mixing, rocking, motion, and/or perfusion. In particular embodiments, the composition of cells, such as engineered T cells, e.g. engineered CD4+ T cells or engineered CD8$^+$ T cells, is cultivated with the surfactant and at least 50%, at least 60%, at least 70%, at least 75%, at least 80%, at least 85%, at least 90%, at least 95%, at least 99%, or at least 99.9% of the T cells survive, e.g., are viable and/or do not undergo necrosis, programed cell death, or apoptosis, during or at least 1 day, 2 days, 3 days, 4 days, 5 days, 6 days, 7 days, or more than 7 days after the cultivation is complete. In particular embodiments, the composition of cells, such as engineered T cells, e.g. engineered CD4$^+$ T cells or engineered CD8$^+$ T cells, is cultivated in the presence of a surfactant and less than 50%, less than 40%, less than 30%, less than 25%, less than 20%, less than 15%, less than 10%, less than 5%, less than 1%, less than 0.1% or less than 0.01% of the cells undergo cell death, e.g., programmed cell death, apoptosis, and/or necrosis, such as due to shearing or shearing-induced stress.

In particular embodiments, a composition of cells, such as engineered T cells, e.g. engineered CD4⁺ T cells or engineered CD8⁺ T cells, is cultivated in the presence of between 0.1 µl/ml and 10.0 µl/ml, between 0.2 µl/ml and 2.5 µl/ml, between 0.5 µl/ml and 5 µl/ml, between 1 µl/ml and 3 µl/ml, or between 2 µl/ml and 4 µl/ml of the surfactant. In some embodiments, the composition of cells, such as engineered T cells, e.g. engineered CD4⁺ T cells or engineered CD8⁺ T cells, is cultivated in the presence of, of about, or at least 0.1 µl/ml, 0.2 µl/ml, 0.4 µl/ml, 0.6 µl/ml, 0.8 µl/ml, 1 µl/ml, 1.5 µl/ml, 2.0 µl/ml, 2.5 µl/ml, 5.0 µl/ml, 10 µl/ml, 25 µl/ml, or 50 µl/ml of the surfactant. In certain embodiments, the composition of cells is cultivated in the presence of or of about 2 µl/ml of the surfactant.

In some embodiments, a surfactant is or includes an agent that reduces the surface tension of liquids and/or solids. For example, a surfactant includes a fatty alcohol (e.g., steryl alcohol), a polyoxyethylene glycol octylphenol ether (e.g., Triton X-100), or a polyoxyethylene glycol sorbitan alkyl ester (e.g., polysorbate 20, 40, 60). In certain embodiments the surfactant is selected from the group consisting of Polysorbate 80 (PS80), polysorbate 20 (PS20), poloxamer 188 (P188). In an exemplary embodiment, the concentration of the surfactant in chemically defined feed media is about 0.0025% to about 0.25% (v/v) of PS80; about 0.0025% to about 0.25% (v/v) of PS20; or about 0.1% to about 5.0% (w/v) of P188.

In some embodiments, the surfactant is or includes an anionic surfactant, a cationic surfactant, a zwitterionic surfactant, or a nonionic surfactant added thereto. Suitable anionic surfactants include but are not limited to alkyl sulfonates, alkyl phosphates, alkyl phosphonates, potassium laurate, triethanolamine stearate, sodium lauryl sulfate, sodium dodecylsulfate, alkyl polyoxyethylene sulfates, sodium alginate, dioctyl sodium sulfosuccinate, phosphatidyl glycerol, phosphatidyl inosine, phosphatidylinositol, diphosphatidylglycerol, phosphatidylserine, phosphatidic acid and their salts, sodium carboxymethylcellulose, cholic acid and other bile acids (e.g., cholic acid, deoxycholic acid, glycocholic acid, taurocholic acid, glycodeoxycholic acid) and salts thereof (e.g., sodium deoxycholate).

In some embodiments, suitable nonionic surfactants include: glyceryl esters, polyoxyethylene fatty alcohol ethers, polyoxyethylene sorbitan fatty acid esters (polysorbates), polyoxyethylene fatty acid esters, sorbitan esters, glycerol monostearate, polyethylene glycols, polypropylene glycols, cetyl alcohol, cetostearyl alcohol, stearyl alcohol, aryl alkyl polyether alcohols, polyoxyethylene-polyoxypropylene copolymers (poloxamers), poloxamines, methylcellulose, hydroxymethyl cellulose, hydroxypropyl cellulose, hydroxypropylmethyl cellulose, noncrystalline cellulose, polysaccharides including starch and starch derivatives such as hydroxyethylstarch (HES), polyvinyl alcohol, and polyvinylpyrrolidone. In certain embodiments, the nonionic surfactant is a polyoxyethylene and polyoxypropylene copolymer and preferably a block copolymer of propylene glycol and ethylene glycol. Such polymers are sold under the tradename POLOXAMER, also sometimes referred to as PLURONIC® F68 or Kolliphor® P188. Among polyoxyethylene fatty acid esters is included those having short alkyl chains. One example of such a surfactant is SOLUTOL® HS 15, polyethylene-660-hydroxystearate.

In some embodiments, suitable cationic surfactants may include, but are not limited to, natural phospholipids, synthetic phospholipids, quaternary ammonium compounds, benzalkonium chloride, cetyltrimethyl ammonium bromide, chitosans, lauryl dimethyl benzyl ammonium chloride, acyl carnitine hydrochlorides, dimethyl dioctadecyl ammomium bromide (DDAB), dioleyoltrimethyl ammonium propane (DOTAP), dimyristoyl trimethyl ammonium propane (DMTAP), dimethyl amino ethane carbamoyl cholesterol (DC—Chol), 1,2-diacylglycero-3-(O-alkyl) phosphocholine, O-alkylphosphatidylcholine, alkyl pyridinium halides, or long-chain alkyl amines such as, for example, n-octylamine and oleylamine.

Zwitterionic surfactants are electrically neutral but possess local positive and negative charges within the same molecule. Suitable zwitterionic surfactants include but are not limited to zwitterionic phospholipids. Suitable phospholipids include phosphatidylcholine, phosphatidylethanolamine, diacyl-glycero-phosphoethanolamine (such as dimyristoyl-glycero-phosphoethanolamine (DMPE), dipalmitoyl-glycero-phosphoethanolamine (DPPE), distearoyl-glycero-phosphoethanolamine (DSPE), and dioleolyl-glycero-phosphoethanolamine (DOPE)). Mixtures of phospholipids that include anionic and zwitterionic phospholipids may be employed in this invention. Such mixtures include but are not limited to lysophospholipids, egg or soybean phospholipid or any combination thereof. The phospholipid, whether anionic, zwitterionic or a mixture of phospholipids, may be salted or desalted, hydrogenated or partially hydrogenated or natural semi-synthetic or synthetic.

In certain embodiments, the surfactant is poloxamer, e.g., poloxamer 188. In some embodiments, a composition of cells is cultivated in the presence of between 0.1 µl/ml and 10.0 µl/ml, between 0.2 µl/ml and 2.5 µl/ml, between 0.5 µl/ml and 5 µl/ml, between 1 µl/ml and 3 µl/ml, or between 2 µl/ml and 4 µl/ml of poloxamer. In some embodiments, the composition of cells is cultivated in the presence of, of about, or at least 0.1 µl/ml, 0.2 µl/ml, 0.4 µl/ml, 0.6 µl/ml, 0.8 µl/ml, 1 µl/ml, 1.5 µl/ml, 2.0 µl/ml, 2.5 µl/ml, 5.0 µl/ml, 10 µl/ml, 25 µl/ml, or 50 µl/ml of the surfactant. In certain embodiments, the composition of cells is cultivated in the presence of or of about 2 µl/ml of poloxamer.

In some aspects, the CD4+ and CD8+ cells are expanded, in some cases each separately expanded or expanded together, until they each reach a threshold amount or cell density. In particular embodiments, the cultivation ends, such as by harvesting cells, when cells achieve a threshold amount, concentration, and/or expansion. In particular embodiments, the cultivation ends when the cell achieve or achieve about or at least a 1.5-fold expansion, a 2-fold expansion, a 2.5-fold expansion, a 3-fold expansion, a 3.5-fold expansion, a 4-fold expansion, a 4.5-fold expansion, a 5-fold expansion, a 6-fold expansion, a 7-fold expansion, a 8-fold expansion, a 9-fold expansion, a 10-fold expansion, or greater than a 10-fold expansion, e.g., with respect and/or in relation to the amount of density of the cells at the start or initiation of the cultivation. In some embodiments, the threshold expansion is a 4-fold expansion, e.g., with respect and/or in relation to the amount of density of the cells at the start or initiation of the cultivation. In some embodiments, the cultivation ends, such as by harvesting cells, when the cells achieve a threshold total amount of cells, e.g., threshold cell count. In some embodiments, the cultivation ends when the cells achieve a threshold total nucleated cell (TNC) count. In some embodiments, the cultivation ends when the cells achieve a threshold viable amount of cells, e.g., threshold viable cell count. In some embodiments, the threshold cell count is or is about or is at least of 50×10⁶ cells, 100×10⁶ cells, 200×10⁶ cells, 300× 10⁶ cells, 400×10⁶ cells, 600×10⁶ cells, 800×10⁶ cells, 1000×10⁶ cells, 1200×10⁶ cells, 1400×10⁶ cells, 1600×10⁶ cells, 1800×106 cells, 2000×106 cells, 2500×106 cells, 3000×106 cells, 4000×106 cells, 5000×106 cells, 10,000×106 cells, 12,000×106 cells, 15,000×106 cells or 20,000×106 cells, or any of the foregoing threshold of viable cells.

In particular embodiments, the cultivation ends when the cells achieve a threshold cell count. In some embodiments, the cultivation ends at, at about, or within 6 hours, 12 hours, 24 hours, 36 hours, 1 day, 2 days, 3 days, 4 days, 5 days, 6 days, or 7 or more days, after the threshold cell count is achieved. In particular embodiments, the cultivation is ended at or about 1 day after the threshold cell count is achieved. In certain embodiments, the threshold density is, is about, or is at least 0.1×106 cells/ml, 0.5×106 cells/ml, 1×106 cells/ml, 1.2×106 cells/ml, 1.5×106 cells/ml, 1.6×106 cells/ml, 1.8×106 cells/ml, 2.0×106 cells/ml, 2.5×106 cells/ml, 3.0×106 cells/ml, 3.5×106 cells/ml, 4.0×106 cells/ml, 4.5×106 cells/ml, 5.0×106 cells/ml, 6×$10^6$ cells/ml, 8×106 cells/ml, or 10×106 cells/ml, or any of the foregoing threshold of viable cells. In particular embodiments, the cultivation ends when the cells achieve a threshold density. In some embodiments, the cultivation ends at, at about, or within 6 hours, 12 hours, 24 hours, 36 hours, 1 day, 2 days, 3 days, 4 days, 5 days, 6 days, or 7 or more days, after the threshold density is achieved. In particular embodiments, the cultivation is ended at or about 1 day after the threshold density is achieved.

In some embodiments, at least a portion of the incubation is carried out under static conditions. In some embodiments, at least a portion of the incubation is carried out with perfusion, such as to perfuse out spent media and perfuse in fresh media during the culture. In some embodiments, the method includes a step of perfusing fresh culture medium into the cell culture, such as through a feed port. In some embodiments, the culture media added during perfusion contains the one or more stimulating agents, e.g. one or more recombinant cytokine, such as IL-2, IL-7 and/or IL-15. In some embodiments, the culture media added during perfusion is the same culture media used during a static incubation.

In some embodiments, subsequent to the incubation, the container, e.g., bag, is re-connected to a system for carrying out the one or more other processing steps of for manufacturing, generating or producing the cell therapy, such as is re-connected to the system containing the centrifugal chamber. In some aspects, cultured cells are transferred from the bag to the internal cavity of the chamber for formulation of the cultured cells.

In some embodiments, the T cells are expanded by adding to a culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

E. Compositions and Formulations

The methods provided herein are capable of producing an output composition of engineered cells (e.g, T cells) with specific phenotypic and functional characteristics. In some embodiments, the output composition can be formulated, for example, to be a therapeutic or pharmaceutical composition or formulation. Thus, also provided are compositions (e.g., output compositions) comprising any of the cells and/or doses of cells, such as unit dose form compositions including the number of cells for administration in a given dose or fraction thereof, including pharmaceutical compositions and formulations. The pharmaceutical compositions and formulations generally include one or more optional pharmaceutically acceptable carrier or excipient. In some embodiments, the dose of cells comprising cells engineered with a recombinant antigen receptor, e.g. CAR or TCR, is provided as a composition or formulation, such as a pharmaceutical composition or formulation. Such compositions can be used in accord with the provided methods, and/or with the provided articles of manufacture or compositions, such as in the prevention or treatment of diseases, conditions, and disorders, or in detection, diagnostic, and prognostic methods. In some embodiments, also provided are any of the unit doses described herein, and/or compositions comprising any of the unit doses of cells described herein. In some embodiments, the composition is an output composition.

In some embodiments, the dose of cells comprising cells engineered with a recombinant antigen receptor, e.g. CAR or TCR, is provided as a composition or formulation, such as a pharmaceutical composition or formulation. Such compositions can be used in accord with adoptive cell therapy methods, including methods for the prevention or treatment of diseases, conditions, and disorders, or in detection, diagnostic, and prognostic methods. In some embodiments, such compositions or formulations can be stored, contained or transferred in the provided biomedical materials vessels, and/or as a component of the provided articles of manufacture.

In some cases, the cells are processed in one or more steps (e.g. carried out in the centrifugal chamber and/or closed system) for manufacturing, generating or producing a cell therapy and/or engineered cells may include formulation of cells, such as formulation of genetically engineered cells resulting from the provided transduction processing steps prior to or after the culturing, e.g. cultivation and expansion, and/or one or more other processing steps as described. In some cases, the cells can be formulated in an amount for dosage administration, such as for a single unit dosage administration or multiple dosage administration. In some embodiments, the provided methods associated with formulation of cells include processing transduced cells, such as cells transduced and/or expanded using the processing steps described above, in a closed system. In some embodiments, the formulated cells can be transferred or introduced into the biomedical material vessels, e.g., vials, provided herein.

In certain embodiments, one or more compositions of cells (e.g., output composition), such as engineered and cultivated T cells, are formulated. In particular embodiments, one or more compositions of cells, such as engineered and cultivated T cells, are formulated after the one or more compositions have been engineered and/or cultivated.

In some embodiments, T cells, such as CD4+ and/or CD8+ T cells, generated by one or more of the processing steps are formulated. In some aspects, a plurality of compositions are separately manufactured, produced or generated, each containing a different population and/or sub-types of cells from the subject, such as for administration separately or independently, optionally within a certain period of time. For example, separate formulations of engineered cells containing different populations or sub-types of cells can include CD8+ and CD4+ T cells, respectively, and/or CD8+− and CD4+-enriched populations, respectively, e.g., CD4+ and/or CD8+ T cells each individually including cells genetically engineered to express the recombinant receptor. In some embodiments, at least one composition is formulated with CD4+ T cells genetically engineered to express the recombinant receptor. In some embodiments, at least one composition is formulated with CD8+ T cells genetically engineered to express the recombinant receptor. In some embodiments, the administration of the dose comprises administration of a first composition comprising a dose of CD8+ T cells or a dose of CD4+ T cells and administration of a second composition comprising the other of the dose of CD4+ T cells and the CD8+ T cells. In some embodiments, a first composition comprising a dose of CD8+ T cells or a dose of CD4+ T cells is administered prior to the second composition comprising the other of the dose of CD4+ T cells and the CD8+ T cells. In some embodiments, the administration of the dose comprises administration of a composition comprising both of a dose of CD8+ T cells and a dose of CD4+ T cells.

In some embodiments, cells (such as engineered cells) are enriched or sorted, e.g., at or near the end of the production process prior to formulation based on surface expression of one or more markers of the desired phenotype, such as CCR7 or CD27 expression, for example, to ensure at least a particular percentage (such as at least at or about, or at or about, 80%, 85%, 90%, 91%, 92%, 93%, 94%, 95%, 96%, 97%, 98%, 99% or 100%) or number of cells (or subset thereof) in the administered therapeutic composition are positive for such marker.

In certain embodiments, the one or more compositions of cells (e.g., output composition), such as engineered and cultivated T cells, are or include two separate compositions, e.g., separate engineered and/or cultivated compositions, of cells. In particular embodiments, two separate compositions of cells, e.g., two separate compositions of CD4+ T cells and CD8+ T cells selected, isolated, and/or enriched from the same biological sample, separately engineered and separately cultivated, are separately formulated. In certain embodiments, the two separate compositions include a composition of CD4+ T cells, such as a composition of engineered and/or cultivated CD4+ T cells. In particular embodiments, the two separate compositions include a composition of CD8+ T cells, such as a composition of engineered and/or cultivated CD8+ T cells. In some embodiments, two separate compositions of CD4+ T cells and CD8+ T cells, such as separate compositions of engineered and cultivated CD4+ T cells and engineered and cultivated CD8+ T cells, are separately formulated. In some embodiments, a single composition of cells is formulated. In certain embodiments, the single composition is a composition of CD4+ T cells, such as a composition of engineered and/or cultivated CD4+ T cells. In some embodiments, the single composition is a composition of CD4+ and CD8+ T cells that have been combined from separate compositions prior to the formulation.

In some embodiments, separate compositions of CD4+ and CD8+ T cells, such as separate compositions of engineered and cultivated CD4+ and CD8+ T cells (e.g., output compositions) are combined into a single composition and are formulated. In certain embodiments, separate formulated compositions of CD4+ and CD8+ T cells are combined into a single composition after the formulation has been performed and/or completed. In particular embodiments, separate compositions of CD4+ and CD8+ T cells, such as separate compositions of engineered and cultivated CD4+ and CD8+ T cells, are separately formulated as separate compositions.

In some embodiments, cells can be formulated into a container, such as a vial, such as any vial in the biomedical materials vessels provided herein. In some embodiments, the cells are formulated between 0 days and 10 days, between 0 and 5 days, between 2 days and 7 days, between 0.5 days, and 4 days, or between 1 day and 3 days after the cells after the threshold cell count, density, and/or expansion has been achieved during the cultivation. In certain embodiments, the cells are formulated at or at or about or within 12 hours, 18 hours, 24 hours, 1 day, 2 days, or 3 days after the threshold cell count, density, and/or expansion has been achieved during the cultivation. In some embodiments, the cells are formulated within or within about 1 day after the threshold cell count, density, and/or expansion has been achieved during the cultivation.

In some embodiments, the cells are formulated in a pharmaceutically acceptable buffer, which may, in some aspects, include a pharmaceutically acceptable carrier or excipient. In some embodiments, the processing includes exchange of a medium into a medium or formulation buffer that is pharmaceutically acceptable or desired for administration to a subject. In some embodiments, the processing steps can involve washing the transduced and/or expanded cells to replace the cells in a pharmaceutically acceptable buffer that can include one or more optional pharmaceutically acceptable carriers or excipients. Exemplary of such pharmaceutical forms, including pharmaceutically acceptable carriers or excipients, can be any described below in conjunction with forms acceptable for administering the cells and compositions to a subject. The pharmaceutical composition in some embodiments contains the cells in amounts effective to treat or prevent the disease or condition, such as a therapeutically effective or prophylactically effective amount.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the cells, preferably those with activities complementary to the cells, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine. In some embodiments, the agents or cells are administered in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

Compositions in some embodiments are provided as sterile liquid preparations, e.g., isotonic aqueous solutions, suspensions, emulsions, dispersions, or viscous compositions, which may in some aspects be buffered to a selected pH. Liquid compositions can comprise carriers, which can be a solvent or dispersing medium containing, for example, water, saline, phosphate buffered saline, polyol (for example, glycerol, propylene glycol, liquid polyethylene glycol) and suitable mixtures thereof. Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

In some embodiments, the formulation buffer contains a cryopreservative. In some embodiments, the cell are formulated with a cyropreservative solution that contains 1.0% to 30% DMSO solution, such as a 5% to 20% DMSO solution or a 5% to 10% DMSO solution. In some embodiments, the cryopreservation solution is or contains, for example, PBS containing 20% DMSO and 8% human serum albumin (HSA), or other suitable cell freezing media. In some embodiments, the cryopreservative solution is or contains, for example, at least or about 7.5% DMSO. In some embodiments, the processing steps can involve washing the transduced and/or expanded cells to replace the cells in a cryopreservative solution. In some embodiments, the cells are frozen, e.g., cryopreserved or cryoprotected, in media and/or solution with a final concentration of or of about 12.5%, 12.0%, 11.5%, 11.0%, 10.5%, 10.0%, 9.5%, 9.0%, 8.5%, 8.0%, 7.5%, 7.0%, 6.5%, 6.0%, 5.5%, or 5.0% DMSO, or between 1% and 15%, between 6% and 12%, between 5% and 10%, or between 6% and 8% DMSO. In particular embodiments, the cells are frozen, e.g., cryopreserved or cryoprotected, in media and/or solution with a final concentration of or of about 5.0%, 4.5%, 4.0%, 3.5%, 3.0%, 2.5%, 2.0%, 1.5%, 1.25%, 1.0%, 0.75%, 0.5%, or 0.25% HSA, or between 0.1% and 5%, between 0.25% and 4%, between 0.5% and 2%, or between 1% and 2% HSA.

In particular embodiments, the composition of enriched T cells, e.g., T cells that have been stimulated, engineered, and/or cultivated, are formulated, cryopreserved, and then stored for an amount of time, for example, in the provided biomedical materials vessel. In certain embodiments, the formulated, cryopreserved cells are stored until the cells are released for infusion. In particular embodiments, the formulated cryopreserved cells are stored for between 1 day and 6 months, between 1 month and 3 months, between 1 day and 14 days, between 1 day and 7 days, between 3 days and 6 days, between 6 months and 12 months, or longer than 12 months. In some embodiments, the cells are cryopreserved and stored for, for about, or for less than 1 days, 2 days, 3 days, 4 days, 5 days, 6 days, or 7 days. In certain embodiments, the cells are thawed and administered to a subject after the storage. In certain embodiments, the cells are stored for or for about 5 days.

In some embodiments, the formulation is carried out using one or more processing step including washing, diluting or concentrating the cells, such as the cultured or expanded cells. In some embodiments, the processing can include dilution or concentration of the cells to a desired concentration or number, such as unit dose form compositions including the number of cells for administration in a given dose or fraction thereof. In some embodiments, the processing steps can include a volume-reduction to thereby increase the concentration of cells as desired. In some embodiments, the processing steps can include a volume-addition to thereby decrease the concentration of cells as desired. In some embodiments, the processing includes adding a volume of a formulation buffer to transduced and/or expanded cells. In some embodiments, the volume of formulation buffer is from 10 mL to 1000 mL or from about 10 mL to about 1000 mL, such as at least or about at least or about 50 mL, 100 mL, 200 mL, 300 mL, 400 mL, 500 mL, 600 mL, 700 mL, 800 mL, 900 mL or 1000 mL.

In some embodiments, the cells are cultured, such as stimulated engineered and/or cultivated in a container, e.g., bag or a centrifugal chamber. In some aspects, the container is a first container and the cultured cells are expressed or transferred from the first container, e.g. bag or centrifugal chamber, to a second container, such as biomedical material vessels, that is operably linked to the first container. In some embodiments, the biomedical material vessels are configured for integration and or operable connection and/or is integrated or operably connected, to the first container, e.g. bag or centrifugal chamber, used for one or more of the previous processing steps. In some embodiments, the biomedical material vessel is connected to the first container, e.g. bag or centrifugal chamber, at an output line or output position. In some cases, the first container, e.g. bag or centrifugal chamber, is connected to the vial of the biomedical material vessel at the inlet tube.

In some embodiments, such processing steps for formulating a cell composition is carried out in a closed system. Exemplary of such processing steps can be performed using a centrifugal chamber in conjunction with one or more systems or kits associated with a cell processing system, such as a centrifugal chamber produced and sold by Biosafe SA, including those for use with the Sepax® or Sepax 2® cell processing systems. An exemplary system and process is described in International Publication Number WO2016/073602. In some embodiments, the method includes effecting expression or transfer from the internal cavity of the centrifugal chamber a formulated composition, which is the resulting composition of cells formulated in a formulation buffer, such as pharmaceutically acceptable buffer, in any of the above embodiments as described. In some embodiments, the expression or transfer of the formulated composition is to a container, such as vials of the biomedical material vessels described herein, that is operably linked as part of a closed system with the centrifugal chamber. In some embodiments, the biomedical material vessels are configured for integration and or operable connection and/or is integrated or operably connected, to a closed system or device that carries out one or more processing steps. In some embodiments, the biomedical material vessel is connected to a system at an output line or output position. In some cases, the closed system is connected to the vial of the biomedical material vessel at the inlet tube. Exemplary closed systems for use with the biomedical material vessels described herein include the Sepax® and Sepax® 2 system.

In some embodiments, the composition can be transferred from the first container, such as a centrifugal chamber or cell processing system, to the provided biomedical material vessels via a multi-port output kit containing a multi-way tubing manifold associated at each end of a tubing line with a port to which one or a plurality of containers, e.g. biomedical material vessels, can be connected for expression of the formulated composition. In some aspects, a desired number or plurality of such vials, can be sterilely connected to one or more, generally two or more, such as at least 3, 4, 5, 6, 7, 8 or more of the ports of the multi-port output. For example, in some embodiments, one or more containers, e.g., biomedical material vessels, can be attached to the ports, or to fewer than all of the ports. Thus, in some embodiments, the system can effect expression of the output composition into a plurality of vials of the biomedical material vessels.

In some aspects, cells can be expressed or transferred to the one or more of the plurality of output containers, e.g., vials of the biomedical material vessels, in an amount for dosage administration, such as for a single unit dosage administration or multiple dosage administration. For example, in some embodiments, the vials of the biomedical material vessels, may each contain the number of cells for administration in a given dose or fraction thereof. Thus, each vial, in some aspects, may contain a single unit dose for administration or may contain a fraction of a desired dose such that more than one of the plurality of vials, such as two of the vials, or 3 of the vials, together constitute a dose for administration.

Thus, the vials in the biomedical materials vessels described herein, generally contain the cells to be administered, e.g., one or more unit doses thereof. The unit dose may be an amount or number of the cells to be administered to the subject or twice the number (or more) of the cells to be administered. It may be the lowest dose or lowest possible dose of the cells that would be administered to the subject.

In some embodiments, each of the vials individually comprises a unit dose of the cells. Thus in some embodiments, each of the containers comprises the same or approximately or substantially the same number of cells. In some embodiments, each unit dose contains at least or about at least $1\times10^6$, $2\times10^6$, $5\times10^6$, $1\times10^7$, $5\times10^7$, $1\times10^8$, $2.5\times10^8$, or $5\times10^8$ engineered cells, total cells, T cells, or PBMCs. In some embodiments, each unit dose contains at least at or about $2.5\times10^7$, at or about $5.0\times10^7$, at or about $1.5\times10^8$, at or about $3.0\times10^8$, at or about $4.5\times10^8$, at or about $8.0\times10^8$ or at or about $1.2\times10^9$ engineered cells, total cells, T cells, or PBMCs. In some embodiments, each unit dose contains no more than at or about $2.5\times10^7$, at or about $5.0\times10^7$, at or about $1.5\times10^8$, at or about $3.0\times10^8$, at or about $4.5\times10^8$, at or about $8.0\times10^8$ or at or about $1.2\times10^9$ engineered cells, total cells, T cells, or PBMCs. In some aspects, exemplary dose of cells that can be contained in the vials include any doses described herein, e.g., in Section IV. In some aspects, exemplary dose of cells that can be administered to a subject include any doses described herein, e.g., in Section IV.

In some embodiments, the volume of the formulated cell composition in each container is 10 mL to 100 mL, such as at least or about at least or about 20 mL, 30 mL, 40 mL, 50 mL, 60 mL, 70 mL, 80 mL, 90 mL or 100 mL. In some embodiments, the cells in the vials can be cryopreserved. In some embodiments, the vials can be stored in liquid nitrogen until further use.

In some embodiments, such cells produced by the method, or a composition comprising such cells, are administered to a subject for treating a disease or condition. The pharmaceutical composition in some embodiments contains agents or cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

The agents or cells can be administered by any suitable means, for example, by bolus infusion, by injection, e.g., intravenous or subcutaneous injections, intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration. In some embodiments, a given dose is administered by a single bolus administration of the cells or agent. In some embodiments, it is administered by multiple bolus administrations of the cells or agent, for example, over a period of no more than 3 days, or by continuous infusion administration of the cells or agent.

For the prevention or treatment of disease, the appropriate dosage may depend on the type of disease to be treated, the type of agent or agents, the type of cells or recombinant receptors, the severity and course of the disease, whether the agent or cells are administered for preventive or therapeutic purposes, previous therapy, the subject's clinical history and response to the agent or the cells, and the discretion of the attending physician. The compositions are in some embodiments suitably administered to the subject at one time or over a series of treatments.

The cells or agents may be administered using standard administration techniques, formulations, and/or devices. Provided are formulations and devices, such as syringes and vials, for storage and administration of the compositions. With respect to cells, administration can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell or an agent that treats or ameliorates symptoms of neurotoxicity), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the agent or cell populations are administered parenterally. The term "parenteral," as used herein, includes intravenous, intramuscular, subcutaneous, rectal, vaginal, and intraperitoneal administration. In some embodiments, the agent or cell populations are administered to a subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the agent or cells in a solvent, such as in admixture with a suitable carrier, diluent, or excipient such as sterile water, physiological saline, glucose, dextrose, or the like.

The formulations to be used for in vivo administration are generally sterile. Sterility may be readily accomplished, e.g., by filtration through sterile filtration membranes.

1. Features of the Output Composition

Among the provided embodiments are methods of producing a cell composition containing genetically engineered cell, such as an output composition. In some aspects, the output composition can be generated upon genetic engineering of an input composition, such as any described herein. In certain embodiments, the methods provided herein include one or more steps for genetically engineering cells from an input composition to generate an output cell composition that contains engineered cells having a particular properties, features and/or characteristics, such as cell phenotypes, e.g., the presence and/or expression of a surface marker, and/or the absence or lack of expression of a surface marker, of the cells in the composition for administration. In some aspects, cells in the output composition include cells that express, e.g., express on the surface of the cell, or do not express, one or more markers associated with certain cell phenotypes, including markers associated or indicative of a less differentiated cell phenotype and/or markers associated with or indicative of a memory cell subtype. In some aspects, cells in the output composition include cells that produce, e.g., i nresponse to stimulation as described herein, one or more cytokine, including cytokines associated or indicative of a less differentiated cell phenotype and/or cytokines associated with or indicative of a memory cell subtype. In some embodiments, the methods provided herein generate an output composition useful for the treatment of disease. In some embodiments, the output composition, or formulation, therapeutic composition, or pharmaceutical composition formulated therefrom, is correlated with progression free survival and/or durable response. In some embodiments, the output composition, or formulation, therapeutic composition, or pharmaceutical composition formulated therefrom, is correlated with progression free survival and/or durable response in patients with high and/or low disease burden, such as described herein.

In certain embodiments, the methods provided herein include one or more steps for genetically engineering cells from a starting and/or input composition to generate a resulting and/or an output cell composition having a defined ratio of recombinant receptor-expressing (receptor$^+$) CD8$^+$ T cells that express or do not express CCR7, CD27 and/or CD45RA to receptor$^+$/CD4$^+$ T cells that express or do not express CCR7, CD27 and/or CD45RA and/or a defined ratio of receptor$^+$/CD8$^+$ T cells that express or do not express CCR7, CD27 and/or CD45RA and/or receptor$^+$/CD4$^+$ T cells that express or do not express CCR7, CD27 and/or CD45RA to another subset of cells in the composition.

In certain embodiments, the methods provided herein include one or more steps for genetically engineering cells from a starting and/or input composition to generate a resulting an/or an output cell composition having a percentage of cells, e.g., CD4+ cells, that produce a IL-2, TNF-alpha, or IFN-gamma.

In particular embodiments, the content, make-up, and/or constitution of the input composition correlates, controls, corresponds, and/or associates with the content, make-up, and/or constitution of the output cell composition. In certain embodiments, the amount, portion, percentage, number, number per volume, number per weight, and/or ratio of cells expressing one or more markers associated with certain cell phenotypes, including markers associated or indicative of a less differentiated cell phenotype and/or markers associated with or indicative of a memory cell subtype, in an input composition correlates, controls, corresponds, and/or associates with the with the content, make-up, and/or constitution of the output cell composition. In particular embodiments, the amount, portion, number, number per volume, number per weight, and/or ratio of CD4$^+$ T cells and/or CD8$^+$ T cells expressing one or more markers associated with certain cell phenotypes, including markers associated or indicative of a less differentiated cell phenotype and/or markers associated with or indicative of a memory cell subtype in an input composition correlates, controls, corresponds, and/or associates with the with the content, make-up, and/or constitution of the output cell composition. In some aspects, the expression or absence of expression of one or more of CCR7, CD27 and/or CD45RA of cells in the input composition is correlated with the expression or absence of expression of one or more of CCR7, CD27 and/or CD45RA of cells in the output composition, e.g., after genetic engineering to express the recombinant receptor. Thus, in some aspects, the number, frequency and/or percentage of cells in the input composition that express or do not express one or more of CCR7, CD27 and/or CD45RA is associated with, correlated to and/or indicative of, the number, frequency and/or percentage of recombinant receptor-expressing engineered cells in the output composition that express or do not express one or more of CCR7, CD27 and/or CD45RA. In some aspects, the absence of expression of an apoptotic marker (e.g., activated caspase 3 or annexin V) in the cells of the input composition is correlated with progression free survival and/or durable response following administration of the output composition (e.g., formulation, therapeutic composition, pharmaceutical composition, such as administered in one or more unit doses, as described herein). Thus, in some aspects, the number, frequency and/or percentage of cells in the input composition that do not express an apoptotic marker (e.g., activated caspase 3, annexin V) is associated with, correlated with an output composition useful treating disease.

In some aspects, the output composition includes a defined ratio of recombinant receptor-expressing (receptor$^+$) CD8$^+$ T cells that express or do not express CCR7, CD27 and/or CD45RA to receptor$^+$/CD4$^+$ T cells that express or do not express CCR7, CD27 and/or CD45RA and/or a defined ratio of receptor$^+$/CD8$^+$ T cells that express or do not express CCR7, CD27 and/or CD45RA and/or receptor$^+$/CD4$^+$ T cells that express or do not express CCR7, CD27 and/or CD45RA to another subset of cells in the composition.

In some embodiments, the output composition comprises a defined ratio of receptor$^+$/CD8$^+$/CCR7$^+$, receptor$^+$/CD8$^+$/CD27$^+$, receptor$^+$/CD8$^+$/CCR7$^+$/CD27$^+$, receptor$^+$/CD8$^+$/CCR7$^+$/CD45RA$^-$ and/or receptor$^+$/CD8$^+$/CCR7$^+$/CD45RA$^+$ cells, to receptor$^+$/CD4$^+$/CCR7$^+$, receptor$^+$/CD4$^+$/CD27$^+$, receptor$^+$/CD4$^+$/CCR7$^+$/CD27$^+$, receptor$^+$/CD4$^+$/CCR7$^+$/CD45RA$^-$ and/or receptor$^+$/CD4$^+$/CCR7$^+$/CD45RA$^+$ cells; or a defined ratio of receptor$^+$/CD8$^+$/CCR7$^+$, receptor$^+$/CD8$^+$/CD27$^+$, receptor$^+$/CD8$^+$/CCR7$^+$/CD27$^+$, receptor$^+$/CD8$^+$/CCR7$^+$/CD45RA$^-$ and/or receptor$^+$/CD8$^+$/CCR7$^+$/CD45RA$^+$ cells and/or receptor$^+$/CD4$^+$/CCR7$^+$, receptor$^+$/CD4$^+$/CD27$^+$, receptor$^+$/CD4$^+$/CCR7$^+$/CD27$^+$, receptor$^+$/CD4$^+$/CCR7$^+$/CD45RA$^-$ and/or receptor$^+$/CD4$^+$/CCR7$^+$/CD45RA$^+$ cells to another subset of cells in the composition. In some embodiments, the output composition comprises cells that do not express markers of apoptosis (e.g., caspase 3, annexin V).

In some embodiments, the defined ratio of receptor$^+$/CD8$^+$/CCR7$^+$, receptor$^+$/CD8$^+$/CD27$^+$, receptor$^+$/CD8$^+$/CCR7$^+$/CD27$^+$, receptor$^+$/CD8$^+$/CCR7$^+$/CD45RA$^-$ and/or receptor$^+$/CD8$^+$/CCR7$^+$/CD45RA$^+$ cells, to receptor$^+$/CD4$^+$/CCR7$^+$, receptor$^+$/CD4$^+$/CD27$^+$, receptor$^+$/CD4$^+$/CCR7$^+$/CD27$^+$, receptor$^+$/CD4$^+$/CCR7$^+$/CD45RA$^-$ and/or receptor$^+$/CD4$^+$/CCR7$^+$/CD45RA$^+$ cells include approximately 1:1 or approximately between 1:3 and 3:1 or approximately between 1:2 and 2:1, receptor$^+$/CD8$^+$/CCR7$^+$: receptor$^+$/CD4$^+$/CCR7$^+$; receptor$^+$/CD8$^+$/CD27$^+$: receptor$^+$/CD4$^+$/CD27$^+$; receptor$^+$/CD8$^+$/CCR7$^+$/CD27$^+$: receptor$^+$/CD4$^+$/CCR7$^+$/CD27$^+$; receptor$^+$/CD8$^+$/CCR7$^+$/CD45RA$^-$: receptor$^+$/CD4$^+$/CCR7$^+$/CD45RA$^-$ cells and/or receptor$^+$/CD8$^+$/CCR7$^+$/CD45RA$^+$: receptor$^+$/CD4$^+$/CCR7$^+$/CD45RA$^+$ cells. In some embodiments, the define ratio of cells does not comprise cells that express markers of apoptosis (e.g., caspase 3, annexin V).

In some embodiments, the defined ratio of receptor$^+$/CD8$^+$/CCR7$^+$, receptor$^+$/CD8$^+$/CD27$^+$, receptor$^+$/CD8$^+$/CCR7$^+$/CD27$^+$, receptor$^+$/CD8$^+$/CCR7$^+$/CD45RA$^-$ and/or receptor$^+$/CD8$^+$/CCR7$^+$/CD45RA$^+$ cells and/or receptor$^+$/CD4$^+$/CCR7$^+$, receptor$^+$/CD4$^+$/CD27$^+$, receptor$^+$/CD4$^+$/CCR7$^+$/CD27$^+$, receptor$^+$/CD4$^+$/CCR7$^+$/CD45RA$^-$ and/or receptor$^+$/CD4$^+$/CCR7$^+$/CD45RA$^+$ cells to another subset of cells in the composition includes at least 15%, 20%, 30%, 40%, 50%, 60%, 70%, 80% or 90% of the total cells in the input composition, or between about 15% and 90%, between about 20% and 80%, between about 30% and 70%, or between about 40% and 60%, each inclusive, of the total receptor-expressing cells (receptor$^+$ cells) in the output composition being receptor$^+$/CD8$^+$/CCR7$^+$, receptor$^+$/CD8$^+$/CD27$^+$, receptor$^+$/CD8$^+$/CCR7$^+$/CD27$^+$, receptor$^+$/CD8$^+$/CCR7$^+$/CD45RA$^-$ and/or receptor$^+$/CD8$^+$/CCR7$^+$/CD45RA$^+$ cells and/or receptor$^+$/CD4$^+$/CCR7$^+$, receptor$^+$/CD4$^+$/CD27$^+$, receptor$^+$/CD4$^+$/CCR7$^+$/CD27$^+$, receptor$^+$/CD4$^+$/CCR7$^+$/CD45RA$^-$ and/or receptor$^+$/CD4$^+$/CCR7$^+$/CD45RA$^+$. In some embodiments, the defined ratio of receptor$^+$/CD8$^+$/CCR7$^+$, receptor$^+$/CD8$^+$/CD27$^+$ and/or receptor$^+$/CD8$^+$/CCR7$^+$/CD27$^+$, and/or receptor$^+$/CD4$^+$/CCR7$^+$, receptor$^+$/CD4$^+$/CD27$^+$ and/or receptor$^+$/CD4$^+$/CCR7$^+$/CD27$^+$ to another subset of cells in the composition includes at least 15%, 20%, 30%, 40%, 50%, 60%, 70%, 80% or 90% of the total cells in the input composition, or between about 15% and 90%, between about 20% and 80%, between about 30% and 70%, or between about 40% and 60%, each inclusive, of the total receptor-expressing cells (receptor$^+$ cells) in the output composition being receptor$^+$/CD8$^+$/CCR7$^+$, receptor$^+$/CD8$^+$/CD27$^+$ and/or receptor$^+$/CD8$^+$/CCR7$^+$/CD27$^+$, and/or receptor$^+$/CD4$^+$/CCR7$^+$, receptor$^+$/CD4$^+$/CD27$^+$ and/or receptor$^+$/CD4$^+$/CCR7$^+$/CD27$^+$.

In some embodiments, the output composition includes at least at or about, or at or about, 75%, 80%, 85%, 90%, 95%, 96%, 97%, 98%, or 99% of the total number of engineered cells (e.g., T cells) in the composition or of the total number of engineered cells (e.g., T cells) in the composition expressing the recombinant receptor, negative for markers of apoptosis (e.g., caspase-3, annexin V). In some embodiments, the marker of apoptosis is activated caspase 3. In some embodiments, the marker of apoptosis is annexin V.

In some embodiments, the output composition includes cell, e.g., T cells, such as engineered T cells, capable of producing one or more cytokines are IL-2, IFN-gamma, and/or TNF-alpha. In some embodiments, the output composition includes CD4$^+$/CAR$^+$ cells capable of producing of IL-2. In some embodiments, the output composition includes CD4$^+$/CAR$^+$ cells capable of producing of TNF-alpha. In some embodiments, the output composition includes CD4+/CAR+ cells capable of producing of IL-2, TNF-alpha, and IFN-gamma. In some embodiments, the output composition includes CD4+/CAR+ cells capable of producing of IL-2 and TNF-alpha. In some embodiments, the output composition includes CD4+/CAR+ cells capable of producing of IL-2 and IFN-gamma. In some embodiments, the output composition includes CD8+/CAR+ cells capable of producing of TNF-alpha. In some embodiments, the output composition includes CD8+/CAR+ cells capable of producing of TNF-alpha and IFN-gamma. In some embodiments, the output composition includes at least at or about, or at or about, 70%, 80%, 85%, 90%, 91%, 92%, 93%, 94%, 95%, 96%, 97%, 98%, 99% or 100% of the total number of CD4+ T cells, such as engineered CD4 T cells expressing a recombinant receptor (e.g., CAR), capable of producing a cytokine selected from interleukin 2 (IL-2) and/or TNF-alpha. In some embodiments, the output composition includes at least at or about, or at or about, 10%, 15%, 20%, 25%, 30%, 40% or more, of the total number of CD4+ T cells, such as engineered CD4 T cells expressing a recombinant receptor (e.g., CAR) that are polyfunctional for producing two or more cytokines selected from among interferon-gamma (IFN-gamma), interleukin 2 (IL-2) and TNF-alpha.

In particular embodiments, the methods provided herein produce or generate a composition of cells that contain genetically engineered cells, e.g., an output cell composition. In certain embodiments, an output cell composition is a cell composition that results from some or all of the steps for genetically engineering cells. In certain embodiments, the output cell composition results from a process of genetically engineering cells of an input cell composition. In certain embodiments, process contains one or more steps for activating, transducing or transfecting, expanding, and/or harvesting cells, such as cells that were obtained from an input cell composition. In certain embodiments, the output cell composition contains cells that have been genetically engineered. In particular embodiments, the cells of the output cell composition have undergone all of the steps for a process of genetic engineering.

In some embodiments, the output cell composition contains cells that include one or more nucleic acids introduced via genetic engineering, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

In some embodiments, the output cell composition contains cells that have been genetically engineered. In particular embodiments, the output cell composition contains engineered T cells. In some embodiments, the engineered T cells include engineered CD4+ T cells and engineered CD8+ T cells. In particular embodiments, the output cell composition contains or includes at least 25%, at least 30%, at least 40%, at least 50%, at least 60%, at least 70%, at least 75%, at least 80%, at least 85%, at least 90%, at least 95%, at least 96%, at least 97%, at least 98%, at least 99%, at least 99.5%, at least 99.9%, or 100% or about 100% engineered T cells. In certain embodiments, the engineered cells express a recombinant receptor. In particular embodiments, the output cell composition contains or includes at least 25%, at least 30%, at least 40%, at least 50%, at least 60%, at least 70%, at least 75%, at least 80%, at least 85%, at least 90%, at least 95%, at least 96%, at least 97%, at least 98%, at least 99%, at least 99.5%, at least 99.9%, or 100% or about 100% T cells that express a recombinant receptor. In some embodiments, the recombinant receptor is a TCR or a CAR. In particular embodiments, the recombinant receptor is a CAR.

In some aspects, the method further involves determining one or more unit doses of a T cell composition for administration to a subject having a disease or conditions, wherein the unit dose comprises all or a portion of the output composition. In some aspects, all or a portion of the output composition can be used as a unit dose for administration to a subject. In some aspects, the methods also include selecting all or a portion of the output composition, and optionally combining with another solution to achieve a unit dose of the T cell composition for administration. In some aspects, the provided embodiments, involve determining one or more unit doses of a cell composition and/or a volume corresponding to such unit doses, such that the unit dose can be contained in the article of manufacture described herein and/or administered to a subject, e.g., for therapeutic purposes. In some aspects, unit dose is based upon number of biologically active engineered T cells having a particular phenotype, and/or, where dose is based upon total numbers of biologically active engineered T cells having a particular phenotype. In some aspects, the unit dose can be any unit dose described herein, e.g., in Section I. In some embodiments, the unit dose comprises all or a portion of the output composition that comprises: a defined number of recombinant receptor-expressing CD8+ T cells that express C—C chemokine receptor type 7 (CCR7) (receptor+/CD8+/CCR7+ cells) and/or a defined number of recombinant receptor-expressing CD4+ T cells that express CCR7 (receptor+/CD4+/CCR7+ cells) and/or a defined ratio of receptor+/CD8+/CCR7+ cells to receptor+/CD4+/CCR7+ cells and/or a defined ratio of receptor+/CD8+/CCR7+ cells and/or receptor+/CD4+/CCR7+ cells to another subset of cells in the composition; a defined number of recombinant receptor-expressing CD8+ T cells that express cluster of differentiation 27 (CD27) (receptor+/CD8+/CD27+ cells) and/or a defined number of recombinant receptor-expressing CD4+ T cells that express CD27 (receptor+/CD4+/CD27+ cells) and/or a defined ratio of receptor+/CD8+/CD27+ cells to receptor+/CD4+/CD27+ cells and/or a defined ratio of receptor+/CD8+/CD27+ cells and/or receptor+/CD4+/CD27+ cells to another subset of cells in the composition; or a defined number of recombinant receptor-expressing CD8+ T cells that express CCR7 and CD27 (receptor+/CD8+/CCR7+/CD27+ cells) and/or a defined number of recombinant receptor-expressing CD4+ T cells that express CCR7 and CD27 (receptor+/CD4+/CCR7+/CD27+ cells) and/or a defined ratio of receptor+/CD8+/CCR7+/CD27+ cells to receptor+/CD4+/CCR7+/CD27+ cells and/or a defined ratio of receptor+/CD8+/CCR7+/CD27+ cells and/or receptor+/CD4+/CCR7+/CD27+ cells to another subset of cells in the composition.

In some embodiments, the output composition is assessed to determine the phenotype(s) (e.g., surface markers, apoptotic markers, cytokine production) of the cells contained in the output composition and the percentage of such phenotypes in the output compostions. In some embodiments, the output compositions for therapeutic use are selected based on one or more percentages of cells with specific phenotypes of interest. In some embodiments, the output composition selected for use as a therapeutic agent has or includes one or more percentages of cells with specific phenotypes (e.g., surface markers, apoptotic markers, cytokine production) according to one or more of the percentages and phenotypes described herein. In some embodiments, if the output composition does not comprise the one or more target percentages of one or more phenotypes described herein, e.g., percentage of specific phenotypes described herein, the output composition may undergo a selection process to select, isolate or enrich the output composition such that the target percentages of phenotypes are attained. In some embodiments, if the output composition cannot undergo further processing to attain the target percentage of one or more phenotypes described herein, the output composition is not used as a therapeutic composition.

In some embodiments, the output composition is crypreserved according to any of the methods for cryopreservation known or described herein.

III. ENGINEERED CELLS EXPRESSING RECOMBINANT RECEPTORS

In some embodiments, the provided methods and articles of manufacture relate to engineered cells, such as immune cells, such as T cells, that express a recombinant receptor. In some aspects, the provided methods involve administering engineered T cells, such as CD3$^+$ T cells, CD4$^+$ T cells and/or CD8$^+$ T cells, that are genetically engineered to express a recombinant receptor, e.g., a chimeric antigen receptor (CAR), including administering compositions of such cells in which a certain or defined percentage or number of cells of a particular phenotype are administered as described herein (e.g. CCR7$^+$ or CD27). In some aspects, the recombinant receptors of the engineered cells can bind and/or target antigens associated with a disease or condition.

A. Recombinant Receptors

Among the receptors are antigen receptors and receptors containing one or more component thereof. The recombinant receptors may include chimeric receptors, such as those containing ligand-binding domains or binding fragments thereof and intracellular signaling domains or regions, functional non-TCR antigen receptors, chimeric antigen receptors (CARs), and T cell receptors (TCRs), such as recombinant or transgenic TCRs, chimeric autoantibody receptor (CAAR) and components of any of the foregoing. The recombinant receptor, such as a CAR, generally includes the extracellular antigen (or ligand) binding domain linked to one or more intracellular signaling components, in some aspects via linkers and/or transmembrane domain(s).

1. Chimeric Antigen Receptors (CARs)

In some embodiments, engineered cells, such as T cells, are provided that express a CAR with specificity for a particular antigen (or marker or ligand), such as an antigen expressed on the surface of a particular cell type. In some embodiments, the antigen is a polypeptide. In some embodiments, it is a carbohydrate or other molecule. In some embodiments, the antigen is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

In particular embodiments, the recombinant receptor, such as chimeric receptor, contains an intracellular signaling region, which includes a cytoplasmic signaling domain or region (also interchangeably called an intracellular signaling domain or region), such as a cytoplasmic (intracellular) region capable of inducing a primary activation signal in a T cell, for example, a cytoplasmic signaling domain or region of a T cell receptor (TCR) component (e.g. a cytoplasmic signaling domain or region of a zeta chain of a CD3-zeta (CD3ζ) chain or a functional variant or signaling portion thereof) and/or that comprises an immunoreceptor tyrosine-based activation motif (ITAM).

In some embodiments, the chimeric receptor further contains an extracellular ligand-binding domain that specifically binds to a ligand (e.g. antigen) antigen. In some embodiments, the chimeric receptor is a CAR that contains an extracellular antigen-recognition domain that specifically binds to an antigen. In some embodiments, the ligand, such as an antigen, is a protein expressed on the surface of cells. In some embodiments, the CAR is a TCR-like CAR and the antigen is a processed peptide antigen, such as a peptide antigen of an intracellular protein, which, like a TCR, is recognized on the cell surface in the context of a major histocompatibility complex (MHC) molecule.

Exemplary antigen receptors, including CARs, and methods for engineering and introducing such receptors into cells, include those described, for example, in international patent application publication numbers WO200014257, WO2013126726, WO2012/129514, WO2014031687, WO2013/166321, WO2013/071154, WO2013/123061, U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) PLoS ONE 8(4): e61338; Turtle et al., Curr. Opin. Immunol., 2012 October; 24(5): 633-39; Wu et al., Cancer, 2012 March 18(2): 160-75. In some aspects, the antigen receptors include a CAR as described in U.S. Pat. No. 7,446,190, and those described in International Patent Application Publication No.: WO/2014055668 A1. Examples of the CARs include CARs as disclosed in any of the aforementioned publications, such as WO2014031687, U.S. Pat. Nos. 8,339,645, 7,446,179, US 2013/0149337, U.S. Pat. Nos. 7,446,190, 8,389,282, Kochenderfer et al., 2013, Nature Reviews Clinical Oncology, 10, 267-276 (2013); Wang et al. (2012) J. Immunother. 35(9): 689-701; and Brentjens et al., Sci Transl Med. 2013 5(177). See also WO2014031687, U.S. Pat. Nos. 8,339,645, 7,446,179, US 2013/0149337, U.S. Pat. Nos. 7,446,190, and 8,389,282.

In some embodiments, the CAR is constructed with a specificity for a particular antigen (or marker or ligand), such as an antigen expressed in a particular cell type to be targeted by adoptive therapy, e.g., a cancer marker, and/or an antigen intended to induce a dampening response, such as an antigen expressed on a normal or non-diseased cell type. Thus, the CAR typically includes in its extracellular portion one or more antigen binding molecules, such as one or more antigen-binding fragment, domain, or portion, or one or more antibody variable domains, and/or antibody molecules. In some embodiments, the CAR includes an antigen-binding portion or portions of an antibody molecule, such as a single-chain antibody fragment (scFv) derived from the variable heavy ($V_H$) and variable light ($V_L$) chains of a monoclonal antibody (mAb).

In some embodiments, the antibody or antigen-binding portion thereof is expressed on cells as part of a recombinant receptor, such as an antigen receptor. Among the antigen receptors are functional non-TCR antigen receptors, such as chimeric antigen receptors (CARs). Generally, a CAR containing an antibody or antigen-binding fragment that exhibits TCR-like specificity directed against peptide-MHC complexes also may be referred to as a TCR-like CAR. In some embodiments, the extracellular antigen binding domain specific for an MHC-peptide complex of a TCR-like CAR is linked to one or more intracellular signaling components, in some aspects via linkers and/or transmembrane domain(s). In some embodiments, such molecules can typically mimic or approximate a signal through a natural antigen receptor, such as a TCR, and, optionally, a signal through such a receptor in combination with a costimulatory receptor.

In some embodiments, the recombinant receptor, such as a chimeric receptor (e.g. CAR), includes a ligand-binding domain that binds, such as specifically binds, to an antigen (or a ligand). Among the antigens targeted by the chimeric receptors are those expressed in the context of a disease, condition, or cell type to be targeted via the adoptive cell therapy. Among the diseases and conditions are proliferative, neoplastic, and malignant diseases and disorders, including cancers and tumors, including hematologic cancers, cancers of the immune system, such as lymphomas, leukemias, and/or myelomas, such as B, T, and myeloid leukemias, lymphomas, and multiple myelomas.

In some embodiments, the antigen (or a ligand) is a polypeptide. In some embodiments, it is a carbohydrate or other molecule. In some embodiments, the antigen (or a ligand) is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

In some embodiments, the CAR contains an antibody or an antigen-binding fragment (e.g. scFv) that specifically recognizes an antigen, such as an intact antigen, expressed on the surface of a cell.

In some embodiments, the antigen (or a ligand) is a tumor antigen or cancer marker. In some embodiments, the antigen (or a ligand) the antigen is or includes αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPRC5D), Her2/neu (receptor tyrosine kinase erbB2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22Ra), IL-13 receptor alpha 2 (IL-13Ra2), kinase insert domain receptor (kdr), kappa light chain, Li cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen is or includes CD20, CD19, CD22, ROR1, CD45, CD21, CD5, CD33, Igkappa, Iglambda, CD79a, CD79b or CD30.

In some embodiments, the antigen is or includes a pathogen-specific or pathogen-expressed antigen. In some embodiments, the antigen is a viral antigen (such as a viral antigen from HIV, HCV, HBV, etc.), bacterial antigens, and/or parasitic antigens.

The term "antibody" herein is used in the broadest sense and includes polyclonal and monoclonal antibodies, including intact antibodies and functional (antigen-binding) antibody fragments, including fragment antigen binding (Fab) fragments, F(ab')$_2$ fragments, Fab' fragments, Fv fragments, recombinant IgG (rIgG) fragments, heavy chain variable ($V_H$) regions capable of specifically binding the antigen, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific or trispecific, antibodies, diabodies, triabodies, and tetrabodies, tandem di-scFv, tandem tri-scFv. Unless otherwise stated, the term "antibody" should be understood to encompass functional antibody fragments thereof also referred to herein as "antigen-binding fragments." The term also encompasses intact or full-length antibodies, including antibodies of any class or sub-class, including IgG and sub-classes thereof, IgM, IgE, IgA, and IgD.

The terms "complementarity determining region," and "CDR," synonymous with "hypervariable region" or "HVR," are known, in some cases, to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known, in some cases, to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4).

The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme); Al-Lazikani et al., (1997) JMB 273,927-948 ("Chothia" numbering scheme); MacCallum et al., J. Mol. Biol. 262: 732-745 (1996), "Antibody-antigen interactions: Contact analysis and binding site topography," J. Mol. Biol. 262, 732-745." ("Contact" numbering scheme); Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme); Honegger A and Pluckthun A, "Yet another numbering scheme for immunoglobulin variable domains: an automatic modeling and analysis tool," J Mol Biol, 2001 Jun. 8; 309(3):657-70, ("Aho" numbering scheme); and Martin et al., "Modeling antibody hypervariable loops: a combined algorithm," PNAS, 1989, 86(23): 9268-9272, ("AbM" numbering scheme).

The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme. The AbM scheme is a compromise between Kabat and Chothia definitions based on that used by Oxford Molecular's AbM antibody modeling software.

Table 1, below, lists exemplary position boundaries of CDR-L1, CDR-L2, CDR-L3 and CDR-H1, CDR-H2, CDR-H3 as identified by Kabat, Chothia, AbM, and Contact schemes, respectively. For CDR-H1, residue numbering is listed using both the Kabat and Chothia numbering schemes. FRs are located between CDRs, for example, with FR-L1 located before CDR-L1, FR-L2 located between CDR-L1 and CDR-L2, FR-L3 located between CDR-L2 and CDR-L3 and so forth. It is noted that because the shown Kabat numbering scheme places insertions at H35A and H35B, the end of the Chothia CDR-H1 loop when numbered using the shown Kabat numbering convention varies between H32 and H34, depending on the length of

TABLE 1

Boundaries of CDRs according to various numbering schemes.

| CDR | Kabat | Chothia | AbM | Contact |
|---|---|---|---|---|
| CDR-L1 | L24--L34 | L24--L34 | L24--L34 | L30--L36 |
| CDR-L2 | L50--L56 | L50--L56 | L50--L56 | L46--L55 |
| CDR-L3 | L89--L97 | L89--L97 | L89--L97 | L89--L96 |
| CDR-H1 (Kabat Numbering[1]) | H31--H35B | H26--H32 . . . 34 | H26--H35B | H30--H35B |
| CDR-H1 (Chothia Numbering[2]) | H31--H35 | H26--H32 | H26--H35 | H30--H35 |

TABLE 1-continued

Boundaries of CDRs according to various numbering schemes.

| CDR | Kabat | Chothia | AbM | Contact |
|---|---|---|---|---|
| CDR-H2 | H50--H65 | H52--H56 | H50--H58 | H47--H58 |
| CDR-H3 | H95--H102 | H95--H102 | H95--H102 | H93--H101 |

[1]Kabat et al. (1991), "Sequences of Proteins of Immunological Interest," 5th Ed. Public Health Service, National Institutes of Health, Bethesda, MD
[2]Al-Lazikani et al., (1997) JMB 273, 927-948

Thus, unless otherwise specified, a "CDR" or "complementary determining region," or individual specified CDRs (e.g., CDR-H1, CDR-H2, CDR-H3), of a given antibody or region thereof, such as a variable region thereof, should be understood to encompass a (or the specific) complementary determining region as defined by any of the aforementioned schemes, or other known schemes. For example, where it is stated that a particular CDR (e.g., a CDR-H3) contains the amino acid sequence of a corresponding CDR in a given $V_H$ or $V_L$ region amino acid sequence, it is understood that such a CDR has a sequence of the corresponding CDR (e.g., CDR-H3) within the variable region, as defined by any of the aforementioned schemes, or other known schemes. In some embodiments, specific CDR sequences are specified. Exemplary CDR sequences of the antibodies are described using various numbering schemes, although it is understood that the antibody can include CDRs as described according to any of the other aforementioned numbering schemes or other numbering schemes known to a skilled artisan.

Likewise, unless otherwise specified, a FR or individual specified FR(s) (e.g., FR-H1, FR-H2, FR-H3, FR-H4), of a given antibody or region thereof, such as a variable region thereof, should be understood to encompass a (or the specific) framework region as defined by any of the known schemes. In some instances, the scheme for identification of a particular CDR, FR, or FRs or CDRs is specified, such as the CDR as defined by the Kabat, Chothia, AbM or Contact method, or other known schemes. In other cases, the particular amino acid sequence of a CDR or FR is given.

The term "variable region" or "variable domain" refers to the domain of an antibody heavy or light chain that is involved in binding the antibody to antigen. The variable regions of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., J. Immunol. 150: 880-887 (1993); Clarkson et al., Nature 352:624-628 (1991).

Among the antibodies included in the CARs are antibody fragments. An "antibody fragment" or "antigen-binding fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; heavy chain variable ($V_H$) regions, single-chain antibody molecules such as scFvs and single-domain antibodies comprising only the $V_H$ region; and multispecific antibodies formed from antibody fragments. In some embodiments, the antigen-binding domain in the CARs is or comprises an antibody fragment comprising a variable heavy chain ($V_H$) and a variable light chain ($V_L$) region. In particular embodiments, the antibodies are single-chain antibody fragments comprising a heavy chain variable ($V_H$) region and/or a light chain variable ($V_L$) region, such as scFvs.

In some embodiments, the antigen or antigen binding domain is CD19. In some embodiments, the scFv contains a $V_H$ and a $V_L$ derived from an antibody or an antibody fragment specific to CD19. In some embodiments, the antibody or antibody fragment that binds CD19 is a mouse derived antibody such as FMC63 and SJ25C1. In some embodiments, the antibody or antibody fragment is a human antibody, e.g., as described in U.S. Patent Publication No. US 2016/0152723.

In some embodiments, the scFv is derived from FMC63. FMC63 generally refers to a mouse monoclonal IgG1 antibody raised against Nalm-1 and -16 cells expressing CD19 of human origin (Ling, N. R., et al. (1987). *Leucocyte typing III.* 302). In some embodiments, the FMC63 antibody comprises CDR-H1 and CDR-H2 set forth in SEQ ID NOS: 38 and 39, respectively, and CDR-H3 set forth in SEQ ID NO: 40 or 54; and CDR-L1 set forth in SEQ ID NO: 35 and CDR-L2 set forth in SEQ ID NO: 36 or 55 and CDR-L3 set forth in SEQ ID NO: 37 or 34. In some embodiments, the FMC63 antibody comprises the heavy chain variable region ($V_H$) comprising the amino acid sequence of SEQ ID NO: 41 and the light chain variable region ($V_L$) comprising the amino acid sequence of SEQ ID NO: 42.

In some embodiments, the scFv comprises a variable light chain containing the CDR-L1 sequence of SEQ ID NO:35, a CDR-L2 sequence of SEQ ID NO:36, and a CDR-L3 sequence of SEQ ID NO:37 and/or a variable heavy chain containing a CDR-H1 sequence of SEQ ID NO:38, a CDR-H2 sequence of SEQ ID NO:39, and a CDR-H3 sequence of SEQ ID NO:40. In some embodiments, the scFv comprises a variable heavy chain region set forth in SEQ ID NO:41 and a variable light chain region set forth in SEQ ID NO:42. In some embodiments, the variable heavy and variable light chains are connected by a linker. In some embodiments, the linker is set forth in SEQ ID NO:56. In some embodiments, the scFv comprises, in order, a $V_H$, a linker, and a $V_L$. In some embodiments, the scFv comprises, in order, a $V_L$, a linker, and a $V_H$. In some embodiments, the scFv is encoded by a sequence of nucleotides set forth in SEQ ID NO:57 or a sequence that exhibits at least 85%, 86%, 87%, 88%, 89%, 90%, 91%, 92%, 93%, 94%, 95%, 96%, 97%, 98%, or 99% sequence identity to SEQ ID NO:57. In some embodiments, the scFv comprises the sequence of amino acids set forth in SEQ ID NO:43 or a sequence that exhibits at least 85%, 86%, 87%, 88%, 89%, 90%, 91%, 92%, 93%, 94%, 95%, 96%, 97%, 98%, or 99% sequence identity to SEQ ID NO:43.

In some embodiments the scFv is derived from SJ25C1. SJ25C1 is a mouse monoclonal IgG1 antibody raised against Nalm-1 and -16 cells expressing CD19 of human origin (Ling, N. R., et al. (1987). *Leucocyte typing III.* 302). In some embodiments, the SJ25C1 antibody comprises CDR-H1, CDR-H2 and CDR-H3 set forth in SEQ ID NOS: 47-49, respectively, and CDR-L1, CDR-L2 and CDR-L3 sequences set forth in SEQ ID NOS: 44-46, respectively. In some embodiments, the SJ25C1 antibody comprises the heavy chain variable region ($V_H$) comprising the amino acid sequence of SEQ ID NO: 50 and the light chain variable region ($V_L$) comprising the amino acid sequence of SEQ ID NO: 51.

In some embodiments, the scFv comprises a variable light chain containing a CDR-L1 sequence of SEQ ID NO:44, a CDR-L2 sequence of SEQ ID NO: 45, and a CDR-L3 sequence of SEQ ID NO:46 and/or a variable heavy chain containing a CDR-H1 sequence of SEQ ID NO:47, a CDR-H2 sequence of SEQ ID NO:48, and a CDR-H3 sequence of SEQ ID NO:49. In some embodiments, the scFv comprises a variable heavy chain region set forth in SEQ ID NO:50 and a variable light chain region set forth in SEQ ID NO:51. In some embodiments, the variable heavy and variable light chain are connected by a linker. In some embodiments, the linker is set forth in SEQ ID NO:52. In some embodiments, the scFv comprises, in order, a $V_H$, a linker, and a $V_L$. In some embodiments, the scFv comprises, in order, a $V_L$, a linker, and a $V_H$. In some embodiments, the scFv comprises the sequence of amino acids set forth in SEQ ID NO:53 or a sequence that exhibits at least 85%, 86%, 87%, 88%, 89%, 90%, 91%, 92%, 93%, 94%, 95%, 96%, 97%, 98%, or 99% sequence identity to SEQ ID NO:53.

In some embodiments, the antigen is CD20. In some embodiments, the scFv contains a $V_H$ and a $V_L$ derived from an antibody or an antibody fragment specific to CD20. In some embodiments, the antibody or antibody fragment that binds CD20 is an antibody that is or is derived from Rituximab, such as is Rituximab scFv.

In some embodiments, the antigen is CD22. In some embodiments, the scFv contains a $V_H$ and a $V_L$ derived from an antibody or an antibody fragment specific to CD22. In some embodiments, the antibody or antibody fragment that binds CD22 is an antibody that is or is derived from m971, such as is m971 scFv.

In some embodiments, the antigen or antigen binding domain is BCMA. In some embodiments, the scFv contains a $V_H$ and a $V_L$ derived from an antibody or an antibody fragment specific to BCMA. In some embodiments, the antibody or antibody fragment that binds BCMA is or contains a $V_H$ and a $V_L$ from an antibody or antibody fragment set forth in International Patent Applications, Publication Number WO 2016/090327 and WO 2016/090320.

In some embodiments, the antigen or antigen binding domain is GPRC5D. In some embodiments, the scFv contains a $V_H$ and a $V_L$ derived from an antibody or an antibody fragment specific to GPRC5D. In some embodiments, the antibody or antibody fragment that binds GPRC5D is or contains a $V_H$ and a $V_L$ from an antibody or antibody fragment set forth in International Patent Applications, Publication Number WO 2016/090329 and WO 2016/090312.

In some embodiments, the CAR contains a TCR-like antibody, such as an antibody or an antigen-binding fragment (e.g. scFv) that specifically recognizes an intracellular antigen, such as a tumor-associated antigen, presented on the cell surface as a MHC-peptide complex. In some embodiments, an antibody or antigen-binding portion thereof that recognizes an MHC-peptide complex can be expressed on cells as part of a recombinant receptor, such as an antigen receptor. Among the antigen receptors are functional non-TCR antigen receptors, such as chimeric antigen receptors (CARs). Generally, a CAR containing an antibody or antigen-binding fragment that exhibits TCR-like specificity directed against peptide-MHC complexes also may be referred to as a TCR-like CAR.

Reference to "Major histocompatibility complex" (MHC) refers to a protein, generally a glycoprotein, that contains a polymorphic peptide binding site or binding groove that can, in some cases, complex with peptide antigens of polypeptides, including peptide antigens processed by the cell machinery. In some cases, MHC molecules can be displayed or expressed on the cell surface, including as a complex with peptide, i.e. MHC-peptide complex, for presentation of an antigen in a conformation recognizable by an antigen receptor on T cells, such as a TCRs or TCR-like antibody. Generally, MHC class I molecules are heterodimers having a membrane spanning α chain, in some cases with three α domains, and a non-covalently associated β2 microglobulin. Generally, MHC class II molecules are composed of two transmembrane glycoproteins, α and β, both of which typically span the membrane. An MHC molecule can include an effective portion of an MHC that contains an antigen binding site or sites for binding a peptide and the sequences necessary for recognition by the appropriate antigen receptor. In some embodiments, MHC class I molecules deliver peptides originating in the cytosol to the cell surface, where a MHC-peptide complex is recognized by T cells, such as generally $CD8^+$ T cells, but in some cases $CD4^+$ T cells. In some embodiments, MHC class II molecules deliver peptides originating in the vesicular system to the cell surface, where they are typically recognized by $CD4^+$ T cells. Generally, MHC molecules are encoded by a group of linked loci, which are collectively termed H-2 in the mouse and human leukocyte antigen (HLA) in humans. Hence, typically human MHC can also be referred to as human leukocyte antigen (HLA).

The term "MHC-peptide complex" or "peptide-MHC complex" or variations thereof, refers to a complex or association of a peptide antigen and an MHC molecule, such as, generally, by non-covalent interactions of the peptide in the binding groove or cleft of the MHC molecule. In some embodiments, the MHC-peptide complex is present or displayed on the surface of cells. In some embodiments, the MHC-peptide complex can be specifically recognized by an antigen receptor, such as a TCR, TCR-like CAR or antigen-binding portions thereof.

In some embodiments, a peptide, such as a peptide antigen or epitope, of a polypeptide can associate with an MHC molecule, such as for recognition by an antigen receptor. Generally, the peptide is derived from or based on a fragment of a longer biological molecule, such as a polypeptide or protein. In some embodiments, the peptide typically is about 8 to about 24 amino acids in length. In some embodiments, a peptide has a length of from or from about 9 to 22 amino acids for recognition in the MHC Class II complex. In some embodiments, a peptide has a length of from or from about 8 to 13 amino acids for recognition in the MHC Class I complex. In some embodiments, upon recognition of the peptide in the context of an MHC molecule, such as MHC-peptide complex, the antigen receptor, such as TCR or TCR-like CAR, produces or triggers an activation signal to the T cell that induces a T cell response, such as T cell proliferation, cytokine production, a cytotoxic T cell response or other response.

In some embodiments, a TCR-like antibody or antigen-binding portion, are known or can be produced by known methods (see e.g. US Published Application Nos. US 2002/0150914; US 2003/0223994; US 2004/0191260; US 2006/0034850; US 2007/00992530; US20090226474; US20090304679; and International PCT Publication No. WO 03/068201).

In some embodiments, an antibody or antigen-binding portion thereof that specifically binds to a MHC-peptide complex, can be produced by immunizing a host with an effective amount of an immunogen containing a specific MHC-peptide complex. In some cases, the peptide of the MHC-peptide complex is an epitope of antigen capable of binding to the MHC, such as a tumor antigen, for example a universal tumor antigen, myeloma antigen or other antigen as described below. In some embodiments, an effective amount of the immunogen is then administered to a host for eliciting an immune response, wherein the immunogen retains a three-dimensional form thereof for a period of time sufficient to elicit an immune response against the three-dimensional presentation of the peptide in the binding groove of the MHC molecule. Serum collected from the host is then assayed to determine if desired antibodies that recognize a three-dimensional presentation of the peptide in the binding groove of the MHC molecule is being produced. In some embodiments, the produced antibodies can be assessed to confirm that the antibody can differentiate the MHC-peptide complex from the MHC molecule alone, the peptide of interest alone, and a complex of MHC and irrelevant peptide. The desired antibodies can then be isolated.

In some embodiments, an antibody or antigen-binding portion thereof that specifically binds to an MHC-peptide complex can be produced by employing antibody library display methods, such as phage antibody libraries. In some embodiments, phage display libraries of mutant Fab, scFv or other antibody forms can be generated, for example, in which members of the library are mutated at one or more residues of a CDR or CDRs. See e.g. US published application No. US20020150914, US2014/0294841; and Cohen CJ. et al. (2003) *J Mol. Recogn.* 16:324-332.

The term "antibody" herein is used in the broadest sense and includes polyclonal and monoclonal antibodies, including intact antibodies and functional (antigen-binding) antibody fragments, including fragment antigen binding (Fab) fragments, F(ab')$_2$ fragments, Fab' fragments, Fv fragments, recombinant IgG (rIgG) fragments, variable heavy chain ($V_H$) regions capable of specifically binding the antigen, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

In some embodiments, the antigen-binding proteins, antibodies and antigen binding fragments thereof specifically recognize an antigen of a full-length antibody. In some embodiments, the heavy and light chains of an antibody can be full-length or can be an antigen-binding portion (a Fab, F(ab')2, Fv or a single chain Fv fragment (scFv)). In other embodiments, the antibody heavy chain constant region is chosen from, e.g., IgG1, IgG2, IgG3, IgG4, IgM, IgA1, IgA2, IgD, and IgE, particularly chosen from, e.g., IgG1, IgG2, IgG3, and IgG4, more particularly, IgG1 (e.g., human IgG1). In another embodiment, the antibody light chain constant region is chosen from, e.g., kappa or lambda, particularly kappa.

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; variable heavy chain ($V_H$) regions, single-chain antibody molecules such as scFvs and single-domain $V_H$ single antibodies; and multispecific antibodies formed from antibody fragments. In particular embodiments, the antibodies are single-chain antibody fragments comprising a variable heavy chain region and/or a variable light chain region, such as scFvs.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., J. Immunol. 150: 880-887 (1993); Clarkson et al., *Nature* 352:624-628 (1991).

Single-domain antibodies are antibody fragments comprising all or a portion of the heavy chain variable domain or all or a portion of the light chain variable domain of an antibody. In certain embodiments, a single-domain antibody is a human single-domain antibody. In some embodiments, the CAR comprises an antibody heavy chain domain that specifically binds the antigen, such as a cancer marker or cell surface antigen of a cell or disease to be targeted, such as a tumor cell or a cancer cell, such as any of the target antigens described herein or known.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some embodiments, the antibody fragments are scFvs.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

Thus, in some embodiments, the chimeric antigen receptor, including TCR-like CARs, includes an extracellular portion containing an antibody or antibody fragment. In some embodiments, the antibody or fragment includes an scFv. In some aspects, the chimeric antigen receptor includes an extracellular portion containing the antibody or fragment and an intracellular signaling region. In some embodiments, the intracellular signaling region comprises an intracellular signaling domain. In some embodiments, the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM).

In some embodiments, the recombinant receptor such as the CAR, such as the antibody portion thereof, further includes a spacer, which may be or include at least a portion of an immunoglobulin constant region or variant or modified version thereof, such as a hinge region, e.g., an IgG4 hinge region, and/or a $C_H1/C_L$ and/or Fc region. In some embodiments, the recombinant receptor further comprises a spacer and/or a hinge region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. In some examples, the spacer is at or about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include IgG4 hinge alone, IgG4 hinge linked to CH2 and CH3 domains, or IgG4 hinge linked to the CH3 domain. Exemplary spacers include, but are not limited to, those described in Hudecek et al. (2013) *Clin. Cancer Res.*, 19:3153, Hudecek et al. (2015) Cancer Immunol Res. 3(2): 125-135 or international patent application publication number WO2014031687. In some embodiments, the spacer has the sequence set forth in SEQ ID NO: 1, and is encoded by the sequence set forth in SEQ ID NO: 2. In some embodiments, the spacer has the sequence set forth in SEQ ID NO: 3. In some embodiments, the spacer has the sequence set forth in SEQ ID NO: 4.

In some aspects, the spacer is a polypeptide spacer that (a) comprises or consists of all or a portion of an immunoglobulin hinge or a modified version thereof or comprises about 15 amino acids or less, and does not comprise a CD28 extracellular region or a CD8 extracellular region, (b) comprises or consists of all or a portion of an immunoglobulin hinge, optionally an IgG4 hinge, or a modified version thereof and/or comprises about 15 amino acids or less, and does not comprise a CD28 extracellular region or a CD8 extracellular region, or (c) is at or about 12 amino acids in length and/or comprises or consists of all or a portion of an immunoglobulin hinge, optionally an IgG4, or a modified version thereof; or (d) consists or comprises the sequence of amino acids set forth in SEQ ID NOS: 1, 3-5, 27-34 or 58, or a variant of any of the foregoing having at least 85%, 86%, 87%, 88%, 89%, 90%, 91%, 92%, 93%, 94%, 95%, 96%, 97%, 98%, 99% or more sequence identity thereto, or (e) comprises or consists of the formula $X_1PPX_2P$, where $X_1$ is glycine, cysteine or arginine and $X_2$ is cysteine or threonine.

In some embodiments, the constant region or portion is of IgD. In some embodiments, the spacer has the sequence set forth in SEQ ID NO: 5. In some embodiments, the spacer has a sequence of amino acids that exhibits at least or at least about 85%, 86%, 87%, 88%, 89%, 90%, 91%, 92%, 93%, 94%, 95%, 96%, 97%, 98%, 99% or more sequence identity to any of SEQ ID NOS: 1, 3, 4 and 5.

The antigen recognition domain generally is linked to one or more intracellular signaling components, such as signaling components that mimic activation through an antigen receptor complex, such as a TCR complex, in the case of a CAR, and/or signal via another cell surface receptor. Thus, in some embodiments, the antigen binding component (e.g., antibody) is linked to one or more transmembrane and intracellular signaling regions. In some embodiments, the transmembrane domain is fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD3γ, CD64, CD80, CD86, CD134, CD137, CD154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s).

Among the intracellular signaling region are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

The receptor, e.g., the CAR, generally includes at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some aspects, the ROR1-binding antibody is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25, or CD16. For example, in some aspects, the CAR includes a chimeric molecule between CD3-zeta (CD3-ζ), or Fc receptor γ and CD8, CD4, CD25 or CD16.

In some embodiments, upon ligation of the CAR, the cytoplasmic domain or intracellular signaling region of the CAR activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling region of an antigen receptor component or costimulatory molecule is used in place of an intact immunostimulatory chain, for example, if it transduces the effector function signal. In some embodiments, the intracellular signaling regions, e.g., comprising intracellular domain or domains, include the cytoplasmic sequences of the T cell receptor (TCR), and in some aspects also those of co-receptors that in the natural context act in concert with such receptor to initiate signal transduction following antigen receptor engagement, and/or any derivative or variant of such molecules, and/or any synthetic sequence that has the same functional capability.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR or CD3 zeta, FcR gamma or FcR beta. In some embodiments, cytoplasmic signaling molecule(s) in the CAR contain(s) a cytoplasmic signaling domain, portion thereof, or sequence derived from CD3 zeta.

In some embodiments, the CAR includes a signaling region and/or transmembrane portion of a costimulatory receptor, such as CD28, 4-1BB, OX40, DAP10, and ICOS. In some aspects, the same CAR includes both the signaling region and costimulatory components.

In some embodiments, the signaling region is included within one CAR, whereas the costimulatory component is provided by another CAR recognizing another antigen. In some embodiments, the CARs include activating or stimulatory CARs, and costimulatory CARs, both expressed on the same cell (see WO2014/055668).

In certain embodiments, the intracellular signaling region comprises a CD28 transmembrane and signaling domain linked to a CD3 (e.g., CD3-zeta) intracellular domain. In some embodiments, the intracellular signaling region comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR in some aspects is one that includes multiple costimulatory domains of different costimulatory receptors.

In some embodiments, the chimeric antigen receptor includes an extracellular portion containing the antibody or fragment described herein. In some aspects, the chimeric antigen receptor includes an extracellular portion containing the antibody or fragment described herein and an intracellular signaling domain. In some embodiments, the antibody or fragment includes an scFv or a single-domain $V_H$ antibody and the intracellular domain contains an ITAM. In some aspects, the intracellular signaling domain includes a signaling domain of a zeta chain of a CD3-zeta (CD3ζ) chain. In some embodiments, the chimeric antigen receptor includes a transmembrane domain disposed between the extracellular domain and the intracellular signaling region.

In some aspects, the transmembrane domain contains a transmembrane portion of CD28. The extracellular domain and transmembrane can be linked directly or indirectly. In some embodiments, the extracellular domain and transmembrane are linked by a spacer, such as any described herein. In some embodiments, the chimeric antigen receptor contains an intracellular domain of a T cell costimulatory molecule, such as between the transmembrane domain and intracellular signaling domain. In some aspects, the T cell costimulatory molecule is CD28 or 4-1BB.

In some embodiments, the CAR contains an antibody, e.g., an antibody fragment, a transmembrane domain that is or contains a transmembrane portion of CD28 or a functional variant thereof, and an intracellular signaling domain containing a signaling portion of CD28 or functional variant thereof and a signaling portion of CD3 zeta or functional variant thereof. In some embodiments, the CAR contains an antibody, e.g., antibody fragment, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g. an IgG4 hinge, such as a hinge-only spacer.

In some embodiments, the transmembrane domain of the receptor, e.g., the CAR is a transmembrane domain of human CD28 or variant thereof, e.g., a 27-amino acid transmembrane domain of a human CD28 (Accession No.: P10747.1), or is a transmembrane domain that comprises the sequence of amino acids set forth in SEQ ID NO: 8 or a sequence of amino acids that exhibits at least or at least about 85%, 86%, 87%, 88%, 89%, 90%, 91%, 92%, 93%, 94%, 95%, 96%, 97%, 98%, 99% or more sequence identity to SEQ ID NO:8; in some embodiments, the transmembrane-domain containing portion of the recombinant receptor comprises the sequence of amino acids set forth in SEQ ID NO: 9 or a sequence of amino acids having at least or at least about 85%, 86%, 87%, 88%, 89%, 90%, 91%, 92%, 93%, 94%, 95%, 96%, 97%, 98%, 99% or more sequence identity thereto.

In some embodiments, the chimeric antigen receptor contains an intracellular domain of a T cell costimulatory molecule. In some aspects, the T cell costimulatory molecule is CD28 or 4-1BB.

In some embodiments, the intracellular signaling region comprises an intracellular costimulatory signaling domain of human CD28 or functional variant or portion thereof, such as a 41 amino acid domain thereof and/or such a domain with an LL to GG substitution at positions 186-187 of a native CD28 protein. In some embodiments, the intracellular signaling domain can comprise the sequence of amino acids set forth in SEQ ID NO: 10 or 11 or a sequence of amino acids that exhibits at least or at least about 85%, 86%, 87%, 88%, 89%, 90%, 91%, 92%, 93%, 94%, 95%, 96%, 97%, 98%, 99% or more sequence identity to SEQ ID NO: 10 or 11. In some embodiments, the intracellular region comprises an intracellular costimulatory signaling domain of 4-1BB or functional variant or portion thereof, such as a 42-amino acid cytoplasmic domain of a human 4-1BB (Accession No. Q07011.1) or functional variant or portion thereof, such as the sequence of amino acids set forth in SEQ ID NO: 12 or a sequence of amino acids that exhibits at least or at least about 85%, 86%, 87%, 88%, 89%, 90%, 91%, 92%, 93%, 94%, 95%, 96%, 97%, 98%, 99% or more sequence identity to SEQ ID NO: 12.

In some embodiments, the intracellular signaling region comprises a human CD3 chain, optionally a CD3 zeta stimulatory signaling domain or functional variant thereof, such as an 112 AA cytoplasmic domain of isoform 3 of human CD3 (Accession No.: P20963.2) or a CD3 zeta signaling domain as described in U.S. Pat. No. 7,446,190 or 8,911,993. In some embodiments, the intracellular signaling region comprises the sequence of amino acids set forth in SEQ ID NO: 13, 14 or 15 or a sequence of amino acids that exhibits at least or at least about 85%, 86%, 87%, 88%, 89%, 90%, 91%, 92%, 93%, 94%, 95%, 96%, 97%, 98%, 99% or more sequence identity to SEQ ID NO: 13, 14 or 15.

In some aspects, the spacer contains only a hinge region of an IgG, such as only a hinge of IgG4 or IgG1, such as the hinge only spacer set forth in SEQ ID NO:1. In other embodiments, the spacer is an Ig hinge, e.g., and IgG4 hinge, linked to a $C_H2$ and/or $C_H3$ domains. In some embodiments, the spacer is an Ig hinge, e.g., an IgG4 hinge, linked to $C_H2$ and $C_H3$ domains, such as set forth in SEQ ID NO:3. In some embodiments, the spacer is an Ig hinge, e.g., an IgG4 hinge, linked to a $C_H3$ domain only, such as set forth in SEQ ID NO:4. In some embodiments, the spacer is or comprises a glycine-serine rich sequence or other flexible linker such as known flexible linkers.

2. T Cell Receptors (TCRs)

In some embodiments, engineered cells, such as T cells, are provided that express a T cell receptor (TCR) or antigen-binding portion thereof that recognizes an peptide epitope or T cell epitope of a target polypeptide, such as an antigen of a tumor, viral or autoimmune protein.

In some embodiments, a "T cell receptor" or "TCR" is a molecule that contains a variable α and β chains (also known as TCRα and TCRβ, respectively) or a variable γ and δ chains (also known as TCRα and TCRβ, respectively), or antigen-binding portions thereof, and which is capable of specifically binding to a peptide bound to an MHC molecule. In some embodiments, the TCR is in the αβ form. Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules.

Unless otherwise stated, the term "TCR" should be understood to encompass full TCRs as well as antigen-binding portions or antigen-binding fragments thereof. In some embodiments, the TCR is an intact or full-length TCR, including TCRs in the αβ form or γδ form. In some embodiments, the TCR is an antigen-binding portion that is less than a full-length TCR but that binds to a specific peptide bound in an MHC molecule, such as binds to an MHC-peptide complex. In some cases, an antigen-binding portion or fragment of a TCR can contain only a portion of the structural domains of a full-length or intact TCR, but yet is able to bind the peptide epitope, such as MHC-peptide complex, to which the full TCR binds. In some cases, an antigen-binding portion contains the variable domains of a TCR, such as variable α chain and variable β chain of a TCR, sufficient to form a binding site for binding to a specific MHC-peptide complex. Generally, the variable chains of a TCR contain complementarity determining regions involved in recognition of the peptide, MHC and/or MHC-peptide complex.

In some embodiments, the variable domains of the TCR contain hypervariable loops, or complementarity determining regions (CDRs), which generally are the primary contributors to antigen recognition and binding capabilities and specificity. In some embodiments, a CDR of a TCR or combination thereof forms all or substantially all of the antigen-binding site of a given TCR molecule. The various CDRs within a variable region of a TCR chain generally are separated by framework regions (FRs), which generally display less variability among TCR molecules as compared to the CDRs (see, e.g., Jores et al., Proc. Nat'l Acad. Sci. U.S.A. 87:9138, 1990; Chothia et al., EMBO J. 7:3745, 1988; see also Lefranc et al., Dev. Comp. Immunol. 27:55, 2003). In some embodiments, CDR3 is the main CDR responsible for antigen binding or specificity, or is the most important among the three CDRs on a given TCR variable region for antigen recognition, and/or for interaction with the processed peptide portion of the peptide-MHC complex. In some contexts, the CDR1 of the alpha chain can interact with the N-terminal part of certain antigenic peptides. In some contexts, CDR1 of the beta chain can interact with the C-terminal part of the peptide. In some contexts, CDR2 contributes most strongly to or is the primary CDR responsible for the interaction with or recognition of the MHC portion of the MHC-peptide complex. In some embodiments, the variable region of the β-chain can contain a further hypervariable region (CDR4 or HVR4), which generally is involved in superantigen binding and not antigen recognition (Kotb (1995) Clinical Microbiology Reviews, 8:411-426).

In some embodiments, a TCR also can contain a constant domain, a transmembrane domain and/or a short cytoplasmic tail (see, e.g., Janeway et al., Immunobiology: The Immune System in Health and Disease, 3rd Ed., Current Biology Publications, p. 4:33, 1997). In some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction.

In some embodiments, a TCR chain contains one or more constant domain. For example, the extracellular portion of a given TCR chain (e.g., α-chain or β-chain) can contain two immunoglobulin-like domains, such as a variable domain (e.g., Vα or Vβ; typically amino acids 1 to 116 based on Kabat numbering Kabat et al., "Sequences of Proteins of Immunological Interest, US Dept. Health and Human Services, Public Health Service National Institutes of Health, 1991, 5th ed.) and a constant domain (e.g., α-chain constant domain or Cα, typically positions 117 to 259 of the chain based on Kabat numbering or β chain constant domain or Cβ, typically positions 117 to 295 of the chain based on Kabat) adjacent to the cell membrane. For example, in some cases, the extracellular portion of the TCR formed by the two chains contains two membrane-proximal constant domains, and two membrane-distal variable domains, which variable domains each contain CDRs. The constant domain of the TCR may contain short connecting sequences in which a cysteine residue forms a disulfide bond, thereby linking the two chains of the TCR. In some embodiments, a TCR may have an additional cysteine residue in each of the α and β chains, such that the TCR contains two disulfide bonds in the constant domains.

In some embodiments, the TCR chains contain a transmembrane domain. In some embodiments, the transmembrane domain is positively charged. In some cases, the TCR chain contains a cytoplasmic tail. In some cases, the structure allows the TCR to associate with other molecules like CD3 and subunits thereof. For example, a TCR containing constant domains with a transmembrane region may anchor the protein in the cell membrane and associate with invariant subunits of the CD3 signaling apparatus or complex. The intracellular tails of CD3 signaling subunits (e.g. CD3γ, CD3δ, CD3ε and CD3ζ chains) contain one or more immunoreceptor tyrosine-based activation motif or ITAM that are involved in the signaling capacity of the TCR complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds.

In some embodiments, the TCR can be generated from a known TCR sequence(s), such as sequences of Vα, chains, for which a substantially full-length coding sequence is readily available. Methods for obtaining full-length TCR sequences, including V chain sequences, from cell sources are well known. In some embodiments, nucleic acids encoding the TCR can be obtained from a variety of sources, such as by polymerase chain reaction (PCR) amplification of TCR-encoding nucleic acids within or isolated from a given cell or cells, or synthesis of publicly available TCR DNA sequences.

In some embodiments, the TCR is obtained from a biological source, such as from cells such as from a T cell (e.g. cytotoxic T cell), T-cell hybridomas or other publicly available source. In some embodiments, the T-cells can be obtained from in vivo isolated cells. In some embodiments, the TCR is a thymically selected TCR. In some embodiments, the TCR is a neoepitope-restricted TCR. In some embodiments, the T-cells can be a cultured T-cell hybridoma or clone. In some embodiments, the TCR or antigen-binding portion thereof or antigen-binding fragment thereof can be synthetically generated from knowledge of the sequence of the TCR.

In some embodiments, the TCR is generated from a TCR identified or selected from screening a library of candidate TCRs against a target polypeptide antigen, or target T cell epitope thereof. TCR libraries can be generated by amplification of the repertoire of Vα and Vβ from T cells isolated from a subject, including cells present in PBMCs, spleen or other lymphoid organ. In some cases, T cells can be amplified from tumor-infiltrating lymphocytes (TILs). In some embodiments, TCR libraries can be generated from CD4+ or CD8+ cells. In some embodiments, the TCRs can be amplified from a T cell source of a normal of healthy subject, i.e. normal TCR libraries. In some embodiments, the TCRs can be amplified from a T cell source of a diseased subject, i.e. diseased TCR libraries. In some embodiments, degenerate primers are used to amplify the gene repertoire of Vα and Vβ, such as by RT-PCR in samples, such as T cells, obtained from humans. In some embodiments, scTv libraries can be assembled from naïve Vα and Vβ libraries in which the amplified products are cloned or assembled to be separated by a linker. Depending on the source of the subject and cells, the libraries can be HLA allele-specific. Alternatively, in some embodiments, TCR libraries can be generated by mutagenesis or diversification of a parent or scaffold TCR molecule. In some aspects, the TCRs are subjected to directed evolution, such as by mutagenesis, e.g., of the α or β chain. In some aspects, particular residues within CDRs of the TCR are altered. In some embodiments, selected TCRs can be modified by affinity maturation. In some embodiments, antigen-specific T cells may be selected, such as by screening to assess CTL activity against the peptide. In some aspects, TCRs, e.g. present on the antigen-specific T cells, may be selected, such as by binding activity, e.g., particular affinity or avidity for the antigen.

In some embodiments, the genetically engineered antigen receptors include recombinant T cell receptors (TCRs) and/or TCRs cloned from naturally occurring T cells. In some embodiments, a high-affinity T cell clone for a target antigen (e.g., a cancer antigen) is identified, isolated from a patient, and introduced into the cells. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al. (2009) Clin Cancer Res. 15:169-180 and Cohen et al. (2005) J Immunol. 175:5799-5808. In some embodiments, phage display is used to isolate TCRs against a target antigen (see, e.g., Varela-Rohena et al. (2008) Nat Med. 14:1390-1395 and Li (2005) Nat Biotechnol. 23:349-354.

In some embodiments, the TCR or antigen-binding portion thereof is one that has been modified or engineered. In some embodiments, directed evolution methods are used to generate TCRs with altered properties, such as with higher affinity for a specific MHC-peptide complex. In some embodiments, directed evolution is achieved by display methods including, but not limited to, yeast display (Holler et al. (2003) Nat Immunol, 4, 55-62; Holler et al. (2000) Proc Natl Acad Sci USA, 97, 5387-92), phage display (Li et al. (2005) Nat Biotechnol, 23, 349-54), or T cell display (Chervin et al. (2008) J Immunol Methods, 339, 175-84). In some embodiments, display approaches involve engineering, or modifying, a known, parent or reference TCR. For example, in some cases, a wild-type TCR can be used as a template for producing mutagenized TCRs in which in one or more residues of the CDRs are mutated, and mutants with an desired altered property, such as higher affinity for a desired target antigen, are selected.

In some embodiments, peptides of a target polypeptide for use in producing or generating a TCR of interest are known or can be readily identified by a skilled artisan. In some embodiments, peptides suitable for use in generating TCRs or antigen-binding portions can be determined based on the presence of an HLA-restricted motif in a target polypeptide of interest, such as a target polypeptide described below. In some embodiments, peptides are identified using available computer prediction models. In some embodiments, for predicting MHC class I binding sites, such models include, but are not limited to, ProPred1 (Singh and Raghava (2001) Bioinformatics 17(12):1236-1237, and SYFPEITHI (see Schuler et al. (2007) Immunoinformatics Methods in Molecular Biology, 409(1): 75-93 2007). In some embodiments, the MHC-restricted epitope is HLA-A0201, which is expressed in approximately 39-46% of all Caucasians and therefore, represents a suitable choice of MHC antigen for use preparing a TCR or other MHC-peptide binding molecule.

HLA-A0201-binding motifs and the cleavage sites for proteasomes and immune-proteasomes using computer prediction models are known. For predicting MHC class I binding sites, such models include, but are not limited to, ProPred1 (described in more detail in Singh and Raghava, ProPred: prediction of HLA-DR binding sites. BIOINFORMATICS 17(12):1236-1237 2001), and SYFPEITHI (see Schuler et al. SYFPEITHI, Database for Searching and T-Cell Epitope Prediction. in Immunoinformatics Methods in Molecular Biology, vol 409(1): 75-93 2007).

In some embodiments, the TCR or antigen binding portion thereof may be a recombinantly produced natural protein or mutated form thereof in which one or more property, such as binding characteristic, has been altered. In some embodiments, a TCR may be derived from one of various animal species, such as human, mouse, rat, or other mammal. A TCR may be cell-bound or in soluble form. In some embodiments, for purposes of the provided methods, the TCR is in cell-bound form expressed on the surface of a cell.

In some embodiments, the TCR is a full-length TCR. In some embodiments, the TCR is an antigen-binding portion. In some embodiments, the TCR is a dimeric TCR (dTCR). In some embodiments, the TCR is a single-chain TCR (sc-TCR). In some embodiments, a dTCR or scTCR have the structures as described in WO 03/020763, WO 04/033685, WO2011/044186.

In some embodiments, the TCR contains a sequence corresponding to the transmembrane sequence. In some embodiments, the TCR does contain a sequence corresponding to cytoplasmic sequences. In some embodiments, the TCR is capable of forming a TCR complex with CD3. In some embodiments, any of the TCRs, including a dTCR or scTCR, can be linked to signaling domains that yield an active TCR on the surface of a T cell. In some embodiments, the TCR is expressed on the surface of cells.

In some embodiments a dTCR contains a first polypeptide wherein a sequence corresponding to a TCR α chain variable region sequence is fused to the N terminus of a sequence corresponding to a TCR α chain constant region extracellular sequence, and a second polypeptide wherein a sequence corresponding to a TCR β chain variable region sequence is fused to the N terminus a sequence corresponding to a TCR β chain constant region extracellular sequence, the first and second polypeptides being linked by a disulfide bond. In some embodiments, the bond can correspond to the native inter-chain disulfide bond present in native dimeric α TCRs. In some embodiments, the interchain disulfide bonds are not present in a native TCR. For example, in some embodiments, one or more cysteines can be incorporated into the constant region extracellular sequences of dTCR polypeptide pair. In some cases, both a native and a non-native disulfide bond may be desirable. In some embodiments, the TCR contains a transmembrane sequence to anchor to the membrane.

In some embodiments, a dTCR contains a TCR α chain containing a variable α domain, a constant α domain and a first dimerization motif attached to the C-terminus of the constant α domain, and a TCR β chain comprising a variable Rdomain, a constant Rdomain and a first dimerization motif attached to the C-terminus of the constant Rdomain, wherein the first and second dimerization motifs easily interact to form a covalent bond between an amino acid in the first dimerization motif and an amino acid in the second dimerization motif linking the TCR α chain and TCR β chain together.

In some embodiments, the TCR is a scTCR. Typically, a scTCR can be generated using methods known, See e.g., Soo Hoo, W. F. et al. PNAS (USA) 89, 4759 (1992); Wülfing, C. and Plückthun, A., J. Mol. Biol. 242, 655 (1994); Kurucz, I. et al. PNAS (USA) 90 3830 (1993); International published PCT Nos. WO 96/13593, WO 96/18105, WO99/60120, WO99/18129, WO 03/020763, WO2011/044186; and Schlueter, C. J. et al. J. Mol. Biol. 256, 859 (1996). In some embodiments, a scTCR contains an introduced non-native disulfide interchain bond to facilitate the association of the TCR chains (see e.g. International published PCT No. WO 03/020763). In some embodiments, a scTCR is a non-disulfide linked truncated TCR in which heterologous leucine zippers fused to the C-termini thereof facilitate chain association (see e.g. International published PCT No. WO99/60120). In some embodiments, a scTCR contain a TCRα variable domain covalently linked to a TCRβ variable domain via a peptide linker (see e.g., International published PCT No. WO99/18129).

In some embodiments, a scTCR contains a first segment constituted by an amino acid sequence corresponding to a TCR α chain variable region, a second segment constituted by an amino acid sequence corresponding to a TCR β chain variable region sequence fused to the N terminus of an amino acid sequence corresponding to a TCR β chain constant domain extracellular sequence, and a linker sequence linking the C terminus of the first segment to the N terminus of the second segment.

In some embodiments, a scTCR contains a first segment constituted by an α chain variable region sequence fused to the N terminus of an α chain extracellular constant domain sequence, and a second segment constituted by a β chain variable region sequence fused to the N terminus of a sequence β chain extracellular constant and transmembrane sequence, and, optionally, a linker sequence linking the C terminus of the first segment to the N terminus of the second segment.

In some embodiments, a scTCR contains a first segment constituted by a TCR β chain variable region sequence fused to the N terminus of a chain extracellular constant domain sequence, and a second segment constituted by an α chain variable region sequence fused to the N terminus of a sequence α chain extracellular constant and transmembrane sequence, and, optionally, a linker sequence linking the C terminus of the first segment to the N terminus of the second segment.

In some embodiments, the linker of a scTCRs that links the first and second TCR segments can be any linker capable of forming a single polypeptide strand, while retaining TCR binding specificity. In some embodiments, the linker sequence may, for example, have the formula —P-AA-P— wherein P is proline and AA represents an amino acid sequence wherein the amino acids are glycine and serine. In some embodiments, the first and second segments are paired so that the variable region sequences thereof are orientated for such binding. Hence, in some cases, the linker has a sufficient length to span the distance between the C terminus of the first segment and the N terminus of the second segment, or vice versa, but is not too long to block or reduces bonding of the scTCR to the target ligand. In some embodiments, the linker can contain from or from about 10 to 45 amino acids, such as 10 to 30 amino acids or 26 to 41 amino acids residues, for example 29, 30, 31 or 32 amino acids. In some embodiments, the linker has the formula —PGGG-(SGGGG)$_5$—P— wherein P is proline, G is glycine and S is serine (SEQ ID NO:22). In some embodiments, the linker has the sequence GSADDAKKDAAKKDGKS (SEQ ID NO:23)

In some embodiments, the scTCR contains a covalent disulfide bond linking a residue of the immunoglobulin region of the constant domain of the α chain to a residue of the immunoglobulin region of the constant domain of the β chain. In some embodiments, the interchain disulfide bond in a native TCR is not present. For example, in some embodiments, one or more cysteines can be incorporated into the constant region extracellular sequences of the first and second segments of the scTCR polypeptide. In some cases, both a native and a non-native disulfide bond may be desirable.

In some embodiments of a dTCR or scTCR containing introduced interchain disulfide bonds, the native disulfide bonds are not present. In some embodiments, the one or more of the native cysteines forming a native interchain disulfide bonds are substituted to another residue, such as to a serine or alanine. In some embodiments, an introduced disulfide bond can be formed by mutating non-cysteine residues on the first and second segments to cysteine. Exemplary non-native disulfide bonds of a TCR are described in published International PCT No. WO2006/000830.

In some embodiments, the TCR or antigen-binding fragment thereof exhibits an affinity with an equilibrium binding constant for a target antigen of between or between about 10-5 and 10-12 M and all individual values and ranges therein. In some embodiments, the target antigen is an MHC-peptide complex or ligand.

In some embodiments, nucleic acid or nucleic acids encoding a TCR, such as a and R chains, can be amplified by PCR, cloning or other suitable means and cloned into a suitable expression vector or vectors. The expression vector can be any suitable recombinant expression vector, and can be used to transform or transfect any suitable host. Suitable vectors include those designed for propagation and expansion or for expression or both, such as plasmids and viruses.

In some embodiments, the vector can be a vector of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), or the pEX series (Clontech, Palo Alto, Calif.). In some cases, bacteriophage vectors, such as XG10, XGT11, λZapII (Stratagene), λEMBL4, and λNM1149, also can be used. In some embodiments, plant expression vectors can be used and include pBI01, pBI101.2, pBI101.3, pBI121 and pBIN19 (Clontech). In some embodiments, animal expression vectors include pEUK-Cl, pMAM and pMAM-neo (Clontech). In some embodiments, a viral vector is used, such as a retroviral vector.

In some embodiments, the recombinant expression vectors can be prepared using standard recombinant DNA techniques. In some embodiments, vectors can contain regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based. In some embodiments, the vector can contain a nonnative promoter operably linked to the nucleotide sequence encoding the TCR or antigen-binding portion (or other MHC-peptide binding molecule). In some embodiments, the promoter can be a non-viral promoter or a viral promoter, such as a cytomegalovirus (CMV) promoter, an SV40 promoter, an RSV promoter, and a promoter found in the long-terminal repeat of the murine stem cell virus. Other known promoters also are contemplated.

In some embodiments, after the T-cell clone is obtained, the TCR alpha and beta chains are isolated and cloned into a gene expression vector. In some embodiments, the TCR alpha and beta genes are linked via a picornavirus 2A ribosomal skip peptide so that both chains are coexpression. In some embodiments, genetic transfer of the TCR is accomplished via retroviral or lentiviral vectors, or via transposons (see, e.g., Baum et al. (2006) Molecular Therapy: The Journal of the American Society of Gene Therapy. 13:1050-1063; Frecha et al. (2010) Molecular Therapy: The Journal of the American Society of Gene Therapy. 18:1748-1757; and Hackett et al. (2010) Molecular Therapy: The Journal of the American Society of Gene Therapy. 18:674-683.

In some embodiments, to generate a vector encoding a TCR, the α and β chains are PCR amplified from total cDNA isolated from a T cell clone expressing the TCR of interest and cloned into an expression vector. In some embodiments, the α and β chains are cloned into the same vector. In some embodiments, the α and β chains are cloned into different vectors. In some embodiments, the generated α and β chains are incorporated into a retroviral, e.g. lentiviral, vector.

3. Chimeric Auto-Antibody Receptor (CAAR)

In some embodiments, the recombinant receptor is a chimeric autoantibody receptor (CAAR). In some embodiments, the CAAR is specific for an autoantibody. In some embodiments, a cell expressing the CAAR, such as a T cell engineered to express a CAAR, can be used to specifically bind to and kill autoantibody-expressing cells, but not normal antibody expressing cells. In some embodiments, CAAR-expressing cells can be used to treat an autoimmune disease associated with expression of self-antigens, such as autoimmune diseases. In some embodiments, CAAR-expressing cells can target B cells that ultimately produce the autoantibodies and display the autoantibodies on their cell surfaces, mark these B cells as disease-specific targets for therapeutic intervention. In some embodiments, CAAR-expressing cells can be used to efficiently targeting and killing the pathogenic B cells in autoimmune diseases by targeting the disease-causing B cells using an antigen-specific chimeric autoantibody receptor. In some embodiments, the recombinant receptor is a CAAR, such as any described in U.S. Patent Application Pub. No. US 2017/0051035.

In some embodiments, the CAAR comprises an autoantibody binding domain, a transmembrane domain, and an intracellular signaling region. In some embodiments, the intracellular signaling region comprises an intracellular signaling domain. In some embodiments, the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM). In some embodiments, the intracellular signaling region comprises a secondary or costimulatory signaling region (secondary intracellular signaling regions).

In some embodiments, the autoantibody binding domain comprises an autoantigen or a fragment thereof. The choice of autoantigen can depend upon the type of autoantibody being targeted. For example, the autoantigen may be chosen because it recognizes an autoantibody on a target cell, such as a B cell, associated with a particular disease state, e.g. an autoimmune disease, such as an autoantibody-mediated autoimmune disease. In some embodiments, the autoimmune disease includes pemphigus vulgaris (PV). Exemplary autoantigens include desmoglein 1 (Dsg1) and Dsg3.

4. Multi-Targeting

In some embodiments, the cells and methods include multi-targeting strategies, such as expression of two or more genetically engineered receptors on the cell, each recognizing the same of a different antigen and typically each including a different intracellular signaling component. Such multi-targeting strategies are described, for example, in International Patent Application Publication No: WO 2014055668 A1 (describing combinations of activating and costimulatory CARs, e.g., targeting two different antigens present individually on off-target, e.g., normal cells, but present together only on cells of the disease or condition to be treated) and Fedorov et al., Sci. Transl. Medicine, 5(215) (December, 2013) (describing cells expressing an activating and an inhibitory CAR, such as those in which the activating CAR binds to one antigen expressed on both normal or non-diseased cells and cells of the disease or condition to be treated, and the inhibitory CAR binds to another antigen expressed only on the normal cells or cells which it is not desired to treat).

For example, in some embodiments, the cells include a receptor expressing a first genetically engineered antigen receptor (e.g., CAR or TCR) which is capable of inducing an activating or stimulating signal to the cell, generally upon specific binding to the antigen recognized by the first receptor, e.g., the first antigen. In some embodiments, the cell further includes a second genetically engineered antigen receptor (e.g., CAR or TCR), e.g., a chimeric costimulatory receptor, which is capable of inducing a costimulatory signal to the immune cell, generally upon specific binding to a second antigen recognized by the second receptor. In some embodiments, the first antigen and second antigen are the same. In some embodiments, the first antigen and second antigen are different.

In some embodiments, the first and/or second genetically engineered antigen receptor (e.g. CAR or TCR) is capable of inducing an activating or stimulating signal to the cell. In some embodiments, the receptor includes an intracellular signaling component containing ITAM or ITAM-like motifs. In some embodiments, the activation induced by the first receptor involves a signal transduction or change in protein expression in the cell resulting in initiation of an immune response, such as ITAM phosphorylation and/or initiation of ITAM-mediated signal transduction cascade, formation of an immunological synapse and/or clustering of molecules near the bound receptor (e.g. CD4 or CD8, etc.), activation of one or more transcription factors, such as NF-κB and/or AP-1, and/or induction of gene expression of factors such as cytokines, proliferation, and/or survival.

In some embodiments, the first and/or second receptor includes intracellular signaling domains of costimulatory receptors such as CD28, CD137 (4-1BB), OX40, and/or ICOS. In some embodiments, the first and second receptor include an intracellular signaling domain of a costimulatory receptor that are different. In one embodiment, the first receptor contains a CD28 costimulatory signaling region and the second receptor contain a 4-1BB co-stimulatory signaling region or vice versa.

In some embodiments, the first and/or second receptor includes both an intracellular signaling domain containing ITAM or ITAM-like motifs and an intracellular signaling domain of a costimulatory receptor.

In some embodiments, the first receptor contains an intracellular signaling domain containing ITAM or ITAM-like motifs and the second receptor contains an intracellular signaling domain of a costimulatory receptor. The costimulatory signal in combination with the activating or stimulating signal induced in the same cell is one that results in an immune response, such as a robust and sustained immune response, such as increased gene expression, secretion of cytokines and other factors, and T cell mediated effector functions such as cell killing.

In some embodiments, neither ligation of the first receptor alone nor ligation of the second receptor alone induces a robust immune response. In some aspects, if only one receptor is ligated, the cell becomes tolerized or unresponsive to antigen, or inhibited, and/or is not induced to proliferate or secrete factors or carry out effector functions. In some such embodiments, however, when the plurality of receptors are ligated, such as upon encounter of a cell expressing the first and second antigens, a desired response is achieved, such as full immune activation or stimulation, e.g., as indicated by secretion of one or more cytokine, proliferation, persistence, and/or carrying out an immune effector function such as cytotoxic killing of a target cell.

In some embodiments, the two receptors induce, respectively, an activating and an inhibitory signal to the cell, such that binding by one of the receptor to its antigen activates the cell or induces a response, but binding by the second inhibitory receptor to its antigen induces a signal that suppresses or dampens that response. Examples are combinations of activating CARs and inhibitory CARs or iCARs. Such a strategy may be used, for example, in which the activating CAR binds an antigen expressed in a disease or condition but which is also expressed on normal cells, and the inhibitory receptor binds to a separate antigen which is expressed on the normal cells but not cells of the disease or condition.

In some embodiments, the cells expressing the recombinant receptor further include inhibitory CARs (iCARs, see Fedorov et al., *Sci. Transl. Medicine,* 5(215) (2013), such as a CAR recognizing an antigen other than the one associated with and/or specific for the disease or condition whereby an activating signal delivered through the disease-targeting CAR is diminished or inhibited by binding of the inhibitory CAR to its ligand, e.g., to reduce off-target effects.

In some embodiments, the two receptors induce, respectively, an activating and an inhibitory signal to the cell, such that ligation of one of the receptor to its antigen activates the cell or induces a response, but ligation of the second inhibitory receptor to its antigen induces a signal that suppresses or dampens that response. Examples are combinations of activating CARs and inhibitory CARs (iCARs). Such a strategy may be used, for example, to reduce the likelihood of off-target effects in the context in which the activating CAR binds an antigen expressed in a disease or condition but which is also expressed on normal cells, and the inhibitory receptor binds to a separate antigen which is expressed on the normal cells but not cells of the disease or condition.

In some aspects, the chimeric receptor is or includes an inhibitory CAR (e.g. iCAR) and includes intracellular components that dampen or suppress an immune response, such as an ITAM- and/or co stimulatory-promoted response in the cell. Exemplary of such intracellular signaling components are those found on immune checkpoint molecules, including PD-1, CTLA4, LAG3, BTLA, OX2R, TIM-3, TIGIT, LAIR-1, PGE2 receptors, EP2/4 Adenosine receptors including A2AR. In some aspects, the engineered cell includes an inhibitory CAR including a signaling domain of or derived from such an inhibitory molecule, such that it serves to dampen the response of the cell, for example, that induced by an activating and/or costimulatory CAR.

In some embodiments, the multi-targeting strategy is employed in a case where an antigen associated with a particular disease or condition is expressed on a non-diseased cell and/or is expressed on the engineered cell itself, either transiently (e.g., upon stimulation in association with genetic engineering) or permanently. In such cases, by requiring ligation of two separate and individually specific antigen receptors, specificity, selectivity, and/or efficacy may be improved.

In some embodiments, the plurality of antigens, e.g., the first and second antigens, are expressed on the cell, tissue, or disease or condition being targeted, such as on the cancer cell. In some aspects, the cell, tissue, disease or condition is multiple myeloma or a multiple myeloma cell. In some embodiments, one or more of the plurality of antigens generally also is expressed on a cell which it is not desired to target with the cell therapy, such as a normal or non-diseased cell or tissue, and/or the engineered cells themselves. In such embodiments, by requiring ligation of multiple receptors to achieve a response of the cell, specificity and/or efficacy is achieved.

IV. ARTICLE OF MANUFACTURE AND KITS

Also provided are articles of manufacture, such as kits and devices, for the administration of the cells to subjects in according to the provided methods for adoptive cell therapy, and for storage and administration of the cells and compositions.

The articles of manufacture include one or more containers, typically a plurality of containers, packaging material, and a label or package insert on or associated with the container or containers and/or packaging, generally including instructions for administration of the cells to a subject.

In some embodiments, provided are articles of manufacture and/or kits that include a composition comprising a therapeutically effective amount of any of the engineered cells described herein, and instructions for administering, to a subject for treating a disease or condition. In some embodiments, the instructions can specify some or all of the elements of the methods provided herein. In some embodiments, the instructions specify particular instructions for administration of the cells for cell therapy, e.g., doses, timing, selection and/or identification of subjects for administration and conditions for administration. In some embodiments, the instructions can be included as a label or package insert accompanying the compositions for administration. In some embodiments the instructions specify determining a dose of the composition to be administered, e.g., one or more unit doses thereof and/or a volume corresponding to such one or more of unit doses The containers generally contain the cells to be administered, e.g., one or more unit doses thereof. The article of manufacture typically includes a plurality of containers, each containing a single unit dose of the cells. The unit dose may be an amount or number of the cells to be administered to the subject in the first dose or twice the number (or more) the cells to be administered in the first or any one or more consecutive dose(s). It may be the lowest dose or lowest possible dose of the cells that would be administered to the subject in connection with the administration method. In some embodiments, the unit dose is the minimum number of cells or number of cells or the minimum number of reference units or the target reference units or reference units within a target range that would be administered in a single dose to any subject having a particular disease or condition or any subject, according to the methods herein.

In some embodiments, the number of cells in the unit dose is the number of cells or number of recombinant receptor-expressing or CAR-expressing cells, or number, percentage, ratio, frequency and/or proportion of such cells of a certain phenotype, e.g. cells that express or do not express one or more markers is selected from CD4, CD8, CCR7, CD27, CD45RA, annexin V, or activated caspase 3, that it is desired to administer to a particular subject in a dose, such as a subject from which the cells have been derived. In some embodiments, the number of cells in the unit dose is the number of cells or number of recombinant receptorexpressing or CAR-expressing cells, or number, percentage, ratio, frequency and/or proportion of such cells of a certain phenotype, e.g., CCR7$^+$, CD27$^+$, CD45RA$^+$, CD45RA$^-$, CD4$^+$, CD8$^+$, apoptosis marker negative (e.g. Annexin V$^-$ or Caspase 3$^-$) cells, or cells that are positive or negative for one or more of any of the foregoing, that it is desired to administer to a particular subject in a dose, such as a subject from which the cells have been derived.

In some embodiments, the number of cells in the unit dose is the number of cells or number of recombinant receptor-expressing or CAR-expressing cells, or number, percentage, ratio and/or proportion of such cells of a certain phenotype, e.g., CCR7$^+$/CD4$^+$, CCR7$^+$/CD8$^+$, CD27$^+$/CD4$^+$, CD27$^+$/CD8$^+$, CD45RA$^+$/CD4$^+$, CD45RA$^+$/CD8$^+$, CCR7$^-$/CD4$^+$, CCR7$^-$/CD8$^+$, CD27$^-$/CD4$^+$, CD27$^-$/CD8$^+$, CD45RA$^-$/CD4$^+$, CD45RA$^-$/CD8$^+$, CCR7$^+$/CD27$^+$/CD4$^+$, CCR7$^+$/CD27$^+$/CD8$^+$, CCR7$^+$/CD45RA$^-$/CD4$^+$, CCR7$^+$/CD45RA$^-$/CD8$^+$, CCR7$^-$/CD45RA$^-$/CD4$^+$, CCR7$^-$/CD45RA$^-$/CD8$^+$, CCR7$^-$/CD27$^-$/CD4$^+$, CCR7$^-$/CD27$^-$/CD8$^+$; and apoptosis marker negative (e.g. Annexin V$^-$ or Caspase 3) cells, that it is desired to administer to a particular subject in a dose, such as a subject from which the cells have been derived. In some embodiments, the defined number of cells include the number of cells or number of recombinant receptor-expressing or CAR-expressing cells, or number, percentage, ratio and/or proportion of such cells of a certain phenotype, e.g., CCR7$^+$/CD4$^+$, CCR7$^+$/CD8$^+$, CD27$^+$/CD4$^+$, CD27$^+$/CD8$^+$, CD45RA$^+$/CD4$^+$, CD45RA$^+$/CD8$^+$, CCR7$^-$/CD4$^+$, CCR7$^-$/CD8$^+$, CD27$^-$/CD4$^+$, CD27$^-$/CD8$^+$, CD45RA$^-$/CD4$^+$, CD45RA$^-$/CD8$^+$, CCR7$^+$/CD27$^+$/CD4$^+$, CCR7$^+$/CD27$^+$/CD8$^+$, CCR7$^+$/CD45RA$^-$/CD4$^+$, CCR7$^+$/CD45RA$^-$/CD8$^+$, CCR7$^-$/CD45RA$^-$/CD4$^+$, CCR7$^-$/CD45RA$^-$/CD8$^+$, CCR7$^-$/CD27$^-$/CD4$^+$, CCR7$^-$/CD27$^-$/CD8$^+$; and apoptosis marker negative (e.g. Annexin V$^-$ or Caspase 3) cells, and/or any subset thereof, and that it is desired to administer to a particular subject in a dose, such as a subject from which the cells have been derived. In some embodiments, the cells have been derived from the subject to be treated by methods as provided herein or in need thereof.

In some embodiments, the instructions specify the dose or number of cells or cell type(s) and/or a frequency, ratio, and/or percentage of cells or cell types, e.g., individual populations, phenotypes, or subtypes, in the cell composition, such as those with the phenotypes of annexin V$^-$/CCR7$^+$/CAR$^+$; annexin V$^-$/CCR7$^+$/CAR$^+$/CD4$^+$; annexin V$^-$/CCR7$^+$/CAR$^+$/CD8$^+$; annexin V$^-$/CD27$^+$/CAR$^+$; annexin V$^-$/CD27$^+$/CAR$^+$/CD4$^+$; annexin V$^-$/CD27$^+$/CAR$^+$/CD8$^+$; annexin V$^-$/CCR7$^+$/CD27$^+$/CAR$^+$; annexin V$^-$/CCR7$^+$/CD27$^+$/CAR$^+$/CD4$^+$; annexin V$^-$/CCR7$^+$/CD27$^+$/CAR$^+$/CD8$^+$; annexin V$^-$/CCR7$^+$/CD45RA$^-$/CAR$^+$; annexin V$^-$/CCR7$^+$/CD45RA$^-$/CAR$^+$/CD4$^+$; annexin V$^-$/CCR7$^+$/CD45RA$^-$/CAR$^+$/CD8$^+$; annexin V$^-$/CCR7$^-$/CD45RA$^-$/CAR$^+$; annexin V$^-$/CCR7$^-$/CD45RA$^-$/CAR$^+$/CD4$^+$; annexin V$^-$/CCR7$^-$/CD45RA$^-$/CAR$^+$/CD8$^+$; annexin V$^-$/CCR7$^-$/CD27$^-$/CAR$^+$, annexin V$^-$/CCR7$^-$/CD27$^-$/CAR$^+$/CD4$^+$; annexin V$^-$/CCR7$^-$/CD27$^-$/CAR$^+$/CD8$^+$; activated caspase 3$^-$/CCR7$^+$/CAR$^+$; activated caspase 3$^-$/CCR7$^+$/CAR$^+$/CD4$^+$; activated caspase 3$^-$/CCR7$^+$/CAR$^+$/CD8$^+$; activated caspase 3$^-$/CD27$^+$/CAR$^+$; activated caspase 3$^-$/CD27$^+$/CAR$^+$/CD4$^+$; activated caspase 3$^-$/CD27$^+$/CAR$^+$/CD8$^+$; activated caspase 3$^-$/CCR7$^+$/CD27$^+$/CAR$^+$; activated caspase 3$^-$/CCR7$^+$/CD27$^+$/CAR$^+$/CD4$^+$; activated caspase 3$^-$/CCR7$^+$/CD27$^+$/CAR$^+$/CD8$^+$; activated caspase 3$^-$/CCR7$^+$/CD45RA$^-$/CAR$^+$; activated caspase 3$^-$/CCR7$^+$/CD45RA$^-$/CAR$^+$/CD4$^+$; activated caspase 3$^-$/CCR7$^+$/CD45RA$^-$/CAR$^+$/CD8$^+$; activated caspase 3$^-$/CCR7$^-$/CD45RA$^-$/CAR$^+$; activated caspase 3$^-$/CCR7$^-$/CD45RA-CAR$^+$/CD4$^+$; activated caspase 3$^-$/CCR7$^-$/CD45RA$^-$/CAR$^+$/CD8$^+$; activated caspase 3$^-$/CCR7$^-$/CD27$^-$/CAR$^+$; activated caspase 3$^-$/CCR7$^-$/CD27$^-$/CAR$^+$/CD4$^+$; and/or activated caspase 3$^-$/CCR7$^-$/CD27$^-$/CAR$^+$/CD8$^+$; or a combination thereof.

In some embodiments, the article of manufacture contains a unit dose of cells containing a defined number, ratio or percentage of engineered CD8$^+$ T cells that express C—C chemokine receptor type 7 (CCR7) and/or a defined number of engineered CD4$^+$ T cells that express CCR7; and/or a defined ratio of CD8$^+$ T cells that express CCR7 and/or CD4$^+$ T cells that express CCR7. In some embodiments, the article of manufacture contains instructions for administering to a subject having a disease or condition, the therapeutic composition, optionally one or more unit doses thereof and/or a volume corresponding to such one or more of unit doses, and/or instructions for assessing any of the phenotypes described herein and/or instructions for determining a dose for administration and/or a volume corresponding to such one or more of unit doses. Exemplary unit doses of defined number, ratio or percentage of CAR$^+$ expressing cells having a specific phenotype include any as described throughout this disclosure.

In some embodiments, each of the containers individually comprises a unit dose of the cells, e.g., including the same or substantially the same number of cells or number of recombinant receptor-expressing or CAR-expressing cells, or number of such cells of a certain phenotype, e.g. CCR7$^+$/CD4$^+$, CCR7$^+$/CD8$^+$, CD27$^+$/CD4$^+$, CD27$^+$/CD8$^+$, CD45RA$^+$/CD4$^+$, CD45RA$^+$/CD8$^+$, CCR7$^-$/CD4$^+$, CCR7$^-$/CD8$^+$, CD27$^-$/CD4$^+$, CD27$^-$/CD8$^+$, CD45RA$^-$/CD4$^+$, CD45RA$^-$/CD8$^+$, CCR7$^+$/CD27$^+$/CD4$^+$, CCR7$^+$/CD27$^+$/CD8$^+$, CCR7$^+$/CD45RA$^-$/CD4$^+$, CCR7$^+$/CD45RA$^-$/CD8$^+$, CCR7$^-$/CD45RA$^-$/CD4$^+$, CCR7$^-$/CD45RA$^-$/CD8$^+$, CCR7$^-$/CD27-/CD4$^+$, CCR7$^-$/CD27$^-$/CD8$^+$; and apoptosis marker negative (e.g. Annexin V$^-$ or Caspase 3$^-$) cells. In some embodiments, each of the containers individually comprises a unit dose of the cells, e.g., including the same or substantially the same number of target reference units or a number of reference units within a target range.

In some embodiments, the article of manufacture or kit comprises a container, optionally a vial comprising a plurality of CD4$^+$ T cells expressing a recombinant receptor, and a container, optionally a vial comprising a plurality of CD8$^+$ T cells expressing a recombinant receptor. In some embodiments, the article of manufacture or kit comprises a container, optionally a vial comprising a plurality of CD4+ T cells expressing a recombinant receptor, and further comprises, in the same container, a plurality of CD8+ T cells expressing a recombinant receptor. In some embodiments, a cryoprotectant is included with the cells. In some aspects the container is a bag.

Suitable containers include, for example, bottles, vials, syringes, and flexible bags, such as infusion bags. In particular embodiments, the containers are bags, e.g., flexible bags, such as those suitable for infusion of cells to subjects, e.g., flexible plastic or PVC bags, and/or IV solution bags. The bags in some embodiments are sealable and/or able to be sterilized, so as to provide sterile solution and delivery of the cells and compositions. In some embodiments, the containers, e.g., bags, have a capacity of at or about or at least at or about 10, 20, 30, 40, 50, 60, 70, 80, 90, 100, 200, 300, 400, 500, or 1000 mL capacity, such as between at or about 10 and at or about 100 or between at or about 10 and at or about 500 mL capacity. In some embodiments, the containers, e.g., bags, are and/or are made from material which is stable and/or provide stable storage and/or maintenance of cells at one or more of various temperatures, such as in cold temperatures, e.g. below at or about or at or about −20° C., −80° C., −120° C., 135° C. and/or temperatures suitable for cryopreservation, and/or other temperatures, such as temperatures suitable for thawing the cells and body temperature such as at or about 37° C., for example, to permit thawing, e.g., at the subject's location or location of treatment, e.g., at bedside, immediately prior to treatment.

The containers may be formed from a variety of materials such as glass or plastic. In some embodiments, the container has one or more port, e.g., sterile access ports, for example, for connection of tubing or cannulation to one or more tubes, e.g., for intravenous or other infusion and/or for connection for purposes of transfer to and from other containers, such as cell culture and/or storage bags or other containers. Exemplary containers include infusion bags, intravenous solution bags, vials, including those with stoppers pierceable by a needle for injection.

The article of manufacture may further include a package insert or label with one or more pieces of identifying information and/or instructions for use. In some embodiments, the information or instructions indicates that the contents can or should be used to treat a particular condition or disease, and/or providing instructions therefor. The label or package insert may indicate that the contents of the article of manufacture are to be used for treating the disease or condition. In some embodiments, the label or package insert provides instructions to treat a subject, e.g., the subject from which the cells have been derived, via a method involving the administration of a first and one or more consecutive doses of the cells, e.g., according to any of the embodiments of the provided methods. In some embodiments, the instructions specify administration, in a first dose, of one unit dose, e.g., the contents of a single individual container in the article of manufacture, followed by one or more consecutive doses at a specified time point or within a specified time window and/or after the detection of the presence or absence or amount or degree of one or more factors or outcomes in the subject.

In some embodiments, the instructions specify administering one or more of the unit doses to the subject. In some embodiments, the instructions specify administration of a dose determined using the methods provided herein. In some embodiments, the instructions specify methods of determining and/or calculating an appropriate dose, based on assessment of expression of cell surface markers.

In some embodiments, the label or package insert or packaging comprises an identifier to indicate the specific identity of the subject from which the cells are derived and/or are to be administered. In the case of autologous transfer, the identity of the subject from which the cells are derived is the same as the identity of the subject to which the cells are to be administered. Thus, the identifying information may specify that the cells are to be administered to a particular patient, such as the one from which the cells were originally derived. Such information may be present in the packaging material and/or label in the form of a bar code or other coded identifier, or may indication the name and/or other identifying characteristics of the subject.

The article of manufacture in some embodiments includes one or more, typically a plurality, of containers containing compositions comprising the cells, e.g., individual unit dose forms thereof, and further include one or more additional containers with a composition contained therein which includes a further agent, such as a cytotoxic or otherwise therapeutic agent, for example, which is to be administered in combination, e.g., simultaneously or sequentially in any order, with the cells. Alternatively, or additionally, the article of manufacture may further include another or the same container comprising a pharmaceutically-acceptable buffer. It may further include other materials such as other buffers, diluents, filters, tubing, needles, and/or syringes.

The term "package insert" is used to refer to instructions customarily included in commercial packages of therapeutic products, that contain information about the indications, usage, dosage, administration, combination therapy, contraindications and/or warnings concerning the use of such therapeutic products.

In some embodiments, the articles of manufacture and/or kits further include one or more reagents for assaying biological samples, e.g., biological samples from subjects who are candidates for administration or who have been administered the therapy, and optionally instructions for use of the reagents or assays. In some embodiments, the article of manufacture and/or kits contain reagents for measuring the level of particular phenotypic markers, e.g., CD4, CD8, CCR7, CD27, and/or CD45RA, and particular markers indicative of apoptosis, such as annexin V and/or caspase 3 cleavage, and instructions for measuring. In some embodiments, the biological sample is or is obtained from a blood, plasma or serum sample. In some embodiments, the reagents can be used prior to the administration of the cell therapy or after the administration of cell therapy, for diagnostic purposes, to identify subjects and/or to assess treatment outcomes and/or toxicities. For example, in some embodiments, the article of manufacture and/or kits further contain reagents for measuring the level of particular cell surface markers or other markers that are associated with toxicity, and instructions for measuring. In some embodiments, the reagents include components for performing an in vitro assay to measure the cell surface markers or other markers, such as an immunoassay, an aptamer-based assay, a histological or cytological assay, or an mRNA expression level assay. In some embodiments, the in vitro assay is selected from among an enzyme linked immunosorbent assay (ELISA), immunoblotting, immunoprecipitation, radioimmunoassay (RIA), immunostaining, flow cytometry assay, surface plasmon resonance (SPR), chemiluminescence assay, lateral flow immunoassay, inhibition assay and avidity assay. In some aspects, the reagent is a binding reagent that specifically binds the cell surface markers or other markers.

In some cases, the binding reagent is an antibody or antigen-binding fragment thereof, an aptamer or a nucleic acid probe. In some embodiments, the reagents include reagents for detecting expression and/or presence of markers such as CD4, CD8, CCR7, CD27, CD45RA, annexin V, or activated caspase 3.

V. DEFINITIONS

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

As used herein, recitation that nucleotides or amino acid positions "correspond to" nucleotides or amino acid positions in a disclosed sequence, such as set forth in the Sequence listing, refers to nucleotides or amino acid positions identified upon alignment with the disclosed sequence to maximize identity using a standard alignment algorithm, such as the GAP algorithm. By aligning the sequences, one skilled in the art can identify corresponding residues, for example, using conserved and identical amino acid residues as guides. In general, to identify corresponding positions, the sequences of amino acids are aligned so that the highest order match is obtained (see, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New. Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; Carrillo et al. (1988) SIAM J Applied Math 48: 1073).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors." Among the vectors are viral vectors, such as retroviral, e.g., gammaretroviral and lentiviral vectors.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

As used herein, "percent (%) amino acid sequence identity" and "percent identity" when used with respect to an amino acid sequence (reference polypeptide sequence) is defined as the percentage of amino acid residues in a candidate sequence (e.g., the subject antibody or fragment) that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software.

Those skilled in the art can determine appropriate parameters for aligning sequences, including any algorithms needed to achieve maximal alignment over the full length of the sequences being compared.

An amino acid substitution may include replacement of one amino acid in a polypeptide with another amino acid. The substitution may be a conservative amino acid substitution or a non-conservative amino acid substitution. Amino acid substitutions may be introduced into a binding molecule, e.g., antibody, of interest and the products screened for a desired activity, e.g., retained/improved antigen binding, decreased immunogenicity, or improved ADCC or CDC.

Amino acids generally can be grouped according to the following common side-chain properties:
  (1) hydrophobic: Norleucine, Met, Ala, Val, Leu, Ile;
  (2) neutral hydrophilic: Cys, Ser, Thr, Asn, Gln;
  (3) acidic: Asp, Glu;
  (4) basic: His, Lys, Arg;
  (5) residues that influence chain orientation: Gly, Pro;
  (6) aromatic: Trp, Tyr, Phe.

In some embodiments, conservative substitutions can involve the exchange of a member of one of these classes for another member of the same class. In some embodiments, non-conservative amino acid substitutions can involve exchanging a member of one of these classes for another class.

As used herein, a composition refers to any mixture of two or more products, substances, or compounds, including cells. It may be a solution, a suspension, liquid, powder, a paste, aqueous, non-aqueous or any combination thereof.

As used herein, a "subject" is a mammal, such as a human or other animal, and typically is human.

VI. EXEMPLARY EMBODIMENTS

Among the provided embodiments are:

1. A therapeutic composition comprising T cells expressing a recombinant receptor, wherein at least at or about, or at or about, 40%, 50%, 60%, 70%, 80%, 85%, 90%, 91%, 92%, 93%, 94%, 95%, 96%, 97%, 98%, 99% or 100% of the total number of T cells in the composition or of the total number of T cells in the composition expressing the recombinant receptor, are surface positive for CCR7 and/or CD27.

2. The therapeutic composition of embodiment 1, wherein at least at or about, or at or about 50% of the total number of T cells in the composition or of the total number of T cells in the composition expressing the recombinant receptor are surface positive for CCR7 and/or CD27.

3. The therapeutic composition of embodiment 1, wherein at least at or about, or at or about 60% of the total number of T cells in the composition or of the total number of T cells in the composition expressing the recombinant receptor are surface positive for CCR7 and/or CD27.

4. The therapeutic composition of embodiment 1, wherein at least at or about, or at or about 70% of the total number of T cells in the composition or of the total number of T cells in the composition expressing the recombinant receptor are surface positive for CCR7 and/or CD27.

5. The therapeutic composition of embodiment 1, wherein at least at or about, or at or about 80% of the total number of T cells in the composition or of the total number of T cells in the composition expressing the recombinant receptor are surface positive for CCR7 and/or CD27.

6. The therapeutic composition of any of embodiments 1-5, wherein:
  the T cells in the composition and/or expressing the recombinant receptor comprise or consist of $CD8^+$ T cells;
  the T cells in the composition and/or expressing the recombinant receptor comprise or consist of $CD4^+$ T cells;
  the T cells in the composition and/or expressing the recombinant receptor comprise or consist of $CD8^+$ and $CD4^+$ T cells;
  the T cells in the composition and/or expressing the recombinant receptor comprise or consist of at least at or about 30%, 50% 95%, 96%, 97%, 98%, or 99% or 100% $CD8^+$ T cells;
  the T cells in the composition and/or expressing the recombinant receptor comprise or consist of at least at or about 30%, 50% 95%, 96%, 97%, 98%, or 99% or 100% $CD4^+$ T cells; and/or
  the T cells in the composition and/or expressing the recombinant receptor comprise or consist of approximately 1:1 or approximately between 1:3 and 3:1 or approximately between 1:2 and 2:1, $CD4^+$:$CD8^+$ T cells.

7. A therapeutic composition comprising T cells expressing a recombinant receptor, wherein at least at or about, or at or about, 80%, 85%, 90%, 91%, 92%, 93%, 94%, 95%, 96%, 97%, 98%, 99% or 100% of the total number of T cells in the composition, or the total number of T cells in the composition expressing the recombinant receptor, are surface positive for CCR7 and/or CD27, optionally wherein:
  the T cells in the composition and/or expressing the recombinant receptor comprise or consist of $CD8^+$ T cells;
  the T cells in the composition and/or expressing the recombinant receptor comprise or consist of $CD4^+$ T cells;
  the T cells in the composition and/or expressing the recombinant receptor comprise or consist of $CD8^+$ and $CD4^+$ T cells;
  the T cells in the composition and/or expressing the recombinant receptor comprise or consist of at least at or about 30%, 50% 95%, 96%, 97%, 98%, or 99% or 100% $CD8^+$ T cells;
  the T cells in the composition and/or expressing the recombinant receptor comprise or consist of at least at or about 30%, 50% 95%, 96%, 97%, 98%, or 99% or 100% $CD4^+$ T cells; and/or
  the T cells in the composition and/or expressing the recombinant receptor comprise or consist of approximately 1:1 or approximately between 1:3 and 3:1 or approximately between 1:2 and 2:1, $CD4^+$:$CD8^+$ T cells.

8. The therapeutic composition of any of embodiments 1-7, the total number of T cells in the composition, or the total number of T cells in the composition expressing the recombinant receptor, are surface positive for CCR7.

9. The therapeutic composition of any of embodiments 1-7, the total number of T cells in the composition, or the total number of T cells in the composition expressing the recombinant receptor, are surface positive for CD27.

10. The therapeutic composition of any of embodiments 1-7, the total number of T cells in the composition, or the total number of T cells in the composition expressing the recombinant receptor, are surface positive for CCR7 and CD27.

11. The composition of any of embodiments 1-10, wherein the composition comprises one or more unit doses of cells.

12. The composition of any of embodiments 1-11, wherein the unit dose or composition comprises between at or about $1\times10^5$ and at or about $1\times10^8$, between at or about $5\times10^5$ and at or about $1\times10^7$, or between at or about $1\times10^6$ and at or about $1\times10^7$ total CD8$^+$ cells that express the recombinant receptor (receptor$^+$/CD8$^+$ cells) or total CD4$^+$ cell that express the recombinant receptor (receptor$^+$/CD4$^+$ cells), total receptor$^+$/CD8$^+$/CCR7$^+$ cells, total receptor$^+$/CD4$^+$/CCR7$^+$ cells, total receptor$^+$/CD8$^+$/CD27$^+$ cells, or total receptor$^+$/CD4$^+$/CD27$^+$ cells, each inclusive and/or wherein the unit dose or composition comprises no more than about $1\times10^8$, no more than about $5\times10^7$, no more than about $1\times10^7$, no more than about $5\times10^6$, no more than about $1\times10^6$, or no more than about $5\times10^5$ total receptor$^+$/CD8$^+$ cells or total receptor$^+$/CD4$^+$ cells, total receptor$^+$/CD8$^+$/CCR7$^+$ cells, total receptor$^+$/CD4$^+$/CCR7$^+$ cells, total receptor$^+$/CD8$^+$/CD27$^+$ cells, or total receptor$^+$/CD4$^+$/CD27$^+$ cells.

13. The composition of any of embodiments 1-12, wherein the composition or unit dose comprises at least about $3\times10^6$, $4\times10^6$, $5\times10^6$, $6\times10^6$, $7\times10^6$, $8\times10^6$, $9\times10^6$, or $1\times10^7$ total receptor$^+$/CD8$^+$/CCR7$^+$ cells or total receptor$^+$/CD8$^+$/CD27$^+$ cells and/or at least about $3\times10^6$, $4\times10^6$, $5\times10^6$, $6\times10^6$, $7\times10^6$, $8\times10^6$, $9\times10^6$, or $1\times10^7$ total receptor$^+$/CD4$^+$/CCR7$^+$ cells or total receptor$^+$/CD4$^+$/CD27$^+$.

14. The composition of any of embodiments 1-13, wherein the composition or unit dose comprises between at or about $3\times10^6$ and at or about $2.5\times10^7$, between at or about $4\times10^6$ and at or about $2\times10^7$, or between at or about $5\times10^6$ and at or about $1\times10^7$ total receptor$^+$/CD8$^+$/CCR7$^+$ cells or total receptor$^+$/CD8$^+$/CD27$^+$ cells and/or between at or about $3\times10^6$ and at or about $2.5\times10^7$, between at or about $4\times10^6$ and at or about $2\times10^7$, or between at or about $5\times10^6$ and at or about $1\times10^7$ total receptor$^+$/CD4$^+$/CCR7$^+$ cells or total receptor$^+$/CD4$^+$/CD27$^+$, each inclusive.

15. The composition of any of embodiments 1-14, wherein at least 15%, 20%, 30%, 40%, 50%, 60%, 70%, 80% or 90% of the total receptor$^+$ cells in the composition or unit dose, or between about 15% and 90%, between about 20% and 80%, between about 30% and 70%, or between about 40% and 60%, each inclusive, of the total receptor$^+$ cells in the composition or unit dose are receptor$^+$/CD8$^+$/CCR7$^+$ or receptor$^+$/CD8$^+$/CD27$^+$; or at least 15%, 20%, 30%, 40%, 50%, 60%, 70%, 80% or 90% of the total receptor$^+$ cells in the composition or unit dose, or between about 15% and 90%, between about 20% and 80%, between about 30% and 70%, or between about 40% and 60%, each inclusive, of the total receptor$^+$ cells in the composition or unit dose are receptor$^+$/CD4$^+$/CCR7$^+$ or receptor$^+$/CD4$^+$/CD27$^+$.

16. The composition of any of embodiments 1-15, wherein the unit dose of cells or composition comprises a defined ratio of receptor$^+$/CD8$^+$/CCR7$^+$ cells to receptor$^+$/CD4$^+$/CCR7$^+$ cells, which ratio optionally is or is approximately 1:1 or is between approximately 1:3 and approximately 3:1.

17. The composition of embodiment 16, wherein the defined number or ratio is further based on expression or absence of expression of CD27 and/or CD45RA on the cells.

18. The composition of embodiment 16 or embodiment 17, wherein the defined number of cells further express or do not express CD27 and/or CD45RA, optionally wherein the defined number of cells further are CD27$^+$ or CD45RA$^-$ cells.

19. The composition of any of embodiments 1-15, wherein the unit dose of cells or composition comprises a defined ratio of receptor$^+$/CD8$^+$/CD27$^+$ cells to receptor$^+$/CD4$^+$/CD27$^+$ cells, which ratio optionally is or is approximately 1:1 or is between approximately 1:3 and approximately 3:1.

20. The composition of embodiment 19, wherein the defined number or ratio is further based on expression or absence of expression of CCR7 and/or CD45RA on the cells.

21. The composition of embodiment 19 or embodiment 20, wherein the defined number of cells further express or do not express CCR7 and/or CD45RA, optionally wherein the defined number of cells further are CCR7$^+$ or CD45RA$^-$ cells.

22. The composition of any of embodiments 1-21, wherein the unit dose of cells or composition comprises a defined number of receptor$^+$/CD8$^+$/CCR7$^+$/CD27$^+$ cells and/or receptor$^+$/CD8$^+$/CCR7$^+$/CD45RA$^-$ cells.

23. The composition of any of embodiments 1-21, wherein the unit dose of cells or composition comprises a defined number of receptor$^+$/CD4$^+$/CCR7$^+$/CD27$^+$ cells and/or receptor$^+$/CD4$^+$/CCR7$^+$/CD45RA$^-$ cells.

24. The composition of any of embodiments 1-23, wherein at least 15%, 20%, 30%, 40%, 50%, 60%, 70%, 80% or 90% of the total receptor$^+$ cells in the unit dose or composition, or between about 15% and 90%, between about 20% and 80%, between about 30% and 70%, or between about 40% and 60%, each inclusive, of the total receptor$^+$ cells in the unit dose or composition are receptor$^+$/CD8$^+$/CCR7$^+$/CD27$^+$, receptor$^+$/CD8$^+$/CCR7$^+$/CD45RA$^-$, receptor$^+$/CD4$^+$/CCR7$^+$/CD27$^+$ or receptor$^+$/CD4$^+$/CCR7$^+$/CD45RA$^-$.

25. The composition of any of embodiments 1-24, wherein the unit dose or number of cells expressing the recombinant receptor comprises between at or about $1\times10^5$ and at or about $5\times10^8$, between at or about $1\times10^5$ and at or about $1\times10^8$, between at or about $5\times10^5$ and at or about $1\times10^7$, or between at or about $1\times10^6$ and at or about $1\times10^7$ total CD3$^+$ cells that express the recombinant receptor (receptor$^+$/CD3$^+$ cells) or total CD3$^+$ cells, each inclusive.

26. The composition of any of embodiments 1-24, wherein the unit dose or number of cells expressing the recombinant receptor comprises no more than about $5\times10^8$, no more than about $1\times10^8$, no more than about $5\times10^7$, no more than about $1\times10^7$, no more than about $5\times10^6$, no more than about $1\times10^6$, or no more than about $5\times10^5$ total receptor$^+$/CD3$^+$ cells or total CD3$^+$ cells.

27. The composition of any of embodiments 1-26, wherein the total number of CD3$^+$ cells, total number of receptor$^+$/CD3$^+$ cells, total number of receptor$^+$/CD8$^+$ cells, total number of receptor$^+$/CD4$^+$ cells, total number of receptor$^+$/CD8$^+$/CCR7$^+$ cells, total number of receptor$^+$/CD4$^+$/CCR7$^+$ cells, total number of receptor$^+$/CD8$^+$/CD27$^+$ cells, total number of receptor$^+$/CD4$^+$/CD27$^+$ cells, total number of receptor$^+$/CD8$^+$/CCR7$^+$/CD27$^+$ cells, total number of receptor$^+$/CD4$^+$/CCR7$^+$/CD27$^+$ cells, total number of receptor$^+$/CD8$^+$/CCR7$^+$/CD45RA$^-$ cells and/or receptor$^+$/CD4$^+$/CCR7$^+$/CD45RA$^-$ cells is the total number of such cells that are live or viable.

28. The composition of any of embodiments 1-27, wherein the total number of CD3$^+$ cells, total number of receptor$^+$/CD3$^+$ cells, total number of receptor$^+$/CD8$^+$ cells, total number of receptor+/CD4+ cells, total number of receptor+/CD8+/CCR7+ cells, total number of receptor+/CD4+/CCR7+ cells, total number of receptor+/CD8+/CCR7+/CD27+ cells, total number of receptor+/CD8+/CD27+ cells, total number of receptor+/CD4+/CD27+ cells, total number of receptor+/CD4+/CCR7+/CD27+ cells, total number of receptor+/CD8+/CCR7+/CD45RA− cells and/or receptor+/CD4+/CCR7+/CD45RA− cells is the total number of such cells that do not express an apoptotic marker and/or is the total number of such cells that are apoptotic marker negative (−), wherein the apoptotic marker is Annexin V or activated Caspase 3.

29. The composition of any of embodiments 1-28, wherein the recombinant receptor is or comprises a chimeric receptor and/or a recombinant antigen receptor.

30. The composition of any of embodiments 1-29, wherein the recombinant receptor is capable of binding to a target antigen that is associated with, specific to, and/or expressed on a cell or tissue of a disease, disorder or condition.

31. The composition of embodiment 30, wherein the disease, disorder or condition is an infectious disease or disorder, an autoimmune disease, an inflammatory disease, or a tumor or a cancer.

32. The composition of embodiment 30 or embodiment 31, wherein the target antigen is a tumor antigen.

33. The composition of any of embodiments 30-32, wherein the target antigen is selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD138, CD171, epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), G Protein Coupled Receptor 5D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22Ra), IL-13 receptor alpha 2 (IL-13Ra2), kinase insert domain receptor (kdr), kappa light chain, L1 cell adhesion molecule (L1-CAM), CE7 epitope of L-CAM, Leucine Rich Repeat Containing 8 Family Member A (LRRC8A), Lewis Y, Melanoma-associated antigen (MAGE)-A1, MAGE-A3, MAGE-A6, mesothelin, c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), vascular endothelial growth factor receptor (VEGFR), vascular endothelial growth factor receptor 2 (VEGFR2), Wilms Tumor 1 (WT-1), a pathogen-specific antigen, or an antigen associated with a universal tag, and/or biotinylated molecules, and/or molecules expressed by HIV, HCV, HBV or other pathogens.

34. The composition of any of embodiments 1-33, wherein the recombinant receptor is or comprises a functional non-TCR antigen receptor or a TCR or antigen-binding fragment thereof.

35. The composition of any of embodiments 1-34, wherein the recombinant receptor is a chimeric antigen receptor (CAR).

36. The composition of any of embodiments 1-35, wherein the recombinant receptor comprises an extracellular domain comprising an antigen-binding domain.

37. The composition of embodiment 36, wherein the antigen-binding domain is or comprises an antibody or an antibody fragment thereof, which optionally is a single chain fragment.

38. The composition of embodiment 37, wherein the fragment comprises antibody variable regions joined by a flexible linker.

39. The composition of embodiment 37 or embodiment 38, wherein the fragment comprises an scFv.

40. The composition of any of embodiments 1-39, wherein the recombinant receptor comprises an intracellular signaling region.

41. The composition of embodiment 40, wherein the intracellular signaling region comprises an intracellular signaling domain.

42. The composition of embodiment 41, wherein the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM).

43. The composition of embodiment 42, wherein the intracellular signaling domain is or comprises an intracellular signaling domain of a CD3 chain, optionally a CD3-zeta (CD3ζ) chain, or a signaling portion thereof.

44. The composition of any of embodiments 40-43, wherein the recombinant receptor further comprises a transmembrane domain disposed between the extracellular domain and the intracellular signaling region.

45. The composition of any of embodiments 40-44, wherein the intracellular signaling region further comprises a costimulatory signaling domain.

46. The composition of embodiment 45, wherein the costimulatory signaling domain comprises an intracellular signaling domain of a T cell costimulatory molecule or a signaling portion thereof.

47. The composition of embodiment 45 or embodiment 46, wherein the costimulatory signaling domain comprises an intracellular signaling domain of a CD28, a 4-1BB or an ICOS or a signaling portion thereof.

48. The composition of any of embodiments 45-47, wherein the costimulatory signaling domain is between the transmembrane domain and the intracellular signaling domain.

49. The composition of any of embodiments 1-48, wherein the T cells are primary T cells obtained from a subject.

50. The composition of any of embodiments 1-49, wherein the T cells are autologous to the subject.

51. The composition of any of embodiments 1-50, wherein the T cells are allogeneic to the subject.

52. An article of manufacture, comprising a container comprising a composition of any of embodiments 1-51, and instructions for administering to a subject having a disease or condition, the therapeutic composition, optionally one or more unit doses thereof and/or a volume corresponding to such one or more of unit doses.

53. An article of manufacture, comprising:
a container, comprising one or more unit doses of cells, present in one or more therapeutic composition, the unit dose comprising a plurality of $CD8^+$ and/or $CD4^+$ T cells expressing (optionally engineered to express) a recombinant receptor, wherein a unit dose of cells comprises a defined number of recombinant receptor-expressing $CD8^+$ T cells that express (optionally surface express) C—C chemokine receptor type 7 (CCR7) (receptor$^+$/$CD8^+$/$CCR7^+$ cells) and/or a defined number of recombinant receptor-expressing $CD4^+$ T cells that express CCR7 (receptor$^+$/$CD4^+$/$CCR7^+$ cells) and/or a defined ratio of receptor$^+$/$CD8^+$/$CCR7^+$ cells to receptor$^+$/$CD4^+$/$CCR7^+$ cells and/or a defined ratio of receptor$^+$/$CD8^+$/$CCR7^+$ cells and/or receptor$^+$/$CD4^+$/$CCR7^+$ cells to another subset of cells in the composition; and
instructions for administering to a subject having a disease or condition, the therapeutic composition, optionally one or more unit doses thereof and/or a volume corresponding to such one or more of unit doses.

54. An article of manufacture, comprising:
a container, comprising one or more unit doses of cells, present in one or more therapeutic composition, the unit dose comprising a plurality of $CD8^+$ and/or $CD4^+$ T cells expressing (optionally engineered to express) a recombinant receptor, wherein a unit dose of cells comprises a defined number of recombinant receptor-expressing $CD8^+$ T cells that express (optionally surface express) cluster of differentiation 27 (CD27) (receptor$^+$/$CD8^+$/$CD27^+$ cells) and/or a defined number of recombinant receptor-expressing $CD4^+$ T cells that express CD27 (receptor$^+$/$CD4^+$/$CD27^+$ cells) and/or a defined ratio of receptor$^+$/$CD8^+$/$CD27^+$ cells to receptor$^+$/$CD4^+$/$CD27^+$ cells and/or a defined ratio of receptor$^+$/$CD8^+$/$CD27^+$ cells and/or receptor$^+$/$CD4^+$/$CD27^+$ cells to another subset of cells in the composition; and
instructions for administering to a subject having a disease or condition, the therapeutic composition, optionally one or more unit doses thereof and/or a volume corresponding to such one or more of unit doses.

55. The article of manufacture of embodiment 53 or embodiment 54, wherein the unit dose of cells comprises the composition of any of embodiments 1-51.

56. The article of manufacture of any of embodiments 53-55, wherein the unit dose of cells comprises a defined number of $CD8^+$/$CCR7^+$ cells; and/or wherein the unit dose of cells comprises a defined number of $CD4^+$/$CCR7^+$ cells.

57. The article of manufacture of any of embodiments 53-55, wherein the unit dose of cells comprises a defined number of $CD8^+$/$CD27^+$ cells; and/or wherein the unit dose of cells comprises a defined number of $CD4^+$/$CD27^+$ cells.

58. The article of manufacture or composition of any of embodiments 52-57,
wherein the unit dose comprises between at or about $1\times10^5$ and at or about $1\times10^8$, between at or about $5\times10^5$ and at or about $1\times10^7$, or between at or about $1\times10^6$ and at or about $1\times10^7$ total $CD8^+$ cells that express the recombinant receptor (receptor$^+$/$CD8^+$ cells) or total $CD4^+$ cell that express the recombinant receptor (receptor$^+$/$CD4^+$ cells), total receptor$^+$/$CD8^+$/$CCR7^+$ cells, total receptor$^+$/$CD4^+$/$CCR7^+$ cells, total receptor$^+$/$CD8^+$/$CD27^+$ cells, or total receptor$^+$/$CD4^+$/$CD27^+$ cells, each inclusive and/or
wherein the unit dose comprises no more than about $1\times10^8$, no more than about $5\times10^7$, no more than about $1\times10^7$, no more than about $5\times10^6$, no more than about $1\times10^6$, or no more than about $5\times10^5$ total receptor$^+$/$CD8^+$ cells or total receptor$^+$/$CD4^+$ cells, total receptor$^+$/$CD8^+$/$CCR7^+$ cells, total receptor$^+$/$CD4^+$/$CCR7^+$ cells, total receptor$^+$/$CD8^+$/$CD27^+$ cells, or total receptor$^+$/$CD4^+$/$CD27^+$ cells.

59. The article of manufacture of any of embodiments 52-58, wherein the unit dose comprises at least about $3\times10^6$, $4\times10^6$, $5\times10^6$, $6\times10^6$, $7\times10^6$, $8\times10^6$, $9\times10^6$, or $1\times10^7$ total receptor$^+$/$CD8^+$/$CCR7^+$ cells or total receptor$^+$/$CD8^+$/$CD27^+$ cells and/or at least about $3\times10^6$, $4\times10^6$, $5\times10^6$, $6\times10^6$, $7\times10^6$, $8\times10^6$, $9\times10^6$, or $1\times10^7$ total receptor$^+$/$CD4^+$/$CCR7^+$ cells or total receptor$^+$/$CD4^+$/$CD27^+$.

60. The article of manufacture of any of embodiments 52-59, wherein the unit dose comprises between at or about $3\times10^6$ and at or about $2.5\times10^7$, between at or about $4\times10^6$ and at or about $2\times10^7$, or between at or about $5\times10^6$ and at or about $1\times10^7$ total receptor$^+$/$CD8^+$/$CCR7^+$ cells or total receptor$^+$/$CD8^+$/$CD27^+$ cells and/or between at or about $3\times10^6$ and at or about $2.5\times10^7$, between at or about $4\times10^6$ and at or about $2\times10^7$, or between at or about $5\times10^6$ and at or about $1\times10^7$ total receptor$^+$/$CD4^+$/$CCR7^+$ cells or total receptor$^+$/$CD4^+$/$CD27^+$, each inclusive.

61. The article of manufacture of any of embodiments 52-60, wherein at least 15%, 20%, 30%, 40%, 50%, 60%, 70%, 80% or 90% of the total receptor$^+$ cells in the unit dose, or between about 15% and 90%, between about 20% and 80%, between about 30% and 70%, or between about 40% and 60%, each inclusive, of the total receptor$^+$ cells in the unit dose are receptor$^+$/$CD8^+$/$CCR7^+$ or receptor$^+$/$CD8^+$/$CD27^+$; or at least 15%, 20%, 30%, 40%, 50%, 60%, 70%, 80% or 90% of the total receptor$^+$ cells in the unit dose, or between about 15% and 90%, between about 20% and 80%, between about 30% and 70%, or between about 40% and 60%, each inclusive, of the total receptor$^+$ cells in the unit dose are receptor$^+$/$CD4^+$/$CCR7^+$ or receptor$^+$/$CD4^+$/$CD27^+$.

62. The article of manufacture of any of embodiments 51-56 and 58-61, wherein the unit dose of cells or composition comprises a defined ratio of receptor$^+$/$CD8^+$/$CCR7^+$ cells to receptor$^+$/$CD4^+$/$CCR7^+$ cells, which ratio optionally is or is approximately 1:1 or is between approximately 1:3 and approximately 3:1.

63. The article of manufacture of embodiment 62, wherein the defined number or ratio is further based on expression or absence of expression of CD27 and/or CD45RA on the cells.

64. The article of manufacture of embodiment 62 or embodiment 63, wherein the defined number of cells further express or do not express CD27 and/or CD45RA, optionally wherein the defined number of cells further are $CD27^+$ or $CD45RA^-$ cells.

65. The article of manufacture of any of embodiments 51-55 and 57-61, wherein the unit dose of cells or composition comprises a defined ratio of receptor$^+$/$CD8^+$/$CD27^+$ cells to receptor$^+$/$CD4^+$/$CD27^+$ cells, which ratio optionally is or is approximately 1:1 or is between approximately 1:3 and approximately 3:1.

66. The article of manufacture of embodiment 65, wherein the defined number or ratio is further based on expression or absence of expression of CCR7 and/or CD45RA on the cells.

67. The article of manufacture of embodiment 65 or embodiment 66, wherein the defined number of cells further express or do not express CCR7 and/or CD45RA, optionally wherein the defined number of cells further are CCR7$^+$ or CD45RA$^-$ cells.

68. The article of manufacture of any of embodiments 51-67, wherein the unit dose of cells comprises a defined number of receptor$^+$/CD8$^+$/CCR7$^+$/CD27$^+$ cells and/or receptor$^+$/CD8$^+$/CCR7$^+$/CD45RA$^-$ cells.

69. The article of manufacture of any of embodiments 51-67, wherein the unit dose of cells comprises a defined number of receptor$^+$/CD4$^+$/CCR7$^+$/CD27$^+$ cells and/or receptor$^+$/CD4$^+$/CCR7$^+$/CD45RA$^-$ cells.

70. The article of manufacture of any of embodiments 51-69, wherein at least 15%, 20%, 30%, 40%, 50%, 60%, 70%, 80% or 90% of the total receptor$^+$ cells in the unit dose, or between about 15% and 90%, between about 20% and 80%, between about 30% and 70%, or between about 40% and 60%, each inclusive, of the total receptor$^+$ cells in the unit dose are receptor$^+$/CD8$^+$/CCR7$^+$/CD27$^+$, receptor$^+$/CD8$^+$/CCR7$^+$/CD45RA$^-$, receptor$^+$/CD4$^+$/CCR7$^+$/CD27$^+$ or receptor$^+$/CD4$^+$/CCR7$^+$/CD45RA$^-$.

71. An article of manufacture, comprising:
  a container, comprising one or more unit doses of cells, present in one or more therapeutic composition, the unit dose comprising a plurality of CD8$^+$ and/or CD4$^+$ T cells expressing, optionally engineered to express, a recombinant receptor, wherein a unit dose of cells comprises a defined number of recombinant receptor-expressing CD8$^+$ T cells that express CCR7 and CD27 (receptor$^+$/CD8$^+$/CCR7$^+$/CD27$^+$ cells) and/or a defined number of recombinant receptor-expressing CD4$^+$ T cells that express CCR7 and CD27 (receptor$^+$/CD4$^+$/CCR7$^+$/CD27$^+$ cells) and/or a defined ratio of receptor$^+$/CD8$^+$/CCR7$^+$/CD27$^+$ cells to receptor$^+$/CD4$^+$/CCR7$^+$/CD27$^+$ cells and/or a defined ratio of receptor$^+$/CD8$^+$/CCR7$^+$/CD27$^+$ cells and/or receptor$^+$/CD4$^+$/CCR7$^+$/CD27$^+$ cells to another subset of cells in the composition; and
  instructions for administering to a subject having a disease or condition, the therapeutic composition, optionally one or more unit doses thereof and/or a volume corresponding to such one or more of unit doses.

72. The article of manufacture of any of embodiments 63, 64 and 66-71, wherein the unit dose of cells comprises a defined number of CD8$^+$/CCR7$^+$/CD27$^+$ cells.

73. The article of manufacture of any of embodiments 63, 64 and 66-71, wherein the unit dose of cells comprises a defined number of CD4$^+$/CCR7$^+$/CD27$^+$ cells.

74. The article of manufacture of any of embodiments 63, 64 and 66-73, wherein the unit dose comprises between at or about $1\times10^5$ and at or about $1\times10^8$, between at or about $5\times10^5$ and at or about $1\times10^7$, or between at or about $1\times10^6$ and at or about $1\times10^7$ total CD8$^+$ cells that express the recombinant receptor (receptor$^+$/CD8$^+$ cells) or total CD4$^+$ cell that express the recombinant receptor (receptor$^+$/CD4$^+$ cells), total receptor$^+$/CD8$^+$/CCR7$^+$/CD27$^+$ cells, or total receptor$^+$/CD4$^+$/CCR7$^+$/CD27$^+$ cells, each inclusive.

75. The article of manufacture of any of embodiments 63, 64 and 66-74, wherein the unit dose comprises no more than about $1\times10^8$, no more than about $5\times10^7$, no more than about $1\times10^7$, no more than about $5\times10^6$, no more than about $1\times10^6$, or no more than about $5\times10^5$ total receptor$^+$/CD8$^+$ cells or total receptor$^+$/CD4$^+$ cells, total receptor$^+$/CD8$^+$/CCR7$^+$/CD27$^+$ cells, or total receptor$^+$/CD4$^+$/CCR7$^+$/CD27$^+$ cells.

76. The article of manufacture of any of embodiments 63, 64 and 66-75, wherein the unit dose comprises at least about $3\times10^6$, $4\times10^6$, $5\times10^6$, $6\times10^6$, $7\times10^6$, $8\times10^6$, $9\times10^6$, or $1\times10^7$ total receptor$^+$/CD8$^+$/CCR7$^+$/CD27$^+$ cells and/or at least about $3\times10^6$, $4\times10^6$, $5\times10^6$, $6\times10^6$, $7\times10^6$, $8\times10^6$, $9\times10^6$, or $1\times10^7$ total receptor$^+$/CD4$^+$/CCR7$^+$/CD27$^+$ cells.

77. The article of manufacture of any of embodiments 63. 64 and 66-76, wherein the unit dose comprises between at or about $3\times10^6$ and at or about $2.5\times10^7$, between at or about $4\times10^6$ and at or about $2\times10^7$, or between at or about $5\times10^6$ and at or about $1\times10^7$ total receptor$^+$/CD8$^+$/CCR7$^+$/CD27$^+$ cells and/or between at or about $3\times10^6$ and at or about $2.5\times10^7$, between at or about $4\times10^6$ and at or about $2\times10^7$, or between at or about $5\times10^6$ and at or about $1\times10^7$ total receptor$^+$/CD4$^+$/CCR7$^+$/CD27$^+$ cells, each inclusive.

78. The article of manufacture of any of embodiments 63, 64 and 66-77, wherein at least 15%, 20%, 30%, 40%, 50%, 60%, 70%, 80% or 90% of the total receptor$^+$ cells in the unit dose, or between about 15% and 90%, between about 20% and 80%, between about 30% and 70%, or between about 40% and 60%, each inclusive, of the total receptor$^+$ cells in the unit dose are receptor$^+$/CD8$^+$/CCR7$^+$/CD27$^+$ or receptor$^+$/CD4$^+$/CCR7$^+$/CD27$^+$.

79. The article of manufacture of any of embodiments 63, 64 and 66-78, wherein the unit dose of cells comprises a defined ratio of receptor$^+$/CD8$^+$/CCR7$^+$/CD27$^+$ cells to receptor$^+$/CD4$^+$/CCR7$^+$/CD27$^+$ cells, which ratio optionally is or is approximately 1:1 or is between approximately 1:3 and approximately 3:1.

80. The article of manufacture of embodiment 79, wherein the defined number or ratio is further based on expression or absence of expression of CD45RA on the cells.

81. The article of manufacture of embodiment 79 or embodiment 80, wherein the defined number of cells further express or do not express CD45RA, optionally wherein the defined number of cells further are CD45RA$^-$ cells.

82. The article of manufacture of any of embodiments 52, 53, 55, 56, 58-64 and 66-81, wherein among a plurality of articles or unit doses, optionally produced according to the same method, the number or ratio of cells that express CCR7 (CCR7$^+$ cells) in the unit dose varies by no more than 40%, by no more than 30%, by no more than 20%, by no more than 10% or by no more than 5%.

83. The article of manufacture of any of embodiments 52-82, wherein the unit dose or number of cells expressing the recombinant receptor comprises between at or about $1\times10^5$ and at or about $5\times10^8$, between at or about $1\times10^5$ and at or about $1\times10^8$, between at or about $5\times10^5$ and at or about $1\times10^7$, or between at or about $1\times10^6$ and at or about $1\times10^7$ total CD3$^+$ cells that express the recombinant receptor (receptor$^+$/CD3$^+$ cells) or total CD3$^+$ cells, each inclusive.

84. The article of manufacture or composition of any of embodiments 52-83, wherein the unit dose or number of cells expressing the recombinant receptor comprises no more than about $5\times10^8$, no more than about $1\times10^8$, no more than about $5\times10^7$, no more than about $1\times10^7$, no more than about $5\times10^6$, no more than about $1\times10^6$, or no more than about $5\times10^5$ total receptor$^+$/CD3$^+$ cells or total CD3$^+$ cells.

85. The article of manufacture of any of embodiments 52-84, wherein the total number of CD3$^+$ cells, total number of receptor$^+$/CD3$^+$ cells, total number of receptor$^+$/CD8$^+$ cells, total number of receptor$^+$/CD4$^+$ cells, total number of receptor$^+$/CD8$^+$/CCR7$^+$ cells, total number of receptor$^+$/CD4$^+$/CCR7$^+$ cells, total number of receptor$^+$/CD8$^+$/CD27$^+$ cells, total number of receptor$^+$/CD4$^+$/CD27$^+$ cells, total number of receptor$^+$/CD8$^+$/CCR7$^+$/CD27$^+$ cells, total number of receptor$^+$/CD4$^+$/CCR7$^+$/CD27$^+$ cells, total number of receptor⁺/CD8⁺/CCR7⁺/CD45RA⁻ cells and/or receptor⁺/CD4⁺/CCR7⁺/CD45RA⁻ cells is the total number of such cells that are live or viable.

86. The article of manufacture of any of embodiments 52-85, wherein the total number of CD3⁺ cells, total number of receptor⁺/CD3⁺ cells, total number of receptor⁺/CD8⁺ cells, total number of receptor⁺/CD4⁺ cells, total number of receptor⁺/CD8⁺/CCR7⁺ cells, total number of receptor⁺/CD4⁺/CCR7⁺ cells, total number of receptor⁺/CD8⁺/CCR7⁺/CD27⁺ cells, total number of receptor⁺/CD8⁺/CD27⁺ cells, total number of receptor⁺/CD4⁺/CD27⁺ cells, total number of receptor⁺/CD4⁺/CCR7⁺/CD27⁺ cells, total number of receptor⁺/CD8⁺/CCR7⁺/CD45RA⁻ cells and/or receptor⁺/CD4⁺/CCR7⁺/CD45RA⁻ cells is the total number of such cells that do not express an apoptotic marker and/or is the total number of such cells that are apoptotic marker negative (−), wherein the apoptotic marker is Annexin V or activated Caspase 3.

87. The article of manufacture of any of embodiments 52-86, wherein the instructions specify administering a plurality of unit doses contained in a plurality of separate compositions.

88. The article of manufacture of embodiment 87, wherein the plurality of separate compositions comprise a first composition comprising one of the CD8⁺ T cells and the CD4⁺ T cells and a second composition comprising the other of the CD8⁺ T cells and the CD4⁺ T cells.

89. The article of manufacture of embodiment 88, wherein the first composition comprises the CD8⁺ T cells.

90. The article of manufacture of embodiment 88, wherein the first composition comprises the CD4⁺ T cells.

91. The article of manufacture of any of embodiments 88-90, wherein the instructions specify administering the composition containing CD8⁺ T cells or one or more unit doses thereof and/or a volume corresponding to such one or more of unit doses and the composition containing CD4⁺ T cells or one or more unit doses thereof and/or a volume corresponding to such one or more of unit doses, no more than 2 hours, no more than 1 hour, no more than 30 minutes, no more than 15 minutes, no more than 10 minutes or no more than 5 minutes apart or simultaneously.

92. The article of manufacture of any of embodiments 88-91, wherein the instructions specify administering the composition containing CD8⁺ T cells or one or more unit doses thereof and/or a volume corresponding to such one or more of unit doses, prior to administering the composition containing CD4⁺ cells or one or more unit doses thereof and/or a volume corresponding to such one or more of unit doses.

93. The article of manufacture of any of embodiments 88-92, wherein the instructions specify administering the composition containing CD4⁺ T cells or one or more unit doses thereof and/or a volume corresponding to such one or more of unit doses, prior to administering the composition containing CD8⁺ cells or one or more unit doses thereof and/or a volume corresponding to such one or more of unit doses.

94. The article of manufacture of any of embodiments 52-93, wherein the recombinant receptor is or comprises a chimeric receptor and/or a recombinant antigen receptor.

95. The article of manufacture or composition of any of embodiments 1-94, wherein the recombinant receptor is capable of binding to a target antigen that is associated with, specific to, and/or expressed on a cell or tissue of a disease, disorder or condition.

96. The article of manufacture or composition of embodiment 95, wherein the disease, disorder or condition is an infectious disease or disorder, an autoimmune disease, an inflammatory disease, or a tumor or a cancer.

97. The article of manufacture or composition of embodiment 95 or embodiment 96, wherein the target antigen is a tumor antigen.

98. The article of manufacture or composition of any of embodiments 95-97, wherein the target antigen is selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD138, CD171, epidermal growth factor protein (EGFR), truncated epidermal growth factor protein (tEGFR), type III epidermal growth factor receptor mutation (EGFR VIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), G Protein Coupled Receptor 5D (GPCR5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22Ra), IL-13 receptor alpha 2 (IL-13Ra2), kinase insert domain receptor (kdr), kappa light chain, L1 cell adhesion molecule (L1-CAM), CE7 epitope of L-CAM, Leucine Rich Repeat Containing 8 Family Member A (LRRC8A), Lewis Y, Melanoma-associated antigen (MAGE)-A1, MAGE-A3, MAGE-A6, mesothelin, c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), vascular endothelial growth factor receptor (VEGFR), vascular endothelial growth factor receptor 2 (VEGFR2), Wilms Tumor 1 (WT-1), a pathogen-specific antigen, or an antigen associated with a universal tag, and/or biotinylated molecules, and/or molecules expressed by HIV, HCV, HBV or other pathogens.

99. The article of manufacture or composition of any of embodiments 1-98, wherein the recombinant receptor is or comprises a functional non-TCR antigen receptor or a TCR or antigen-binding fragment thereof.

100. The article of manufacture or composition of any of embodiments 1-99, wherein the recombinant receptor is a chimeric antigen receptor (CAR).

101. The article of manufacture or composition of any of embodiments 1-100, wherein the recombinant receptor comprises an extracellular domain comprising an antigen-binding domain.

102. The article of manufacture or composition of embodiment 101, wherein the antigen-binding domain is or comprises an antibody or an antibody fragment thereof, which optionally is a single chain fragment.

103. The article of manufacture or composition of embodiment 102, wherein the fragment comprises antibody variable regions joined by a flexible linker.

104. The article of manufacture or composition of embodiment 102 or embodiment 103, wherein the fragment comprises an scFv.

105. The article of manufacture or composition of any of embodiments 1-104, wherein the recombinant receptor comprises an intracellular signaling region.

106. The article of manufacture or composition of embodiment 105, wherein the intracellular signaling region comprises an intracellular signaling domain.

107. The article of manufacture or composition of embodiment 106, wherein the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM).

108. The article of manufacture or composition of embodiment 107, wherein the intracellular signaling domain is or comprises an intracellular signaling domain of a CD3 chain, optionally a CD3-zeta (CD3ζ) chain, or a signaling portion thereof.

109. The article of manufacture or composition of any of embodiments 1-108, wherein the recombinant receptor further comprises a transmembrane domain disposed between the extracellular domain and the intracellular signaling region.

110. The article of manufacture or composition of any of embodiments 1-109, wherein the intracellular signaling region further comprises a costimulatory signaling domain.

111. The article of manufacture or composition of embodiment 110, wherein the costimulatory signaling domain comprises an intracellular signaling domain of a T cell costimulatory molecule or a signaling portion thereof.

112. The article of manufacture or composition of embodiment 110 or embodiment 111, wherein the costimulatory signaling domain comprises an intracellular signaling domain of a CD28, a 4-1BB or an ICOS or a signaling portion thereof.

113. The article of manufacture or composition of any of embodiments 110-112, wherein the costimulatory signaling domain is between the transmembrane domain and the intracellular signaling domain.

114. The article of manufacture or composition of any of embodiments 1-113, wherein the T cells are primary T cells obtained from a subject.

115. The article of manufacture or composition of any of embodiments 1-114, wherein the T cells are autologous to the subject.

116. The article of manufacture or composition of any of embodiments 1-114, wherein the T cells are allogeneic to the subject.

117. A method of treatment, comprising administering to a subject having a disease or condition one or more unit doses of a therapeutic composition of embodiment 1 or embodiment 7 or a therapeutic composition comprising a plurality of CD8$^+$ and/or CD4$^+$ T cells engineered to express a recombinant receptor and/or a volume corresponding to such unit doses, optionally wherein:
the unit dose of cells comprises a defined number of recombinant receptor-expressing CD8$^+$ T cells that express C—C chemokine receptor type 7 (CCR7) (receptor$^+$/CD8$^+$/CCR7$^+$ cells) and/or a defined number of recombinant receptor-expressing CD4$^+$ T cells that express CCR7 (receptor$^+$/CD4$^+$/CCR7$^+$ cells) and/or a defined ratio of receptor$^+$/CD8$^+$/CCR7$^+$ cells to receptor$^+$/CD4$^+$/CCR7$^+$ cells and/or a defined ratio of receptor$^+$/CD8$^+$/CCR7$^+$ cells and/or receptor$^+$/CD4$^+$/CCR7$^+$ cells to another subset of cells in the composition; and/or
among a group of subjects treated according to the method, the number or ratio of cells that express CCR7 (CCR7$^+$ cells) in the unit dose varies by no more than 40%, by no more than 30%, by no more than 20%, by no more than 10% or by no more than 5%.

118. The method of embodiment 117, wherein the unit dose of cells comprises a defined number of CD8$^+$/CCR7$^+$ cells.

119. The method of embodiment 117, wherein the unit dose of cells comprises a defined number of CD4$^+$/CCR7$^+$ cells.

120. A method of treatment, comprising administering to a subject having a disease or condition one or more unit doses of a therapeutic composition of embodiment 1 or embodiment 7, or a therapeutic composition comprising a plurality of CD8$^+$ and/or CD4$^+$ T cells engineered to express a recombinant receptor and/or a volume corresponding to such unit doses, optionally wherein:
the unit dose of cells comprises a defined number of recombinant receptor-expressing CD8$^+$ T cells that express cluster of differentiation 27 (CD27) (receptor$^+$/CD8$^+$/CD27$^+$ cells) and/or a defined number of recombinant receptor-expressing CD4$^+$ T cells that express CD27 (receptor$^+$/CD4$^+$/CD27$^+$ cells) and/or a defined ratio of receptor$^+$/CD8$^+$/CD27$^+$ cells to receptor$^+$/CD4$^+$/CD27$^+$ cells and/or a defined ratio of receptor$^+$/CD8$^+$/CD27$^+$ cells and/or receptor$^+$/CD4$^+$/CD27$^+$ cells to another subset of cells in the composition; and/or
among a group of subjects treated according to the method, the number or ratio of cells that express CD27 (CD27$^+$ cells) in the unit dose varies by no more than 40%, by no more than 30%, by no more than 20%, by no more than 10% or by no more than 5%.

121. The method of embodiment 120, wherein the unit dose of cells comprises a defined number of CD8$^+$/CD27$^+$ cells.

122. The method of embodiment 120, wherein the unit dose of cells comprises a defined number of CD4$^+$/CD27$^+$ cells.

123. The method of any of embodiments 117-122, wherein the unit dose comprises between at or about $1 \times 10^5$ and at or about $1 \times 10^8$, between at or about $5 \times 10^5$ and at or about $1 \times 10^7$, or between at or about $1 \times 10^6$ and at or about $1 \times 10^7$ total CD8$^+$ cells that express the recombinant receptor (receptor$^+$/CD8$^+$ cells) or total CD4$^+$ cell that express the recombinant receptor (receptor$^+$/CD4$^+$ cells), total receptor$^+$/CD8$^+$/CCR7$^+$ cells, total receptor$^+$/CD4$^+$/CCR7$^+$ cells, total receptor$^+$/CD8$^+$/CD27$^+$ cells, or total receptor$^+$/CD4$^+$/CD27$^+$ cells, each inclusive.

124. The method of any of embodiments 117-123, wherein the unit dose comprises no more than about $1 \times 10^8$, no more than about $5 \times 10^7$, no more than about $1 \times 10^7$, no more than about $5 \times 10^6$, no more than about $1 \times 10^6$, or no more than about $5 \times 10^5$ total receptor$^+$/CD8$^+$ cells or total receptor$^+$/CD4$^+$ cells, total receptor$^+$/CD8$^+$/CCR7$^+$ cells, total receptor$^+$/CD4$^+$/CCR7$^+$ cells, total receptor$^+$/CD8$^+$/CD27$^+$ cells, or total receptor$^+$/CD4$^+$/CD27$^+$ cells.

125. The method of any of embodiments 117-124, wherein the unit dose comprises at least about $3 \times 10^6$, $4 \times 10^6$, $5 \times 10^6$, $6 \times 10^6$, $7 \times 10^6$, $8 \times 10^6$, $9 \times 10^6$, or $1 \times 10^7$ total receptor$^+$/CD8$^+$/CCR7$^+$ cells or total receptor$^+$/CD8$^+$/CD27$^+$ cells and/or at least about $3\times10^6$, $4\times10^6$, $5\times10^6$, $6\times10^6$, $7\times10^6$, $8\times10^6$, $9\times10^6$, or $1\times10^7$ total receptor/CD4/CCR7$^+$ cells or total receptor$^+$/CD4$^+$/CD27$^+$.

126. The method of any of embodiments 117-125, wherein the unit dose comprises between at or about $3\times10^6$ and at or about $2.5\times10^7$, between at or about $4\times10^6$ and at or about $2\times10^7$, or between at or about $5\times10^6$ and at or about $1\times10^7$ total receptor$^+$/CD8$^+$/CCR7$^+$ cells or total receptor$^+$/CD8$^+$/CD27$^+$ cells and/or between at or about $3\times10^6$ and at or about $2.5\times10^7$, between at or about $4\times10^6$ and at or about $2\times10^7$, or between at or about $5\times10^6$ and at or about $1\times10^7$ total receptor$^+$/CD4$^+$/CCR7$^+$ cells or total receptor$^+$/CD4$^+$/CD27$^+$, each inclusive.

127. The method of any of embodiments 117-126, wherein at least 15%, 20%, 30%, 40%, 50%, 60%, 70%, 80% or 90% of the total receptor$^+$ cells in the unit dose, or between about 15% and 90%, between about 20% and 80%, between about 30% and 70%, or between about 40% and 60%, each inclusive, of the total receptor$^+$ cells in the unit dose are receptor$^+$/CD8$^+$/CCR7$^+$ or receptor$^+$/CD8$^+$/CD27$^+$; or at least 15%, 20%, 30%, 40%, 50%, 60%, 70%, 80% or 90% of the total receptor$^+$ cells in the unit dose, or between about 15% and 90%, between about 20% and 80%, between about 30% and 70%, or between about 40% and 60%, each inclusive, of the total receptor$^+$ cells in the unit dose are receptor$^+$/CD4$^+$/CCR7$^+$ or receptor$^+$/CD4$^+$/CD27$^+$.

128. The method of any of embodiments 117-119 and 123-127, wherein the unit dose of cells comprises a defined ratio of receptor$^+$/CD8$^+$/CCR7$^+$ cells to receptor$^+$/CD4$^+$/CCR7$^+$ cells, which ratio optionally is or is approximately 1:1 or is between approximately 1:3 and approximately 3:1.

129. The method of any of embodiments 117-119 and 123-128, wherein the defined number or ratio is further based on expression or absence of expression of CD27 and/or CD45RA on the cells.

130. The method of any of embodiments 120-127, wherein the unit dose of cells comprises a defined ratio of receptor$^+$/CD8$^+$/CD27$^+$ cells to receptor$^+$/CD4$^+$/CD27$^+$ cells, which ratio optionally is or is approximately 1:1 or is between approximately 1:3 and approximately 3:1.

131. The method of any of embodiments 120-127 and 130, wherein the defined number or ratio is further based on expression or absence of expression of CCR7 and/or CD45RA on the cells.

132. The method of embodiment 131, wherein the unit dose of cells comprises a defined number of receptor$^+$/CD8$^+$/CCR7$^+$/CD27$^+$ cells and/or receptor$^+$/CD8$^+$/CCR7$^+$/CD45RA$^-$ cells.

133. The method of any of embodiments 129, 131 or 132, wherein at least 15%, 20%, 30%, 40%, 50%, 60%, 70%, 80% or 90% of the total receptor$^+$ cells in the unit dose, or between about 15% and 90%, between about 20% and 80%, between about 30% and 70%, or between about 40% and 60%, each inclusive, of the total receptor$^+$ cells in the unit dose are receptor$^+$/CD8$^+$/CCR7$^+$/CD27$^+$ or receptor$^+$/CD8$^+$/CCR7$^+$/CD45RA$^-$.

134. The method of embodiment 131, wherein the unit dose of cells comprises a defined number of receptor$^+$/CD4$^+$/CCR7$^+$/CD27$^+$ cells and/or receptor$^+$/CD4$^+$/CCR7$^+$/CD45RA$^-$ cells.

135. The method of any of embodiments 129, 131 or 132, wherein at least 15%, 20%, 30%, 40%, 50%, 60%, 70%, 80% or 90% of the total receptor$^+$ cells in the unit dose, or between about 15% and 90%, between about 20% and 80%, between about 30% and 70%, or between about 40% and 60%, each inclusive, of the total receptor$^+$ cells in the unit dose are receptor$^+$/CD4$^+$/CCR7$^+$/CD27$^+$ or receptor$^+$/CD4$^+$/CCR7$^+$/CD45RA$^-$.

136. A method of treatment, the method comprising administering to a subject having a disease or condition one or more unit doses of a composition of embodiment 1 or embodiment 7.

137. The method of embodiment 136, wherein:
the unit dose of cells comprises a defined number of recombinant receptor-expressing CD8$^+$ T cells that express CCR7 and CD27 (receptor$^+$/CD8$^+$/CCR7$^+$/CD27$^+$ cells) and/or a defined number of recombinant receptor-expressing CD4$^+$ T cells that express CCR7 and CD27 (receptor$^+$/CD4$^+$/CCR7$^+$/CD27$^+$ cells) and/or a defined ratio of receptor$^+$/CD8$^+$/CCR7$^+$/CD27$^+$ cells to receptor$^+$/CD4$^+$/CCR7$^+$/CD27$^+$ cells and/or a defined ratio of receptor$^+$/CD8$^+$/CCR7$^+$/CD27$^+$ cells and/or receptor$^+$/CD4$^+$/CCR7$^+$/CD27$^+$ cells to another subset of cells in the composition; and
among a group of subjects treated according to the method, the number or ratio of cells that express CCR7 (CCR7$^+$ cells) in the unit dose varies by no more than 40%, by no more than 30%, by no more than 20%, by no more than 10% or by no more than 5%.

138. A method of treatment, the method comprising administering to a subject having a disease or condition a therapeutic composition comprising a plurality of CD8$^+$ and/or CD4$^+$ T cells engineered to express a recombinant receptor and/or a volume corresponding to such unit doses, wherein:
the unit dose of cells comprises a defined number of recombinant receptor-expressing CD8$^+$ T cells that express CCR7 and CD27 (receptor$^+$/CD8$^+$/CCR7$^+$/CD27$^+$ cells) and/or a defined number of recombinant receptor-expressing CD4$^+$ T cells that express CCR7 and CD27 (receptor$^+$/CD4$^+$/CCR7$^+$/CD27$^+$ cells) and/or a defined ratio of receptor$^+$/CD8$^+$/CCR7$^+$/CD27$^+$ cells to receptor$^+$/CD4$^+$/CCR7$^+$/CD27$^+$ cells and/or a defined ratio of receptor$^+$/CD8$^+$/CCR7$^+$/CD27$^+$ cells and/or receptor$^+$/CD4$^+$/CCR7$^+$/CD27$^+$ cells to another subset of cells in the composition; and
among a group of subjects treated according to the method, the number or ratio of cells that express CCR7 (CCR7$^+$ cells) in the unit dose varies by no more than 40%, by no more than 30%, by no more than 20%, by no more than 10% or by no more than 5%.

139. The method of any of embodiments 129 and 131-138, wherein the unit dose of cells comprises a defined number of CD8$^+$/CCR7$^+$/CD27$^+$ cells.

140. The method of any of embodiments 129 and 131-138, wherein the unit dose of cells comprises a defined number of CD4$^+$/CCR7$^+$/CD27$^+$ cells.

141. The method of any of embodiments 129 and 131-140, wherein the unit dose comprises between at or about $1\times10^5$ and at or about $1\times10^8$, between at or about $5\times10^5$ and at or about $1\times10^7$, or between at or about $1\times10^6$ and at or about $1\times10^7$ total CD8$^+$ cells that express the recombinant receptor (receptor$^+$/CD8$^+$ cells) or total CD4$^+$ cell that express the recombinant receptor (receptor$^+$/CD4$^+$ cells), total receptor$^+$/CD8$^+$/CCR7$^+$/CD27$^+$ cells, or total receptor$^+$/CD4$^+$/CCR7$^+$/CD27$^+$ cells, each inclusive.

142. The method of any of embodiments 129 and 131-141, wherein the unit dose comprises no more than about $1\times10^8$, no more than about $5\times10^7$, no more than about $1\times10^7$, no more than about $5\times10^6$, no more than about $1\times10^6$, or no more than about $5\times10^5$ total receptor$^+$/CD8$^+$ cells or total receptor⁺/CD4⁺ cells, total receptor⁺/CD8⁺/CCR7⁺/CD27⁺ cells, or total receptor⁺/CD4⁺/CCR7⁺/CD27⁺ cells.

143. The method of any of embodiments 129 and 131-142, wherein the unit dose comprises at least about $3\times10^6$, $4\times10^6$, $5\times10^6$, $6\times10^6$, $7\times10^6$, $8\times10^6$, $9\times10^6$, or $1\times10^7$ total receptor⁺/CD8⁺/CCR7⁺/CD27⁺ cells; and/or at least about $3\times10^6$, $4\times10^6$, $5\times10^6$, $6\times10^6$, $7\times10^6$, $8\times10^6$, $9\times10^6$, or $1\times10^7$ total receptor⁺/CD4⁺/CCR7⁺/CD27⁺ cells.

144. The method of any of embodiments 129 and 131-143, wherein the unit dose comprises between at or about $3\times10^6$ and at or about $2.5\times10^7$, between at or about $4\times10^6$ and at or about $2\times10^7$, or between at or about $5\times10^6$ and at or about $1\times10^7$ total receptor⁺/CD8⁺/CCR7⁺/CD27⁺ cells; and/or between at or about $3\times10^6$ and at or about $2.5\times10^7$, between at or about $4\times10^6$ and at or about $2\times10^7$, or between at or about $5\times10^6$ and at or about $1\times10^7$ total receptor⁺/CD4⁺/CCR7⁺/CD27⁺ cells, each inclusive.

145. The method of any of embodiments 129 and 131-144, wherein at least 15%, 20%, 30%, 40%, 50%, 60%, 70%, 80% or 90% of the total receptor⁺ cells in the unit dose, or between about 15% and 90%, between about 20% and 80%, between about 30% and 70%, or between about 40% and 60%, each inclusive, of the total receptor⁺ cells in the unit dose are receptor⁺/CD8⁺/CCR7⁺/CD27⁺ or receptor⁺/CD4⁺/CCR7⁺/CD27⁺.

146. The method of any of embodiments 129 and 131-145, wherein the unit dose of cells comprises a defined ratio of receptor⁺/CD8⁺/CCR7⁺/CD27⁺ cells to receptor⁺/CD4⁺/CCR7⁺/CD27⁺ cells, which ratio optionally is or is approximately 1:1 or is between approximately 1:3 and approximately 3:1.

147. The method of any of embodiments 129 and 131-146, wherein the defined number or ratio is further based on expression or absence of expression of CD45RA on the cells.

148. The method of any of embodiments 129 and 131-147, wherein the defined number of cells further express or do not express CD45RA, optionally wherein the defined number of cells further are CD45RA⁻ cells.

149. The method of any of embodiments 117-148, wherein the unit dose comprises between at or about $1\times10^5$ and at or about $5\times10^8$, between at or about $1\times10^5$ and at or about $1\times10^8$, between at or about $5\times10^5$ and at or about $1\times10^7$, or between at or about $1\times10^6$ and at or about $1\times10^7$ total CD3⁺ cells that express the recombinant receptor (receptor⁺/CD3⁺ cells) or total CD3⁺ cells, each inclusive.

150. The method of any of embodiments 117-149, wherein the unit dose comprises no more than about $5\times10^8$, no more than about $1\times10^8$, no more than about $5\times10^7$, no more than about $1\times10^7$, no more than about $5\times10^6$, no more than about $1\times10^6$, or no more than about $5\times10^5$ total receptor⁺/CD3⁺ cells or total CD3⁺ cells.

151. The method of any of embodiments 117-150, wherein the total number of CD3⁺ cells, total number of receptor⁺/CD3⁺ cells, total number of receptor⁺/CD8⁺ cells, total number of receptor⁺/CD4⁺ cells, total number of receptor⁺/CD8⁺/CCR7⁺ cells, total number of receptor⁺/CD4⁺/CCR7⁺ cells, total number of receptor⁺/CD8⁺/CD27⁺ cells, total number of receptor⁺/CD4⁺/CD27⁺ cells, total number of receptor⁺/CD8⁺/CCR7⁺/CD27⁺ cells, total number of receptor⁺/CD4⁺/CCR7⁺/CD27⁺ cells, total number of receptor⁺/CD8⁺/CCR7⁺/CD45RA⁻ cells and/or receptor⁺/CD4⁺/CCR7⁺/CD45RA⁻ cells is the total number of such cells that are live or viable.

152. The method of any of embodiments 117-151, wherein the total number of CD3⁺ cells, total number of receptor⁺/CD3⁺ cells, total number of receptor⁺/CD8⁺ cells, total number of receptor⁺/CD4⁺ cells, total number of receptor⁺/CD8⁺/CCR7⁺ cells, total number of receptor⁺/CD4⁺/CCR7⁺ cells, total number of receptor⁺/CD8⁺/CD27⁺ cells, total number of receptor⁺/CD4⁺/CD27⁺ cells, total number of receptor⁺/CD8⁺/CCR7⁺/CD27⁺ cells, total number of receptor⁺/CD4⁺/CCR7⁺/CD27⁺ cells, total number of receptor⁺/CD8⁺/CCR7⁺/CD45RA⁻ cells and/or receptor⁺/CD4⁺/CCR7⁺/CD45RA⁻ cells is the total number of such cells that do not express an apoptotic marker and/or is the total number of such cells that are apoptotic marker negative (−), wherein the apoptotic marker is Annexin V or activated Caspase 3.

153. The method of any of embodiments 117-152, comprising administering a plurality of unit doses contained in a plurality of separate compositions.

154. The method of any of embodiments 117-153, wherein the plurality of separate compositions comprise a first composition comprising one of the CD8⁺ T cells and the CD4⁺ T cells and a second composition comprising the other of the CD8⁺ T cells and the CD4⁺ T cells.

155. The method of embodiment 154, wherein the first composition comprises the CD8⁺ T cells.

156. The method of embodiment 154, wherein the first composition comprises the CD4⁺ T cells.

157. The method of any of embodiments 154-156, comprising administering the composition containing CD8⁺ T cells or one or more unit doses thereof and/or a volume corresponding to such one or more of unit doses and the composition containing CD4⁺ T cells or one or more unit doses thereof and/or a volume corresponding to such one or more of unit doses, no more than 2 hours, no more than 1 hour, no more than 30 minutes, no more than 15 minutes, no more than 10 minutes or no more than 5 minutes apart or simultaneously.

158. The method of any of embodiments 154-157, comprising administering the composition containing CD8⁺ T cells or one or more unit doses thereof and/or a volume corresponding to such one or more of unit doses, prior to administering the composition containing CD4⁺ cells or one or more unit doses thereof and/or a volume corresponding to such one or more of unit doses.

159. The method of any of embodiments 154-158, comprising administering the composition containing CD4⁺ T cells or one or more unit doses thereof and/or a volume corresponding to such one or more of unit doses, prior to administering the composition containing CD8⁺ cells or one or more unit doses thereof and/or a volume corresponding to such one or more of unit doses.

160. The method of any of embodiments 117-159, wherein the recombinant receptor is or comprises a chimeric receptor and/or a recombinant antigen receptor.

161. The method of any of embodiments 117-160, wherein the recombinant receptor is capable of binding to a target antigen that is associated with, specific to, and/or expressed on a cell or tissue of a disease, disorder or condition.

162. The method of embodiment 161, wherein the disease, disorder or condition is an infectious disease or disorder, an autoimmune disease, an inflammatory disease, or a tumor or a cancer.

163. The method of embodiment 161 or embodiment 162, wherein the target antigen is a tumor antigen.

164. The method of any of embodiments 161-163, wherein the target antigen is selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD138, CD171, epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), G Protein Coupled Receptor 5D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22Ra), IL-13 receptor alpha 2 (IL-13Ra2), kinase insert domain receptor (kdr), kappa light chain, L1 cell adhesion molecule (L1-CAM), CE7 epitope of L-CAM, Leucine Rich Repeat Containing 8 Family Member A (LRRC8A), Lewis Y, Melanoma-associated antigen (MAGE)-A1, MAGE-A3, MAGE-A6, mesothelin, c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), vascular endothelial growth factor receptor (VEGFR), vascular endothelial growth factor receptor 2 (VEGFR2), Wilms Tumor 1 (WT-1), a pathogen-specific antigen, or an antigen associated with a universal tag, and/or biotinylated molecules, and/or molecules expressed by HIV, HCV, HBV or other pathogens.

165. The method of any of embodiments 117-164, wherein the recombinant receptor is or comprises a functional non-TCR antigen receptor or a TCR or antigen-binding fragment thereof.

166. The method of any of embodiments 117-165, wherein the recombinant receptor is a chimeric antigen receptor (CAR).

167. The method of any of embodiments 117-166, wherein the recombinant receptor comprises an extracellular domain comprising an antigen-binding domain.

168. The method of embodiment 167, wherein the antigen-binding domain is or comprises an antibody or an antibody fragment thereof, which optionally is a single chain fragment.

169. The method of embodiment 168, wherein the fragment comprises antibody variable regions joined by a flexible linker.

170. The method of embodiment 168 or embodiment 169, wherein the fragment comprises an scFv.

171. The method of any of embodiments 117-161, wherein the recombinant receptor comprises an intracellular signaling region.

172. The method of embodiment 171, wherein the intracellular signaling region comprises an intracellular signaling domain.

173. The method of embodiment 172, wherein the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM).

174. The method of embodiment 173, wherein the intracellular signaling domain is or comprises an intracellular signaling domain of a CD3 chain, optionally a CD3-zeta (CD3ζ) chain, or a signaling portion thereof.

175. The method of any of embodiments 117-174, wherein the recombinant receptor further comprises a transmembrane domain disposed between the extracellular domain and the intracellular signaling region.

176. The method of any of embodiments 117-175, wherein the intracellular signaling region further comprises a costimulatory signaling domain.

177. The method of embodiment 176, wherein the costimulatory signaling domain comprises an intracellular signaling domain of a T cell costimulatory molecule or a signaling portion thereof.

178. The method of embodiment 176 or embodiment 177, wherein the costimulatory signaling domain comprises an intracellular signaling domain of a CD28, a 4-1BB or an ICOS or a signaling portion thereof.

179. The method of any of embodiments 176-178, wherein the costimulatory signaling domain is between the transmembrane domain and the intracellular signaling domain.

180. The method of any of embodiments 117-179, wherein the T cells are primary T cells obtained from a subject.

181. The method of any of embodiments 117-180, wherein the T cells are autologous to the subject.

182. The method of any of embodiments 117-180, wherein the T cells are allogeneic to the subject.

183. A method of determining a unit dose of engineered T cells for treating a subject, the method comprising:
(a) assessing, in a therapeutic composition comprising a plurality of $CD8^+$ and/or $CD4^+$ T cells engineered to express a recombinant receptor, the number, percentage or ratio of T cells that express the recombinant receptor and CCR7 (receptor$^+$/CCR7$^+$);
(b) based on the number, percentage or ratio of receptor$^+$/CCR7$^+$ cells, determining one or more unit doses of cells for administration to a subject having a disease or conditions, wherein the unit dose comprises a defined number of recombinant receptor-expressing $CD8^+$ T cells that express C—C chemokine receptor type 7 (CCR7) (receptor$^+$/CD8$^+$/CCR7$^+$ cells) and/or a defined number of recombinant receptor-expressing $CD4^+$ T cells that express CCR7 (receptor$^+$/CD4$^+$/CCR7$^+$ cells) and/or a defined ratio of receptor$^+$/CD8$^+$/CCR7$^+$ cells to receptor$^+$/CD4$^+$/CCR7$^+$ cells and/or a defined ratio of receptor$^+$/CD8$^+$/CCR7$^+$ cells and/or receptor$^+$/CD4$^+$/CCR7$^+$ cells to another subset of cells in the composition.

184. A method of determining a unit dose of engineered T cells for treating a subject, the method comprising:
(a) assessing, in a therapeutic composition comprising a plurality of $CD8^+$ and/or $CD4^+$ T cells engineered to express a recombinant receptor, the number, percentage or ratio of T cells that express the recombinant receptor and CD27 (receptor$^+$/CD27$^+$); and
(b) based on the number, percentage or ratio of receptor$^+$/CD27$^+$ cells, determining one or more unit doses of cells for administration to a subject having a disease or conditions, wherein the unit dose comprises a defined number of recombinant receptor-expressing CD8$^+$ T cells that express cluster of differentiation 27 (CD27) (receptor$^+$/CD8$^+$/CD27$^+$ cells) and/or a defined number of recombinant receptor-expressing CD4$^+$ T cells that express CD27 (receptor$^+$/CD4$^+$/CD27$^+$ cells) and/or a defined ratio of receptor$^+$/CD8$^+$/CD27$^+$ cells to receptor$^+$/CD4$^+$/CD27$^+$ cells and/or a defined ratio of receptor$^+$/CD8$^+$/CD27$^+$ cells and/or receptor$^+$/CD4$^+$/CD27$^+$ cells to another subset of cells in the composition.

185. A method of producing a composition comprising a unit dose of a T cell composition, the method comprising:
(a) assessing, in a therapeutic composition comprising a plurality of CD8$^+$ and/or CD4$^+$ T cells engineered to express a recombinant receptor, the number, percentage or ratio of T cells that express the recombinant receptor and CCR7 and/or CD27 (receptor$^+$/CCR7$^+$ and/or receptor$^+$/CD27$^+$); and
(b) filling a container with all or a portion of the composition and optionally another solution to achieve a unit dose of the T cell composition, wherein the unit dose comprises a defined number of recombinant receptor-expressing CD8$^+$ T cells that express C—C chemokine receptor type 7 (CCR7) (receptor$^+$/CD8$^+$/CCR7$^+$ cells) and/or a defined number of recombinant receptor-expressing CD4$^+$ T cells that express CCR7 (receptor$^+$/CD4$^+$/CCR7$^+$ cells) and/or a defined ratio of receptor$^+$/CD8$^+$/CCR7$^+$ cells to receptor$^+$/CD4$^+$/CCR7$^+$ cells and/or a defined ratio of receptor$^+$/CD8$^+$/CCR7$^+$ cells and/or receptor$^+$/CD4$^+$/CCR7$^+$ cells to another subset of cells in the composition, or a defined number of recombinant receptor-expressing CD8$^+$ T cells that express cluster of differentiation 27 (CD27) (receptor$^+$/CD8$^+$/CD27$^+$ cells) and/or a defined number of recombinant receptor-expressing CD4$^+$ T cells that express CD27 (receptor$^+$/CD4$^+$/CD27$^+$ cells) and/or a defined ratio of receptor$^+$/CD8$^+$/CD27$^+$ cells to receptor$^+$/CD4$^+$/CD27$^+$ cells and/or a defined ratio of receptor$^+$/CD8$^+$/CD27$^+$ cells and/or receptor$^+$/CD4$^+$/CD27$^+$ cells to another subset of cells in the composition.

186. A method of producing a therapeutic composition comprising a unit dose of a T cell composition, the method comprising filling a container with all or a portion of a T cell composition, the T cell composition comprising T cells comprising a recombinant receptor that specifically binds an antigen associated with a disease or condition, to achieve a unit dose of the T cell composition, wherein the unit dose comprises a defined number of recombinant receptor-expressing CD8$^+$ T cells that express C—C chemokine receptor type 7 (CCR7) (receptor$^+$/CD8$^+$/CCR7$^+$ cells) and/or a defined number of recombinant receptor-expressing CD4$^+$ T cells that express CCR7 (receptor$^+$/CD4$^+$/CCR7$^+$ cells) and/or a defined ratio of receptor$^+$/CD8$^+$/CCR7$^+$ cells to receptor$^+$/CD4$^+$/CCR7$^+$ cells and/or a defined ratio of receptor$^+$/CD8$^+$/CCR7$^+$ cells and/or receptor$^+$/CD4$^+$/CCR7$^+$ cells to another subset of cells in the composition.

187. A method of producing a therapeutic composition comprising a unit dose of a T cell composition, the method comprising filling a container with all or a portion of a T cell composition, the T cell composition comprising T cells comprising a recombinant receptor that specifically binds an antigen associated with a disease or condition, to achieve a unit dose of the T cell composition, wherein the unit dose comprises a defined number of recombinant receptor-expressing CD8$^+$ T cells that express cluster of differentiation 27 (CD27) (receptor$^+$/CD8$^+$/CD27$^+$ cells) and/or a defined number of recombinant receptor-expressing CD4$^+$ T cells that express CD27 (receptor$^+$/CD4$^+$/CD27$^+$ cells) and/or a defined ratio of receptor$^+$/CD8$^+$/CD27$^+$ cells to receptor$^+$/CD4$^+$/CD27$^+$ cells and/or a defined ratio of receptor$^+$/CD8$^+$/CD27$^+$ cells and/or receptor$^+$/CD4$^+$/CD27$^+$ cells to another subset of cells in the composition.

188. The method of any of embodiments 184-187, wherein the unit dose of cells comprises a defined number of CD8$^+$/CCR7$^+$ cells.

189. The method of any of embodiments 184-188, wherein the unit dose of cells comprises a defined number of CD4$^+$/CCR7$^+$ cells.

190. The method of any of embodiments 184-189, wherein the unit dose comprises between at or about $1\times10^5$ and at or about $1\times10^8$, between at or about $5\times10^5$ and at or about $1\times10^7$, or between at or about $1\times10^6$ and at or about $1\times10^7$ total CD8$^+$ cells that express the recombinant receptor (receptor$^+$/CD8$^+$ cells) or total CD4$^+$ cell that express the recombinant receptor (receptor$^+$/CD4$^+$ cells), total receptor$^+$/CD8$^+$/CCR7$^+$ cells, total receptor$^+$/CD4$^+$/CCR7$^+$ cells, total receptor$^+$/CD8$^+$/CD27$^+$ cells, or total receptor$^+$/CD4$^+$/CD27$^+$ cells, each inclusive.

191. The method of any of embodiments 184-180, wherein the unit dose comprises no more than about $1\times10^8$, no more than about $5\times10^7$, no more than about $1\times10^7$, no more than about $5\times10^6$, no more than about $1\times10^6$, or no more than about $5\times10^5$ total receptor$^+$/CD8$^+$ cells or total receptor$^+$/CD4$^+$ cells, total receptor$^+$/CD8$^+$/CCR7$^+$ cells, total receptor$^+$/CD4$^+$/CCR7$^+$ cells, total receptor$^+$/CD8$^+$/CD27$^+$ cells, or total receptor$^+$/CD4$^+$/CD27$^+$ cells.

192. The method of any of embodiments 184-191, wherein the unit dose comprises at least about $3\times10^6$, $4\times10^6$, $5\times10^6$, $6\times10^6$, $7\times10^6$, $8\times10^6$, $9\times10^6$, or $1\times10^7$ total receptor$^+$/CD8$^+$/CCR7$^+$ cells or total receptor$^+$/CD8$^+$/CD27$^+$ cells and/or at least about $3\times10^6$, $4\times10^6$, $5\times10^6$, $6\times10^6$, $7\times10^6$, $8\times10^6$, $9\times10^6$, or $1\times10^7$ total receptor/CD4/CCR7$^+$ cells or total receptor$^+$/CD4$^+$/CD27$^+$.

193. The method of any of embodiments 184-192, wherein the unit dose comprises between at or about $3\times10^6$ and at or about $2.5\times10^7$, between at or about $4\times10^6$ and at or about $2\times10^7$, or between at or about $5\times10^6$ and at or about $1\times10^7$ total receptor$^+$/CD8$^+$/CCR7$^+$ cells or total receptor$^+$/CD8$^+$/CD27$^+$ cells and/or between at or about $3\times10^6$ and at or about $2.5\times10^7$, between at or about $4\times10^6$ and at or about $2\times10^7$, or between at or about $5\times10^6$ and at or about $1\times10^7$ total receptor$^+$/CD4$^+$/CCR7$^+$ cells or total receptor$^+$/CD4$^+$/CD27$^+$, each inclusive.

194. The method of any of embodiments 184-193, wherein at least 15%, 20%, 30%, 40%, 50%, 60%, 70%, 80% or 90% of the total receptor$^+$ cells in the unit dose, or between about 15% and 90%, between about 20% and 80%, between about 30% and 70%, or between about 40% and 60%, each inclusive, of the total receptor$^+$ cells in the unit dose are receptor$^+$/CD8$^+$/CCR7$^+$ or receptor$^+$/CD8$^+$/CD27$^+$; or at least 15%, 20%, 30%, 40%, 50%, 60%, 70%, 80% or 90% of the total receptor$^+$ cells in the unit dose, or between about 15% and 90%, between about 20% and 80%, between about 30% and 70%, or between about 40% and 60%, each inclusive, of the total receptor$^+$ cells in the unit dose are receptor$^+$/CD4$^+$/CCR7$^+$ or receptor$^+$/CD4$^+$/CD27$^+$.

195. The method of any of embodiments 184-194, wherein the unit dose of cells comprises a defined ratio of receptor$^+$/CD8$^+$/CCR7$^+$ cells to receptor$^+$/CD4$^+$/CCR7$^+$ cells, which ratio optionally is or is approximately 1:1 or is between approximately 1:3 and approximately 3:1.

196. The method of any of embodiments 184-195, wherein the unit dose further comprises a defined number of cells comprising cells that express or do not express CD27 and/or CD45, optionally wherein the unit dose further comprises a defined number of cells comprising CD27$^+$ or CD45RA$^-$ cells.

197. The method of any of embodiments 184-196, further comprising assessing in the therapeutic composition the number, percentage or ratio of T cells that express or do not express CD27 and/or CD45RA, optionally the number, percentage or ratio of T cells that are CD27$^+$ or CD45RA$^-$.

198. The method of embodiment 196 or embodiment 197, wherein the unit dose of cells comprises a defined number of receptor$^+$/CD8$^+$/CCR7$^+$/CD27$^+$ cells and/or receptor$^+$/CD8$^+$/CCR7$^+$/CD45RA$^-$ cells.

199. The method of embodiment 196 or embodiment 197, wherein the unit dose of cells comprises a defined number of receptor$^+$/CD4$^+$/CCR7$^+$/CD27$^+$ cells and/or receptor$^+$/CD4$^+$/CCR7$^+$/CD45RA$^-$ cells.

200. The method of any of embodiments 196-199, wherein at least 15%, 20%, 30%, 40%, 50%, 60%, 70%, 80% or 90% of the total receptor$^+$ cells in the unit dose, or between about 15% and 90%, between about 20% and 80%, between about 30% and 70%, or between about 40% and 60%, each inclusive, of the total receptor$^+$ cells in the unit dose are receptor$^+$/CD8$^+$/CCR7$^+$/CD27$^+$, receptor$^+$/CD8$^+$/CCR7$^+$/CD45RA$^-$, receptor$^+$/CD4$^+$/CCR7$^+$/CD27$^+$ or receptor$^+$/CD4$^+$/CCR7$^+$/CD45RA$^-$.

201. A method of determining a unit dose of engineered T cells for treating a subject, the method comprising:
 (a) assessing, in a therapeutic composition comprising a plurality of CD8$^+$ and/or CD4$^+$ T cells engineered to express a recombinant receptor, the number, percentage or ratio of T cells that express the recombinant receptor and CCR7 and CD27 (receptor$^+$/CCR7$^+$/CD27$^+$);
 (b) based on the number, percentage or ratio of receptor$^+$/CCR7$^+$/CD27$^+$ cells, determining one or more unit doses of cells of cells for administration to a subject having a disease or conditions, wherein the unit dose comprises a defined number of recombinant receptor-expressing CD8$^+$ T cells that express CCR7 and CD27 (receptor$^+$/CD8$^+$/CCR7$^+$/CD27$^+$ cells) and/or a defined number of recombinant receptor-expressing CD4$^+$ T cells that express CCR7 and CD27 (receptor$^+$/CD4$^+$/CCR7$^+$/CD27$^+$ cells) and/or a defined ratio of receptor$^+$/CD8$^+$/CCR7$^+$/CD27$^+$ cells to receptor$^+$/CD4$^+$/CCR7$^+$/CD27$^+$ cells and/or a defined ratio of receptor$^+$/CD8$^+$/CCR7$^+$/CD27$^+$ cells and/or receptor$^+$/CD4$^+$/CCR7$^+$/CD27$^+$ cells to another subset of cells in the composition.

202. A method of producing a composition comprising a unit dose of a T cell composition, the method comprising:
 (a) assessing, in a therapeutic composition comprising a plurality of CD8$^+$ and/or CD4$^+$ T cells engineered to express a recombinant receptor, the number, percentage or ratio of T cells that express the recombinant receptor and CCR7 and CD27 (receptor$^+$/CCR7$^+$/CD27$^+$); and
 (b) filling a container with all or a portion of the composition and optionally another solution to achieve a unit dose of the T cell composition, wherein the unit dose comprises a defined number of recombinant receptor-expressing CD8$^+$ T cells that express CCR7 and CD27 (receptor$^+$/CD8$^+$/CCR7$^+$/CD27$^+$ cells) and/or a defined number of recombinant receptor-expressing CD4$^+$ T cells that express CCR7 and CD27 (receptor$^+$/CD4$^+$/CCR7$^+$/CD27$^+$ cells) and/or a defined ratio of receptor$^+$/CD8$^+$/CCR7$^+$/CD27$^+$ cells to receptor$^+$/CD4$^+$/CCR7$^+$/CD27$^+$ cells and/or a defined ratio of receptor$^+$/CD8$^+$/CCR7$^+$/CD27$^+$ cells and/or receptor$^+$/CD4$^+$/CCR7$^+$/CD27$^+$ cells to another subset of cells in the composition.

203. A method of producing a therapeutic composition comprising a unit dose of a T cell composition, the method comprising filling a container with all or a portion of a T cell composition, the T cell composition comprising T cells comprising a recombinant receptor that specifically binds an antigen associated with a disease or condition, to achieve a unit dose of the T cell composition, wherein the unit dose comprises a defined number of recombinant receptor-expressing CD8$^+$ T cells that express CCR7 and CD27 (receptor$^+$/CD8$^+$/CCR7$^+$/CD27$^+$ cells) and/or a defined number of recombinant receptor-expressing CD4$^+$ T cells that express CCR7 and CD27 (receptor$^+$/CD4$^+$/CCR7$^+$/CD27$^+$ cells) and/or a defined ratio of receptor$^+$/CD8$^+$/CCR7$^+$/CD27$^+$ cells to receptor$^+$/CD4$^+$/CCR7$^+$/CD27$^+$ cells and/or a defined ratio of receptor$^+$/CD8$^+$/CCR7$^+$/CD27$^+$ cells and/or receptor$^+$/CD4$^+$/CCR7$^+$/CD27$^+$ cells to another subset of cells in the composition.

204. The method of any of embodiments 201-203, wherein the unit dose of cells comprises a defined number of CD8$^+$/CCR7$^+$/CD27$^+$ cells.

205. The method of any of embodiments 201-203, wherein the unit dose of cells comprises a defined number of CD4$^+$/CCR7$^+$/CD27$^+$ cells.

206. The method of any of embodiments 201-205, wherein the unit dose comprises between at or about $1 \times 10^5$ and at or about $1 \times 10^8$, between at or about $5 \times 10^5$ and at or about $1 \times 10^7$, or between at or about $1 \times 10^6$ and at or about $1 \times 10^7$ total CD8$^+$ cells that express the recombinant receptor (receptor$^+$/CD8$^+$ cells) or total CD4$^+$ cell that express the recombinant receptor (receptor$^+$/CD4$^+$ cells), total receptor$^+$/CD8$^+$/CCR7$^+$/CD27$^+$ cells, or total receptor$^+$/CD4$^+$/CCR7$^+$/CD27$^+$ cells, each inclusive.

207. The method of any of embodiments 201-206, wherein the unit dose comprises no more than about $1 \times 10^8$, no more than about $5 \times 10^7$, no more than about $1 \times 10^7$, no more than about $5 \times 10^6$, no more than about $1 \times 10^6$, or no more than about $5 \times 10^5$ total receptor$^+$/CD8$^+$ cells or total receptor$^+$/CD4$^+$ cells, total receptor$^+$/CD8$^+$/CCR7$^+$/CD27$^+$ cells, or total receptor$^+$/CD4$^+$/CCR7$^+$/CD27$^+$ cells.

208. The method of any of embodiments 201-207, wherein the unit dose comprises at least about $3 \times 10^6$, $4 \times 10^6$, $5 \times 10^6$, $6 \times 10^6$, $7 \times 10^6$, $8 \times 10^6$, $9 \times 10^6$, or $1 \times 10^7$ total receptor$^+$/CD8$^+$/CCR7$^+$/CD27$^+$ cells and/or at least about $3 \times 10^6$, $4 \times 10^6$, $5 \times 10^6$, $6 \times 10^6$, $7 \times 10^6$, $8 \times 10^6$, $9 \times 10^6$, or $1 \times 10^7$ total receptor$^+$/CD4$^+$/CCR7$^+$/CD27$^+$ cells.

209. The method of any of embodiments 201-208, wherein the unit dose comprises between at or about $3 \times 10^6$ and at or about $2.5 \times 10^7$, between at or about $4 \times 10^6$ and at or about $2 \times 10^7$, or between at or about $5 \times 10^6$ and at or about $1 \times 10^7$ total receptor$^+$/CD8$^+$/CCR7$^+$/CD27$^+$ cells and/or between at or about $3 \times 10^6$ and at or about $2.5 \times 10^7$, between at or about $4 \times 10^6$ and at or about $2 \times 10^7$, or between at or about $5 \times 10^6$ and at or about $1 \times 10^7$ total receptor$^+$/CD4$^+$/CCR7$^+$/CD27$^+$ cells, each inclusive.

210. The method of any of embodiments 201-209, wherein at least 15%, 20%, 30%, 40%, 50%, 60%, 70%, 80% or 90% of the total receptor$^+$ cells in the unit dose, or between about 15% and 90%, between about 20% and 80%, between about 30% and 70%, or between about 40% and 60%, each inclusive, of the total receptor$^+$ cells in the unit dose are receptor$^+$/CD8$^+$/CCR7$^+$/CD27$^+$ or receptor$^+$/CD4$^+$/CCR7$^+$/CD27$^+$.

211. The method of any of embodiments 201-210, wherein the unit dose of cells comprises a defined ratio of receptor⁺/CD8⁺/CCR7⁺/CD27⁺ cells to receptor⁺/CD4⁺/CCR7⁺/CD27⁺ cells, which ratio optionally is or is approximately 1:1 or is between approximately 1:3 and approximately 3:1.

212. The method of any of embodiments 201-211, wherein the unit dose further comprises a defined number of cells comprising cells that express or do not express CD45, optionally wherein the unit dose further comprises a defined number of cells comprising CD45RA⁻ cells.

213. The method of any of embodiments 201-212, further comprising assessing in the therapeutic composition the number, percentage or ratio of T cells that express or do not express CD45RA, optionally the number, percentage or ratio of T cells that are CD45RA⁻.

214. A method for generating a cell composition comprising genetically engineered cells, the method comprising:
 i) providing, from a biological sample from a subject, an input composition comprising a target percentage of CD8⁺ T cells that express or do not express CCR7, CD27 and/or CD45RA and/or a target percentage of CD4⁺ T cells that express or do not express CCR7, CD27 and/or CD45RA;
 ii) introducing, into the input composition, a polynucleotide encoding a recombinant receptor; and
 iii) stimulating the cells in the input composition, prior to, during and/or subsequent to said introducing, wherein stimulating comprises incubating the cells in the presence of one or more stimulating agents, said stimulating results in activation and/or proliferation of the cells;
 wherein the method produces an output composition comprising a defined ratio of recombinant receptor-expressing (receptor⁺) CD8⁺ T cells that express or do not express CCR7, CD27 and/or CD45RA to receptor⁺/CD4⁺ T cells that express or do not express CCR7, CD27 and/or CD45RA and/or a defined ratio of receptor⁺/CD8⁺ T cells that express or do not express CCR7, CD27 and/or CD45RA and/or receptor⁺/CD4⁺ T cells that express or do not express CCR7, CD27 and/or CD45RA to another subset of cells in the composition.

215. A method for generating a cell composition comprising genetically engineered cells, the method comprising introducing, into an input composition, a polynucleotide encoding a recombinant receptor, wherein the input composition comprises a target percentage of CD8⁺ T cells that express or do not express CCR7, CD27 and/or CD45RA and/or a target percentage of CD4⁺ T cells that express or do not express CCR7, CD27 and/or CD45RA provided from a biological sample from a subject, and the input composition is stimulated, prior to, during and/or subsequent to said introducing by incubating the cells in the presence of one or more stimulating agents, said stimulation results in activation and/or proliferation of the cells; and wherein the method produces an output composition comprising a defined ratio of recombinant receptor-expressing (receptor⁺) CD8⁺ T cells that express or do not express CCR7, CD27 and/or CD45RA to receptor⁺/CD4⁺ T cells that express or do not express CCR7, CD27 and/or CD45RA and/or a defined ratio of receptor⁺/CD8⁺ T cells that express or do not express CCR7, CD27 and/or CD45RA and/or receptor⁺/CD4⁺ T cells that express or do not express CCR7, CD27 and/or CD45RA to another subset of cells in the composition.

216. A method for generating a cell composition comprising genetically engineered cells, the method comprising:
 i) isolating, from a biological sample obtained from a subject, a target number of CD8⁺ T cells that express or do not express CCR7, CD27 and/or CD45RA and/or a target number of CD4⁺ T cells that express or do not express CCR7, CD27 and/or CD45RA, thereby generating an input composition;
 ii) introducing, into the input composition, a polynucleotide encoding a recombinant receptor; and
 iii) stimulating the cells in the input composition, prior to, during and/or subsequent to said introducing, wherein stimulating comprises incubating the cells in the presence of one or more stimulating agents, said stimulating results in activation and/or proliferation of the cells;
 wherein the method produces an output composition comprising a defined ratio of recombinant receptor-expressing (receptor⁺) CD8⁺ T cells that express or do not express CCR7, CD27 and/or CD45RA to receptor⁺/CD4⁺ T cells that express or do not express CCR7, CD27 and/or CD45RA and/or a defined ratio of receptor⁺/CD8⁺ T cells that express or do not express CCR7, CD27 and/or CD45RA and/or receptor⁺/CD4⁺ T cells that express or do not express CCR7, CD27 and/or CD45RA to another subset of cells in the composition.

217. A method for generating a cell composition comprising genetically engineered cells, the method comprising introducing, into an input composition, a polynucleotide encoding a recombinant receptor, wherein the input composition is generated by isolating, from a biological sample obtained from a subject, a target number of CD8⁺ T cells that express or do not express CCR7, CD27 and/or CD45RA and/or a target number of CD4⁺ T cells that express or do not express CCR7, CD27 and/or CD45RA, and the input composition is stimulated, prior to, during and/or subsequent to said introducing by incubating the cells in the presence of one or more stimulating agents, said stimulation results in activation and/or proliferation of the cells; and wherein the method produces an output composition comprising a defined ratio of recombinant receptor-expressing (receptor⁺) CD8⁺ T cells that express or do not express CCR7, CD27 and/or CD45RA to receptor⁺/CD4⁺ T cells that express or do not express CCR7, CD27 and/or CD45RA and/or a defined ratio of receptor⁺/CD8⁺ T cells that express or do not express CCR7, CD27 and/or CD45RA and/or receptor⁺/CD4⁺ T cells that express or do not express CCR7, CD27 and/or CD45RA to another subset of cells in the composition.

218. The method of any of embodiments 214-217, wherein the input composition comprises a target percentage of CD8⁺ T cells that express or do not express CCR7, CD27 and/or CD45RA and/or a target percentage of CD4⁺ T cells that express or do not express CCR7, CD27 and/or CD45RA.

219. The method of any of embodiments 214-217, wherein the input composition comprises a target percentage of CD4⁺/CCR7⁺, CD4⁺/CD27⁺, CD4⁺/CCR7⁺/CD27⁺, CD4⁺/CCR7⁺/CD45RA⁻, CD4⁺/CCR7⁺/CD45RA⁺, CD8⁺/CCR7⁺, CD8⁺/CD27⁺, CD8⁺/CCR7⁺/CD27⁺, CD8⁺/CCR7⁺/CD45RA⁻ and/or CD8⁺/CCR7⁺/CD45RA⁺ cells.

220. The method of any of embodiments 214-219, wherein the output composition comprises a defined ratio of receptor⁺/CD8⁺/CCR7⁺, receptor⁺/CD8⁺/CD27⁺, receptor⁺/CD8⁺/CCR7⁺/CD27⁺, receptor⁺/CD8⁺/CCR7⁺/CD45RA⁻ and/or receptor⁺/CD8⁺/CCR7⁺/CD45RA⁺ cells, to receptor⁺/CD4⁺/CCR7⁺, receptor⁺/CD4⁺/CD27⁺, receptor⁺/CD4⁺/CCR7⁺/CD27⁺, receptor⁺/CD4⁺/CCR7⁺/CD45RA⁻ and/or receptor⁺/CD4⁺/CCR7⁺/CD45RA⁺ cells; or
 a defined ratio of receptor⁺/CD8⁺/CCR7⁺, receptor⁺/CD8⁺/CD27⁺, receptor⁺/CD8⁺/CCR7⁺/CD27⁺, receptor⁺/CD8⁺/CCR7⁺/CD45RA⁻ and/or receptor⁺/CD8⁺/CCR7⁺/CD45RA⁺ cells and/or receptor⁺/CD4⁺/CCR7⁺, receptor⁺/CD4⁺/CD27⁺, receptor⁺/CD4⁺/CCR7⁺/CD27⁺, receptor⁺/CD4⁺/CCR7⁺/CD45RA⁻ and/or receptor⁺/CD4⁺/CCR7⁺/CD45RA⁺ cells to another subset of cells in the composition.

221. The method of any of embodiments 214-219, further comprising determining one or more unit doses of a T cell composition for administration to a subject having a disease or conditions, wherein the unit dose comprises all or a portion of the output composition that comprises:
  a defined number of recombinant receptor-expressing CD8⁺ T cells that express C—C chemokine receptor type 7 (CCR7) (receptor⁺/CD8⁺/CCR7⁺ cells) and/or a defined number of recombinant receptor-expressing CD4⁺ T cells that express CCR7 (receptor⁺/CD4⁺/CCR7⁺ cells) and/or a defined ratio of receptor⁺/CD8⁺/CCR7⁺ cells to receptor⁺/CD4⁺/CCR7⁺ cells and/or a defined ratio of receptor⁺/CD8⁺/CCR7⁺ cells and/or receptor⁺/CD4⁺/CCR7⁺ cells to another subset of cells in the composition;
  a defined number of recombinant receptor-expressing CD8⁺ T cells that express cluster of differentiation 27 (CD27) (receptor⁺/CD8⁺/CD27⁺ cells) and/or a defined number of recombinant receptor-expressing CD4⁺ T cells that express CD27 (receptor⁺/CD4⁺/CD27⁺ cells) and/or a defined ratio of receptor⁺/CD8⁺/CD27⁺ cells to receptor⁺/CD4⁺/CD27⁺ cells and/or a defined ratio of receptor⁺/CD8⁺/CD27⁺ cells and/or receptor⁺/CD4⁺/CD27⁺ cells to another subset of cells in the composition; or
  a defined number of recombinant receptor-expressing CD8⁺ T cells that express CCR7 and CD27 (receptor⁺/CD8⁺/CCR7⁺/CD27⁺ cells) and/or a defined number of recombinant receptor-expressing CD4⁺ T cells that express CCR7 and CD27 (receptor⁺/CD4⁺/CCR7⁺/CD27⁺ cells) and/or a defined ratio of receptor⁺/CD8⁺/CCR7⁺/CD27⁺ cells to receptor⁺/CD4⁺/CCR7⁺/CD27⁺ cells and/or a defined ratio of receptor⁺/CD8⁺/CCR7⁺/CD27⁺ cells and/or receptor⁺/CD4⁺/CCR7⁺/CD27⁺ cells to another subset of cells in the composition.

222. The method of embodiment 221, wherein the unit dose of cells comprises a defined number of CD8⁺/CCR7⁺ cells, CD4⁺/CCR7⁺ cells, CD8⁺/CD27⁺ cells, CD4⁺/CD27⁺ cells, CD8⁺/CCR7⁺/CD27⁺ cells and/or CD4⁺/CCR7⁺/CD27⁺ cells.

223. The method of embodiment 221 or embodiment 222, wherein the unit dose comprises between at or about $1 \times 10^5$ and at or about $1 \times 10^8$, between at or about $5 \times 10^5$ and at or about $1 \times 10^7$, or between at or about $1 \times 10^6$ and at or about $1 \times 10^7$, each inclusive, total receptor⁺/CD8⁺ cells or total receptor⁺/CD4⁺ cells, total receptor⁺/CD8⁺/CCR7⁺ cells, total receptor⁺/CD4⁺/CCR7⁺ cells, total receptor⁺/CD8⁺/CD27⁺ cells, total receptor⁺/CD4⁺/CD27⁺ cells, total receptor⁺/CD8⁺/CCR7⁺/CD27⁺ cells, or total receptor⁺/CD4⁺/CCR7⁺/CD27⁺ cells.

224. The method of any of embodiments 221-223, wherein the unit dose comprises at least about $3 \times 10^6$, $4 \times 10^6$, $5 \times 10^6$, $6 \times 10^6$, $7 \times 10^6$, $8 \times 10^6$, $9 \times 10^6$, or $1 \times 10^7$ total receptor⁺/CD8⁺/CCR7⁺ cells or total receptor⁺/CD8⁺/CD27⁺ cells; and/or at least about $3 \times 10^6$, $4 \times 10^6$, $5 \times 10^6$, $6 \times 10^6$, $7 \times 10^6$, $8 \times 10^6$, $9 \times 10^6$, $1 \times 10^6$, or $1 \times 10^7$ total receptor/CD4/CCR7⁺ cells or total receptor⁺/CD4⁺/CD27⁺; and/or at least about $3 \times 10^6$, $4 \times 10^6$, $5 \times 10^6$, $6 \times 10^6$, $7 \times 10^6$, $8 \times 10^6$, $9 \times 10^6$, or $1 \times 10^7$ total receptor⁺/CD8⁺/CCR7⁺/CD27⁺ cells and/or at least about $3 \times 10^6$, $4 \times 10^6$, $5 \times 10^6$, $6 \times 10^6$, $7 \times 10^6$, $8 \times 10^6$, $9 \times 10^6$, or $1 \times 10^7$ total receptor⁺/CCR7⁺/CD27⁺ cells.

225. The method of any of embodiments 221-224, wherein the unit dose comprises between at or about $3 \times 10^6$ and at or about $2.5 \times 10^7$, between at or about $4 \times 10^6$ and at or about $2 \times 10^7$, or between at or about $5 \times 10^6$ and at or about $1 \times 10^7$ total receptor⁺/CD8⁺/CCR7⁺ cells or total receptor⁺/CD8⁺/CD27⁺ cells; and/or between at or about $3 \times 10^6$ and at or about $2.5 \times 10^7$, between at or about $4 \times 10^6$ and at or about $2 \times 10^7$, or between at or about $5 \times 10^6$ and at or about $1 \times 10^7$ total receptor⁺/CD4⁺/CCR7⁺ cells or total receptor⁺/CD4⁺/CD27⁺, and/or between at or about $3 \times 10^6$ and at or about $2.5 \times 10^7$, between at or about $4 \times 10^6$ and at or about $2 \times 10^7$, or between at or about $5 \times 10^6$ and at or about $1 \times 10^7$ total receptor⁺/CD8⁺/CCR7⁺/CD27⁺ cells and/or between at or about $3 \times 10^6$ and at or about $2.5 \times 10^7$, between at or about $4 \times 10^6$ and at or about $2 \times 10^7$, or between at or about $5 \times 10^6$ and at or about $1 \times 10^7$ total receptor⁺/CD4⁺/CCR7⁺/CD27⁺ cells, each inclusive.

226. The method of any of embodiments 221-225, wherein at least 15%, 20%, 30%, 40%, 50%, 60%, 70%, 80% or 90% of the total receptor⁺ cells in the unit dose, or between about 15% and 90%, between about 20% and 80%, between about 30% and 70%, or between about 40% and 60%, each inclusive, of the total receptor⁺ cells in the unit dose are receptor⁺/CD8⁺/CCR7⁺ or receptor⁺/CD8⁺/CD27⁺; and/or at least 15%, 20%, 30%, 40%, 50%, 60%, 70%, 80% or 90% of the total receptor⁺ cells in the unit dose, or between about 15% and 90%, between about 20% and 80%, between about 30% and 70%, or between about 40% and 60%, each inclusive, of the total receptor⁺ cells in the unit dose are receptor⁺/CD4⁺/CCR7⁺ or receptor⁺/CD4⁺/CD27⁺; and/or at least 15%, 20%, 30%, 40%, 50%, 60%, 70%, 80% or 90% of the total receptor⁺ cells in the unit dose, or between about 15% and 90%, between about 20% and 80%, between about 30% and 70%, or between about 40% and 60%, each inclusive, of the total receptor⁺ cells in the unit dose are receptor⁺/CD8⁺/CCR7⁺/CD27⁺ or receptor⁺/CD4⁺/CCR7⁺/CD27⁺.

227. The method of any of embodiments 221-226, wherein the unit dose of cells comprises a defined ratio of receptor⁺/CD8⁺/CCR7⁺ cells to receptor⁺/CD4⁺/CCR7⁺ cells, which ratio optionally is or is approximately 1:1 or is between approximately 1:3 and approximately 3:1; and/or a defined ratio of receptor⁺/CD8⁺/CD27⁺ cells to receptor⁺/CD4⁺/CD27⁺ cells, which ratio optionally is or is approximately 1:1 or is between approximately 1:3 and approximately 3:1; and/or a defined ratio of receptor⁺/CD8⁺/CCR7⁺/CD27⁺ cells to receptor⁺/CD4⁺/CCR7⁺/CD27⁺ cells, which ratio optionally is or is approximately 1:1 or is between approximately 1:3 and approximately 3:1.

228. The method of any of embodiments 221-227, wherein the unit dose further comprises a defined number of cells comprising cells that express or do not express CD45, optionally wherein the unit dose further comprises a defined number of cells comprising CD45RA⁻ cells.

229. The method of embodiment 228, wherein the unit dose of cells comprises a defined number of receptor⁺/CD4⁺/CCR7⁺/CD45RA⁻ cells and/or receptor⁺/CD8⁺/CCR7⁺/CD45RA⁻ cells.

230. The method of any of embodiments 221-229, wherein at least 15%, 20%, 30%, 40%, 50%, 60%, 70%, 80% or 90% of the total receptor⁺ cells in the unit dose, or between about 15% and 90%, between about 20% and 80%, between about 30% and 70%, or between about 40% and 60%, each inclusive, of the total receptor⁺ cells in the unit dose are receptor⁺/CD4⁺/CCR7⁺/CD45RA⁻ or receptor⁺/CD8⁺/CCR7⁺/CD45RA⁻.

231. The method of any of embodiments 214-230, wherein prior to the providing or isolating, the method comprises determining the number, number per volume, number per weight, and/or percentage of the CD8⁺ T cells that express or do not express CCR7, CD27 and/or CD45RA and/or CD4+ T cells that express or do not express CCR7, CD27 and/or CD45RA.

232. The method of any of embodiments 214-231, wherein the one or more stimulating agent is capable of activating T cells, CD4+ T cells and/or CD8+ T cells; is capable of inducing a signal through a TCR complex; and/or is capable of inducing proliferation of T cells, CD4+ T cells and/or CD8+ T cells.

233. The method of any of embodiments 214-232, wherein the one or more stimulating agent comprises a primary agent that binds to a member of a TCR complex, optionally that specifically binds to CD3.

234. The method of embodiment 233, wherein the one or more stimulating agent further comprises a secondary agent that specifically binds to a T cell costimulatory molecule.

235. The method of embodiment 234, wherein the costimulatory molecule is selected from the group consisting of CD28, CD137 (4-1-BB), OX40, or ICOS.

236. The method of embodiment 234 or embodiment 235, wherein the primary and secondary agents comprise antibodies, optionally wherein the one or more stimulating agent comprises incubation with an anti-CD3 antibody and an anti-CD28 antibody.

237. The method of any of embodiments 214-236, wherein the one or more stimulating agents are present on the surface of a solid support, optionally a bead.

238. The method of any of embodiments 214-237, wherein the one or more stimulating agent is selected from the group consisting of CD3-binding molecules; CD28-binding molecules; recombinant IL-2; recombinant IL-15; and recombinant IL-7, a vaccine comprising an antigen specifically recognized by the antigen receptor, and an anti-idiotype antibody that specifically binds the antigen receptor or combinations thereof.

239. The method of any of embodiments 183-238, wherein the therapeutic composition is a composition according to embodiment 1.

240. The methods of any of embodiments 183-239, further comprising administering to a subject having a disease or condition, the therapeutic composition, optionally one or more unit doses thereof and/or a volume corresponding to such one or more of unit doses.

241. The method of any of embodiments 183-240, wherein among a group of subjects treated according to the method, the number or ratio of cells that express CCR7 (CCR7+ cells) in the unit dose varies by no more than 40%, by no more than 30%, by no more than 20%, by no more than 10% or by no more than 5%.

242. The method of any of embodiments 183-241, wherein the unit dose comprises between at or about $1 \times 10^5$ and at or about $5 \times 10^8$, between at or about $1 \times 10^5$ and at or about $1 \times 10^8$, between at or about $5 \times 10^5$ and at or about $1 \times 10^7$, or between at or about $1 \times 10^6$ and at or about $1 \times 10^7$ total CD3+ cells that express the recombinant receptor (receptor+/CD3+ cells) or total CD3+ cells, each inclusive.

243. The method of any of embodiments 183-242, wherein the unit dose comprises no more than about $5 \times 10^8$, no more than about $1 \times 10^8$, no more than about $5 \times 10^7$, no more than about $1 \times 10^7$, no more than about $5 \times 10^6$, no more than about $1 \times 10^6$, or no more than about $5 \times 10^5$ total receptor+/CD3+ cells or total CD3+ cells.

244. The method of any of embodiments 183-243, wherein the total number of CD3+ cells, total number of receptor+/CD3+ cells, total number of receptor+/CD8+ cells, total number of receptor+/CD4+ cells, total number of receptor+/CD8+/CCR7+ cells, total number of receptor+/CD4+/CCR7+ cells, total number of receptor+/CD8+/CD27+ cells, total number of receptor+/CD4+/CD27+ cells, total number of receptor+/CD8+/CCR7+/CD27+ cells, total number of receptor+/CD4+/CCR7+/CD27+ cells, total number of receptor+/CD8+/CCR7+/CD45RA− cells and/or receptor+/CD4+/CCR7+/CD45RA− cells is the total number of such cells that are live or viable.

245. The method of any of embodiments 183-244, wherein the total number of CD3+ cells, total number of receptor+/CD3+ cells, total number of receptor+/CD8+ cells, total number of receptor+/CD4+ cells, total number of receptor+/CD8+/CCR7+ cells, total number of receptor+/CD4+/CCR7+ cells, total number of receptor+/CD8+/CD27+ cells, total number of receptor+/CD4+/CD27+ cells, total number of receptor+/CD8+/CCR7+/CD27+ cells, total number of receptor+/CD4+/CCR7+/CD27+ cells, total number of receptor+/CD8+/CCR7+/CD45RA− cells and/or receptor+/CD4+/CCR7+/CD45RA− cells is the total number of such cells that do not express an apoptotic marker and/or is the total number of such cells that are apoptotic marker negative (−), wherein the apoptotic marker is Annexin V or activated Caspase 3.

246. The method of any of embodiments 240-245, comprising administering a plurality of unit doses contained in a plurality of separate compositions.

247. The method of embodiment 246, wherein the plurality of separate compositions comprise a first composition comprising one of the CD8+ T cells and the CD4+ T cells and a second composition comprising the other of the CD8+ T cells and the CD4+ T cells.

248. The method of embodiment 247, wherein the first composition comprises the CD8+ T cells.

249. The method of embodiment 247, wherein the first composition comprises the CD4+ T cells.

250. The method of any of embodiments 247-249, comprising administering the composition containing CD8+ T cells or one or more unit doses thereof and/or a volume corresponding to such one or more of unit doses and the composition containing CD4+ T cells or one or more unit doses thereof and/or a volume corresponding to such one or more of unit doses, no more than 2 hours, no more than 1 hour, no more than 30 minutes, no more than 15 minutes, no more than 10 minutes or no more than 5 minutes apart or simultaneously.

251. The method of any of embodiments 247-250, comprising administering the composition containing CD8+ T cells or one or more unit doses thereof and/or a volume corresponding to such one or more of unit doses, prior to administering the composition containing CD4+ cells or one or more unit doses thereof and/or a volume corresponding to such one or more of unit doses.

252. The method of any of embodiments 247-250, comprising administering the composition containing CD4+ T cells or one or more unit doses thereof and/or a volume corresponding to such one or more of unit doses, prior to administering the composition containing CD8+ cells or one or more unit doses thereof and/or a volume corresponding to such one or more of unit doses.

253. The method of any of embodiments 183-252, wherein the recombinant receptor is or comprises a chimeric receptor and/or a recombinant antigen receptor.

254. The method of any of embodiments 183-253, wherein the recombinant receptor is capable of binding to a target antigen that is associated with, specific to, and/or expressed on a cell or tissue of a disease, disorder or condition.

255. The method of embodiment 254, wherein the disease, disorder or condition is an infectious disease or disorder, an autoimmune disease, an inflammatory disease, or a tumor or a cancer.

256. The method of embodiment 254 or embodiment 255, wherein the target antigen is a tumor antigen.

257. The method of any of embodiments 254-256, wherein the target antigen is selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD138, CD171, epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), G Protein Coupled Receptor 5D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22Ra), IL-13 receptor alpha 2 (IL-13Ra2), kinase insert domain receptor (kdr), kappa light chain, L1 cell adhesion molecule (L1-CAM), CE7 epitope of L-CAM, Leucine Rich Repeat Containing 8 Family Member A (LRRC8A), Lewis Y, Melanoma-associated antigen (MAGE)-A1, MAGE-A3, MAGE-A6, mesothelin, c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), vascular endothelial growth factor receptor (VEGFR), vascular endothelial growth factor receptor 2 (VEGFR2), Wilms Tumor 1 (WT-1), a pathogen-specific antigen, or an antigen associated with a universal tag, and/or biotinylated molecules, and/or molecules expressed by HIV, HCV, HBV or other pathogens.

258. The method of any of embodiments 183-257, wherein the recombinant receptor is or comprises a functional non-TCR antigen receptor or a TCR or antigen-binding fragment thereof.

259. The method of any of embodiments 183-258, wherein the recombinant receptor is a chimeric antigen receptor (CAR).

260. The method of any of embodiments 183-259, wherein the recombinant receptor comprises an extracellular domain comprising an antigen-binding domain.

261. The method of embodiment 260, wherein the antigen-binding domain is or comprises an antibody or an antibody fragment thereof, which optionally is a single chain fragment.

262. The method of embodiment 261, wherein the fragment comprises antibody variable regions joined by a flexible linker.

263. The method of embodiment 261 or embodiment 262, wherein the fragment comprises an scFv.

264. The method of any of embodiments 183-263, wherein the recombinant receptor comprises an intracellular signaling region.

265. The method of embodiment 264, wherein the intracellular signaling region comprises an intracellular signaling domain.

266. The method of embodiment 265, wherein the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM).

267. The method of embodiment 266, wherein the intracellular signaling domain is or comprises an intracellular signaling domain of a CD3 chain, optionally a CD3-zeta (CD3ζ) chain, or a signaling portion thereof.

268. The method of any of embodiments 183-267, wherein the recombinant receptor further comprises a transmembrane domain disposed between the extracellular domain and the intracellular signaling region.

269. The method of any of embodiments 183-268, wherein the intracellular signaling region further comprises a costimulatory signaling domain.

270. The method of embodiment 269, wherein the costimulatory signaling domain comprises an intracellular signaling domain of a T cell costimulatory molecule or a signaling portion thereof.

271. The method of embodiment 259 or embodiment 270, wherein the costimulatory signaling domain comprises an intracellular signaling domain of a CD28, a 4-1BB or an ICOS or a signaling portion thereof.

272. The method of any of embodiments 269-271, wherein the costimulatory signaling domain is between the transmembrane domain and the intracellular signaling domain.

273. The method of any of embodiments 183-272, wherein the T cells are primary T cells obtained from a subject.

274. The method of any of embodiments 183-273, wherein the T cells are autologous to the subject.

275. The method of any of embodiments 183-274, wherein the T cells are allogeneic to the subject.

276. An output composition produced by the method of any of embodiments 183-275.

277. A unit dose determined or produced by the method of any of embodiments 201-213 and 221-276.

278. A pharmaceutical composition comprising the unit dose of embodiment 277.

279. The pharmaceutical composition of embodiment 278, further comprising a pharmaceutical carrier.

280. A method of treatment, comprising administering to a mammalian subject all or a portion of the output composition of embodiment 276, a unit dose of embodiment 277 or a pharmaceutical composition of embodiment 278 or embodiment 279.

281. Use of all or a portion of the output composition of embodiment 276, a unit dose of embodiment 277 or a pharmaceutical composition of embodiment 278 or embodiment 279 for treating cancer.

282. Use of all or a portion of the output composition of embodiment 276, a unit dose of embodiment 277 or a pharmaceutical composition of embodiment 278 or embodiment 279 in the manufacture of a medicament for treating cancer.

283. The output composition of embodiment 276, a unit dose of embodiment 277 or a pharmaceutical composition of embodiment 278 or embodiment 279 for use in treating cancer.

VII. EXAMPLES

The following examples are included for illustrative purposes only and are not intended to limit the scope of the invention.

Example 1 Assessment of Cell Attributes and Phenotypes of Anti-CD19 CAR-Expressing T Cells and Pharmacokinetic (PK) Parameters, Response and Toxicity The relationship between cellular phenotypes of T cells engineered to express a chimeric antigen receptor (CAR) and pharmacokinetic (PK) parameters, response and toxicity outcomes of the cells upon administration to subjects were assessed.

A. Attributes of Therapeutic T Cell Composition

Exemplary therapeutic T cell compositions containing autologous T cells expressing a chimeric antigen-receptor (CAR) specific for CD19 were generated. The anti-CD19 CAR contained an anti-CD19 scFv derived from a murine antibody (variable region derived from FMC63, $V_L$-linker-$V_H$ orientation), an immunoglobulin-derived spacer, a transmembrane domain derived from CD28, a costimulatory region derived from 4-1BB, and a CD3-zeta intracellular signaling domain. The viral vector further contained sequences encoding a truncated receptor, which served as a surrogate marker for CAR expression; separated from the CAR sequence by a T2A ribosome skip sequence. The generated therapeutic T cell compositions, used for administration in subjects with Relapsed and Refractory Non-Hodgkin's Lymphoma (NHL) described below, were assessed for greater than one hundred phenotypic, functional, and cell health related attributes, using flow cytometry and in vitro assays. Cells were assessed before and after engineering, for various attributes.

Exemplary attributes that were assessed are set forth in Table E1. Phenotypic attributes generally associated with memory phenotypic composition and cell health phenotypes were examined using flow cytometry. T cell functionality was assessed using in vitro antigen-specific bioassays. Characterization and release testing was conducted on therapeutic T cell compositions that had undergone a representative number of freeze-thaw cycles.

TABLE E1

Representative characterization attributes measured in therapeutic cell compositions containing anti-CD19 CAR T cells Viability
Active intracellular caspase-3
Annexin V
CCR7 (C-C chemokine receptor type 7)
Inflammatory cytokines such as TNF-α (tumor necrosis factor α)

For generation of cell compositions for administration, autologous cells were isolated from the subjects via leukapheresis. Leukapheresis samples were subjected to a process for generation of CAR-expressing cells. The process involved washing of cells using an automated wash and immunoaffinity based selection for purification of CD4+ and CD8+ T cells, resulting in two compositions, enriched for CD8+ (in which a median of 99%, Inter Quartile Range (IQR) 98-100%, of cells were CD8+) and CD4+ (in which a median of 99%, IQR 99-100%, cells were CD4+) cells, respectively.

Cells of the enriched CD4+ and CD8+ compositions were separately subjected to lentiviral transduction with a vector encoding an anti-CD19 CAR with a 4-1BB costimulatory domain. Transduced populations then were separately incubated in the presence of stimulating reagents for cell expansion. Expanded CD8+ and CD4+ cells were formulated and cryopreserved separately and stored prior to administration. To minimize variations, between lots and/or cell compositions derived from different patients, such as those having different patient attributes, in parameters indicative of cell health, cells were held at constant volumes across lots. Cell products exhibited a tight range of viable cell concentrations (based on an assessment of cell compositions for one group of subjects, CD8+: median $31 \times 10^6$ cells/mL, IQR $28\text{-}40 \times 10^6$ cells/mL, N=38; CD4+: median $35 \times 10^6$ cells/mL, IQR $31\text{-}40 \times 10^6$, N=36).

At the site of administration, cell compositions were thawed and administered separately, according to a target volume of each composition corresponding to the number of CD8+ CAR+ and CD4+ CAR+ cells in the appropriate dose (such as for DL1, containing $5 \times 10^7$ total CAR-expressing T cells ($2.5 \times 10^7$ each of CAR-expressing CD4+ and CAR-expressing CD8+ cells), or DL2, containing $1 \times 10^8$ total CAR-expressing T cells ($5 \times 10^7$ each of CAR-expressing CD4+ and CAR-expressing CD8+ cells)).

Parameters indicative of health of the CAR-expressing T cells in the compositions for administration were assessed, such as by measuring, post-thaw, viability, cell surface Annexin V expression and levels of active intracellular Caspase 3. The median percentage of Annexin V-expressing cells was 11% (IQR 9-18%; N=33) of CD8+ CAR+ T cells and 10% (IQR 8-17%; N=31) of CD4+ CAR+ T cells. Caspase 3 expression was observed to be similar to Annexin V expression.

The quantities of CAR+CD4+ and CAR+ CD8+ T cells in the composition for administration were precisely controlled. The number of cells actually administered to an exemplary set of subjects was observed to be within 8% or less of the target number of cells for a given dose:
  $2.4\text{-}2.7 \times 10^7$ (target±8%) CD4+ CAR+ T cells and $2.4\text{-}2.7 \times 10^7$ (target±8%) CD8+ CAR+ T cells for subjects administered cells at DL1 (n=48)
  $4.6\text{-}5.1 \times 10^7$ (target±8%) CD4+ CAR+ T cells or $4.6\text{-}5.1 \times 10^7$ (target±8%) CD8+ CAR+ T cells for subjects administered cells at DL2 (n=20).

The range of administered dose was found to have low variability in a different exemplary set of subjects:
  $48\text{-}52 \times 10^6$ CD3+ CAR+ T cell at DL1 (n=34)
  $96\text{-}101 \times 10^6$ CD3+ CAR+ T cells at DL2 (n=29)
  $24\text{-}27 \times 10^6$ CD4+ CAR+ or CD8+ CAR+ T cells at DL1 (n=34)
  $46\text{-}51 \times 10^6$ CD4+ CAR+ or CD8+ CAR+ T cells at DL2 (n=29).

As shown in FIG. 1A, CAR-expressing T cell compositions administered to subjects were observed to exhibit high T cell purity and low variance between lots. In view, e.g., of process and product controls, therapeutic cell compositions containing CAR T cells were observed to have low lot-to-lot variability in cell-specific T cell function.

Figure 1B:
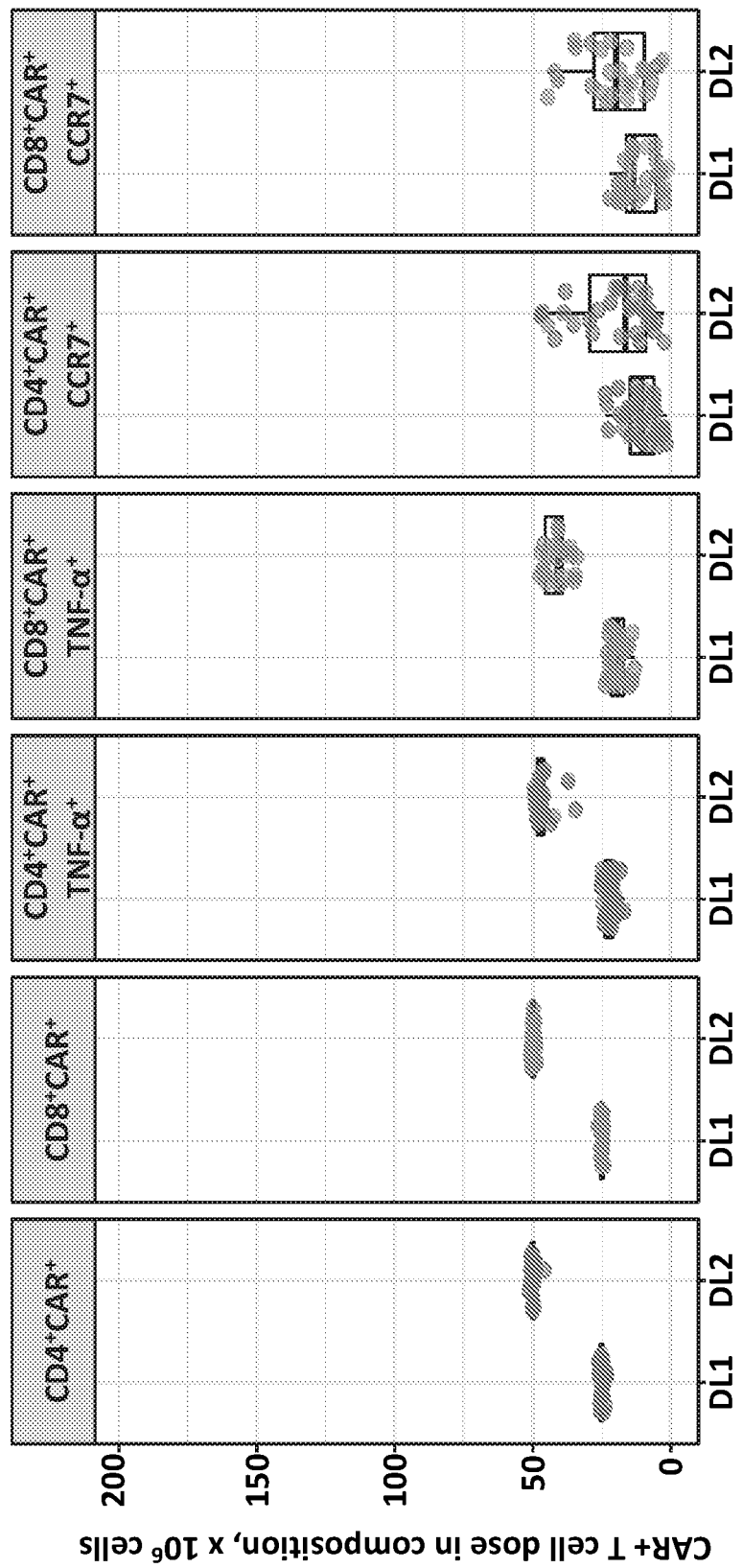
FIG. 1B shows the number of CD4$^+$ CAR$^+$ and CD8$^+$ CAR$^+$ cells, CD4$^+$ CAR$^+$ TNF-$\alpha^+$ cells and CD8$^+$ CAR$^+$ TNF-$\alpha^+$, CD4$^+$CAR$^+$CCR7$^+$ cells and CD8$^+$CAR$^+$CCR7$^+$ cells present in CAR T cell compositions for administration at DL1 and DL2.
Figure 1C:
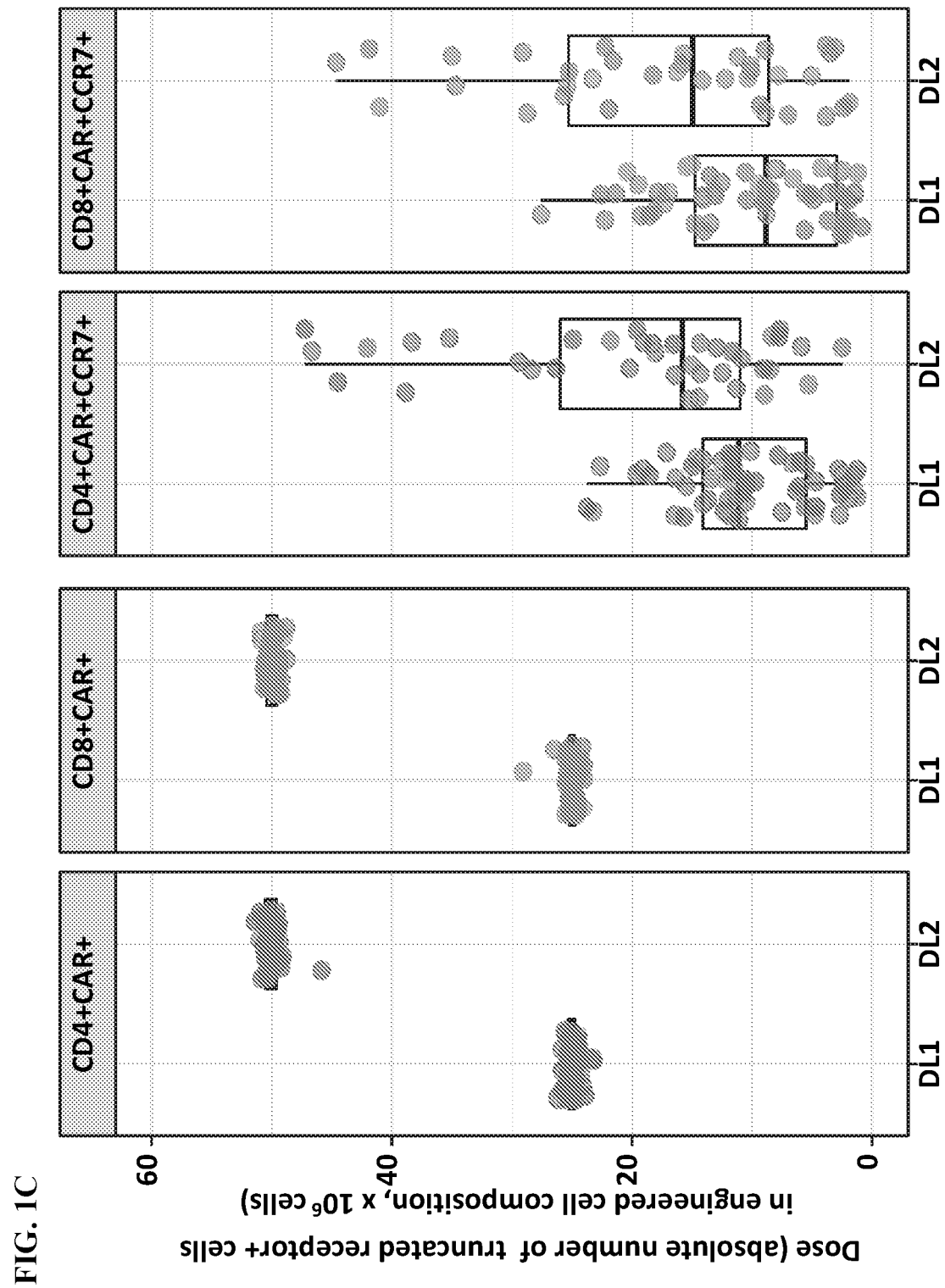
FIG. 1C shows the number of CD4$^+$ CAR$^+$ and CD8$^+$ CAR$^+$ cells, CD4$^+$CAR$^+$CCR7$^+$ cells and CD8$^+$ CAR$^+$CCR7$^+$ cells present in CAR T cell compositions for administration at DL1 and DL2.

In vitro antigen-specific cytokine accumulation and intracellular cytokine staining (ICS) showed a similar low variance between lots for cytokine production for multiple cytokines (IL-2, TNF-α and IFN-γ). In an exemplary ICS experiment, cells from compositions were stimulated with CD19, stained for cytokines, including TNF-α, and surface proteins, including C—C chemokine receptor type 7 (CCR7) as a memory phenotype marker, and analyzed by flow cytometry. The number of cells in the composition for administration that were positive for the cytokines or surface proteins was determined. FIG. 1B shows the number of CD4$^+$ CAR$^+$ and CD8$^+$ CAR$^+$ cells, CD4$^+$ CAR$^+$ TNF-α$^+$ and CD8$^+$ CAR$^+$ TNF-α$^+$ cells, CD4$^+$CAR$^+$CCR7$^+$ and CD8$^+$CAR$^+$CCR7$^+$ and present in CAR T cell compositions for administration at DL1 and DL2. FIG. 1C shows another figure depicting the number of CD4$^+$ CAR$^+$ cells, CD8$^+$ CAR$^+$ cells, CD4$^+$CAR$^+$CCR7$^+$ cells and CD8$^+$CAR$^+$CCR7$^+$ cells in the controlled dose compositions, on a different scale. These results are summarized in Table E2. The results show low variability in the number of CD4$^+$ CAR$^+$ and CD8$^+$ CAR$^+$ cells, CD4$^+$ CAR$^+$ TNF-α$^+$ and CD8$^+$ CAR$^+$ TNF-α+ cells, CD4$^+$CAR$^+$CCR7$^+$ and CD8$^+$CAR$^+$CCR7$^+$ cells. For example, a tight range for the number of cells positive for TNF-α production was observed (n=61).

A parameter indicative of production by CAR$^+$ cells of tumor necrosis factor alpha (TNFα) after stimulation with CD19 showed a narrow range among different lots, with relative standard deviation (RSD) of 37% for CD4$^+$ CAR$^+$ T cells (N=59) and 51% for CD8$^+$ CAR$^+$ T cells (N=61).

The results were consistent with an observation that at least three aspects of the manufacturing and control process of the cell composition contributed to the low variability between compositions and consistent cell health: a precise, consistent flat dose of administered CD4$^+$ and CD8$^+$ cells; control and optimization of CD4$^+$ and CD8$^+$ T cell culture conditions that result in low between-composition lot variability of phenotypes (e.g., CCR7) and in vitro function (e.g., IL-2, TNF-α and IFN-γ production after antigen stimulation); and constant formulation and volume of composition. The results also showed that tight control of the number of CD4$^+$ and CD8$^+$ CAR$^+$ T cells in the therapeutic composition for administration in subjects, allows the identification of attributes of cells in the engineered cell composition (see FIG. 1C) and potential association with pharmacokinetics (PK) and clinical outcomes such as response and toxicity.

B. Administration of Anti-CD19 CAR$^+$ T Cell Composition

The therapeutic CAR$^+$ T cell composition described above was administered to subjects with relapsed or refractory (R/R) aggressive non-Hodgkin's lymphoma (NHL) in a clinical study. Specifically, a cohort of adult human subjects with R/R NHL, including diffuse large B-cell lymphoma (DLBCL) de novo or transformed from indolent lymphoma (NOS), high-grade B-cell lymphoma (including double/triple hit), DLBCL transformed from chronic lymphocytic leukemia (CLL) or marginal zone lymphomas (MZL), primary mediastinal large b-cell lymphoma (PMBCL), and follicular lymphoma grade 3b (FLG3B), were administered with anti-CD19 CAR-expressing T cell compositions. Outcomes were separately assessed for a core subset of subjects within the full cohort (excluding those subjects with a poor performance status (ECOG 2), DLBCL transformed from marginal zone lymphomas (MZL) and/or chronic lymphocytic leukemia (CLL, Richter's), and excluding those subjects with primary mediastinal large b-cell lymphoma (PMBCL), and follicular lymphoma grade 3b (FLG3B) (core cohort)). The core cohort included subjects with DLBCL, NOS and transformed follicular lymphoma (tFL) or high grade B-cell lymphoma (double/triple hit) or high-grade B-cell lymphoma, with MYC and BCL2 and/or BCL6 rearrangements with DLBCL histology (double/triple hit) and with Eastern Cooperative Oncology Group performance status (ECOG PS) of 0 or 1. The analysis at this time point presented in this example is based on assessment of a total of 91 subjects in the full cohort (88 (65 from the CORE cohort) assessed for response and 91 (67 from the CORE cohort) assessed for safety) that had been administered the anti-CD19 CAR-expressing cells.

TABLE E2

| Controlled dose, T cell phenotypes, and cell specific function (×10$^6$ cells) | | | | | | | | | | | |
|---|---|---|---|---|---|---|---|---|---|---|---|
| CD4$^+$CAR$^+$ | | CD8$^+$CAR$^+$ | | CD4$^+$CAR$^+$TNF-α$^+$ | | CD8$^+$CAR$^+$TNF-α$^+$ | | CD4$^+$CAR$^+$CCR7$^+$ | | CD8$^+$CAR$^+$CCR7$^+$ | |
| DL1 | DL2 | DL1 | DL2 | DL1 | DL2 | DL1 | DL2 | DL1 | DL2 | DL1 | DL2 |
| Median 25.1 | 50.0 | 25.0 | 49.9 | 22.4 | 47.3 | 19.4 | 41.0 | 10.6 | 16.6 | 13.5 | 19.9 |
| IQR 24.7-25.4 | 49.6-50.4 | 24.8-25.3 | 49.6-50.3 | 21.1-23.8 | 46.1-48.4 | 17.1-21.7 | 39.3-45.5 | 6.2-14.7 | 9.0-29.4 | 5.4-16.2 | 9.6-27.9 |

The anti-CD19 CAR contained an anti-CD19 scFv derived from a murine antibody (variable region derived from FMC63, V$_L$-linker-V$_H$ orientation), an immunoglobulin-derived spacer, a transmembrane domain derived from CD28, a costimulatory region derived from 4-1BB, and a CD3-zeta intracellular signaling domain. The viral vector further contained sequences encoding a truncated receptor, which served as a surrogate marker for CAR expression; separated from the CAR sequence by a T2A ribosome skip sequence.

The cryopreserved cell compositions containing anti-CD19 CAR-expressing cells were thawed prior to intravenous administration. The therapeutic T cell dose was administered as a defined cell composition by administering the formulated CD4$^+$ CAR$^+$ cell population and the formulated CD8$^+$ CAR$^+$ population separately administered at a target ratio of approximately 1:1. Subjects were administered a single or double dose of CAR-expressing T cells (each single dose via separate infusions of CD4$^+$ CAR-expressing T cells and CD8$^+$ CAR-expressing T cells, respectively) as follows: a single dose of dose level 1 (DL1) containing 5×10$^7$ total CAR-expressing T cells, or a single dose of dose level 2 (DL2) containing 1×10$^8$ total CAR-expressing T cells. In some cases, the subjects were administered a double dose of DL1 in which each dose was administered approximately fourteen (14) days apart, administered on day 1 and day 14, including one subject that inadvertently received two DL2 doses via the two-dose schedule, due to a dosing error. The dose level and the target numbers of T cell subsets for the administered composition at DL1 and DL2 are set forth in Table E3. In the core cohort, 34 subjects were administered DL1, and 27 subjects were administered DL2.

TABLE E3

Target dose level and number of T cell subsets for cell compositions containing anti-CD19 CAR T cells

| Dose level | Helper T cell ($T_H$) Dose (CD4$^+$CAR$^+$) | Cytotoxic T Cell ($T_C$) Dose (CD8$^+$CAR$^+$) | Total T Cell Dose (CD3$^+$ CAR$^+$) |
|---|---|---|---|
| 1 | 25 × 10$^6$ | 25 × 10$^6$ | 50 × 10$^6$ |
| 2 | 50 × 10$^6$ | 50 × 10$^6$ | 100 × 10$^6$ |

C. Safety and Response Outcomes after Treatment

Table E4 shows the overall response and safety outcomes for the full cohort and the core cohort at the two dose levels. The objective response rate (ORR) was 74%, including 52% subjects who showed a complete response (CR). The incidence of any grade of cytokine release syndrome (CRS) was 35%, with 1% severe CRS; and the incidence of any grade of neurotoxicity (NT) was 19%, with 1% severe NT.

TABLE E4

Response and Safety After CAR$^+$ Cell Administration

| | FULL All Dose Levels | CORE Levels$^a$ | DL1 | DL2 |
|---|---|---|---|---|
| Best Overall Response (BOR), n$^b$ | 88 | 65 | 34 | 27 |
| ORR, % (95% CI) | 74 (63, 83) | 80 (68, 89) | 77 (59, 89) | 82 (62, 94) |
| CR, % (95% CI) | 52 (41, 63) | 55 (43, 68) | 47 (30, 65) | 63 (42, 81) |
| Safety, n$^c$ | 91 | 67 | 34 | 29 |
| Any CRS, % (95% CI) | 35 (25, 46) | 36 (24, 48) | 41 (25, 59) | 24 (10, 44) |
| sCRS (grade 3-4), % (95% CI) | 1 (0, 6) | 1 (0, 8) | 38 (0, 15) | 0 |
| Any NT, % (95% CI) | 19 (11, 28) | 21(12, 33) | 24 (11, 41) | 17 (6, 36) |
| sNT(grade 3-4), % (95% CI) | 12 (6, 21) | 15 (7, 26) | 21 (9, 38) | 7 (1, 23) |

$^a$Four patients treated on DL1D (dose level 1 two-dose schedule) with similar outcomes.
$^b$Includes patients with event of PD, death, or 28-day restaging scans. One patient did not have restaging scans available.
$^c$Includes all subjects who have received at least one dose of conforming CAR-expressing cell product 28 days prior to data snapshot date or died.

D. Pharmacokinetic Assessment

Numbers of CAR$^+$ T cells in peripheral blood and bone marrow at time points before administration (pre-treatment or pre-lymphodepleting chemotherapy (LDC)) and various time points post-treatment (with day of administration as day 1) in 86 subjects in the DLBCL cohort with evaluable PK, by flow cytometry using an antibody specific for the truncated receptor used as a surrogate marker, and quantitative polymerase chain reaction (qPCR) using primers specific for a woodchuck hepatitis virus post-transcriptional regulatory element (WPRE) present in the vector encoding the chimeric antigen receptor (CAR). The area under the curve plotting numbers per microliter for the indicated CAR$^+$ cell population between days 0 and 28 (AUC$_{0-28}$; CAR$^+$ cells*day/μL blood), the maximum or peak blood concentration of CAR$^+$ cells ($C_{max}$; CAR$^+$ cells/μL blood) and the time to $C_{max}$ ($T_{max}$; days) were assessed.

Figure 2:
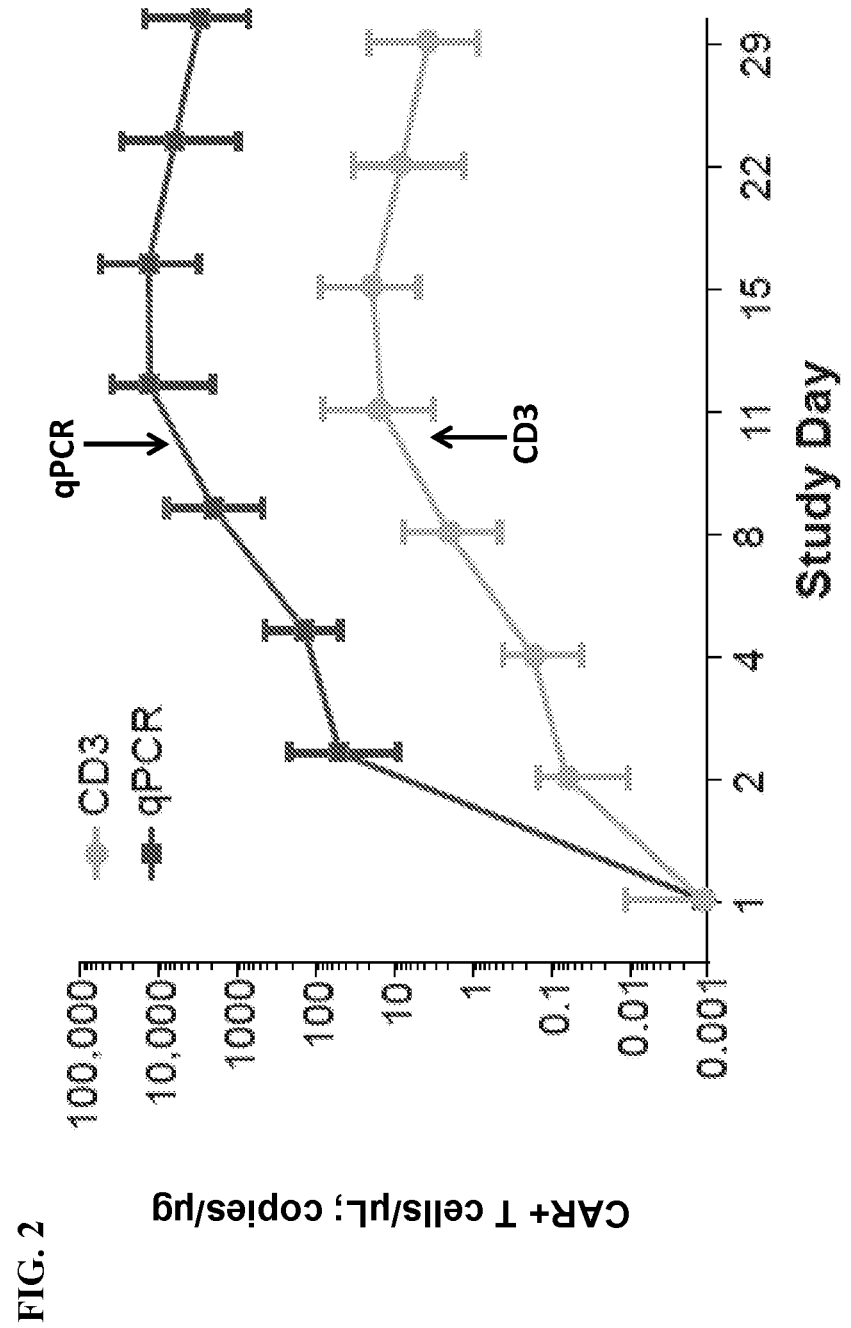
FIG. 2 depicts the median (±quartiles) number of CAR-expressing CD3$^+$ cells/μL blood, assessed by flow cytometry using an antibody specific for a truncated receptor (CD3, circle; N=87); or median (±quartiles) number of copies integrated CAR transgene/μg genomic DNA, assessed by quantitative polymerase chain reaction (qPCR) using primers specific for a woodchuck hepatitis virus post-transcriptional regulatory element (WPRE) present in the vector encoding the CAR (qPCR, square; N=85) in blood samples from 87 subjects that have been administered anti-CD19 CAR-expressing cells. The cutoff for CAR$^+$ cell detection in flow cytometry was set at ≥25 events in the CAR$^+$ gate, and limit of detection for qPCR was ≥12.5 copies of CAR transgene per g of genomic DNA.

An exemplary graph depicting the detected numbers of CAR T cells per microliter of blood at various indicated time-points, as assessed by qPCR or flow cytometry is shown in FIG. 2. As shown in FIG. 2, levels of CAR-expressing cells in samples from subjects were observed both by flow cytometry-based assays and qPCR-based assays.

Example 2 Association Between Cell Attributes of Anti-CD19 CAR-Expressing T Cells and Pharmacokinetic (PK) Parameters, Response and Toxicity The relationship between the assessed cellular attributes of T cells engineered to express a chimeric antigen receptor (CAR) and pharmacokinetic (PK) parameters, response and toxicity outcomes of the cells upon administration to subjects, as determined in Example 1, was evaluated.

A. Relationship Between Pharmacokinetics/CAR$^+$ T Cell Exposure and Cell Phenotype Attributes of Administered Therapeutic Cell Composition Relationships were assessed between certain phenotypic attributes of the CAR$^+$ T cells in the therapeutic compositions administered, and parameters associated with pharmacokinetics (PK) or CAR$^+$ T cell exposure and cytokine production.

In particular, due to the low variability among therapeutic cell compositions engineered from cells derived from, and formulated for administration to, different subjects, it was possible to detect phenotypes (e.g., CCR7$^+$ expression and cytokine production) associated with pharmacokinetic parameters (e.g., AUC), clinical response outcomes and toxicity outcomes (e.g., CRS or NT).

Cell surface expression levels or the absence of expression of cell surface markers that can be indicative of certain T cell subtypes, such as memory cell subtypes, including C—C chemokine receptor type 7 (CCR7), CD27 and CD45RA, were assessed by flow cytometry. Surface expression levels of CD3, CD4, CD8, CD28, and/or and truncated receptor used as a surrogate marker, also were assessed; the presence of activated caspase 3 was assessed as a measure of apoptotic cells. Cytokine production (μg/mL) was assessed in CD8 cells after stimulation with CD19 (antigen specific for the expressed CAR). Expression of the markers and cytokine production were correlated with the area under the curve plotting numbers of CAR$^+$ T cells (or subsets thereof) detected in the blood of subjects, between days 0 and 28 post-administration (AUC28; day 0 as the day of dosing) and the maximum or peak blood concentration of CAR$^+$ cells ($C_{max}$) post-administration. The correlations were assessed using univariate, multivariate, and machine learning based analyses.

Among the active caspase 3-negative (non-apoptotic) cells in the therapeutic cell composition administered, the total percentage or number of CCR7$^+$ cells, CD27$^+$ cells, CCR7$^+$CD27$^+$ cells, or CD45RA-CCR7$^+$ cells, among CD4 or CD8 CAR$^+$ T cells, in the composition administered were observed to be positively correlated with CD4 or CD8 $C_{max}$ and AUC$_{0-28}$. The total percentage or number of CD45RA-CCR7$^+$ cells was observed to be negatively correlated with CD4 or CD8 $C_{max}$ and AUC$_{0-28}$. The total percentage or number of CCR7$^-$CD27$^-$ cells was observed to be negatively correlated with CD4 $C_{max}$ and AUC$_{0-28}$. In vitro IL-2 production levels upon stimulation with CD19 were observed to be correlated with CD8 $C_{max}$ and AUC$_{0-28}$.

Figure 3A:
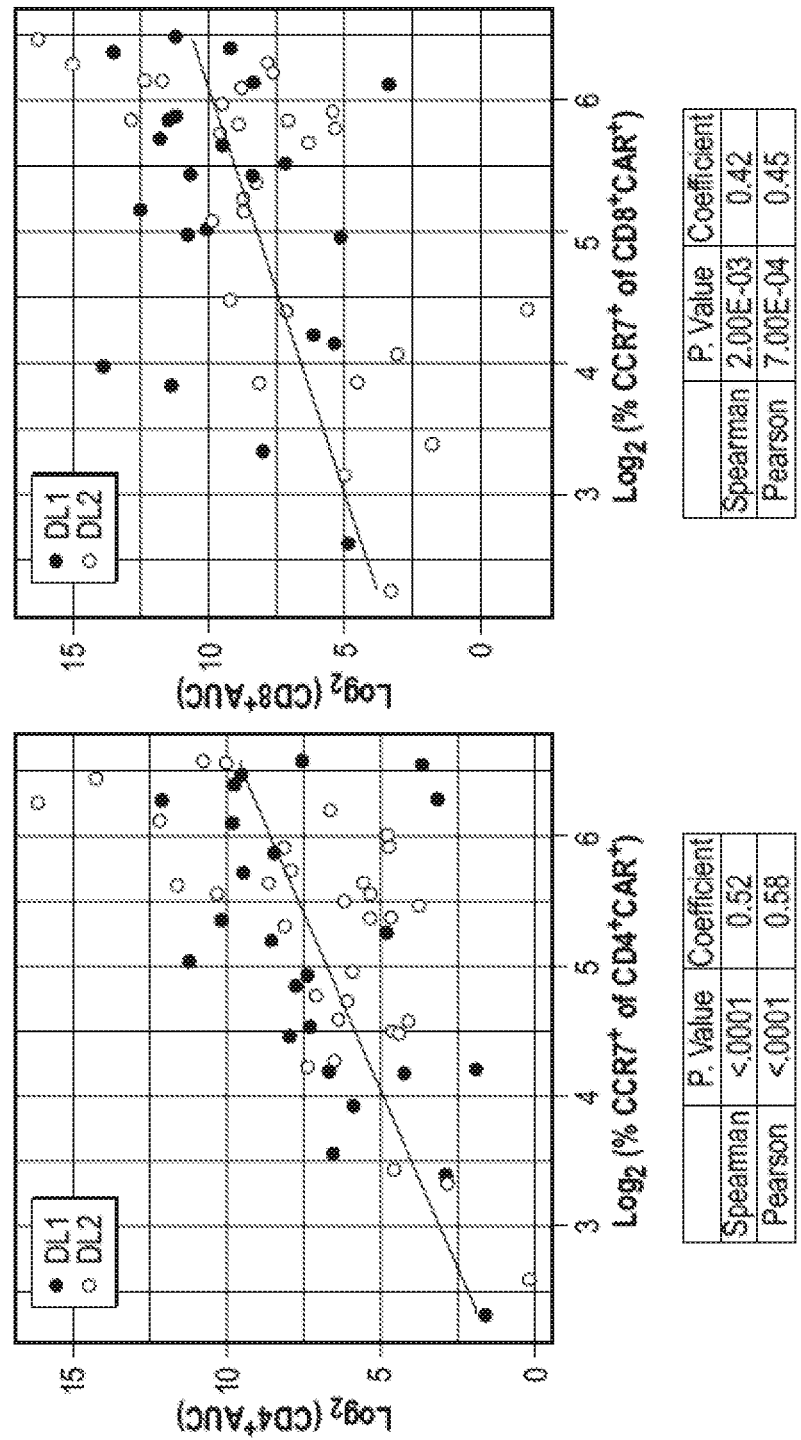
FIG. 3A shows a plot of percentage CCR7$^+$ cells (among CD4$^+$ CAR$^+$ and CD8$^+$CAR$^+$ cell populations) against pharmacokinetic parameters of CD4$^+$ CAR$^+$ cells and CD8$^+$ CAR$^+$ cells, respectively (as indicated by AUC$_{0-28}$ of CD4$^+$ CAR$^+$ or AUC$_{0-28}$ of CD8$^+$ CAR$^+$ cells in blood for subjects administered the cell therapy). Each dot represents an individual patient, with shading of individual dots indicating whether the patient received dose level 1 (DL1) or dose level 2 (DL2).
Figure 3B:
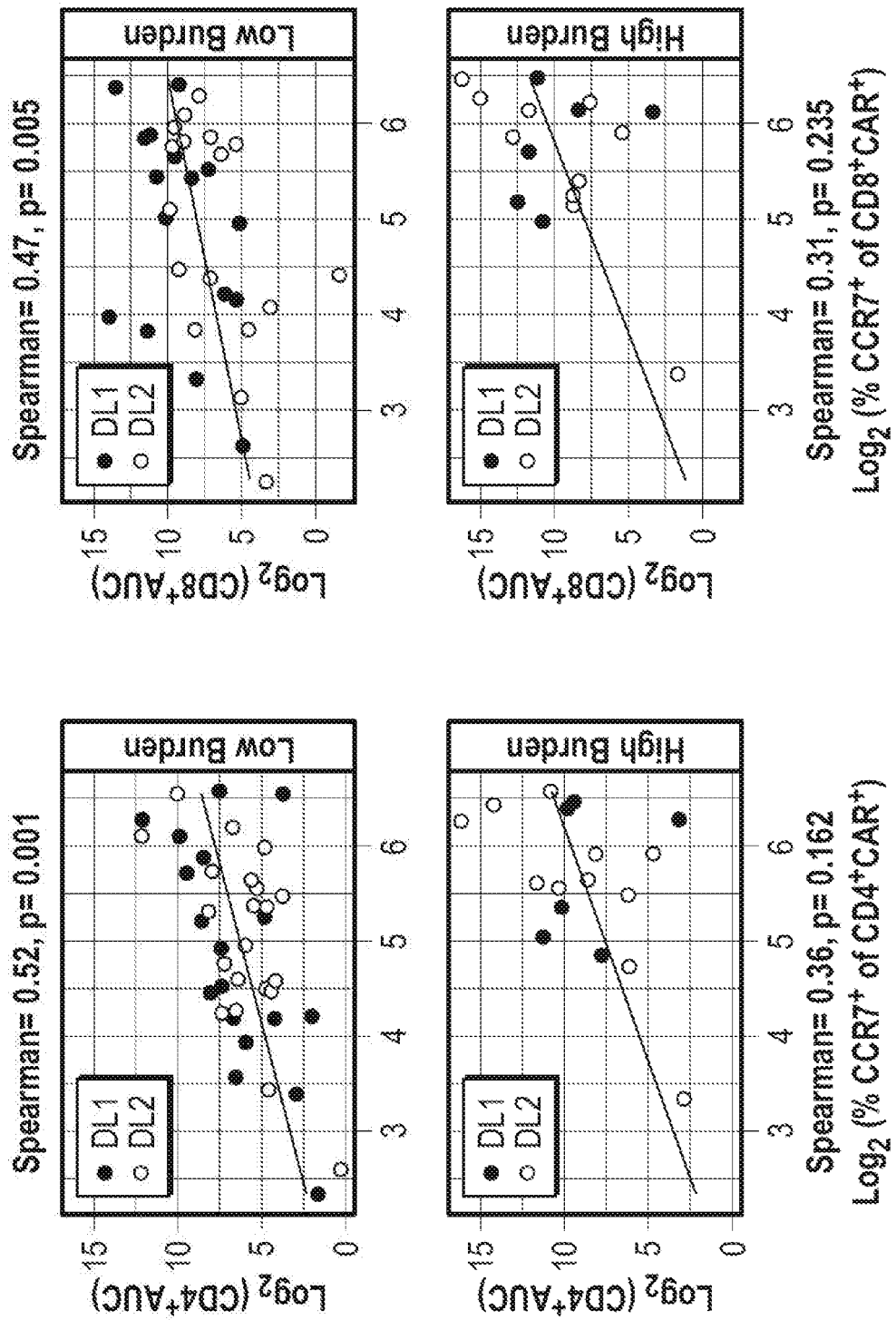
FIG. 3B shows similar plots, indicated separately for subjects observed to exhibit high (in this assessment, indicated by a sum of the products of diameters (SPD) value of greater than or equal to 50 cm$^2$) or low (SPD value of less than 50 cm$^2$) pre-treatment tumor burden (assessed at the time of pre-treatment lymphodepleting chemotherapy).
Figure 3C:
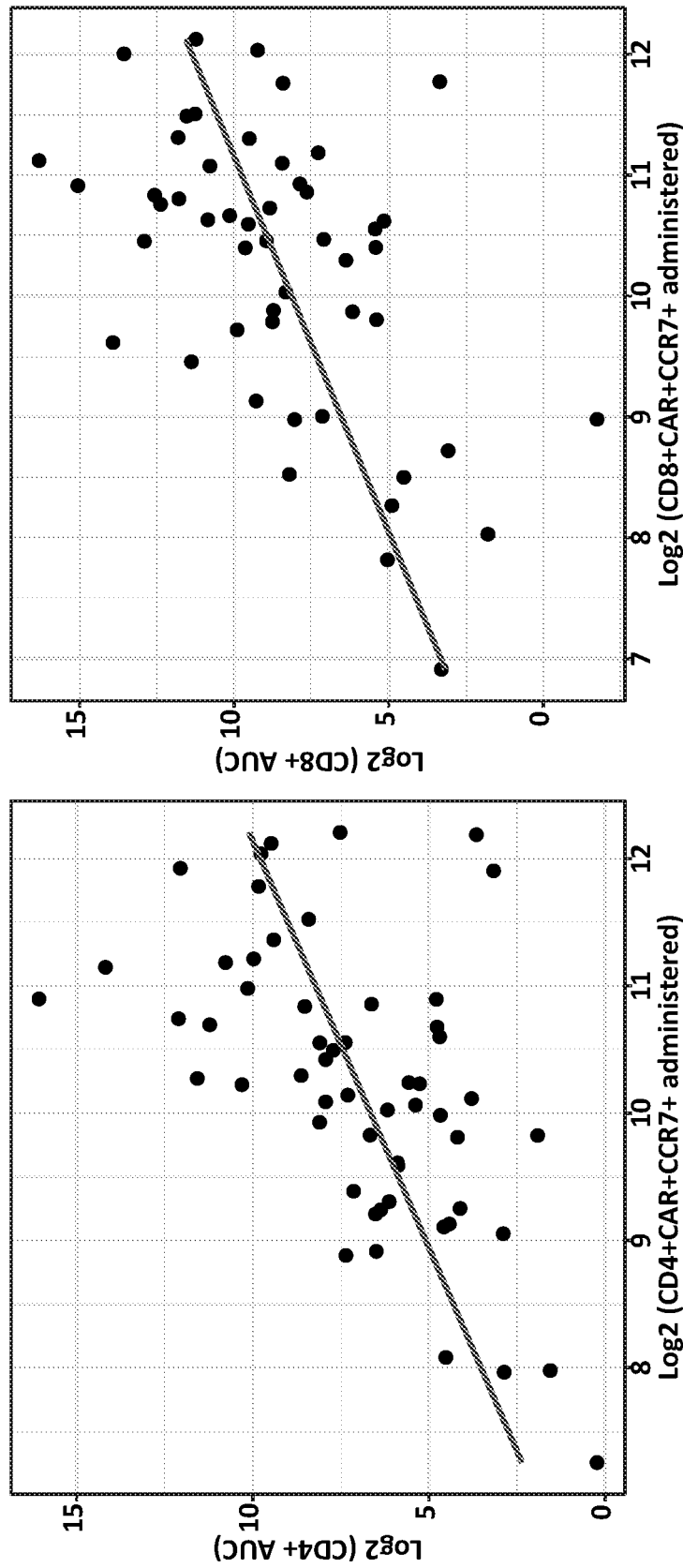
FIG. 3C depicts a plot of the number of CD4$^+$CAR$^+$CCR7$^+$ cells and CD8$^+$CAR$^+$CCR7$^+$ cells against AUC$_{0-28}$ of CD4$^+$ CAR$^+$ or AUC$_{0-28}$ of CD8$^+$ CAR$^+$ cells in blood for subjects administered the cell therapy), with the correlation coefficients and associated p-values.
Figure 3D:
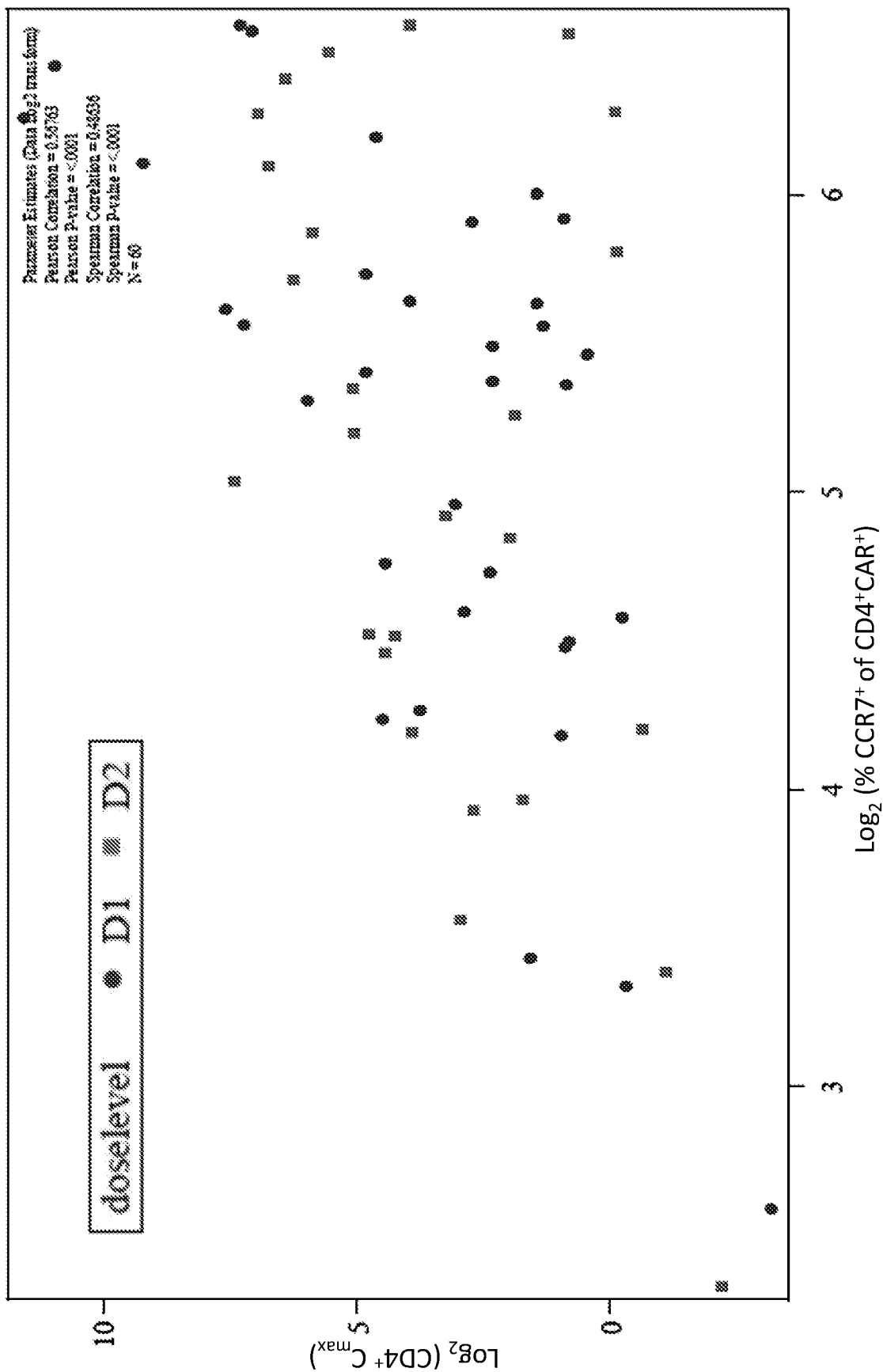
Figure 3F:
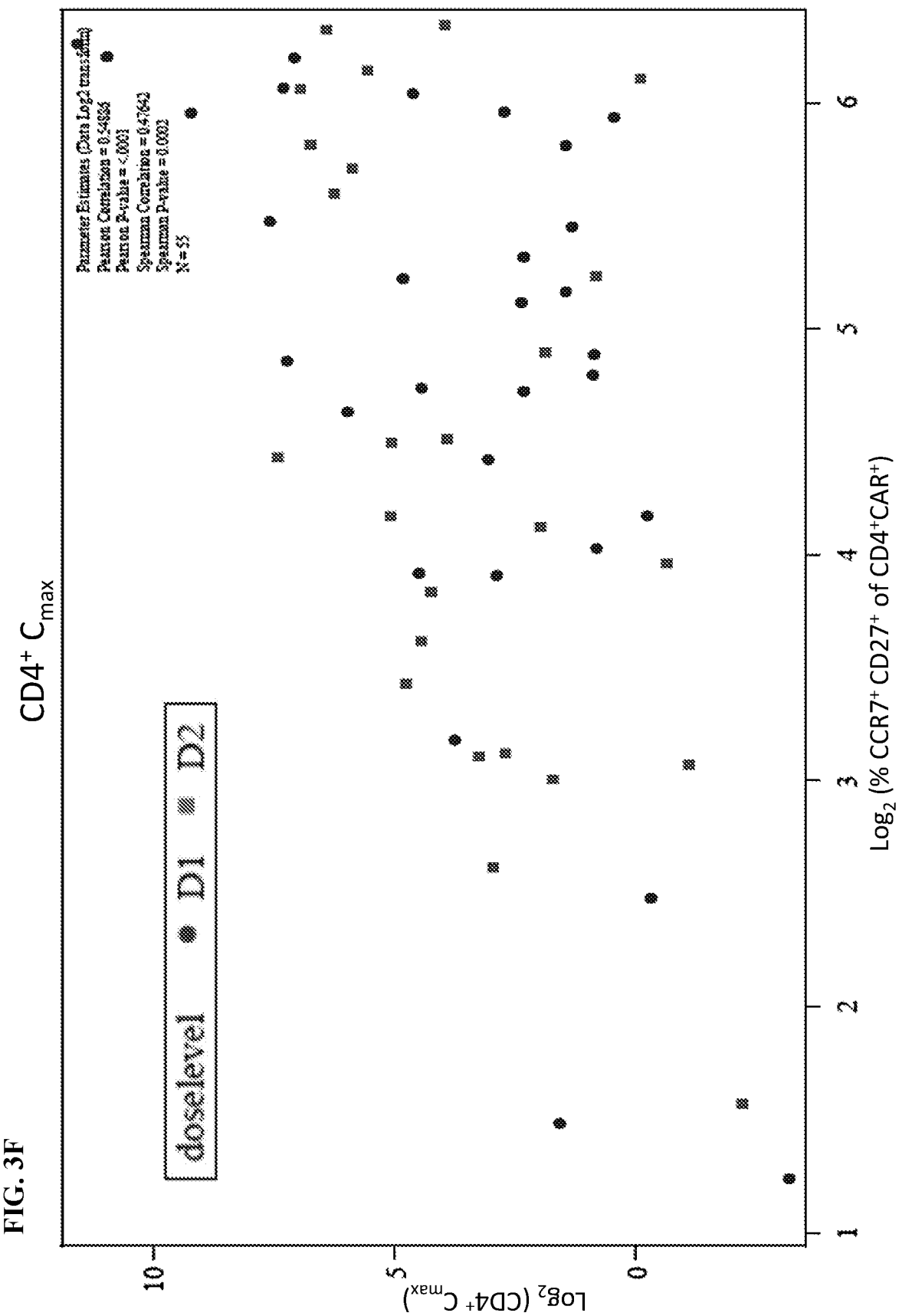
Figure 3G:
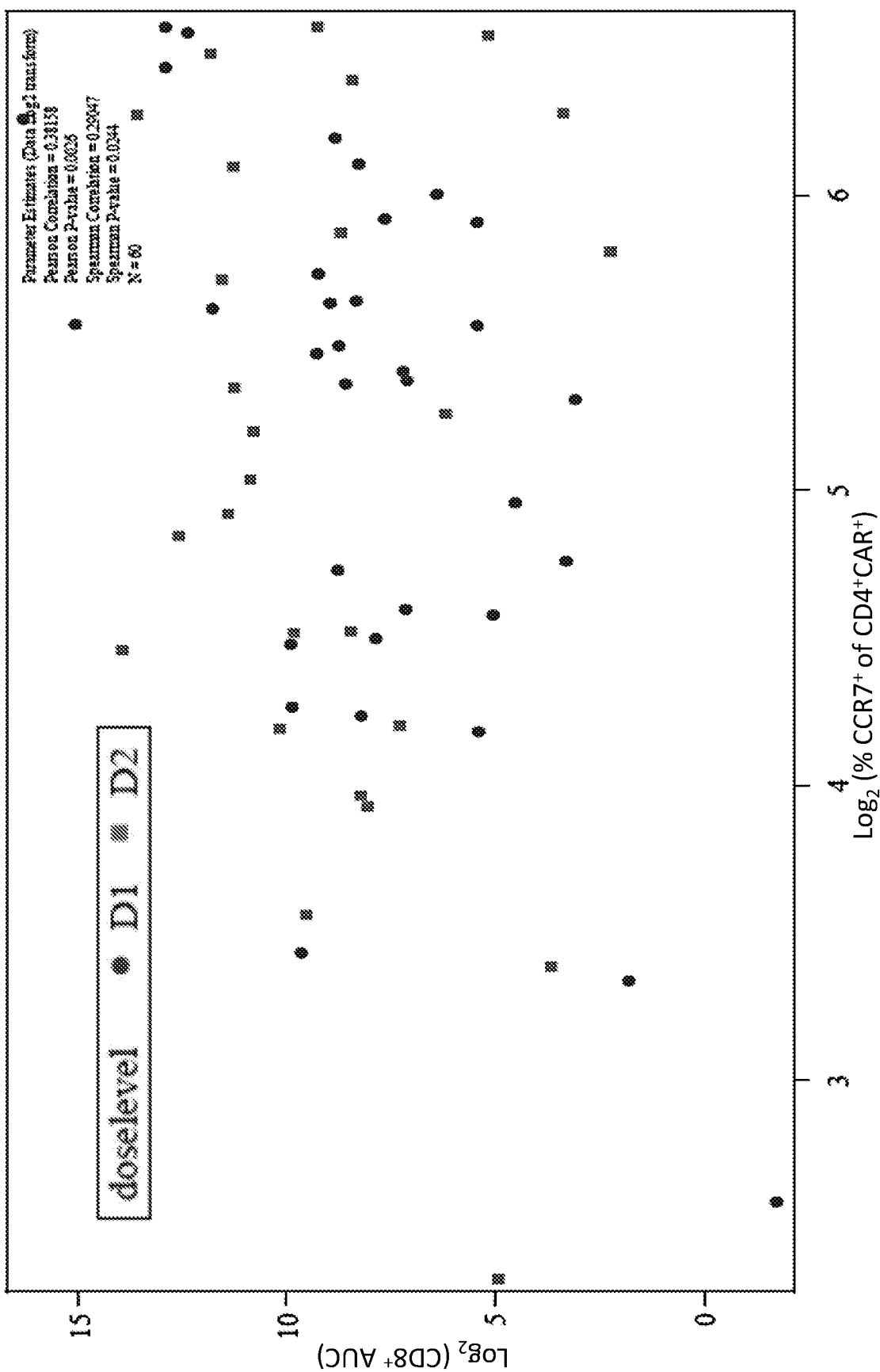
Figure 3H:
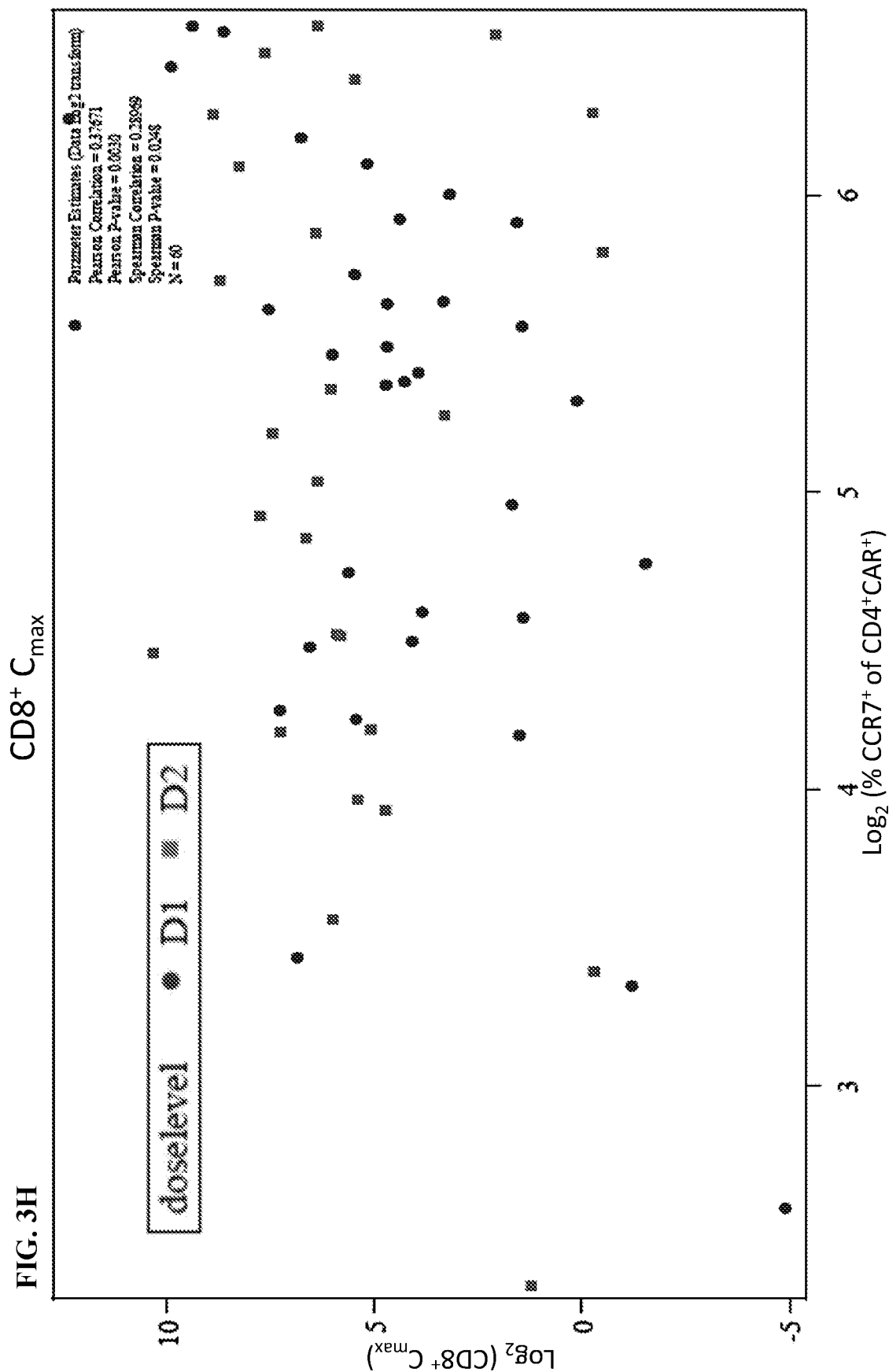
Figure 3I:
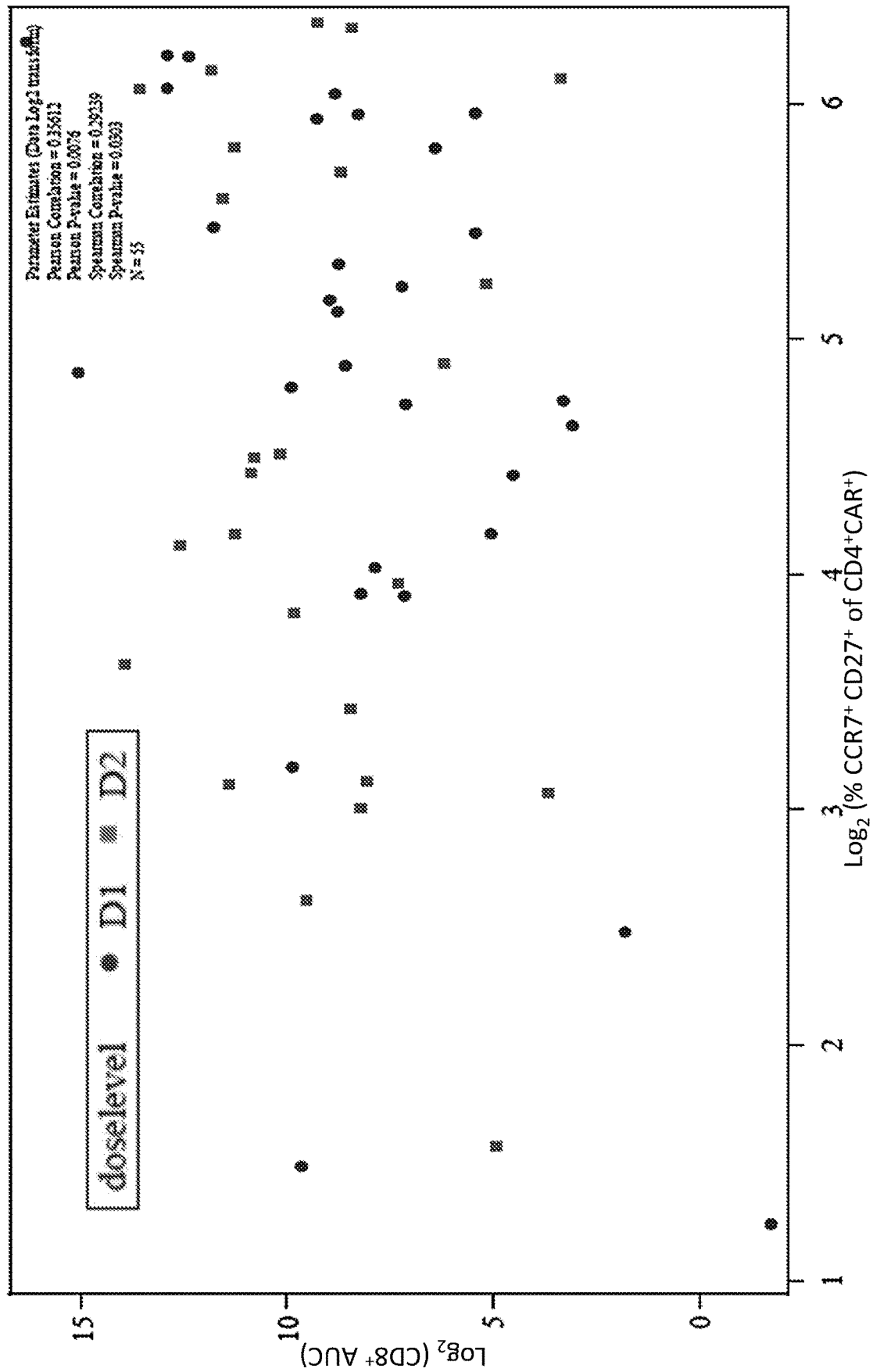
Figure 3J:
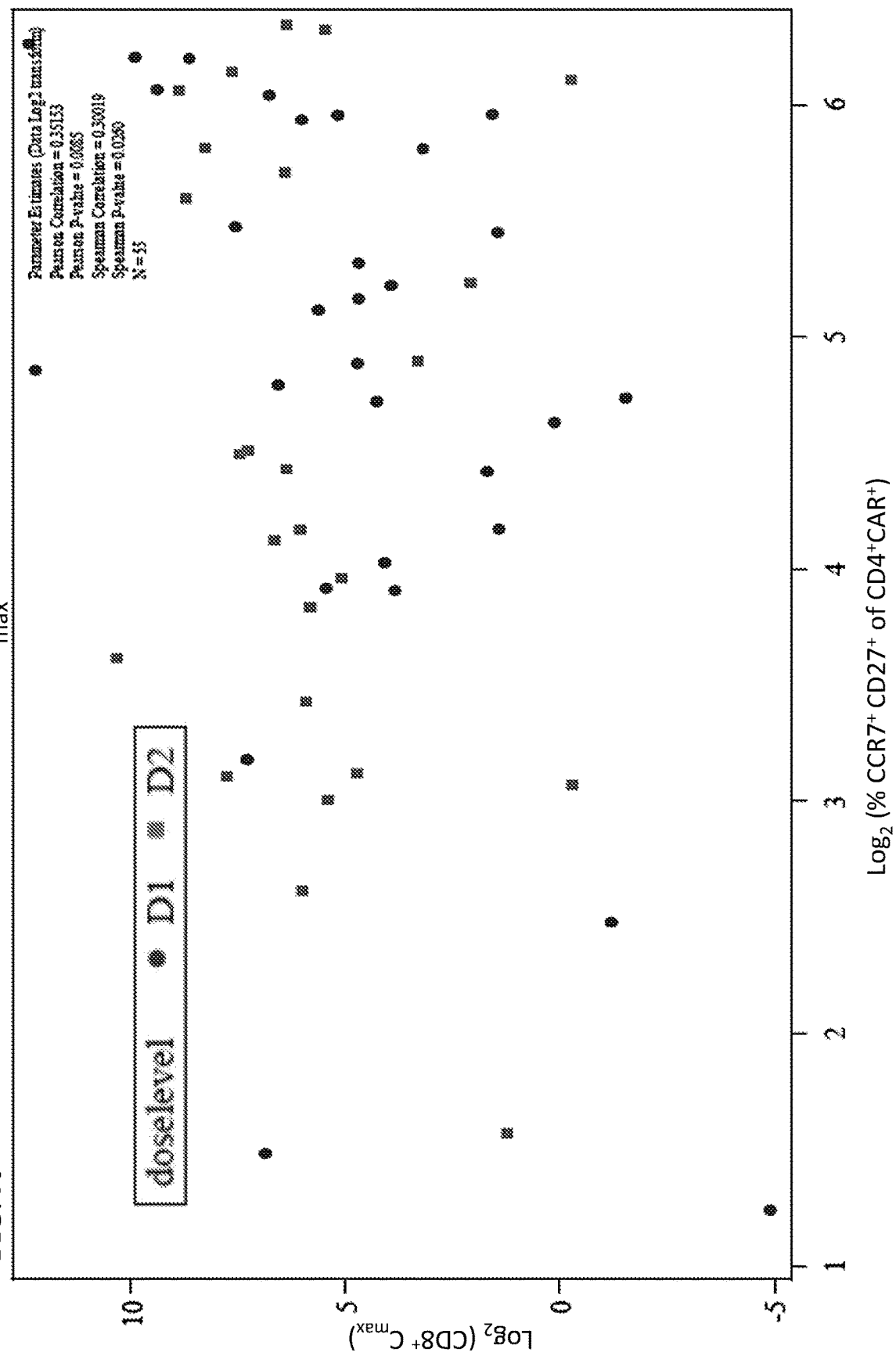

FIG. 3A shows results of a study assessing relationship of percentage CCR7$^+$ cells (among CD4$^+$ CAR$^+$ and CD8$^+$ CAR$^+$ cell populations) and pharmacokinetics of CD4$^+$ CAR$^+$ cells and CD8$^+$ CAR$^+$ cells, respectively (as indicated by AUC$_{0-28}$ of CD4$^+$ or AUC$_{0-28}$ CD8$^+$CAR$^+$ cells in blood for subjects administered the cell therapy). Each dot represents an individual patient, with shading of individual dots indicating whether the patient received dose level 1 (DL1) or dose level 2 (DL2)). In FIG. 3B, such analysis is shown with results indicated separately for subjects observed to exhibit high (in this assessment, indicated by a sum of the products of diameters (SPD) value of greater than or equal to 50 cm$^2$) or low (SPD value of less than 50 cm$^2$) pre-treatment tumor burden (assessed at the time of pre-treatment lymphodepleting chemotherapy). The percentage of CCR7$^+$ cells among CD4$^+$ CAR$^+$ cells in the dose administered was observed to be positively correlated with the CD4$^+$ AUC$_{0-28}$, and the percentage of CCR7$^+$ cells among CD8$^+$ CAR$^+$ cells in the dose administered was observed to be positively correlated with the CD8$^+$ AUC$_{0-28}$. Additionally, therapeutic engineered cell compositions generated from cells derived from subjects in the "high" pre-treatment disease burden group were observed generally to exhibit a higher percentage of CCR7$^+$ cells, among the CD8$^+$ and CD4$^+$ compositions. FIG. 3C shows the results for assessing the relationship between the total number of CCR7$^+$CD4$^+$ CAR$^+$ and CCR7$^+$ CD8$^+$ CAR$^+$ cells and the AUC$_{0-28}$ of CD4$^+$ and AUC$_{0-28}$ CD8$^+$ CAR$^+$ cells in blood for subjects administered the cell therapy, respectively.

In a further assessment of the relationship between attributes of CD4$^+$ CAR$^+$ T cells and the AUC$_{0-28}$ and C$_{max}$ of CD4$^+$ or CD8$^+$ CAR$^+$ T cells, the percentage of CD4$^+$ CAR$^+$ T cells that are CCR7$^+$ or CCR7$^+$CD27$^+$ were observed to be correlated with PK parameters (AUC$_{0-28}$ and C$_{max}$) of CD4$^+$ CAR$^+$ T cells (FIGS. 3A, 3D-3F) and CD8$^+$ CAR$^+$ T cells (FIGS. 3G-3J). The results are consistent with an observation that CD4$^+$ CAR$^+$ T cell help can support the expansion of CD8$^+$ CAR$^+$ T cells.

The results were consistent with an observation that representation in the therapeutic cell compositions of cells expressing certain phenotypic markers, such as those indicative of T cell subtypes, such as memory compartment subtypes, e.g., CCR7 and/or CD27, positively correlated with pharmacokinetic parameters such as those indicative of degree of exposure to CAR$^+$ T cells, such as AUC$_{0-28}$ and/or C$_{max}$ in subjects administered the defined cell composition. In some aspects, CD45RA$^-$ CCR7$^-$ or CCR7$^-$ CD27$^-$ cells in the CAR$^+$ T cell composition was negatively correlated with the pharmacokinetic parameters.

B. Relationship Between Pharmacokinetics/CAR$^+$ T Cell Exposure, Clinical Response, Toxicity and Cell Phenotype Attributes of Administered Therapeutic Cell Composition The relationship between certain phenotypic attributes of the CAR$^+$ T cells in the therapeutic compositions and parameters associated with pharmacokinetics (PK) or CAR$^+$ T cell exposure, cytokine production, clinical response outcomes and toxicity outcomes were assessed. In an analysis of therapeutic compositions generated from and administered to an exemplary group of subjects, compositions with elevated frequency of cells expressing markers indicative of memory T cell subtypes exhibited a strong correlation with cytokine production following in vitro CD19 stimulation.

Cell surface expression levels of various markers, presence of activated caspases, cytokine production in CD4$^+$ and CD8$^+$ cells after stimulation with CD19, pharmacokinetic (PK) parameters after administration (AUC$_{0-28}$ and C$_{max}$) were determined as described above. Expression of the markers and cytokine production were correlated with AUC$_{0-28}$, C$_{max}$, and clinical response outcomes (including progression-free survival and durable response) and toxicity outcomes (cytokine release syndrome (CRS) or neurotoxicity (NT)), determined from evaluable subjects in the core cohort described above who had been administered the particular CAR$^+$ T cell composition. The correlations were assessed using univariate, multivariate, and machine learning based analyses. A heatmap was generated indicating nominal p-values for various attributes of the cells and the association with toxicity, response or pharmacokinetic (PK) parameters.

Figure 4A:
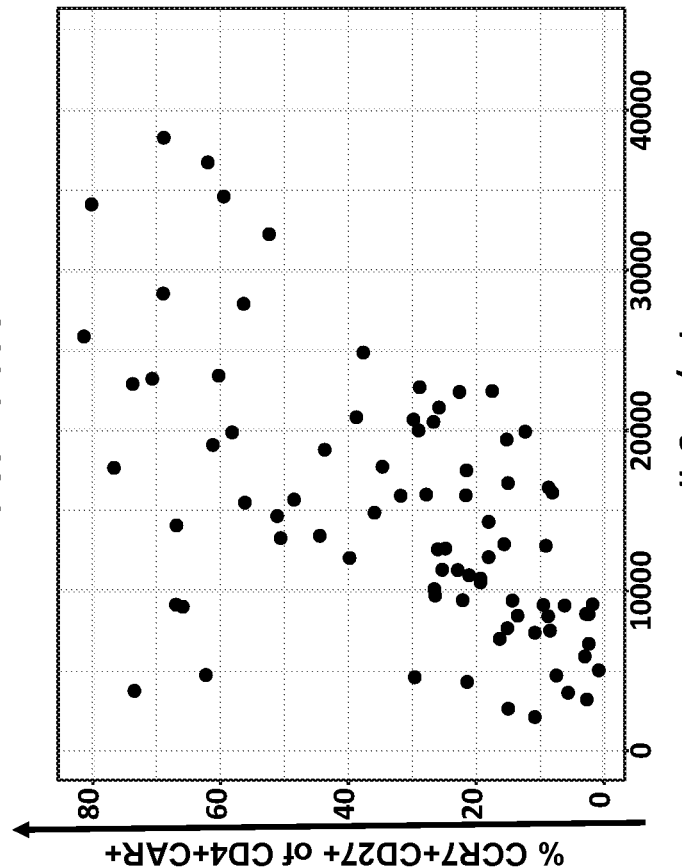
FIGS. 4A-4B depict a plot of the percentage of CCR7$^+$CD27$^+$ cells among CD4$^+$CAR$^+$ cells against IFNγ (FIG. 4A) and IL-2 (FIG. 4B) secretion by the CD4$^+$ CAR$^+$ composition upon stimulation with the antigen recognized by the CAR (CD19).
Figure 4B:
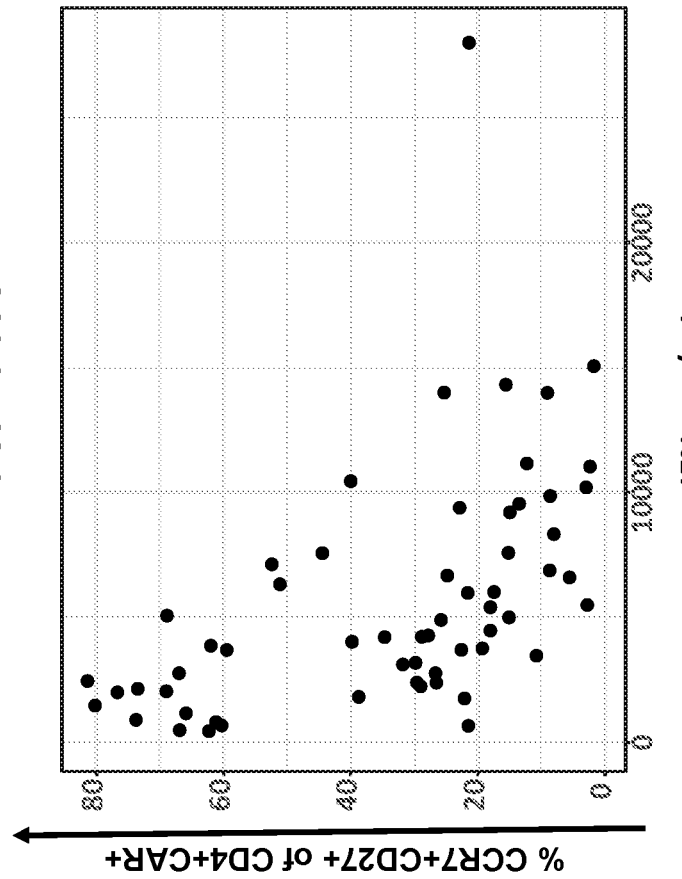
Figure 6A:
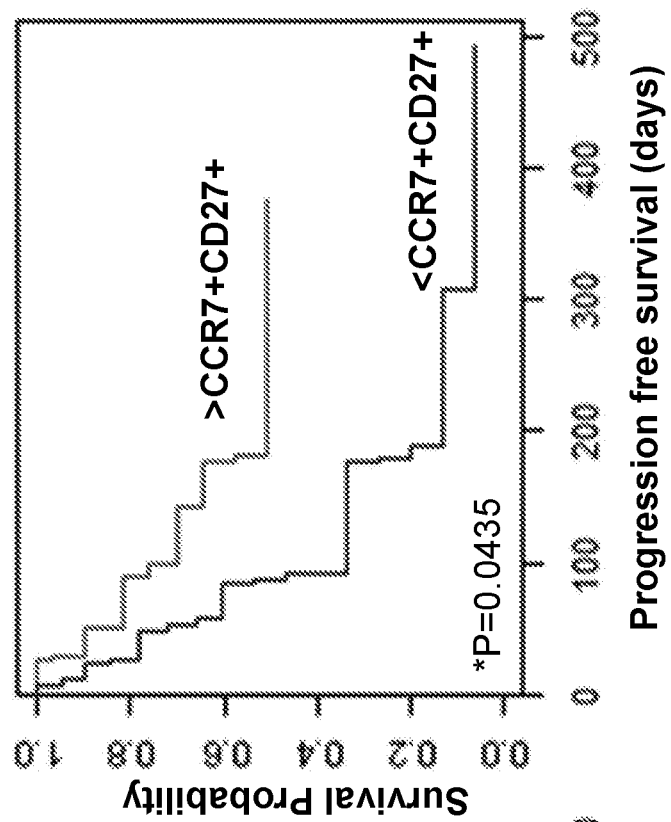
Figure 6B:
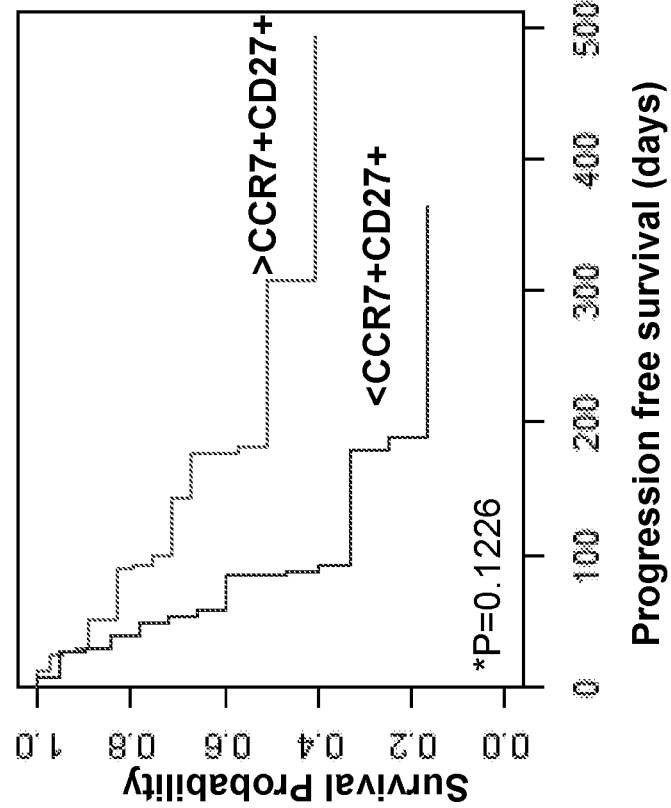

The results showed an association between certain functional profiles, safety events and durable response and the frequency of cells expressing markers indicative of a less differentiated T cell state, e.g., CCR7$^+$CD27$^+$. Specifically, compositions with high frequency of CCR7$^+$ cells, a marker indicative of central memory T cell subtype, exhibited increased IL-2 production (Spearman $\rho=0.55$, P<0.0001). As shown in FIGS. 4A-4B, CD4$^+$ CAR-expressing T cell compositions containing increased frequencies of less differentiated CCR7$^+$CD27$^+$ CAR$^+$ T cells secrete reduced IFN$\gamma$ (FIG. 4A) and increased IL-2 (FIG. 4B). In contrast, compositions with high frequencies of cells expressing markers associated with effector differentiated T cell subtypes exhibited increased IFN$\gamma$ production ($\rho=0.51$, P<0.0001) and IL-13 production ($\rho=0.45$, P<0.0001). As shown in FIGS. 5A-5B, CD8$^+$ CAR-expressing T cell compositions containing increased frequencies of less differentiated CCR7$^+$CD27$^+$ CAR$^+$ T cells produce low levels of some cytokines associated with Th2, such as IL-5 (FIG. 5A) and IL-13 (FIG. 5B).

The correlations between memory phenotype in the composition and function translated to a positive correlation between central memory subset composition and peak in vivo expansion of CAR$^+$ cells ($\rho=0.42$, P=0.002), and progression-free survival (PFS) (Kaplan-Meier survival estimate, P=0.0164) that were observed. FIGS. 6A-6D show the Kaplan-Meier survival curves for subjects who were administered CAR$^+$ T cell compositions, divided into groups that were administered compositions containing a frequency of CCR7$^+$CD27$^+$ CAR$^+$ T cells among CD4$^+$ CAR$^+$ T cells (FIG. 6A for progression free survival, FIG. 6C for duration of response) and among CD8$^+$ CAR$^+$ T cells (FIG. 6B for progression free survival, FIG. 6D for duration of response) that is above or below a certain threshold level. Higher CCR7$^+$CD27$^+$ memory cells in the composition was observed to be correlated with longer progression free survival.

Figure 7B:
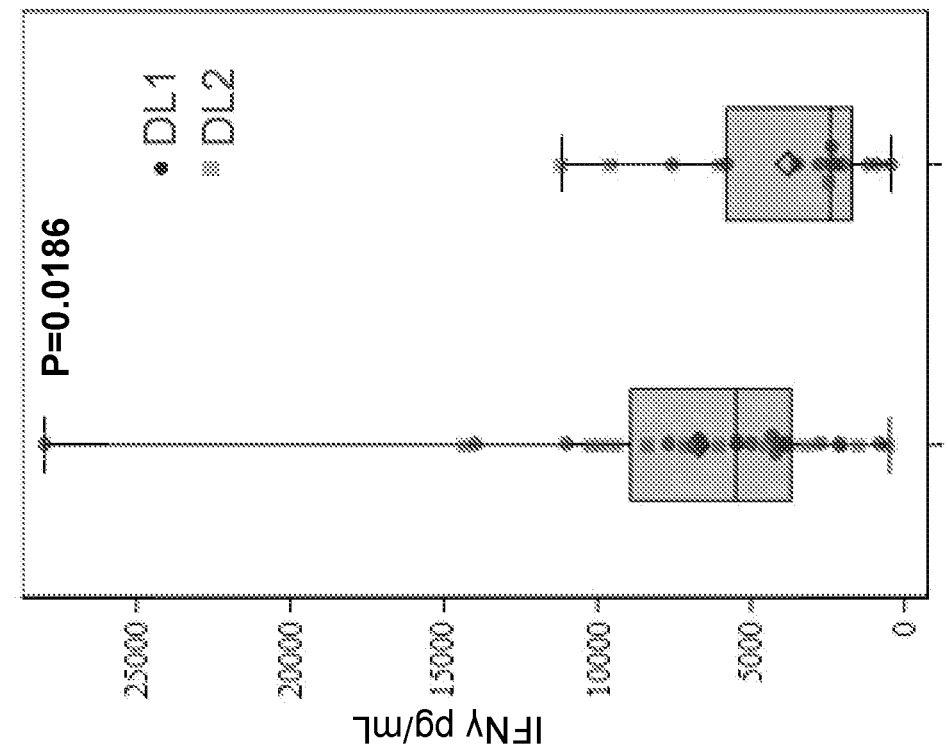
FIGS. 7A-7B show boxplots depicting the percentage of CCR7$^+$CD27$^+$ cells among CD4$^+$ CAR$^+$ cells (FIG. 7A) or IFNγ secretion by CD4$^+$ CAR$^+$ cells (FIG. 7B) in cell compositions administered to for subjects as a function of whether the subject went on to develop cytokine release syndrome (CRS; grade 0 vs. grade 1 or higher).
Figure 7A:
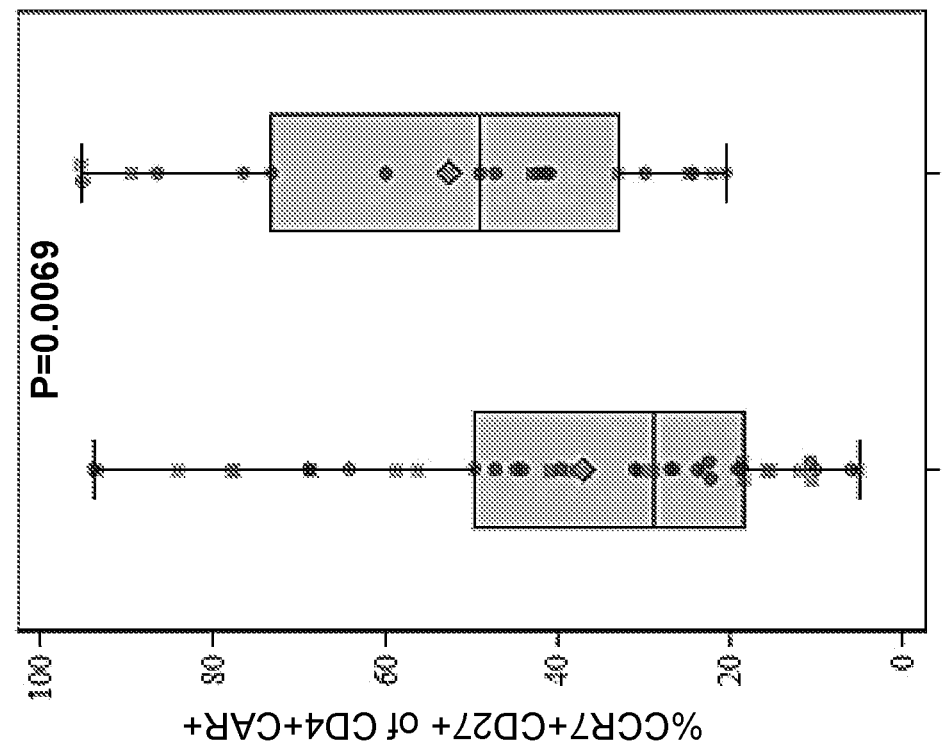

In addition, CD4$^+$ CAR$^+$ T cell compositions containing an increased frequency of a central memory subpopulation demonstrated relationships with whether the subject went on to develop a toxicity following administration of the therapeutic composition, either cytokine release syndrome (CRS, Grade 1 or higher, P=0.0069; FIG. 7A) or severe neurotoxicity (NT, Grade 3 or higher, P=0.0014, FIG. 7C). CD4$^+$ CAR$^+$ T cell compositions with reduced IFN$\gamma$ production were associated with CRS (Grade 1 or higher, P=0.0186; FIG. 7B) or severe NT (Grade 3 or higher, P=0.0055, FIG. 7D).

Figure 8B:
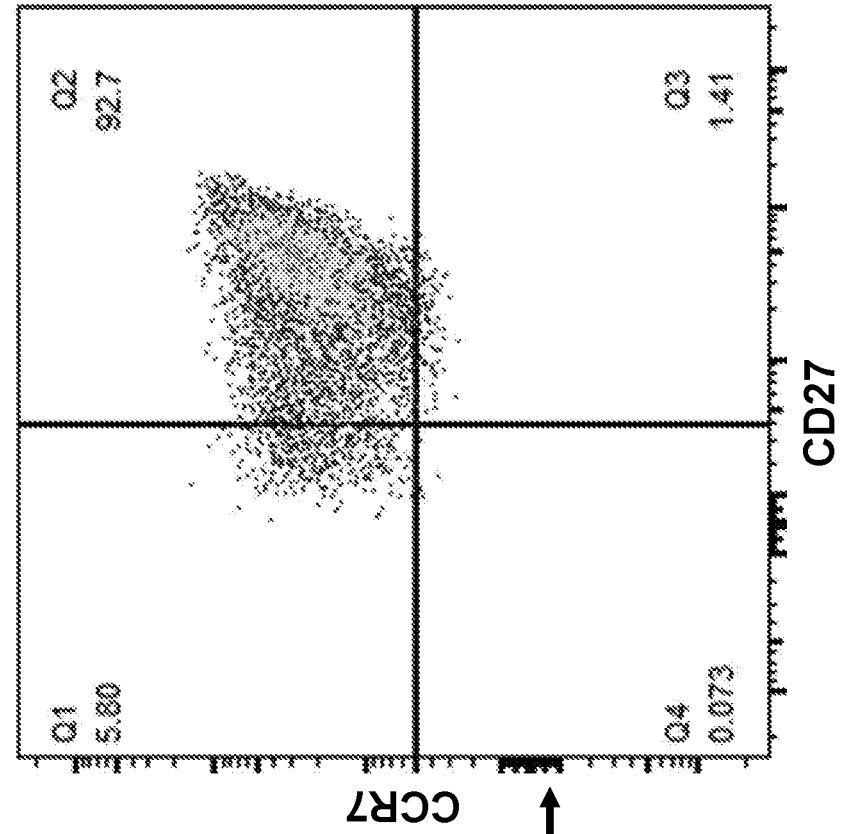
FIG. 8B shows an exemplary flow cytometry plot for a cell subtype identified from the analysis (within the boundary of the shape drawn on FIG. 8A) for CCR7 and CD27 expression.
Figure 8A:
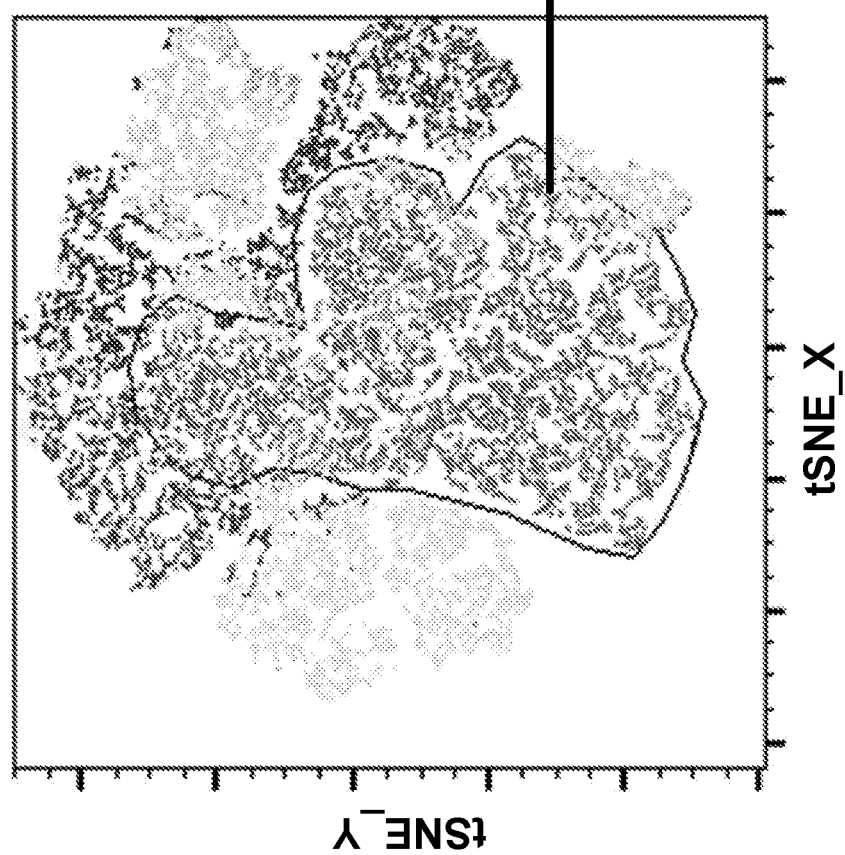
FIG. 8A shows an exemplary multiparameter phenotype analysis based on a t-distributed stochastic neighbor embedding (tSNE).

The results showed a relationship between engineered cell composition attributes and PK, safety and response outcome of the administered cells. The compositions with high frequency of CCR7$^+$ cells were observed to have increased peak CAR$^+$ cell expansion and persistence after administration consistent with an observation that less differentiated CAR$^+$ T cells contribute to pharmacokinetic parameters and progression free survival. The results are consistent with an observation that phenotype and functional attributes and profiles associated with a less differentiated T cell exhibited a relationships with increased likelihood of NT or CRS, and improved durability of response C. Multiparameter Phenotype Analysis An exemplary multiparameter phenotype analysis was performed based on a t-distributed stochastic neighbor embedding (tSNE), to identify different cell subtype population using flow cytometry. The tSNE analysis involved nonlinear dimensionality reduction to represent the results in a two-dimensional space, including collapsing multiple cell attributes onto a two-dimensional plot, and identifying 6 different cell subtypes on the two-dimensional plot (see FIG. 8A). The two attributes that were predominantly present in the plot were identified. As shown, a memory T cell subset, expressing both CCR7 and CD27 (within the boundary of the shape drawn on FIG. 8A, flow cytometry plot for CCR7 and CD27 expression shown in FIG. 8B) was identified among $CD4^+$ and $CD8^+$ $CAR^+$ T cells. As shown above in FIGS. 4A-4B and 5A-5B, the identified cells exhibited a distinct functional profile.

D. Conclusion

CAR+ T cell compositions administered to the subjects exhibited low variability, were pure and contained a precise dose, allowing identification of relationships between various cell attributes and clinical outcomes, such as response and toxicity. Cell populations expressing markers associated with memory phenotypes exhibited specific functional profiles (e.g., cytokine production), with $CCR7^+CD27^+CD4^+$ CAR T cells producing reduced IFNγ and increased IL-2, and $CCR7^+CD27^+CD8^+$ CAR T cells producing reduced IL-5 and IL-13. The administered cell compositions containing $CAR^+$ T cells in a less differentiated state, based on phenotypes such as $CCR7^+CD27^+$ expression and functional profiles such as cytokine production, were observed to be associated with pharmacokinetic parameters, safety events and increased durable response.

Further, among the embodiments provided herein are those involving methods and compositions providing for low variability between lots of therapeutic cell compositions (such as those produced from starting populations across a range of different patients), such as those containing anti-CD19 $CAR^+$ cells. Among the provided embodiments are those based on the ability, e.g., which may be due in part to such low degrees of variability, to stratify patients according to disease burden and/or to identify certain T cell phenotypes or phenotypic attributes that may be associated with one or more outcomes following administration, such as pharmacokinetic parameters of the anti-CD19 $CAR^+$ cells, e.g., factors indicative of exposure of the patient to CAR-T cells following administration of the treatment, including maximum exposure levels or exposure over time, such as measured by AUC.

In some embodiments, such parameters include one or more markers indicative of subtypes of one or more T cell compartments, such as attributes related to markers indicative of memory subtypes, including central memory T cell phenotype, such as $CCR7^+$ or $CD27^+$ expression or percentage and/or of $CCR7^+$ and/or $CD27^+$ cells. In some aspects, such results support dosing based on expression of one or more of such markers and/or attributes, such as by administering a cell composition, including a cell composition expressing a recombinant receptor (e.g. CAR), in which at least a certain percentage of cells are positive for one or more such markers, e.g., CCR7 and/or CD27, and/or by administering a dose in which a particular number or percentage of cells expressing such markers, e.g., CCR7 and/or CD27, are indicated for administration, e.g., across a number of subjects or indication. Among such embodiments are those in which dosing is based on a defined number or fixed dose of recombinant receptor (e.g. CAR)-expressing cells that are $CCR7^+$. In some aspects, such approaches may limit or decrease dose-to-dose variability among subjects administered the therapeutic composition. In some aspects, such approaches permit the targeting and/or control of particular pharmacokinetic attributes, such as degree of $CAR^+$ T cell levels or exposure in the patient, e.g., over time or at peak. In some aspects, such parameters are targeted to be within an acceptable therapeutic window or range, such as one observed to be associated with at least a desired probability of a particular response or efficacy outcome and below a certain probability or risk of one or more adverse effects or toxicity outcomes, for an administered therapeutic T cell composition.

Example 3 Identification of Molecular Signatures of $CAR^+$ T Cell Compositions Associated with Durable Response Genomic characterization studies, such as transcriptomic and epigenomic analyses, were performed in addition to assessment of various functional attribute to identify molecular signatures in $CAR^+$ T cell compositions that are associated with clinical response, e.g., durable clinical response upon $CAR^+$ T cell administration.

Figure 9A:
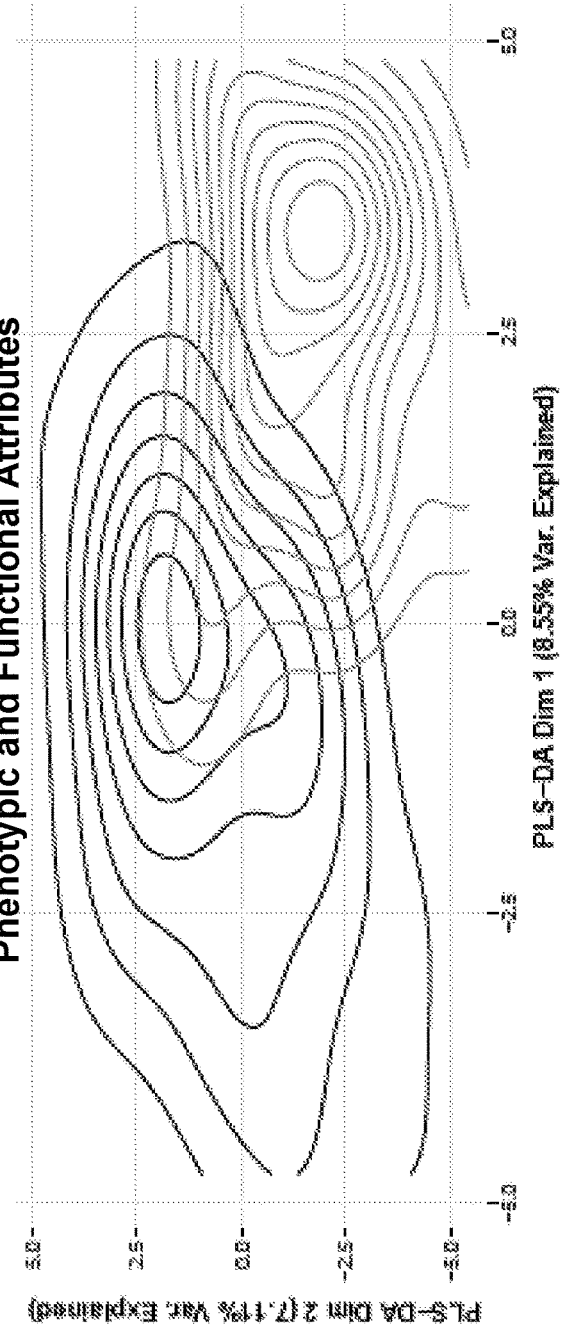
FIGS. 9A-9C show exemplary partial least squares-discriminant analysis (PLS-DA) assessment of phenotypic and functional attributes (FIG. 9A) and transcriptomic (FIG. 9B) and epigenomic analyses (FIG. 9C) to identify variables that discriminate between subjects that exhibited complete response (CR) and subjects that exhibited progressive disease (PD) or partial response (PR), at 6 months after administration of the CAR$^+$ T cell composition.
Figure 9B:
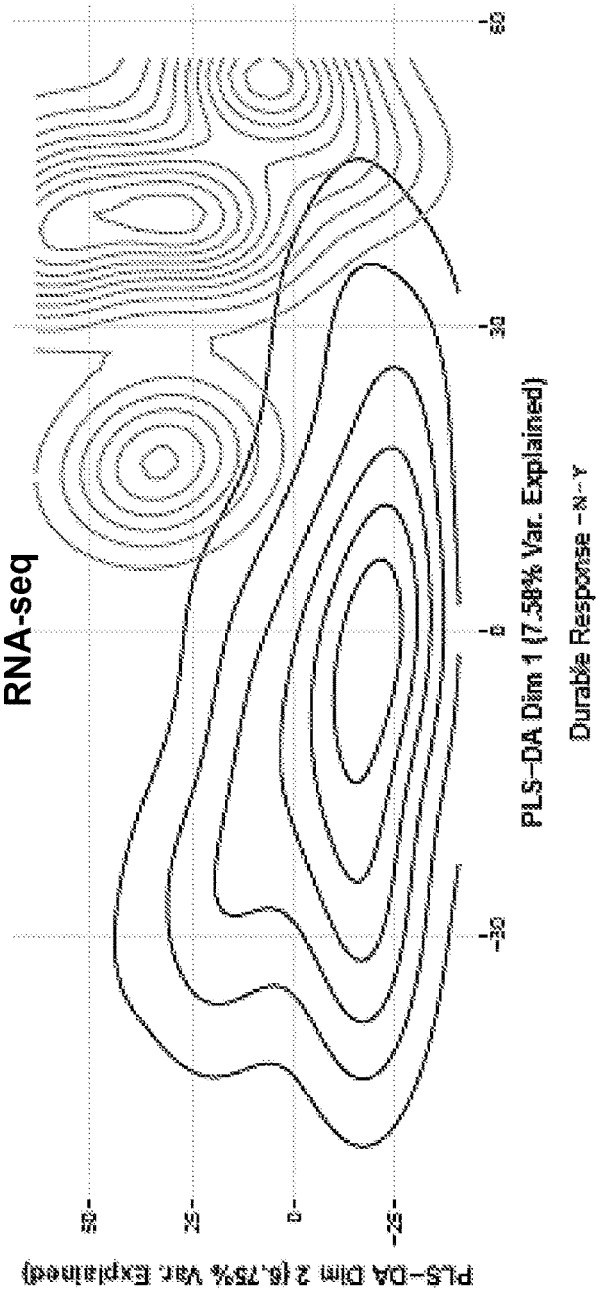
Figure 9C:
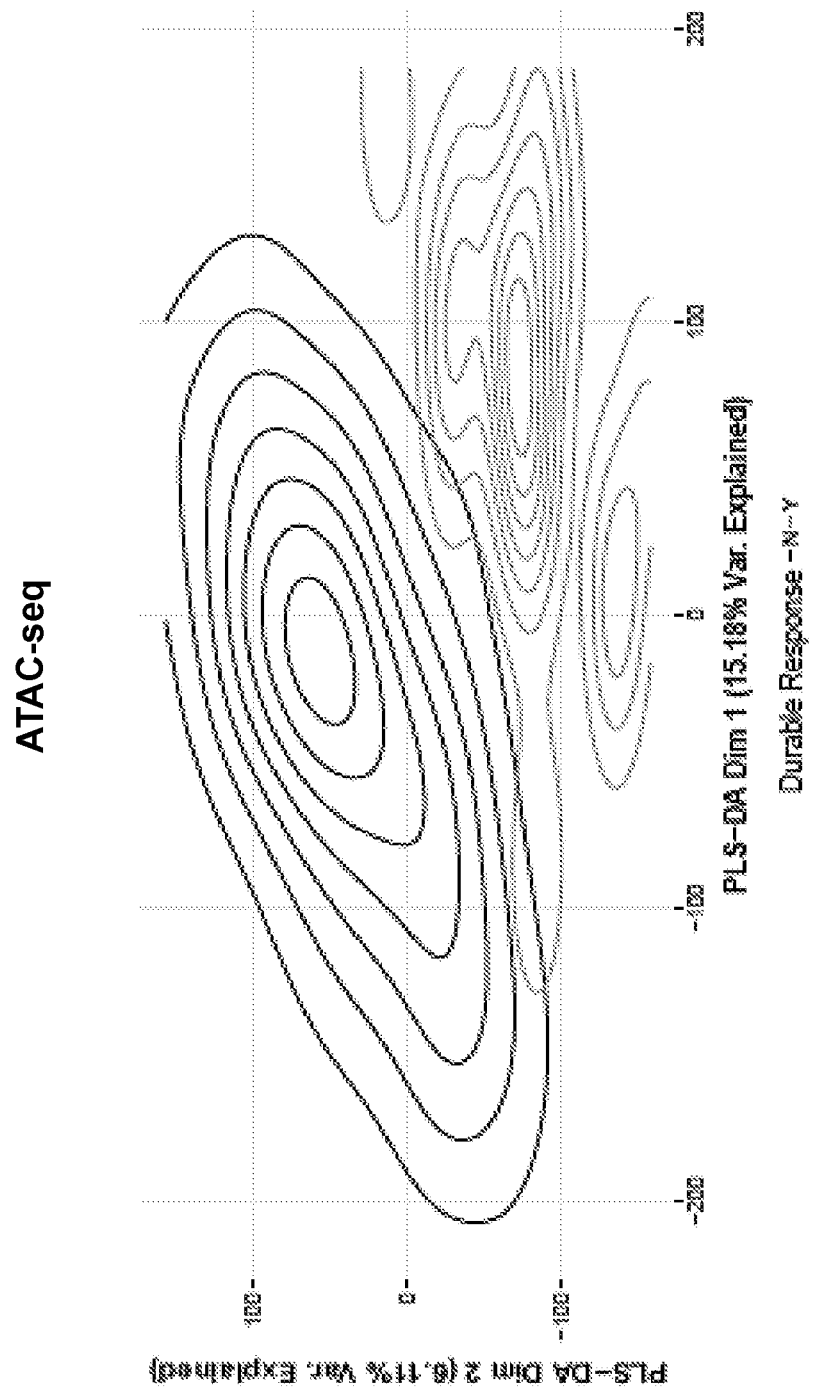

Engineered cell compositions containing $CAR^+$ T cells generated as described above in Example 1, were subject to analysis of approximately 100 phenotypic and functional attributes, assessment of expression of approximately 20,000 transcript by high-throughput RNA sequencing (RNA-seq) and assessment of chromatin accessibility at approximately 100,000 regulatory regions by assay for transposase-accessible chromatin using sequencing (ATAC-seq). The attributes were analyzed by partial least squares-discriminant analysis (PLS-DA) to identify variables that discriminate between subjects that exhibited complete response (CR) and subjects that exhibited progressive disease (PD) or partial response (PR), at 6 months after administration of the $CAR^+$ T cell composition. As shown in FIGS. 9A-9C, assessment of phenotypic and functional attributes and transcriptomic and epigenomic analyses can be used to identify molecular signatures of engineered $CAR^+$ T cell compositions that are associated with durable clinical response (e.g., CR at 6 months), in subjects that had been administered the engineered cell compositions. The results are consistent with an observation that molecular signatures that correlate with efficacy and safety can be identified based on genomic characterization of engineered cell compositions.

Example 4 Association Between Memory Cell Subtype Attributes in T Cell Compositions Before and after Enineering to Express a Chimeric Antigen Receptor (CAR)

Various cell attributes, including expression of markers indicative of memory subtypes, such as CCR7, CD27 and/or CD45RA, were assessed in T cell compositions from a subject prior to engineering, and engineered therapeutic cell compositions expressing a chimeric antigen receptor (CAR). The association between the attributes in the two populations were assessed.

$CD4^+$ and $CD8^+$ T cells were selected by immunoaffinity-based enrichment from leukapheresis of human peripheral blood mononuclear cells (PBMC) from a plurality of subjects. A composition of such selected T cells (before genetic engineering, designated "pre-engineering composition") were assessed for various attributes, including expression of cell surface markers indicative of certain T cell subtypes, such as memory cell subtypes, including C—C chemokine receptor type 7 (CCR7), CD27 and CD45RA, and surface expression of CD3, CD4, CD8, CD28, and/or truncated receptor used as a surrogate marker, and the presence of activated caspase 3 was assessed as a measure of apoptotic cells. The selected T cells were subject to genetic engineering to express an anti-CD19 CAR, after activation by incubation with anti-CD3 and anti-CD28 antibody-coated beads in the presence of cytokines, followed by transduction with a lentiviral vector encoding an anti-CD19 CAR, described in Example 1.A above. The resulting cell compositions were expanded and cryopreserved (after genetic engineering, designated "engineered cell composition"), and assessed for cell attributes as described above. Spearman's rank-order correlation coefficients for pairwise correlations between the cell attributes in the pre-engineering composition and the engineered cell composition were determined.

Figure 10A:
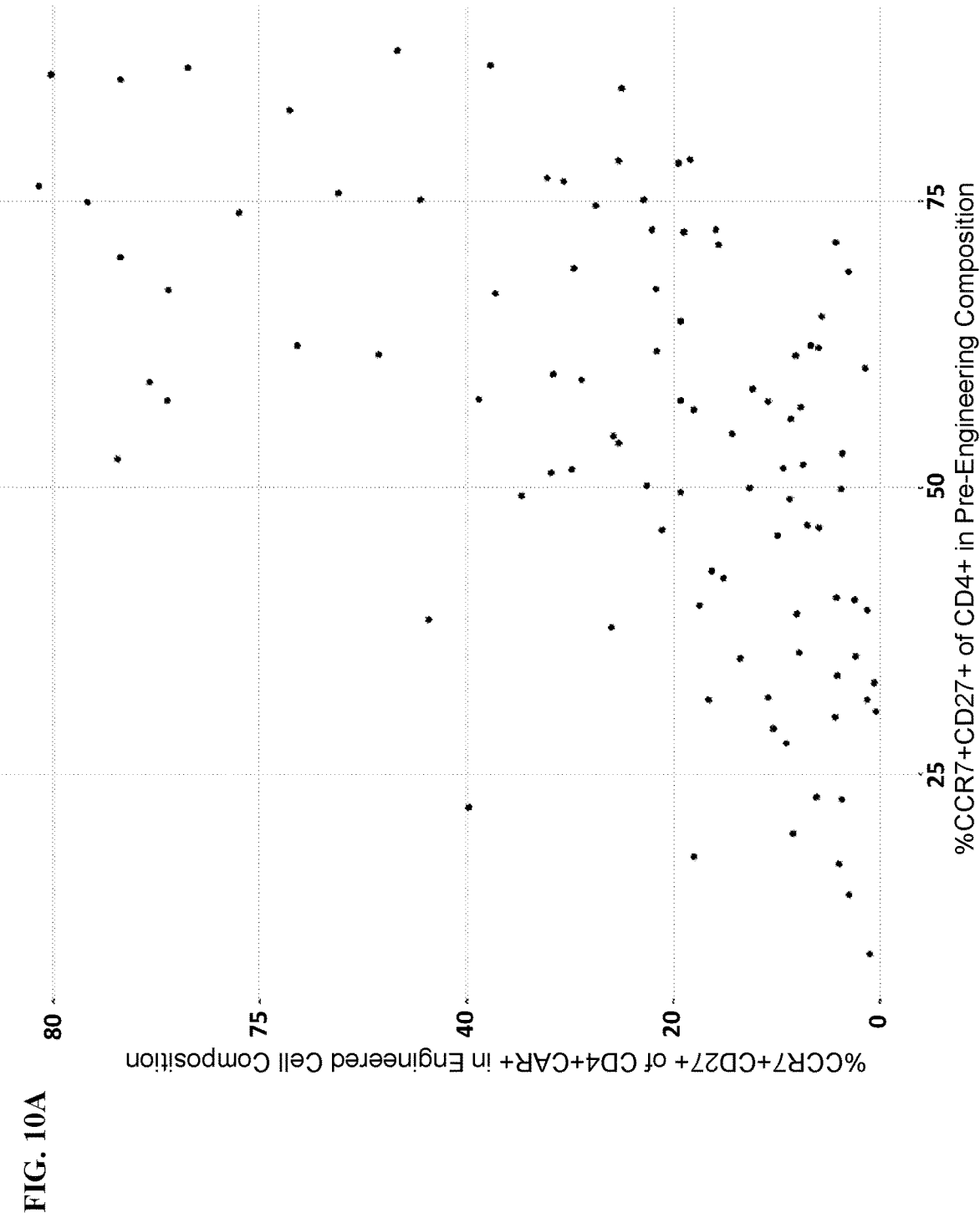
FIG. 10A shows a plot of the frequency of CD4$^+$CCR7$^+$CD27$^+$ cells in pre-engineering compositions against the frequency of CD4$^+$CAR$^+$CCR7$^+$CD27$^+$ cells in the engineered cell compositions (Spearman's rank-order correlation coefficient: 0.591).
Figure 10B:
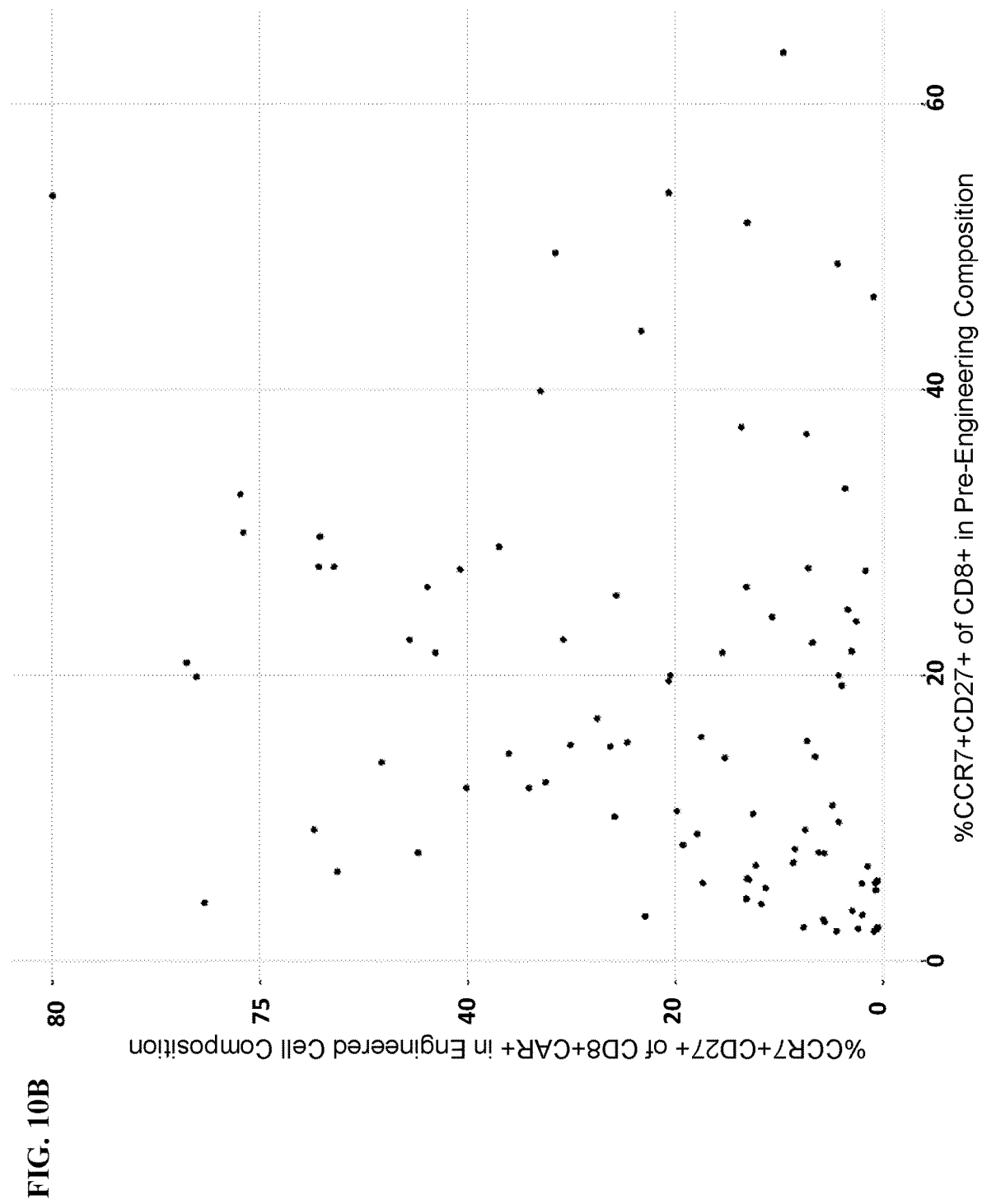
FIG. 10B shows a plot of the frequency of CD8$^+$CCR7$^+$CD27$^+$ cells in pre-engineering compositions and the frequency of CD8$^+$CAR$^+$CCR7$^+$CD27$^+$ cells in the engineered cell compositions (Spearman's rank-order correlation coefficient: 0.357).

FIGS. 10A-10B show exemplary results of the correlation between the frequency of $CD4^+CCR7^+CD27^+$ cells in pre-engineering compositions and the frequency of $CD4^+CAR^+CCR7^+CD27^+$ cells in the engineered cell compositions (FIG. 10A; Spearman's rank-order correlation coefficient: 0.591), and the frequency of $CD8^+CCR7^+CD27^+$ cells in pre-engineering compositions and the frequency of $CD8^+CAR^+CCR7^+CD27^+$ cells in the engineered cell compositions (FIG. 10B; Spearman's rank-order correlation coefficient: 0.357). The results showed that expression of one or more markers indicative of memory cell subtypes, e.g., CCR7 and/or CD27, in the engineered cell composition for administration in some cases were associated with the expression of the markers in the pre-engineering cell composition. The results were consistent with a finding that an engineered cell composition containing a specific number or percentage of cells expressing marker(s) indicative of memory cell subtypes, e.g., CCR7 and/or CD27, can be generated based on the number or percentage of cells expressing marker(s) in the pre-engineering composition.

Example 5: Assessment of Naïve-Like Markers in Engineered T Cell Compositions Containing CAR+ T Cells Engineered compositions of primary T cells containing T cells expressing chimeric antigen receptors (CARs) were produced by two parallel processes that utilized a stimulatory reagent composed of paramagnetic polystyrene-coated beads with attached anti-CD3 and anti-CD28 antibodies to activate T cells prior to transduction with a viral vector. In both processes, cells were engineered by lentiviral transduction to express the same anti-BCMA CAR. The CAR contained an scFv antigen-binding domain specific for BCMA, a CD28 transmembrane region, a 4-1BB costimulatory signaling region, and a CD3-zeta derived intracellular signaling domain. The processes differed in their duration and in the conditions for expansion of cells. The produced T cell compositions were assessed for cell surface markers.

In both processes, separate compositions of CD4+ and CD8+ cells were selected from isolated PBMCs from a leukapheresis sample from a human donor, and the selected cell compositions were cryopreserved. The separate compositions of CD4+ and CD8+ T cells were subsequently thawed and mixed at a ratio of 1:1 of viable CD4+ T cells to viable CD8+ T cells. Approximately $300 \times 10^6$ T cells ($150 \times 10^6$ CD4+ and $150 \times 10^6$ CD8+ T cells) of the mixed input cell composition were stimulated by incubating the cells for 18-30 hours in the presence of anti-CD3/anti-CD28 antibody conjugated beads at a 1:1 bead to cell ratio in serum free media. The media also contained recombinant IL-2, IL-7, and IL-15. Following the stimulation, the cells were washed and resuspended in the serum free media containing additives as well as recombinant IL-2, IL-7 and IL-15.

In one process (an exemplary non-expanded process), the cells from the stimulated cell composition were then transduced with a lentiviral vector encoding the anti-BCMA CAR by spinoculation. After the spinoculation, the cells were washed and resuspended in the serum free media containing recombinant IL-2, IL-7 and IL-15. The cells of the resuspended compositions were incubated at about 37.0° C. in an incubator. At about 96 hours after initiation of the stimulation, cells were rinsed twice in the presence of a magnetic field to remove the anti CD3/anti-CD28 antibody conjugated paramagnetic beads, and formulated in a solution containing 10% DMSO. The formulated cell composition was transferred to a bag or vial and was stored at approximately −80° C.

In another process (an exemplary expanded process), following the incubation, approximately $100 \times 10^6$ viable cells from the stimulated cell composition were concentrated in the serum free media containing recombinant IL-2, IL-7 and IL-15. The cells were transduced with a lentiviral vector encoding the same anti-BCMA CAR as described above by spinoculation at approximately 1600 g for 60 minutes. After spinoculation, the cells were resuspended in the serum free media containing recombinant IL-2, IL-7, and IL-15, and incubated for about 18 to 30 hours at about 37° C. The cells were then cultivated for expansion by transfer to a bioreactor (e.g. a rocking motion bioreactor) in about 500 mL of the exemplary serum free media containing twice the concentration of IL-2, IL-7, and IL-15 as used during the incubation and transduction steps. When a set viable cell density was achieved, perfusion was initiated, where media was replaced by semi-continuous perfusion with continual mixing. The cells were cultivated the next day in the bioreactor until a threshold cell density of about $3 \times 10^6$ cells/ml was achieved, which typically occurred in a process involving 6-7 days of expansion. The anti-CD3 and anti-CD28 antibody conjugated paramagnetic beads were removed from the cell composition by exposure to a magnetic field. The cells were then collected, and formulated and cryoprotected as described above.

Figure 11A:
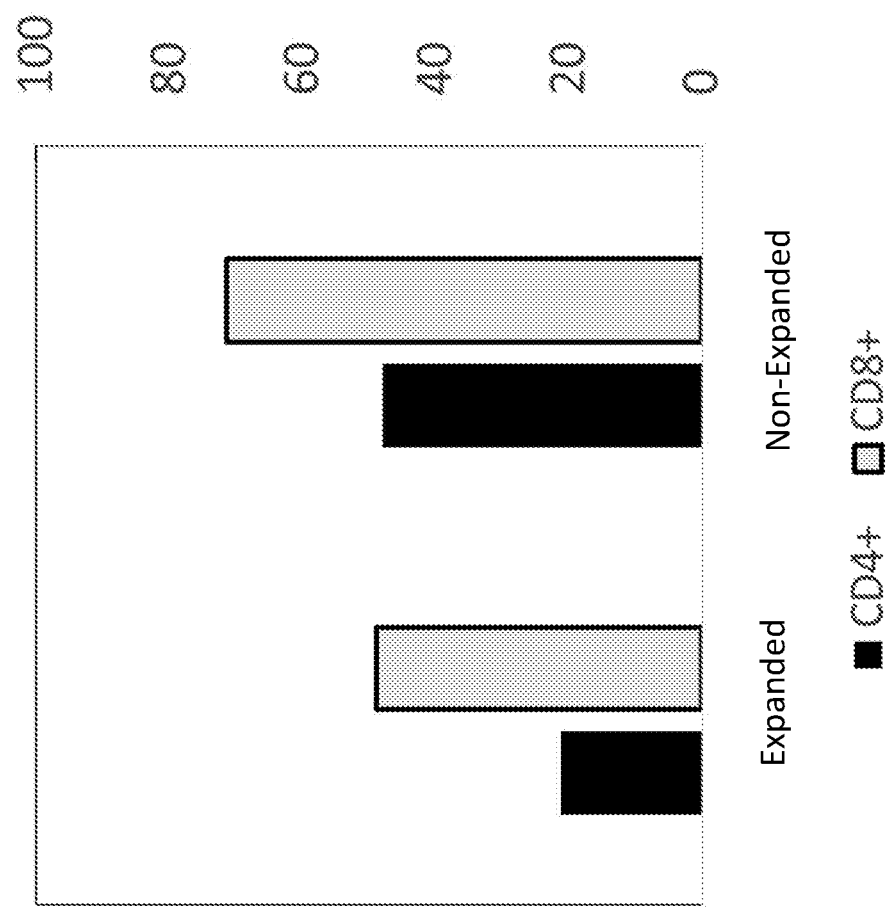
FIGS. 11A-11D depict results from CAR+ T cell compositions generated from exemplary expanded and non-expanded processes involving a bead-based stimulatory reagent (Bead) and incubation in basal media (Bead-Basal Media), or an oligomeric stimulatory reagent (Oligomer).
Figure 11B:
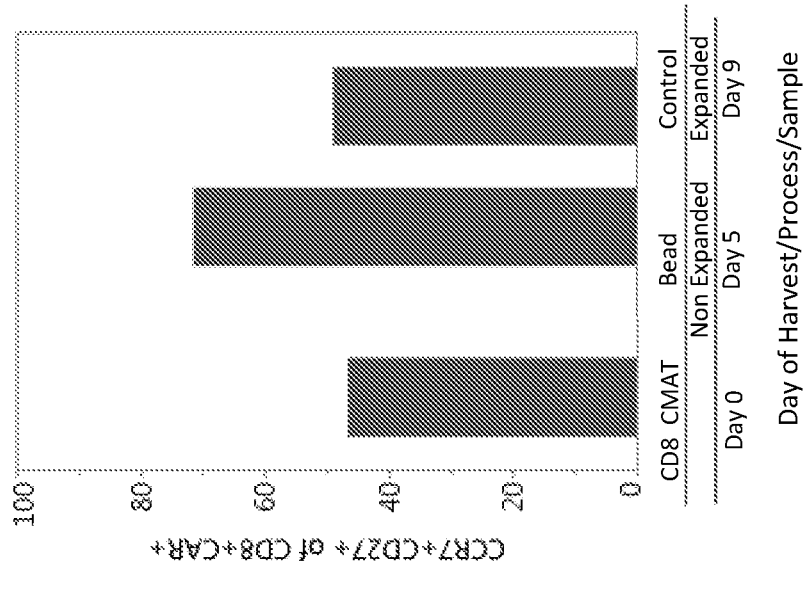
Figure 11C:
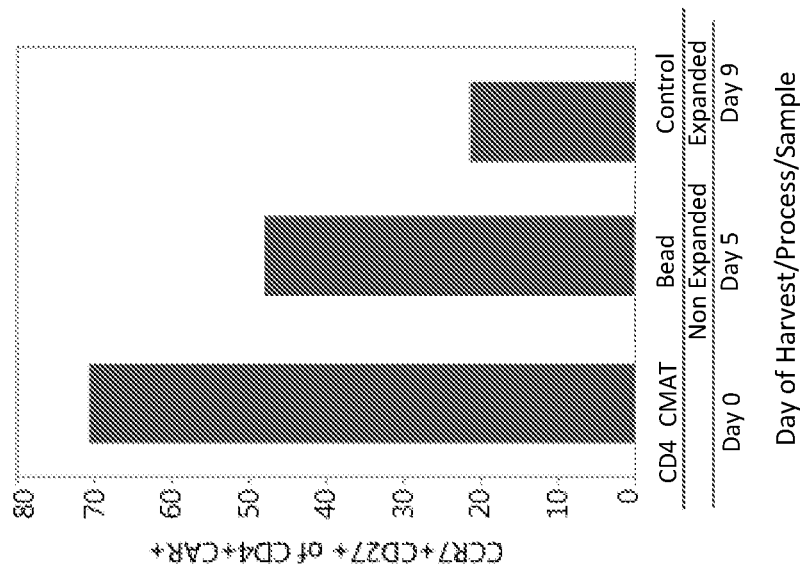

T cell compositions produced using the exemplary expanded and non-expanded processes were stained with reagent recognizing surface markers including CD4, CD8, CCR7 and CD27 and assessed by flow cytometry. The percentage of CD4+ $CAR^+$ and CD8+ $CAR^+$ T cells surface positive for both CCR7 and CD27 staining are shown in FIG. 11A. FIG. 11B and FIG. 11C depict the percentage of CCR7+CD27+ cells among CD4+ $CAR^+$ T cells and CD8+ $CAR^+$, respectively, in the produced T cell compositions, compared to the percentage of CCR7+CD27+ cells in the input compositions prior to the incubation with the anti-CD3/anti-CD28 antibody conjugated bead stimulatory reagent. As shown, a greater percentage of CCR7+CD27+ were observed in the T cell compositions produced from the exemplary non-expanded process as compared to the exemplary expanded process. These results are consistent with engineered cell compositions generated from the exemplary non-expanded processes having a greater portion of cells with a naïve-like, less differentiated phenotype than cell compositions generated by the exemplary expanded process.

Figure 11D:
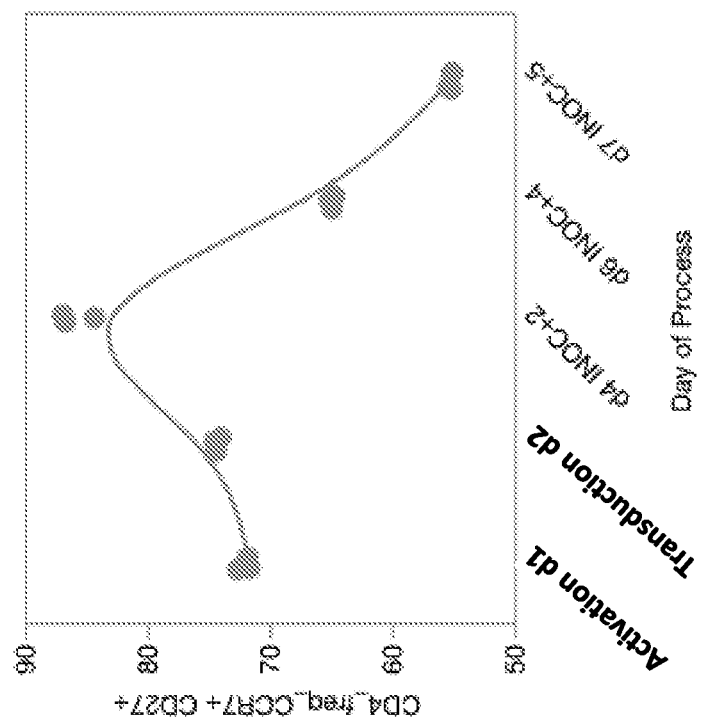

Further analysis of cells generated by the exemplary expanded process from a representative donor at various days during the process of manufacture, including at activation, transduction or at various times after initiation of cultivation (inoc+2, inoc+4 or inoc+5), demonstrate expansion of cells is associated with a more differentiated phenotype as determined by a decreased percentage of CCR7+ CD27+ cells (FIG. 11D).

Example 6: Assessment of T Cell Clonality Using Sequencing and Analysis Methods

Compositions of T cells were assessed for T cell clonal abundance, using single cell sequencing of T cell receptor (TCR) pairs, before and after genetic engineering to express a chimeric antigen receptor (CAR).

Autologous T cells were isolated from the subjects via leukapheresis by immunoaffinity based selection for purification of CD4$^+$ and CD8$^+$ T cells, resulting in two compositions, enriched for CD8$^+$ and CD4+ T cells, respectively. Cells of the enriched CD4$^+$ and CD8$^+$ compositions were activated with anti-CD3/anti-CD28 paramagnetic beads and then were separately subjected to lentiviral transduction with a vector encoding an anti-CD19 CAR. The anti-CD19 CAR contained an anti-CD19 scFv derived from a murine antibody (variable region derived from FMC63), an immunoglobulin-derived spacer, a transmembrane domain derived from CD28, a costimulatory region derived from 4-1BB, and a CD3-zeta intracellular signaling domain. Transduced populations then were separately incubated in the presence of stimulating reagents for cell expansion. Expanded CD8$^+$ and CD4$^+$ compositions containing CAR-expressing T cells were formulated and cryopreserved separately and stored.

T cell clonality of the isolated CD4+ and CD8+ T cell compositions before engineering (CMAT) and of the CD4+ and CD8+ therapeutic CAR+T cell compositions after engineering by the process described above was assessed. To assess T cell clonality, the cells were subject to single-cell αβ-paired TCR sequencing, generally as described in WO2016044227, WO2016176322 and WO2012048340. Based on barcoded single-cell sequencing of TCR genes, T cell clonality and diversity of the identified clones in a cell population were determined. In some cases, the Shannon index was used as a threshold to filter clones ("Shannon-adjusted clonality"), which preserves inter-sample relationships while eliminating sample noise. See, Chaara et al. (2018) Front Immunol 9:1038).

Figure 12:
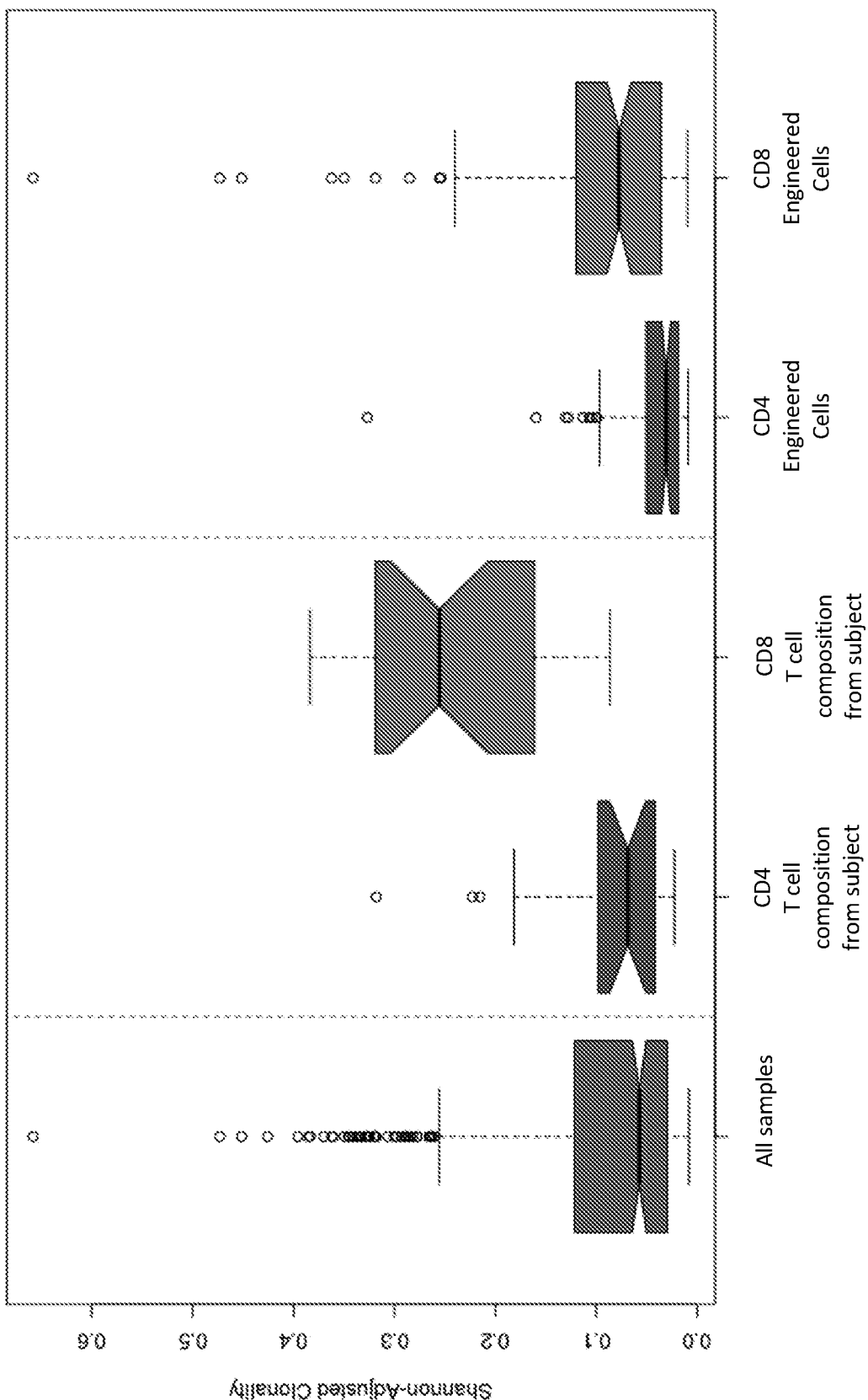
FIG. 12 shows the T cell clonality of the isolated CD4+ and CD8+ T cell compositions before engineering and of the CD4+ and CD8+ therapeutic CAR+ T cell compositions after engineering (Shannon index applied).

FIG. 12 shows the clonality of the each sample after applying the Shannon index. As shown in FIG. 12, the clonality of CD4 and CD8 cells differed among T cell compositions before and after the genetic engineering, with the engineered CAR+ T cell compositions exhibiting a reduced clonality compared to the T cells in the compositions prior to initiation of the process for engineering the cells.

CD4+ and CD8+ therapeutic CAR$^+$ T cell compositions after genetic engineering were sorted by flow cytometry expression of a factor indicative of apoptosis, such as surface staining with Annexin V (Annexin V−) or caspase 3 cleavage (indicating non-apoptotic cells), and for expression of various surface markers including CD45RA, CCR7, CD27, CD4 and CD8. The phenotype of the cells was correlated to the degree of clonality of the cells. It was observed that, in both the CD4+ and CD8+ therapeutic CAR$^+$ T cell compositions, the presence of apoptotic marker-negative cells that were CCR7$^-$/CD27$^-$ positively correlated highly with the clonality of the cells in the composition. Likewise, the presence of apoptotic marker-negative cells that were CCR7+ or CCR7+/CD27+ negatively correlated with the clonality of cells in each of the CD4+ and CD8+ therapeutic CAR+ T cell compositions. These results are consistent with an observation that clonality of cells may be inversely correlated with less differentiated, naïve-like cells, such as determined by CCR7 and/or CD27 positivity.

Example 7 Assessment of the Relationship Between Cell Phenotypic and Functional Attributes and Response Exemplary therapeutic T cell compositions containing autologous T cells expressing a chimeric antigen-receptor (CAR) specific for CD19 were generated and administered to patients as described in Example 1. Starting samples, enriched CD4+ or CD8+ input T cell compositions and generated therapeutic T cell compositions expressing an anti-CD19 CAR were assessed for a variety of attributes, including for various phenotypic, function and cell health related attributes, using flow cytometry.

Figure 13A:
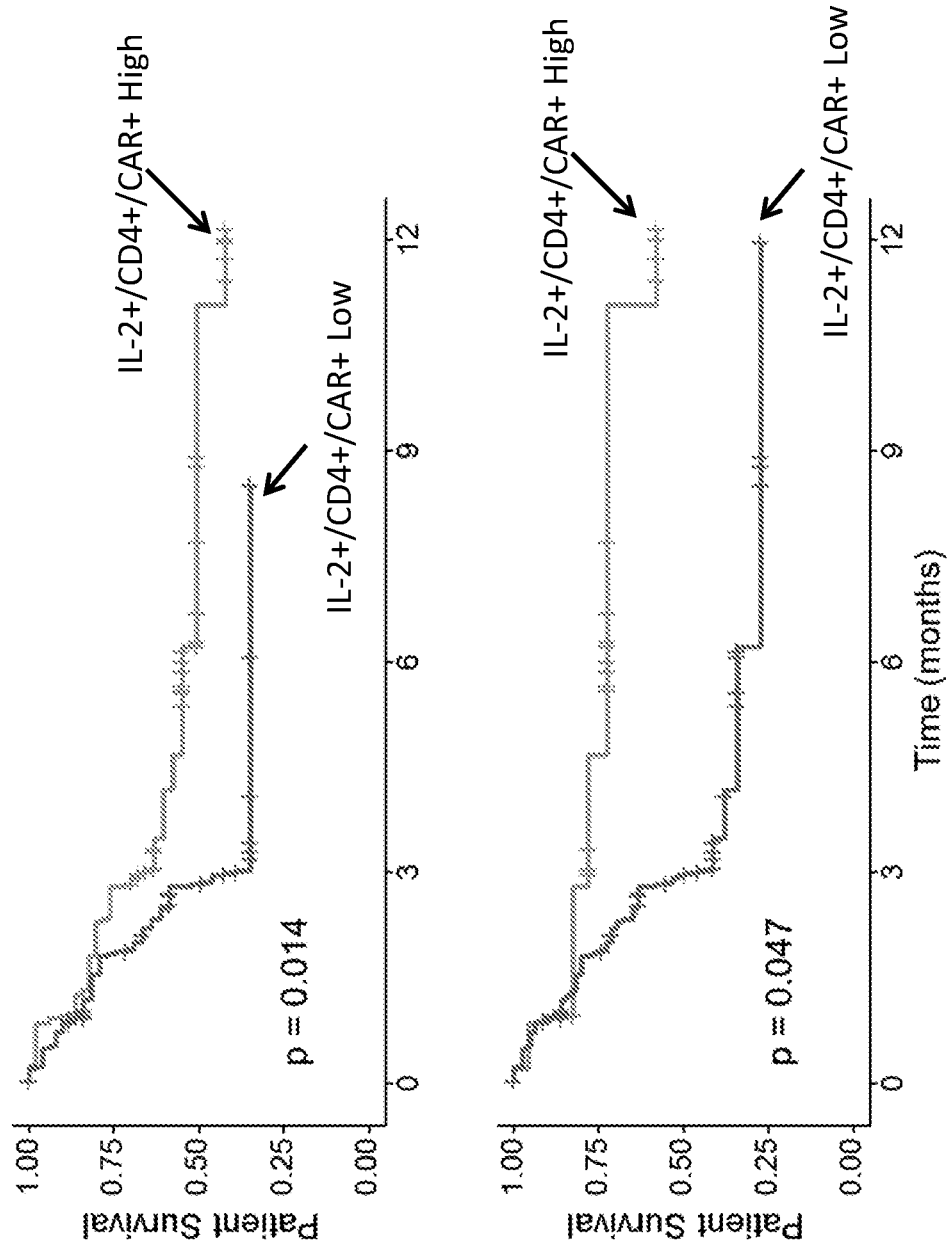
FIGS. 13A and 13B show progression free survival curves (Cox Proportional Hazard (top) and optimal split (bottom)) for patients with a "high" or "low" percentage of cells producing IL-2 or TNFα, respectively, in CD4$^+$/CAR$^+$ T cells of the therapeutic composition as determined using maximally selected rank statistics.
Figure 13B:
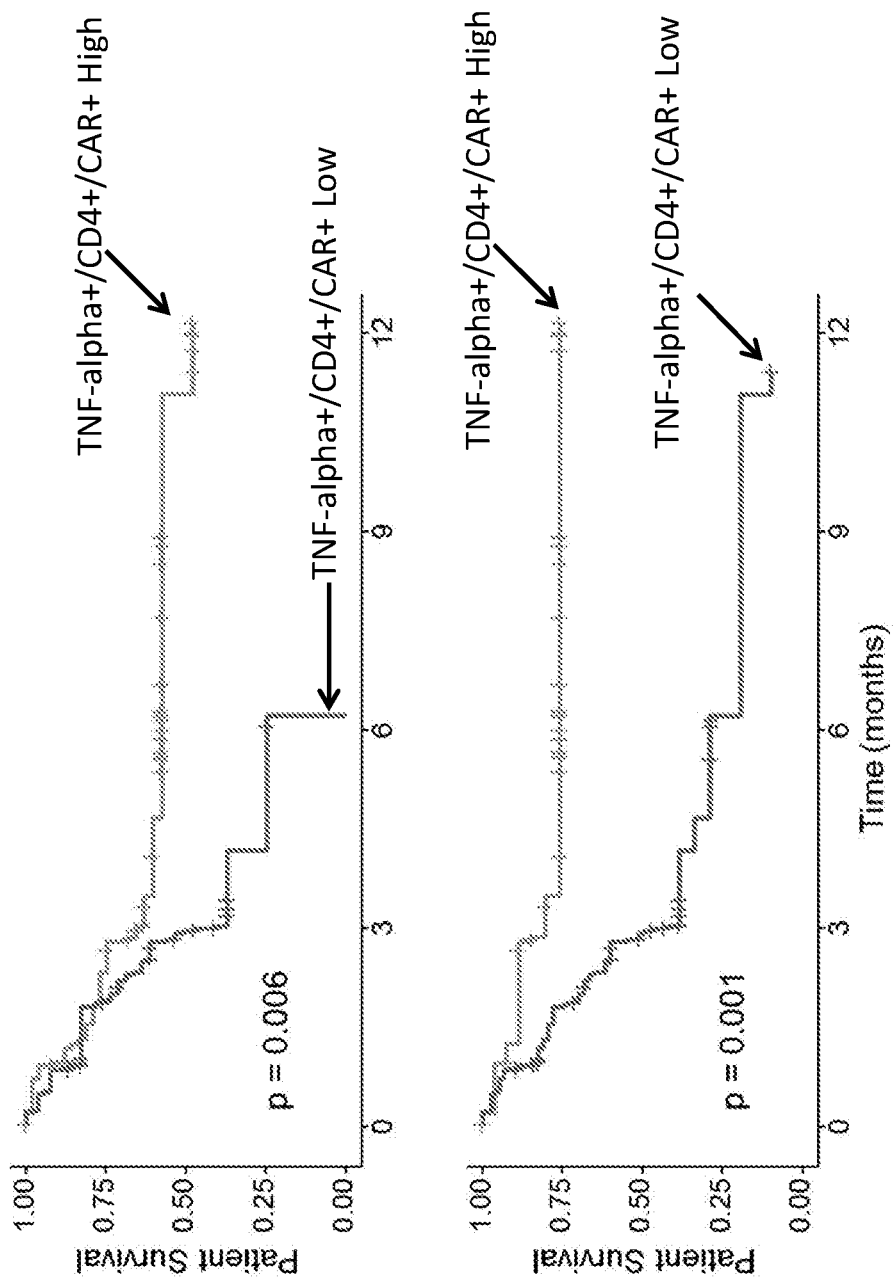

The attributes of generated CAR$^+$ T cell compositions were analyzed via univariate analysis for relationship to response outcome as assessed by comparing progression free survival (PFS) of subjects administered the therapeutic T cell compositions. Among the top variable attributes identified was the ability of CD4+ CAR$^+$ T cells to produce IL-2 and TNF-alpha cytokines in a non-CAR antigen-specific manner, such as in a flow-based method intracellular cytokine staining (ICS) assay, in response to PMA/ionomycin in the presence of Golgi inhibitor. In particular, FIGS. 13A and 13B show PFS curves (Cox Proportional Hazard (top) and optimal split (bottom)) for patients with a "high" or "low" percentage of cells producing IL-2 and TNFα production, respectively, in CD4$^+$/CAR$^+$ T cells of the therapeutic composition, as determined using maximally selected rank statistics. As shown in FIGS. 13A and 13B, groups administered therapeutic T cell compositions containing higher levels of CD4+/CAR$^+$ IL-2 or TNFα production showed improved survival compared to subjects administered therapeutic T cell compositions containing a lower percentage of such cells.

Figure 14:
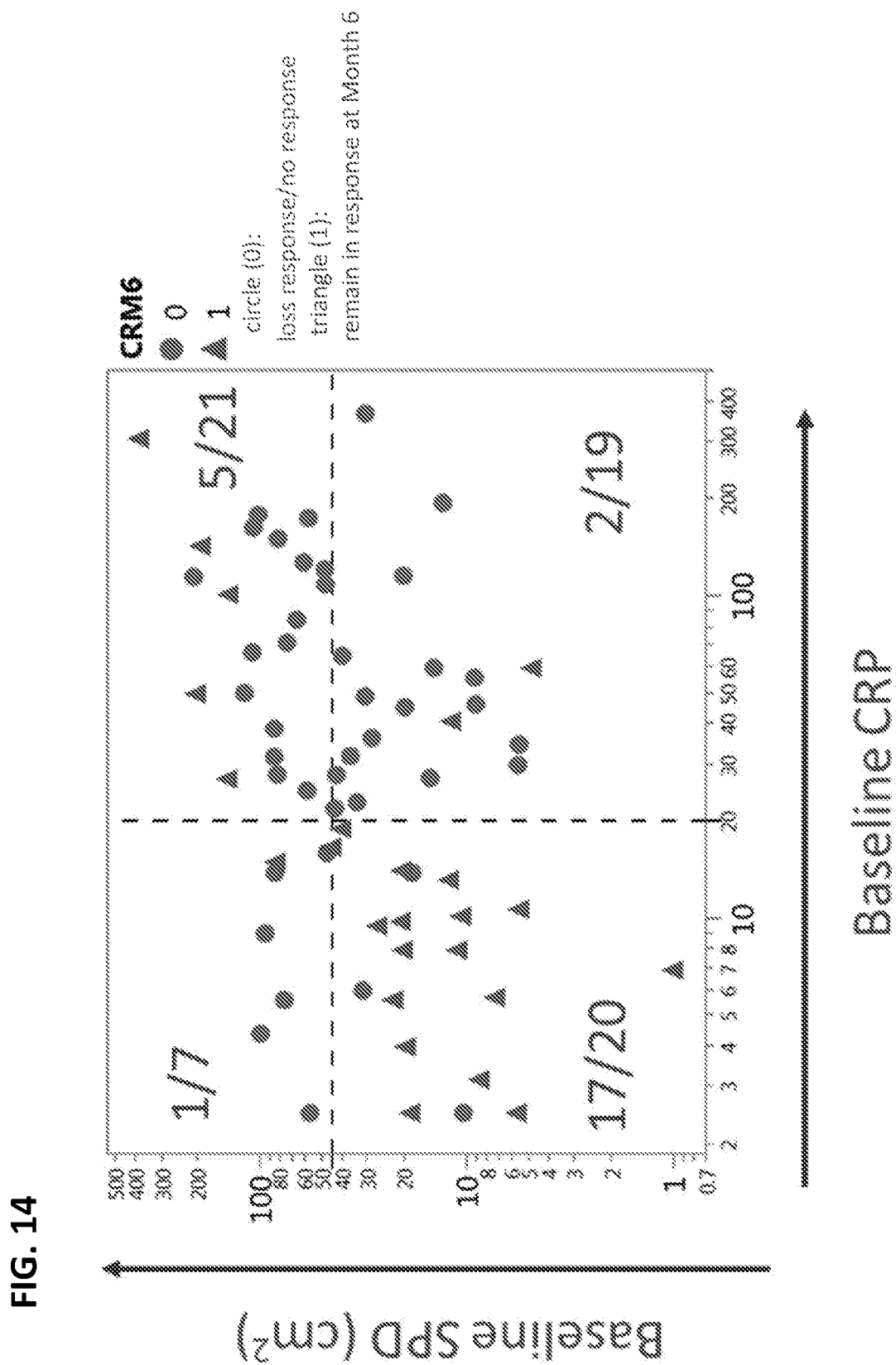
FIG. 14 shows the relationship of clinical outcome to baseline sum of the products of diameters (SPD) and baseline C-reactive protein (CRP) levels in subjects exhibiting a complete response (CR) (triangles) or loss of response/no response (circles)) at 6 months.
Figure 15:
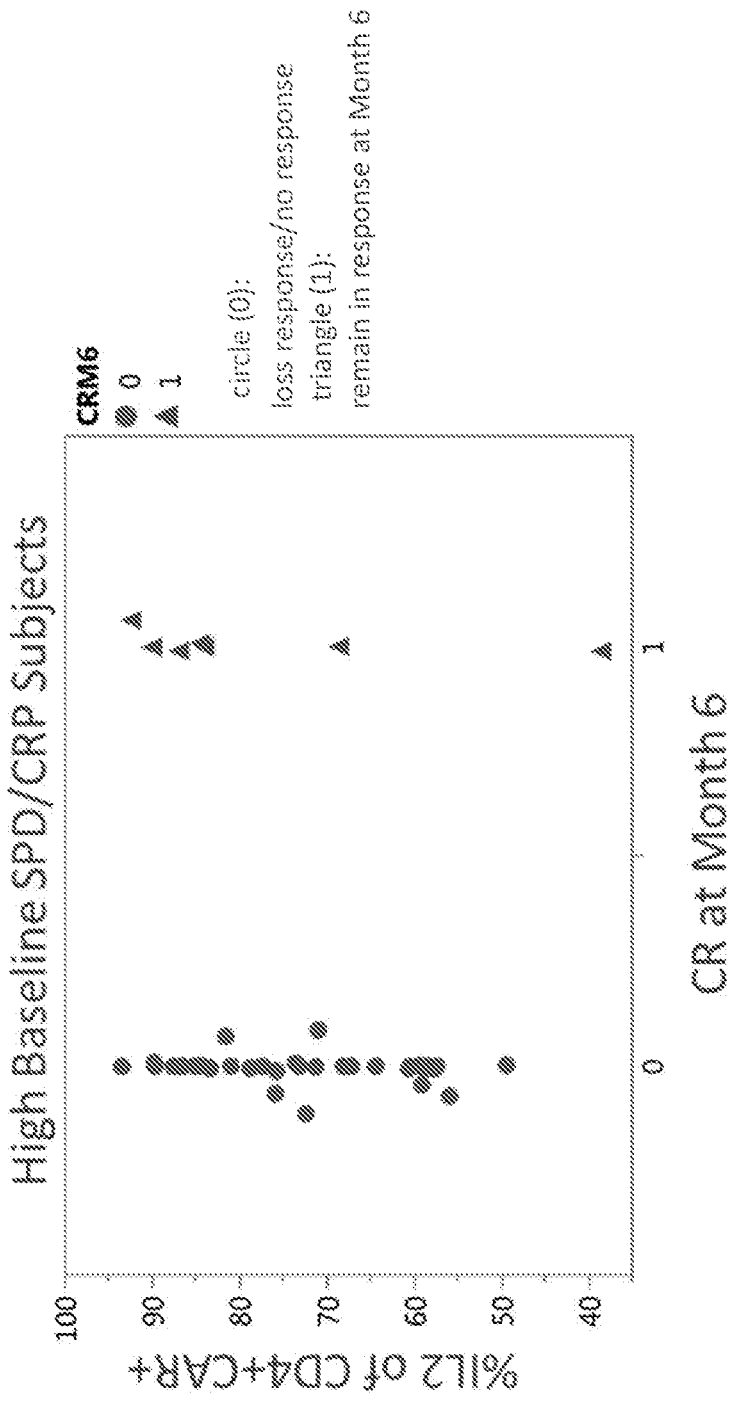
FIG. 15 shows the percentage of IL-2/CD4+/CAR+ cells in therapeutic T cell compositions generated from high baseline SPD/CRP subjects exhibiting a complete response (CR) (triangles; 1) or loss of response/no response (circles; 0)) at 6 months.

Prior to the administration of the CAR$^+$ therapeutic T cell compositions, subjects were assessed for tumor burden by monitoring baseline serum levels of sum of products (SPD) as described in Example 2. Baseline serum levels of C reactive protein (CRP) were also determined. After administration of the CAR-expressing T cell compositions to subjects substantially as described in Example 1, clinical outcome was determined for each subject at 6 months after administration and correlated to disease burden. FIG. 14 depicts clinical outcome correlated to SPD or CRP levels in subjects exhibiting a complete response (CR) (triangles) or loss of response/no response (circles)) at 6 months. As shown in FIG. 14, patients with lower disease burden, as indicated by low baseline SDP (less than 50 cm$^2$) and low CRP values (less than 20 mg/L in baseline samples), had a lower risk of loss of response at 6 months compared to patients with high disease burden, as indicated by higher baseline SPD and CRP values. For patients with high disease burden, therapeutic T cell compositions with increased frequency of CD4+ CAR+ T cells producing IL-2 expression correlated with maintained response at 6 months (FIG. 15) Similar results were observed for TNF-alpha. These data are consistent with an observation that certain functional attributes of CD4+ CAR-expressing T cells, such as the ability to produce IL-2 and TNFα, correlate positively with maintained clinical response, particularly in subjects with high disease burden or baseline levels of SPD or CRP about a threshold.

Figure 16:
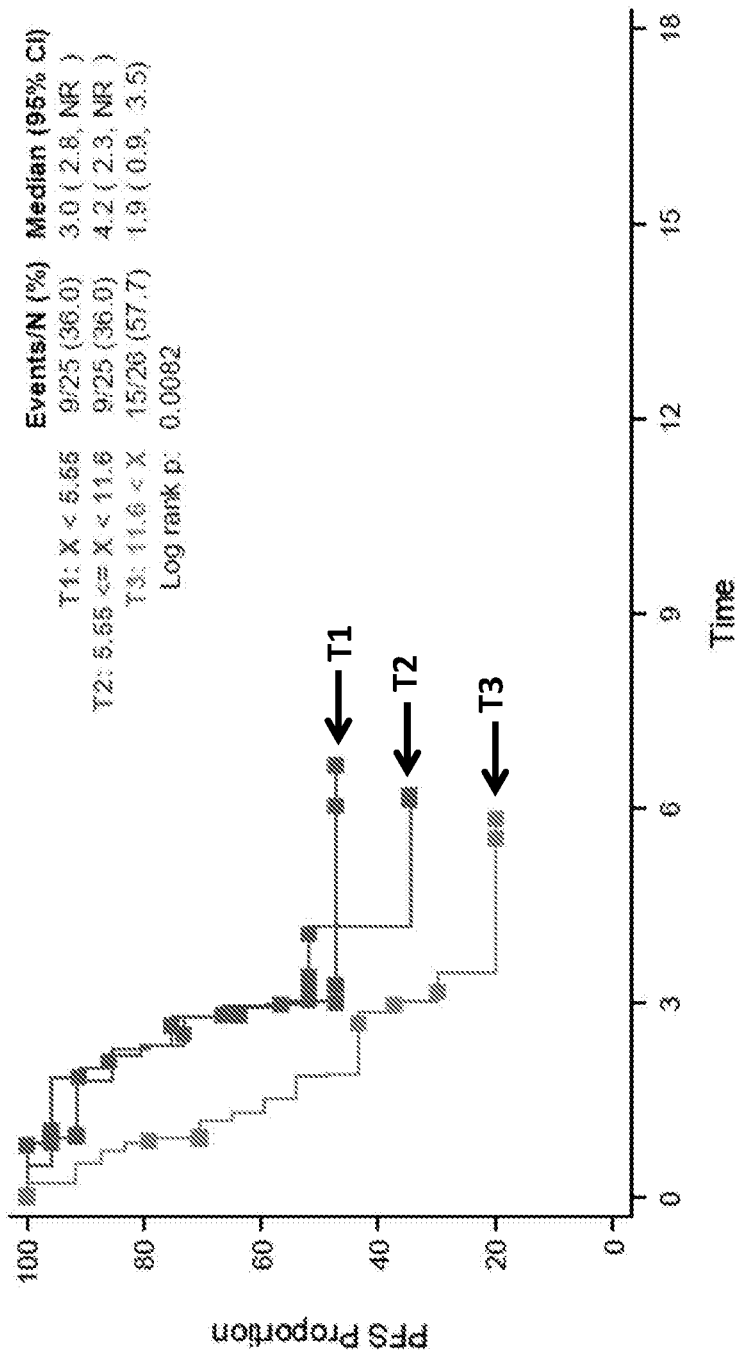
FIG. 16 shows progression free survival curves for exemplary tertile cut-off values for cells positive for the apoptotic marker activated caspase 3 in the input compositions.

Cell health of input compositions selected and enriched for CD4+ or CD8+(prior to the engineering with the anti-CD19 CAR) was assessed by flow cytometry for markers of apoptosis (e.g., activated caspase 3). The relationship between cell health and response was assessed. As shown in FIG. 16 among a plurality of enriched T cell input compositions, exemplary tertile cut-off values for cells positive for the apoptotic marker (e.g. activated caspase 3) in the input compositions demonstrated the relationship between percent apoptotic cells in the starting T cell material used to generate the therapeutic T cell composition and probability of PFS. The results are consistent with an inverse correlation between percent apoptotic marker+ cells in the starting material and improved progression free survival (PFS).

Figure 17:
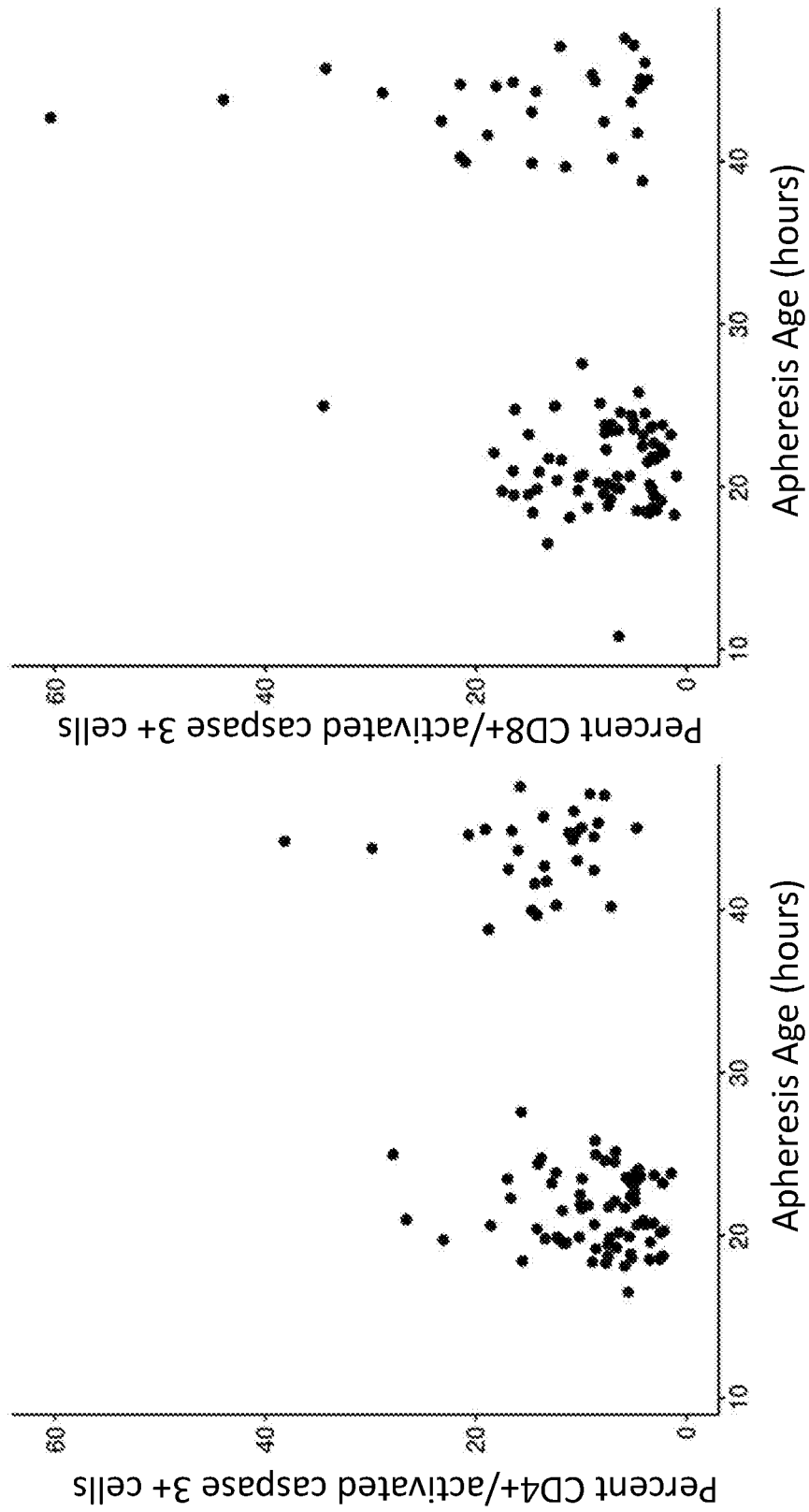
FIG. 17 shows the percent of cells positive for apoptotic marker activated caspase 3 caspase 3 in enriched input T cells compositions as a function of age of the starting apheresis sample, i.e. samples varying in the length of time (e.g. in hours) between apheresis and its further processing before enrichment of T cells. The left plot shows the percentage of CD4+/activated caspase 3+ cells and the right plot shows the percentage of CD8+/activated caspase 3+ cells.

FIG. 17 shows the percent of cells positive for an apoptotic marker (e.g. activated caspase 3) in enriched input T cells compositions using a process substantially described in Example 1, as a function of age of the starting apheresis sample, i.e. samples varying in the length of time (e.g. in hours) between apheresis and its further processing before enrichment of T cells. These data are supportive of a positive correlation between apheresis age and the presence of cells positive for an apoptotic marker.

The correlation between the presence of cells positive for an apoptotic marker (e.g. activated caspase 3) in the enriched CD8+ or CD4+ T cell starting material and various other parameters or attributes of the transduced material or of process or product features are summarized in Table E5. These data further support the finding that the starting T cell material apoptotic profile is correlated with the therapeutic composition quality.

TABLE E5

Indicated attribute correlation with activated caspase 3 in starting T cell material

| Attribute | Correlation Coefficient | P value |
|---|---|---|
| Transduced Material Viability | −0.49 | 3.32E−08 |

TABLE E5-continued

Indicated attribute correlation with activated caspase 3 in starting T cell material

| Attribute | Correlation Coefficient | P value |
|---|---|---|
| Total Doublings | 0.46 | 1.00E−06 |
| Viability | −0.42 | 2.56E−06 |
| Apheresis Age | 0.38 | 4.26E−05 |
| Viable Cell Concentration | −0.37 | 3.31E−05 |
| CCR7+ CD27+ | −0.37 | 1.93E−05 |
| IL-2 secretion | −0.26 | 3.78E−03 |

The above results are supportive of a model in which certain correlative variables associated with features of a process and/or generated $CAR^+$ therapeutic T cell composition may predict or indicate the likelihood that a subject is likely to exhibit PFS that is durable. Using conditional inference trees to recursively partition survival curves, in which partitions were performed recursively until no further splits were significant as determined using permutations to infer multiplicity adjusted p-values (Bonferroni correction), a decision tree of variables that correlate to durability of PFS was developed. The model inferred an improved likelihood of durability of response in which variables included a low level of apoptotic marker$^+$/CD3$^+$/CAR$^+$ cells in starting T cell material (e.g. enriched CD8+ T cells), a relatively low numbers of doublings of the cells during a process for producing the therapeutic T cell compositions, and a relatively low percentage of CAR+CD4+ cells among cells of the therapeutic T cell composition negative for cytokines (e.g. IL-2 or TNF) following antigen-independent stimulation (e.g. responsive to PMA/Ionomycin in an intracellular cytokine assay).

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

Sequences

| # | SEQUENCE | ANNOTATION |
|---|---|---|
| 1 | ESKYGPPCPPCP | spacer (IgG4hinge) (aa) |
| 2 | GAATCTAAGTACGGACCGCCCTGCCCCCCTTGCCCT | spacer (IgG4hinge) (nt) |
| 3 | ESKYGPPCPPCPGQPREPQVYTLPPSQEEMTKNQVSLTCLVKGFYPSDI AVEWESNGQPENNYKTTPPVLDSDGSFFLYSRLTVDKSRWQEGNVFSCS VMHEALHNHYTQKSLSLSLGK | Hinge-CH3 spacer |
| 4 | ESKYGPPCPPCPAPEFLGGPSVFLFPPKPKDTLMISRTPEVTCVVVDVS QEDPEVQFNWYVDGVEVHNAKTKPREEQFNSTYRVVSVLTVLHQDWLNG KEYKCKVSNKGLPSSIEKTISKAKGQPREPQVYTLPPSQEEMTKNQVSL TCLVKGFYPSDIAVEWESNGQPENNYKTTPPVLDSDGSFFLYSRLTVDK SRWQEGNVFSCSVMHEALHNHYTQKSLSLSLGK | Hinge-CH2-CH3 spacer |

| # | SEQUENCE | ANNOTATION |
|---|---|---|
| 5 | RWPESPKAQASSVPTAQPQAEGSLAKATTAPATTRNTGRGGEEKKKEKE KEEQEERETKTPECPSHTQPLGVYLLTPAVQDLWLRDKATFTCFVVGSD LKDAHLTWEVAGKVPTGGVEEGLLERHSNGSQSQHSRLTLPRSLWNAGT SVTCTLNHPSLPPQRLMALREPAAQAPVKLSLNLLASSDPPEAASWLLC EVSGFSPPNILLMWLEDQREVNTSGFAPARPPPQPGSTTFWAWSVLRVP APPSPQPATYTCVVSHEDSRTLLNASRSLEVSYVTDH | IgD-hinge-Fc |
| 6 | LEGGGEGRGSLLTCGDVEENPGPR | T2A |
| 7 | MLLLVTSLLLCELPHPAFLLIPRKVCNGIGIGEFKDSLSINATNIKHFK NCTSISGDLHILPVAFRGDSFTHTPPLDPQELDILKTVKEITGFLLIQA WPENRTDLHAFENLEIIRGRTKQHGQFSLAVVSLNITSLGLRSLKEISD GDVIISGNKNLCYANTINWKKLFGTSGQKTKIISNRGENSCKATGQVCH ALCSPEGCWGPEPRDCVSCRNVSRGRECVDKCNLLEGEPREFVENSECI QCHPECLPQAMNITCTGRGPDNCIQCAHYIDGPHCVKTCPAGVMGENNT LVWKYADAGHVCHLCHPNCTYGCTGPGLEGCPTNGPKIPSIATGMVGAL LLLLVVALGIGLFM | tEGFR |
| 8 | FWVLVVVGGVLACYSLLVTVAFIIFWV | CD28 (amino acids 153-179 of Accession No. P10747) |
| 9 | IEVMYPPPYLDNEKSNGTIIHVKGKHLCPSPLFPGPSKPFWVLVVVGGV LACYSLLVTVAFIIFWV | CD28 (amino acids 114-179 of Accession No. P10747) |
| 10 | RSKRSRLLHSDYMNMTPRRPGPTRKHYQPYAPPRDFAAYRS | CD28 (amino acids 180-220 of P10747) |
| 11 | RSKRSRGGHSDYMNMTPRRPGPTRKHYQPYAPPRDFAAYRS | CD28 (LL to GG) |
| 12 | KRGRKKLLYIFKQPFMRPVQTTQEEDGCSCRFPEEEEGGCEL | 4-1BB (amino acids 214-255 of Q07011.1) |
| 13 | RVKFSRSADAPAYQQGQNQLYNELNLGRREEYDVLDKRRGRDPEMGGKP RRKNPQEGLYNELQKDKMAEAYSEIGMKGERRRGKGHDGLYQGLSTATK DTYDALHMQALPPR | CD3 zeta |
| 14 | RVKFSRSAEPPAYQQGQNQLYNELNLGRREEYDVLDKRRGRDPEMGGKP RRKNPQEGLYNELQKDKMAEAYSEIGMKGERRRGKGHDGLYQGLSTATK DTYDALHMQALPPR | CD3 zeta |
| 15 | RVKFSRSADAPAYKQGQNQLYNELNLGRREEYDVLDKRRGRDPEMGGKP RRKNPQEGLYNELQKDKMAEAYSEIGMKGERRRGKGHDGLYQGLSTATK DTYDALHMQALPPR | CD3 zeta |
| 16 | RKVCNGIGIGEFKDSLSINATNIKHFKNCTSISGDLHILPVAFRGDSFT HTPPLDPQELDILKTVKEITGFLLIQAWPENRTDLHAFENLEIIRGRTK QHGQFSLAVVSLNITSLGLRSLKEISDGDVIISGNKNLCYANTINWKKL FGTSGQKTKIISNRGENSCKATGQVCHALCSPEGCWGPEPRDCVSCRNV SRGRECVDKCNLLEGEPREFVENSECIQCHPECLPQAMNITCTGRGPDN CIQCAHYIDGPHCVKTCPAGVMGENNTLVWKYADAGHVCHLCHPNCTYG CTGPGLEGCPTNGPKIPSIATGMVGALLLLLVVALGIGLFM | tEGFR |
| 17 | EGRGSLLTCGDVEENPGP | T2A |
| 18 | GSGATNFSLLKQAGDVEENPGP | P2A |
| 19 | ATNFSLLKQAGDVEENPGP | P2A |
| 20 | QCTNYALLKLAGDVESNPGP | E2A |
| 21 | VKQTLNFDLLKLAGDVESNPGP | F2A |
| 22 | -PGGG-(SGGGG)5-P- wherein P is proline, G is glycine and S is serine | Linker |
| 23 | GSADDAKKDAAKKDGKS | Linker |
| 24 | atgcttctcctggtgacaagccttctgctctgtgagttaccacaccag cattcctcctgatccca | GMCSFR alpha chain signal sequence |

-continued

| # | SEQUENCE | ANNOTATION |
|---|---|---|
| 25 | MLLLVTSLLLCELPHPAFLLIP | GMCSFR alpha chain signal sequence |
| 26 | MALPVTALLLPLALLLHA | CD8 alpha signal peptide |
| 27 | Glu Pro Lys Ser Cys Asp Lys Thr His Thr Cys Pro Pro Cys Pro | Hinge |
| 28 | Glu Arg Lys Cys Cys Val Glu Cys Pro Pro Cys Pro | Hinge |
| 29 | ELKTPLGDTHTCPRCPEPKSCDTPPPCPRCPEPKSCDTPPPCPRCPEPK SCDTPPPCPRCP | Hinge |
| 30 | Glu Ser Lys Tyr Gly Pro Pro Cys Pro Ser Cys Pro | Hinge |
| 31 | Glu Ser Lys Tyr Gly Pro Pro Cys Pro Pro Cys Pro | Hinge |
| 32 | Tyr Gly Pro Pro Cys Pro Pro Cys Pro | Hinge |
| 33 | Lys Tyr Gly Pro Pro Cys Pro Pro Cys Pro | Hinge |
| 34 | Glu Val Val Val Lys Tyr Gly Pro Pro Cys Pro Pro Cys Pro | Hinge |
| 35 | RASQDISKYLN | CDR L1 |
| 36 | SRLHSGV | CDR L2 |
| 37 | GNTLPYTFG | CDR L3 |
| 38 | DYGVS | CDR H1 |
| 39 | VIWGSETTYYNSALKS | CDR H2 |
| 40 | YAMDYWG | CDR H3 |
| 41 | EVKLQESGPGLVAPSQSLSVTCTVSGVSLPDYGVSWIRQPPRKGLEWLG VIWGSETTYYNSALKSRLTIIKDNSKSQVFLKMNSLQTDDTAIYYCAKH YYYGGSYAMDYWGQGTSVTVSS | VH |
| 42 | DIQMTQTTSSLSASLGDRVTISCRASQDISKYLNWYQQKPDGTVKLLIY HTSRLHSGVPSRFSGSGSGTDYSLTISNLEQEDIATYFCQQGNTLPYTF GGGTKLEIT | VL |
| 43 | DIQMTQTTSSLSASLGDRVTISCRASQDISKYLNWYQQKPDGTVKLLIY HTSRLHSGVPSRFSGSGSGTDYSLTISNLEQEDIATYFCQQGNTLPYTF GGGTKLEITGSTSGSGKPGSGEGSTKGEVKLQESGPGLVAPSQSLSVTC TVSGVSLPDYGVSWIRQPPRKGLEWLGVIWGSETTYYNSALKSRLTIIK DNSKSQVFLKMNSLQTDDTAIYYCAKHYYYGGSYAMDYWGQGTSVTVSS | scFv |
| 44 | KASQNVGTNVA | CDR L1 |
| 45 | SATYRNS | CDR L2 |
| 46 | QQYNRYPYT | CDR L3 |
| 47 | SYWMN | CDR H1 |
| 48 | QIYPGDGDTNYNGKFKG | CDR H2 |
| 49 | KTISSVVDFYFDY | CDR H3 |
| 50 | EVKLQQSGAELVRPGSSVKISCKASGYAFSSYWMNWVKQRPGQGLEWIG QIYPGDGDTNYNGKFKGQATLTADKSSSTAYMQLSGLTSEDSAVYFCAR KTISSVVDFYFDYWGQGTTVTVSS | VH |
| 51 | DIELTQSPKFMSTSVGDRVSVTCKASQNVGTNVAWYQQKPGQSPKPLIY SATYRNSGVPDRFTGSGSGTDFTLTITNVQSKDLADYFCQQYNRYPYTS GGGTKLEIKR | VL |
| 52 | GGGGSGGGGSGGGGS | Linker |

| # | SEQUENCE | ANNOTATION |
|---|---|---|
| 53 | EVKLQQSGAELVRPGSSVKISCKASGYAFSSYWMNWVKQRPGQGLEWIG<br>QIYPGDGDTNYNGKFKGQATLTADKSSSTAYMQLSGLTSEDSAVYFCAR<br>KTISSVVDFYFDYWGQGTTVTVSSGGGGSGGGGSGGGGSDIELTQSPKF<br>MSTSVGDRVSVTCKASQNVGTNVAWYQQKPGQSPKPLIYSATYRNSGVP<br>DRFTGSGSGTDFTLTITNVQSKDLADYFCQQYNRYPYTSGGGTKLEIKR | scFv |
| 54 | HYYYGGSYAMDY | HC-CDR3 |
| 55 | HTSRLHS | LC-CDR2 |
| 56 | QQGNTLPYT | LC-CDR3 |
| 57 | gacatccagatgacccagaccacctccagcctgagcgccagcctgggcg<br>accgggtgaccatcagctgccgggccagccaggacatcagcaagtacct<br>gaactggtatcagcagaagcccgacggcaccgtcaagctgctgatctac<br>cacaccagccggctgcacagcggcgtgcccagccggtttagcggcagcg<br>gctccggcaccgactacagcctgaccatctccaacctggaacaggaaga<br>tatcgccacctacttttgccagcagggcaacacactgccctacacccttt<br>ggcggcggaacaaagctggaaatcaccggcagcacctccggcagcggca<br>agcctggcagcggcgagggcagcaccaagggcgaggtgaagctgcagga<br>aagcggccctggcctggtggcccccagccagagcctgagcgtgacctgc<br>accgtgagcggcgtgagcctgcccgactacggcgtgagctggatccggc<br>agccccccaggaagggcctggaatggctgggcgtgatctggggcagcga<br>gaccacctactacaacagcgccctgaagagccggctgaccatcatcaag<br>gacaacagcaagagccaggtgttcctgaagatgaacagcctgcagaccg<br>acgacaccgccatctactactgcgccaagcactactactacggcggcag<br>ctacgccatggactactggggccagggcaccagcgtgaccgtgagcagc | Sequence encoding scFv |
| 58 | X₁PPX₂P<br>X₁ is glycine, cysteine or arginine<br>X₂ is cysteine or threonine | Hinge |
| 59 | GSTSGSGKPGSGEGSTKG | Linker |

What is claimed:

1. A method of treatment, the method comprising administering to a subject having lymphoma or leukemia a unit dose of a therapeutic composition comprising a plurality of CD8$^+$ and/or CD4$^+$ T cells engineered to express a recombinant receptor, wherein the recombinant receptor is a chimeric antigen receptor directed to CD19, wherein:
   the plurality of CD8+ and/or CD4+ T cells have been isolated from the peripheral blood of the subject and engineered with the recombinant receptor; and
   the unit dose of cells comprises between $1\times10^5$ and $1\times10^8$ total recombinant receptor-expressing CD8$^+$ T cells that express CD27 and CCR7 (receptor$^+$/CD8$^+$/CCR7$^+$/CD27$^+$ T cells) and/or recombinant receptor-expressing CD4$^+$ T cells that express CCR7 and CD27 (receptor$^+$/CD4$^+$/CCR7$^+$/CD27$^+$ T cells).

2. The method of claim 1, wherein the T cells expressing the recombinant receptor that are surface positive for CD27 and CCR7 are also surface negative for CD45RA.

3. The method of claim 1, wherein at least 15% of the total receptor$^+$ T cells in the composition are receptor$^+$/CD8$^+$/CCR7$^+$/CD27$^+$ or receptor$^+$/CD4$^+$/CCR7$^+$/CD27$^+$.

4. The method of claim 1, wherein, prior to the administering, the method further comprises assaying the therapeutic composition comprising a plurality of CD8$^+$ and/or CD4$^+$ T cells engineered to express a recombinant receptor for the percentage of T cells expressing the recombinant receptor that are surface positive for CD27 and CCR7.

5. The method of claim 1, wherein the unit dose comprises between $3\times10^6$ and $2.5\times10^7$ total receptor$^+$/CD8$^+$/CCR7$^+$/CD27$^+$ viable T cells and/or between $3\times10^6$ and $2.5\times10^7$ total receptor$^+$/CD4$^+$/CCR7$^+$/CD27$^+$ viable T cells, each inclusive.

6. The method of claim 1, wherein between 15% and 90% of the total receptor$^+$ T cells in the unit dose are receptor$^+$/CD8$^+$/CCR7$^+$/CD27$^+$ or receptor$^+$/CD4$^+$/CCR7$^+$/CD27$^+$, each inclusive.

7. The method of claim 1, wherein the defined ratio of receptor*/CD8+/CCR7+/CD27+ T cells to receptor*/CD4+/CCR7+/CD27+ T cells is between 1:3 and 3:1.

8. The method of claim 1, wherein the unit dose of cells is administered as a plurality of unit doses contained in separate compositions.

9. The method of claim 8, wherein the separate compositions comprise a first composition comprising one of the CD8$^+$ T cells and the CD4$^+$ T cells and a second composition comprising the other of the CD8$^+$ T cells and the CD4$^+$ T cells.

10. A method for treatment of a subject, the method comprising: (A) assaying an engineered cell composition comprising T cells expressing a recombinant receptor for the percentage of T cells expressing the recombinant receptor that are surface positive for a phenotype that is CD27 and CCR7, wherein the recombinant receptor is a chimeric antigen receptor directed to CD 19, and wherein the T cells have been isolated from the peripheral blood of the subject and engineered with the chimeric antigen receptor; and (B) administering to a subject having lymphoma or leukemia a therapy, the administering selected from: (1) if the percentage of T cells surface positive for the phenotype of cells of the engineered T cell composition is at or above a threshold value, administering to the subject one or more unit doses of cells of the engineered cell composition comprising T cells expressing the recombinant receptor that are surface positive for the phenotype; or (2) if the percentage of T cells surface positive for the phenotype of cells of the engineered T cell composition is below a threshold value, administering a therapy selected from (a) one or more unit doses of cells of the engineered cell composition and an agent capable of increasing expansion, proliferation or efficacy of T cells of the engineered cell composition in the subject, or (b) an increased dose of cells of the engineered cell composition; wherein the threshold value of the percentage of T cells surface positive for the phenotype is about 15 percent of the total number of T cells in the composition or of the total number of T cells in the composition expressing the recombinant receptor that are surface positive for CD27 and CCR7.

11. The method of claim 10, wherein the unit dose comprises between $3\times10^6$ and $2.5\times10^7$ total receptor$^+$/CD8$^+$/CCR7$^+$/CD27$^+$ viable T cells and/or between $3\times10^6$ and $2.5\times10^7$ total receptor$^+$/CD4$^+$/CCR7$^+$/CD27$^+$ viable T cells, each inclusive.

12. The method of claim 10, wherein between 15% and 90% of the total receptor$^+$ T cells in the unit dose are receptor$^+$/CD8$^+$/CCR7$^+$/CD27$^+$ or receptor$^+$/CD4$^+$/CCR7$^+$/CD27$^+$, each inclusive.

13. The method of claim 10, wherein the ratio of receptor*/CD8+/CCR7+/CD27+ T cells to receptor*/CD4+/CCR7+/CD27+ T cells is between 1:3 and 3:1.

14. The method of claim 10, wherein the unit dose comprises between $1\times10^5$ and $5\times10^8$ total CD3$^+$ viable T cells that express the recombinant receptor (receptor$^+$/CD3$^+$ cells) or total CD3$^+$ viable T cells, each inclusive.

15. The method of claim 10, wherein the unit dose of cells is administered as a plurality of unit doses contained in separate compositions.

16. The method of claim 15, wherein the separate compositions comprise a first composition comprising one of the CD8$^+$ T cells and the CD4$^+$ T cells and a second composition comprising the other of the CD8$^+$ T cells and the CD4$^+$ T cells.

17. A method of treatment, the method comprising administering to a subject having lymphoma or leukemia a unit dose of a therapeutic composition comprising a plurality of CD8$^+$ and/or CD4$^+$ T cells engineered to express a recombinant receptor, wherein:
the plurality of CD8+ and/or CD4+ T cells have been isolated from the peripheral blood of the subject and engineered with the recombinant receptor; and
the unit dose of cells comprises between $3\times10^6$ and $2.5\times10^7$ recombinant receptor-expressing CD8$^+$ T cells that express CD27 and CCR7 (receptor$^+$/CD8$^+$/CCR7$^+$/CD27$^+$ T cells) and/or recombinant receptor-expressing CD4$^+$ T cells that express CCR7 and CD27 (receptor$^+$/CD4$^+$/CCR7$^+$/CD27$^+$ T cells).

18. The method of claim 17, wherein at least 15% of the total receptor$^+$ cells in the unit dose are receptor$^+$/CD8$^+$/CCR7$^+$/CD27$^+$ or receptor$^+$/CD4$^+$/CCR7$^+$/CD27$^+$.

19. The method of claim 17, wherein between 15% and 90% of the total receptor$^+$ cells in the unit dose are receptor$^+$/CD8$^+$/CCR7$^+$/CD27$^+$ or receptor$^+$/CD4$^+$/CCR7$^+$/CD27$^+$, each inclusive.

20. The method of claim 17, wherein the ratio of receptor*/CD8+/CCR7+/CD27+ T cells to receptor+/CD4+/CCR7+/CD27+ T cells is between 1:3 and 3:1.

* * * * *

UNITED STATES PATENT AND TRADEMARK OFFICE
CERTIFICATE OF CORRECTION

PATENT NO. : 12,161,670 B2  
APPLICATION NO. : 16/770510  
DATED : December 10, 2024  
INVENTOR(S) : Kedar Himanshu Dave Page 1 of 1

It is certified that error appears in the above-identified patent and that said Letters Patent is hereby corrected as shown below:

On the Title Page

In Column 1, Item (72), Line 8, delete "Seattle, CA (US);" and insert -- Seattle, WA (US); --

In the Claims

Column 290, Line 38, In Claim 7, delete "defined"

Column 290, Line 39, In Claim 7, delete "receptor*/CD8+/CCR7+/CD27+" and insert -- receptor+/CD8+/CCR7+/CD27+ --

Column 290, Lines 39-40, In Claim 7, delete "receptor*/CD4+/CCR7+/CD27+" and insert -- receptor+/CD4+/CCR7+/CD27+ --

Column 290, Line 56, In Claim 10, delete "CD 19" and insert -- CD19 --

Column 291, Lines 22-23, In Claim 13, delete "receptor*/CD8+/CCR7+/CD27+" and insert -- receptor+/CD8+/CCR7+/CD27+ --

Column 291, Lines 23-24, In Claim 13, delete "receptor*/CD4+/CCR7+/CD27+" and insert -- receptor+/CD4+/CCR7+/CD27+ --

Column 292, Lines 27-28, In Claim 20, delete "receptor*/CD8+/CCR7+/CD27+" and insert -- receptor+/CD8+/CCR7+/CD27+ --

Column 292, Lines 28-29, In Claim 20, delete "receptor*/CD4+/CCR7+/CD27+" and insert -- receptor+/CD4+/CCR7+/CD27+ --

Signed and Sealed this  
Twenty-fifth Day of February, 2025

Coke Morgan Stewart  
*Acting Director of the United States Patent and Trademark Office*